United States Patent
Patterson et al.

(10) Patent No.: US 7,136,758 B2
(45) Date of Patent: Nov. 14, 2006

(54) VIRTUAL LIBRARY SEARCHABLE FOR POSSIBLE COMBINATORIALLY DERIVED PRODUCT MOLECULES HAVING DESIRED PROPERTIES WITHOUT THE NECESSITY OF GENERATING PRODUCT STRUCTURES

(76) Inventors: David E. Patterson, 2808 Regent St., Apt. B, Berkeley, CA (US) 94705; Richard D. Cramer, 48 Camino de Milagro, Sante Fe, NM (US) 87506

( * ) Notice: Subject to any disclaimer, the term of this patent is extended or adjusted under 35 U.S.C. 154(b) by 0 days.

(21) Appl. No.: 09/866,543

(22) Filed: May 25, 2001

(65) Prior Publication Data
US 2002/0099526 A1    Jul. 25, 2002

Related U.S. Application Data

(60) Division of application No. 08/903,217, filed on Jul. 20, 1997, now Pat. No. 6,240,374, which is a continuation-in-part of application No. 08/657,147, filed on Jun. 3, 1996, now abandoned, which is a continuation-in-part of application No. 08/592,132, filed on Jan. 26, 1996, now Pat. No. 6,185,506.

(51) Int. Cl.
*G01N 33/48* (2006.01)
*G06F 7/48* (2006.01)

(52) U.S. Cl. .......................... 702/19; 702/22; 702/27; 702/30; 702/32; 703/11; 707/102; 435/DIG. 51

(58) Field of Classification Search .... 435/DIG. 1–50, 435/DIG. 51; 702/19, 20, 22, 27, 30; 703/1, 703/11; 707/6, 7
See application file for complete search history.

(56) References Cited

U.S. PATENT DOCUMENTS

| | | | | |
|---|---|---|---|---|
| 4,642,762 A | * | 2/1987 | Fisanick | 707/3 |
| 4,811,217 A | * | 3/1989 | Tokizane et al. | 707/3 |
| 5,025,388 A | * | 6/1991 | Cramer et al. | 700/293 |
| 5,056,035 A | * | 10/1991 | Fujita | 703/12 |
| 5,157,736 A | * | 10/1992 | Boyer et al. | 382/113 |
| 5,270,170 A | * | 12/1993 | Schatz et al. | 435/7.37 |
| 5,307,287 A | * | 4/1994 | Cramer et al. | 703/2 |
| 5,345,516 A | * | 9/1994 | Boyer et al. | 382/113 |
| 5,386,507 A | * | 1/1995 | Teig et al. | 715/836 |
| 5,418,944 A | * | 5/1995 | DiPace et al. | 707/3 |
| 5,424,963 A | * | 6/1995 | Turner et al. | 703/6 |
| 5,434,796 A | * | 7/1995 | Weininger | 703/12 |
| 5,463,564 A | * | 10/1995 | Agrafiotis et al. | 700/268 |
| 5,500,807 A | * | 3/1996 | Lavin et al. | 702/22 |
| 5,526,281 A | * | 6/1996 | Chapman et al. | 702/22 |
| 5,555,366 A | * | 9/1996 | Teig et al. | 711/169 |
| 5,574,656 A | * | 11/1996 | Agrafiotis et al. | 700/268 |
| 5,577,239 A | * | 11/1996 | Moore et al. | 707/3 |
| 5,583,973 A | * | 12/1996 | DeLisi et al. | 345/420 |
| 5,619,421 A | * | 4/1997 | Venkataraman et al. | 702/27 |
| 5,752,019 A | * | 5/1998 | Rigoutsos et al. | 707/3 |
| 5,806,062 A | * | 9/1998 | Chen et al. | 707/4 |
| 5,880,972 A | * | 3/1999 | Horlbeck | 702/27 |
| 6,253,168 B1 | * | 6/2001 | Griffey et al. | 703/12 |

FOREIGN PATENT DOCUMENTS

WO    WO9607943    *    9/1994

OTHER PUBLICATIONS

Cohen et al. Molecular Modeling Software and Methods for Medicinal chemistry: J Med Chem 33 (3) 883-898, 1990.*
Rothstein et al. Group Build: A Fragment Based Method for de Novo . . . J Med Cham 36(12) 1700-1709, 1993.*

* cited by examiner

*Primary Examiner*—Mary K. Zeman
(74) *Attorney, Agent, or Firm*—Laurence Weinberger

(57) ABSTRACT

The problem of how to select out of a large chemically accessible universe molecules representative of the diversity of that universe is resolved by the discovery of a method to validate molecular structural descriptors. Using the validated descriptors, optimally diverse subsets can be selected. In addition, from the universe, molecules with characteristics similar to a selected molecule can be identified. The validated descriptors also enable the generation of a huge virtual library of potential product molecules which could be formed by combinatorial arrangement of structural variations and cores. In this virtual library it is possible to search billions of possible product compounds in relatively short time frames.

7 Claims, 44 Drawing Sheets

8B
REMOVE NON-DIVERSE REACTANTS:
  3D STRUCTURE GENERATION
  TOPOMERIC CONFORMER
    ALIGNMENT
  CoMFA FIELD GENERATION:
    HYDROGEN BOND FIELD
      GENERATION
    ROTATABLE BOND FIELD
      ATTENUATION
  CALCULATE FIELD
    DIFFERENCES
  CLUSTER
  REACTANT SELECTION FROM
    EACH CLUSTER

SYBYL: SELECTOR &
  CONCORD 3.2.1
    SPECIALIZED SOFTWARE:
    APPENDIX "A"
    (SYBYL: CoMFA
      STERIC & MSS)

SYBYL: HIERCHICAL
  CLUSTER – MSS
SYLBL: MSS

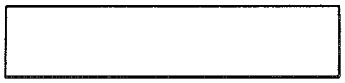
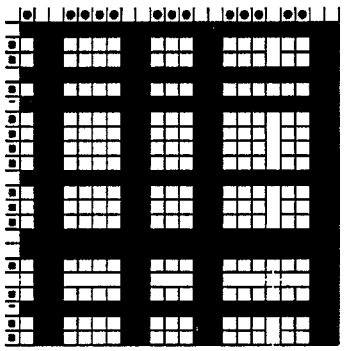

8C
COMBINE REACTANTS TO BUILD PRODUCTS

SYBYL: LEGION MSS

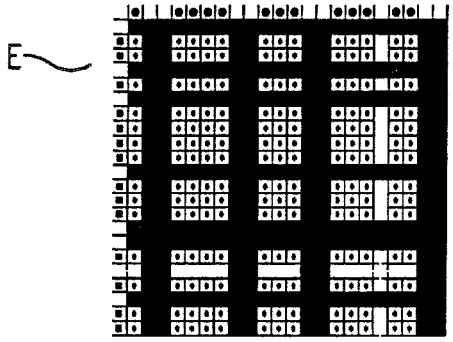

8D
REMOVE PRODUCTS:
  NON-DIVERSITY REASONS
  GENERAL CRITERIA:

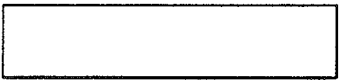

SYBYL: SPL SCRIPTS
  ON MSS

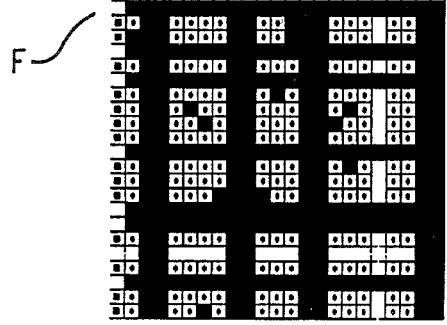

FIG.11(b)

VIRTUAL LIBRARY SEARCHABLE FOR POSSIBLE COMBINATORIALLY DERIVED PRODUCT MOLECULES HAVING DESIRED PROPERTIES WITHOUT THE NECESSITY OF GENERATING PRODUCT STRUCTURES

This application is a divisional application of application Ser. No. 08/903,217 filed Jul. 20, 1997, to be issued on May 29, 2001 as U.S. Pat. No. 6,240,374, which was a continuation-in-part of application Ser. No. 08/657,147 filed Jun. 3, 1996 now abandoned which was a continuation-in-part of application Ser. No. 08/592,132 filed Jan. 26, 1996 which issued Feb. 6, 2001 as U.S. Pat. No. 6,185,506 entitled A Method For Selecting An Optimally Diverse Library Of Small Molecules Based On Validated Molecular Structural Descriptors.

A portion of the disclosure of this patent document contains material which is subject to copyright protection. The copyright owner has no objection to the facsimile reproduction by anyone of the patent document or the patent disclosure, as it appears in the U.S. Patent and Trademark Office but otherwise reserves all copyright rights whatsoever.

TECHNICAL FIELD

This invention relates to the field of molecular structure/activity analysis and more specifically to: 1) a method of validating molecular structural descriptors; 2) a method using validated molecular descriptors to design an optimally diverse combinatorial screening library; 3) a method of merging libraries derived from different combinatorial chemistries; 4) a method using validated molecular descriptors of generating a searchable virtual library of molecules which can be combinatorially derived; 5) methods of searching the virtual library for combinatorially derived product molecules which meet specified criteria; and 6) methods of following up and optimizing identified leads. The screening libraries designed by the methods of this invention are constructed to ensure that an optimal structural diversity of compounds is represented. The search methods of the invention ensure that the same diversity space is not oversampled and that compounds can be identified having a high likelihood of possessing the same structure and/or activity of a lead compound. In particular, the invention describes the design of libraries of small molecules to be used for pharmacological testing.

BACKGROUND ART

Statement of the Problem

While the present invention is discussed with detailed reference to the search for and identification of pharmacologically useful chemical compounds, the invention is applicable to any attempt to search for and identify chemical compounds which have some desired physical or chemical characteristic(s). The broader teachings of this invention are easily recognized if a different functional utility or useful property describing other chemical systems is substituted below for the term "biological activity".

Starting with the serendipitous discovery of penicillin by Fleming and the subsequent directed searches for additional antibiotics by Waksman and Dubos, the field of drug discovery during the post World War II era has been driven by the belief that nature would provide many needed drugs if only a careful and diligent search for them was conducted. Consequently, pharmaceutical companies undertook massive screening programs which tested samples of natural products (typically isolated from soil or plants) for their biological properties. In a parallel effort to increase the effectiveness of the discovered "lead" compounds, medicinal chemists learned to synthesize derivatives and analogs of the compounds. Over the years, as biochemists identified new enzymes and biological reactions, large scale screening continued as compounds were tested for biological activity in an ever rapidly expanding number of biochemical pathways. However, proportionately fewer and fewer lead compounds possessing a desired therapeutic activity have been discovered. In an attempt to extend the range of compounds available for testing, during the last few years the search for unique biological materials has been extended to all corners of the earth including sources from both the tropical rain forests and the ocean. Despite these and other efforts, it is estimated that discovery and development of each new drug still takes about 12 years and costs on the order of 350 million dollars.

Beginning approximately twenty-five years ago, as bioscientists learned more about the chemical and stereochemical requirements for biological interactions, a variety of semi-empirical, theoretical, and quantitative approaches to drug design were developed. These approaches were accelerated by the availability of powerful computers to perform computational chemistry. It was hoped that the era of "rational drug design" would shorten the time between significant discoveries and also provide an approach to discovering compounds active in biological pathways for which no drugs had yet been discovered. In large part, this work was based on the accumulated observation of medicinal chemists that compounds which were structurally similar also possessed similar biological activities. While significant strides were made using this approach, it too, like the mass screening programs, failed to provide a solution to the problem of rapidly discovering new compounds with activities in the ever increasing number of biological pathways being elucidated by modern biotechnology.

During the past four or five years, a revised screening approach has been under development which, it was hoped, would accelerate the pace of drug discovery. In fact, the approach has been remarkably successful and represents one of the most active areas in biotechnology today. This new approach utilizes combinatorial libraries against which biological assays are screened. Combinatorial libraries are collections of molecules generated by synthetic pathways in which either: 1) two groups of reactants are combined to form products; or 2) one or more positions on core molecules are substituted by a different chemical constituent/moiety selected from a large number of possible constituents.

Two fundamental ideas underlie combinatorial screening libraries. The first idea, common to all drug research, is that somewhere amongst the diversity of all possible chemical structures there exist molecules which have the appropriate shape and binding properties to interact with any biological system. The second idea is the belief that synthesizing and testing many molecules in parallel is a more efficient way (in terms of time and cost) to find a molecule possessing a desired activity than the random testing of compounds, no matter what their source. In the broadest context, these ideas require that, since the binding requirements of a ligand to the biological systems under study (enzymes, membranes, receptors, antibodies, whole cell preparations, genetic materials, etc.) are not known, the screened compounds should possess as broad a range of characteristics (chemical and physical) as possible in order to increase the likelihood of finding one that is appropriate for any given biological target. This requirement for a screening library is reflected in the term "diversity"-essentially a way of suggesting that the library should contain as great a dissimilarity of compounds as possible.

However, as is immediately apparent, a combinatorial approach to synthesizing molecules generates an immense number of compounds many with a high degree of structural similarity. In fact, the number of compounds synthetically accessible with known organic reactions exceeds by many orders of magnitude the numbers which can actually be made and tested. One area where these ideas were first explored is in the design of peptide libraries. For a library of five member peptides synthesized using the 20 naturally occurring amino acids, 3,200,000, ($20^5$) different peptides may be constructed. The number of combinatorial possibilities increases even more dramatically when non-peptide combinatorial libraries are considered. With non-peptide libraries, the whole synthetic chemical universe of combinatorial possibilities is available. Library sizes ranging from $5 \times 10^7$ to $4 \times 10^{12}$ molecules are now being discussed. The enormous universe of chemical compounds is both a blessing and a curse to medicinal chemists seeking new drugs. On the one hand, if a molecule exists with the desired biological activity, it should be included in the chemical universe. On the other hand, it may be impossible to find. Thus, the principal focus of recent efforts has been to define smaller screening subsets of molecules derivable from accessible combinatorial syntheses without losing the inherent diversity of an accessible universe.

To date, in order to narrow the focus of the search and reduce the number of compounds to be screened, attention has been directed to designing biologically specific libraries. Thus, many combinatorial screening libraries existing in the prior art have been designed based on prior knowledge about a particular biological system such as a known pharmacophore (a geometric arrangement of structural fragments abstracted from molecular structures known to have activity). Even with this knowledge, molecules are included in these prior art libraries based on intuition—"seat of the pants" estimations of likely similarity based on an intuitive "feel" for the systems under study. This procedure is essentially pseudo-random screening, not rational library design. Several biotechnology startup companies have developed just such proprietary libraries, and success using combinatorial libraries has been achieved by sheer effort. In one example 18 libraries containing 43 million compounds were screened to identify 27 active compounds[1]. With library searches of this magnitude, it is most likely that the enormous number of inactive molecules [$(43 \times 10^6)-27$] must have included staggering numbers of redundantly inactive molecules—molecules not significantly distinguishable from one another—even in libraries designed with a particular biological target in mind. Clearly, when searching for a lead molecule which interacts with an uncharacterized biological target, approaches requiring knowledge of the biological targets will not work. But finding such a lead is exactly the case for which it is hoped general purpose screening libraries can be designed. If the promise of combinatorial chemistry is ever to be fully realized, some rational and quantitative method of reducing the astronomical number of compounds accessible in the combinatorial chemistry universe to a number which can be usefully tested is required. In other words, the efficiency of the search process must be increased. For this purpose, a smaller rationally designed screening library, which still retains the diversity of the combinatorially accessible compounds, is absolutely necessary.

Thus, there are two criteria which must be met by any screening library subset of some universe of combinatorially accessible compounds. First, the diversity, the dissimilarity of the universe of compounds accessible by some combinatorial reaction, must be retained in the screening subset. A subset which does not contain examples of the total range of diversity in such a universe would potentially miss critical molecules, thereby frustrating the very reason for the creation of the subset. Second, for efficient screening, the ideal subset should not contain more than one compound representative of each aspect of the diversity of the larger group. If more than one example were included, the same diversity would be tested more than once. Such redundant screening would yield no new information while simultaneously increasing the number of compounds which must be synthesized and screened. Therefore, the fundamental problem is how to reduce to a manageable number the number of compounds that need to be synthesized and tested while at the same time providing a reasonably high probability that no possible molecule of biological importance is overlooked. (In this regard, it should be recognized that the only way of absolutely insuring that all diversity is represented in a library is to include and test all compounds.) A conceptual analogy to the problem might be: what kind of filter can be constructed to sort out from the middle of a blinding snowstorm individual snowflakes which represent all the classes of crystal structures which snowflakes can form?

The fundamental question plaguing progress in this area has been whether the concept of the diversity of molecular structure can be usefully described and quantified; that is, how is it possible to compare/distinguish the physical and chemical properties determinative of biological activity of one molecule with that of another molecule? Without some way to quantitatively describe diversity, no meaningful filter can be constructed. Fortunately, for biological systems, the accumulated wisdom of bioscientists has recognized a general principle alluded to earlier which provides a handle on this problem. As framed by Johnson and Maggiora[2], the principle is simply stated as: "structurally similar molecules are expected to exhibit similar (biological) properties." Based on this principle, quantifying diversity becomes a matter of quantifying the notion of structural similarity. Thus, for design of a screening subset of a combinatorial library (hereafter referred to as a "combinatorial screening library"), it should only be necessary to identify which molecules are structurally similar and which structurally dissimilar. According to the selection criteria outlined above, one molecule of each structurally similar group in the combinatorially accessible chemical universe would be included in the library subset. Such a library would be an optimally diverse combinatorial screening library. The problem for medicinal chemists is to determine how the intuitively perceived notions of structural similarity of chemical compounds can be validly quantified. Once this question is satisfactorily answered, it should be possible to rationally design combinatorial screening libraries.

Prior Art Approaches

Many descriptors of molecular structure have been created in the prior art in an attempt to quantify structural similarity and/or dissimilarity. As the art has recognized, however, no method currently exists to distinguish those descriptors that quantify useful aspects of similarity from those which do not. The importance of being able to validate molecular descriptors has been a vexing problem restricting advances in the art, and, before this invention, no generally applicable and satisfactory answer had been found. The problem may be conceptualized in terms of a multidimensional space of structurally derivable properties which is populated by all possible combinatorially accessible chemical compounds. Compounds lying "near" one another in any one dimension may lie "far apart" from one another in another dimension. The difficulty is to find a useful design space—a quantifiable dimensional space (metric space) in which compounds with similar biological properties cluster; ie., are found measurably near to each other. What is desired is a molecular structural descriptor which, when applied to the molecules of the chemical universe, defines a dimensional space in which the "nearness" of the molecules with respect to a specified characteristic (ie.; biological activity) in the chemical universe is preserved in the dimensional space. A molecular structural descriptor (metric) which does not have this property is useless as a descriptor of molecular diversity. A valid descriptor is defined as one which has this property.

In light of the above, it should be noted that there is a difference between a descriptor being valid and being perfect. There may or may not be a "perfect" metric which precisely and quantitatively maps the diversity of compounds (much less those of biological interest). However, a good approximation is sufficient for purposes of designing a combinatorial screening library and is considered valid/useful. Acceptance of this validation/usefulness criteria is essentially equivalent to saying that, if there is a high probability that if one molecule is active (or inactive), a second molecule is also active (or inactive), then most of the time sampling one of the pair will be sufficient. Restating this same principle with a slightly different emphasis highlights another feature, namely: the design criteria for combinatorial screening libraries should yield a high probability that, for any given inactive molecule, it is more probable to find an active molecule somewhere else rather than as a near neighbor of that inactive molecule. While this is a probabilistic approach, it emphasizes that a good approximation to a perfect metric is sufficient for purposes of designing a combinatorial screening library as well as in other situations where the ability to discriminate molecular structural difference and similarities is required. A perfect descriptor (certainty) for pharmacological searching is not needed to achieve the required level of confidence as long as it is valid (maps a subspace where biological properties cluster).

The typical prior art approach for establishing selection criteria for screening library subsets relied on the following clustering paradigm: 1) characterization of compounds according to a chosen descriptor(s) (metric[s]); 2) calculation of similarities or "distances" in the descriptor (metric) between all pairs of compounds; and 3) grouping or clustering of the compounds based on the descriptor distances. The idea behind the paradigm is that, within a cluster, compounds should have similar activities and, therefore, only one or a few compounds from each cluster, which will be representative of that cluster, need be included in a library. The actual clustering is done until the prior art user feels comfortable with the groupings and their spacing. However, with no knowledge of the validity/usefulness of the descriptor employed, and no guidance with respect to the size or spacing of clusters to be expected from any given descriptor, prior art clustering has been, at best, another intuitive "seat of the pants" approach to diversity measurement.

The prior art describes the construction and application of many molecular structural descriptors while all the while tacitly acknowledging that little progress has been made towards solving the fundamental problem of establishing their validity. The field has nevertheless proceeded based on the belief/faith that, by incorporating in the descriptors certain measures which had been recognized in QSAR studies as being important contributors to defining structure-activity relationships, valid/useful descriptors would be produced. In a leading method representative of this prior art approach to defining a similarity descriptor, E. Martin et al.[3] construct a metric for quantifying structural similarity using measures that characterize lipophilicity, shape and branching, chemical functionality, and receptor recognition features. (For the reasons set forth later in relation to the present invention, Martin et al. applied their metric to the reactants which would be used in combinatorial synthesis.) This large set of measures is used to generate a statistically blended metric consisting of a total of 16 properties for each individual reactant studied (5 shape descriptors, 5 measures of chemical functionality, 5 receptor binding descriptors, and one lipophilicity property). This generates a 16 dimensional property space. The 16 properties are simultaneously displayed in a circular "Flower Plots" graphical environment, where each property is assigned a petal. All the plots together visually display how the diversity of the studied reactants is distributed through the computed property space. Martin acknowledges that the plots ". . . cannot, of course, prove that the subset is diverse in any 'absolute' sense, independent of the calculated properties." (Martin at 1434)

In another approach relating to peptoid design, Martin et al.[4] have characterized the varieties of shape that an unknown receptor cavity might assume by a few assemblages of blocks, called "polyominos". Candidates for a combinatorial design are classified by the types of polyominos into which they can be made to fit, or "docked". The 7 flexible polyomino shape descriptors are added to the previously defined 16 descriptors to yield a 23 dimensional property space. Martin has demonstrated that the docking procedure generates for a methotrexate ligand in a cavity of dihydrofolate reductase nearly the correct structure as that established by X-ray diffraction studies. The docking procedure, which must be applied to every design candidate for each polyomino, requires a considerable amount of CPU time (is computationally expensive). However, a problem with this approach is the conceptually severe (unjustified) approximation of representing all possible irregularly shaped receptor cavities by only about a dozen assemblies of smooth-sided polyomino cubes. Martin has also presented no validation of the approach, which in this case, would be a demonstration that molecules which fit into the same polyominos tend to have similar biological properties.

One approach which has been taken to try to empirically assess the relative validity of prior art metrics has been to survey the metrics to see if any of them appeared to be superior to any others as judged by clustering analysis. Y. C. Martin et al.[5] have reported that 3D fingerprints, collections of fragments defined by pairs of atoms and their accessible interatomic distances, perform no better than collections of 2D fragments in defining clusters that separate biologically active from inactive compounds. As will be seen later, some of this work pointed towards the possible validity of one metric, but the authors concentrated on the comparative clustering aspects and did not follow up on the broader import of the data.

W. Hemdon[6] among others has pointed out that an experimentally determined similarity QSAR is, by definition, a good test of the validity of that similarity concept for the biological system from which it is derived and may have some usefulness in estimating diversity for that system. However, QSARs essentially map only the space of a particular receptor, do not provide information about the validity of other descriptors, and would be generally inapplicable to construction of a combinatorial screening library designed for screening unknown receptors or those for which no QSAR data was available.

Finally, D. Chapman et al.[7] have used their "Compass" 3D-QSAR descriptor which is based on the three dimensional shape of molecules, the locations of polar functionalities on the molecules, and the fixation entropies of the molecules to estimate the similarity of molecules. Essentially, using the descriptor, they try to find the molecules which have the maximum overlap (in geometric/cartesian space) with each other. The shape of each molecule of a series is allowed to translate and rotate relative to each other molecule and the internal degrees of freedom are also allowed to rotate in an iterative procedure until the shapes with greatest or least overlap similarity are identified. Selecting 20 maximally diverse carboxylic acids based on seeking the maximally diverse alignment of each of the 3000 acids considered took approximately 4 CPU computing weeks by their method. No indication was given of whether their descriptor was valid in the sense defined above, and, clearly, such a procedure would be too time consuming to apply to a truly large combinatorial library design.

One way in which many of the prior art approaches attempt to work around the problem of not knowing if a molecular structural descriptor is valid is to try, when clustering, to maximize as much as possible the distance between the clusters from which compounds will be selected for inclusion in the screening library subset. The thinking behind this approach is that, if the clusters are far enough apart, only molecules diverse from each other will be chosen. Conversely, it is thought that, if the clusters are close together, oversampling (selection of two or more molecules representative of the same elements of diversity) would likely occur. However, as we have seen, if the metric used in the cluster analysis is not initially valid (does not define a subspace in which molecules with similar biological activity cluster), then no amount of manipulation will prevent the sample from being essentially random. Worse yet, an invalid metric might not yield a selection as good as random! The acknowledgment by Martin quoted above is a recognition of the prior art's failure to yet discover a general method for validating descriptors.

Another related problem in the prior art is the failure to have any objective manner of ascertaining when the library subset under design has an adequate number of members; that is, when to stop sampling. Clearly, if nothing is known about the distribution of the diversity of molecules, one arbitrary stopping point is as good as any other. Any stopping point may or may not sample sufficiently or may oversample. In fact, the prior art has not recognized a coherent quantitative methodology for determining the end point of selection. Essentially, in the prior art, a metric is used to maximize the presumed differences between molecules (typically in a clustering analysis), and a very large number of molecules are chosen for inclusion in a screening library subset based on the belief that there is safety in numbers; that sampling more molecules will result in sampling more of the diversity of a combinatorially accessible chemical space. As pointed out earlier, however, only by including all possible molecules in a library will one guarantee that all of the diversity has been sampled. Short of such total sampling, users of prior art library subsets constructed along the lines noted above do not know whether a random sample, a representative sample, or a highly skewed sample has been screened.

Several other problems flow from the inability to rationally select a combinatorial screening library for optimal diversity and these are related both to the chemistry used to create the combinatorial library and the screening systems used. First, because many more molecules may have to be synthesized than may be needed, mass synthetic schemes have to be devised which create many combinations simultaneously. In fact, there is a good deal of disagreement in the prior art as to whether compounds should be synthesized individually or collectively or in solution or on solid supports. Within any synthetic scheme, an additional problem is keeping track of and identifying the combinations created. It should be understood that, where relatively small (molecular weight of less than about 1500) organic molecules are concerned, generally standard, well known, organic reactions are used to create the molecules. In the case of peptide like molecules, standard methods of peptide synthesis are employed. Similarly for polysaccharides and other polymers, reaction schemes exist in the prior art which are well known and can be utilized. While the synthesis of any individual combinatorial molecule may be straightforward, much time and effort has been and is still being expended to develop synthetic schemes in which hundreds, thousands, or tens of thousands of combinatorial combinations can be synthesized simultaneously.

In many synthetic schemes, mixtures of combinatorial products are synthesized for screening in which the identity of each individual component is uncertain. Alternatively, many different combinatorial products may be mixed together for simultaneous screening. Each additional molecule added to a simultaneous screen means that many fewer individual screening operations have to be performed. Thus, it is not unusual that a single assay may be simultaneously tested against up to 625 or more different molecules. Not until the mixture shows some activity in the biological screening assay will an attempt be made to identify the components. Many approaches in the prior art therefore face "deconvolution" problems; ie. trying to figure out what was in an active mixture either by following the synthetic reaction pathway, by resynthesizing the individual molecules which should have resulted from the reaction pathway, or by direct analysis of duplicate samples. Some approaches even tag the carrier of each different molecule with a unique molecular identifier which can be read when necessary. All these problems are significantly decreased by designing a library for optimal diversity.

Another major problem with the inclusion of multiple and potentially non-diverse compounds in the same screening mixture is that many assays will yield false positives (have an activity detected above a certain established threshold) due to the combined effect of all the molecules in the screening mixture. The absence of the desired activity is only determined after expending the time, effort, and expense of identifying the molecules present in the mixture and testing them individually. Such instances of combined reactivity are reduced when the screening mixture can be selected from molecules belonging to diverse groups of an optimally designed library since it is not as likely that molecules of different (diversity) structures would likely produce a combined effect.

It is clear that a great deal of cleverness has been expended in actually manufacturing the combinatorial libraries. While the basic chemistry of synthesizing any given molecule is straight forward, the next advance in the development of combinatorial chemistry screening libraries will be optimization of the design of the libraries.

Further problems in the prior art arise in the attempt to follow up leads resulting from the screening process. As noted above, many libraries are designed with some knowledge of the receptor and its binding requirements. While, within those constraints, all possible combinatorial molecules are synthesized for screening, finding a few molecules with the desired activity among such a library yields no information about what active molecules might exist in the universe accessible with the same combinatorial chemistry but outside the limited (receptor) library definition. This is an especially troubling problem since, from serendipitous experience, it is well known that sometimes totally unexpected molecules with little or no obvious similarity to known active molecules exhibit significant activity in some biological systems. Thus, even finding a candidate lead in a library whose design was based on knowledge of the receptor is no guarantee that the lead can be followed to an optimal compound. Only a rationally designed combinatorial screening library of optimal diversity can approach this goal.

For prior art library subsets designed around the use of some descriptor to cluster compounds, similar problems may exist. In such a library design, one or at most a few compounds will have been selected from each cluster. Only if the descriptor is valid, does such a selection procedure make sense. If the descriptor is not valid, each cluster will contain molecules representative of many different diversities and selecting from each cluster will still have resulted in a random set of molecules which do not sample all of the diversity present. Since the prior art does not possess a generally applicable method of validating descriptors, all screening performed with prior art libraries is suspect and may not have yielded all the useful information desired about the larger chemical universe from which the library subsets were selected.

Finally, as the expense in time and effort of creating and screening combinatorial libraries increases, the question of the uniqueness of the libraries becomes ever more critical. Questions can be asked such as: 1) does library "one" cover the same diversity of chemical structures as library "two"; 2) if libraries "one" and "two" cover both different and identical aspects of diversity, how much overlap is there; 3) what about the possible overlap with libraries "three", "four", "five", etc.? To date, the prior art has been unable to answer these questions. In fact, assumptions have been made that as long as different chemistries were involved (ie., proteins, polysaccharides, small organic molecules), it was unlikely that the same diversity space was being sampled. However, such an assumption contradicts the well known reality that biological receptors can recognize molecular similarities arising from different structures. When screening for compounds possessing activity for undefined biological receptors, there is no way of telling a priori which chemistry or chemistries is most likely to produce molecules with activity for that receptor. Thus, screening with as many chemistries as possible is desired but is only really practical if redundant sampling of the same diversity space in each chemistry can be avoided. The prior art has not provided any guidance towards the resolution of these problems.

BRIEF SUMMARY OF THE INVENTION

In order to select a screening subset of a combinatorially accessible chemical universe which is representative of all the structural variation (diversity) to be found in the universe, it is necessary to have the means to describe and compare the molecular structural diversity in the universe. The first aspect of the present invention is the discovery of a generalized method of validating descriptors of molecular structural diversity. The method does not assume any prior knowledge of either the nature of the descriptor or of the biological system being studied and is generally applicable to all types of descriptors of molecular structure. This discovery enables several related advances to the art.

The second aspect of the invention is the discovery of a method of generating a validated three dimensional molecular structural descriptor using CoMFA fields. To generate these field descriptors required solving the alignment problem associated with these measurements. The alignment problem was solved using a topomeric procedure.

A third aspect of the invention is the discovery that validated molecular structural descriptors applicable to whole molecules can be used both to: 1) quantitatively define a meaningful end-point for selection in defining a single screening library (sampling procedure); and 2) merge libraries so as not to include molecules of the same or similar diversity. It is shown that a known metric (Tanimoto 2D fingerprint similarity) can be used in conjunction with the sampling procedure for this purpose.

A fourth aspect of the invention is the discovery of a method of using validated reactant and whole molecule molecular structural descriptors to rationally design a combinatorial screening library of optimal diversity. In particular, the shape sensitive topomeric CoMFA descriptor and the atom group Tanimoto 2D similarity descriptor may be used in the library design. As a benefit of designing a combinatorial screening library of optimal diversity based on validated molecular descriptors, many prior art problems associated with the synthesis, identification, and screening of mixtures of combinatorial molecules can be reduced or eliminated.

A fifth aspect of the invention is the use of validated molecular structural descriptors to guide the search for optimally active compounds after a lead compound has been identified by screening. In the case of a screening library designed for optimal diversity using validated descriptors, a great deal of the information necessary for lead optimization flows directly from the library design. In the case where a lead has been identified by screening a prior art library or through some other means, validated descriptors provide a method for identifying the molecular structural space nearest the lead which is most likely to contain compounds with the same or similar activity.

A sixth aspect of this invention is the discovery of a method for generating, using validated molecular descriptors, a virtual library of product molecules derivable from combinatorial reactions (or which may be represented by a combinatorial SLN [CSLN]) in which the characteristics of product molecules can be searched and compared without the actual construction of the product molecules. This virtual library allows the searching of billions of possible product molecules in reasonable amounts of time.

A seventh aspect of this invention is the discovery that, using validated molecular descriptors, the virtual library can be searched over billions of possible product molecules in ways to yield both optimally diverse screening libraries and to follow up on lead explosions. Using the virtual library, a much larger fraction of the chemically accessible universe can be searched for molecules of interest.

An eighth aspect of this invention is the discovery of a way to search, using validated molecular descriptors, the virtual library for possible molecules which have similar structures and/or activities to a query molecule which is not necessarily derived from a combinatorial synthesis. This discovery opens up a whole new method for seeking molecules with similar characteristics to a previously identified molecule.

It is an object of this invention to define a general process which may be used with randomly selected literature data sets to validate molecular structural descriptors.

It is a further object of this invention to define a process to derive CoMFA steric fields (and, if desired, additional relevant fields) using topomeric alignment so that the resulting descriptor is valid.

It is a further object of this invention to teach that topomeric alignments may be used to describe molecular conformations.

It is a further object of this invention to define a general process for using a validated molecular descriptor to establish a meaningful end-point for the sampling of compounds thereby avoiding the oversampling of compounds representing the same molecular structural characteristics.

It is yet a further object of this invention to design an optimally diverse combinatorial screening library using multiple validated molecular structural descriptors.

It is a further object of this invention to use the topomeric CoMFA molecular structural descriptor as a reactant descriptor in the design of an optimally diverse combinatorial screening library.

It is a further object of this invention to use the Tanimoto 2D similarity molecular structural descriptor as a product descriptor in the design of an optimally diverse combinatorial screening library.

It is a further object of this invention to define a method for merging assemblies of molecules (libraries), both those designed by the methods of this invention and others not designed by the methods of this invention, in such a manner that molecules representing the same or similar diversity space are not likely to be included.

It is a further object of this invention to define methods for the use of validated molecular structural descriptors to guide the search for optimally active compounds after a lead compound has been identified by screening or some other method.

It is a further object of this invention to generate a virtual library, using validated molecular descriptors, of potential product molecules derivable from combinatorial reactions (or which may be represented by a combinatorial SLN [CSLN]) which can be searched for molecules having desired characteristics.

It is a further object of this invention to define methods for creating optimal diversity screening libraries as subsets of the virtual library.

It is still a further object of this invention to locate within the virtual library possible product molecules similar in structure and/or activity to lead compounds.

These and further objects of the invention will become apparent from the detailed description of the invention which follows.

BRIEF DESCRIPTION OF DRAWINGS

FIGS. 11A through 11C are schematics of the combinatorial screening library design process.

DISCLOSURE OF INVENTION

Figure 1A:
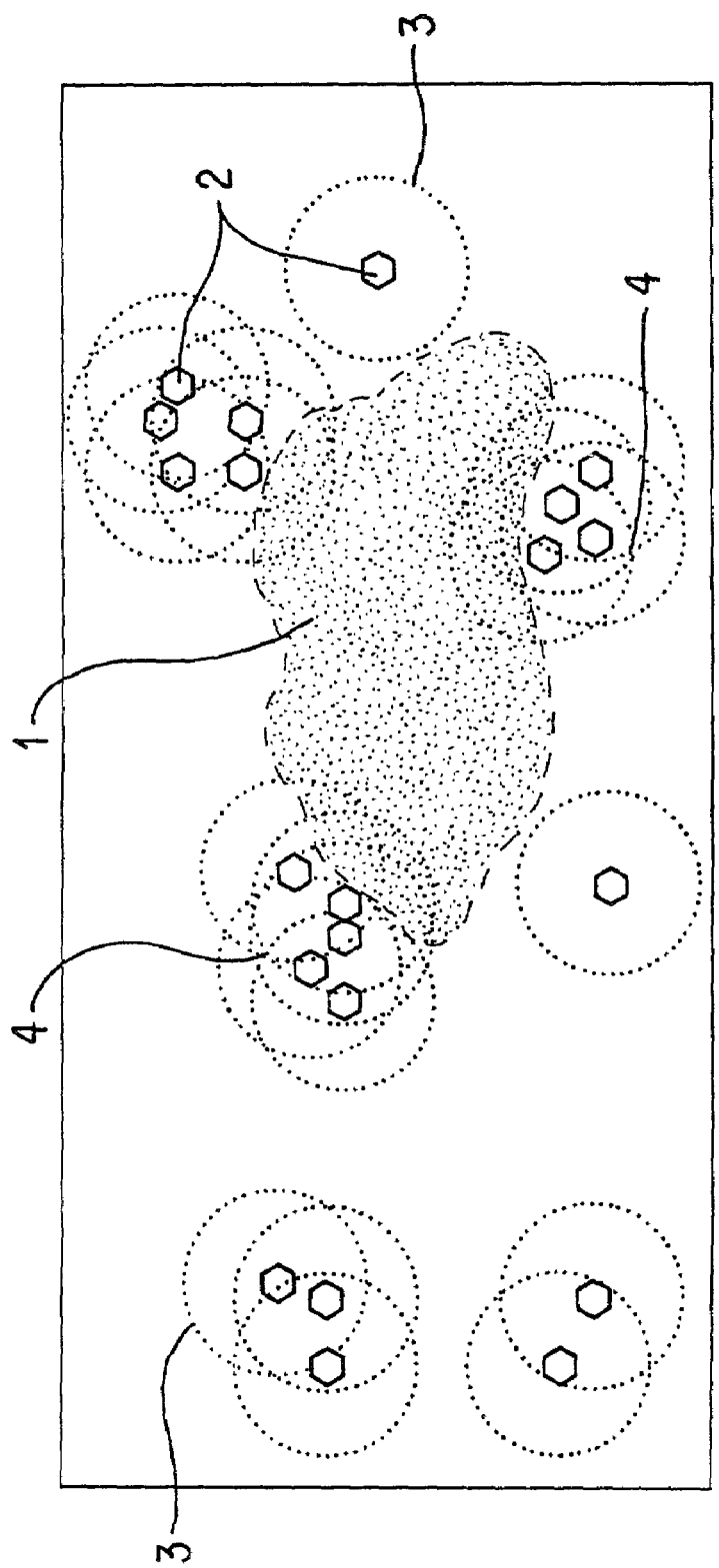
FIG. 1 schematically shows the distribution of molecular structures around and about an island of biological activity in a hypothetical two dimensional metric space for a poorly designed prior art library and for an efficiently designed optimally diverse screening library.

1. Computational Chemistry Environment
2. Definitions
3. Validating Metrics
   A. Theoretical Considerations—Neighborhood Property
   B. Construction, Application, and Analysis Of Patterson Plots
4. Topomeric CoMFA Descriptor
   A. Topomeric Alignment
      i. General Topomeric Allignment
      ii. Specialized Allignment for Chiral and Equivalent Atoms
   B. Calculation Of CoMFA and Hydrogen Bonding Fields
   C. Validation Of Topomeric CoMFA Descriptor
5. Tanimoto Fingerprint Descriptor
   A. Neighborhood Property
   B. Applicability Of Tanimoto To Different Biological Systems
   C. Comparison of Sigmoid and Patterson Plots
6. Comparison of Tanimoto and Topomeric CoMFA Metrics
7. Additional Validation Results
8. Combinatorial Library Design Utilizing Validated Metrics
   A. Removal Of Reactants For Non-Diversity Reasons
      i. General Removal Criteria
      ii. Biologically Based Criteria5
   B. Removal of Non-Diverse Reactants
   C. Identification (Building) Of Products
   D. Removal Of Products For Non-Diversity Reasons
   E. Removal of Non-Diverse Products
9. Lead Compound Optimization
   A. Advantages Resulting From Product Filter
   B. Advantages Resulting From Reactant Filter
   C. Additional Optimization Methods Using Validated Metrics
10. Merging Libraries
11. Other Advantages of Optimally Diverse Libraries
12. Virtual Library Construction & Searching
    A. Derivation of the Database (Virtual Library) of Compounds
    B. Overview of Methodology
    C. Overview of Virtual Library Construction
    D. Virtual Library Construction
       i. Representation of the Database of Compounds
       ii. Application of A First Metric (Topomeric CoMFA)
       iii. Application of A Second Metric (Tanimoto Fingerprint)
       iv. Summary of Method & Scope of Chemistry
    E. Searching the Virtual Library
       i. Example Search Routine of Virtual Library—Tanimoto Similarity
       ii. Design Screening Libraries (Subsets of the Virtual Library)
          (a) Subset Screening Library Based On Topomeric Fields and Tanimoto
          (b) Subset Based on Tanimoto Similarity
          (c) Subset Based on Topomeric Fields
          (d) Subset Based on Combined Metric
       iii. Designing Lead Optimizations
          (a) Search Based on Tanimoto Similarity
          (b) Searches Based on Topomer Similarity
          (c) Topomeric (3D) Searching of Arbitrary Molecular Structures
          (d) Topomeric (3D) Searching of Core Structures

1. Computational Chemistry Environment

Generally, all calculations and analyses to conduct combinatorial chemistry screening library design and follow up are implemented in a modern computational chemistry environment using software designed to handle molecular structures and associated properties and operations. For purposes of this Application, such an environment is specifically referenced. In particular, the computational environment and capabilities of the SYBYL and UNITY software programs developed and marketed by Tripos, Inc. (St. Louis, Mo.) are specifically utilized. Unless otherwise noted, all software references and commands in the following text are references to functionalities contained in the SYBYL and UNITY software programs. Where a required functionality is not available in SYBYL or UNITY, the software code to implement that functionality is provided in an Appendix to this Application. Software with similar functionalities to SYBYL and UNITY are available from other sources, both commercial and non-commercial, well known to those in the art. A general purpose programmable digital computer with ample amounts of memory and hard disk storage is required for the implementation of this invention. In performing the methods of this invention, representations of thousands of molecules and molecular structures as well as other data may need to be stored simultaneously in the random access memory of the computer or in rapidly available permanent storage. The inventors use a Silicon Graphics, Inc. Challenge-M computer having a single 150 Mhz R4400 processor with 128 Mb memory and 4 Gb hard disk storage space. As the size of the virtual library increases, a corresponding increase in hard disk storage and computational power is required. For these tasks, access to several gigabytes of storage and Silicon Graphics, Inc. processors in the R4400 to R10000 range are useful.

2. Definitions

The words or phrases in capital letters shall, for the purposes of this application, have the meanings set forth below:

2D MEASURES shall mean a molecular representation which does not include any terms which specifically incorporate information about the three dimensional features of the molecule. 2D is a misnomer used in the art and does not mean a geometric "two dimensional" descriptor such as a flat image on a piece of paper. Rather, 2D descriptors take no account of geometric features of a molecule but instead reflect only the properties which are derivable from its topology; that is, the network of atoms connected by bonds.

2D FINGERPRINTS shall mean a 2D molecular measure in which a bit in a data string is set corresponding to the occurrence of a given 2–7 atom fragment in that molecule. Typically, strings of roughly 900 to 2400 bits are used. A particular bit may be set by many different fragments.

COMBINATORIAL SCREENING LIBRARY shall mean a subset of molecules selected from a combinatorial accessible universe of molecules to be used for screening in an assay.

MOLECULAR STRUCTURAL DESCRIPTOR shall mean a quantitative representation of the physical and chemical properties determinative of the activity of a molecule. The term METRIC is synonymous with MOLECULAR STRUCTURAL DESCRIPTOR and is used interchangeably throughout this Application.

PATTERSON PLOTS shall mean two dimensional scatter plots in which the distance between molecules in some metric is plotted on the X axis and the absolute difference in some biological activity for the same molecules is plotted on the Y axis.

SIGMOID PLOTS shall mean two dimensional plots for which the proportion of molecular pairs in which the second molecule is also active is plotted on the Y axis and the pairwise Tanimoto similarity is plotted in intervals on the X axis.

TOPOMERIC ALIGNMENT shall mean conformer alignment based on a set of alignment rules.

3. Validating Metrics

A. Theoretical Considerations—Neighborhood Property

As noted above, the similarity principle suggests a way to quantify the concept of diversity by quantifying structural similarity. While the prior art devised many structural descriptors, no one has been able to explicitly show that any of the descriptors are valid. It is possible with the method of this invention to determine the validity of any metric by applying it to presently existing literature data sets, for which values of biological activity and molecular structure are known. Once the validity has been determined, the metric may be used with confidence in designing combinatorial screening libraries and in following up on discovered leads. Examples of these applications will be given below.

The present invention is the first to recognize that the similarity principle also provides a way to validate metrics. Specifically, the similarity principle requires that any valid descriptor must have a "neighborhood property". That is: the descriptor must meet the similarity principle's constraint that it measure the chemical universe in such a way that similar structures (as defined by the descriptor) have substantially similar biological properties. Or stated slightly differently: within some radius in descriptor space of any given molecule possessing some biological property, there should be a high probability that other molecules found within that radius will also have the same biological property. If a descriptor does not have the neighborhood property, it does not meet the similarity principle, and can not be valid. Regardless of the computations involved or the intentions of the users, using prior art descriptors without the neighborhood property results, at best, in random selection of compounds to include in screening libraries.

Figure 1B:
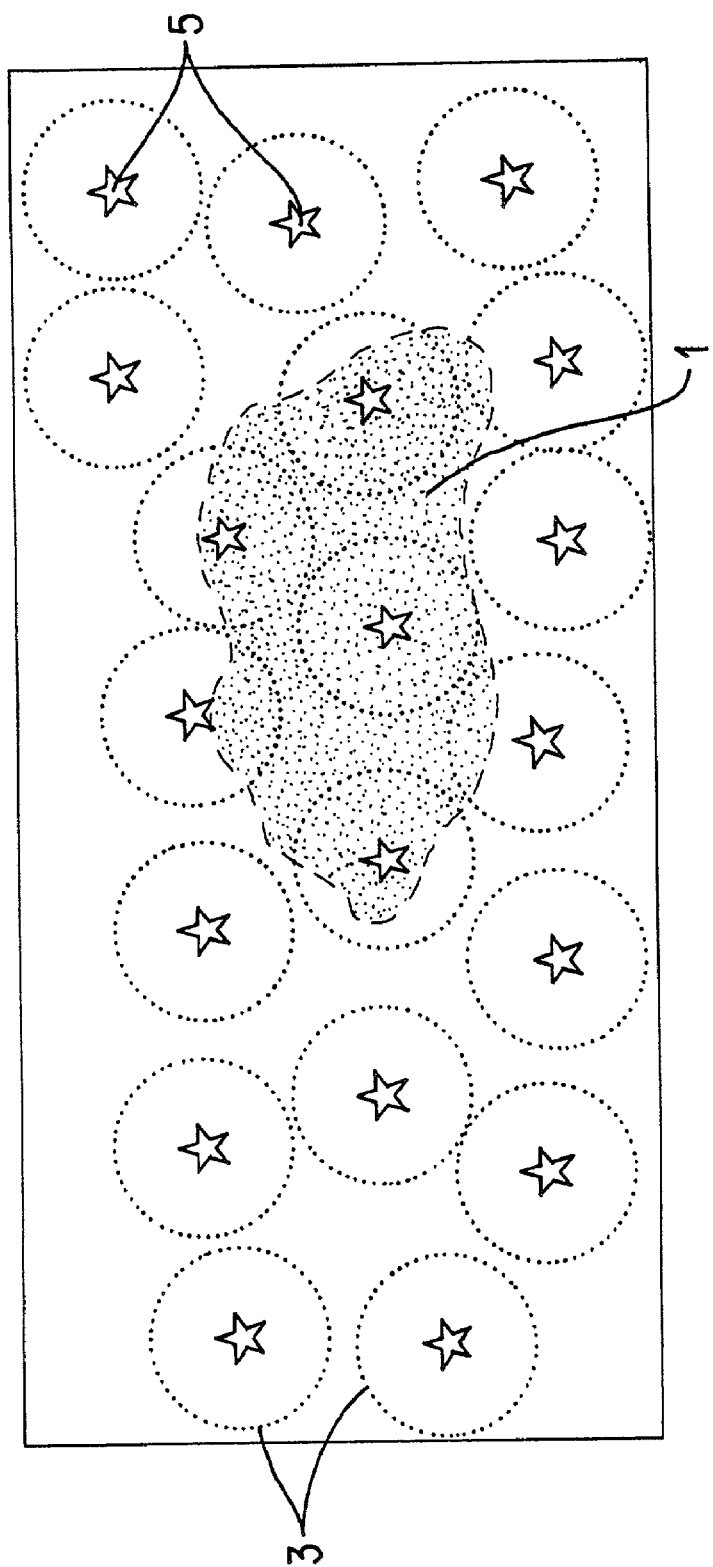

The importance of the neighborhood property to the design of combinatorial screening libraries is schematically illustrated in FIG. 1. FIG. 1A and FIG. 1B show an "island" 1 of biological activity plotted in some relevant two dimensional molecular descriptor space. In FIG. 1A the molecules 2 of a typical prior art library are plotted as hexagons. Around each hexagon a circle 3 describes the area of the metric space (the neighborhood) in which molecules of similar structural diversity to the plotted molecule would be found. Since the prior art metric used to select these molecules was not valid, the molecules are essentially distributed at random in the metric space. The circles 3 (neighborhoods) of similar structural diversity of several of the molecules overlap at 4 indicating that they sample the same diversity space. Clearly, there is no guarantee that the island area will be adequately sampled or that a great deal of redundant testing will not be involved with such a library design.

In FIG. 1B the molecules 5 of a optimally designed library are plotted as stars along with their corresponding circles 3 of similar structural diversity. Since a valid molecular descriptor with the neighborhood property was used to select the molecules, molecules were identified which not only sampled that part of the descriptor space accessible with the molecular structures available but also did not sample the same descriptor space more than once. Clearly, the likelihood of sampling the "island" 1 is greater when it is possible to identify the unique neighborhood 3 around each sample molecule and choose molecules that sample different areas. FIG. 1B represents an optimally diverse design.

A method to quantitatively analyze whether any given metric obeys the neighborhood principle has been discovered. In the prior art, absolute values of biological activity have always been considered the dependent variable with the structural metric as the independent variable. This is the case for traditional QSARs (quantitative structure activity relationships). Note however, that the similarity principle requires that for any pair of molecules, differences in activity are related to differences in structure. In particular, small differences in structure should be associated with small differences in activity. However, the converse is not necessarily true; large differences in activity are not necessarily associated with large differences in structure. The first novel feature of the present invention is that it uses differences in both measures: biological differences and structural (metric) differences. There is no rationale present in the prior art suggesting that the use of both differences in such a manner would be useful. Thus, instead of looking at the values assigned by the metric to each molecule, the absolute differences in the metric values for each pair of molecules are the independent variables and the absolute differences in biological activity for each pair of molecules are the dependent variables. The absolute value is used since it is the difference, not its sign, which is important.

Figure 2:
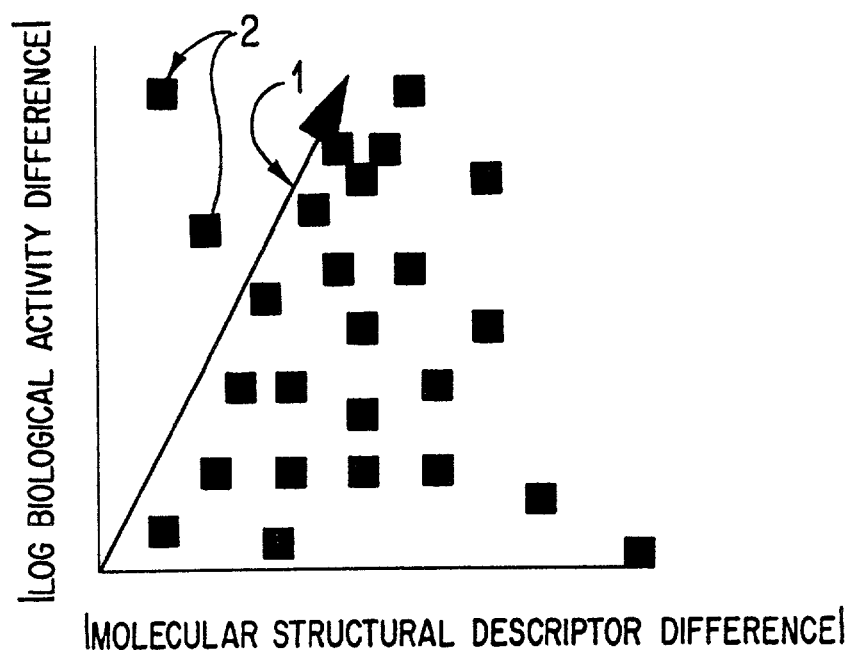
FIG. 2 shows a theoretical scatter plot (Patterson Plot) for a metric having the neighborhood property in which the X axis shows distances in some metric space calculated as the absolute value of the pairwise differences in some candidate molecular descriptor and the Y axis shows the absolute value of the pairwise differences in biological activity.

For a metric possessing the neighborhood property, a scatter plot of pairwise absolute differences in descriptors for each set of molecules versus pairwise absolute differences in biological activity for the same set of molecules (Patterson plot) will have a characteristic appearance as shown in FIG. 2. Note that it is important that pairwise absolute differences for all molecules in a data set are used, that is; the absolute metric "distance" between every molecule and every other molecule is plotted. Accordingly, there are $n(n-1)/2$ pairwise comparisons for every data set containing $n$ compounds. The use of pairwise differences for every possible pair reflects all the relationships between all structural changes with all activity changes for the molecules under study.

Line 1 on the graph of FIG. 2 depicts a special case where there is a strictly linear relationship between differences in metric distance and differences in biological activity. However, the neighborhood property does not imply a linear correlation (corresponding to points lying on a straight line) and need not imply anything about large property differences causing large biological activity differences. (Generally, the line should be linear for only very small changes in molecular structure and would exhibit a complex shape overall depending on the nature of the biological interaction. However, for purposes of discussion and analysis, it is useful to employ a straight line as a first approximation.) The slope of line 1 will vary depending on the biological activity of the measured system. Thus, the lower right trapezoid (LRT) {defined by the vertices [0,0], [actual metric value, max. bio. value], [max. metric value, max. bio. value], and [max. metric value, 0]} of the plot may be populated as shown in any number of ways.

The upper left triangle (ULT) of the plot (above the line) should not be populated at all as long as the descriptor completely characterizes the compound and there are no discontinuities in the behavior of the molecules. However, in the real world, some population of the space (as indicated by points 2) above the line would be expected since there are known discontinuities in the behavior of real molecular ligands. For instance, it is well known amongst medicinal chemists that adding one methyl group can cause some very active compounds to lose all sign of activity.

Figure 3:
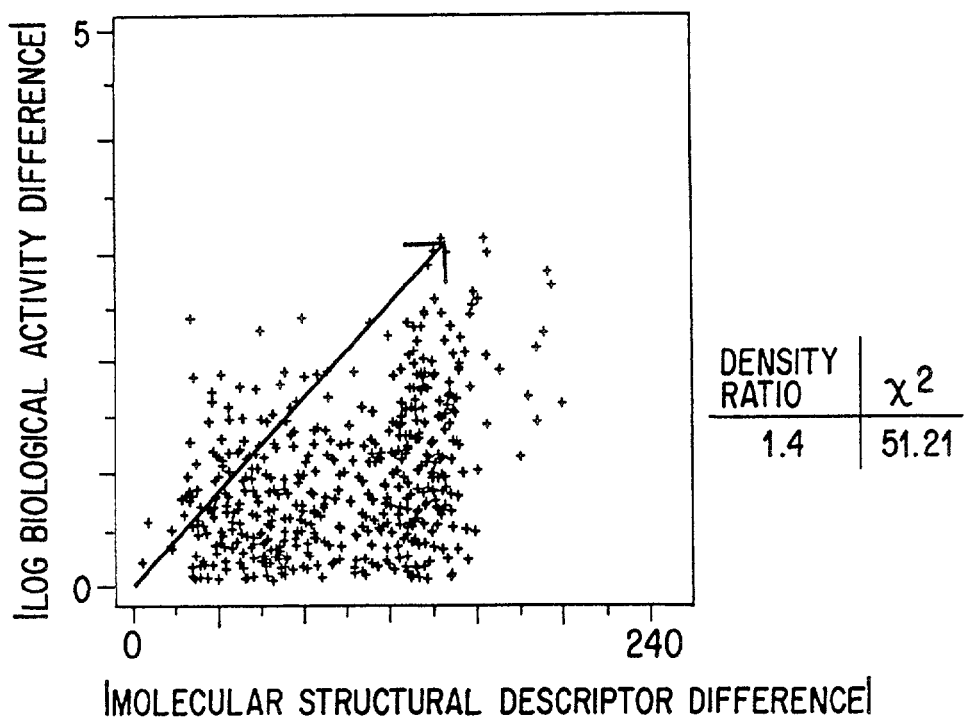
FIG. 3 shows a Patterson plot for an illustrative data set.

FIG. 3 shows a Patterson plot of a real world example. Points lying above the solid line near the Y axis reflect a metric space where a small difference in metric property (structure) produces a large difference in biological property. These points clearly violate the similarity principle/neighborhood rule. Thus, in the real world sometimes relatively small differences in structure can produce large differences in activity. If some points lie above the line, the metric is less ideal, but, clearly still useful. The major criteria and the key point to recognize is that for a metric to be valid the upper left triangle will be substantially less populated than the lower right trapezoid.

Thus, it should be recognized that for any receptor, the presence of some particular side group or combination of side groups may produce a discontinuity in the receptor response. Generally, however, any (metric) descriptor displaying the above characteristic of predominantly populating the lower right trapezoid (such as in FIG. 3) will possess the neighborhood property, and the demonstration that a metric possesses such behavior indicates the validity/usefulness of that metric. Conversely, a descriptor in which the points in the difference plot are uniformly distributed (equal density of points in ULT and LRT) does not obey the neighborhood principle and is invalid as a metric. While a brief glance at the difference plots may quickly indicate validity or non-validity, visual analysis may be misleading. As it turns out, data points in the plot frequently overlap so that visually only one point is seen where there may be two (or more). A quantitative analysis of the data distribution, therefore, yields a more accurate picture. An objective validation procedure for determining the validity/usefulness of metrics from Patterson plots of real world data including a method for assessing its statistical significance is set forth below.

Viewing the metric data in this way requires no knowledge about either the actual value of the biological activities or the actual values assigned by the descriptor under review. Because all pairwise differences are displayed, all possible gradations of molecular structural diversity and activity are represented and utilized. Consequently, there is no arbitrary lower limit set on the usable data.

B. Construction, Application. and Analysis of Patterson Plots

For purposes of objectively examining metrics for validity, it is first necessary to accurately determine the slope (placement) of the line which divides a Patterson plot into the two areas, a lower right trapezoid (LRT) and an upper left triangle (ULT). The triangle is defined by the points [0,0], [actual metric value, max. bio. value], and [0, max. bio. value]. The trapezoid is defined by the points [0,0], [actual metric value, max. bio. value], [max. metric value, max. bio. value], and [max. metric value, 0]. For a metric to be a valid and a useful measure of molecular diversity, the density of points in the lower right trapezoid should be significantly greater than the density in the upper left triangle. To determine the correct placement of the line, the variation in the density of points is used. The line must always pass through (0,0) at the lower left corner of a Patterson plot since no change in any metric must imply no change in the biological activity. As noted earlier, considering a straight line is only a first approximation. A "perfect" metric, which totally describes the structure activity relationship of the biological system, would display a complex line reflecting the biological interaction. As a first approximation, a "useful" straight line can be found which meaningfully reflects the variation in the density of points.

The preferred search for the correct/useful line tests only those slopes which a particular data set can distinguish; specifically those drawn from [0,0] to each point [actual metric value, max bio value]. The process starts by drawing the line to a point having the smallest actual metric value [smallest metric value, max. bio. value] and continues for all of the values observed for actual metric value up to the largest [largest metric value, max. bio. value]; ie, subsequent lines are of decreasing slope. (In the limiting case of drawing the line to [largest metric value, max. bio. value] the trapezoid becomes a triangle.) When searching for the correct diagonal, it is defined to be the one which yields the highest density (number of data points/unit graph area) for a lower right triangle, which for this process is defined to have its vertices at [0,0], [actual metric value, 0], and [actual metric value, max bio. value]. Thus, the line is identified based on the density of points under this triangle, but the evaluation ratios for the metric are calculated based on the density within the trapezoid compared to the density of the entire plot (sum of triangle and trapezoid areas). The software necessary to implement this procedure (as well as to determine the $X^2$ values to be discussed below) is contained in Appendix "A". There may be other procedures for determining the placement of the line since the line is only a first approximation. Any such procedure must meet two tests: 1) it must consistently distinguish between diversity descriptors; and 2) it must clearly distinguish/recognize meaningless diversity descriptors. The procedure described here clearly meets both tests. (The preferred search for the placement of the line is as described above. However, the lines shown in the Figures accompanying this description were found slightly differently. For the Figures, the search was started by requiring that the diagonal also pass through the point defined by the largest descriptor difference and the maximum biological activity difference [max.metric value, max. bio. value]. The line was then systematically tilted towards the vertical trying each of 100 evenly spaced steps (in terms of the Y/X ratio). As in the preferred method, the line yielding the highest density for the LRT was drawn. The line placements yielded by the two methods are not substantially different. All numerical values reported in this specification were obtained from Patterson plots in which the preferred line drawing process was used.)

Figure 4:
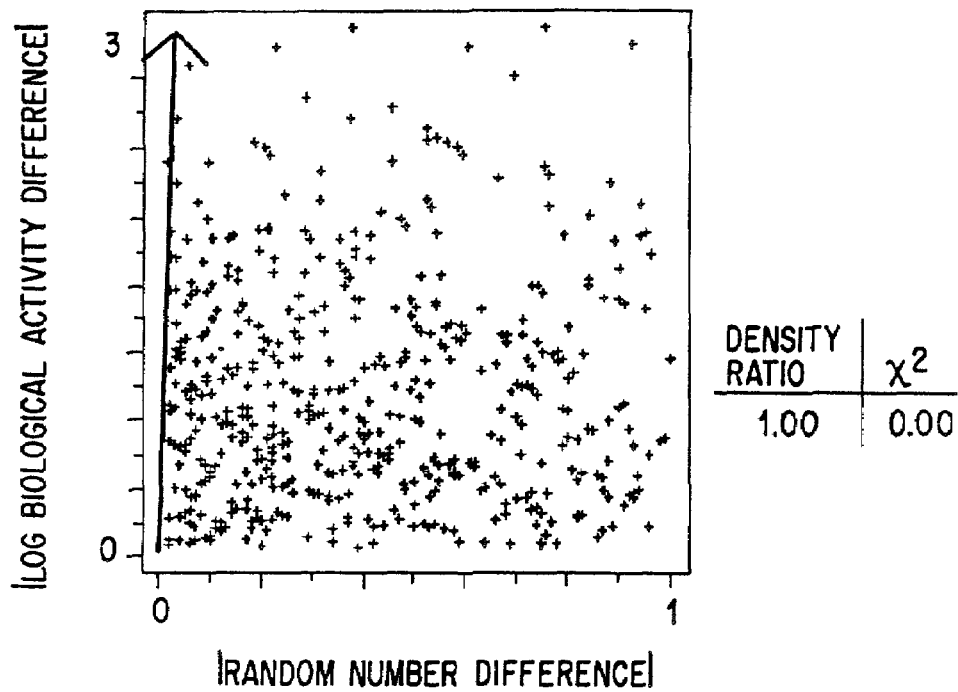
FIG. 4 shows a Patterson plot for the same data set as in FIG. 3 but where the diversity descriptor values (X axis) associated with each molecule have been replaced by random numbers.
Figure 5:
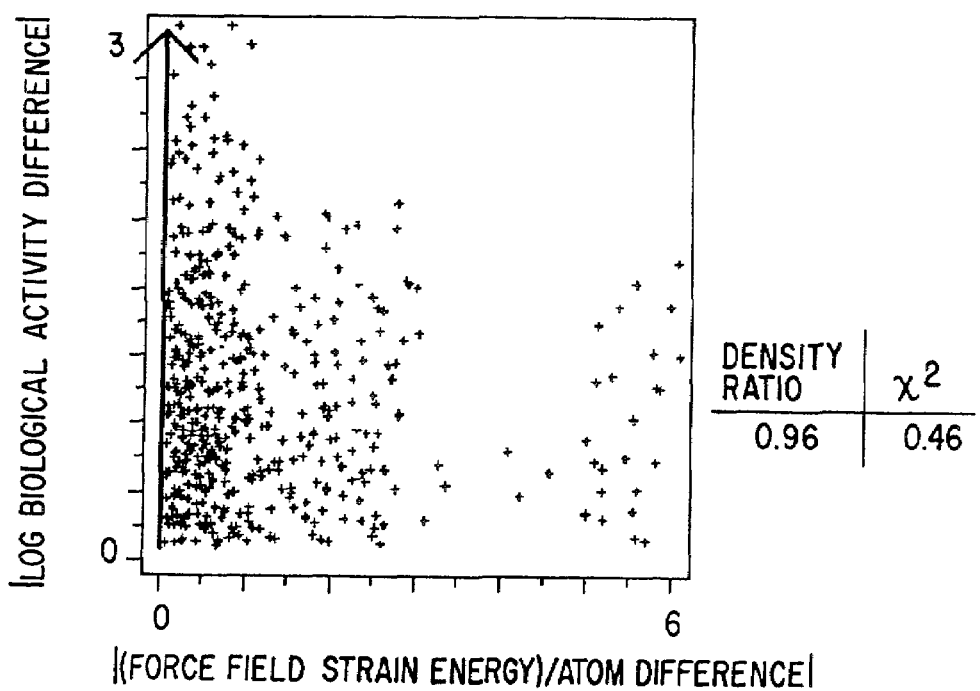
FIG. 5 shows a Patterson plot for the same data set as in FIG. 3 but where the diversity descriptor values (X axis) associated with each molecule have been replaced by a normalized force field strain energy/atom value.

The Patterson plot showing the diagonal for an exemplary data set used to validate the topomeric CoMFA descriptor (discussed in Section 4.C. below) is shown in FIG. 3. For comparison, FIGS. 4 and 5 show Patterson plots for two other variations of the same data which would not be expected to be valid molecular "measurements" useful as diversity metrics. For FIG. 4, in place of the actual metric values of FIG. 3, random numbers were generated for the diversity descriptor values of each compound and the Patterson plot generated from the differences in these random numbers. As expected from a random number assignment, no line can be found by the procedure which enriches the density in the triangle and the best ratio is not significantly different from 1.0. The best line is always reported by the procedure, which in this case corresponds to a nearly vertical line drawn to the point [minimum metric value, max. bio. value]. For randomly distributed values, this line yields the highest density for the test triangle since the X axis value and, therefore, the area of the tested triangle, is at a minimum. It is possible with some random data sets that this line, although nearly vertical, might include a couple points under the line. The placement of the line at this position is essentially an artifact of the procedure which results from an inability to find any other line which enriches the density in the tested triangle.

Because random numbers are not "real" metrics, an example of a "real molecular measurement" that is unlikely to be a valid diversity metric was examined. For the Patterson plot of FIG. 5, a force field strain energy (for the topomeric conformations using the standard Tripos force field) was calculated for each of the compounds in the same data set as was used for FIGS. 3 and 4. Because force field strain energy tends to increase with the number of atoms and thus, correlate roughly with the occasionally useful molecular weight, to normalize the value, the force field energy was divided by the number of atoms in each molecule. As expected, just as with random numbers, no optimum line could be found. This is essentially a confirmation that the points in the graph were also distributed randomly. Again, the best ratio is not significantly different from 1.0.

To objectively quantify the validity/usefulness determination, the ratio of the density of points in the lower right trapezoid to the average density of points is determined. This value can vary from somewhere above 0 but significantly less than 1, through 1 (equal density of points in each area) to a maximum of 2 (all the points in the lower right trapezoid, and the upper triangle and lower trapezoid are equal in area [limiting case of trapezoid merging into triangle]). According to the theoretical considerations discussed above, a ratio very near or equal to 1 (approximately equal densities) would indicate an invalid metric, while a ratio (significantly) greater than 1 would indicate a valid metric. The value of this ratio is set forth next to each Patterson plot in FIGS. 3 (real data), 4 (random numbers substituted), and 5 (force field energy substituted) under the column "Density Ratio". Clearly, the topomeric CoMFA data of FIG. 3 reflect a valid metric (ratio much larger than 1), while the random numbers of FIG. 4 and force field energies of FIG. 5 reflect a meaningless invalid metric (ratio very near 1). As will be discussed below, a density ratio of 1.1 is a useful threshold of validity/usefulness for a molecular diversity descriptor.

The statistical significance of the Patterson plot data can also be determined by a chi-squared test at any chosen level of significance. In this case the data are handled as:

$$X^2 = \frac{(\text{Actual } LRT \text{ Count} - \text{Expected } LRT \text{ Count})^2}{\text{Expected } LRT \text{ Count}}$$

$$\text{where: Expected } LRT \text{ Count} = \frac{LRT \text{ Area}}{\text{Total Area}} \times \text{Total Count}$$

The chi-squared values for the Patterson plots of FIGS. 3, 4, and 5 are also set forth next to the plots under the column $X^2$. For 95% confidence limits and one degree of freedom, the chi-squared value is 3.84. The chi-squared values confirm the visual inspection and density ratio observations that the CoMFA metric is valid and the other two "constructed" metrics are invalid. A full set of topomeric CoMFA, random number, and force field data are discussed below under validation of the topomeric CoMFA descriptor.

The analysis of metrics using the difference plot of this invention is a powerful tool with which to examine metrics and data sets. First, the analysis can be used with any system and requires no prior assumptions about the range of activities or structures which need to be considered. Second, the plot extracts all the information available from a given data set since pairwise differences between all molecules are used. The prior art believed that not much information, if any, could be extracted from literature data sets since, generally, there is not a great deal of structural variety in each set. On the contrary, as will be shown below, using the Patterson plot method of this invention, a metric can be validated based on just such a limited data set. As will also be demonstrated below, metrics can be applied to literature data sets to determine the validity of the metrics. This ability opens up vast amounts of pre-existing literature data for analysis. Since in any analysis there is always a risk of making an improper determination due to sampling error when too few data sets are used or too narrow a variety of biological systems (activities) are included, the ability to use much of the available literature is a significant advance in the art. Also, the fact that the validation analysis methodology of this invention is not dependent on the study of a specific biological system, strongly implies that a validated metric is very likely to be applicable to molecular structures of unknown biological activity encountered in designing combinatorial screening libraries or making other diversity based selections. Or stated slightly differently, there is a high degree of confidence that metrics validated across many chemistries and biologies can be used in situations where nothing is known about the biological system under study.

4. Topomeric CoMFA Descriptor

Many of the prior art descriptors are essentially 2D in nature. That this is the case with the prior art probably reflects three underlying reasons. First, the rough general associations between fragments and biological properties were validated statistically decades ago.[8] Second, 2D fragment keys or "fingerprints" are widely available since they are used by all commercial molecular database programs to compare structures and expedite retrieval. Third, no one in the prior art has yet met the challenge of figuring out how to formulate and validate an appropriate three dimensional molecular structural descriptor. The situation in the prior art before the present invention is very similar to the field of QSAR about ten years ago. Then, the prior art had long recognized the desirability of three dimensional descriptors but had not been able to implement any. When a 3D technique (CoMFA) became available[9], its widespread acceptance[10] and application[11] confirmed the expected importance of 3D descriptors in general.

It has been discovered that a CoMFA approach to generating a molecular structural descriptor using a specially developed alignment procedure, topomeric alignment, produces a three dimensional descriptor of molecules which is shown to be valid by the method outlined above. In addition, this new descriptor provides a powerful tool with which to design combinatorial screening libraries. It is equally useful any time selection based on diversity from within a congeneric series is required. A full description of CoMFA and the generation of molecular interaction energies is contained in U.S. Pat. Nos. 5,025,388 and 5,307,287. The disclosures of these patents are incorporated in this Application. The usual challenge in applying CoMFA to a known set of molecules is to determine the proper alignment of the molecular structures with respect to each other. Two molecules of identical structure will have substantially different molecular interaction energies if they are translated or rotated so as to move their atoms more than about 4 Å from their original positions. Thus, alignment is hard enough when applying CoMFA to analyze a set of molecules which interact with the same biological receptor. The more difficult question is how to "align" molecules distributed in multidimensional chemistry space to create a meaningful descriptor with respect to arbitrary and unknown receptors against which the molecules will ultimately be tested. The topomeric alignment procedure was developed to correct the usual CoMFA alignments which often over-emphasize a search for "receptor-bound", "minimum energy", or "field-fit" conformations. It has been discovered that, when congenericity exists, a meaningful alignment results from overlaying the atoms that lie within some selected common substructure and arranging the other atoms according to a unique canonical rule with any resulting steric collisions ignored. When CoMFA fields are generated for molecules so aligned, it has been discovered that the resulting field differences are a valid molecular structural descriptor.

Two major advantages are achieved by applying the topomeric CoMFA metric to the reactants proposed for use in a combinatorial synthesis rather than the products resulting from the synthesis. First, the computational time/effort is dramatically reduced. Instead of analyzing for diversity a combinatorial matrix of product compounds (R1×R2× R3 . . . ) only the values for the sum of the reactants (R1+R2+R3 . . . ) need to be computed. For example, assuming 2000 reactants for R1 and 2000 reactants for R2, only 4000 calculations need be performed on the reactants versus $2000^2$ (4,000,000) if calculations on the combinatorial products were performed. Second, by identifying reactants which explore similar diversity space, it is only necessary to choose one of each reactant representative of each diversity. This immediately reduces the number of combinatorial products which need to be considered and synthesized.

A. Topomeric Alignment

Usually a CoMFA modeler seeks low energy conformations. However, if alignment with unknown receptors is desired (such as is the case in designing combinatorial screening libraries for general purpose screening), then the major goal in conformer generation must be that molecules having similar topologies should produce similar fields. In fact, topomeric CoMFA fields may be used as a validated diversity descriptor to identify molecules with similar or dissimilar structures anytime there is a problem of having more compounds than can be easily dealt with. Thus, its applicability extends well beyond its use in combinatorial chemistry to all situations where it is necessary to analyze an existing group of compounds or specify the creation of new ones. The topomeric alignment procedure is especially applicable to the design of a combinatorial screening library. Typically, as noted earlier, in the creation of combinatorially derived compounds there is often an invariant central core to which a variety of side chains (contributed by reactants of a particular class) are attached at the open valences. Within the combinatorial products, this central core tethers each of the side chains contributed by any set of reactants into the same relative position in space. In the language of CoMFA alignments, the side chains contributed by each reactant can thus be oriented by overlapping the bond that attaches the side chain to the central core and using a topomeric protocol to select a representative conformation of the side chain. Nowhere does the prior art suggest that a topomeric protocol could possibly yield a meaningful alignment. Indeed, the prior art inherently teaches away from the idea because the topomerically derived conformers often may be energetically inaccessible and incapable of binding to any receptor.

The idea of a topomeric conformer is that it is rule based. The exact rules may be modified for specific circumstances. In fact, once it is appreciated from the teaching of this invention that a particular topomeric protocol is useful (yields a valid molecular descriptor), other such protocols may be designed and their use is considered within the teaching of this disclosure.

i. General Topomeric Alignment

With the exception of two specialized situations (molecules containing chiral atoms or requiring a choice between two equivalent atoms) which will be discussed in section 4(A)(ii) below, the following topologically-based rules will generate a single, consistent, unambiguous, aligned topomeric conformation for any molecule. The software necessary to implement this procedure is contained in Appendix "A". The starting point for a topomeric alignment of a molecule is a CONCORD generated three dimensional model which is then FIT as a rigid body onto a template 3D model by least-squares minimization of the distances between structurally corresponding atoms. By convention, the template model is originally oriented so that one of its atoms is at the Cartesian origin, a second lies along the X axis, and a third lies in the XY plane.

Torsions are then adjusted for all bonds which: 1) are single and acyclic; 2) connect polyvalent atoms; and 3) do not connect atoms that are polyvalent within the template model structure since adjusting such bonds would change the template-matching geometry. Unambiguous specification of a torsion angle about a bond also requires a direction along that bond and two attached atoms. In this situation, for acyclic bonds the direction "away from the FIT atoms" is always well-defined.

The following precedence rules then determine the two attached atoms. From each candidate atom, begin growing a "path", atom layer by atom layer, including all branches but ending whenever another path is encountered (occurrence of ring closure). At the end of the bond that is closer to the FIT atoms, choose the attached atom beginning the shortest path to any FIT atom. If there are several ways to choose the atom, first choose the atom with the lowest X. If there are still several ways to choose the atom, choose next the atom with the lowest Y, and finally, if necessary, the lowest Z coordinate (coordinate values differing by some small value, typically less than 0.1 Angstroms, are considered as identical). At the other end of the bond, choose the atom beginning the path that contains any ring. When more than one path contains a ring, choose the atom whose path has the most atoms. If there are several ways to choose the path, in precedence order choose the path with the highest sum of atomic weights, and finally, if still necessary, the atom with the highest X, then highest Y, then highest Z coordinate. The new setting of the torsional value depends only on whether the bonds to the chosen atoms are cyclic or not. If neither are cyclic, the setting is 180 degrees; if one is cyclic, the setting is 90 degrees; and if both are cyclic, the setting is 60 degrees. Any steric clashes that may result from these settings are ignored.

Figure 6A:
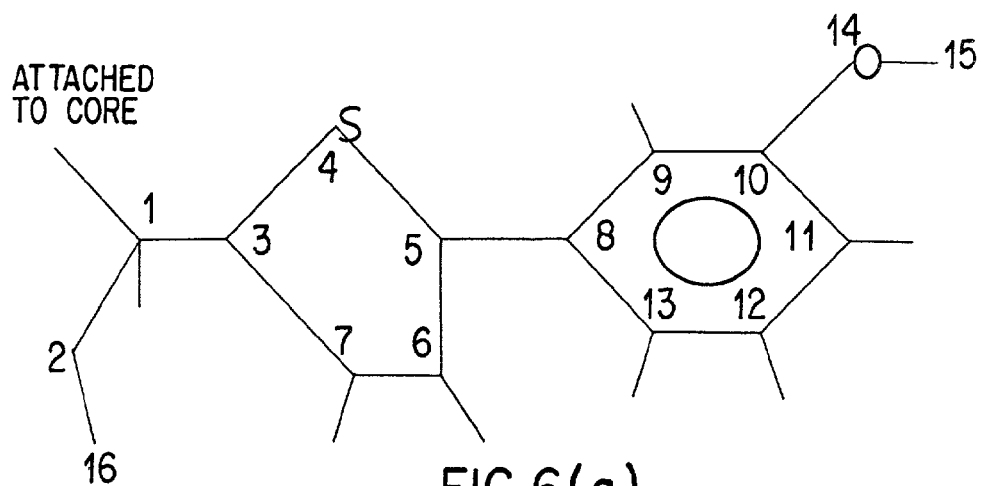
FIGS. 6A through 6D shows four molecular structures numbered and marked in accordance with the topomeric alignment rule.

As an illustrative example, consider generation of the topomeric conformer for the side chain shown in FIG. 6(A), in which atom 1 is attached to some core structure by the upper left-most bond. Assuming that the alignment template for this fragment involves atom 1 only, there are three bonds whose torsions require adjustment, those connecting atoms pairs 1-3; 5-8; and 10-14. (Adding atom 3 to the alignment template would make atom 1 "polyvalent within the template model structure", so that the 1-3 bond would then not be altered.) The atom whose attached atoms will move (in the torsion adjustment) is the second atom noted in each atom pair. For example, if a torsional change were applied to the 14-10 bond instead of the 10-14 bond as shown in FIG. 6A, all of the molecule except atoms 10, 14 and 15 (and 13 by symmetry) would move. Correspondingly, if a torsional change were applied to the 10-14 bond instead of the 14-10 bond, only atom 15 would move.

Figure 6B:
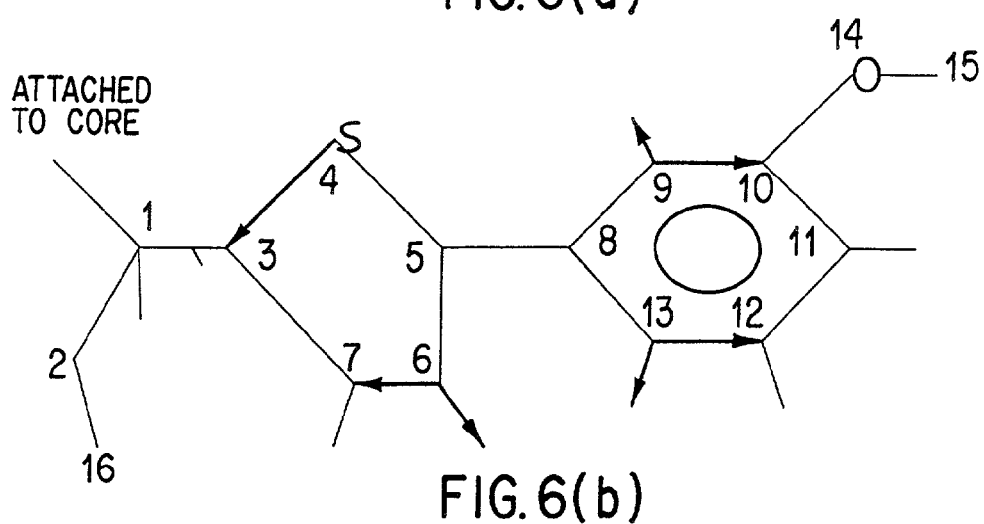
Figure 6C:
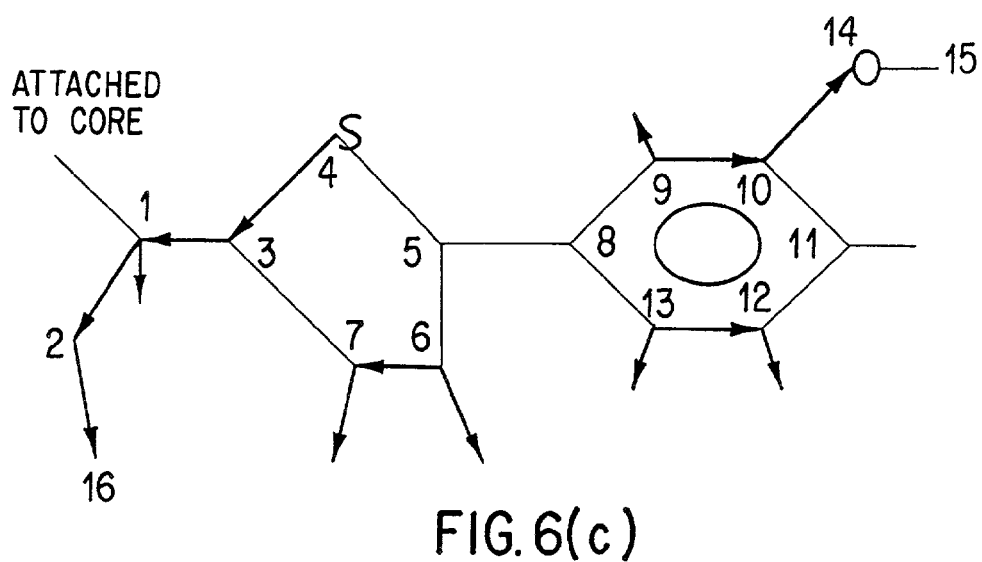

To define a torsional change, atoms attached to each of the bonded atoms must also be specified. For example, setting torsion about the bond 5-8 to 60 degrees would yield four different conformers depending on whether it is the 6-5-8-13, 6-5-8-9, 4-5-8-9, or 4-5-8-13 dihedral angle which becomes 60 degrees. To make such a choice, "paths" are grown from each of the candidate atoms, in "layers", each layer consisting of all previously unvisited atoms attached to any existing atom in any path. In choosing among the four attached-atom possibilities of the 5-8 bond, FIG. 6(B) shows the four paths after the first layer of each is grown, and FIG. 6(C) shows the final paths. In FIG. 6(C), notice within the rings that, not only is the bond between 3 and 7 not crossed, but also atom 11 is not visited because the third layer seeks to include 11 from two paths, so both fail. The attached atoms chosen for the torsion definition becomes the ones that begin the highest-ranking paths according to the rules stated above. For example, in FIG. 6(C), attached atom 4 outranks atom 6 because its path is the only one reaching the alignment template, and atom 9 outranks atom 13 because its path has more atoms, so that it is the 4-5-8-9 torsion which is set to a prescribed value. For the same reasons, the other complete torsions become 9-10-14-15, attached 1-3-4 and attached 1-2-16. The other decision rules would need to be applied if atom 9 was, instead of carbon, an aromatic nitrogen (with the consequent loss of the attached hydrogen) so that the 9 and 13 paths have the same number of atoms. In this case, the 9 path still takes priority, since it has the higher molecular weight. If instead atom 14 is deleted, so that the 9 and 13 paths are topologically identical, the 9 path again takes priority because atom 9 has the same X coordinate but a larger Y coordinate than does atom 13.

As for the dihedral angle values themselves, torsion 4-5-8-9 is set to 60 degrees, because both the 4-5 and 8-9 bonds are within a ring; torsions 9-10-14-15 and attached-1-3-4 become 90°, because only the 3-4 and 9-10 bonds respectively are cyclic; and the attached-1-2-16 dihedral becomes 180° since none of the bonds are cyclic. It should be noted that this topomeric alignment procedure will not work with molecules containing chiral centers since, for each chiral center, two possible three dimensional configurations are possible for the same molecule, and, clearly, each configuration by the above rules would yield a different topomeric conformer.

ii. Specialized Allignment for Chiral and Equivalent Atoms

Figure 6D:
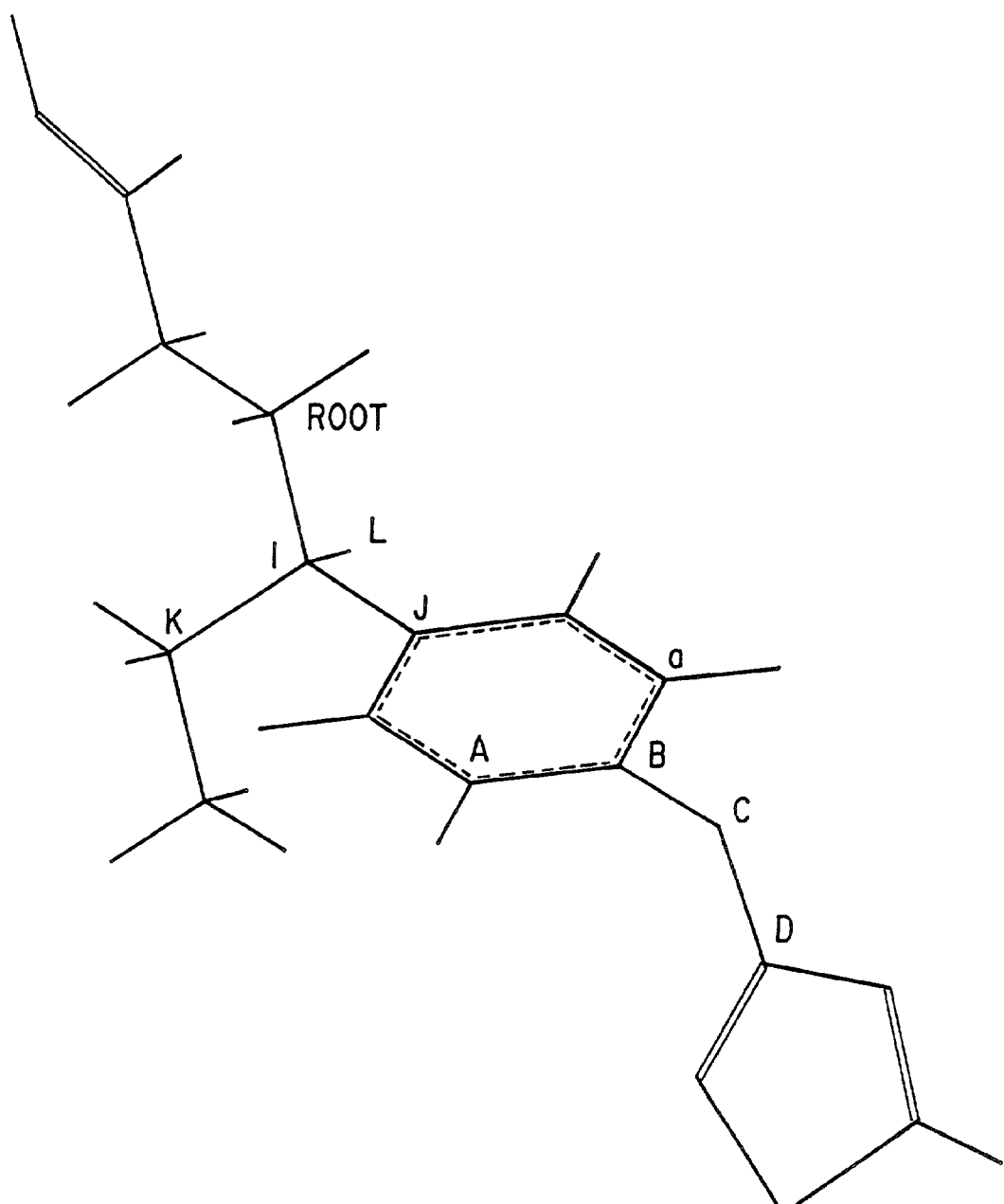

In order to resolve the ambiguity introduced by a chiral center or centers in a molecule, a specialied topermic allignment rule must be adopted. FIG. 6(D) shows a side chain whose attachment atom is marked as "Root" and in which atom I is chiral. Atom I has four non-equivalent attachments, indicated by Root, J, K, and L. Although the absolute configuration of such a chiral atom is not usually specified, an allingment methodology of an explicit 3D model must necessarily consistently select one of the two possible conformations, even if arbitrarily chosen. Proceeding as taught above, generating the topomeric conformation for the side chain leads to selection of atom J (the largest of the attachments rooted by J, K, and L) as the atom defining the Root-I torsion and thus fixes the position of J. However the relative positions of K and L remain ambiguous. Unless such "prochiral" atoms (including pyramidally hydrolyzed nitrogen) are recognized and a configuration explicitly assigned, side chains which are topologically identical may seem to be very different in shape.

The procedure used to make sure that the actual topomeric 3D models generated around chiral centers are as similar as possible is as follows: first, form a list of all such chiral centers including pyramidal nitrogen (many algorithms for doing this are described in the literature and are found in any modelling software); second, after an individual torsion has been set, as described earlier, if the third atom of the four in the torsion list is one of the chiral centers, [in FIG. 6(D) the configuration of atom I will be adjusted just after the torsion about Root-I has been set] proceed to replace the fourth atom on the torsion list [J in FIG. 6(D)] with the next highest attachment atom [following the earlier description this will be atom K in FIG. 6(D)]. If the dihedral angle value for the new torsion is greater than 180 degrees, then the relative position of atoms K and L must be exchanged To exchange the positions of atoms K and L, generate the plane defined by the second (Root) through fourth (J) atoms on the torsion that was initially set. Finally, reflect the coordinates of all the atoms attached to the third atom (I) through that plane. This topomeric procedure will generate a consistent topomeric allignment for all side chains containing chiral centers.

A second specialized topomeric allignment problem which may be encontered is the requirement to select between two equivalent atoms. This situation is also illustrated in FIG. 6(D) where there are two candidate attachment atoms, "A" and "a", for the torsion A(a)-B-C-D. Topologically atoms "A" and "a" are identical, but a different position for the five-membered ring, hence a very different shape, will be generated depending on whether "A" or "a" is used to assign the torsion of A(a)-B-C-D. The following rule is used to ensure that the choice between "A" and "a" is made consistently. Measure the two dihedral angles defined by the atom lists Root-B-C-A and Root-B-C-a. (Although these atoms are obviously not directly connected, the dihedral angle values are well-defined.) Of the two possibilities, select the atom to define the torsion for which the torsional value lies between 170 and 350 degrees.

Using the selection rules set out above, the critical point is that the use of a single topomerically aligned conformer in computing a CoMFA three dimensional descriptor has been found to yield a validated descriptor. While other approaches to conformer selection such as averaging many representative conformers or classifying a representative set by their possible interactions with a theoretically averaged receptor (such as in the polyomino docking) are possible, it has been found that topomerically aligned conformers yield a validated descriptor which, as will be seen below, produces clustering highly consistent with the accumulated wisdom of medicinal chemistry.

B. Calculation Of CoMFA and Hydrogen Bonding Fields

The basic CoMFA methodology provides for the calculation of both steric and electrostatic fields. It has been found up to the present point in time that using only the steric fields yields a better diversity descriptor than a combination of steric and electrostatic fields. There appear to be three factors responsible for this observation. First is the fact that steric interactions-classical bioisosterism-are certainly the best defined and probably the most important of the selective non-covalent interactions responsible for biological activity. Second, adding the electrostatic interaction energies may not add much more information since the differences in electrostatic fields are not independent of the differences in steric fields. Third, the addition of the electrostatic fields will halve the contribution of the steric field to the differences between one shape and another. This will dilute out the steric contribution and also dilute the neighborhood property. Clearly, reducing the importance of a primary descriptor is not a way to increase accuracy. However, it is certainly possible that in a given special situation the electrostatic contribution might contribute significantly to the overall "shape". Under these unique circumstances, it would be appropriate to also use the electrostatic interaction energies or other molecular characterizers, and such are considered within the scope of this disclosure. For instance, in some circumstances a topomeric CoMFA field which incorporates hydrogen bonding interactions, characterized as set forth below, may be useful.

The steric fields of the topomerically aligned molecular side chain reactants are generated almost exactly as in a standard CoMFA analysis using an $sp^3$ carbon atom as the probe. As in standard CoMFA, both the grid spacing and the size of the lattice space for which data points are calculated will depend on the size of the molecule and the resolution desired. The steric fields are set at a cutoff value (maximum value) as in standard CoMFA for lattice points whose total steric interaction with any side-chain atom(s) is greater than the cutoff value. One difference from the usual CoMFA procedure is that atoms which are separated from any template-matching atom by one or more rotatable bonds are set to make reduced contributions to the overall steric field. An attenuation factor (1—"small number"), preferably about 0.85, is applied to the steric field contributions which result from these atoms. For atoms at the end of a long molecule, the attenuation factor produces very small field contributions (ie: $[0.85]^N$) where N is the number of rotatable bonds between the specified atom and the alignment template atom. This attenuation factor is applied in recognition of the fact that the rotation of the atoms provides for a flexibility of the molecule which permits the parts of the molecule furthest away from the point of attachment to assume whatever orientation may be imposed by the unknown receptor. If such atoms were weighted equally, the contributions to the fields of the significant steric differences due to the more anchored atoms (whose disposition in the volume defined by the receptor site is most critical) would be overshadowed by the effects of these flexible atoms.

The derivation of a hydrogen-bond field is slightly different from the standard CoMFA measurement. The intent of the hydrogen-bonding descriptor is to characterize similarities and differences in the abilities of side chains to form hydrogen-bonds with unknown receptors. Like the successful use of the topomeric conformation to characterize steric interactions, the topomeric conformation is also an appropriate way to characterize the spatial position of a side chain's hydrogen-bonding groups. However, unlike a steric field, hydrogen-bonding is a spatially localized phenomenon whose strength is also difficult to quantitate. Therefore, it is appropriate to represent a hydrogen-bonding field as a bitset, much like a 2D fingerprint, or as an array of 0 or 1 values rather than as an array of real numbers like a CoMFA field.

The hydrogen-bonding loci for a particular side chain are specified using the DISCO approach of "extension points" developed by Y. Martin[12] and coworkers, wherein, for example, a carbonyl oxygen generates two hydrogen-bond accepting loci at positions found by extending a line passing from the oxygen nuclei through each of the two "lone-pair" locations to where a complementary hydrogen-bond donating atom on the receptor would optimally be. It is not possible with a bitset representation to attenuate the effects of atoms by the number of intervening rotatable bonds. Instead, uncertainty about the location of a hydrogen-bonding group can be represented by setting additional bits for grid locations spatially adjacent to the single grid location that is initially set for each hydrogen-bonding locus. In other words, each hydrogen-bonding locus sets bits corresponding to a cube of grid points rather than a single grid point. The validation results shown in Table 4 were obtained for a cube of 27 grid locations for each hydrogen bonding locus. The single bitset representing a topomeric hydrogen-bonding fingerprint has twice as many bits as there are lattice points, in order to discriminate hydrogen-bond accepting and hydrogen bond-donating loci. The difference between two topomeric hydrogen-bonding fingerprints is simply their Tanimoto coefficient which now represents a difference in actual field values. Software which implements the hydrogen-bonding field calculations is provided in Appendix "B".

C. Validation of Topomeric CoMFA Descriptor

Figure 7A:
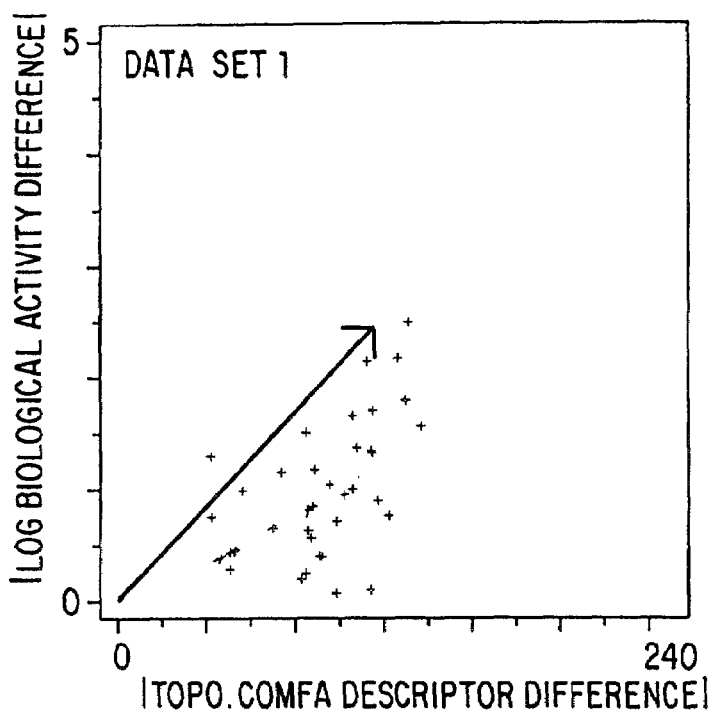
FIGS. 7(a) through 7(t) are a complete set of Patterson plots for the twenty data sets used for the validation studies of the topomeric CoMFA descriptor.
Figure 7B:
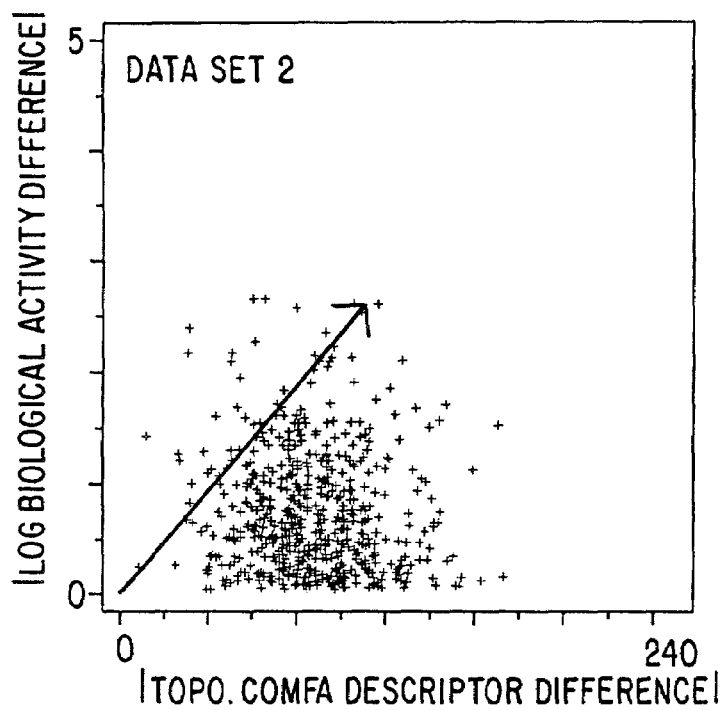
Figure 7C:
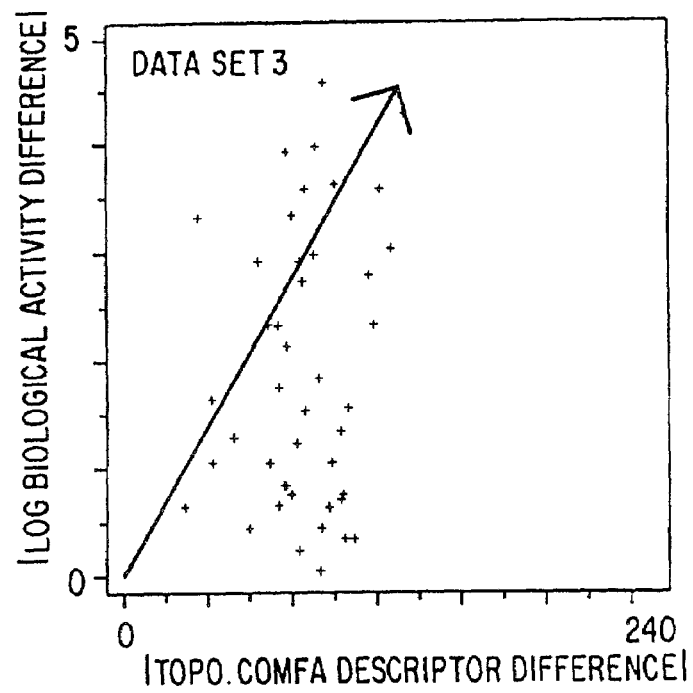
Figure 7D:
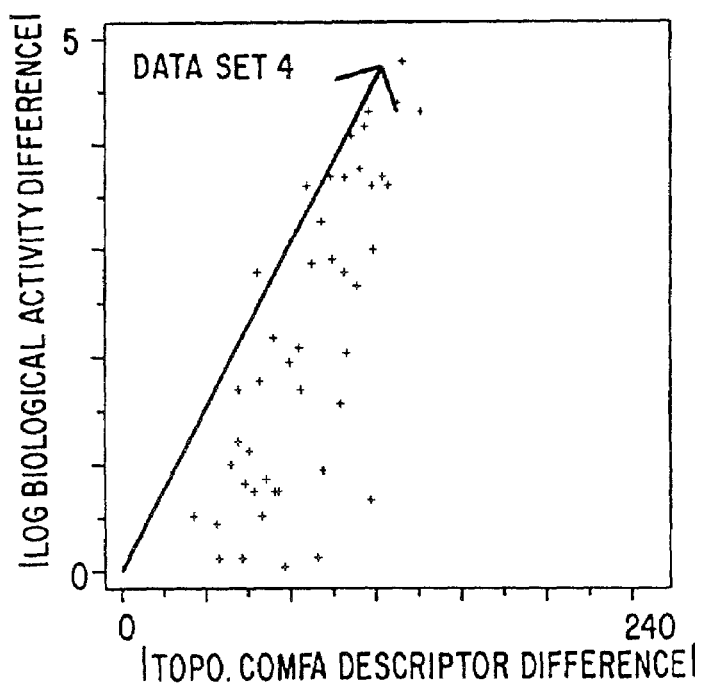
Figure 7E:
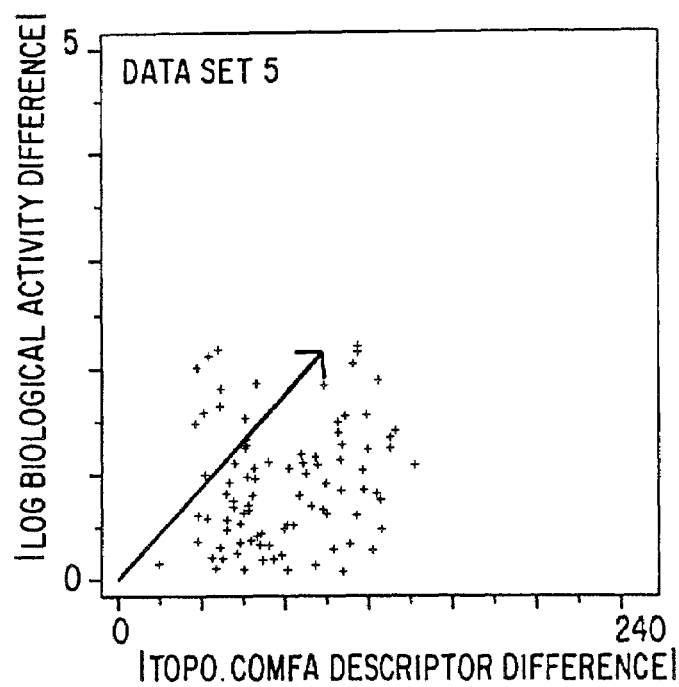
Figure 7F:
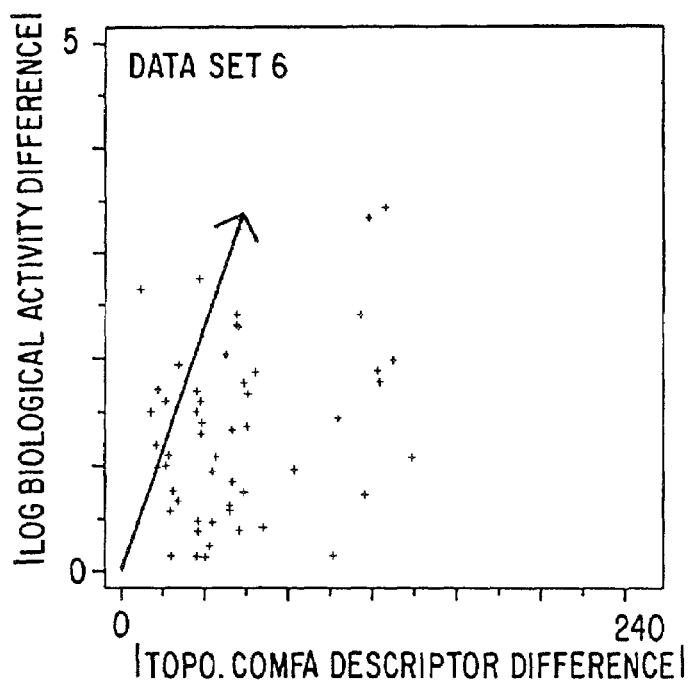
Figure 7G:
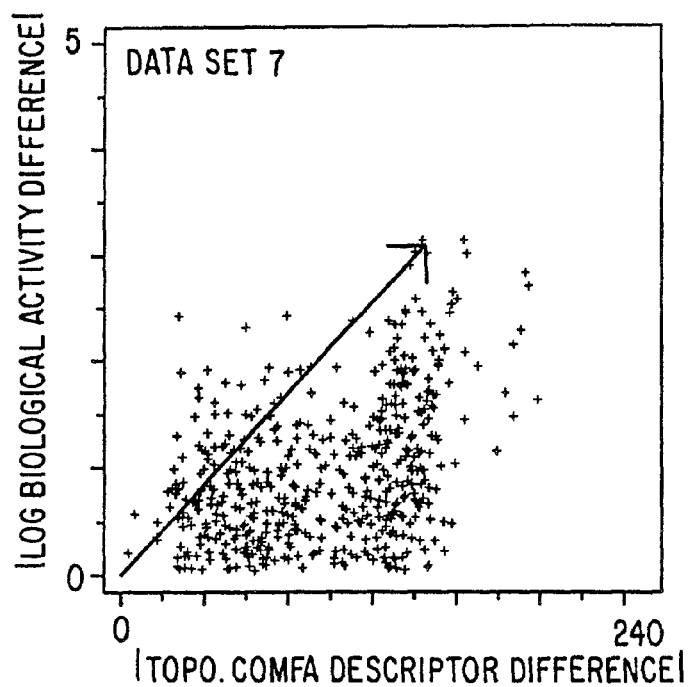
Figure 7H:
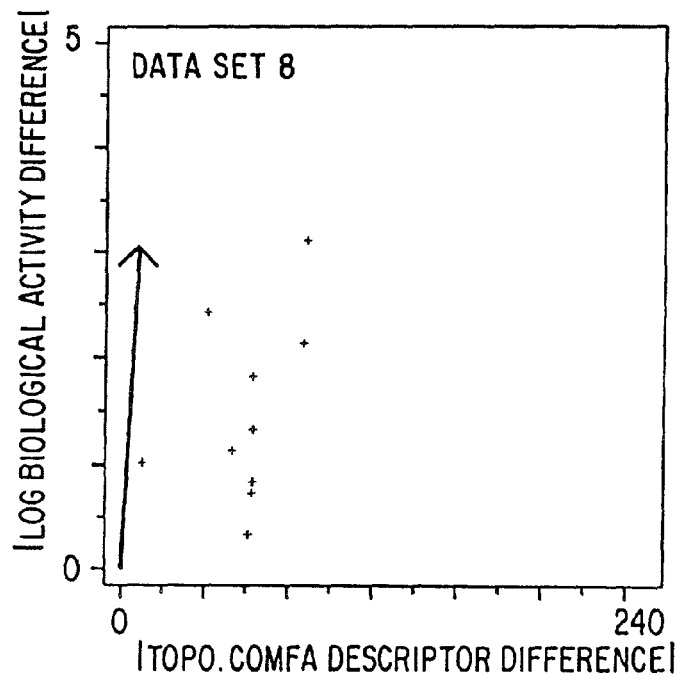
Figure 7I:
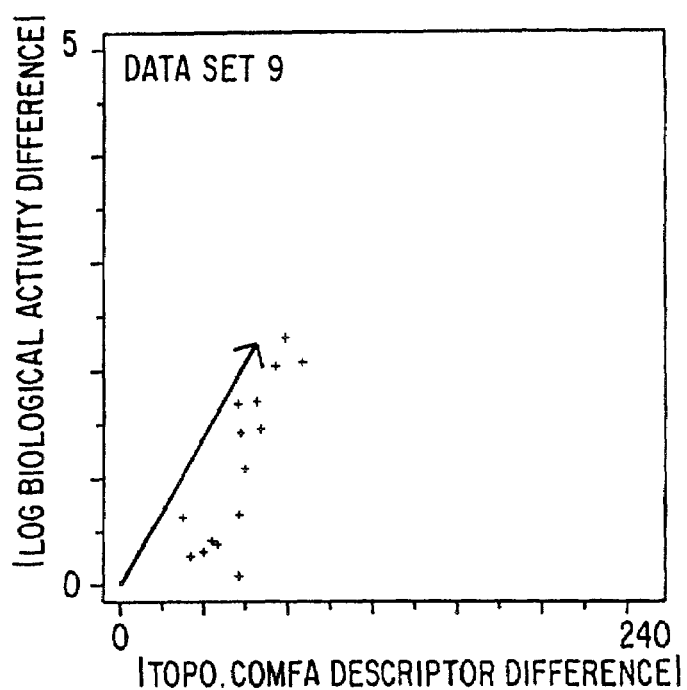
Figure 7J:
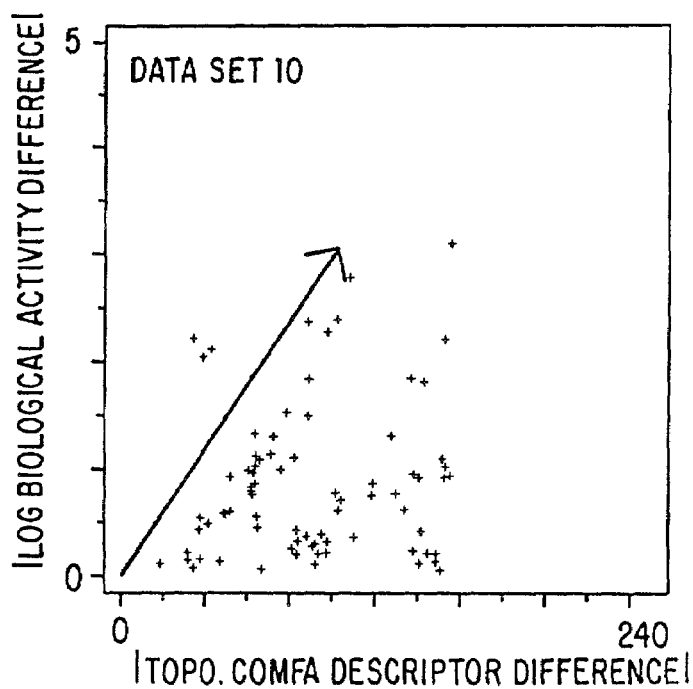
Figure 7K:
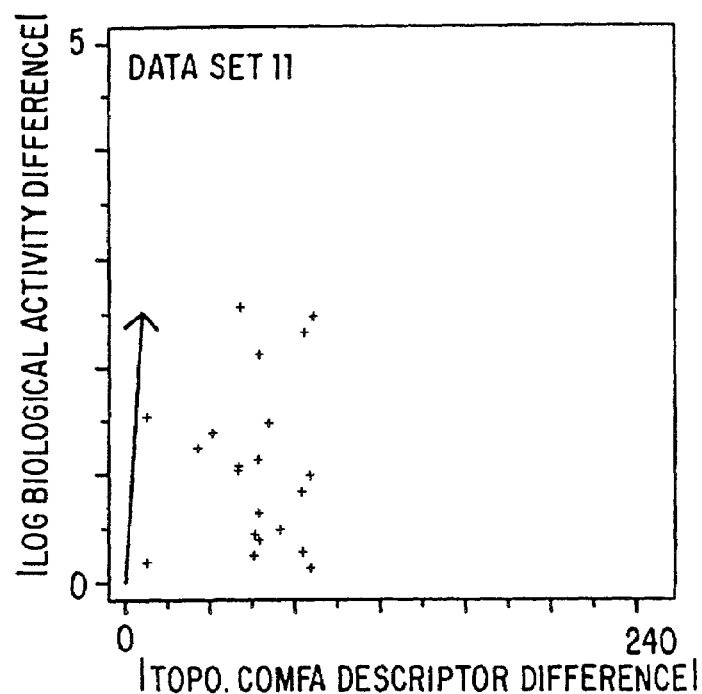
Figure 7L:
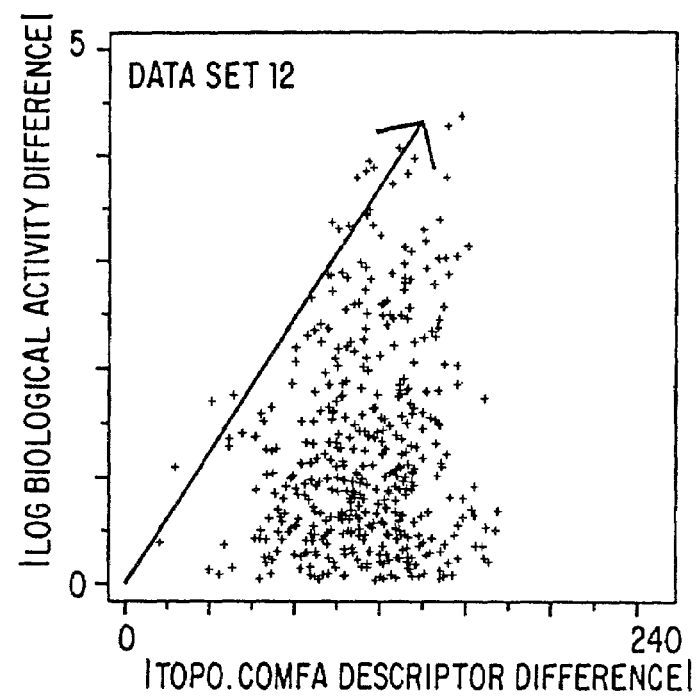
Figure 7M:
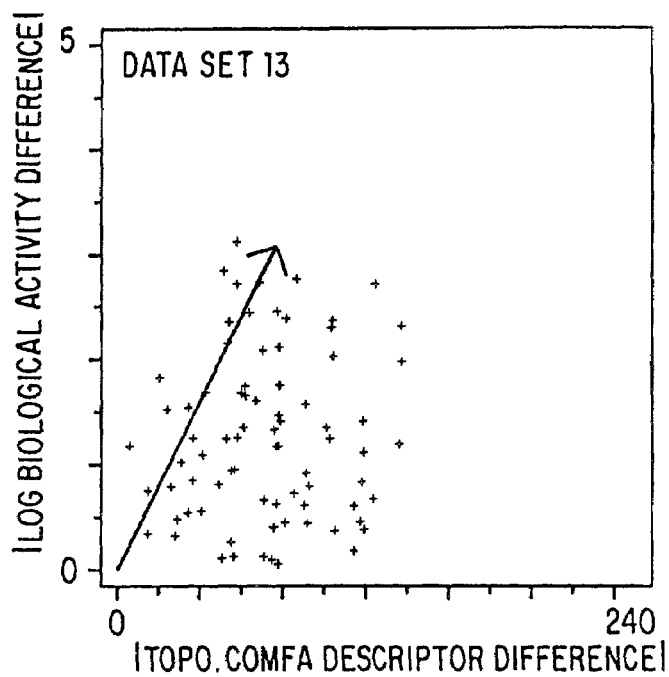
Figure 7N:
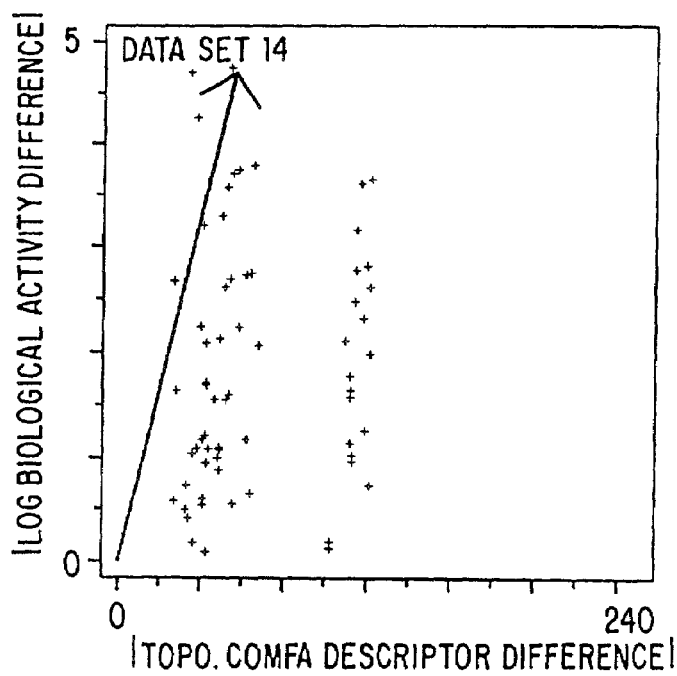
Figure 7O:
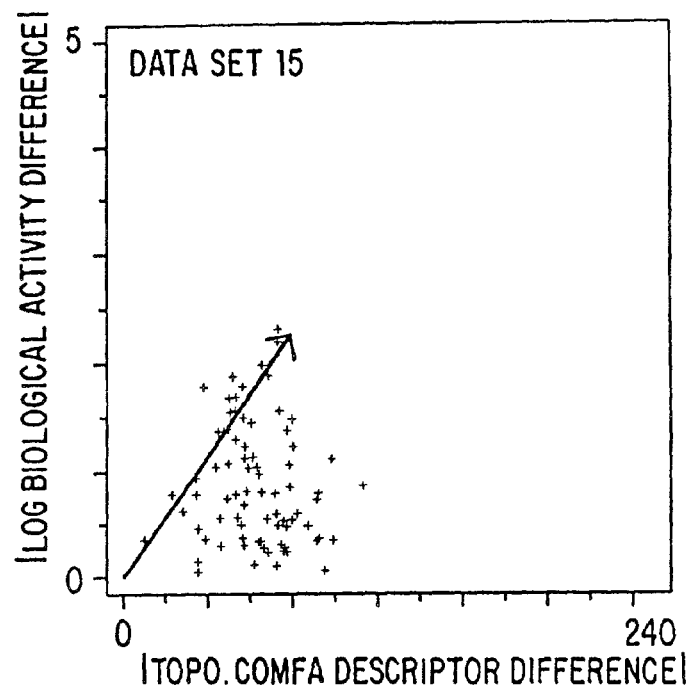
Figure 7P:
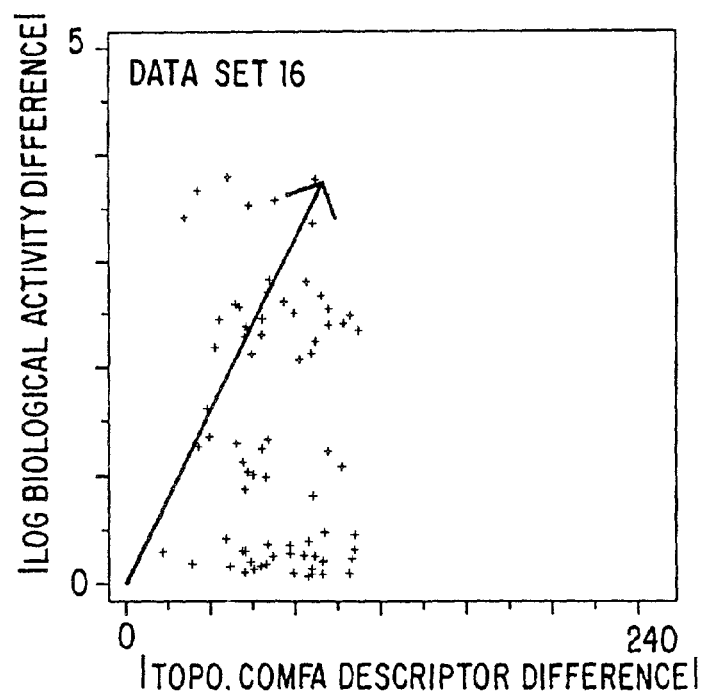
Figure 7Q:
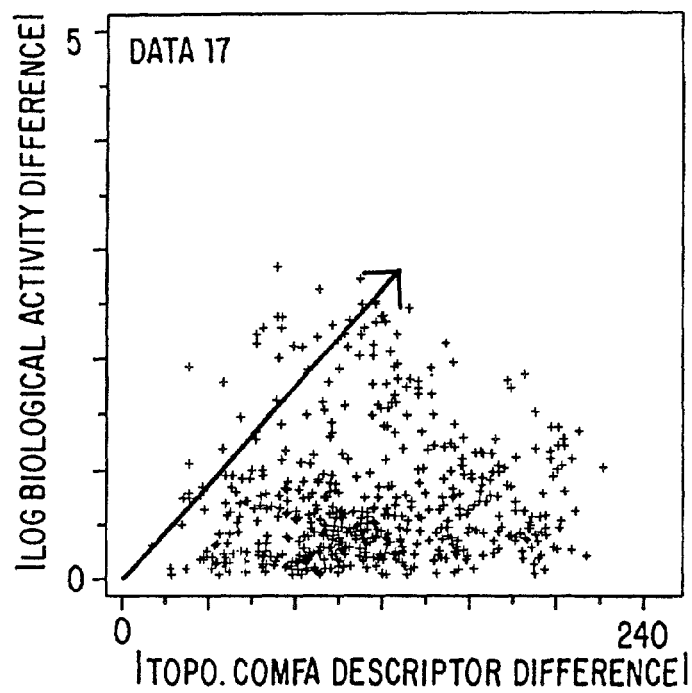
Figure 7R:
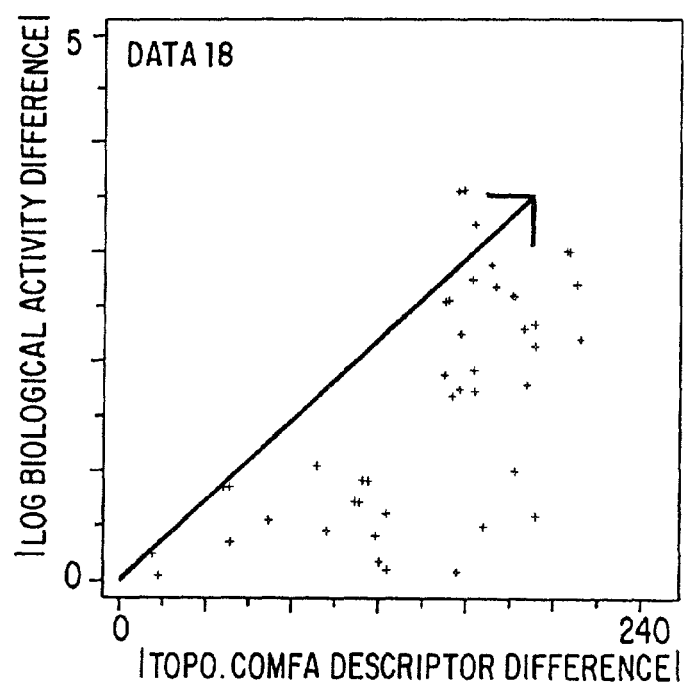
Figure 7S:
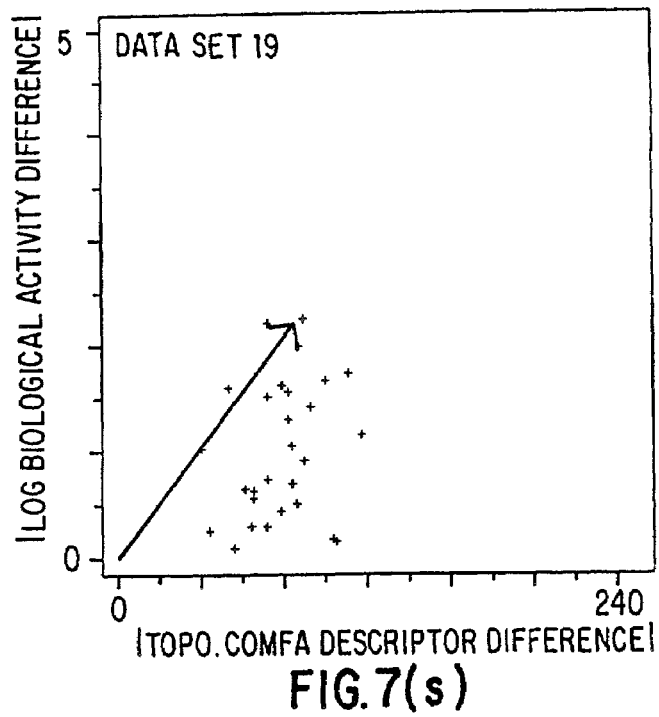
Figure 7T:
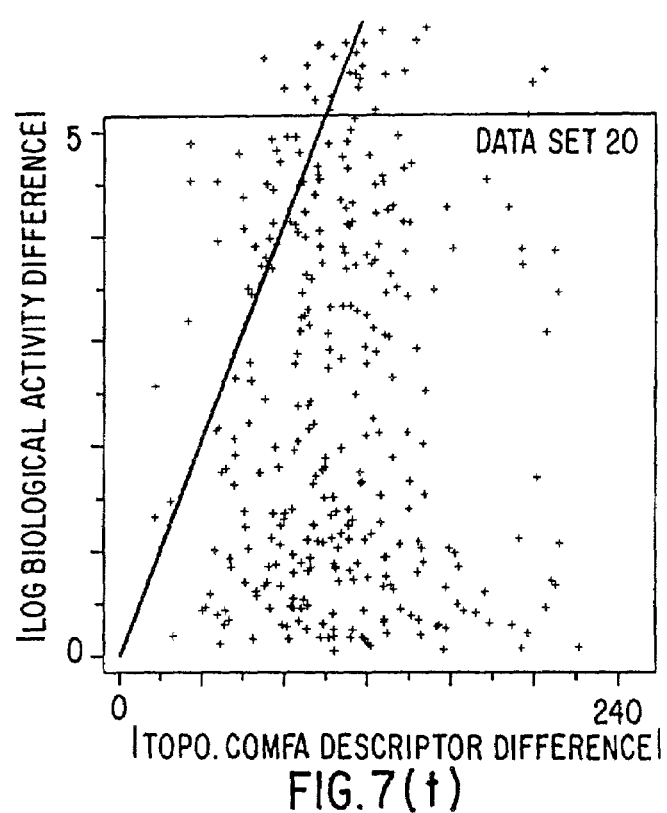

The validity of topomerically aligned CoMFA fields as a molecular structural descriptor, which can be used to describe the diversity of compounds, was confirmed on twenty data sets randomly chosen from the recent biochemical literature. The data sets spanned several different types of ligand-receptor binding interactions. The only criteria for the data sets were: 1) the reported biological activities must span at least two orders of magnitude; 2) the structural variation must be "monovalent" (only one difference per molecule); 3) the molecules contain no chiral centers; and 4) no page turning was required for data entry in order to reduce the likelihood of entry errors. Each data set was analyzed independently. The identification of the data sets is set forth in Appendix "C". The structural variations of the side chains of the core templates were entered as the Sybyl Line Notations of the corresponding thiols. (Sybyl Line Notations [SLNs] define molecular structures.) An-SH was substituted for the larger common template portion of each molecule and provided the two additional atoms needed for 3D orientation. According to the validation method of this invention the Patterson plots constructed as discussed above for the twenty data sets are shown in FIGS. 7(a)–7(t).

In 17 of the 20 cases, visual inspection of the plots suggests that the density of points in the lower right trapezoid is, indeed, greater than the density in the upper left triangle as predicted for a metric descriptor obeying the neighborhood rule. Also, for reasons noted earlier, some points do fall above the line as would be expected for the real world. However, the relative rarity of points in the upper left triangle of the plots indicates that "small steric field differences are not likely to produce large differences in bioactivity", the neighborhood rule. Thus, the distribution of points in the Patterson plots across all the randomly selected data sets is remarkably consistent with the theoretical prediction for a valid/useful diversity metric. It can be easily seen that the topomeric CoMFA metric is validated/useful.

Table 1 contains the density ratios from the quantitative analysis of the twenty data sets. The density ratios of the two test metrics (random number assignments and molecular force field energy divided by number of atoms for the diversity descriptor values) described earlier are presented for comparison. $X^2$ values reflecting the statistical significance of the ratios are also set forth next to the corresponding ratios.

TABLE 1

Patterson Plot Ratios and Associated $X^2$

| No. | Reference | CoMFA Ratio | CoMFA $X^2$ | Random Ratio | Random $X^2$ | Energy Ratio | Energy $X^2$ |
|---|---|---|---|---|---|---|---|
| 1 | Uehling | 1.71 | 10.27 | 0.98 | 0.01 | 0.98 | 0.02 |
| 2 | Strupczewski | 1.39 | 57.33 | 1.01 | 0.02 | 0.97 | 0.47 |
| 3 | Siddiqi | 1.44 | 6.26 | 0.92 | 0.01 | * | * |
| 4 | Garratt-1 | 1.72 | 13.01 | 1.02 | 0.02 | 1.00 | 0.00 |
| 5 | Garratt-2 | 1.37 | 8.02 | 1.04 | 0.11 | 0.97 | 0.07 |
| 6 | Heyl | 1.04 | 0.08 | 0.99 | 0.01 | 0.97 | 0.05 |
| 7 | Cristalli | 1.40 | 51.21 | 1.00 | 0.00 | 0.96 | 0.46 |
| 8 | Stevenson | 0.95 | 0.02 | 0.98 | 0.00 | 0.98 | 0.01 |
| 9 | Doherty | 1.63 | 3.54 | 1.02 | 0.01 | 0.96 | 0.02 |
| 10 | Penning | 1.45 | 10.33 | 0.99 | 0.01 | 1.00 | 0.00 |
| 11 | Lewis | 0.95 | 0.04 | 1.05 | 0.05 | 0.97 | 0.02 |
| 12 | Krystek | 1.64 | 119.92 | 1.00 | 0.00 | 0.97 | 0.49 |
| 13 | Yokoyama-1 | 1.18 | 1.88 | 1.00 | 0.00 | 0.93 | 0.41 |
| 14 | Yokoyama-2 | 1.23 | 2.62 | 1.02 | 0.02 | 0.99 | 0.01 |
| 15 | Svensson | 1.27 | 3.72 | 1.04 | 0.00 | 0.99 | 0.00 |
| 16 | Tsutsumi | 1.38 | 6.50 | 0.94 | 0.02 | 0.96 | 0.06 |
| 17 | Chang | 1.34 | 45.55 | 1.01 | 0.12 | 0.99 | 0.03 |
| 18 | Rosowsky | 1.71 | 12.46 | 0.95 | 0.10 | 1.00 | 0.00 |
| 19 | Thompson | 1.47 | 3.96 | 1.06 | 0.09 | 1.00 | 0.00 |
| 20 | Depreux | 1.22 | 10.85 | 0.98 | 0.07 | * | * |
|  | MEAN | 1.38 | 18.38 | 1.00 | 0.03 | 0.98 | 0.12 |
|  | STND. DEVIATION | 0.24 | 29.43 | 0.04 | 0.04 | 0.02 | 0.19 |

* Data sets 3 and 20 are not reported for the force field energy because one of the structures in each data set (in the topomeric conformation) had a very strained energy greater than 10 kcal/mole-atom, which produced a discontinuously large metric difference.

The chi-squared distributions for 1 degree of freedom are:

| P = | .75 | .90 | .95 | .99 | .999 |
|---|---|---|---|---|---|
| $X^2$ = | 1.32 | 2.71 | 3.84 | 6.64 | 10.83 |

Figure 8A:
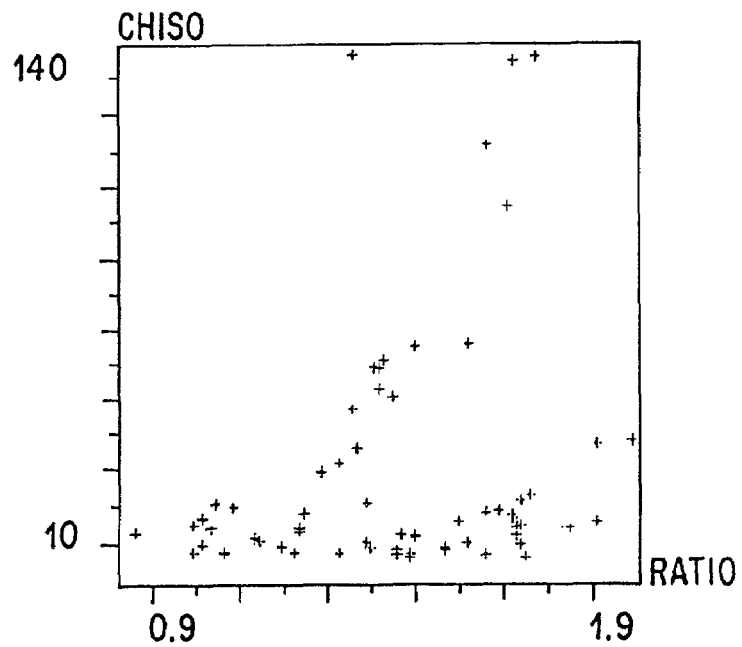
FIGS. 8A and 8B show the two scatter plots displaying the relation between $X^2$ values and their corresponding density ratio values for the tested metrics over the twenty random data sets.
Figure 8B:
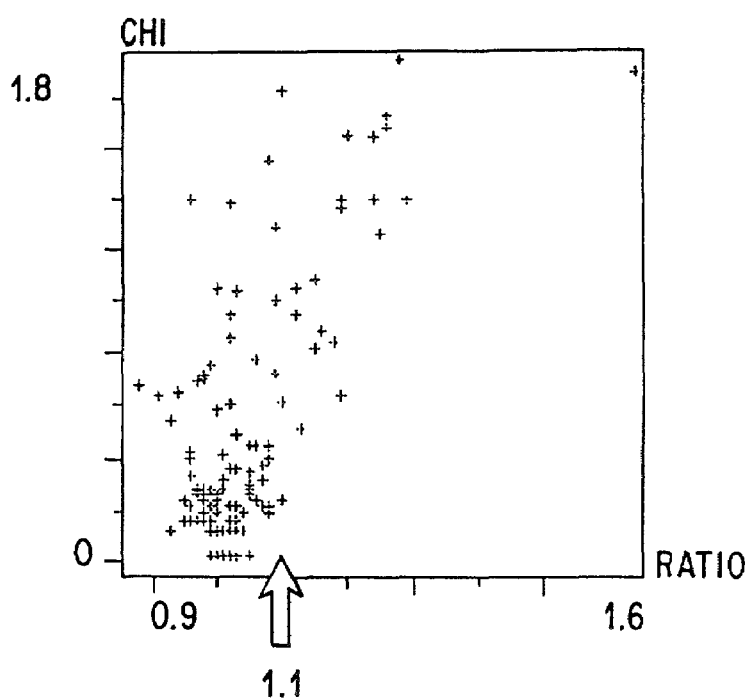

Typically, a confidence level of 95% is considered appropriate in statistical measures A metric is considered valid/useful for an individual data set if the Patterson plot ratio is greater than 1.1; that is, there is greater than a 10% difference in the density between the ULT and LRT. The use of 1.1 as a decisional criteria is confirmed by an examination of the scatter diagrams of $X^2$ values versus their corresponding ratios as shown in FIGS. 8A and 8B. (The value of X is actually plotted in FIG. 8B in order to separate the data points.) FIG. 8A shows the plot of $X^2$s having a value of greater than 3.84 (95% confidence limits) versus their corresponding ratios, while FIG. 8B shows the plot of $X^2$s (plotted as $\sqrt{X^2}$) having a value less than 3.84 versus their corresponding ratios. A ratio value of greater than 1.1 (FIG. 8A) clearly includes most of the statistically significant ratios, while a ratio value of less than 1.1 clearly includes most of the statistically insignificant ratios. While this is not a perfect dividing point and there is some overlap, there is also some distortion of the $X^2$ values due to limited population sizes as discussed below. Overall, the value of 1.1 provides a reasonable decision point.

As noted earlier, the validity of a metric should not be determined on the basis of one data set from the literature. A single literature data set usually presents only a limited range of structure/activity data and examines only a single biological activity. To obtain a proper sense of the overall validity/quality of a metric, its behavior over many data sets representing many different biological activities must be considered. It should be expected that randomly selected data sets that due to biological variability, an otherwise valid metric may appear invalid for some particular set. An examination of the data in Table 1 confirms this observation.

Except for data sets 6, 8, and 11, the ratios in Table 1 clearly confirm for the topomeric CoMFA metric that the density of points in the LRT is greater than in the ULT, and the $X^2$ values confirm the significance of the plots. At the same time, the data for the two test metrics clearly demonstrates with great sensitivity that this validation technique yields exactly the results expected for a meaningless metric; specifically, a density ratio substantially equal to 1 and no significance as determined by the $X^2$ test. Contrary to accepted notions in the prior art, with the discovery of this invention, random literature data sets can be used to validate metrics. The type of publicly unavailable data set (as will be discussed in relation to the Abbott data set below) where the bioactivity or inactivity for each molecule in the set has been experimentally verified is not required.

Sets 6, 8, and 11 are the exceptions which help establish the rule. It is realistic to expect that randomly selected data sets would include some where molecular edge (typically a collision with receptor atoms) or other distorting effects would be present. For set 6, one experimental value was so inconsistent with other reported values that the authors even called attention to that fact. In addition to a problematic experimental value, all the structural changes are rather small but some of the biological changes are fairly large. Something very unusual is clearly happening with this system. For set 8, there is simply not enough data. Only 5 compounds (10 differences) were included and this proved insufficient to analyze even with the sensitivity of the Patterson plot. For data set 11, there were two contributing factors. First, the data set was small (only 7 compounds). Second, this set is a good example of an edge effect where a methyl group protruding from the molecules interacts with the receptor site in a unique manner which dramatically alters the activity Generally, the $X^2$ values support the significance (or lack of significance) of the ratio values. However, for data sets 9, 13, 14, and 15 the 95% confidence limit is not met. As with all statistical tests, $X^2$ is sensitive to the sample size of the population. For these data sets the N was simply too low. This sensitivity is well demonstrated by the difference in $X^2$ for sets 14 and 20. The ratio values of the two sets are virtually identical, but the $X^2$s differ significantly since set 14 has few points and set 20 many points. Thus, $x^2$ may be used to confirm the significance of a ratio value, but, on the other hand, can not be used to discredit a ratio value when too few data points are present. It can be clearly seen that the topomeric CoMFA metric appears to define a useful dimensional space (measures chemistry space) better for some of the target sets than for others.

As was discussed above, a metric need not be perfect to be valid. Even using an imperfect metric significantly increases the probability that molecules can be properly characterized based on structural differences. As the quality of the metric increases, the probability increases. Thus, metrics which appear valid by the above analysis with respect to only a few test data sets are still useful. Metrics, like topomeric CoMFA, which are valid for 85% (17/20) of the data sets yield a higher probability that structurally diverse molecules can be identified.

Only with respect to data sets 6, 8, and 11 does the topomeric CoMFA metric not appear to provide a useful measure. Considering the fact that some of the data sets have limited samples and that a very wide range of biological interactions is represented, it is not unexpected that random variations like this will appear. The critically important aspect of this analysis is the fact that the metric is valid over a truly diverse range of types of ligand-substrate interactions. This strongly confirms its generally applicability as a valid measure of the diversity of molecules which can be used to select optimally diverse molecules from large data sets such as for use in combinatorial screening library design.

Another important aspect of the invention can be derived from these plots. Upon close examination it can be seen that molecules having topomeric CoMFA differences (distances) of less than approximately 80–100 generally have activities within 2 log units of each other. This provides a quantitative definition of the radius of an area encompassing molecules possessing similar characteristics (similarly diverse) in topomeric CoMFA metric space-the neighborhood radius. Because the topomeric CoMFA metric is a valid molecular structural descriptor, it is known that molecules with similar structure and activity will cluster in topomeric CoMFA space. Topormeric CoMFA distances can, therefore, be usefully used as a diversity measure in selecting which molecules of a proposed combinatorial synthesis should be retained in the combinatorial screening library in order to have a high probability that most of the diversity available in that combinatorial synthesis is represented in the library. Thus, for a combinatorial screening library, only one example of a molecular pair having a pairwise distance from the other of less than approximately 80–100 kcal/mole (belonging to the same diversity cluster) would be included. However, every molecule of a pair having a pairwise distance greater than approximately 80–100 would be included. Of course, the "fineness" of the resolution (the radius of the neighborhood in metric space) can be changed by using a different activity difference. The Patterson plot permits by direct inspection the determination of a neighborhood distance appropriate to any chosen biological activity difference. It is suggested, however, that for a reasonable search of chemistry space for biologically significant molecules, a difference of 2 log units is appropriate. The exact value chosen can be adjusted to the circumstances. Clearly, the opportunity for real world perturbing effects to dominate the measure is magnified by using less than 2 log units difference in biological activity. This is another example of the general signal to noise ratio problem often encountered in measurements of biological systems. For more accurate signal detection less perturbed by unusual effects, the data sets would ideally contain biological activity values spread over a wider range than what is usually encountered. The neighborhood radius predicted from an analysis of the topomeric CoMFA metric can now be used to cluster molecules for use in selecting those of similar structure and activity (such as is desired in designing a combinatorial screening library of optimal diversity).

The teachings of this disclosure so far may be summarized as follows: 1) a generalizable method for validating metric descriptors has been taught; 2) a specific descriptor, topomeric CoMFA, has been described; and 3) the topomeric CoMFA descriptor has been validated over a diverse sampling of different types of biological interactions from published data sets.

The extraordinary power inherent in the validation method to quantitatively determine a significant neighborhood radius is further demonstrated by a remarkable result obtained in the analysis of a data set of potential reactants for a combinatorial synthesis (all 736 commercially available thiols) from the chemical literature. The results were obtained by "complete linkage" hierarchical cluster analysis of the resulting steric field matrices, using "CoMFA_STD" or "NONE" scaling. (CoMFA_STD implies block standardization of each field, but without rescaling of the individual "columns" corresponding to particular lattice points, which here produces the same clusters as no scaling). For clustering the "distance" between any two molecules is calculated as the root sum of the squared differences in steric field values over all of the lattice intersections defined by the CoMFA "region".

In this example, cluster analysis using topomeric CoMFA fields produced a classification of reagents that makes sense to an experienced medicinal chemist. For example, when the topomerically aligned CoMFA fields of the 736 thiols are clustered, stopping when the smallest distance between clusters is about 91 kcal/mole (within the "neighborhood" distance of 80–100 found for these fields in the validation studies), 231 discrete clusters result differing from each other in steric size by at least a —$CH_2$— group. Upon inspection of the clustering, an experienced analyst will immediately recognize that at this clustering level of 231, a natural break occurs, ie: the separation between cluster level 231 and level 232 was greater than any encountered between levels 158 and 682. Further inspection of these results showed that, with perhaps ten exceptions, each cluster contained only compounds having a very similar 2D topology or connectivity, while different clusters always contained compounds having dissimilar 2D topology. Indeed, so logical was the grouping that it was possible to provide a characteristic and distinctive systematic name for each of the 238 clusters using mostly traditional or 2D chemical nomenclature as shown in Appendix "D". It is striking that this entirely automatic clustering procedure, based only on differences among the topomeric steric fields of 3D models of single conformers, generates a classification that coincides so well with chemical experience as embodied in an independently generated 2D nomenclature. From a pragmatic point of view, this result may also be said to validate the validation procedure in the eyes of an experienced medicinal chemist who will tend to judge a metric by whether its assessments of molecular similarity and diversity agree with his/her own experience.

The critical aspect of this clustering result is that the structurally most logical clustering was generated with a nearest neighbor separation of 91, in the middle of the 80–100 neighborhood distance determined from the validation procedure to be a good measure of similarity among the molecules in topomeric CoMFA metric space. That is, the neighborhood distance of approximately 80–100 (corresponding to an approximate 2 log biological difference) predicted from the topomeric CoMFA validation, generates, when used in a clustering analysis, logical systematic groupings of similar chemical structures. The exact size of the neighborhood radius useful for clustering analysis will vary depending upon: 1) the log range of activity which is to be included; and 2) the metric used since, in the real world, different metrics yield different distance values for the same differences in biological activity. As seen, the topomeric CoMFA metric can be used to distinguish diverse molecules from one another—the very quantitative definition of diversity lacking in the prior art which is necessary for the rationale construction of an optimally diverse combinatorial screening library.

The discovered validation method of this invention is not limited to the topomeric CoMFA field metric but is generalizable to any metric. Thus, once any metric is constructed, its validity can be tested by applying the metric to appropriate literature data sets and generating the corresponding Patterson plots. If the metric displays the neighborhood behavior and is valid/useful according to the analysis of the Patterson plots set forth above, the neighborhood radius is easily determined from the Patterson plots once an activity difference is selected. This neighborhood radius can then be used to stop a clustering analysis when the distance between clusters approaches the neighborhood radius. The resulting clusters are then representative of different aspects of molecular diversity with respect to the clustered property/metric. It should be noted that a metric, by definition, is only used to describe something which has a difference on a measurement scale. This necessarily implies a "distance" in some coordinate system. Mathematical transformations of the distances yielded by any metric are still "distances" and can be used in the preparation of the Patterson plots. For instance, the topomeric CoMFA field distances could be transformed into principal component scores and would still represent the same measure.

Since the validity of the metric is not dependent on the particular chemical/biological assays used to establish its validity, the metric can be applied to assemblies of chemical compounds of unknown activity. Clustering of these assemblies using the validated neighborhood radius for the metric will yield clusters of compounds representative of the different aspects of molecular diversity found in the assemblies. (It should be understood that active molecules for any given assay may or may not reside in more than one cluster, and the cluster(s) containing the active compound(s) in one assay may not include the active compound(s) in a different assay.)

As mentioned above, when designing an efficient combinatorial screening library, one wishes to avoid including more than one molecule which is representative of the same structural diversity. Therefore, if a single molecule is included from each cluster derived as above, a true sample of the diversity represented by all the molecules is achieved without overlap. This is what is meant by designing a combinatorial screening library for optimal diversity. The methodologies of the present invention for the first time enable the achievement of such a design.

5. Tanimoto Fingerprint Descriptor

There are other measures of molecular similarity which are not metrics, that is, they do not correspond to a distance in some coordinate system but for which differences between molecules can be calculated. One such measure is the Tanimoto[13] fingerprint similarity measure. This is one of the 2D measurements frequently used in the prior art to cluster molecules or to partially construct other molecular descriptors. (Technically descriptors containing a Tanimoto term are not metrics since the Tanimoto is not a metric). 2D fingerprint measures were originally constructed to rapidly screen molecular data bases for molecules having similar structural components. For the present purposes, a string of 988 has been found convenient and sufficiently long. A Tanimoto 2D fingerprint similarity measure (Tanimoto coefficient) between two molecules is defined as:

$$\frac{\text{No. Of Bits Occuring} \in \text{Both Molecules}}{\text{No. Of Bits} \in \text{Either Molecule}}$$

The Tanimoto fingerprint simply expresses the degree to which the substructures found in both compounds is a large fraction of the total substructures.

A. Neighborhood Property

At an American Chemical Society meeting in April, 1995, Brown, Martin, and Bures[3] of Abbott Laboratories presented clustering data generated in an attempt to determine which, if any, of the common descriptors available in the prior art produced "better clustering". "Better clustering" was defined as a greater tendency for active molecules to be found in the same cluster. One of the measures used was the Tanimoto 2D fingerprint coefficient calculated from the structures of the entire molecules (not just the side chains). Proprietary and publicly unavailable data sets were used by the Abbott group which covered a large number of compounds for which the activity or lack of activity in four assays had been experimentally verified over many years of pharmacological research. Although used as an analytical tool to measure clustering effectiveness and not itself a focus of the presentation, one of the graphs Martin presented plotted the "proportion of molecular pairs in which the second molecule is also active" against the "pairwise Tanimoto similarity between active molecules and all molecules" (hereafter referred to as a "sigmoid plot"). From the resulting graph Martin et al. essentially found that if the Tanimoto coefficient of molecule A (an active molecule) with respect to molecule B is greater than approximately 0.85, then there was a high probability that molecule B will also be active; ie., the activity of molecule B can be usefully predicted by the activity of molecule A and vice versa. While not recognized or taught by the Abbott group at the time, the present inventors recognized that, for a very restricted data set, the Abbott group had data suggesting that the Tanimoto coefficient displayed a neighborhood property.

B. Applicability of Tanimoto to Different Biological Systems

In order to determine whether the Tanimoto coefficient reflects a neighborhood property over a range of different biological assays, 11,400 compounds from Index Chemicus containing 18 activity measures with 10 or more structures were analyzed. (Index Chemicus covers novel compounds reported in the literature of 32 journals.) Lack of a reported activity was assumed to be an inactivity although, in reality, the absence of a report of activity probably means that the compound was just untested in that system. For comparison purposes, this assumption is a more difficult test in which to discriminate a trend than with the Abbott data base where it was experimentally known whether or not a molecule was active or inactive. However, all that is absolutely needed for this analysis is a high likelihood of having compounds that are "similar enough" in fingerprints to also be "similar enough" in biological activity. The converse, "similar biological activity must have similar fingerprints", is patently untrue and is not tested. Table 2 shows the structures and activities analyzed.

TABLE 2

Index Chemicus Activities

| Set No. | No. Anal. | Biological Activity |
|---|---|---|
| 1 | 30 | Antianaphylactic |
| 2 | 12 | Antiasthmatic |
| 3 | 71 | Antibacterial |
| 4 | 16 | Anticholinergic |
| 5 | 55 | Antifungal |
| 6 | 17 | Anti-inflammatory |
| 7 | 21 | Antimicrobial |
| 8 | 13 | B-adrenergic |
| 9 | 21 | Bronchodilator |
| 10 | 34 | Ca Antagonistic |
| 11 | 18 | Cytotoxic |
| 12 | 133 | Enzyme Inhibiting |
| 13 | 210 | Nematocidal |
| 14 | 12 | Opioid Rcptr. Bind |
| 15 | 39 | Platelet Aggr. Inh. |
| 16 | 11 | Radioprotective |
| 17 | 13 | Renin Inhibiting |
| 18 | 11 | Thrombin Inhib. |

Figure 9A:
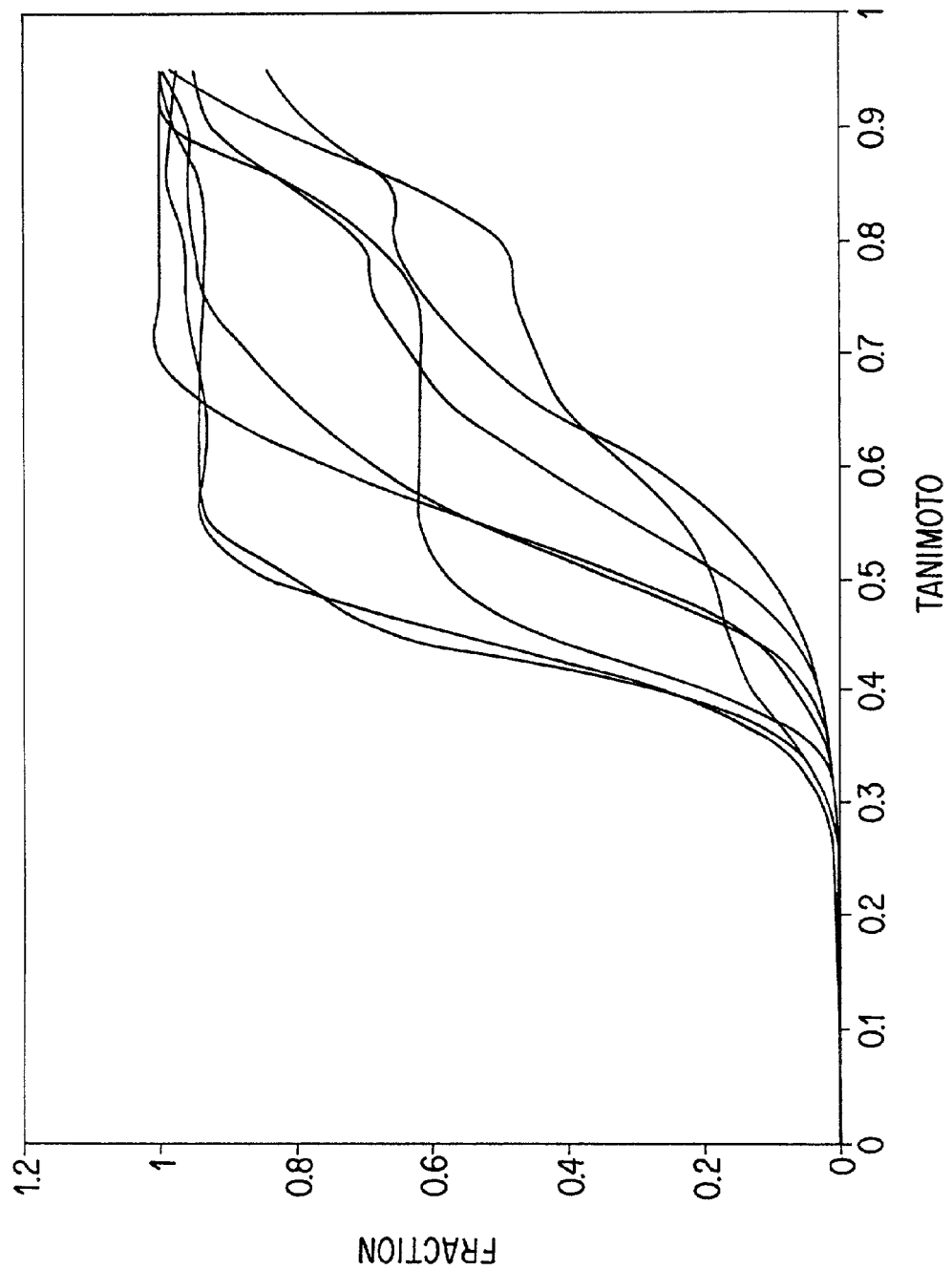
FIGS. 9A through 9C show the graphs of the Tanimoto similarity measure vs. the pairwise frequency of active molecules for 18 groups examined from Index Chemicus.
Figure 9B:
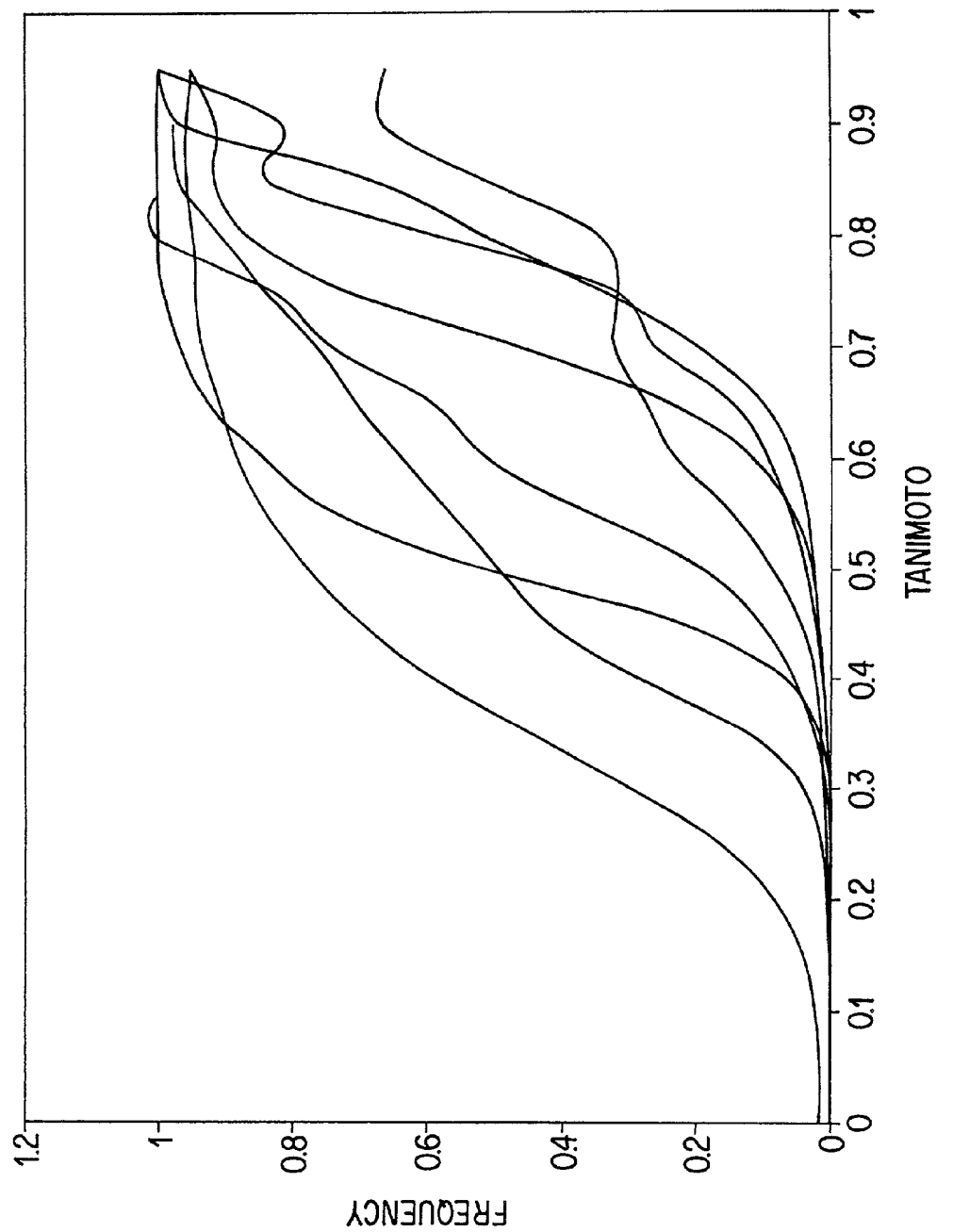
Figure 9C:
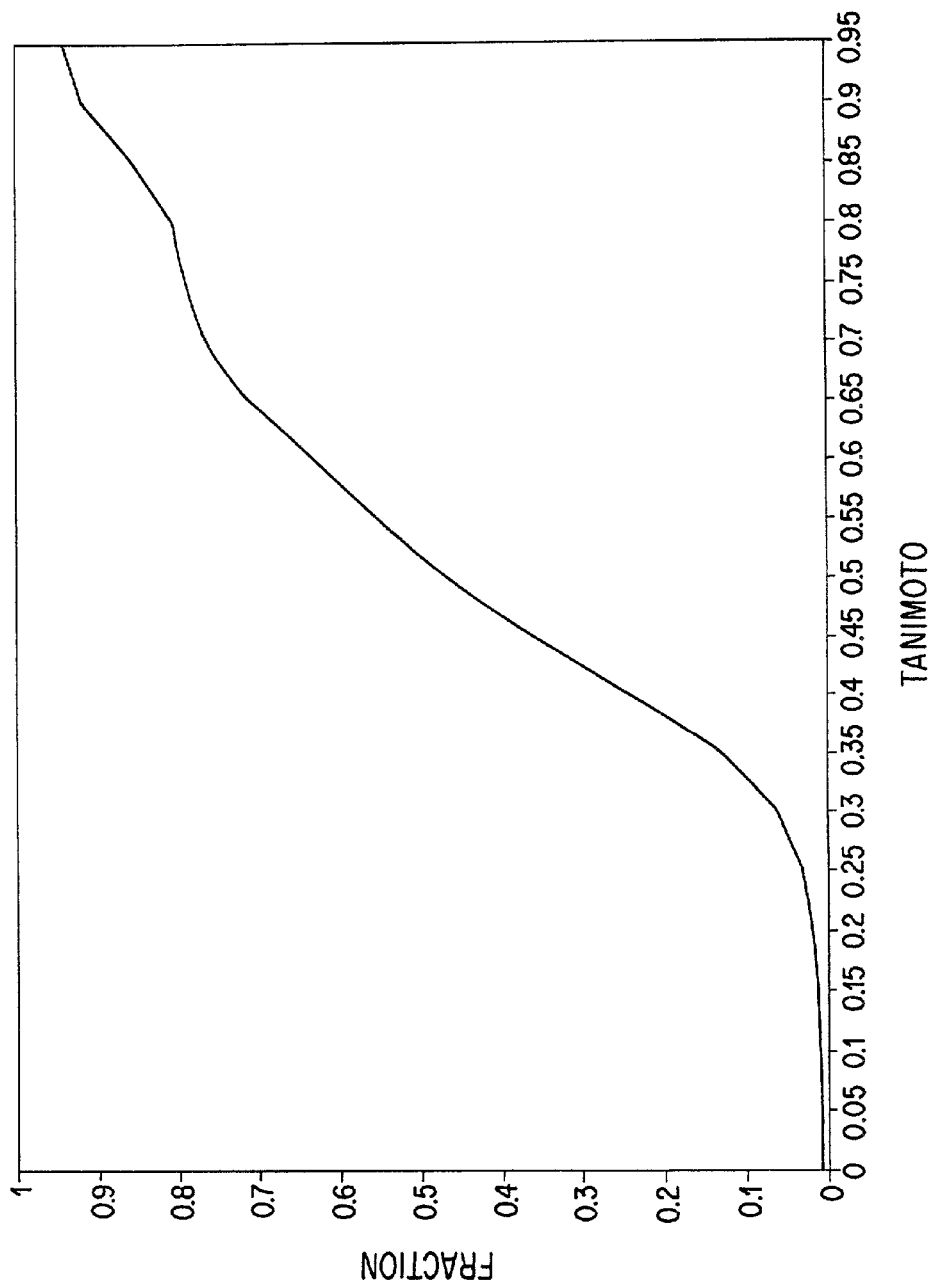

To convert this data to sigmoid plots, the data lists were examined for everything which was active, and a Tanimoto coefficient calculated (on the whole molecule) between every active molecule and everything else in the list. For plotting, the value of the number of molecules which were a given value (X) away from an active compound was determined. The proportion (frequency of such molecules) was plotted on the vertical axis and the Tanimoto coefficient on the horizontal axis. The bin widths for the X axis are 0.05 Tanimoto difference units wide, and the activity from Index Chemicus was simply "active" or "inactive". FIGS. 9A and 9B show the resulting plots for 16 of the 18 data sets broken down into sets of 8 (replication of these Figures in the priority applications did not pick up the ninth curve in each Figure, so that the ninth curve in each set has been ommitted from this application). Many of the curves have a sigmoid shape, but the inflection points clearly differ. Also, it is not clear what effect excluding the differences between active and inactive molecules has on the shape of the curves. To get an overall view, FIG. 9C shows the cumulative plot for both series of 9 activities. This plot generally indicates that, given an active molecule, the probability of an additional molecule, which falls within a Tanimoto similarity of 0.85 of the active, also being active is, itself, approximately 0.85. Stated slightly differently, when a Tanimoto similarity descriptor is summed over an arbitrary assortment of molecules and biological activities, it is clear that molecules having a Tanimoto similarity of approximately 0.85 are likely to share the same activity. Thus, the Tanimoto similarity displays a neighborhood behavior (neighborhood distance of approximately 0.15) when applied to a large enough number of arbitrary sets of compounds. As will be discussed later, one of the more powerful aspects of the Patterson plot validation method is that it can provide a relative ranking of metrics and distinguish on what type of data sets each may be more useful. In this regard, it will be seen that the whole molecule Tanimoto coefficient as a diversity descriptor has unanticipated and previously unknown drawbacks.

However, one of the principle features of the present invention, neither taught by the Abbott researchers nor recognized by anyone in the prior art, is that the Tanimoto descriptor can be used in a unique manner in the construction of a combinatorial screening library. In fact, as will be seen, it has been discovered that this descriptor can be used to provide an important end-point determination for the construction and merging of such libraries and, in addition, is a useful descriptor for constructing and searching the virtual library.

C. Comparison of Sigmoid and Patterson Plots

It is important to understand the difference in the types of information about descriptors and the neighborhood property which is yielded by the Abbott sigmoid plot and the generalized validation method and Patterson plot of the present invention.

To make a sigmoid plot, the molecules must be first be divided into two categories, active molecules and inactive molecules, based on a cut off value chosen for the biological activity. One molecule of a pair must be active (as defined by the cut off value) before the pair is included in the sigmoid plot. Pairs in which neither molecule has any activity, as well as those pairs in which neither molecule has an activity greater than the cut off value, do not contribute information to the sigmoid plot. Thus, the sigmoid plot does not use all of the information about the chemical data set under study. In fact, it uses a limited subset of data derivable from the more general Patterson plot described above. As a consequence very large sets of data (or sets for which both the activity and inactivity in an assay are experimentally known) are needed to get statistically significant results from the sigmoid plots.

By comparison, the Patterson plot clearly displays a great deal more information inherent in the data set which is relevant to evaluating the metric. Most importantly, the validity and usefulness of the metric can be quickly established by examining the Patterson plots resulting from application of the metric to random data sets. As will be shown in the next section, a metric may reflect a neighborhood property (such as in a sigmoid plot), but at the same time may not be a particularly valid/useful metric or may have limited utility. In Patterson plot analysis, all pairs of molecules and their associated activities or inactivities contribute to the validity analysis and to the determinations of the neighborhood radius. Thus, in a Patterson plot, it is easy to see what percentage of the total data set is included when the neighborhood definition is changed by choosing a different biological difference range. This has important consequences for choosing the correct neighborhood radius for clustering.

Figure 10A:
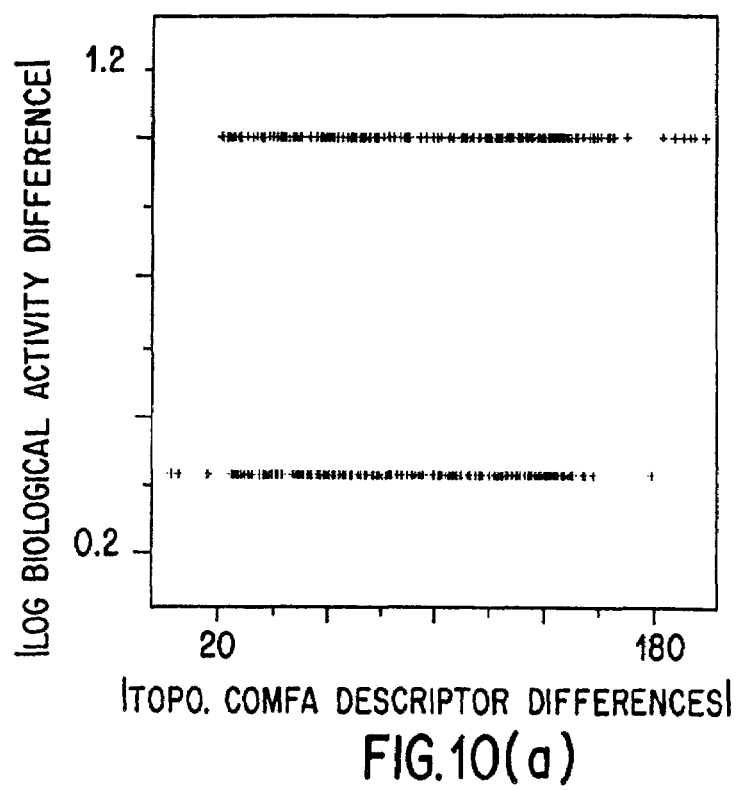
FIGS. 10A and 10B show a Patterson plot of the Cristalli data set using only those values which would have been used for a Tanimoto sigmoid plot of the same data set alongside a Patterson plot of the complete data set.
Figure 10B:
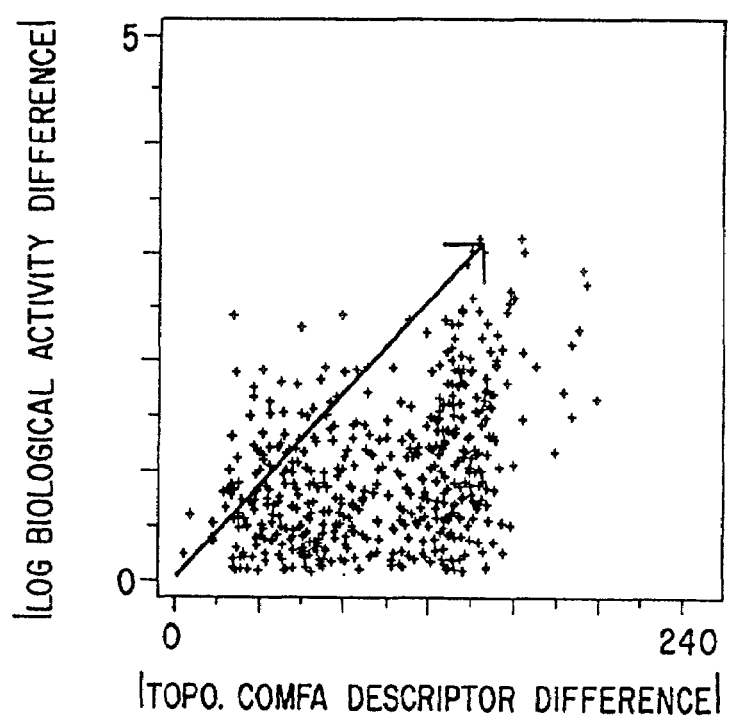

To better see the relationship between the information available from each type of plot, FIG. 10A shows a Patterson plot for the Cristalli data set reconstructed under the Abbott sigmoid plot simplification that the 32 molecules were either "active" (activity=1) or "inactive" (activity=0). The cut off value for biological activity was chosen to be 60 µM. Thus, "active" molecules were those with an Al agonist potency of 60 µM or less, and "inactive" molecules were those with a potency greater than 60 µM. With this Abbott simplification, only two differences in bioactivities can occur for a pair of molecules: both active or inactive, difference=0; or one active and the other inactive, difference=1. The result of constructing a Patterson plot for this impoverished data set thus must appear as two parallel lines, as shown in FIG. 10A alongside the Patterson plot for the full Cristalli data set in FIG. 10B. Although a triangle and trapezoid should still be anticipated within such a reduced plot, the active/inactive classification so limits the observable biological differences that no pattern whatsoever is apparent. The very limited nature of the information retained is clearly seen. In particular, by only looking at molecular pairs in which one molecule is active above a predetermined cut off value, the sigmoid plot totally fails to take into account all the information about the behavior of the metric with respect to non-active pairs (in which one or both molecules have activities less than the cut off value) contained in the distribution of points in the Patterson plot. As a major consequence, the Patterson plot is: 1) able to derive information from much less data; and 2) much more sensitive to all the nuances contained in the data.

6. Comparison of Tanimoto and Topomeric CoMFA Metrics

Having recognized that both the topomeric CoMFA and Tanimoto coefficient metrics display the neighborhood property, a comparison (between Table 1 and columns 3 and 4 of Table 3) of the application of the two metrics to identical data sets yields interesting insights into their respective sensitivities. The prior art practice of using the value of (1—Tanimoto coefficient) as a distance was followed when performing the analysis. For columns 3 and 4 of able 3, Patterson plots were constructed using the Tanimoto distances of the whole molecules represented in the 20 data sets which had been used for the topomeric CoMFA analysis. Patterson plots were also constructed using the Tanimoto distances of just the side chains (as was done with the topomeric CoMFA metric) of the molecules for the same 20 data sets. In Table 3 are shown the Tanimoto fingerprint density ratios for the whole molecule and side chain Tanimoto metrics and the corresponding $X^2$ values for the 20 data sets.

TABLE 3

Patterson Plot Ratios and Associated $X^2$

| No. | Reference | Col. 1 Side Chain Tanimoto Fingerprint Ratio | Col. 2 Side Chain Tanimoto Fingerprint $X^2$ | Col. 3 Whole Molecule Tanimoto Fingerprint Ratio | Col. 4 Whole Molecule Tanimoto Fingerprint $X^2$ |
|---|---|---|---|---|---|
| 1 | Uehling | 1.89 | 14.22 | 1.55 | 6.22 |
| 2 | Strupczewski | 1.70 | 143.48 | 1.41 | 59.61 |
| 3 | Siddiqi | 1.04 | 0.08 | 1.04 | 0.07 |
| 4 | Garratt-1 | 1.60 | 8.10 | 1.07 | 0.19 |
| 5 | Garratt-2 | 1.89 | 36.05 | 1.08 | 0.50 |
| 6 | Heyl | 1.71 | 13.83 | 1.01 | 0.00 |
| 7 | Cristalli | 1.75 | 144.54 | 1.31 | 30.27 |
| 8 | Stevenson | 0.94 | 0.05 | 1.07 | 0.04 |
| 9 | Doherty | 1.73 | 4.03 | 1.05 | 0.04 |
| 10 | Penning | 1.97 | 37.03 | 1.53 | 12.73 |
| 11 | Lewis | 1.64 | 4.80 | 1.01 | 0.00 |
| 12 | Krystek | 1.01 | 0.04 | 1.23 | 16.31 |
| 13 | Yokoyama-1 | 1.48 | 9.94 | 1.01 | 0.00 |
| 14 | Yokoyama-2 | 1.37 | 18.94 | 1.70 | 16.03 |
| 15 | Svensson | 1.64 | 16.61 | 1.02 | 0.02 |
| 16 | Tsutsumi | 1.74 | 21.56 | 1.58 | 14.35 |
| 17 | Chang | 1.34 | 145.00 | 1.13 | 8.36 |
| 18 | Rosowsky | 1.04 | 0.06 | 1.01 | 0.00 |
| 19 | Thompson | 1.72 | 7.83 | 1.17 | 0.68 |
| 20 | Depreux | 1.60 | 64.22 | 1.18 | 6.73 |
|  | MEAN | 1.54 | 34.62 | 1.21 | 8.61 |
|  | STANDARD DEVIATION | 0.32 | 49.85 | 0.23 | 14.57 |

Surprisingly the whole molecule Tanimoto appears to be a good descriptor for only 50% of the data sets (10/20 data sets with a ratio greater than 1.1). At first glance this is surprising in light of the original Abbott data, but, on second consideration, it is consistent with the observed significant individual variability of the plots obtained from the Index Chemicus analysis in FIGS. 9A and 9B. The Patterson plots confirm that the Tanimoto coefficient does display a neighborhood property for some data sets, but clearly it is less valid/useful for other sets. And it is not as consistent as the topomeric CoMFA or the side chain Tanimoto descriptor which were valid 85% (17/20) and 80% (16/20) of the time respectively. Upon inspection of the whole molecule Tanimoto data, it can be seen that the 10 data sets which do not have ratios greater than 1.1 all have a small Tanimoto range and/or contain relatively few compounds. The $X^2$ values for these data sets also confirm the lack of statistical significance. Essentially, the whole molecule Tanimoto is a less discriminating diversity measurement than the others and would appear to need, at the very least, more data and/or a greater range of values. The method of this invention clearly provides much more information and insight into the validation of the Tanimoto metric than did the Abbott style sigmoid plot.

For the majority of sets, 80% (16/20), the side chain Tanimoto metric also appears to be valid/useful. This is an extraordinarily surprising result since this metric has always been thought of in the prior art as useful only as a measure of whole molecule similarity. Overall, it compares favorably with topomeric CoMFA. A very interesting aspect, however, is that the sets for which validity is not apparent are not identical for the topomeric CoMFA and side chain Tanimoto metrics. The side chain Tanimoto metric does not appear valid with respect to sets 3, 8, 12, and 18. Clearly set 8 had too little data for either the topomeric CoMFA or the side chain Tanimoto descriptors. The most interesting comparison involves sets 3, 12, and 18 which validated the topomeric CoMFA metric but for which the side chain Tanimoto metric appears invalid. Upon inspection, these sets all contained substituents in which only the position of a particular side chain varied. Since the topomeric CoMFA metric is sensitive to the relative spatial orientations of the side chains, while the Tanimoto metric is only sensitive to the presence or absence of the side chains, the sterically driven topomeric CoMFA metric was sensitive to the differences in these sets while the Tanimoto was insensitive. In certain circumstances the Tanimoto may be a useful descriptor of molecular diversity for use on the reactants in a combinatorial synthesis; a result totally at odds with the wisdom of the prior art. Clearly, however, the differences in sensitivities between the metrics should be considered when applying them.

Further, considering the five metrics already discussed above (topomeric CoMFA, whole molecule Tanimoto, side chain Tanimoto, random numbers, and force field energy) it is clear that the validation method of this invention can be used to rank the relative quality (validity/usefulness) of the metrics. In addition, when enough metrics have been examined by the method of this invention, it will be possible to choose metrics appropriate to the type of molecular structural differences which it is desired to analyze. Correspondingly, when a metric, which has been validated over a very wide range of data sets and biological activities, yields surprising results (appears invalid) when applied to a new data set, one potential interpretation may be that the data are in error. This highlights another feature of the invention, the ability to reliably suggest that some experimental observations are generating unusual data. Instead of using a data set to validate a metric, the previously validated metric is used to examine the reliability of the data set. By constructing Patterson plots and checking the associated $X^2$ value for significance, experimental scientists have another tool with which they may independently assess their data, especially in situations where new biological activities are being investigated.

7. Additional Validation Results

Considering that the validation method of this invention has shown that both the topomeric CoMFA metric and the Tanimoto metric define metric spaces where biological properties cluster (that is; the metrics are sensitive to biologically relevant molecular strucutral differences), a descriptor combining the two metrics was construcuted. A combined descriptor has been identified which is the best diversity descriptor discovered to date. This descriptor has been validated and has been found to be far superior to any previously considered metric in its ability to identify a neighborhood of similarity for design purposes. This descriptor, a weighted combination of the topomeric CoMFA descriptor and the Tanimoto descriptor, defines a distance measure as:

$$\sqrt{(1-\text{Tanimoto})^2 + (0.003 \times \text{topomericCoMFA})^2}$$

This descriptor has a ratio greater than 1.1 in all 20 out of the 20 test data sets, and, in fact, averages a ratio of 1.55. In all 20 data sets for a neighborhood distance of 0.240 (corresponding to a biological activity difference of 2 log units) not one single point was found above the line in the Patterson plot. Although this may appear as a "perfect" metric, it is doubted that this level will be maintained as more and more data sets are added to the validation group. However, it is believed that it will continue to be the strongest of the presently known descriptors. At the present time, the results of performing validation studies on the combined descriptor and other possible metrics using the Patterson plot method of this invention and the 20 described data sets result in the following data:

TABLE 4

| | | Patterson Plot Ratios | | | | | | |
|---|---|---|---|---|---|---|---|---|
| No. | Reference | HB | LOGP | MR | AP | CONN | AUTO | COMBO |
| 1 | Uehling | 1.83 | 1.09 | 1.07 | 1.55 | 1.19 | 1.66 | 1.87 |
| 2 | Strupczewski | 1.48 | 1.00 | 0.99 | 1.40 | 1.05 | 1.20 | 1.47 |
| 3 | Siddiqi | 1.47 | 0.97 | 0.92 | 1.00 | 1.07 | 1.00 | 1.48 |
| 4 | Garratt-1 | a | 1.01 | 1.01 | 0.90 | 1.11 | 1.14 | 1.68 |
| 5 | Garratt-2 | a | 1.01 | 1.00 | 0.97 | 1.09 | 1.09 | 1.50 |
| 6 | Heyl | 1.24 | 0.98 | 0.95 | 1.11 | b | 1.01 | 1.34 |
| 7 | Cristalli | 1.22 | 1.06 | 0.99 | 1.27 | 0.98 | 1.17 | 1.44 |
| 8 | Stevenson | a | 1.03 | 1.03 | 1.02 | 1.02 | 1.02 | 1.60 |
| 9 | Doherty | 1.07 | 1.00 | 1.01 | 1.18 | 1.02 | 1.28 | 1.78 |
| 10 | Penning | 1.72 | 1.00 | 0.97 | 1.05 | 1.00 | 1.36 | 1.67 |
| 11 | Lewis | *0.57 | 1.00 | 1.02 | 0.97 | 1.15 | 1.14 | 1.62 |
| 12 | Krystek | 1.69 | 0.85 | 0.85 | 1.43 | 1.01 | 1.00 | 1.75 |
| 13 | Yokoyama-1 | *0.71 | d | 1.01 | 1.25 | 1.01 | 0.99 | 1.52 |
| 14 | Yokoyama-2 | 1.00 | 1.00 | 0.99 | 1.25 | 1.05 | 0.99 | 1.57 |
| 15 | Svensson | *0.31 | 1.01 | 0.99 | 1.31 | 1.08 | 1.00 | 1.39 |
| 16 | Tsutsumi | 1.67 | 1.04 | 0.95 | 1.18 | 1.00 | 0.95 | 1.52 |
| 17 | Chang | 1.35 | 1.00 | 1.00 | 1.00 | c | 1.20 | 1.36 |
| 18 | Rosowsky | 1.44 | 1.03 | 0.96 | 1.23 | 1.08 | 1.21 | 1.66 |
| 19 | Thompson | a | 1.12 | 0.99 | 0.87 | 1.02 | 1.01 | 1.47 |
| 20 | Depreux | *0.44 | 1.02 | 0.99 | 0.99 | 1.01 | 0.98 | 1.26 |
| | MEAN | *1.43 | 1.01 | 0.98 | 1.15 | 1.05 | 1.12 | 1.55 |
| | STANDARD DEVIATION | *0.27 | 0.05 | 0.05 | 0.19 | 0.06 | 0.17 | 0.16 |

HB = Topomeric Hydrogen Bonding
LOGP = Calculated Log P
MR = Molar Refractivity
COMBO = Combined Topomeric CoMFA & Tanimoto
AP = Atom Pairs[14]
AUTO = Autocorrelation[15]
CONN = Connectivity Indices[16]
*Asterisked values are excluded in computing the mean. These values are all artifacts, the result of there being no more than two distinguishable values of the molecular descriptor within the particular series, hence only two possible values of the x variable in a Patterson plot.
[a]No Hydrogen bonding groups exist to define the metric under HB
[b]Too many groups for s/w to handle under CONN
[c]One hexavalent atom confuses the computation under CONN
[d]A LOGP could not be calculated for the molecules in this data set Combining the data from Table 4 with the data from Tables 1 and 3 permits the relative ranking of some known metrics:

| VALIDITY/USEFULNESS RANK: | No. Of Ratios > 1.1 |
|---|---|
| USEFUL | |
| Combined Topomeric Steric CoMFA and Tanimoto | 20/20 |
| Topomeric Steric CoMFA | 17/20 |
| Tanimoto 2D Fingerprints (Side Chain) | 16/20 |
| Topomeric HBond Spatial Fingerprints | 10/12 |
| LESS USEFUL: | |
| Tanimoto 2D Fingerprints (Whole Molecule) | 10/20 |
| Atom Pairs (R. Sheridan) | 11/20 |
| Autocorrelation | 9/20 |
| NOT USEFUL - INVALID: | |
| Connectivity Indices | 3/18 |
| (Health Design Implementation, first 10) | |
| Partition Coefficient (CLOGP) | 1/19 |
| Molar Refractivity (CMR) | 0/20 |
| Force Field Strain Energy | 0/18 |
| Random Numbers | 0/20 |

Note:
A denominator of less than 20 indicates that the metric could not be calculated for all 20 data sets.

8. Combinatorial Library Design Utilizing Validated Metrics

The starting point for the design of any combinatorial screening library is the choice of synthetic reaction scheme involving the selection of the core molecule and the possible reactants which could be used with any specific chemistry. As mentioned earlier, well known and understood organic reactions are generally utilized. Initially, information about the chemical structure of all the reactants (and cores, when appropriate) and the synthetic chemistry involved (what products can be built) is input as a database in the computer in a form recognizable by the computational software. Using the insights gained from the discovery of the validation method of this invention, it is now possible to design general purpose combinatorial screening libraries of optimal diversity.

Conceptually, the design process may be thought of as a filtering process in which the molecules available in a combinatorially accessible chemical universe are run through consecutive filters which remove different subsets of the universe according to specified criteria. The goal is to filter out (reduce the numbers of) as many compounds as possible while still retaining those compounds which are necessary to completely sample the molecular diversity of the combinatorially accessible universe. The basic design method of this invention along with several ancillary considerations is shown schematically in FIG. 11 using the filter analogy. For this example only two sets of reactants are considered with one reactant of each set being contributed to each final product molecule. The reactants are shown forming the top row and first column of a combinatorial matrix A. Only a portion of the possible combinatorial matrix is shown, the remainder being indicated by the sections connected to the matrix by dots. One set of reactants is represented by circles 1, and the other set by squares 2. Each empty matrix location represents one possible combinatorial product which can be formed from the two sets of reactants. (The matrix of possible products would be a rectangular prism for three sets of reactants, and a multidimensional prism for higher orders of reactant sets.) As the design process is implemented, the number of products to be included in the screening library design is reduced by each filter 4. Beside each filter step is indicated the corresponding text section describing that filter. Also set out opposite each filtering step is an indication of the software and its source required to implement that step.

A. Removal of Reactants for Non-Diversity Reasons

In designing screening libraries derived from combinatorially accessible chemical universes, practical and end use considerations as well as diversity concerns can be used to reduce the number of reactants which will be used to combinatorially specify the product molecules. These practical and end-use criteria can be divided into those of general applicability and those of more specific applicability for a particular type of screening library (such as for drug discovery). The following discussion is not meant to be limiting, but rather is intended to suggest the types of selections which may be made.

i. General Removal Criteria

As a first consideration, reactants with unusual elements (such as the metals) are normally excluded when considering the synthesis of organic molecules. In addition, tautomerization of structures can cause problems when searching a universe of reactants data base either by missing structures that are actually present or by finding a specific functional group which is really not there. The most common example of this is the keto-enol tautomerism. Thus, possible tautomeric reactants must be examined and improper forms eliminated from consideration. Generally, reactants may be provided in solvent, as salts with counter-ions, or in hydrated forms. Before their structures can be analyzed for diversity purposes, the salt counter-ions, solvent, and/or other species (such as water) should be removed from the molecular structure to be used.

Figure 11A:
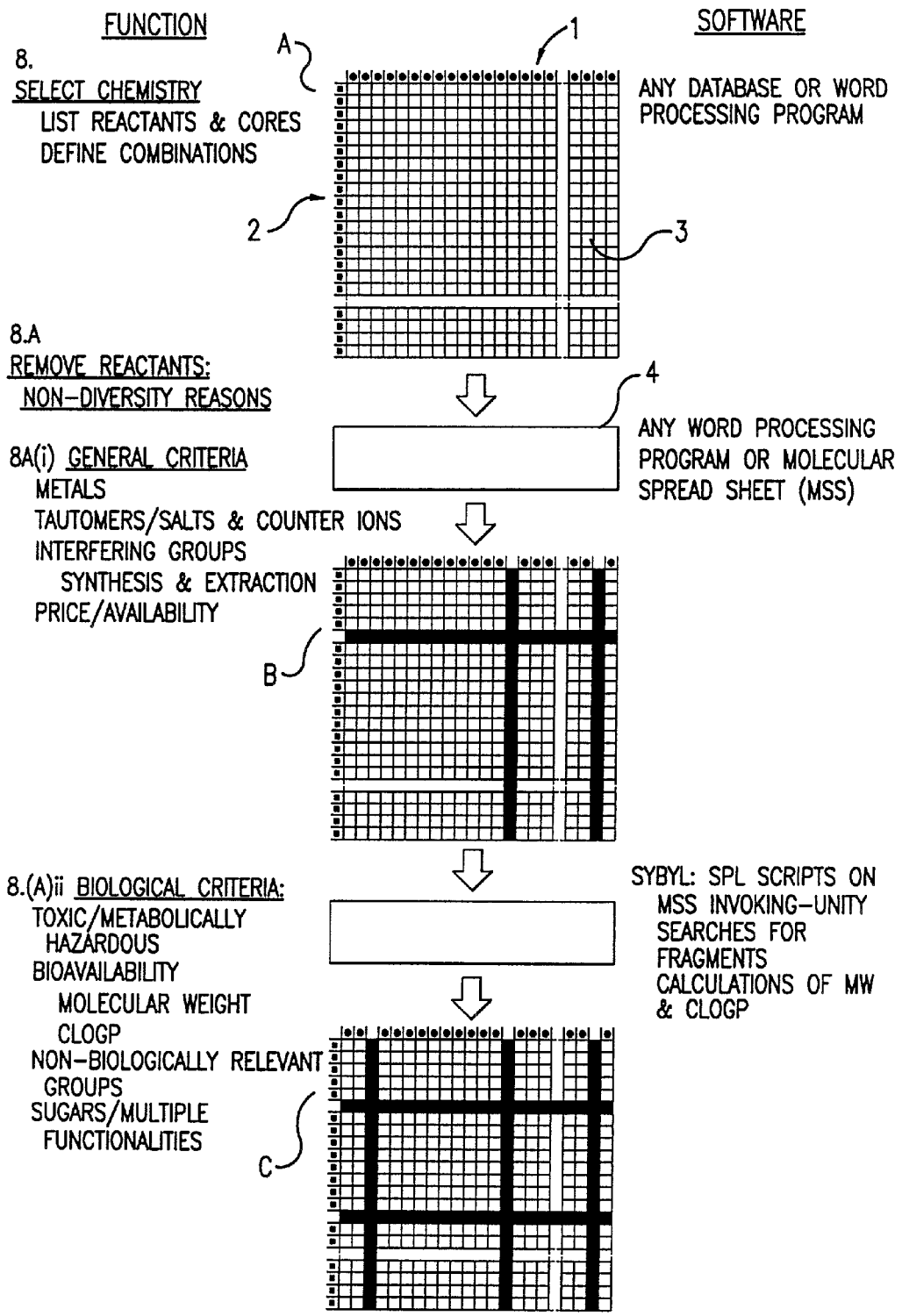
Figure 11C:
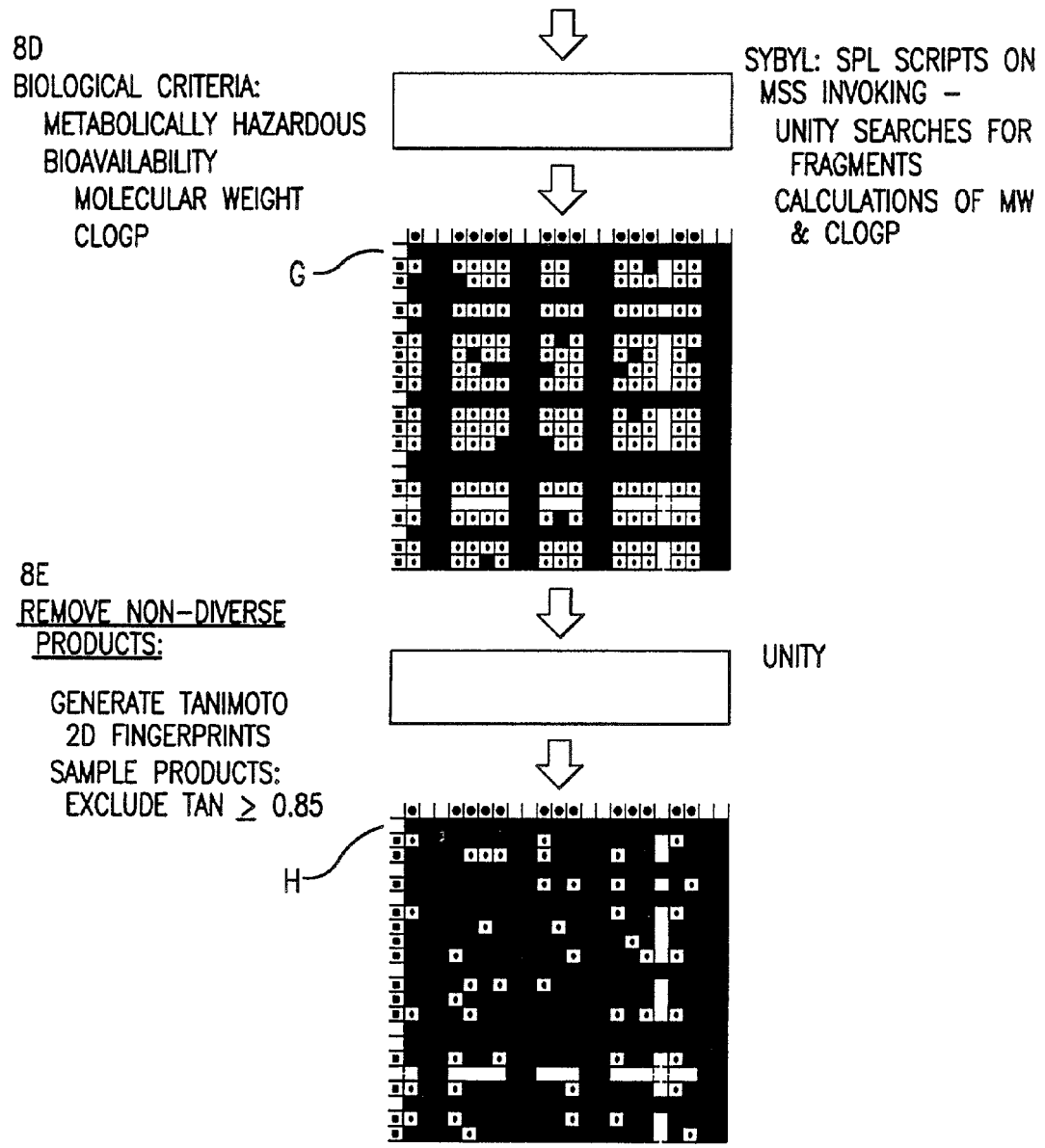

Additionally, reactants may contain chemical groups which would interfere with or prevent the synthetic reaction in which it is desired to use them. Clearly, either different reaction conditions must be used or these reactants removed from consideration. Sometimes, while the synthesis may be possible, extraction of the products resulting from some reactants may be difficult using the proposed synthetic conditions. Again, if possible, another synthetic scheme must be used or the reactants removed from consideration. Price and availability are not insignificant considerations in the real world. Some reactants may need to be specially synthesized for the combinatorial synthesis or are otherwise very expensive. In the prior art, expensive reactants would typically be eliminated before proceeding further with the library design unless they were felt to be particularly advantageous. One of the advantages of the method of this invention is that the decision whether to include expensive reactants may be postponed until the molecular structures have been analyzed by a validated descriptor. With confidence that the validated descriptor permits clustering of molecules representing similar diversity, often another, less expensive, reactant can be selected to represent the diversity cluster which also includes the expensive molecule. The specifics of any particular contemplated combinatorial synthesis may suggest additional appropriate filtering criteria at this level. In FIG. 11 the effect on the number of possible products of removing only a few reactants is easily seen in matrix B. For each reactant removed, whole rows and columns of possible products are excluded.

ii. Biologically Based Criteria

A library designed for screening potential pharmacological agents imposes it own limitations on the type and size of molecules. For instance, for drug discovery, toxic or metabolically hazardous reactants or those containing heavy metals (organometallics) would usually be excluded at this stage. In addition, the likely bioavailability of any synthetic compound would be a reasonable selection criteria. Thus, the size of the reactants needs to be considered since it is well known that molecules above a given range of molecular weights generally are not easily absorbed. Accordingly, the molecular weight for each reactant is calculated. Since the final molecular weight for a bioavailable drug typically ranges from 100 to 750 and since, by definition, at least two reactants are used in a combinatorial synthesis, reactants having a size over some set value are excluded. Typically, those above 600 are excluded at this stage at the present time. A lower value could be used, but it is felt that there is no reason to restrict the diversity unduly at this stage in the design process. Once again, of course, this value can be adjusted depending on the chemistry involved.

Another aspect of bioavailability is the diffusion rate of a compound across membranes such as the intestinal wall. Reactants not likely to cross membranes (as determined by a calculated LogP or other measure) would usually be eliminated. At the present time, although the CLOGP for reactants makes only a partial contribution to the product CLOGP, it is believed that if any reactant has a CLOGP greater than 10, it will not make a usable product. Accordingly, the CLOGP is calculated for each reactant and only those with CLOGP$\leq$10 are kept. Again, in any particular case, a different value of CLOGP could be utilized. For those reactants for which it is difficult or impossible to calculate a LOGP, it is assumed the CLOGP would be less than 10 so that the reactants are kept in the library design at this point. As will be discussed later, a CLOGP will also be calculated on the products.

Other reactants are considered undesirable due to the presence of structural groups not considered "bio-relevant". Bio-relevance is judged by comparison with known drugs and by the experience of medicinal chemists involved in the design of the library. It is hoped that a future formal analysis of drug databases will yield further information about which groups should be excluded. Exclusion on this basis should be minimized since one of the goals of the combinatorial library design process is to find biologically active molecules through the exploration of combinatorial chemistry space which might not otherwise be found. Other removal criteria may be based on whether possible reactants involved sugars or had multiple functionalities. At the present time, the compounds shown in Table 5 are believed to be undesirable and are generally excluded at the initial stage of library design.

TABLE 5

Biologically Non-Relevant Groups

| GROUP DEFINITION | SYBYL Line Notation (SLN) | Reason(s) For Exclusion |
|---|---|---|
| BOC | C(OC(=O)N)(CH3)(CH3)CH3 | Stability |
| FMOC | C[1]H:C[2]:C(:CH:CH:CH@1)CH(CH2OC(=O)N)\ C[22]:C@2:CH:CH:CCH:CH:@22 | Stability |
| Hydrolyzable acyclic groups | Lvg.-[!r]C(-Any)-[!r]Lvg{Lvg:O\|N\|Br\|Cl\|I} | Stability |
| Silicon, Aluminium, Calcium | Si, Al, Ca | Unfashionable |
| Polyhydroxyls/sugars | HOCC(OH)COH | Extraction Difficulties |
| Allyl halides | HaloC(Any)C=:Any{Halo:Br\|Cl\|I} | Stability, alkylating agent |
| Benzyl halides | HaloC(Any)C=:Any{Halo:Br\|Cl\|I} | Stability, alkylating agent |
| Phenacyl halides | HaloC(Any)C=:Any{Halo:Br\|Cl\|I} | Stability, alkylating agent |
| Alpha-halo carbonyls | HaloC(Any)C=:Any{Halo:Br\|Cl\|I} | Stability, alkylating agent |
| Acyl halides | Csp(=O)Hal{Csp:C\|S\|P} | Stability, alkylating agent |
| Phosphyl halides | Csp(=O)Hal{Csp:C\|S\|P} | Stability, alkylating agent |
| Thio halides | Csp(=O)Hal{Csp:C\|S\|P} | Stability, alkylating agent |
| Carbamates | NoroC(=O)Hal{Noro:N\|O\|S} | Stability, alkylating agent |
| Chloroformates | NoroC(=O)Hal{Noro:N\|O\|S} | Stability, alkylating agent |
| Isocyanates | N=C=Het | Stability, alkylating agent |
| Thioisocyanates | N=C=Het | Stability, alkylating agent |
| Diimides | N=C=Het | Stability, alkylating agent |
| Sulfonating agents | Het(=O)(=O))Lvg{Lvg:OHev\|Hal} | Stability, alkylating agent |
| Phosphorylating agents | Het(=O)(=O))Lvg{Lvg:OHev\|Hal} | Stability, aklylating agent |
| Epoxides, etc. | C[1]HetC@1 | Stability, alkylating agent |
| Diazos | Any~N[F]~N[F] | Stability, toxicity |

TABLE 5-continued

Biologically Non-Relevant Groups

| GROUP DEFINITION | SYBYL Line Notation (SLN) | Reason(s) For Exclusion |
|---|---|---|
| Azides | Any~N[F]~N[F]~Oorn[F]{Oorn:O\|N} | Stability, toxicity |
| Nitroso | Any~N[F]~N[F]~Oorn[F]{Oorn:O\|N} | Toxicity |
| Mustards | HaloC(Any)C(Any)Lvg{Lvg:Het\|Halo}{Halo:Br\|Cl\|I} | Stability, alkylating agent |
| 2-halo ethers | HaloC(Any)C(Any)Lvg{Lvg:Het\|Halo}{Halo:Br\|Cl\|I} | Stability, alkylating agent |
| Quaternary Nitrogens | Hev~Norp(~Hev)(~Hev)~Hev{Norp:P\|N} | Extraction difficulties |
| Quaternary Phosphorus | Hev~Norp(~Hev)(~Hev)~Hev{Norp:P\|N} | Extraction difficulties |
| Acid anhydrides | Het=Any-[!r]O-[!r]Any=Het | Stability, alkylating agent |
| Aldehyde | CCH=O | Stability, alkylating agent |
| Polyfluorinates | FC(F)C(F)F | Unfashionable |
| Michael acceptor | O=C(Nothet)-C=Any(H)Nothet{Nothet:C\|H} | Toxicity |
| Trialkylphosphines | P(C)(C)C | Stability |
| Other Triaryls | Any:Any-[!r]Any(-!r]Any:Any)\ (-[!r]Any:Any)Lvg{Lvg:Het\|Hal} | Stability |
| Alpha-dicarbonyls | Oorn=[!r]Any(AnyHev)-C=[!r]Oorn{Oorn:O\|N} | Stability |

The choice of whether to eliminate some reactants based on such general and specific considerations will vary with the given situation. Except in the case of toxic materials, it is recognized that any other limiting selection decreases the diversity of the combinatorial library and potentially eliminates active molecules. As always, when eliminating reactants at the very beginning of library design, the problem boils down to a question of probabilities: what is the likelihood of missing a significant lead molecule? In the real world, what is desired at the very least is a high probability that it is unlikely that such a molecule will be missed if the selection criteria under consideration are implemented. The application of many of these selection criteria (price, availability, toxicity, bioavailability, diffusion, and non-biologically relevant structural groups) can occur before, during, or after the screening library has been selected based on other criteria. Clearly, however, the earlier these selection criteria are applied, the greater will be the reduction in the number of combinatorial possibilities which will need to be evaluated later in the design process. As will be discussed below, not only are these criteria applied at the reactant level, but some of them will also be applied again at the product level. Reduction of the number of reactants (for the reasons set forth above) in the early stages of the library design process is indicated in FIG. 11 at matrix C.

B. Removal of Non-Diverse Reactants

As noted earlier, an ideal combinatorial screening library will: 1) have molecules representing the entire range of diversity present in the chemical universe accessible with a given set of combinatorial materials; and 2) will not have two examples of the same diversity when one will suffice. The goal is to obtain as complete a sampling of the diversity of chemical space as is possible with the fewest number of molecules, and, coincidentally, at lowest cost. In selecting a subset of a possible combinatorial universe to include in a screening library, there are two opportunities based on diversity considerations to reduce the number of included molecules. The first opportunity occurs when selecting reactants for the combinatorial synthesis. The fewer the number of reactants, the much fewer the number of combinatorial possibilities. The second opportunity occurs after all the combinatorial possibilities from the chosen reactants (and core) have been selected. The method of the present invention utilizes both opportunities by using validated metrics appropriate to each situation.

Any metric which has been shown by the Patterson plot validation methodology to be valid/useful when applied to reactants may be used at this stage of the library design process. However, there are a number of reasons to use a metric which reflects the steric diversity of the combinatorially accessible chemical universe. The principle reason is that the accumulated observation of biological systems is that ligand-substrate binding is primarily governed by three dimensional considerations. Before a reactive side group can get to the active site, before appropriate electrostatic interactions can occur, before appropriate hydrogen bonds can be formed, and before hydrophobic effects can come into play, the ligand molecule must basically "fit" into the three dimensional site of the substrate. Thus a principal consideration in designing screening libraries should be to sample as much of the three dimensional (steric) diversity of the combinatorial universe as is possible. The initial method of the present invention does this by utilizing the validated topomeric CoMFA metric to analyze the steric properties of the proposed reactants.

Figure 12:
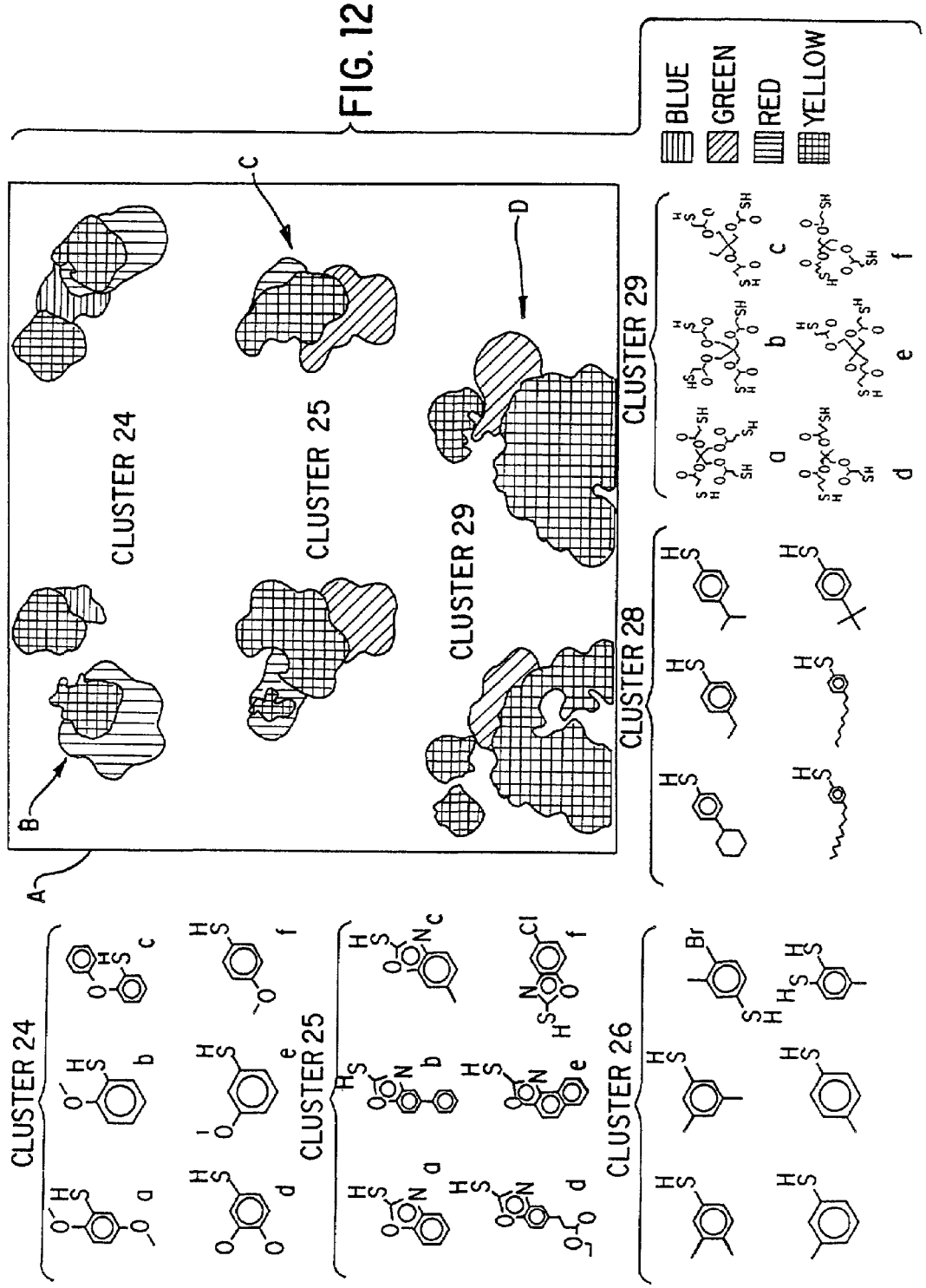
FIG. 12 shows a comparison of the volumes of space occupied by different molecules which are determined to be similar according to the Tanimoto 2D fingerprint descriptor but which are determined to be dissimilar according to the topomeric CoMFA field descriptor.

A second reason for applying a steric metric to the reactants is that all of the three dimensional variability of the products resulting from a combinatorial synthesis resides in the substituents added by the reactants since the core three dimensional structure is common to all molecules in any particular combinatorial synthesis. In a sense it would be redundant to measure the contribution to each product molecule of a core which is common to all the products. A third reason for applying a three dimensional metric to the reactants is that a sterically sensitive metric distinguishes differences among molecules that are not revealed using other presently known metrics. For instance, the topomeric CoMFA metric is more sensitive to the volume and shape of the space occupied by a molecule than is, for instance, either the side chain or whole molecule Tanimoto descriptor. FIG. 12 provides an illustrative example of this feature drawn from the thiol study which confirms what was seen in the Patterson plots of the topomeric CoMFA and Tanimoto whole molecule descriptor. FIG. 12 shows three clusters labeled 24, 25, and 29 for which the Tanimoto whole molecule fingerprint metric does not indicate any substantial difference in molecular structure among the molecules, labeled (a) through (f), making up each of the clusters. The large panel A in the upper right of FIG. 12 shows orthogonal 3D views of the volume differences within clusters 24, 25, and 29 comparing each of the molecules that are not in the majority steric field cluster. For example, the Cluster 24 figure B at the top shows four contours (yellow, green [hidden], red, and blue) indicating the differences in volumes occupied by compounds 24(a), 24(b), 24(c) and 24(f) compared to compounds 24(d) and 24(e) which are found in the same steric field cluster, number 10. The middle C and bottom D figures in the large panel A show similar distinguishable volume differences for Clusters 25 and 29. While the whole molecule Tanimoto metric does not distinguish much difference between the molecules within each of these clusters, it is readily apparent from FIG. 12, even to an untrained eye, that the molecules in the clusters represent very different types of structural diversity; that is, significantly different three dimensional volumes are occupied by the molecules within each whole molecule Tanimoto determined cluster. The topomeric CoMFA metric clearly shows steric differences that are not indicated by the 2D Tanimoto. As seen earlier, a side chain Tanimoto similarity descriptor also does not distinguish steric differences amongst some molecules. A metric responsive to steric differences is, therefore, clearly preferred as a diversity discriminator for reactants.

The initial method for selecting reactants based on diversity is shown schematically at the third filter in FIG. 11. A diversity selection based on three dimensional steric measures begins by: 1) generating 3D structures for the reactants; 2) aligning the 3D molecular structures according to the topomeric alignment rules; 3) generating CoMFA steric field values for the reactants including, if desired, hydrogen bonding fields, and applying a rotatable bond attenuation factor; and 4) calculating pairwise topomeric CoMFA differences for every pair of reactants. At this point the steric diversity of the reactant space has been mapped into the topomeric CoMFA metric space. From the validation of the topomeric CoMFA metric, it was found that the neighborhood radius for an apparent activity difference of 2 log units was defined by a distance of approximately 80–100 topomeric CoMFA units (kcal/mole). Therefore, at this point, the method of the invention clusters (using hierarchical clustering) the reactants in topomeric CoMFA space so that reactants having a pairwise difference of less than approximately 80–100 units are assigned to the same cluster. Put another way, clustering is continued until the inter-cluster separation is greater than approximately 80–100 units. (If desired, there is some leeway in choosing the exact neighborhood radius in and about the neighborhood range to use for any given biological system. An experienced practioner of the clustering art will easily be able to determine, by noting the natural breaks in the clustering, where about the 80–100 range best clustering is obtained.) This process will produce clusters having reactants whose product activities will only rarely differ by more than approximately 2 log units. If reactant clusters having products activities differing by a greater or lesser amount are desired, the neighborhood distance used may be increased or decreased accordingly. The effect on the neighborhood distance of choosing such other activity range can be seen by viewing the Patterson validating plots for the topomeric CoMFA descriptor.

The clustering process now identifies groups (clusters) of reactants having steric diversity from one another but also having the same steric properties within each cluster. Or put in terms familiar to medicinal chemists, the molecules of each cluster should be bioisosters. For purposes of designing a combinatorial screening library which has within it molecules representing the full range of steric diversity present in the universe of reactants, it is now only necessary to select one reactant from each cluster for inclusion in the library. A reasonable way to select the one reactant from each cluster would be to select the lowest priced or most readily available one. However, additional criteria may be considered. The diverse reactants remaining at matrix D need not be adjacent to each other on the combinatorial matrix and are only shown this way for graphic convenience. At this point the first stage of library design has been completed.

While the use of a topomeric CoMFA metric to measure the three dimensional structural diversity of the reactants has been discussed, it should be apparent that any metric: 1) reflective of the three dimensional properties of molecules; and 2) validated as taught above, could be applied to the reactants to be used in a combinatorial synthesis in the manner taught above. The teaching of this invention is not limited to the use of the topomeric CoMFA metric, but also includes the use on reactants of all validated three dimensional metrics. As seen earlier, at the present time initial studies of topomeric hydrogen bonding fields indicate that it should be a very useful metric. For those reactants expected to form large number of hydrogen bonds, this may be the metric of choice. The hydrogen bonding metric would be used as an adjunct to the topomeric CoMFA metric in those situations. There may be situations where a sterically sensitive metric is not needed, in which case it should be clear that any valid metric appropriate to reactants could be used.

C. Identification (Building) of Products

Once the set of diverse reactants has been identified by the above method, the structures of the product molecules can be combinatorially determined based on the synthetic reaction scheme and any desired cores. The reactants are used to build the structures of the combinatorial products using LEGION and are stored in molecular spread sheets. In matrix E the products which can still be built from the available reactants are shown as asterisks in each matrix location.

D. Removal of Products for Non-Diversity Reasons

After the possible product structures have been identified, another opportunity exists to reduce the number of products due to general non-diversity considerations. These considerations will generally be related to the particular chemistry involved and might relate to product instabilities, cyclic structures, etc. (Matrix F)

During the building of the combinatorial product molecules, the size of the product molecules increase and various combinations of core and substituents will affect the likely diffusion of the molecule (and may even form one of the biologically undesirable molecular groupings). Thus, in order to eliminate molecules which would not be used as drugs, the product molecules should be examined with many of the same selection criteria applied to reactants. In particular, molecular weights should be calculated and those compounds which have molecular weights over a predetermined value should be rejected. Typically, a value of 750 is used at this time as a representative weight above which bioavailability may become a problem. In addition, CLOGP should be calculated and any proposed molecule with a value under −2.5 or over 7.5 rejected. The number of structures eliminated at this point will depend in part both on the chemistry involved and the molecular weight range retained at the reactant stage. These additional product structures which are eliminated are reflected in matrix G.

E. Removal of Non-Diverse Products

As noted, a second opportunity based on diversity considerations to reduce the number of molecules to be included in the combinatorial screening library occurs after the products of a proposed combinatorial synthesis have been "built" by the software in the computer. Such an additional reduction is usually necessary since the number of combinatorial products at this stage may still be astronomically large. This is reflected in matrix G. In addition, it makes no sense to screen any more molecules than is absolutely necessary, and redundancy may occur in the products for several reasons. In a simple case, if two diverse reactants may react independently at each of two possible sites on a symmetric core molecule, two identical product molecules will be generated. In a more complex case, it is possible that one combination of core and reactants is similar (due to the similarities of structures contained in the core to the structure of the reactants) to another combination of core and reactants. That is, when the reactants are combined with the core molecule, it is possible that substructures within the core can combine with different substituents to form similar structures. Clearly, it would be redundant to screen both. How to select product molecules has been a vexing problem in the prior art, and this is one reason why the prior art has basically been concerned with clustering criteria. The general approach taken in the prior art to avoid oversampling combinatorial product molecules representing the same diversity has been to cluster the molecules and then maximize the distance between clusters with whatever metric was applied to the products.

Based upon an understanding developed from the theoretical considerations of validating a metric outlined above, the library design method of this invention again makes use of the neighborhood principle to solve this problem. However, it is important to understand that, unlike some methods of the prior art, the method of this invention specifically does not use a metric to cluster product molecules. Rather, the neighborhood definition may be used to decide which product molecules to retain in the final screening library and, correspondingly, when the appropriate number of product molecules have been selected for inclusion in the library. Essentially, starting with one product molecule, additional molecules are selected as far apart as possible (in the validated metric space) from any molecule already in the library until the next molecule to be selected would fall within the neighborhood distance of a molecule already included. Additional molecules are not included because to do so would include two or more molecules within the library representing the same structural diversity. Therefore, the neighborhood principle is used as a sampling rule to insure that molecules representative of the same diversity or otherwise too similar are not included in the library. The resulting combinatorial screening library is not redundant and has not oversampled the diversity space.

In the present invention, the Tanimoto 2D whole molecule similarity coefficient is used for the final product selection. As was seen above, this metric possesses the neighborhood property. Accordingly, from the combinatorial products either a first product is arbitrarily chosen for inclusion in the library or an initial seed of one or more products may be specified. (If an arbitrary product molecule is chosen, Tanimoto coefficients are calculated for all other molecules to the first molecule and a second molecule with the smallest Tanimoto coefficient [greatest distance—least similarity] from the first is chosen for inclusion.) For the efficient selection of additional molecules to be included, the distance (1—Tan. Coeff.) between each additional molecule and all molecules already included in the library is calculated. For each additional molecule, the distance to the closest molecule already in the library is identified. These closest distances for each additional molecule are compared, and the additional molecule whose closest distance is the greatest is selected next for inclusion; that is, the molecule which is farthest away from the closest molecule in the library is selected. A new set of distances is calculated and the process continued, selecting one molecule at a time, until no more molecules remain which are farther away than 0.15 ([1–0.85] the definition of a Tanimoto "distance" using the neighborhood value of 0.85). While this example is presented in terms of the Tanimoto similarity coefficient, any validated whole molecule metric and its neighborhood definition may be used with this sampling procedure.

As noted earlier, the value of 0.85 for the Tanimoto neighborhood definition originally appeared in the sigmoid plots. To confirm whether this is the correct neighborhood definition for the Tanimoto metric, the Patterson plots for the whole molecule Tanimoto in which the $X^2$ indicated significance were used to calculate the neighborhood value. The metric distances corresponding to 2-log and 3-log biological differences were determined by dividing the slope of the density determined line by the values 2 and 3 respectively. Over the data sets, the average metric distance for a 2 log biological difference was 0.14 and the average metric distance for a 3-log biological difference was 0.21. Since the Tanimoto distance of (1—Tan. Coeff.) is plotted in the Patterson plot, these values correspond to a 2-log similarity of 0.86 and a 3-log similarity of 0.79. This confirms the reasonableness of using 0.85 in the sampling process. Also, as discussed earlier, it is reasonable to have more confidence in the definition of the neighborhood derived from the Patterson plots which utilize all the molecular data. As noted with reference to selection of a neighborhood distance using the topomeric CoMFA metric on reactants, there may be a situation where a different biological activity may be appropriate and a correspondingly different neighborhood distance used for product selection.

Figure 13:
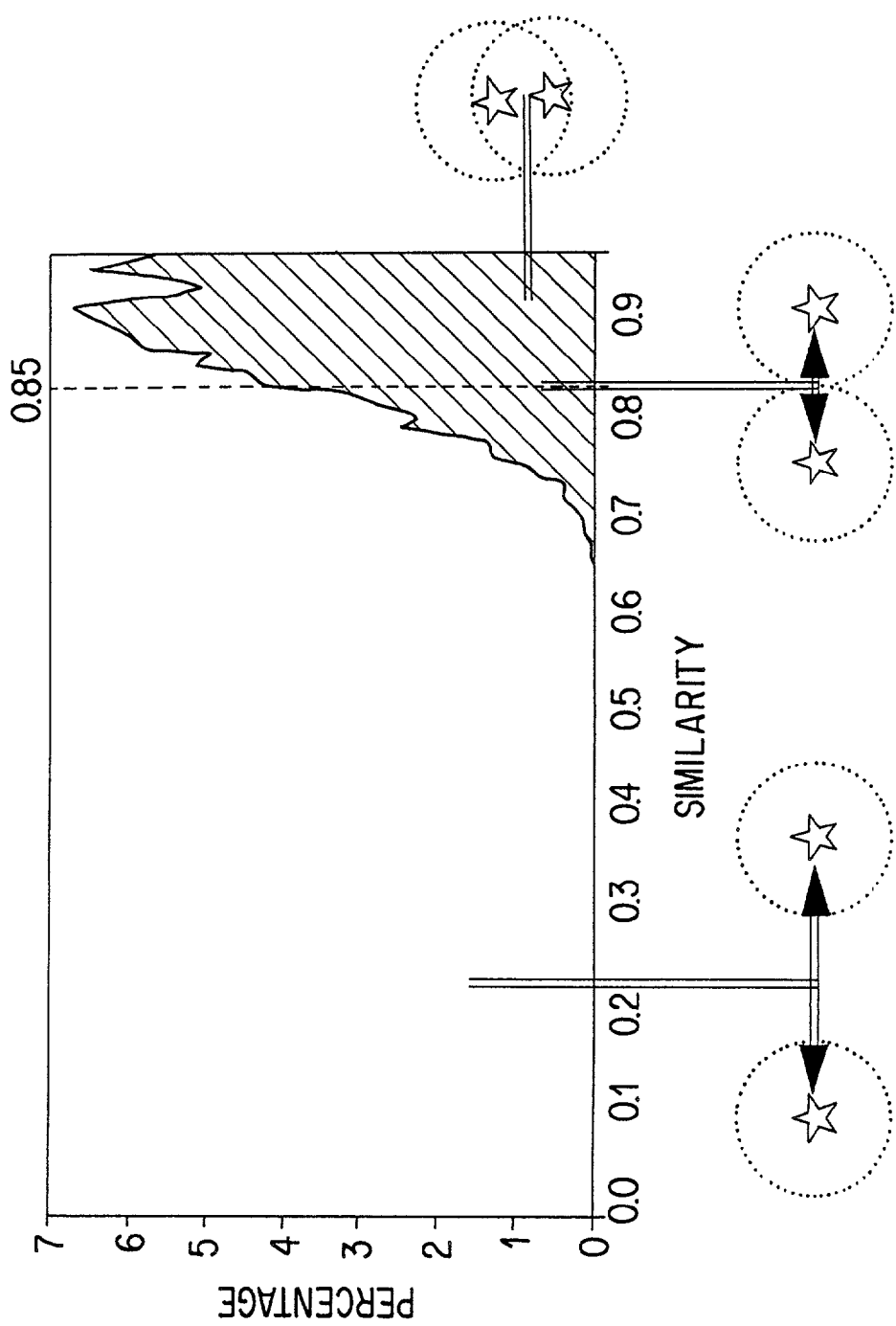
FIG. 13 shows a plot of the Tanimoto 2D pairwise similarities for a typical combinatorial product universe.

Conceptually this selection process is reflected in FIG. 13. FIG. 13 shows a plot of the Tanimoto 2D pairwise similarities for a typical combinatorial product universe in which there has been some selection of reactants based on diversity. As can be seen, a very large percentage of the products have similar structures (Tanimoto coefficients >0.85). The sampling process outlined above results in the following. Molecules having pairwise similarities above approximately 0.85 have overlapping neighborhood radii as shown at 1 and one of each pair is excluded from the library. Molecules having pairwise similarities of approximately 0.85 have almost touching but not overlapping neighborhood radii as shown at 2 and are included in the library. Molecules having pairwise similarities significantly less than approximately 0.85 have no overlapping neighborhood radii as shown at 3 and are also included in the library. Excluding molecules with a Tanimoto similarity greater than 0.85 will eliminate a significant number of molecules in this representative product assembly. This reduction is also reflected in matrix H. While the circles of similarity shown in FIG. 13 represent convenient conceptualizations of the neighborhood distance concept, it should be remembered that most metrics will not define a space in which the "distance" corresponds to an area or volume. In particular, a Tanimoto similarity space does not have this property, yet the "similarity" to a neighbor can be defined and is very useful.

Figure 14:
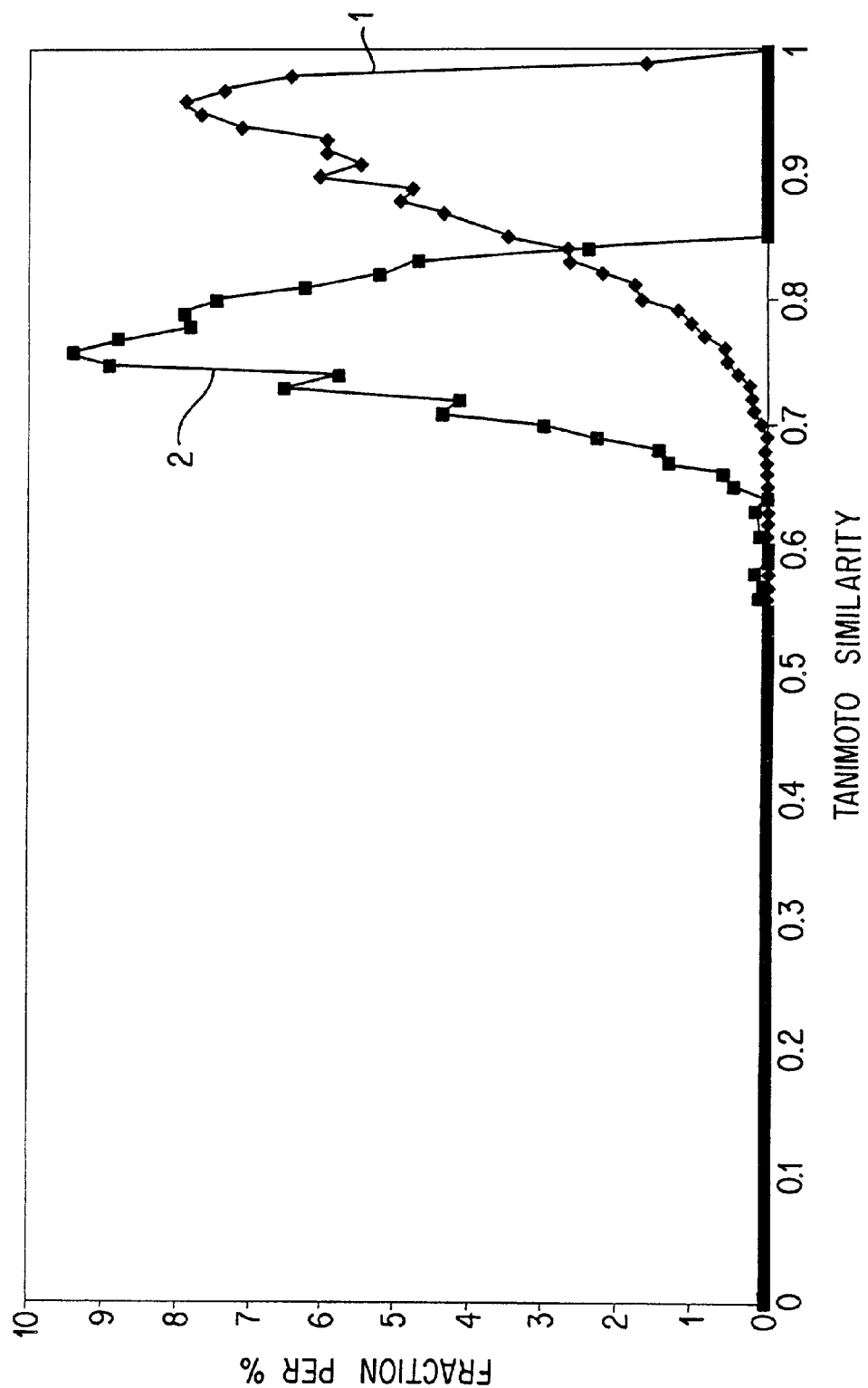
FIG. 14 shows the distribution of molecules resulting from a combinatorial screening library design plotted according to their Tanimoto 2D pairwise similarity after reactant filtering and after final product selection.

A specific example illustrates the dramatic power of the final selection stage in the design process. A proposed combinatorial screening library was designed using thiols and sulfonyl chlorides as reactants. (Many of the same thiols were considered in the study discussed earlier.) The original 716 thiols and 223 sulfonyl chlorides considered would make 159,668 potential products. Topomeric CoMFA analysis indicated that 170 thiols and 61 sulfonyl chloride reactants represented diverse molecules for the purposes of this design and should be used in further library design. 10,370 combinatorial products were now possible. Graph 1 of FIG. 14 shows the Tanimoto similarity distribution of the 10,370 possible products. It can be seen that a large percentage of the possible products were at least 0.85 similar to each other. Following the final stage selection process of the method of this invention, 1,656 product molecules were selected none of which was 0.85 similar to the other. Graph 2 of FIG. 14 shows the plot of the Tanimoto similarities of the final library design products. (The Y axis of the graph is plotted in fraction per % so that the integrated totals are proportional to 10,370 and 1,656 respectively.) The remarkable selectivity of the sampling process is immediately apparent. The products of the designed library have a clearly different similarity profile than the non-selected products. In addition, there has been a greater than 6:1 reduction in the number of product compounds. Thus, from a possible universe of 159,668 potential combinatorial products, 1,656 have been identified which represent the structural diversity of the large ensemble. An approximate 100:1 reduction has been achieved without sacrificing the diversity of the combinatorially accessible universe. As a result of the library design, only the 1,656 compounds have to be synthesized. In addition, these same 1,656 compounds can be tested in any number of biological assays with a high degree of assurance that even in assays with unknown biological activity requirements, these compounds will present the diversity of compounds accessible through this combinatorial universe to the biological assays. Thus there is not only a savings in time and expense in the synthesis and testing of the identified molecules in the library, but it is not necessary to change library design (with concomitant time and expense) each time it is desired to screen a different biological assay. Over time, using the library design of this invention and the process for merging libraries discussed below, it will be possible to build up an optimally diverse combinatorial screening library based on many different combinatorially accessible universes, and this combined library will represent the first real general purpose screening library available to the art—a realization of a long sought after, and previously believed unattainable, goal.

Clearly, other validated whole molecule metrics and their associated neighborhood distances can be used with the sampling process described above to select product molecules for inclusion in a screening library. However, it makes no sense to use the same metric for the products as was used for the reactants. For instance, in the case of the topomeric CoMFA metric, no information would be gained if the metric was used again with the products since all the steric information from the reactants has been transferred to the products. What is critical is that the combinatorial screening library should be constructed by including product molecules which do not fall within the neighborhood radius of other molecules and excluding product molecules which fall within the neighborhood radius of previously chosen molecules. At the end of the design process of this invention, a list of product structures and the reactant sources for each is available in the computer and can be output either in electronically readable or visually discernable form. This data defines the combinatorial screening library. The list of reactants is supplied to synthetic organic chemists. Actual synthesized molecules are then available for testing in the biological assays, typically on multiple well plates. The list of products from each library design can be used to create a definition of a larger combinatorial screening library when merged with other such libraries as discussed below.

The combinatorial screening library designed by the method of this invention is both locally diverse (no two reactants representing the same steric space are present) and globally diverse (no two products having overall similar structures are present). Such a library thus meets the desired combinatorial screening library criteria of being representative of the diversity of the entire combinatorially accessible chemistry universe while at the same time not containing more than one sample of each diversity present (no oversampling). An optimally diverse combinatorial screening library has thus been achieved. By designing an optimally diverse screening library, a reduction in the number of combinatorially generated structures which need to be synthesized and tested of substantially greater than $10^2$–$10^3$ should be possible.

9. Lead Compound Optimization

Unless an entire combinatorially accessible chemical universe is screened, a lead molecule found from screening a library will rarely be the most active or the optimal molecule desired. Therefore, extensive additional work is usually required searching for a related compound possessing the greatest activity or some combination of activity and another desirable feature such as bioavailability. Most of the time, the design of the screening library from which the compound was identified provides little, if any, help in this search. Again, medicinal chemists must resort to traditional methods of lead development. Combinatorial screening libraries based on the methods of this invention provide the means for a directed search of the chemistry space in a way not possible with prior art libraries.

This feature results directly from the fact that the libraries are constructed at each level by selecting molecules which are representative samples of particular molecular diversities. Thus, once a lead is identified, it is a straightforward matter to identify and test compounds representative of the same and/or closely related diversity; ie., it is known how to identify molecules within the neighborhood of the active lead, as defined by the validated metrics used to construct the screening library. Furthermore, the synthetic chemical methods used to construct the screening library are already known and tested and can be used to synthesize additional molecules of the same or similar molecular structural diversity. Since time is always of the essence, especially in exploring a newly discovered biological target, a rational follow up search through an optimally designed library of this invention permits homing in on crucial molecular structures directly and quickly. Not only does this procedure speed up the development process, but it also avoids wasting the time and effort synthesizing and analyzing large numbers of compounds not in the neighborhood of the lead compound which would be erroneously tried prior to knowledge of this invention.

Because the libraries of this invention have been constructed using two selection steps based on molecular structural differences, each step provides an opportunity to identify and explore compounds having similar structural features.

A. Advantages Resulting from Product Filter

Due to the way the final product molecules were selected for inclusion in the library, all compounds with a Tanimoto similarity of approximately 0.85 or greater to a compound already in the library were excluded. Therefore, the first place to look for compounds likely to have the same activity as the lead compound is in the group of all compounds in the combinatorial universe from which the lead was identified having a Tanimoto coefficient with respect to the lead compound of approximately 0.85 or greater. Then, since each of these initial compounds will also have an associated group of different compounds within approximately 0.85 Tanimoto similarity of themselves, this larger group forms the second layer of what can be an expanding area of similar compounds to investigate. How far outwards from the lead compound the search is carried (each time searching within a Tanimoto coefficient of approximately 0.85) will be determined by the success of these additional compounds showing activity in the same assay as the lead compound. Thus, the library design itself identifies and permits a directed search for compounds from the utilized combinatorial universe most likely to have activity similar to the lead compound. The same procedure is followed if another valid metric, not the Tanimoto similarity) was used to create the library. Then all compounds within the neighborhood distance to a compound already in the library were excluded and the first place to look would be for compounds which fall within the neighborhood distance. The process is exactly identical to that followed using the Tanimoto descriptor.

B. Advantages Resulting From Reactant Filter

Two consequences flow from the selection of only one reactant from each cluster. First, combinatorial products containing that reactant may or may not be the most active with respect to any particular given biological screening test. There is no way to guarantee that the reactant that yields the most active product will be selected from the cluster. For any reasonably sized cluster, the probabilities of finding the reactant that yields the most active product would not be greatly increased even if two reactants from that cluster were chosen, and, the size of the library to be tested would have been doubled.

However, the second consequence of selecting only one reactant from each cluster presents the flip side of the selection coin. Once a lead compound is identified, the library design immediately indicates from which diverse clusters the reactant molecules were chosen. All the other possible reactants (in the combinatorial chemical universe under study) representing similar aspects of diversity are included in the clusters from which the reactants were chosen. For lead optimization, compounds containing the other reactants from the identified cluster(s) can be synthesized and tested. The library design itself assures that the exploration of these reactants is likely to yield compounds with similar activity to the lead compound. Thus the reactant selection process not only reduces the number of molecules that need to be screened, but simultaneously identifies the molecular structures which should be subsequently explored to find the compound with the highest activity similar to the identified lead. No other prior art library design process provides so much information for lead optimization.

C. Additional Optimization Methods Using Validated Metrics

The knowledge that a metric is valid, and what that implies for the metric space as discussed earlier, immediately enables methods for lead optimization not previously possible. In particular, knowing that a metric will define a design space where compounds with similar biological properties are found measurably near each other (the definition of a valid metric), now permits for the first time the quantitative examination of the array of molecules used in any screening assay to determine whether any molecules are measurably close to the identified lead compound. One aspect of this approach has already been discussed in sections 9.A and 9.B and certainly works best with an optimal library designed by the method of this invention. In addition, however, validated metrics will permit useful examination of any assemblage of compounds whether or not the lead compound is identified from within the assemblage. There is no restriction on the source of the additional compounds to be examined and they may range from prior art screening libraries to chemical databases. Once a lead is identified, a validated metric would be used to map the lead and all other compounds in the assemblage to be examined into the metric space; ie, the metric characteristics/values are determined for all possible compounds. For reactants (possible substituents) a metric validated on reactants would be used. For whole molecules, a metric validated on whole molecules would be used. Metric differences between the lead molecule and all the other molecules would then be calculated. All molecules with metric distances to the lead within the neighborhood distance of the validated metric should have similar biological activities. Again, if the metric distances from each molecule thus identified as falling within the neighborhood distance of the lead are then calculated with respect to all other molecules (excluding the lead and each other), a second layer of molecules is identified which should have activity similar to the active neighbors of the lead molecule. Additional layers may be similarly identified and explored experimentally. Depending on the structures involved, at least two layers would normally be explored. Thus, because validated metrics are now available, lead optimization will much less often be the hit or miss procedure characteristic of the prior art.

An extension of this procedure yields yet another major advance. In the prior art it was not possible to tell how far away from the lead (in structural terms) one should explore in the search for a compound more active than the lead. In terms of the two dimensional activity island analogy of FIG. 1, no procedure existed for exploring the shape or extent of the island of activity. Without knowledge of the island's shape and extent, not only was it impossible to know by how far a compound missed the island, but even when an active compound was found, it was also not possible to know if the island had been sufficiently explored; that is, whether all compounds representing the range of diversity spanned by the activity island had been identified. In other words, had everyplace been explored that should have been?

With the molecules identified by the expansion procedure outlined above, it will now be possible to map the island. Starting with molecules within the neighborhood distance of the lead, molecules would be synthesized and tested for activity. If all the molecules within the neighborhood distance ("nearest neighbors") show activity, each still falls within the boundary of the island, and the next layer of molecules in the neighborhood distance expansion would be synthesized and tested. If only some of the nearest neighbor molecules show activity, the neighborhood radius of the lead must span an edge of the activity island, and only molecules falling within the neighborhood distance of these nearest neighbor active molecules would be included in the next layer of the expansion and synthesized and tested. Again, some of the newly tested molecules may show activity and some may not. This process of nearest neighbor molecule identification and testing should be repeated until no molecule in the next expansion layer shows any activity. The active molecules determined by this procedure will define the limits and shape of the activity island in terms of structural differences.

The resolution obtainable with this procedure depends upon how well the structural diversity of the activity island is represented by the molecules in the original assemblage. That is, if only a portion of the activity island structural diversity is represented in the assemblage of molecules, that is the only part of the island which can be explored. Alternatively, perhaps only the island's rough outline can be perceived. Within the constraints of the diversity present in the assemblage, exploration of the full extent of the island and of the space within its boundaries can be accomplished with the guidance of the validated metric with which the island is mapped. To explore the island further it is only necessary to identify molecular structures not included within the original assemblage with which to test the unknown territory. In some cases in order to distinguish particular structural differences, it may be necessary to consider additional sources of structurally diverse molecules and, perhaps, to map the lead and additional compounds in more than one metric space. Thus, possible structures can be proposed and examined with the validated metric. If the proposed structures fall within the neighborhood distance of an active molecule, they can be experimentally tested. If those are active, further structures can be proposed and again examined to determine whether they fall within the neighborhood distance of the newly identified active molecule. If they do, they would be experimentally tested. Repeating this cycle of identification and testing will ultimately yield a higher resolution map of the island and assure the searcher that the island has been thoroughly explored and no activity peak has been missed.

The availability of validated metrics enables yet another method of rationally directed lead optimization from a knowledge of the structure of a lead molecule which was not identified from screening an optimally diverse combinatorial screening library. Essentially, the reactant screening process is utilized backwards to identify similar molecular structures, and then the product screening process is utilized to confirm structural similarity of proposed products to the lead. Two cases are important. The first involves lead molecules which can be synthesized directly from reactants. In this method, the lead molecule would be analyzed to determine from what constituent reactants it may be synthesized. These reactants would then be characterized using a reactant metric such as topomeric CoMFA. Molecules in databases of potential reactants would be characterized using the reactant metric and searched for reactants falling within the neighborhood radius of each of the original reactants. The identified reactants will provide a basis for building proposed products having the same structural characteristics (diversity) as the original lead compound. However, before the product is synthesized, its similarity in metric space to the lead would be checked using a product appropriate metric to make sure that it falls within the neighborhood radius of the lead.

The second case involves lead compounds in which substituent groups are bonded to a central or core molecule. The reactants which form the basis of the substituents as well as the core molecule would then be characterized using appropriate validated metrics. Again, molecules in databases of possible reactants and core molecules would be characterized with validated metrics and searched for molecules falling within the neighborhood radius of each of the original reactants and core. The molecules thus identified would provide a basis for building proposed products with structural diversity similar to the lead compound. Again, before synthesis, the proposed products would be evaluated with an appropriate metric to confirm that they fall within the neighborhood distance of the lead compound.

Since it is known that molecules resulting from different chemistries and involving different constituents often show activity in the same biological assay, it would be desirable to search as wide a range of molecules as possible when performing the searches outlined above to identify additional molecules that are within the neighborhood distance of some lead compound. Clearly, when contemplating these procedures, it must be recognized that the universe of all accessible chemical substances, even under the constraints of molecular weight that characterize a useful drug, numbers trillions of structures. While such unprecedented directed searches are only now possible with validated metrics, until the discovery and creation of the virtual library discussed later, even with today's powerful computers, the practicality of such large searches depended on preorganizing the trillions of candidate structures in such a way that the vast majority of candidates could be excluded, to the greatest extent possible, at the start of the search.

For instance, one such useful preorganization involves dividing the candidates into series of molecules accessible by some common synthetic route, and thus describable in terms of a core and reactants. (Typically, the synthetic route used to create the lead would be the first investigated and other sets of alternative routes explored secondarily.) A combinatorial SYBYL Line Notation (cSLN) affords a useful description of such a series of molecules.

Molecules represented by a cSLN would be considered for overall similarity to an active lead molecule in the manner discussed above. Using validated metrics, it is most efficient to: 1) first identify each of the individual lists of reactants within the cSLN with the most similar side chain within the active lead; 2) next, to consider the similarity of the "core" within the lead (the atoms remaining after the side chains are identified) to the non-variant core within the cSLN; and 3) then, if the "core" similarity is not so low that this series of molecules can immediately be excluded, to order the variation lists by similarity to the corresponding side chains within the lead. The advantage of such a partitioning and preordering by similarity is the ability to break off the search as soon as no remaining member of the series would be likely to be sufficiently similar.

As an overly simplistic example, consider the series of sixteen possible dihalogenated methanes which may be represented by a cSLN as: X2CH2X1{X1:F|C1|Br|I}\{X2:F|C1|Br|I}.) If bromobenzene were the "active lead" and the dihalomethanes were the series to be considered, an appropriate metric that indicated the lack of similarity of the aromatic core of bromobenzene to the methylene core of the dihalomethanes would immediately eliminate all dihalomethanes without considering each of the sixteen individual possibilities. However, if ethyl bromide were the "active lead", an appropriate metric might show that the methylene and ethylene moieties were sufficiently similar to warrant consideration of the individual methylene dihalides, and preordering of the variation list might immediately lead to dibromomethane as the most similar dihalomethane to ethyl bromide (the first bromine atom being identical to the ethyl bromide bromine, and the second bromine atom probably being the most similar to the $CH_3$ of the ethyl bromide). In this hypothetical example only one molecule instead of sixteen would need to be considered in identifying similar molecules most likely to lie within the same neighborhood as the lead. Within actual cSLNs (each possibly representing perhaps millions of structures by including more points of variation and many more and larger variations at each point), the speed enhancement obtainable from this searching strategy would be many orders of magnitude greater than sixteen.

There may be other variations of the applications of the methods outlined above which are not yet recognized at the present time since the concepts and applications of this invention are still so new. However, reasonable extrapolations/techniques of molecular discovery which follow from the disclosure of the present invention and, in particular, from the ability to validate metrics, are considered within the teaching of this application.

10. Merging Libraries

The final selection (sampling) methodology of this invention has broader uses than yet described. So far, this disclosure has been primarily concerned with the design of a combinatorial screening library based upon either sets of reactants or sets of reactants and central cores. Each combinatorial screening library based on these materials only explores the diversity of that part of the chemical universe accessible with those compounds. Unless as much of the diversity of the entire combinatorially accessible chemical universe is explored in a screening library as is possible, there is no assurance that a molecule possessing activity with respect to any particular unknown biological assay will be found. Clearly, the useful diversity of the combinatorially accessible chemical universe can only be explored with as many sets of reactants attached to as many cores as is possible. Stated slightly differently, there may be large parts of the diversity of the chemical universe not explored by one or even a few combinatorial schemes. Thus, combinatorial screening libraries based on multiple reactants and multiple cores would be desirable. Just such libraries can now be created through the use of the virtual library discussed later. However, even with screening libraries constructed with the method of this invention discussed above, the simple addition to each other of many such libraries will quickly increase the total number of molecules which need to be screened. Worse yet, since many of the possible reactants used for combinatorial synthesis with different cores have similar structures, and since many of the possible cores used for combinatorial synthesis may differ little from each other, it is highly likely that much of the same diversity is represented to a greater or lesser extent in each of the libraries generated from these materials. Simply combining the libraries would again result in oversampling of the same diversity space. It would clearly be more useful and economical (efficient) in terms of time, money, and opportunity to use additional screening to explore different aspects of the diversity of the chemical universe.

Another significant feature of this invention is the recognition that the neighborhood selection (sampling) criteria also provides a method to combine combinatorial screening libraries to avoid this oversampling problem. Starting with an arbitrary first library, using a validated metric which can be applied to whole molecules, each molecule of a second library is added to the first library if the molecule does not fall within the neighborhood radius of any molecule in the first library as supplemented by all the added molecules from the second library. This process is continued until all the molecules in the second library have been examined. In this manner, only molecules representative of a different aspect of diversity are added from the second library to the first. Each successive library is added in the same manner.

The molecules in a final combined library formed from smaller libraries selected according to the method of this invention represent diverse molecular compounds and have the optimal diversity which is desired of a general combinatorial screening library. However, even if the groups of molecules to be merged have not been selected by the methods of this invention, they may be merged according to the above procedure if first, a subset of each group of molecules is selected according to the product sampling method of the design process. This will insure that similar molecules within each group are eliminated. The resulting merged library will not be optimally diverse, but it should not redundantly sample the diversity present in the separate groups.

Figure 15:
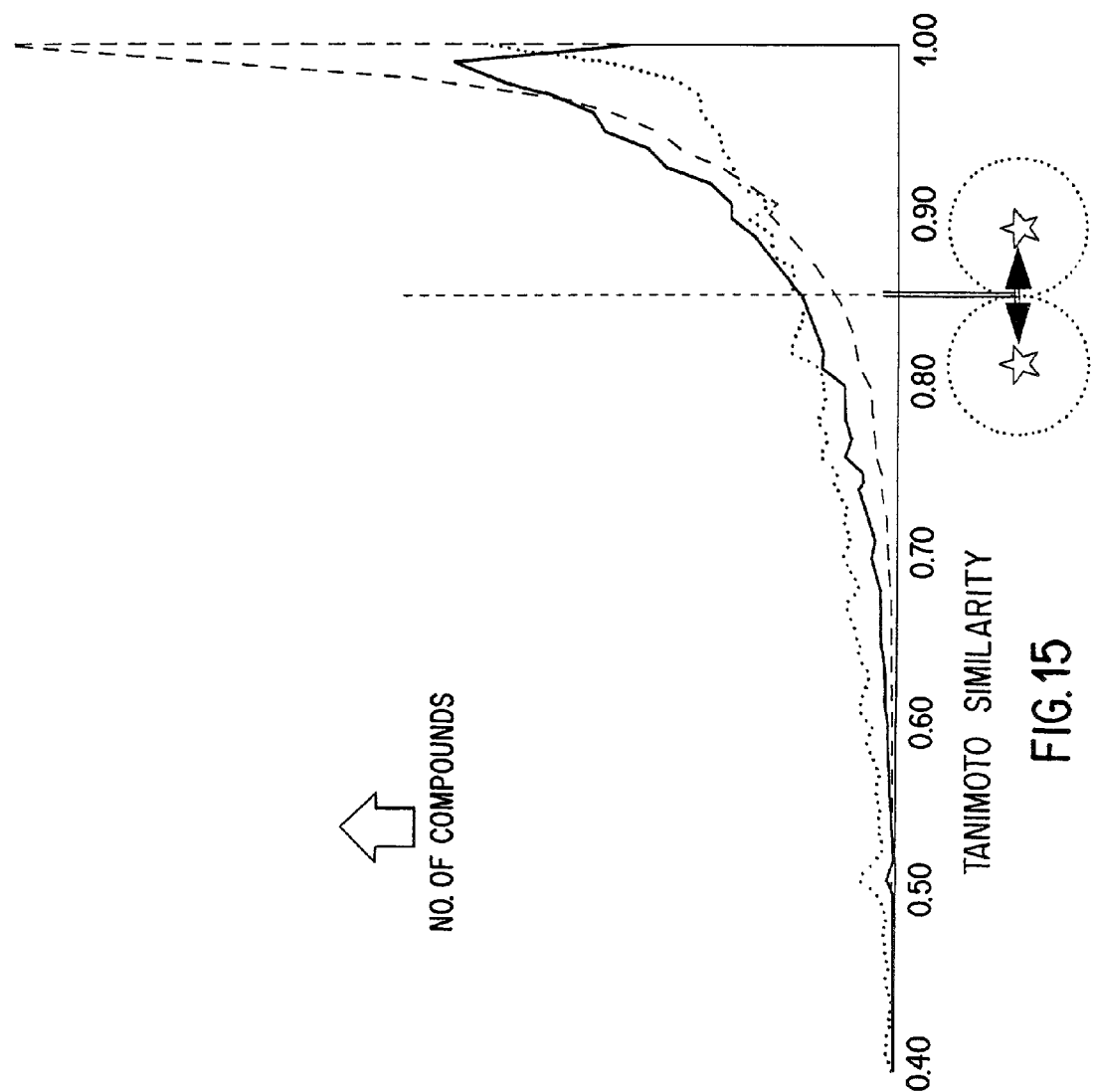
FIG. 15 shows the distribution of molecules plotted according to their Tanimoto 2D pairwise similarity of three database libraries (Chapman & Hall) from the prior art.

The 2D Tanimoto fingerprint metric is useful in performing the library additions. The 2D Tanimoto similarity coefficient of each molecule in the first library to all molecules in a subsequent library are calculated. Each molecule of the second library is added to the first library if the molecule does not fall within a 0.85 Tanimoto coefficient (the neighborhood radius) of any molecule in the first library as supplemented by all the added molecules from the second library. As long as the metric used for sampling and endpoint determination is valid (has the neighborhood property), this selection method guarantees a combined library in which all of the accessible diversity space is represented with little likelihood of oversampling. An example of three prior art libraries not designed with the method of this invention which might be merged using the neighborhood sampling criteria is shown in FIG. 15. FIG. 15 shows the distribution of molecules plotted according to their Tanimoto 2D pairwise similarity of the Chapman & Hall Dictionary of Natural Products, Dictionary of Pharmacological Agents, and Dictionary of Organic Compounds (CD ROM Versions). It is immediately clear from FIG. 15 that simply adding the three libraries together would produce a combined library in which most of the compounds would be very similar to each other (Tanimoto similarities >0.85). Further redundant similarity would be expected from a comparison of the similarities between the molecules in the three libraries! The position of the 0.85 similarity point to the bulk of the molecules in each library indicates that, most of the molecules in these databases would be excluded from a combined library formed by merging the databases by the procedure outline above.

11. Other Advantages of Optimally Diverse Libraries

There are additional benefits achieved by designing combinatorial libraries according to the method of this invention. For instance, as noted earlier, one of the difficulties of screening several compounds simultaneously is the possibility of non-specific activity being detected due to the contributory effect of the combination of compounds. In fact, the likelihood of this effect is increased when compounds of the same molecular structural and chemical diversity are tested in the same assay. With the libraries of this invention, it will be possible to design the assay combinations so that only compounds representing different aspects of diversity are tested together. While this procedure can not guarantee that no combination effects will occur, it makes it much less likely. Another benefit achieved is that complex deconvolutions will generally be unnecessary. Deconvolution problems are accepted in the prior art as a necessary evil due to the enormous number of molecules which must be synthesized and screened since virtually all combinatorial possibilities are included in the libraries. Clearly, with smaller optimally diverse combinatorial screening libraries covering the same search territory as the larger prior art libraries, it is possible with the aid of computer controlled robots and data bases to individually synthesize and track each compound.

As mentioned at the beginning of this disclosure, the methods of this invention are also applicable to problems outside the specific area of drug research. The notion of choosing compounds based on diversity is a general concept with many applications and is applicable any time the problem is presented of having more compounds than can usefully be tested/used. The example was given earlier of determining what compounds had the same structural diversity as a previously identified (biologically active) compound. Of course, with the methods of this invention, the activity may be any chemical activity. In addition, the universe of chemicals from which only some are to be selected does not have to result from a combinatorial synthesis, but may result from any synthesis or no synthesis at all. An example of the later would be the solution to the question of selecting molecules of similar diversity from among those in a large corporate or catalog data base. In these cases, an appropriate metric (remembering that different metrics are applicable in different circumstances) would be applied to all the compounds and clustering would result in compounds of the same diversity. The methods of this invention, including metric validation, topomeric CoMFA metric characterization, end-point neighborhood sampling, lead compound optimization, and library design can all be applied separately and together to solve the selection problem.

12. Virtual Library Construction & Searching

The two step sequential design process for selecting optimally diverse product molecule libraries set out so far in this application is necessarily computationally time consuming, limited to consideration of one set of synthetic reactions at a time, and eliminates at the first stage reactants which might be capable of generating products which would pass the product stage neighborhood filtering criteria. The process is computationally time consuming since, for any given set of reactants, the steric metric must first be computed, the resulting descriptors clustered, and a selection of reactants made based on the neighborhood rule. Only after this first stage can the possible product molecules be determined, a second product metric calculated, and selection made of the final library members.

The process is limited to one set of synthetic reactions at a time in the following sense. First, a particular organic chemical reaction scheme is identified as well as the core and possible reactants which may be used in the scheme. Each sequential step of library design is sequentially implemented and results in an optimally diverse library for that reaction. For a slightly different core which involves the same chemical reaction scheme and the same reactants, the entire process including all calculations must be repeated. Each combination of core and reactants generates a different library. In the method of the above referenced patent application, the resulting libraries, individually derived, are then combined. This process also adds additional time to the assemblage of a larger optimally diverse library. Finally, the product stage of the design is constrained by the reactant stage; that is, since it is desirable to generate as many diverse products as possible, some products may be sufficiently diverse (as confirmed by the product neighborhood metric) when created from similar reactants (those failing within a topomeric neighborhood cluster) by virtue of the mere combination of the reactants into the products, and such products should be included in the library.

In addition, consideration of the above techniques of optimally diverse library design, lead optimization, and merging libraries all point to the distinct advantages of being able to explore the diversity of combinatorially accessible chemical universes using/including as many reactions, core, and reactants as possible. Thus, it was recognized that, ideally, library design and lead optimization would be most useful if all combinatorially accessible molecules could be meaningfully searched. The sheer number of molecules involved (trillions) would seem to suggest that even with today's fastest computers, such a library design and searching would be unachievable. However, using the power and utility of validated metrics, a way to create and search a data base containing representations of products from as many combinatorial reactions and reactants as desired (a huge combinatorially accessible universe) has been discovered. This data base is essentially a virtual library of combinatorial products because, as will be explained below, all information necessary and sufficient to search across and construct all possible product molecules is contained within the virtual library even though the structure of each combinatorial product is not explicitly contained within the virtual library.

The virtual library can be used not only to select screening libraries, to find molecules with similar structures to a lead compound, to perform lead explosions, but, through the use of validated metrics, it can also be used to search for and select compounds likely to have similar biological or other physical properties from across the broader chemical universe. In fact, as will be seen below, use of the virtual library opens up possibilities for searching the accessible chemical universe in ways not heretofore possible.

With respect to the selection of screening libraries, it has been discovered that the same approach to design as previously described can be performed more efficiently and more exactly by combining the formerly separate steps of topomeric selection of reagents and Tanimoto selection of products into one step which operates on the entire set of all possible products from the reaction under consideration. Another advantage of this approach is that generally a larger group of diverse compounds are identified; that is: the significant (active) metric space is sampled more extensively. Additionally, the method by which the maximally diverse set is selected can be modified to yield results which more readily suit the practical issues of laboratory synthesis. As a consequence of this discovery, an efficient method for identifying molecules of interest from the billions of possible products obtainable from combinatorial syntheses has been discovered. Indeed, use of the virtual library is not limited to finding molecules derivable from known synthetic combinatorial reactions, but is generally applicable to molecular selection. As with the selection methodology discussed above, the ability to create and search the virtual library relies upon the power of the neighborhood property of validated metrics to distinguish the similarity or dissimilarity of molecular properties between molecules.

The creation of a virtual library using validated molecular descriptors enables methods to identify compounds of interest from many possible compounds and is particularly applicable to identifying compounds of interest from extraordinarily large numbers of compounds. The application of these novel methods speeds the searching operation and in some ways extends the types of searching criteria which may be used. Most importantly, construction of a virtual library makes it possible to identify compounds of interest by an exhaustive search through all possible compounds from a series of known synthetic reactions—thus providing a capability which does not currently exist otherwise. In particular, the virtual library provides a large number and variety of ways to select a subset of compounds from a very large number of compounds. The number of compounds from which to make the selection is likely to range in the trillions of compounds, based only on known synthetic reactions and commercially available reagents appropriate for each reaction.

The following disclosure of the method of constructing and searching a virtual library will be discussed with respect to those compounds accessible through combinatorial syntheses. However, as noted above, the virtual library is not limited to such combinatorial compound universes and these universes are disclosed by way of an example of the methodology of the discovery, not a limitation thereof.

The significant aspect of being able to create a virtual library using validated metrics is the ability to identify from the large universe of compounds those with related properties and/or structural characteristics without having to examine individual structures; in other words, to do structural searches without directly comparing (looking at) structures. This is made possible by precalculating, as much as possible, characteristics for the component parts of the product structures. Clearly, then, the beginning point for this method is the construction of a database, or "virtual library", of possible chemical compounds, products, which can be synthesized from a common reaction.

A. Derivation of the Database (Virtual Library) of Compounds

The database of compounds, "virtual library", to which the method of this invention may be applied is an assembly of the combinatorially derived product structures resulting from any number of synthetic reactions. In initial applications tens of reactions are used to construct the database (virtual library) of interest. The total number of possible product compounds becomes astronomically large very quickly. For instance, there are approximately 500 commercially available molecules having reactive diamino groups and approximately 15,000 commercially available reactants which will react independently with each of the amino groups. Combinatorially there can therefore be generated 15,000×15,000×500 (112 billion) possible product molecules from this one reaction scheme alone.

B. Overview of Methodology

A fundamental part of the discovery of how to create and use a virtual library is a method to precompute properties based on $1+N_1+N_2+N_3+\ldots N_M$ structural variations which can be used to exactly, or with useful degree of approximation, predict the $1 \times N_1 \times N_2 \times N_3 \times \ldots N_M$ product structure properties which arise from all combinations of the structural variations about the 1 core at all M substitution sites. In the earlier part of this disclosure, the variable parts of a combinatorially derived molecule were referred to either by reference to their source (reactants) or their molecular configuration when attached to the core (side chains). When discussing creation and searching of a virtual library, the more generic term "structural variations" is appropriate for the groups appended to a core. The reasons for adopting this term will become clear later during the discussion of searching the virtual library with respect to non-combinatorially derived structures.

Figure 16:
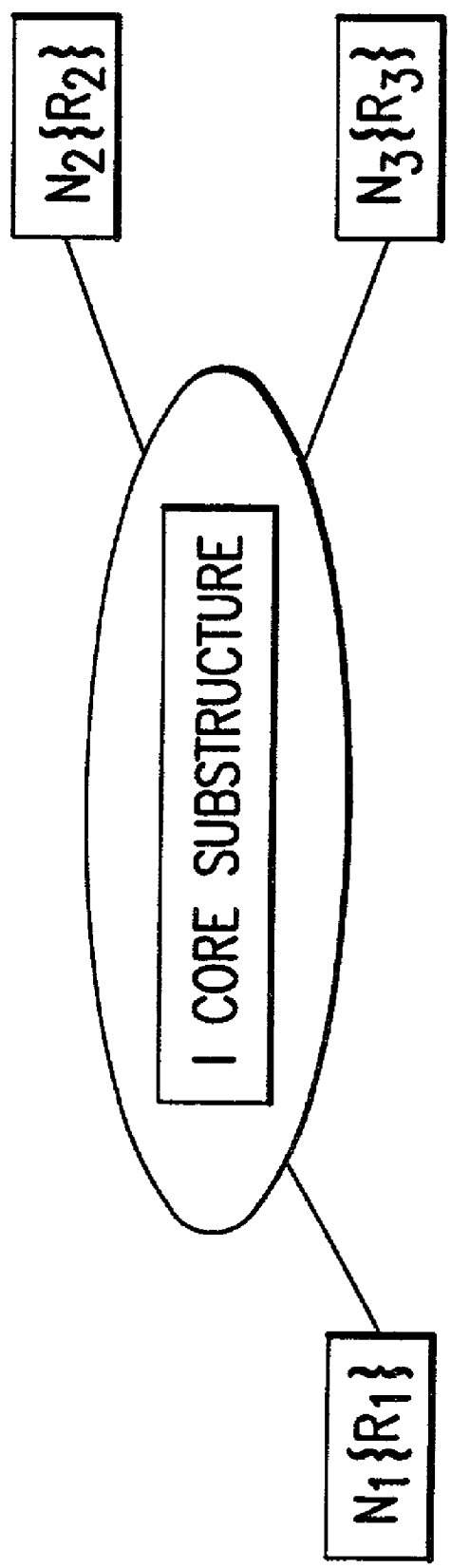
FIG. 16 shows a schematic representation of sets of possible reactants attached to a central core.

FIG. 16 shows in schematic form a representation of three structural variations attached to a central core. In FIG. 16, each possible product structure arises from combining the core substructure with exactly one of the $N_1$ choices in the set of structural variations $\{R_1\}$, exactly one of the $N_2$ structural variations in the set $\{R_2\}$, etc.

For many properties, such as molecular weight and price, or count of rotatable bonds, or number of H-bond donors and acceptors, the values associated with the product compound are exactly the sum of the appropriately created structural variations.

For some properties, such as logP, the assumption of additivity is inexact but adequate for the purpose of selecting a small subset from a very large number of possible products. For other properties, particularly the topomeric shape descriptor, the comparison of two product compounds' properties requires a decision on how to match each structural variations's descriptor in the first product to one structural variations's descriptor in the second product such that each structural variation is referenced exactly once.

There are also some properties (such as molecular fingerprints) which are representative of the whole combinatorial product molecule and can not be represented by the sum of the constituent structural variations. The method for deriving these properties will be discussed below. Generally, however, by this method a virtual library containing descriptions of the structures of all possible combinatorially generated products can be created from a knowledge of the properties of the structural variations.

C. Overview of Virtual Library Construction

Figure 17:
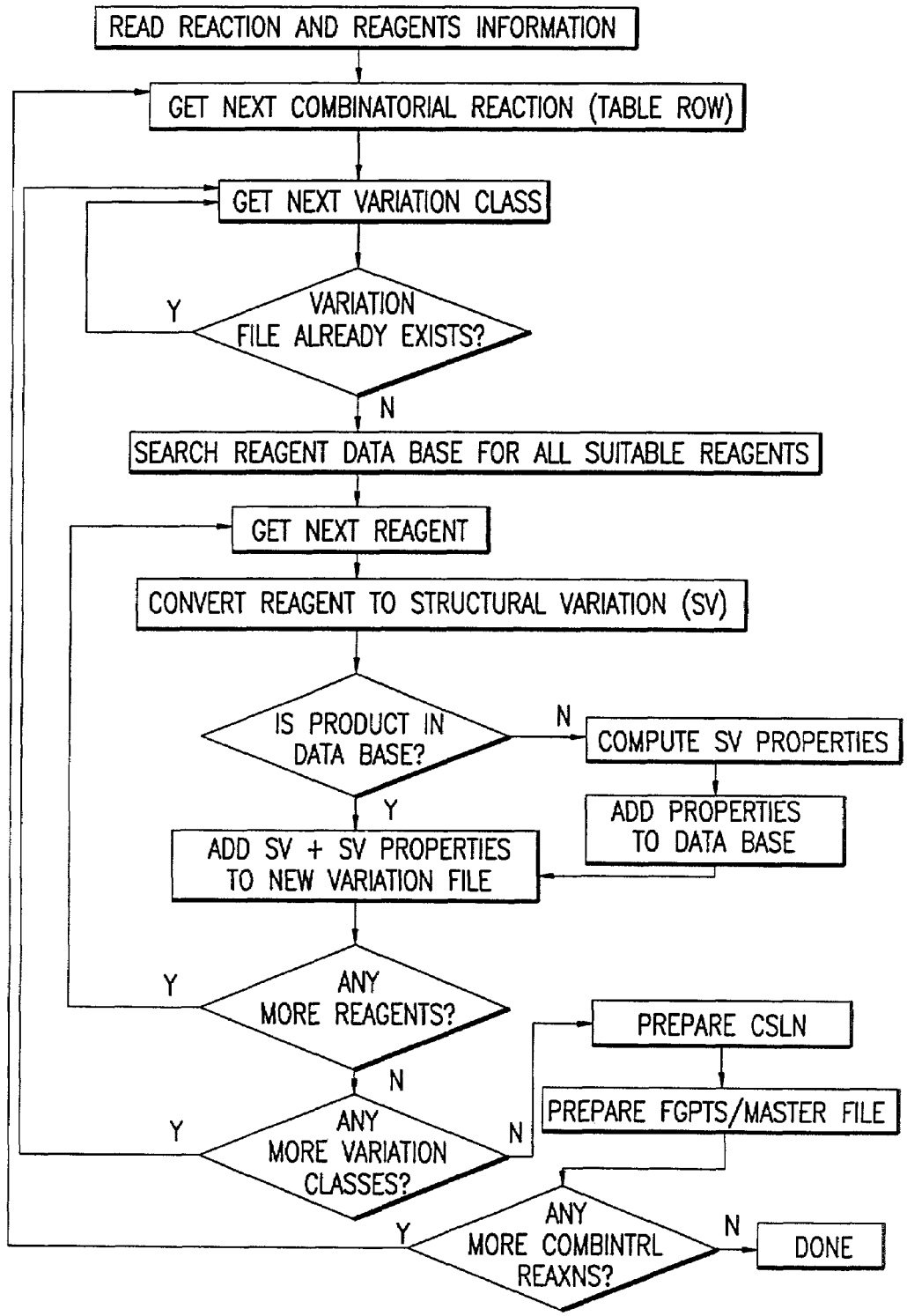
FIG. 17 is a flowchart summarizing the overall process of virtual library construction.

Initially information on the reactions to be included and the reagents which may be used with those reactions needs to be gathered and entered. In addition, the reagents need to be converted to their corresponding structural variations. The overall process of virtual library construction is summarized in the flowchart of FIG. 17. The first step in the creation of the virtual library is to create for each possible structural variation (variable part) a file containing various parameters/characteristics associated with that structural variation. Typically the file may contain information on the price, source, availability, MW, and logP. In addition, the metric characteristics for the structural variation resulting from the application of validated metrics to the structural variation structure are included in the file. Other characteristics which might be used for searching may be added to the file. Similar files are created for core structures. As with the earlier discussion of designing optimally diverse libraries, any validated metric may be chosen to characterize the structural variations or cores. For purposes of discussion of the virtual library, the same metrics, topomeric CoMFA and Tanimoto fingerprints, will be used as in the examples earlier.

The second step in creation of the virtual library is a description of the chemical transformation represented by the chosen chemistry. The virtual library is then created by combinatorially combining all structural variations in the chemical transformation to generate virtual library descriptions of all possible product molecules.

Substantial effort is required to produce the representation of the structural variations forming the database from a given reaction. The software provided as Appendix "E" and Appendix "F" to this application is used in conjunction with the commercial software products, Selector and Legion, to compute properties of the structural variations and to combine two or more such lists of structural variations along with a core structure to produce the representation of all possible products.

Particular skill is required to convert the chemist's description of reaction conditions and reaction validation into a set of selection criteria applied to a database of available reagents, by which only those reagents which are actually likely to yield the desired product in the specific reaction conditions are included. (Here "reagents" refers to chemical starting materials which undergo reaction to produce the products. A reagent corresponds to a molecule used in a structural variation in the method, after some rearrangement of bonds.) Additionally, methods for automating chemical judgment to derive the list of reagents and to compute the properties such as the topomeric shape descriptor have been developed. Finally, a key concept in constructing the virtual library is to organize the process of library definition so that it depends on a relatively small number of parameters which can be stored in a table so that each row in the table defines all the information that is necessary to specify a combinatorial library. While the following discussion addresses formation of the virtual library in terms of chemical transformations, cores, and reagents and/or structural variations which may be used, it should be appreciated that data in the virtual library may be generated by any cores and structural variations as long as the resulting compounds can be described by a cSLN. Thus, even product molecules which can not be synthesized by a known combinatorial reaction can be included in the virtual library and their structures searched.

D. Virtual Library Construction

The first phase of construction of a combinatorial library to be included in the virtual library takes as input a description of the chemical transformation represented by that combinatorial library and a list of available reagents and produces as output all the part structures (a/k/a structural variations) found in the list of available reagents which are appropriate for the chemical transformation, along with all structure-invariant physicochemical properties of those fragments that might be useful in different types of subclass (subset) searches. As is apparent from the earlier discussion, the same general and biologically based elimination criteria can be applied to the proposed structural variations before selection of the structural variations for inclusion in the virtual library. Alternatively, structural variations which would be eliminated by the general or biologically based criteria can be flagged but still included. Having the structural variations flagged, few potential product structures are eliminated from the virtual library, but the products containing particular types of undesirable structural variations can still be removed during selection.

In the course of this process, data are entered and recorded permanently into three tables:

REACTIONS (a Molecular Spreadsheet)=information about a reaction scheme. Each record corresponds to a reaction. A typical reaction would be: "reaction of each nitrogen of a diamine with various reagents such as acids (acylation) or ketones (reductive amnination)".

REAGENTS (a Molecular Spreadsheet)=information about a particular set of reagents used in some instance of a reaction. Each record corresponds to a particular logical reagent structure search in a database of such reagents, presumably a set of reagent structures which will all react in the same way. For example, there are sixteen reagent records for the diamine reaction, enumerating each of eight reactant classes that might react with each of the two nitrogens. One record for example describes a reaction with epoxides, that could be ring opened nucleophilically (and regioselectively) by an amine to yield a beta-amino alcohol.

RDATA (an Oracle Table)=invariant physicochemical data computed about structural variations, typically the varying portions in a CSLN, with one record for each structural variation encountered in any cSLN constructed. Thus data need not be recomputed when such structural variations are reencountered, a substantial savings in processing time. For example, records will be added describing the properties of a —CH2CH (OH)R chain (structural variation) for each (new) epoxide-R reagent retrieved by the example record just given for the REAGENTS spreadsheet.

Entering a new reaction into the system involves inputting the data for a new row to REACTIONS and at least two new rows to REAGENTS. This data entry operation is the only required data entry in preparation for virtual library production.

All these operations of table preparation are carried out by the SPL script getacd.core (Appendix E) and executed within the commercially available software product SYBYL. The code for producing the topomeric CoMFA field descriptor of each structural variation is provided as Appendix F, CTOPS.

i. Representation of the Database of Compounds

The virtual library database of compounds for any one synthetic reaction is represented as a set of chemically bonded (connected) structural variations where the connecting elements may consist of a common core (one or more atoms which are identified in all members of the set). More than two variable sites may be involved. The list of structural alternatives therefore contains two or more elements, each of which represents a specific molecular fragment and a number of associated molecular properties. Table 6 and Table 7 below are produced by getacd.core. For each combinatorial scheme a set of files is generated. For a di-substitution scheme the first file defines the combinatorial scheme, and the second and third files describe the structural variations which can be utilized at the two sites. For a tri-substituted scheme, there will be a set of four files: the first defining file, and three additional files describing the structural variations for each of the three sites. The number of files in each set of files is clearly determined by the combinatorial scheme involved.

In Table 6, the information following #@CORE describes the core, the information following #@CONNECTOR describes the location of attachment of each of the two varying sites, and the #@QUERY line shows an example of how the list of structural variations may be specified. Essentially this QUERY describes how to combinatorially construct product molecules out of the structural variations and is used after searching of the data base is complete to generate actual product structures.

TABLE 6

Sample cSLN File

SYBYL/3DB HITLIST
Created: Date Time
@CLASS STRLIST
@DATABASE NONE
@SOURCE VDB_BUILDER
@SUPPLIER
@PRICE
@FCD
@MW 85.062
@LOGP −1.05
@CORE X1C(=O)CH2NHC(=O)X2
@CONNECTOR 1,X1=2;11,X2=9
@QUERY
Y_01C(=O)CH2NHC(=O)Y_02{Y_02:FC(F)(F)C[5]:C:C(:CH:CH:CH:@5)C(F)(F)F<V
=6>}\
{Y_01:FC(F)(F)C[5]:CH:C(:CH:C(:CH:@5)OCH3)NH<V=19 >} ii. Application of A First Metric (Topomeric CoMFA)

Table 7 shows the format in which the structural variations for the first variable site are listed, including both the structure in Sybyl Line Notation (SLN) and a set of related properties such as SUPPLIER, PRICE, molecular weight MW, estimate of hydrophobicity LOGP, and a field, CTOPS, which in encoded form represents the novel shape descriptor, the topomeric field (the steric field of the topomeric conformation) for the corresponding structural variation. Information on only two possible structural variations is shown. For the diamino example above, this structural variation file would contain all of the structural variations which react with an amino group, approximately 15,000 entries.

A second file similar in appearance to that of Table 7 which lists all the structural variations which may occur at the second site is also created.

iii. Application of A Second Metric (Tanimoto Fingerprint)

Figure 18:
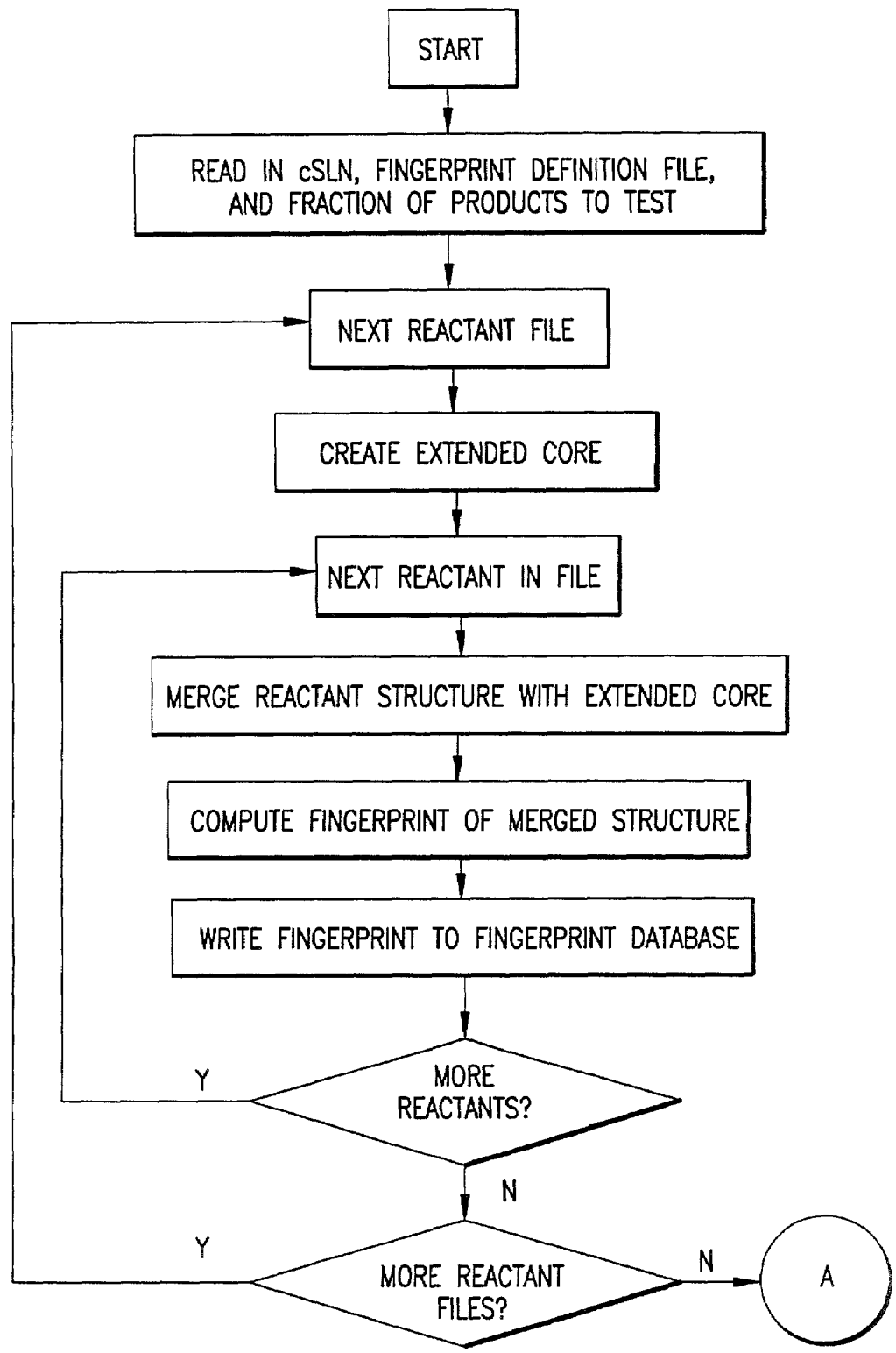
FIGS. 18, 19, and 20 are a flowchart summarizing the overall process of applying the Tanimoto fingerprint metric for use in the virtual library.
Figure 19:
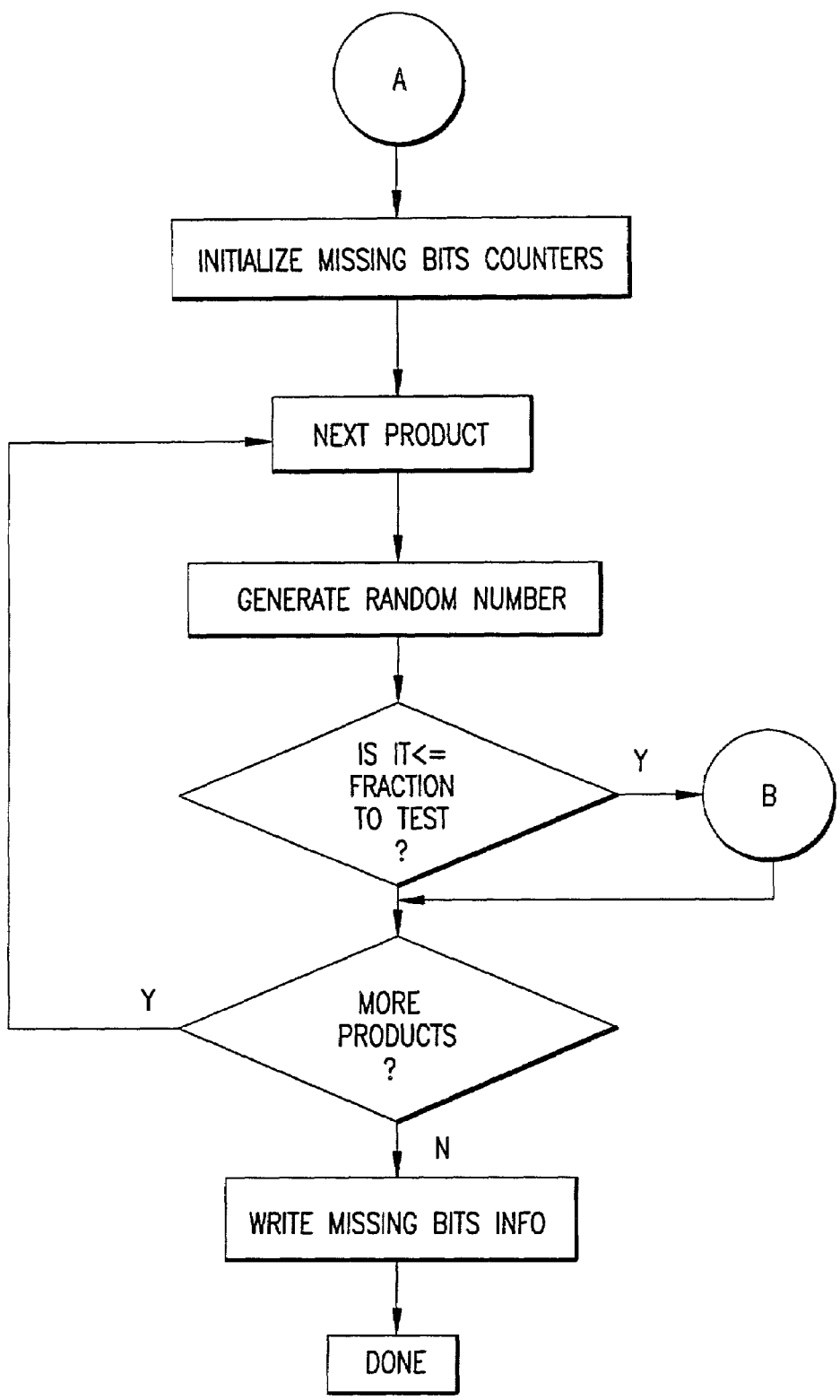
Figure 20:
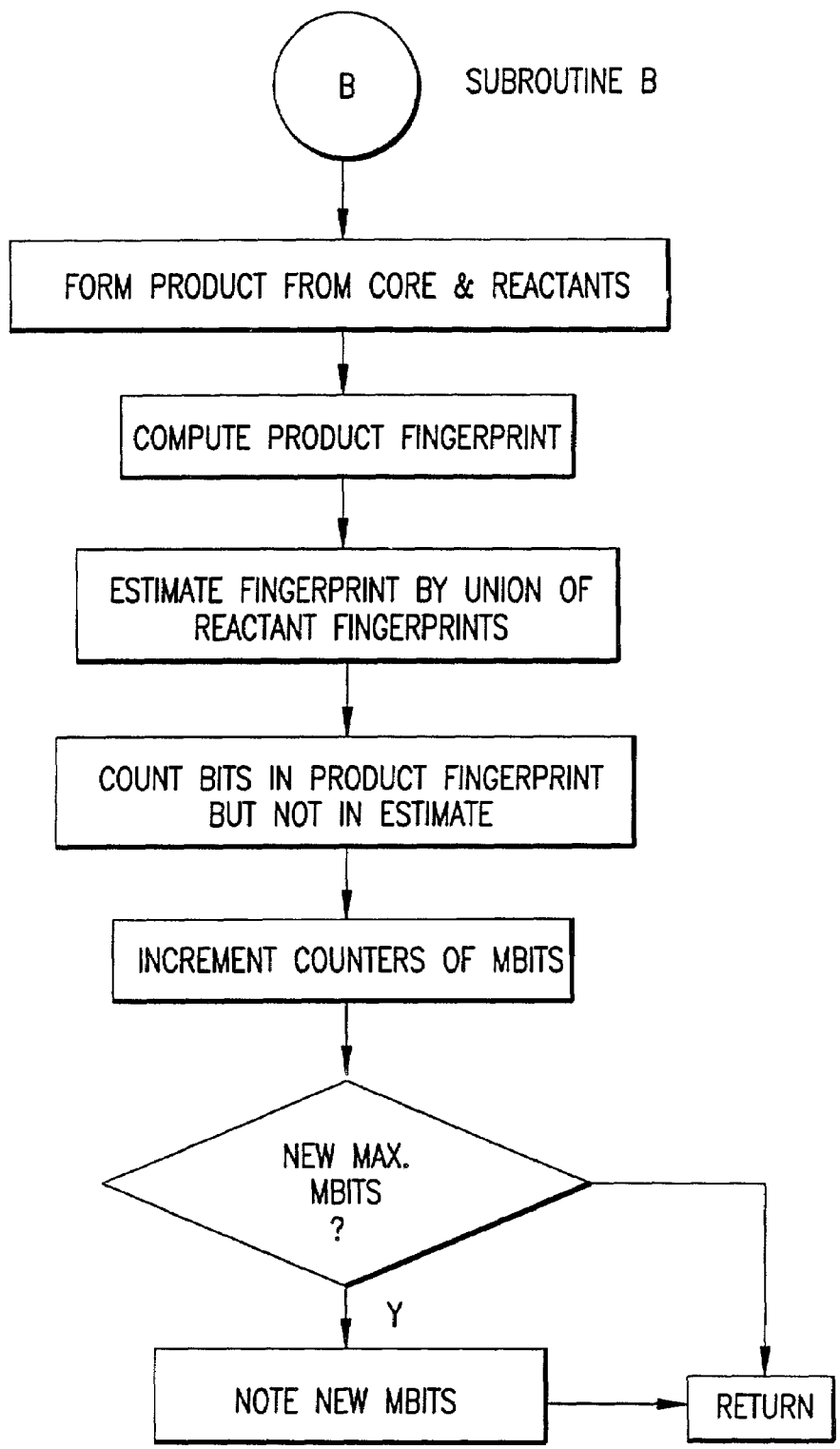

The overall process of applying the Tanimoto fingerprint metric for use in the virtual library is summarized in the flowchart of FIGS. 18, 19, and 20. As mentioned above, certain properties (molecular descriptors) of the product molecules can not be simply computed as the sum of the associated properties of the substructures used to form the product molecule. One of the most important and challenging to compute of these molecular descriptors is the molecular fingerprint. This product descriptor can not be calculated

TABLE 7

Structural Variations At First Site

FC(F)(F)C[5]:CH:C(:CH:C(:CH:@5)OCH3)NHR1<FCD=TRIPOS___0393;PRICE=101.4
;SUPPLIER=ALDRICH;MW=190.14;LOGP=2.33;CTOPS=1111111111111111111111
1111111111111111111111111111111111111111111111111111111111111111111111
1111111111111111111111111111111111111111111111111111111111111111111111
1111111111111111111111111111111111111111111111111111111111111111111111
1111111111111111111111111111111111111111111111111111111111111111111111
11111111111111111111111111a1111111113f21111111141111111111111111111111111
111111111111111111111111111111111111111111111112f11111111ffe11111114ff11111
11ff311111112f11111111111111111111111111111111111111111111111111111112ff111
1115ff31111112ff21111111fff1111111ff41111111111111111111111111111111111111
11111121111111fff1111111fff21111111fff1111111fff1111111942111111111111111111
11111111111111111111111111111111ff1111111114ff11111111711111111111111111111
1111111111111111111111111111111111111111111111111111111111111111111111
1111111111111111111111111111111111111111111111111111111111111111111111
11111111111111111111111111111111111111111111111111>
FC(F)(F)C[5]:CH:C(:CH:C(:CH:@5)C(F)(F)F)NHR1<FCD=TRIPOS___0394;PRICE=14
.84;SUPPLLER=ALDRICH;MW=228.12;LOGP=3.32;CTOPS=1111111111111111111
1111111111111111111111111111111111111111111111111111111111111111111111
1111111111111111111111111111111111111111111111111111111111111111111111
1111111111111111111111111111111111111111111111111111111111111111111111
1111111111111111111111111111111111111111111111111111111111111111111111
11111111111111111111111111a1111111113f2111111114111111111111111111111111111
111111111111111111111111111111111111111112f11111112f11111111ffe11111114ff1111
1111ff311111112f111111111111111111111111111111111111111111111111111112ff11
111115ff11111112ff21111111fff1111111ff41111111111111111111111111111111111111
11111111111111fff1111111fff1111111fff1111111fff11111119421111111111111111111
111111111111111111111111111111111ff21111111ff4111111113f1111111111111111111
111111111111111111111111111111111111111111111111111111111111111111211111
1111111111111111111111111111111111111111111111111111111111111111111111
1111111111111111111111111111111111111111111111111111> as the simple additive results of the descriptor of its pieces. For fingerprints, any fragment which is not fully contained within the core alone or within one structural variation alone will not be represented by treating each piece separately. Therefore, a fingerprint descriptor is computed for an extended core consisting of the structural variation at site $R_1$ and including the substructures which consist of:

1) the structural variation;
2) the common core substructure; and
3) all invariant atoms contiguously connected to the core occurring in structural variations at sites other than $R_1$.

This process is repeated for all sites.

Thus, in FIG. 16, if each selection in $\{R_2\}$ includes an OCH2 group connected to the core and each selection in $\{R_3\}$ contains a CH connected to the core, the fingerprints corresponding to a selection from $\{R_1\}$ will describe the substructure formed by this selection connected to the core and also including an OCH2 connected to the core at site 2 and a CH connected to the core at site 3.

For the standard definition of 2D fingerprints, this method can yield an exact result of the product fingerprint whenever the shortest connected path through the extended core is 5 atoms or more by OR-ing (a Boolean algebra manipulation) the fingerprints of each of the 3 structural variations in the example above. There is no need to include a separate fingerprint for the core, since it is contained in all the structural alternative descriptors. There is no hazard of duplication, since a fingerprint with a few exceptions notes only the presence of a connected fragment, not the number of occurrences. That is; either a bit is set in the fingerprint for that structure or it is not set. Duplicate occurrences of the same structure can not set the bit twice. In the few cases, such as ring and halogen structural features, where a count is maintained, correction for these bits of the fingerprint may be accomplished by explicit correction by count of structural variations plus core.

In some cases the extended core is not large enough to assure exact construction of the product fingerprint from that of the pieces (i.e. some relevant fragments start in one structural variation, span the extended core and reach into the individual alternatives at another site). To create and explicitly fingerprint every compound is in fact possible for a set of one million products. For the creation of a virtual library with initially tens of millions of products and ultimately hundreds of millions and even hundreds of billions of product compounds, explicit fingerprint computation is not feasible in any realistic time frame. For this scale of virtual library creation an approximation is both acceptable and necessary. Finally, since the purpose of the creation of the virtual library is to provide a basis for searching for molecules matching some subset criteria, the approximation method must ensure that such searches are reliable.

For the approximation, a random sample of a statistically significant fraction (typically for a very large virtual library, 0.001) of the products is taken. Each sample product is checked to see how many bits are in the product but not in the fingerprint composed from the pieces. The largest observed difference value, MBITS, is maintained for future calculations and is used to identify, for example, all products which might be similar to a given structure in the extreme case in which all MBITS missing bits were in fact those which would make every product most similar.

The Tanimoto is defined as (#bits in common)/(#bits in either) for the similarity of two compounds' fingerprints. In the case at hand, the estimated product fingerprint might have as many as MBITS bits which are actually present in the product fingerprint but missing from the estimate. In the worst case, every one of those bits would be in common with the bits in the query compound's fingerprints. Since Tanimoto=(#bits in common)/(#bits in either), in our worst case this is (apparent #bits in common +MBITS)/(#bits in either), since every one of the MBITS bits is already represented in the #bits in either but is not present in the apparent #bits in common (i.e. the #bits in common based on the estimated product fingerprint).

By adopting this approach, an upper bound is calculated on the largest possible Tanimoto between two compounds. The actual product fingerprint cannot yield a higher Tanimoto than this, and almost always yields some value between the apparent Tanimoto and the upper bound. In some cases this estimates the largest possible Tanimoto to be greater than the actual maximum of 1.0; it serves no purpose to correct for this!

An example may be useful. Details of the computations are provided in the attached code, dbcslnprepro, but to illustrate the concept assume that what is desired is a subset of compounds defined as those with a Tanimoto similarity of 0.80 or higher to a specified reference compound. By the methods of this invention the fingerprints of every one of the 2000 structural variations at two sites (1000 each) have been precomputed. An estimate can be made of the fingerprints of every one of the 1,000,000 possible products by OR-ing the two site's fingerprints for every selection of one from each site. For a specific possible product the number of common bits is 78 and the "# of bits in either" is 100, so that the apparent Tanimoto is 78/100 which is below the cutoff of 0.80 and the product would not be selected. However, if the MBITS is 3, then the worst case could have 78+3=81 bits in common out of 100 bits in either, and the largest possible Tanimoto would be 81/100 which is greater than the cutoff. If it is desired to err on the side of not missing any possible products, this value would be accepted even though the apparent Tanimoto is too small.

The results of the fingerprint calculations discussed above are added as two additional fields to the structural variation files: fpcard and fp, which together represent the two-dimensional fingerprint of the structural alternative and everything to which it is connected in all of the resulting products; this additional structure being needed to more fully represent the fingerprint of a product compound by that of the structural variations which combine to form it. At the minimum, the common structural portion by which the alternative's structure is augmented is that of the core. Appendix G contains the code dbslnprepro which calculates and adds fpcard and fp.

When the fingerprint terms, fpcard and fp, are added to the file structure shown in Table 7, the complete file format for each structural variation follows the form:

TABLE 8

FC(F)(F)C[5];CH:C(:CH:C(:CH:@5)OCH3)NHR1<FCD=TRIPOS___0393;PRICE=101.4;SUPPLIER=ALDRICH;MW=190.14;LOGP=2.33;CTOPS=111111111111111111111111111111111111111111111111111111111111111111111111111111111111111111

TABLE 8-continued

```
1111111111111111111111111111111111111111111111111111111111111111
1111111111111111111111111111111111111111111111111111111111111111
1111111111111111111111111111111111111111111111111111111111111111
1111111111111111111111111a111111113f21111111141111111111111111111111111
11111111111111111111111111111111111111111111112f11111111ffe11111114ff11111
11ff311111112f11111111111111111111111111111111111111111111111111112fff111
1115ff31111112ff21111111fff1111111ff41111111111111111111111111111111111111
11111121111111fff1111111fff21111111fff1111111fff1111111194211111111111111111111
111111111111111111111111111111111ff1111111114ff11111111711111111111111111111
1111111111111111111111111111111111111111111111111111111111111111
1111111111111111111111111111111111111111111111111111111111111111
11111111111111111111111111111111111111111111111111111;fpcard=141;fp=08000020
20000008002080008804080481000000008003280c42a101000000100f888044011824c809000
4000200080000e008800420204002810000000000112010a80000400111800000c2184c0060a8
0618048000181020000000002000000024812010a024008c80004010000052000011847e0c000
38e7c10100>
FC(F)(F)C[5]:CH:C(:CH:C(:CH:@5)C(F)(F)F)NHR1<FCD=TRIPOS___0394;PRICE=14
.84;SUPPLLER=ALDRICH;MW=228.12;LOGP=3.32;CTOPS=11111111111111111111
1111111111111111111111111111111111111111111111111111111111111111
1111111111111111111111111111111111111111111111111111111111111111
1111111111111111111111111111111111111111111111111111111111111111
1111111111111111111111111111111111111111111111111111111111111111
1111111111111111111111111a111111113f21111111141111111111111111111111111
11111111111111111111111111111111111112f11111112f11111111ffe11111114ff111
1111ff311111112f111111111111111111111111111111111111111111111111112ff11
111115ff11111112ff21111111fff1111111ff411111111111111111111111111111111111
111111111111111fff1111111fff1111111fff1111111fff111111194211111111111111111111
11111111111111111111111111111111111111ff21111111ff411111113f111111111111111111
1111111111111111111111111111111111111111111111111111111111111211111
1111111111111111111111111111111111111111111111111111111111111111
111111111111111111111111111111111111111111111111;fpcard=121;fp=0800002
0200000080000800088000804800000000008003280442a0010000000100f008044011024c80900
04000200080000e00800042000400281000000000001001288000040011190004082184800608
8806180480001010200000000020000002081201080200084800040000000042000001847c0c0
003cff810100>
```

When initially constructed the virtual library consisted of the files described above. However, since the fingerprint metric is calculated for each set of structural variations attached to a specific core, separate structural variations files containing the fingerprint data were required for each combination of core with the structural variations. The virtual library therefore contained a great deal of redundant data (structural variation files repetitively containing the same non-fingerprint data). Accordingly, a more efficient virtual library is constructed by locating the fingerprint files associated with each structural variation file and different cores in separate files. Thus, only one copy of each structural variation file (like Table 7) is required, and there is an associated fingerprint file containing fpcard and fp for every core with which the structural variation file is used. The virtual library keeps track of all the individual files in a master file. For instance, on one line of the master file is kept the information that the Table 6 file is associated with its appropriate structural variation files and fingerprint files. Each line of the master file relates one Table 6 like file (CSLN) file with the appropriate structural variation files and fingerprint files. The same structural variation files may now be used with more than one cSLN as long as the same type of chemical reaction is involved. Appendix G contains the code dbcslnprepro (a/k/a "power") which calculates fpcard and fp, writes the fingerprint files, and updates the master file.

Clearly, the data associated with each structural variation in each file can be directly expanded to include the results of the application of any other validated metric to the structural variation.

iv. Summary of Method & Scope of Chemistry

Creation of a virtual library of structural variation files along with one definition file is all that is needed to describe all the products of a combinatorial synthesis, that is; all possible products of the combinatorial synthesis are now described using only descriptors of the structural variations. As many additional combinatorial synthesis may be added to the virtual library as is desired. Clearly, the larger the number, the more comprehensive will be the universe of accessible compounds which can be searched. In this manner the $N_1 \times N_2 \times N_3 \times \ldots$ number of products may be analyzed using only the $N_1+N_2+N_3+ \ldots$ number of structural variations. This ability to search a geometrically large number of product structures by searching through only the arithmetic sum of their parts is the key feature of the virtual library and is possible because of the identification and use of validated descriptors possessing the neighborhood property. Clearly, this same method is equally applicable to any large assembly of compounds not derived from a combinatorial synthetic scheme which can be described as combinations of structural variations. Any number of additional fields containing information about the structural variation may be added to the file format, and may be meaningfully used as part of the search criteria for subset selection.

There is special merit in assuring that each product which a user may select from this database (virtual library) corresponds to a known synthetic route and known available reagents. However, the routines which the user applies to select subsets of the virtual library, described below, do not depend on this. Neither does the representation itself inherently depend on the assumption of known synthesis pathway. Therefore it can be applied to any situation in which the set of compounds of interest can be expressed concisely as a core and points of enumerated structural variations. This makes the scope of the method, in principle, cover virtually all of small molecule chemistry. In the limit, any molecule is divisible into such a representation where there may be only one "structural variation" known in each list. In fact, the practical advantages of the invention will only obtain when the number of structural variations is large.

E. Searching the Virtual Library

The techniques of constructing and searching the virtual library present the molecular researcher with powerful methods of discovery not previously possible and represent another major advance in the state of the art. Since the virtual library is constructed for purposes of finding molecular similarities in structure and function, a unique feature of the virtual library is that you can ask questions of similarity in two fundamental ways—providing, essentially, two sides of the same coin. The first way is in the design of screening libraries—subsets of the virtual library where what is sought are all those product molecules meeting some set of similarity criteria and not their structurally and/or functionally equivalent neighbors (as illustrated in FIG. 1B). The second way is in expanding on a lead compound (lead explosion)—subsets of the virtual library where what is sought are all those product molecules meeting some set of similarity criteria to the lead and all the structurally and/or functionally equivalent neighbors. Clearly, as a given line of inquiry is followed, the search for the desired subsets may, at any given level of detail, take on aspects of one or the other of these two methods of inquiry. For instance, a search for all product molecules matching a lead compound may result in 10 million possibilities. In order to make the synthesis and actual screening more efficient, out of these 10 million, a screening library may be selected which does not sample the same neighborhood space more than once. This ability to perform different types of similarity searches underlies the discussion which follows.

Any of the characteristics associated in the virtual library file with each structural variation may be searched separately or in conjunction with other characteristics. Since validated metrics are used as descriptors for each structural variation, it is possible using only the data contained in the structural variation files to quickly identify those product molecules which could be formed from the structural variations similar in structure and biological activity to known molecules (such as lead compounds) or arbitrarily chosen molecules (screening libraries). With the virtual library, a structural search can be carried out without having to actually generate and compare any explicit structures of any possible product molecules. Subset libraries (screening libraries) representing molecules with selected characteristics can thereby be directly created by a search of the virtual library, and product structures created and generated only for those molecules included in the subset library. It is important to understand that the virtual library can be formed from any number of combinatorial synthetic schemes or can include molecules which, while not based on a combinatorial synthetic scheme, may be expressed in the form of a cSLN. Methods of including and searching such molecules will be discussed below. Not only does the discovery of a way to create the virtual library make it possible to search an extraordinarily large number of possible molecular structures, but it also makes it possible to do the searching in an extremely efficiently manner and in a very short period of time.

Since a variety of data associated with each structural variation, including that resulting from the application of validated metrics, is stored in the virtual library, the range of questions (searches) and the types of answers (subset libraries) one can ask of and receive from the virtual library is virtually unlimited and the number of possible product molecules examined to answer the questions is extraordinarily large. As emphasized earlier, the virtual library associates precomputed metric values with each structural variation. Library searching is based on the discovery that the metric characteristics of product molecules can be usefully estimated by the metric values of the structural variations used to form the products. As has been seen above, in the case of the Tanimoto fingerprint, it was also necessary to take into consideration in preparing the precomputed metric values some estimation of the core structure. For topomeric field searching, a useful method of comparison involves taking the root mean sum of squares differences between the metric field values of one structural variation and another. This value can then be compared to a chosen neighborhood distance to determine similarity. Finally, it should be recognized that in discussing core structures used in combinatorial arrangements, for purposes of creating and searching the virtual library, it is possible to consider a singe bond as a core structure. In such a case, the structural variations would be combinatorially combined across a single bond.

As presently implemented by the inventors, the virtual library has to date 170 billion possible product compounds representing 70,000 combinatorial reaction schemes over various cores, and it is being expanded monthly. The sheer size of the virtual library suggests that search times must be similarly enormous. However, using the search methodology described below, made possible by the construction of the virtual library based on validated metrics, real world searching rates of greater than 200–500 million compounds per hour have been routinely achieved with a single processor. Higher rates are achievable on a parallel processing computer with multiple processors such as are now available from several vendors including Silicon Graphics, Inc.

i. Example Search Routine of Virtual Library—Tanimoto Similarity

Figure 21:
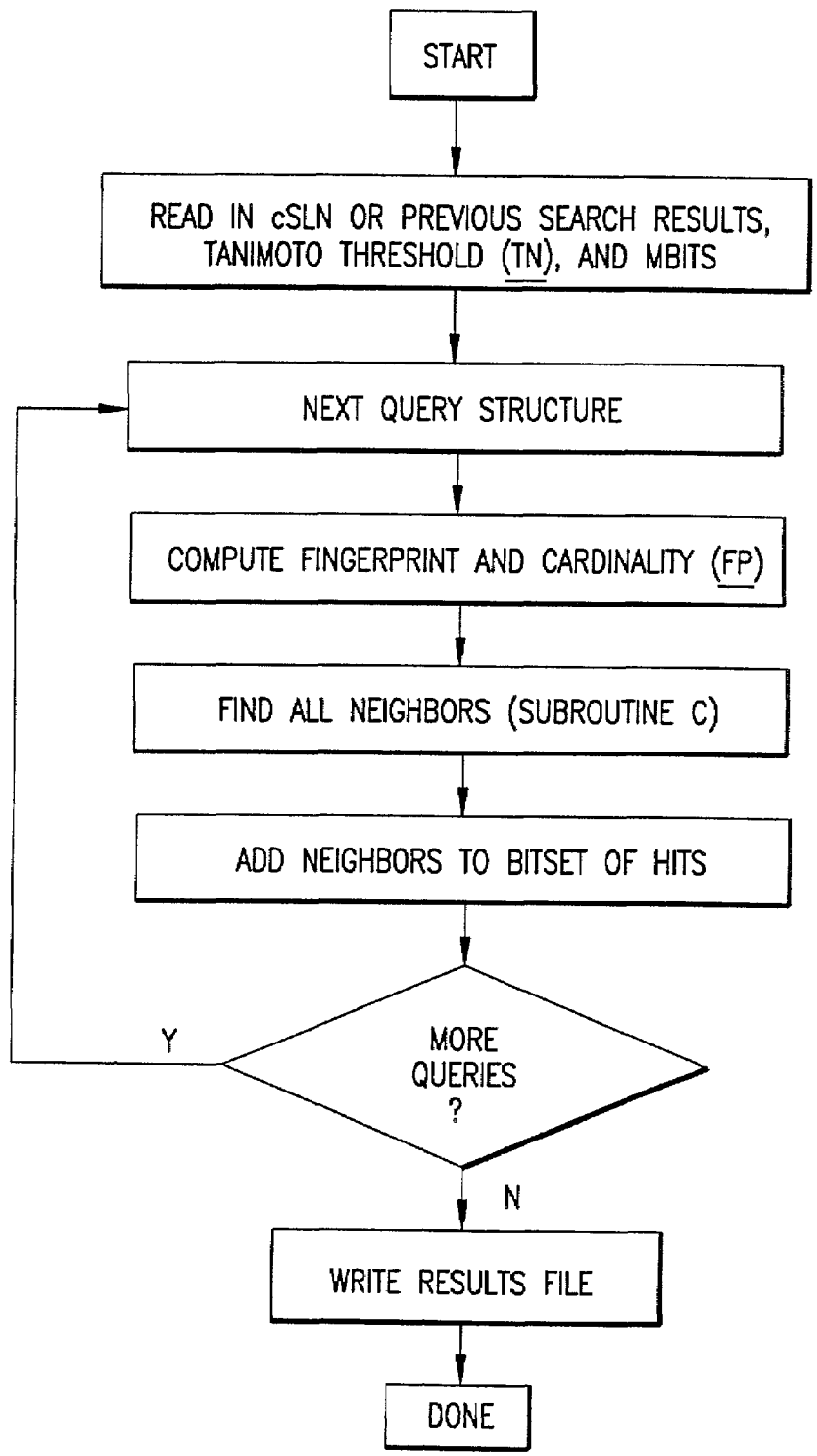
FIGS. 21, 22, and 23 are a flowchart summarizing the overall process of using the Tanimoto fingerprint metric to search for molecules.
Figure 22:
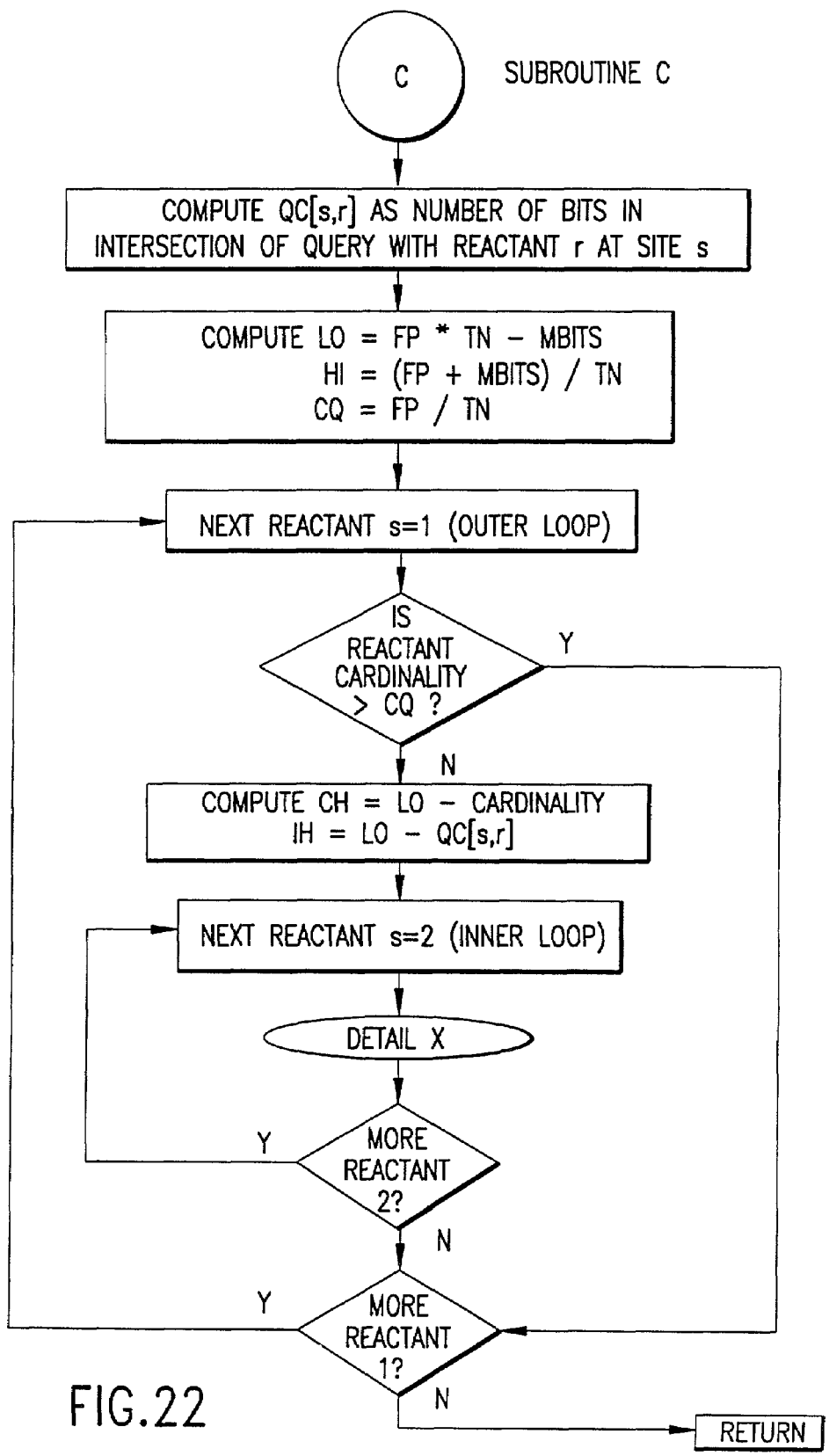
Figure 23:
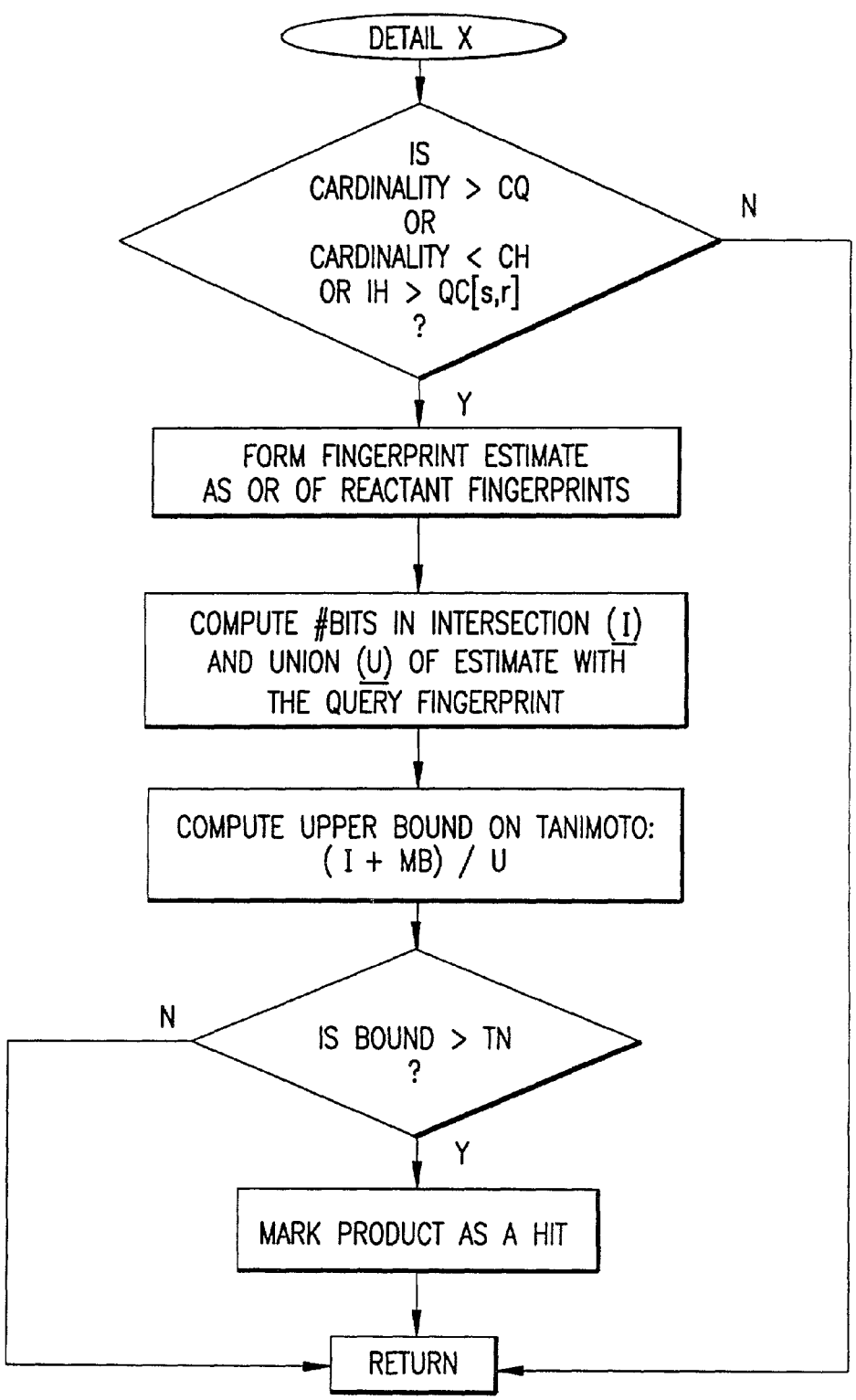

A brief overview of a typical search utilizing 2D fingerprints (a validated metric) will highlight the general approach used for all searches of the virtual library, which at their most fundamental level, rely on the values of the neighborhood distances found for the validated metrics. The overall process of using the Tanimoto fingerprint metric to search for molecules is summarized in the flowchart of FIGS. 21, 22, and 23. A typical library based on the combinatorial synthetic scheme utilizing a reactive diamino core will be used again as an example. As noted, this synthetic scheme alone contributes approximately 112 billion compounds to the virtual library data base. The question typically presented will ask whether the virtual library contains any molecules having a structure likely to yield a biological activity close to that of some known compound. To complete the search nothing need be known about the actual chemical compound for which close structures are desired, provided a 2D fingerprint for the molecule is supplied. Of course, generally, the molecular structure of the known molecule is provided and the software calculates the 2D fingerprint. A particularly important consideration is that the known molecule need not have resulted from a combinatorial synthesis and can, in fact, have any possible structure. The searching method of this invention independently searches each set of associated files generated by the virtual library construction method of the invention; in the case of the diamino example, a set of three files as outlined earlier. The reason each must be searched independently is that the searching program utilizes a knowledge of the number of sites (at which structural variations occurred in the synthetic scheme) to analyze the closeness of structure to the test molecule.

Based on knowledge of the neighborhood property of the validated Tanimoto metric, any molecule falling within a neighborhood Tanimoto similarity of 0.85 of another molecule should possess similar structural and biological characteristics. For this example, a Tanimoto similarity of 0.85 provides the basic selection criteria for examining the virtual library data base. Continuing with the example above, the fingerprint of the known molecule would first be compared to the fingerprint contained in every structural variation occurring at each of the two sites (2×15,000). The method determines how many of the bits set by the known molecule would be set by each structural variation. For all 15,000 choices at varying site $R_1$ (all 15,000 structural variations at $R_1$) the method compares the known molecule's fingerprints to the structural variation fingerprint. The same is then done for all 15,000 structural variations at site $R_2$. Then, for each one of the 15,000 choices at varying site $R_1$ the number of the matching bits set by that structural variation is added to the number of the matching bits for each one of the structural variations at $R_2$. For the entire set of structural variations at $R_1$ and $R_2$, this involves only the integer addition of 15,000× 15,000 terms and may be typically accomplished within fractions of a minute.

As each addition is completed, the resulting sum is compared to the Tanimoto neighborhood criteria. Suppose 100 bits were set by the known molecule. If the sum of bits totaled 65 and the neighborhood Tanimoto criteria of 0.85 (85 out of 100) were used, it would not be possible for any combination of those structural variations to form a molecule which would closely match the structure of the known molecule.

As noted above, the method also provides a check (MBITS) on the approximation routine used to calculate the fingerprints of the product molecules which would be formed from the two structural variations at sites $R_1$ and $R_2$. In this example, a typical MBITS value of 4 is assumed. Adding the 4 MBITS to the 65 only yields 69 which is clearly not within the required degree of Tanimoto neighborhood. However, had the bits from the structural variations added to 82, then the addition of the MBITS 4 would yield a total of 86, and the molecule formed from those structural variations would be considered close enough to check further. To confirm a match, the fingerprints from the two structural variations involved are OR-ed (Boolean) so that commonly set bits are counted only once and then compared to the fingerprint of the known molecule. Only if the resulting number when added to the MBITS term is greater than 85, is the product molecule represented by the two variations considered a match and included in a subset library resulting from the search. While these additional calculations take extra time, it is only necessary to perform them on structural variation combinations which pass the first level of screening (set bits >85). Therefore, typically only thousands of extra additions need to be calculated instead of millions, and the method is very fast. By the method of this invention hundreds of millions of possible compounds may be searched within a couple hours of computer time.

This testing procedure is continued through every set of structural variation virtual library files. Different sets of files resulting from other two site synthetic schemes would be checked in a similar fashion. When the known molecule was tested against a file set constructed from a synthetic scheme having three sites at which a structural variation could occur, the sum of the matching fingerprints contributed from three structural variations would be used and tested against the fingerprint of the known molecule in an identical manner. The actual method embodied in the software, performs many quick checks on each set of structural variation files and quickly ascertains whether that set of files could yield a product structure with the required structural characteristics (fingerprint in this example). If the quick check indicates that the set of files could not yield the known molecule, the search is quickly advanced to the next set of files. In fact, on a parallel processing machine, many simultaneous searches are performed. Thus, the time to search the entire virtual library is relative short.

Several points are extremely important. First, the characteristic of the known molecule is checked against only files associated with the structural variations. Thus, a set of associated files containing 2,000 structural variations (where 1,000 structural variations may occur at each of two sites) requires the examination of only 2,000 structural variations to accomplish a search of 1,000,000 (1,000×1,000) possible product molecules. Second, during the search only the structural variations which would contribute to a molecule having the desired structural characteristics are identified. Only after all such structural variations are identified, are the actual product molecules assembled from the structural variations and their entire structure specified for inclusion in the desired subset. Third, it does not matter whether the known molecule could be synthesized by a known combinatorial scheme. The information derived from a search such as in the example, would identify those molecules which could be derived from a combinatorial scheme which most likely have the same structural and biological characteristics as the known molecule. However, in creating the virtual library, all that is required is that the compounds can be described by a CSLN. The searching method of this invention, could equally well find one or more of these molecules not derived from a combinatorial synthetic scheme as being likely to have the same structural and biological characteristics of the known molecule. The only difference in this later case is that no information about a possible synthetic route is available from the results of the search.

Clearly, the greater the number of compounds specified in the entire virtual library data base whether based on known combinatorial synthetic schemes or resulting from other synthetic pathways and expressed as a CSLN, the greater the likelihood of finding molecules with similar structural and biological characteristics. Fourth, such structural searches require the use of validated metrics exhibiting a neighborhood property to characterize both the structural variations and the known molecule. Fifth, once the virtual library data base is constructed based on the method of this invention, there are any number of different types of searches which can be run. The software code provided with this application permits many such searches as outlined in the descriptions of the code below.

ii. Design Screening Libraries (Subsets of the Virtual Library)

In the current invention, one single method is used to select among all possible products from one or more reactions which share a common core substructure. A bitset is used to represent all the possible products (generally in the tens of millions). One may choose to limit the design subset selection to those compounds which are made of reagents from a specified subset of suppliers, to those of suitable price, to those of suitable molecular weight, logP, etc. One may seed the design with a set of preselected products. One may remove all products in the neighborhood of a subset of compounds as a preface to the design run.

The design process, once all the above initial subset operations have been performed, is extremely simple:

select a compound to add to the design, and remove its neighbors from further consideration continue until no other compounds are left The selection may be random, or may be directed to maximize use of a reagent once selected (this matches the practical requirements for a laboratory two-step synthesis in which maximum use of the first step's intermediate structures offers a substantial advantage in speed and cost). In principle, any rule can be invoked to prioritize which compound to select next, since any remaining compound is allowable at every step. Examples of this type of search are given below.

(a) Subset Screening Library Based On Topomeric Fields and Tanimoto

Figure 24:
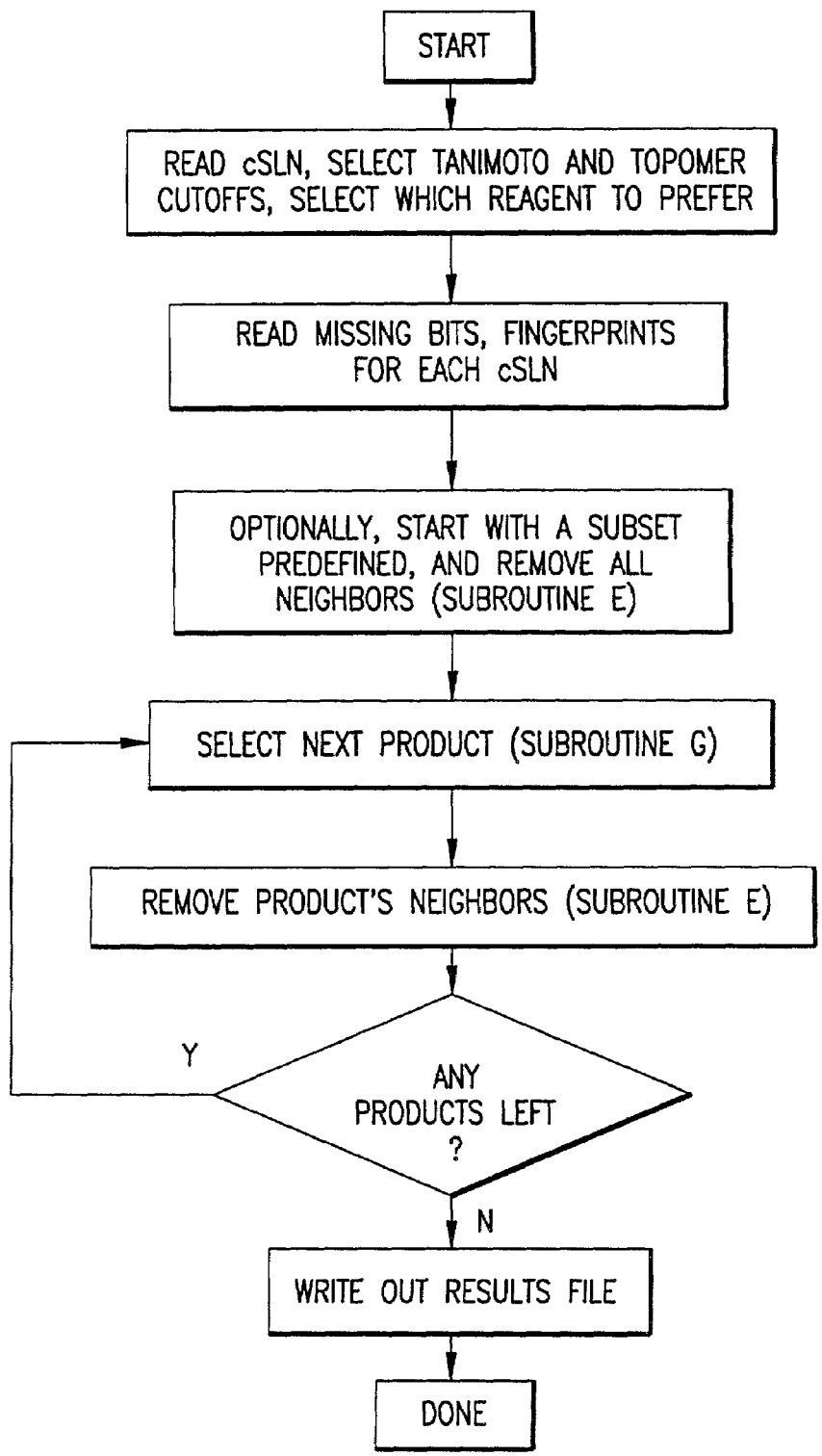
FIGS. 24, 25, and 26 are a flowchart summarizing the overall process of using both the topomeric CoMFA and Tanimoto metrics to search for molecules in the virtual library.
Figure 25:
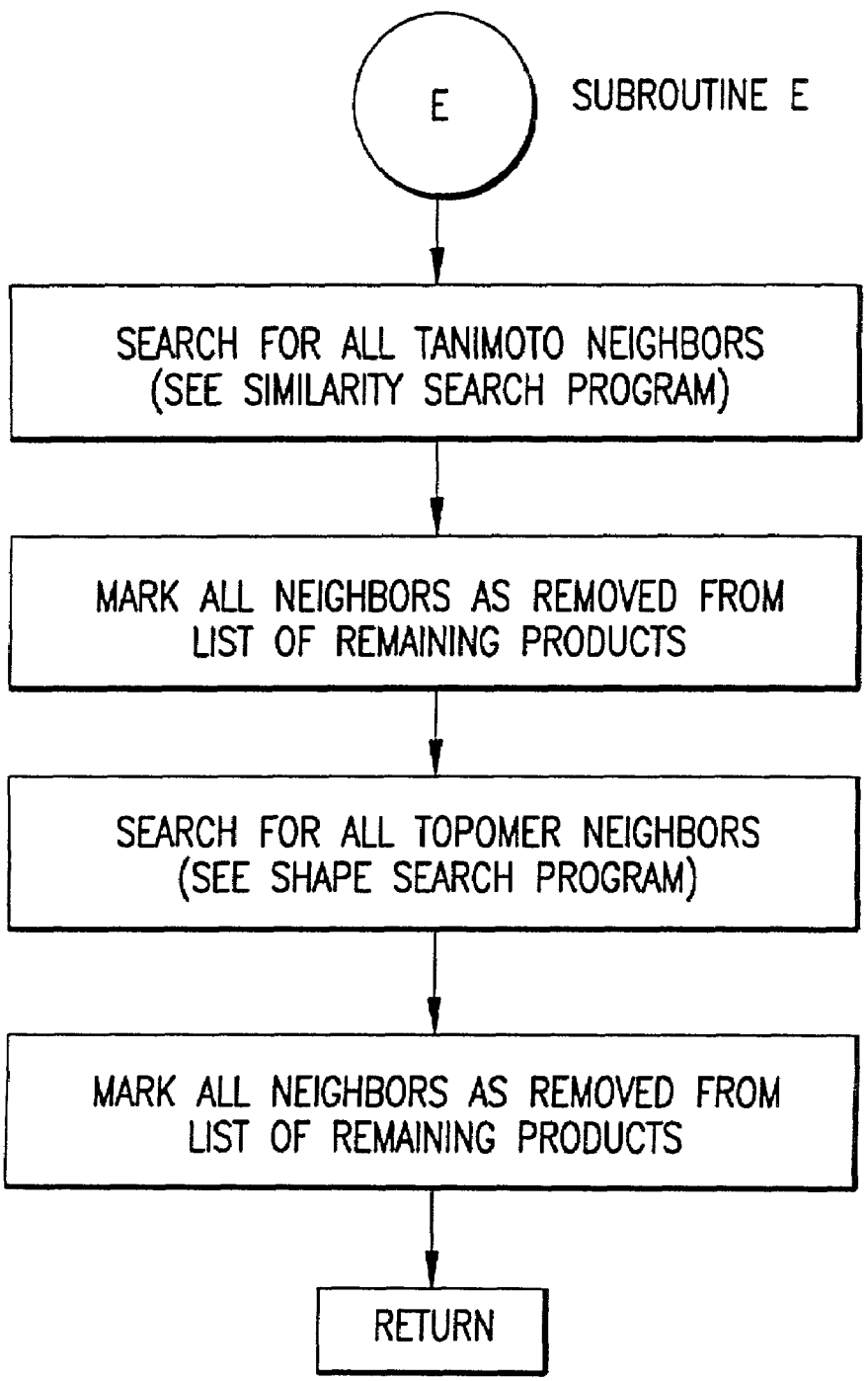
Figure 26:
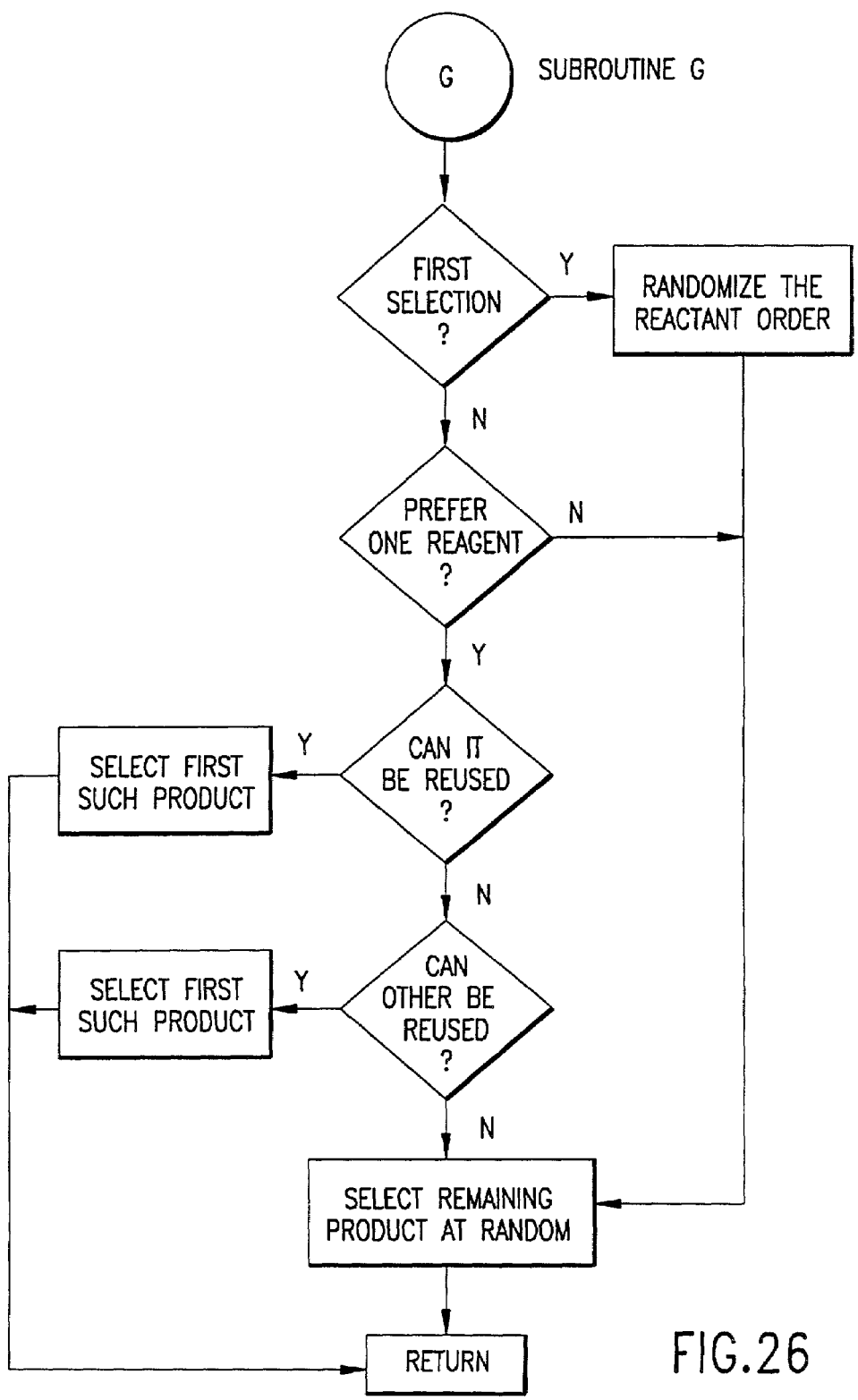
Figure 27:
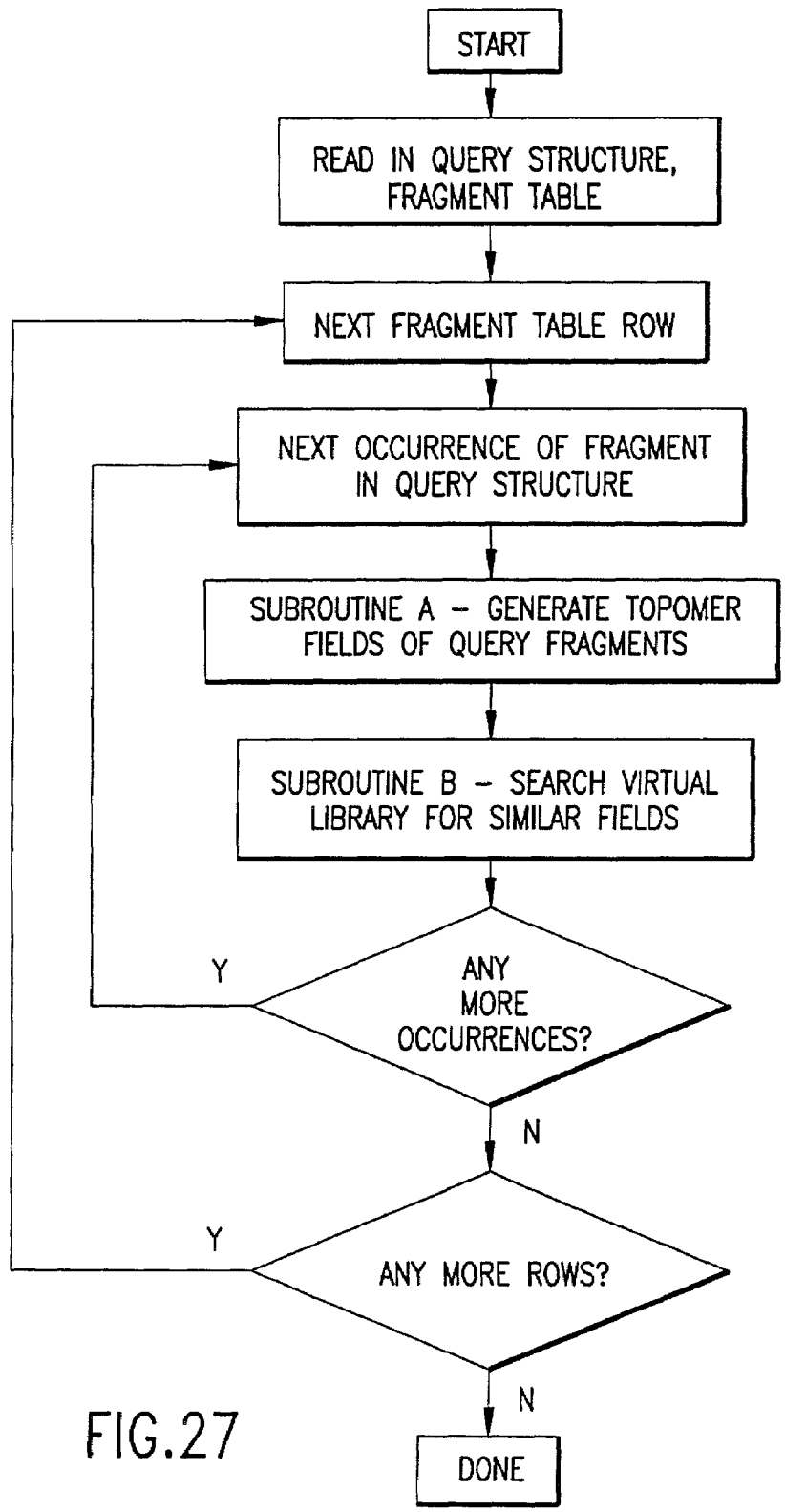
FIGS. 27, 28, 29, and 30 are a flowchart summarizing the overall process for topomeric searches of arbitrary query molecules.
Figure 28:
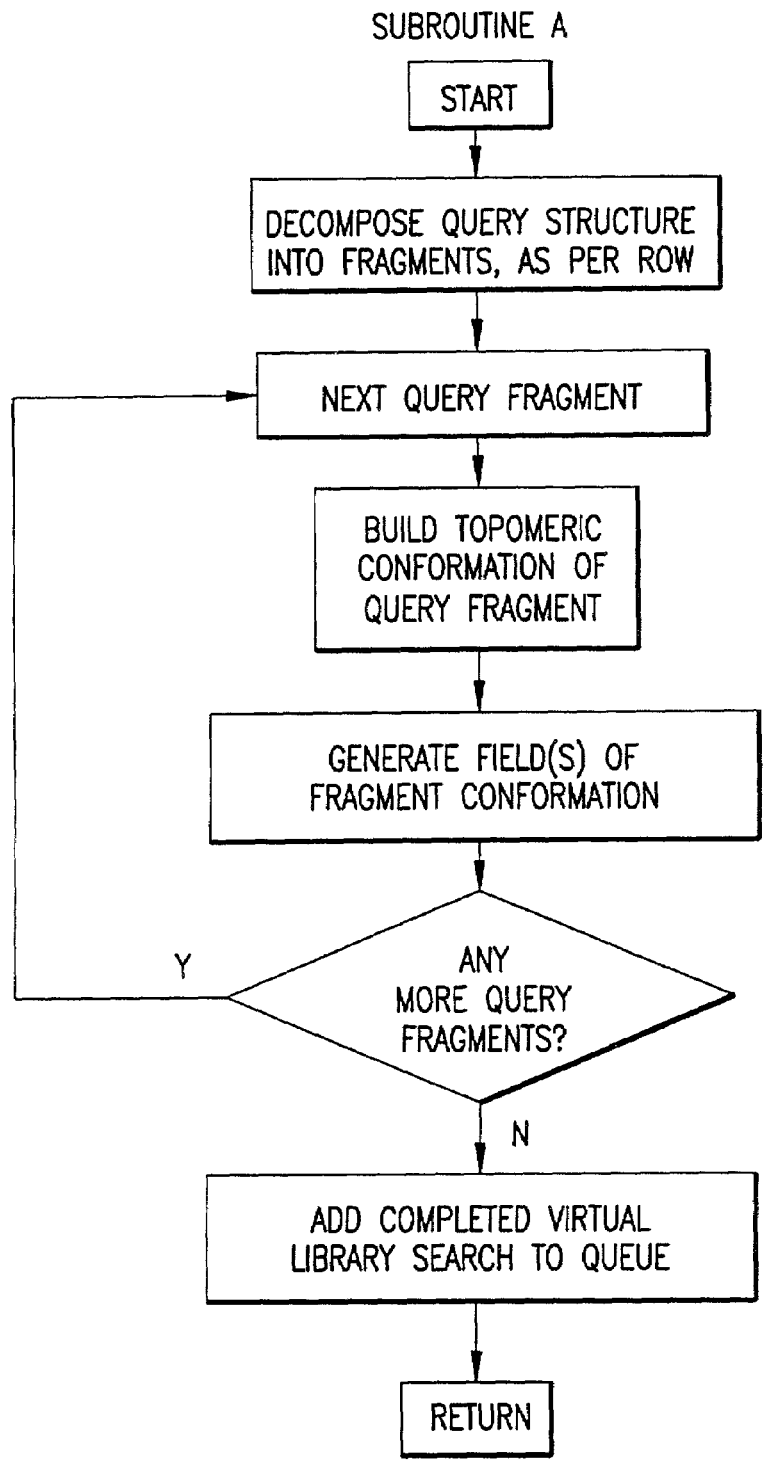
Figure 29:
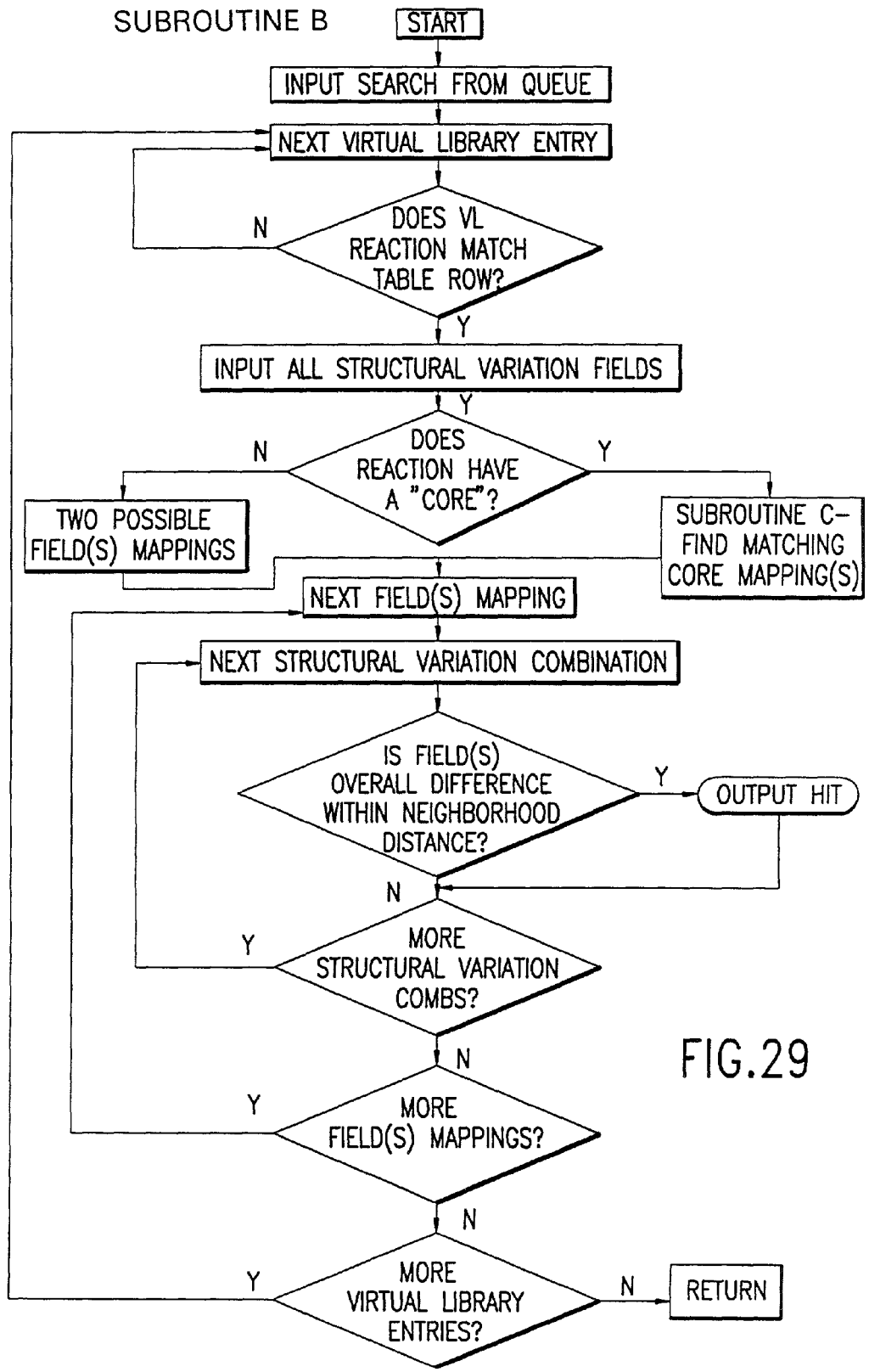
Figure 30:
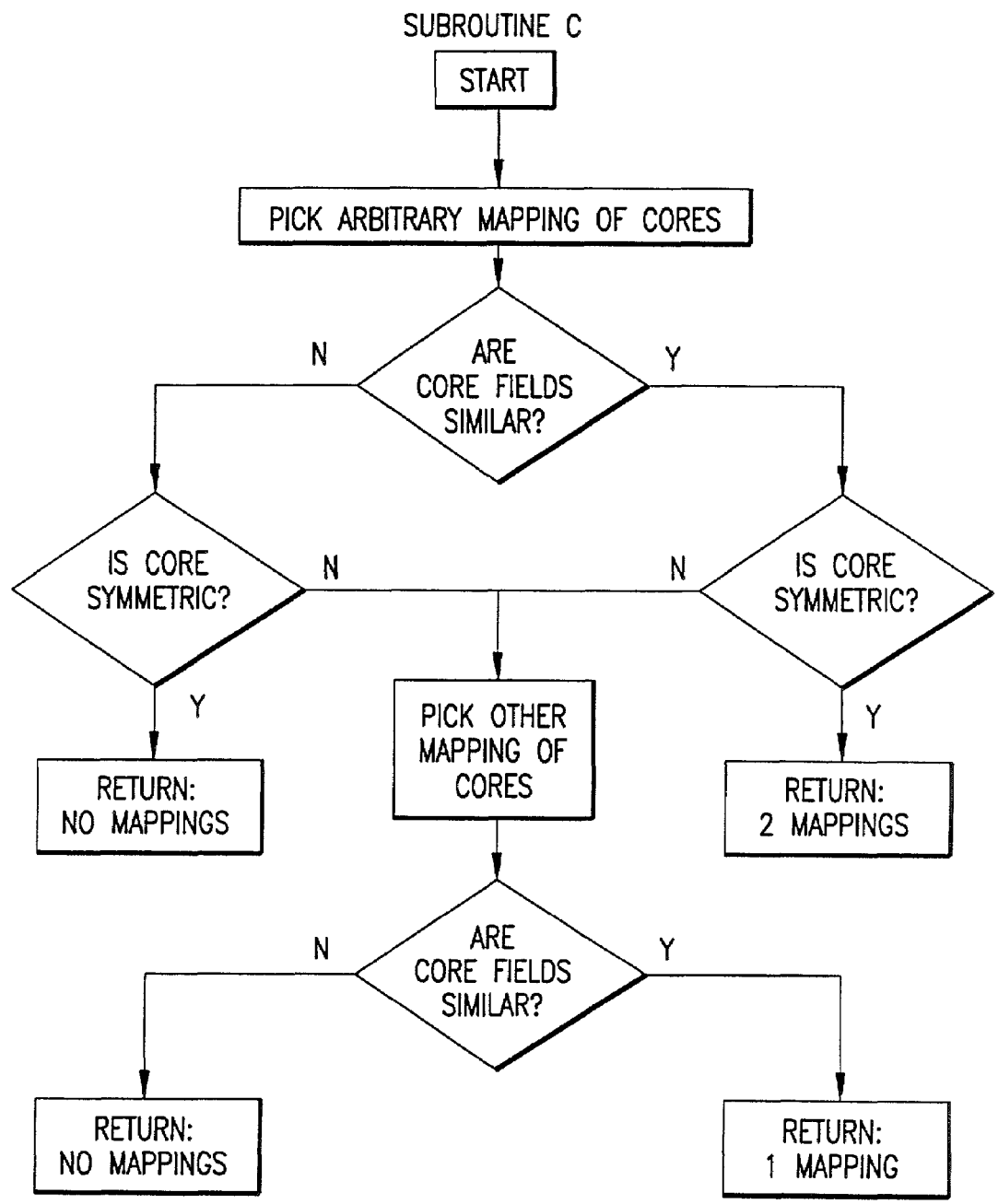

A selection of a screening library based on the same criteria as were discussed in the first part of this application is easily implemented using the virtual library. The library members are identified based on topomers (is the distance too small in topomer space) and on Tanimoto similarity separately, as was done in the earlier disclosed method. However, every reagent is always allowed, unlike the earlier method in which only a small subset of reagents made it through the reagent filter to the product stage. The earlier methods selected products based on maximal dissimilarity of product Tanimoto at each selection. Since by using the virtual library only the final selection set (all possible combinatorially created molecules meeting the selection criteria) is used, and does not depend upon or rely upon the ordering within a selected set (of reagents), the virtual library method is more flexible and in practice faster than the earlier disclosed method. In fact, since the product selection is not constrained by reagent stage selection, somewhat larger screening libraries result from using the virtual library. The overall process of using both the topomeric CoMFA and Tanimoto metrics to search for molecules in the virtual library is summarized in the flowchart of FIGS. 24, 25, and 26. Code to implement this search, db_des, is contained in Appendix K. A more extensive description of the code may be found in section G which follows.

(b) Subset Based on Tanimoto Similarity

A subset of the virtual library chosen just based on Tanimoto similarity/dissimilarity of product molecules, which could be created meeting some initial selection criteria, can be directly chosen. Code to implement this search, dbcslqs, is contained in Appendix I. A more extensive description of the code may be found in section G which follows.

(c) Subset Based on Topomeric Fields

A subset of the virtual library chosen just based on topomeric CoMFA field similarity/dissimilarity of product molecules, which could be created meeting some initial selection criteria, can be directly chosen. Code to implement this search, db_qstop, is contained in Appendix J. A more extensive description of the code may be found in section G which follows.

(d) Subset Based on Combined Metric

A subset of the virtual library may be based as well upon the combined topomeric-fingerprint metric described earlier. Code to implement this search, db_both, is contained in Appendix L. A more extensive description of the code may be found in section G which follows.

iii. Designing Lead Optimizations

The various techniques of lead optimization to explore the island of activity were discussed earlier. The same techniques used with the virtual library are much more powerful since a vastly larger chemical universe is being investigated. Generally, any property associated with a structural variation in the virtual library can be used to expand and define the product molecules sought.

Subsets of molecules from the virtual library database may be selected based on descriptors typically including, but not limited to, the following:

reagent identifier reagent supplier reagent or product molecular weight reagent or product price reagent or product estimated logP reagent shape contribution; product shape contribution under certain restrictions reagent or product 2D fingerprint product substructural features Subsets may be selected by applying by the following methods, including, but not limited to, simple filters, by requiring that filters meet a specific degree of similarity to reference compounds, or by applying proprietary design tools. Specifically, the initial modes of subset selection may include:

substructural searching, to identify compounds which have a set of required structural features, is perhaps the most often used method of chemical database subset selection 3D feature searching, to add interatomic distance requirements to the substructural searching, is also familiar to experts in chemical database searching similarity searching, to find subsets which are substantially like a reference compound, is widely used as well and corresponds to application of a neighborhood principle applied to 2D fingerprints or—planned extensions—atom pair distance fingerprints, etc.

scalar searches corresponding to traditional nonstructural database queries, to find compounds with for example logP between 5 and 8 and molecular weight under 500 and price above 750.

maximum dissimilarity queries, which are used primarily to order a large subset of compounds such that as one reads down the ordered list, compounds are less distinct from each other as a group STIGMATA (a procedure popularized by the scientists at Parke Davis) queries, in which compounds are selected based on the presence of specific bits in a fingerprint (2D, atom pair, pharmacophore triplets, etc.). Commonly such a query is derived by reference to a set of desirable compounds, from which the bits present in all compounds in the set are derived.

design queries (scalar, topomer, fingerprint, arbitrary weightings of any of these) of either of two types:
gridding methods, in which the objective is to have one compound within each specific "hypercube" of the design space
neighborhood methods, in which the objective is to obtain a set in which no two compounds are overly similar, and in which no "holes" exist needlessly (a) Search Based on Tanimoto Similarity Details of a typical lead optimization using the Tanimoto metric were highlighted under section 12(E)(i) above. Essentially, what is sought is a list of all compounds to be found within the Tanimoto neighborhood of the lead. Code to implement this type of search, db_sim, is contained in Appendix H. A more extensive description of the code may be found in section G which follows.

(b) Searches Based on Topomer Similarity

The notion of topomer similarity of a pair of molecules is well defined if the molecules have some common "core". An enhanced method has also been discovered which allows arbitrary structures as search queries not just those which result from a combinatorial synthesis. Therefore, to find molecules similar to some target within the virtual library, the following three phase operation as summarized in the flowchart of FIGS. 27, 28, 29, and 30 must be performed:

1) Determine which of the "common core" substructures (where the core may consist of a single bond and any single bond is equivalent to any other single bond for topomer searching) within the virtual library are wholly contained within the search target molecule. This can be done by any standard searching program, such as Tripos' Unity package.

2) For each of the common cores found, remove that common core from the search target. The atoms remaining will comprise one or more side chains. Generate the topomeric conformations of each of the side chains, using the same code that is used to build topomeric conformations during library ("all possible products") generation. Generate the topomeric conformation of the core.

3) Using these topomeric conformations of each of the target molecule's side chains, search the combinatorial libraries corresponding to the previously identified common cores for all side chains whose sum of corresponding side chain topomeric differences is less than the neighborhood radius within the typical neighborhood range of 80–100 kcal/mol. (91 kcal/mol.) Alternatively, the root sum of square differences between the fields may be used to determine the selection criteria. The procedure is shown in the flowsheet of FIGS. 27, 28, 29, and 30 and described below.

(c) Topomeric (3D) Searching of Arbitrary Molecular Structures

In addition to searching the virtual library as outlined above, it is possible to conduct searches which were heretofore impossible by any means. In particular, a critical question which frequently occurs in chemical research, and especially in biological research, can now be addressed by the discovery and creation embodied in the virtual library. The problem, as it is usually presented, takes the form: given an arbitrary query molecule (generally one previously found to exhibit a desired activity), find biologically similar molecules, that is molecules of similar 3D shape and activity, that can readily be made and tested. Generally, such a query molecule will not have resulted from a combinatorial synthesis, and, in fact, no knowledge of a possible synthetic route to the molecule may be available. As an example, suppose that compounds similar in 3D shape to but structurally different from the structure (written in SLN) CH3C(=O)NHCH(CH3)CH2NHCH2CH2OH are desirable, perhaps because this hypothetical structure was reported to be highly active in a competitive pharmaceutical preparation.

As described earlier, the topomeric 3D shape data within the Virtual Libraries actually describe fragments (structural variations) of molecules. To find similarly shaped molecules within the virtual library, the query molecule must be fragmented and the shapes of its fragments compared with the shapes of corresponding fragments (structural variations) in the virtual library. The difficulty is that a query molecule can be fragmented in so very many ways for searching against the virtual library containing in excess of $10^{12}$ molecules. (The example given has nine bonds connecting heavy atoms, so there are nine two-fragment combinations that could be considered, 9×8=72 three-fragment combinations, 9×8×7=504 four-fragment combinations, etc.) Given this situation, what is needed is a way to emphasize those fragmentations that are most likely to conform to efficient synthetic routes from available starting materials, without requiring the searcher of the virtual library to have any knowledge of what synthetic routes it includes.

The solution to this problem which can be uniquely achieved with the virtual library is a "fragmentation table", where each row constitutes a rule of the following sort: "for each occurrence of this particular structural feature combination (structural variation) in the query molecule, decompose the query molecule in a particular way specified in terms of this structural feature, and search only those combinatorial libraries that utilize specified reactions (sequences) and/or building blocks, mapping specified query fragments onto specified classes of building blocks". Each such query decomposition found generates a search of the virtual library, returning all those products whose sum of squares of differences in shape between corresponding product and query fragments is less than a user specified neighborhood distance threshold. Passing the query molecule (by means of a suitable computer program) against all the rows of this table generates all searches.

To illustrate this approach with a simple example, one row in the table might have as its structural feature C(=O)—[!r]NH (amide bond, where [!r] states that the preceding bond must not be cyclic). This row would specify cleavage between the N and C of any matching fragment within the query, for our example query yielding the fragments CH3C(=O)— and —NHCH(CH3)CH2NHCH2CH2OH, and the characteristics that a matching subset library should have (primary or secondary amine reacting with an acid, acid chloride, isocyanate, chloroformate). The similarity searching engine then returns all products in the virtual library formed from amines close enough in shape to —NHCH(CH3)CH2NHCH2CH2OH and acylating reagents close enough in shape to CH3C(=O)—.

Note that the amide bond is a synthetic convenience, not an absolute arbiter of shape similarity. Molecules in which the amide bond is "reversed" might also be sufficiently shape similar overall to have biological similarity to the query molecule, despite the local differences in shape resulting from the NH to C=O mismatch. Indeed, any reaction that forms a single acyclic bond might contain bioisosteres of our query molecule within its virtual library. On the other hand, an amide library would contain both the most accessible and also the largest number of bioisosteres and so this is the library that should first be searched.

Another row in the fragmentation table might designate a query decomposition into three fragments, with a structural feature R—[!r]NXN—[!r]R. Application of this row to our query molecule would generate CH3C(=O)—, —NHCH(CH3)CH2NH—, and —CH2CH2OH. When searching the "diamine" library (about 10^11 structures) for similarity using these fragments, the "core" or diamine component is searched first for fragments similar in shape to —NHCH(CH3)CH2NH— (see below for a description of the special features of core shape similarity). Core shape similarity is much rarer than side-chain shape similarity and so an efficient search process considers core similarity before considering side chain similarity.

An example of what a few rows in a typical fragmentation table look like is shown below. The description of the individual named columns are as follows:

CLASS_ID=equivalent in meaning and value to CLASS_ID in the REACTIONS table. Identifies a particular reaction sequence as it would be carried out in the laboratory. Only those virtual library records whose CLASS_ID matches this value will actually be searched.

PRIORITY=Allows a searcher to control the depth of a search. Lower values correspond to reactions which are less general, but whose products are more likely to resemble a matching query. Deeper searches will also consider rows having higher values of PRIORITY.

SLN=the structural pattern that will be matched within the query molecule. Each match found within the query molecule generates a decomposition of the query into fragments for topomeric similarity searching, as detailed elsewhere.

REACTANTS=Allows the developer of this table to limit application of a particular row to reactions involving particular classes of reactants.

ATOMS=Specifies, by reference to the fragment description with the SLN column, the bonds in the query whose breaking will generate the fragments to be used in topomeric field similarity searching.

The three rows shown illustrate the three examples discussed elsewhere in this description: Row 1—diamine derivatization; Row 3—amide formation; Row 7—thioether cleavage. For clarity the information for these rows is broken into three sections:

| | 1<br>CLASS_ID | 2<br>PRIORITY | 3<br>SLN | 4<br>REACTANTS | 5<br>ATOMS |
|---|---|---|---|---|---|
| ROW1 | 5 | 2.00 | Hev-[!R]NXN-[!R]Hev | X1=RN=C=O, ClC(=O)OR, Epoxide, Ald/Ket, RC(=O)Cl, RCOOH, RCOO[-], RSO2Cl, ArF(activated), N:CHal, C=CCX, H X2=RN=C=O, ClC(=O)OR, Epoxide, Ald/Ket, RC(=O)Cl, RCOOH, RCOO[-], RSO2Cl, ArF(activated), N:CHal, C=CCX, H | 1,2 5,4 |
| ROW3 | 6 | 2.00 | HevHev(=O)-[!R]NHev | X1=Amine(~3) X2=RCOOH, RN=C=O, ClC(=O)OR, RC(=O)Cl, RCOO[-], RSO2Cl, ArF(activated), N:CHal, C=CCX | 4,2 2,4 |
| ROW7 | 22 | 2.00 | CS-[!R]HevHev | X1=RSH X2=RN=C=S, RN=C=O, RSO2Cl, RCl, ArF(activated), N:CHal, RBr | 2,3 3,2 |

The power and utility of topomeric steric field analysis of fragmented structures is highlighted by a recent analysis of the structures of Tagamet and Zantac (H2 antagonists). Tagamet and Zantac were each fragmented according to Row 7 of the fragmentation table and the topomeric steric fields calculated. The metric distance (difference in metric values) for the two compounds was 127.

Figure 31:
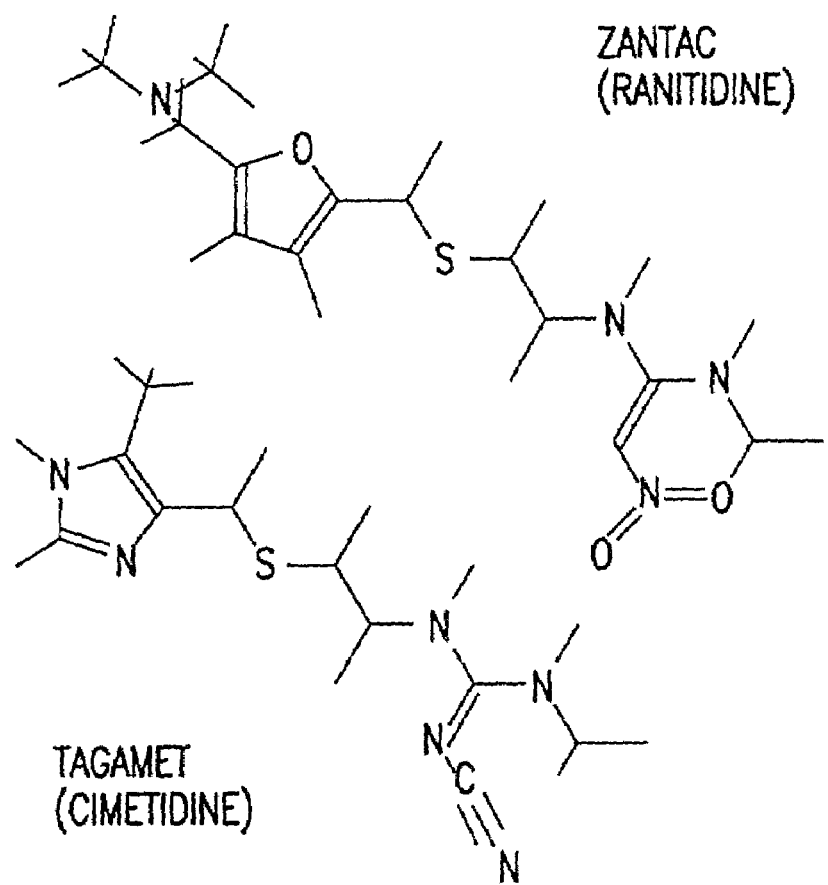
FIG. 31 shows the topomeric conformations of Tagamet and Zantac.

Remembering that a range of 80–100 defines a neighborhood distance for an approximate log2 biological difference for the topomeric CoMFA descriptor, the value of 127 strongly suggests that Tagamet and Zantac should have similar biological activities. Such knowledge would have been very useful to those either seeking to protect molecules with similar structure/activity to the known molecule or to those seeking to find molecules which look similar to the receptor but which are not entirely structurally identical to the known molecule. It should be noted that other widely used diversity approaches, 2D fingerprints and pharmacophoric patterns show a remarkable lack of similarity between the drugs. Indeed, in the topomeric configuration generated by the methods of this invention, Tagamet and Zantac look very similar even to the unaided eye as shown in FIG. 31.

(d) Topomeric (3D) Searching of Core Structures

An ancillary problem when attempting to find molecules in the virtual library (constructed principally from combinatorial chemistries) which are structurally and biologically similar to a given query molecule, is the treatment of the central core to which structural variations can be attached. The virtual library defines the shape similarity of two molecules as the sum of the similarities of comparable fragments. "Core" fragments are any fragments that have multiple attachment bonds to other fragments, in contrast to "side chain" fragments which have only one attachment bond.

Overall molecular shape will be affected most by the relative positions of core attachment bonds. Consider the three possible bivalent phenyl cores, ortho, meta, and para. These will be quite similar in their intrinsic shapes—only a hydrogen changes place—but the molecules derived from the three cores will be very different in shape if the side chains are at all bulky. Therefore in considering the shape similarities of cores the relative positions of attachment bonds must be weighted far more heavily than the shape differences themselves.

The prior art has attempted to deal with this problem. Lauri and Bartlett[17] have described CAVEAT, which in the nomenclature of this disclosure would be considered a "core similarity" searching system that considers only relative attachment bonds, not shape, of all theoretically constructible cyclic cores. In their work, the relative geometry of two attachment bonds is expressed in terms of their distance, angle, and torsions. In contrast the present inventors have found that a much more self-consistent shape classification of, for example, all 750 commercially offered diamines, is obtained when one of the attachment bonds is aligned on the X-axis (as in the standard topomer conformation, described earlier) and the differences calculated as the root mean square of summed differences in the x, y, and z coordinates of the two ends of the other attachment bond. (The conformation used in this procedure is the topomeric conformation of the core with a methyl group replacing the more distant attachment bond.) This procedure differentiates cyclic from acyclic fragments much more strongly than it differs among the linear acyclic moieties pentylyl, hexylyl, and heptylyl.

In addition to this RMS difference in x, y, and z, the differences in steric (and any other fields) also contribute to the bioisosteric differences between two cores. Because there are potentially two or more possible attachment bonds in a core, there are two or more ways in which two or more cores may be compared. So the difference in fields is taken as the least of these possible differences. The combination of two descriptors in considering the difference between two core structures, the attachment bond differences and the field differences, introduces a relative weighting concern. In practice it has been found in clustering experiments like those described for the thiols that the internally most self-consistent classification of 750 diamines results from numerically equal weighting of the two RMS differences.

Thus, the successful generation of a topomeric descriptor for cores involves two advances. In comparison with the procedure for side chains, the relative position of attachment points has been introduced, for example, to distinguish ortho phenylene from para phenylene. In comparison with the treatment of attachment points previously described by Bartlett et al., the use of differences in x, y, z coordinates, rather than relative geometries such as distances and solid angles, provides a stronger differentiation needed between, for example, cyclic and acyclic cores.

G. Code Attachments

The following software code comprising the main sections of the invention is described below and is attached in the Appendices. In addition, necessary auxiliary code is also set forth in the Appendices. All together, all code necessary to fully disclose an enabling embodiment of the invention in the computational chemistry environment specified earlier is set forth in the several appendices. In some cases new code is provided which differs from that in the priority documents to include enhancements described in the text. In particular, as the virtual library has been expanded, it has been found that the larger number of compounds identified from the searches is more conveniently handled which can deal with bitsets rather than as ASCII text. The additional auxiliary code required to manipulate the bitsets is contained in Appendix R. However, the use of bitsets is a computation convenience and does not involve any change in the construction or searching of the virtual library.

Appendix A:

One section of the code in this Appendix generates topomeric conformations, and another section generates the best slope line for Patterson plots.

Appendix B: This code calculates the hydrogen bond variation to be applied to the CoMFA steric field.

Appendix E: getacd.core This code handles the first phase of the construction of the virtual library.

Appendix F: SYB_MGEN_GPLS_CoMFA_HEX *** CTOPS This code calculates the topomeric CoMFA field of each structural variation and adds it to the structural variation files. It also allows the computation and use of other than just steric fields. This Sybyl expression generator, written in C, in invoked from SPL by a call % comfa_hex (Row Column). It returns an ASCII hexadecimal representation (0–9, a–f) for each CoMFA grid point in row "Row" and CoMFA column "Column" in the string which is seen as CTOPS in the input files.

The encoding is as shown in the subroutine lookup_my_comfa_code( ). As indicated, a missing value is assigned "0" and all legitimate values are assigned a number according to their numerical value. The binning is not quite linear; since the CoMFA values are infrequently between 10 and 30 this was empirically found to reproduce the exact CoMFA distances very well. The distances arising from this CTOPS description were validated against data sets to confirm that the encoding and decoding introduced no significant round-off problems. The distance corresponding to the coded topomer field values of CTOPS are seen in the dbcsln_des routine called WhatsTheDifference( ).

Appendix G: dbcslnprepro

This program takes the description of the common core and solicits for each substituted position the SLN for the extended core. From this, and the list of structural variations, it computes the fingerprint and the fingerprint's cardinality for each structural variation and appends this as the fpcard and fp fields.

Additionally, the program creates a specified fraction of product compounds and computes their fingerprints exactly. The actual product fingerprint is compared to the fingerprint estimated from the pieces, and any discrepancy is noted by counting how many tested products have 0 missing bits, how many have 1, etc. The largest observed value is used as the MBITS parameter for the reaction. The new version of this code performs the same functions as the original code except that it writes separate files for fpcard and fp. In addition, it forms a master file to keep track of the association of all the files.

Appendix H: dbcslnsim

This program takes one or more SLN structures as queries, along with the MBITS and the desired Tanimoto similarity, and the output of the dbcslnprepro run. It produces a listing of all products which may be above the Tanimoto cutoff value, by listing the index of each structural variation and both the apparent Tanimoto and the maximum possible Tanimoto (it is the maximum possible Tanimoto which defines the results). This code now reads master files and can read bitsets output from other files.

Appendix I: dbcslnQS

This program takes the results of the dbcslnprepro program, along with the MBITS and the Tanimoto similarity neighborhood, to select a designed subset based on Tanimoto similarity alone. Additional options allow one to remove from consideration products with a parameter outside of the desired range (such as molecular weight or logP or price), and to remove all products whose enumerated fields for one or more reagents are not in a list of acceptable choices (such as supplier).

The design selection consists of first removing products from consideration based on range of variables or acceptability of reagent. An initial selection is made, normally by random selection among all remaining products. Every product whose maximum possible Tanimoto similarity is above the cutoff is removed from further consideration. A product is then selected from among all remaining products, either randomly or by rule to continue using one of the reagents (R1, R2,etc) so long as possible (so long as any product remains using that reagent). This selected product's neighbors are removed from further consideration also, and this simple loop continues until no products remain or a maximum specified number of selections have been made. The loop is simply: select, remove neighbors in Tanimoto space.

Appendix J: dbclsn_qstop

This program takes the results of the dbcslnprepro program, along with a value to define the topomeric similarity neighborhood, to select a designed subset based on topomeric similarity alone.

This program operates exactly like dbcslnQS, except that the step at which neighbors are removed is based on topomeric similarity based on the CTOPS fields of the reagents, rather than the estimate of Tanimoto similarity. Thus after a selection it scans all remaining products to find every one which has a distance within the similarity radius, and marks these neighbors as unavailable for further consideration.

(Note that this is equivalent to doing a topomeric similarity search for each selection. The results are not returned to the user, since their use is to make potential selections disappear!)

Appendix K: dbcsln_des

This program takes the results of the dbcslnprepro program, along with the MBITS and the Tanimoto similarity neighborhood, plus a value to define the topomeric similarity neighborhood to select a designed subset based on Tanimoto similarity and topomeric similarity acting independently. This corresponds closely to the method of designed subset selection in the earlier described method. This code now reads and writes master files and bitsets.

This program operates exactly like dbcslnQS, except that in addition to removing every Tanimoto neighbor of the selected compound, we also remove the topomeric neighbors. Thus after a selection it scans all remaining products to find every one which has a distance within the Tanimoto range, removes them, scans all remaining products to find every one which has a distance within the topomer range, and removes them.

This is equivalent to doing the dbcslnQS and dbclsn_qstop one after another in the innermost loop where neighbors are identified and removed. By setting either the Tanimoto or topomer neighborhood radius to be zero, one should be able to achieve the same results as dbclsn_qstop or dbcslnQS in fact.

Appendix L: dbcsln_both

This program takes the results of the dbcslnprepro program, along with the MBITS and a way to scale topomeric distance, plus a similarity cutoff for the combined descriptor of topomer and Tanimoto, to select a designed subset based on Tanimoto similarity and topomeric similarity acting as one combined descriptor.

This program operates exactly like dbcslnQS, except that the removal of neighbors is not based on either Tanimoto or topomeric distance by itself.

This utilizes the new, combined descriptor described earlier. It is not directly equivalent to either dbcslnQS or dbclsn_qstop in this sense. This code now reads and writes master files and bitsets.

Appendix M: dbcslntohits

This program takes the index results of dbcslnQS, dbclsn_qstop, dbcsln_both, dbcsln_des, or dbcslnsim and generates a full product structure SLN hitlist for them. This hitlist of products is suitable for treatment just as any set of chemical compounds—it loses its combinatorial identity as it becomes an assembly of independent chemicals. The new version of this code can now work with bitsets.

Appendix N: CODATA

This is a header file to declare variables.

Appendix O: DB_UTL

This code is a set of subroutines used in many places, and, in particular, by the design programs.

Appendix P: ELIMATE

This code is a set of subroutines used in many places, and, in particular, by the design programs.

Appendix Q: FILTER

This code contains subroutines for filtering undesired characteristics from product molecules.

Appendix R: dbcsln_bitset

This code provides the additional routines need and called by the other code to handle bitsets.

Appendix S: topsim

This code performs a topomeric CoMFA search for molecules similar to a query compound.

Appendix T: topsetup.core

This code performs the fragmentation required to implement a topomeric search of a query molecule not necessarily derived from a combinatorial synthesis.

From the proceeding description of the construction, generation, and searching of a virtual library, it should be clear that there are many variations which may be employed and, having taught how to generate and search one specific embodiment, all equivalent embodiments are considered within the scope of this disclosure.

While the preceding written description is provided as an aid in understanding, it should be understood that the source code listings appended to this application constitute a complete disclosure of the best mode currently known to the inventors of the methods of constructing and searching the virtual library and obtaining selected subsets of molecules with specified characteristics.

Thus, while this invention has been particularly described with reference to the drug lead identification art, it is clear that the validation of molecular structural descriptors and their use in selecting structurally diverse sets of chemical compounds can be applied anywhere a large number of compounds is encountered from which a representative subset is desired. Since the implications and advances in the art provided by the methods of this invention are still so new, the entire range of possible uses for the methods of this invention can not be fully described at the present time. However, such as yet identified uses are considered to fall under the teachings and claims of this invention if validated molecular structural descriptors are employed to characterize the diversity of molecules.

REFERENCES CITED

1. Seligmann, B. (1995) *Synthesis, Screening, Identification of Positive Compounds and Optimization of Leads from Combinatorial Libraries: Validation of Success*, p. 69–70. Symposium: "Exploiting Molecular Diversity: Small Molecule Libraries for Drug Discovery", La Jolla, Calif. Jan. 23–25, 1995 [conference summary available from Wendy Warr & Associates, 6 Berwick Court, Cheshire, UK CW4 7HZ]
2. Johnson, M. and Maggiora, G. (Editors) *Concepts and Applications of Molecular Similarity*, John Wiley, New York, 1990
3. Martin, E., Blaney, J., Siani, M., Spellmeyer, D., Wong, A., and Moos, W. (1995) *Measuring Diversity: Experimental Design of Combinatorial Libraries for Drug Discovery.* J. Med. Chem. 38, 1431–1436
4. Martin, E., Blaney, J., Siani, M. and Spellmeyer, D. (1995) *Measuring diversity: Experimental design of combinatorial libraries for drug discovery.* Abstract, ACS Meeting, Anaheim, Calif. COMP 32, and Martin, E. (1995) *Measuring Chemical Diversity: Random Screening or Rationale Library Design*, p. 27–30. Symposium: "Exploiting Molecular Diversity: Small Molecule Libraries for Drug Discovery", La Jolla, Calif. Jan. 23–25, 1995 [conference summary available from Wendy Warr & Associates, 6 Berwick Court, Cheshire, UK CW4 7HZ]
5. Brown, R., Bures, M., and Martin, Y. (1995) *Similarity and cluster analysis applied to molecular diversity.* Abstract, ACS Meeting, Anaheim, Calif. COMP 3
6. Herndon, W. (1995). *Similarity and Dissimilarity of Molecular Structures.* p. 25–27. Symposium: "Exploiting Molecular Diversity: Small Molecule Libraries for Drug Discovery", La Jolla, Calif. Jan. 23–25, 1995 [conference summary available from Wendy Warr & Associates, 6 Berwick Court, Cheshire, UK CW4 7HZ]
7. Chapman, D. and Ross, M. (1994) Poster at the symposium: "Chemical and Biomolecular Diversity", San Diego, Calif. Dec. 14–16, 1994, and Ross, M. (1995) *Assessing Diversity (Or Lack Of It) in Chemical Libraries.* p. 63–65. Symposium: "Exploiting Molecular Diversity: Small Molecule Libraries for Drug Discovery", La Jolla, Calif. Jan. 23–25, 1995 [conference summary available from Wendy Warr & Associates, 6 Berwick Court, Cheshire, UK CW4 7HZ]
8. Cramer, R., Redl, G., and Berkoff, C. (1974) *Substructural Analysis: A Novel Approach to the Problem of Drug Design.* J. Med. Chem. 17, 533
9. U.S. Pat. No. 5,025,388 (1988) and Cramer, Patterson, D., and Bunce, J. (1988) *Comparative Molecular Field Analysis (CoMFA). Effect of Shape on Binding of Steroids to Carrier Proteins.* J. Am Chem. Soc. 110, 5959–5967
10. Kubinyi, H. Editor (1993) 3D QSAR in *Drug Design, Theory, Methods, and Applications.* ESCOM, Leiden, Holland
11. Dean, P. Editor (1995) *Molecular Similarity in Drug Design.* Chapter 12, Kim, K. *Comparative molecular field analysis (ComFA).* p. 291–324. Chapman & Hill, London, UK
12. Y. Martin, M. Bures, E. Danaher, J. DeLazzer, I. Lico, P. Pavlik (1993) *A Fast Approach to Pharmacophore Mapping and its Application to Dopaminergic and Benziodiazepine Agonists.* J. Comp.-Aid. Mol. Des. 7, 83–102
13. P. Willett, V. Winterman (1986) *A comparison of some measures for the determination of intermolecular structural similarity.* Quantitative Structure-Activity Relationships 5, 18–23
14. R. P. Sheridan, R. B. Nachbar, B. L. Bush (1994) *Extending the trend vector: The trend matrix and sample-based partial least squares.* J. Comp.-Aid. Mol. Des. 8, 323–340
15. G. Moreau, P. Broto (1980) (no title given). Nouv. J. Chim. 4, 757–7644
16. L. B. Kier, L. H. Hall (1976) *Molecular Connectivity in Chemistry and Drug Research.* Academic Press, NY
17. Georges Lauri, Paul A. Bartlett (1994) CAVAT: *A Program to Facilitate the Design of Organic Molecules.* J. Comp.-Aid. Mol. Des. 8, 51–66

APPENDIX "A"

```

@expression_generator CHOM_THIS_BUILD_3D
#================================================
=================================================
# top level routine for generating topomeric conformer
# CHOM!INIT_BIULD_3D must be called beforehand
# returns true unless something went wrong

globalvar CHOM!Align
localvar ma msav rid pat tpat p sln noth zs a1 n capsln \
        polypat patats mpats allpatats
localvar polyats mat1 mat2 schns rbs sybat aneigh ans i \
        mcore jbds tors msln
   setvar ma $1
   setvar rid $3
   setvar capsln $CHOM!Align[ SLN ]
   setvar polypat $CHOM!polypat
   setvar mcore $CHOM!Align[ MINIT ]
   setvar msln $CHOM!Align[ MSLN ]
# fix NO2's (egad what a pain)
   setvar pat %search2d( %sln( $ma ) N(=O)O ALL 0 y )
   while $pat
      setvar pat %sln_rgroup_sybid( $ma %arg( 1 $pat ) 1 3 )
      modify bond type %bonds( %cat( %arg( 1 $pat ) \
           "=" %arg( 2 $pat ) ) ) 2 >$nulldev
      modify atom type %arg( 2 $pat ) o.2 >$nulldev
      setvar pat %search2d( %sln( $ma ) N(=O)O ALL 0 y )
   endwhile
   if $CHOM!Align[DEBUG]
      label id *
   endif
# basic optimization
```

```
switch $2
case NOBUILD)
   ;;
case CONCORD)
   if %not( %chom_concord( $ma ))
        goto bad_energy
   endif
   ;;
case MINIMIZE)
   MAXIMIN $ma DONE INTERACTIVE >$nulldev
   if %gt( $maximin2_energy 1000 )
        goto bad_energy
   endif
   ;;
endswitch
setvar CHOM!Align[ RBDS ]
# done, if only 3d coord, but for CoMFA ..
if %streql( $4 "A" )
# detect (pro)chiral atoms for adjustment, adjusting and
#      removing any of pre-defined chirality
   setvar CHOM!Align[CHIRAL] %set_create( %atoms({chiral(*,RS)}) )
# find a 2D hit
   setvar pat %search2d( %cat( %sln( $ma ) ) $capsln NoDup 0 y )
   if %not( $pat )
      echo $capsln not found in %sln( $ma ) from Row $rid .. skipping
      return
   endif
   setvar pat %arg(1 $pat )
# now find the (first) pattern that matches the aligning fragment AND whose
# atoms are contained by this SLN hit
   setvar allpatats %set_create( %sln_rgroup_sybid( \
        $ma $pat %range( 1 %sln_atom_count( $capsln ) ) ) )
   setvar mpats %search2d( %cat( %sln( $ma ) ) $msln NoDup 0 y )
```

```
    for pat in $mpats
        if %not( %set_diff( %set_create( %sln_rgroup_sybid( $ma $pat \
            %range( 1 %sln_atom_count( $capsln ) ) ) ) $allpatats ) )
            break
        endif
    endfor
    setvar polyats %set_create( %sln_rgroup_sybid( $ma $pat $polypat ) )
# allow user supplied routine to adjust initial conformer
    if $CHOM!Align[ FIX_CF_CALLBACK ]
        $CHOM!Align[ FIX_CF_CALLBACK ] $ma $allpatats
    endif
# collect all atoms for MATCH and
# and all the info on roots of torsions needing setting
#              ( = = all bonds to atoms that are
# polyvalent within the aligning fragment, except bonds that are (1)
# in rings or (2) connected to some other atom polyvalent within the
# aligning fragment).
    setvar mat1
    setvar mat2
    setvar schns
    setvar rbds %set_create( %bonds({rings()}) )
    for a in %range( 1 %sln_atom_count( $msln ) )
        setvar mat1 $mat1 $CHOM!patats[ $a ]
        setvar sybat %sln_rgroup_sybid( $ma $pat $a )
        setvar mat2 $mat2 $sybat
# build torsion root lists
        if %set_and( $sybat "$polyats" )
            setvar aneigh %set_create( %atom_info( $sybat NEIGHBORS ) )
            setvar ans %set_diff( $aneigh $polyats )
            for i in %set_unpack( "$ans" )
                if %eq( %count( %atom_info( $i NEIGHBORS ) ) 1 )
                    goto notoroot
                endif
```

```
            if $rbds
                if %set_and( $rbds %bonds( %cat( $i "=" $sybat ) ) )
                    goto notoroot
                endif
            endif
            setvar tors %set_diff( $aneigh $i )
# if there are multiple possible torsional root,
#       get one that is part of the root main chain
            if %gt( %set_size( "$tors" ) 1 )
                if %set_and( "$tors" $polyats )
                    setvar tors %set_and( $tors $polyats )
                endif
            endif
# if there are still multiple choices, just have to pick arbitrarily
            if $tors
                setvar tors %arg( 1 %set_unpack( $tors ) )
                setvar schns $schns %cat( $sybat "," $tors "," $i )
            endif
notoroot:
            endfor
        endif
    endfor
    setvar dofit MATCH %cat( $mcore "(" %set_create( $mat1 ) ")" ) \
        %cat( $ma "(" %set_create( $mat2 ) ")" )
    $dofit >$nulldev
if $CHOM!Align[DEBUG]
    echo %prompt( INT 1 " " " " )
endif
# do FIT
    if %gt( $MATCH_RMS $CHOM!Align[ FITRMS ] )
        setvar CHOM!BadRows %set_or( "$CHOM!BadRows" $rid )
        echo Bad geometric alignment (MATCH_RMS = $MATCH_RMS) \
            for Row $rid .. skipping
```

```
        return
    endif
# side chain alignments ..
    switch $CHOM!Align[ ALICYC ]
case User_Macro)
        $CHOM!Align[ ALIDATA ] $ma $CHOM!ALIGN[ MCORE ]
;;
case All_trans)
case With_Templates)
        setvar nojrings TRUE
        for i in $schns
            setvar jbds %set_unpack( $i )
# can set "side chain" bonds only if connecting bond is not cyclic
            if %set_and( "$rbds" "%bonds( %cat( %arg( 3 $jbds ) \
                = %arg( 1 $jbds ) ) )" )
                setvar nojrings
            else
                CHOM!AllTrans $jbds
            endif
        endfor
if $CHOM!Align[DEBUG]
  echo %prompt( INT 1 " " " " )
endif
        if %streql( $CHOM!Align[ ALICYC ] With_Templates )
            setvar f %open( $CHOM!Align[ ALIDATA ] "r" )
            setvar buff %read( $f )
            setvar slnma %cat( %sln( $ma ) )
            while $buff
# each line of text should have pattern, SLN IDs for the 4 torsion atoms,
#           and a torsion value to set
                if %eq( %count( $buff ) 5 )
                    setvar torpat %search2d( $slnma %arg( 1 $buff ) NoDup 0 y )
                    for t in $torpat
```

```
                MODIFY TORSION %sln_rgroup_sybid( $ma $t %arg( 2 $buff ) \
                    %arg( 3 $buff ) %arg( 4 $buff ) ) %arg( 5 $buff ) >$nulldev
                endfor
            endif
          endwhile
          %close( $f )
        endif
  ;;
    endswitch
  endif
# do a bump check?
  if $CHOM!Align[BUMPS]
     if %atoms({bumps(*,*)})
        echo Bad steric contacts in aligned conformer for \
            Row $rid .. skipping
        return
     endif
  endif
# partial charges ..
  switch $CHOM!Align[ CHARGE ]
case None)
 ;;
case User_Macro)
     exec $CHOM!Align[ CHARGEDATA ] $ma
 ;;
case )
     CHARGE $ma COMPUTE $CHOM!Align[ CHARGE ] | >$nulldev
 ;;
  endswitch
  %return( TRUE )
  return
bad_energy:
  echo Minimization failed -- skipping molecule
```

```
    return
.
#=================================================
=========================================
@macro ALLTRANS chom
# assumes default molecule, takes argument atoms $1 and $2
# where $1 is the JOINed atom of the core, $2 is the atom that
#   the rest of the substituent is to be trans to,
#   and $3 is the JOINed atom of the substituent
# starts from that atom and sets all side chains
#   to a trans conformation
# where choices exist, the largest chain is set to trans
#   and secondary chains "fall whereever they fall"
# manages chain branchings
# ignores ring bonds
globalvar CHOM!Err CHOM!Align
localvar bds b bdset a1 a2 tmp sbonds sats rbond pbds torsion ringbonds
localvar doit chir cats rgjoined b2set tval
if %and( "$batch" "$CHOM!Err" )
    RETURN
endif
# warn if angles will be ambiguous
#   setvar chir %set_create( %atoms({chiral(*,RS)}) )
# check input for legality
    setvar tmp %set_create( %atom_info( $1 NEIGHBORS ) )
    if %not( %eq( 2 %count( %set_unpack( %set_and( \
            "$tmp" %cat( $2 "," $3 ) ) ) ) ) )
      echo Bad input to ALLTRANS (atoms $2 $3 not bonded to $1)
      return
    endif
# save key bonds
    setvar rbond %bonds( %cat( $3 "=" $1 ) )
    setvar sats %conn_atoms( $3 $1 )
```

```
    if %not( $sats )
#      echo No substituent atoms found in ALLTRANS
       return
    endif
    setvar sats $3 $sats
    setvar sbonds %set_create( %bonds( %cat( \
              "{TO_ATOMS(" %set_create($sats) ")}" )) )
# define the other bonds that might need adjusting
    setvar bds %set_create( %bonds( (*-{RINGS()})&<1> ) )
    setvar bds %set_and( "$sbonds" "$bds" )
    if %not( $bds )
       return
    endif
# discard bonds to primary atoms
    setvar mval %set_create( %atoms( \
         <H>+<o.2>+<F>+<I>+<Cl>+<Br>+<n.1>+<LP>+<Du> ) )
    setvar pds %set_create( %bonds( %cat( "{TO_ATOMS(" $mval ")}" ) ) )
    setvar bds %set_diff( $bds $pds )
    setvar CHOM!Align[ RBDS ] %set_or( $bds "$CHOM!Align[ RBDS ]" )
    setvar ringbonds %set_create(%bonds({RINGS()}) )
# walk all the important bonds
 for b in %set_unpack( $bds )
    setvar doit TRUE
# if this is the JOIN bond, already have some info
    if %eq( $b $rbond )
     setvar a0 $2
     setvar a1 $1
     setvar a2 $3
# still need to be SURE we're not monovalent
     if %or( "%eq( 1 %count( %atom_info( $a1 NEIGHBORS ) ) )" \
           "%eq( 1 %count( %atom_info( $a2 NEIGHBORS ) ) )" )
        setvar doit
     endif
```

```
    else
      setvar bdat %bond_info( $b ORIGIN TARGET )
      setvar a1 %arg( 1 $bdat )
      setvar a2 %arg( 2 $bdat )
      if %or( "%eq( 1 %count( %atom_info( $a1 NEIGHBORS ) ) )" \
              "%eq( 1 %count( %atom_info( $a2 NEIGHBORS ) ) )" )
        setvar doit
      endif
      if $doit
# which end leads to root atom? if necessary flip a1,a2 to make that one be a1
        if %set_and( "%set_create( %conn_atoms( $a2 $a1 ) )" $1 )
          setvar tmp $a1
          setvar a1 $a2
          setvar a2 $tmp
        endif
        setvar a0path %trans_path( $a1 $a2 $1 )
        setvar a0 %arg( 1 $a0path )
      endif
    endif
    if $doit
      setvar a3path %trans_path( $a2 $a1 $CHOM!ALIGN[ attached ] )
      setvar a3 %arg( 1 $a3path )
      setvar b2set %bonds( %cat( $a0 "=" $a1 "," $a2 "=" $a3 ) )
      setvar rgjoined %set_and( "$ringbonds" %set_create( $b2set ) )
      setvar nrgjoined %count( %set_unpack( "$rgjoined" ) )
      setvar b2 %arg( 2 $b2set )
      if %eq( 0 $nrgjoined )
        setvar torsion 180
      else
        if %eq( 1 $nrgjoined )
              setvar torsion 90
        else
              setvar torsion 60
```

```
        endif
      endif
      modify torsion $a0 $a1 $a2 $a3 $torsion >$nulldev
      if %set_and( "$cats" $a2 )
        MEASURE TORSION %arg( 2 $a3path ) $a1 $a2 $a3 >$nulldev |
        setvar torsion $measure_torsion
        while %lt( $torsion 0 )
              setvar torsion %math( $torsion + 360 )
        endwhile
        if %gt( 180 $torsion )
           CHOM!Reflect $a2 $a1 %arg( 1 $a3path ) \
                %arg( 2 $a3path ) %arg( 3 $a3path )
        endif
      endif
      setvar CHOM!Align[ CHIRAL ] %set_diff( "$CHOM!Align[ CHIRAL ]" $a2 )
    endif
  endfor
#.
@macro Reflect CHOM
#==========================================================
======================
# does a controlled inversion, to convert prochiral atom to topmeric sterreoform
localvar arefl
  DEFINE PLANE %cat( $1 "," $2 "," $3 ) P1 "" >$nulldev
  setvar arefl $4
  setvar arefl %set_or( $arefl "%set_create( %conn_atoms( $4 $1 ) )" )
  if $5
       setvar arefl %set_or( $arefl $5 )
       setvar arefl %set_or( $arefl "%set_create( %conn_atoms( $5 $1 ) )" )
  endif
  REFLECT $arefl P1 >$nulldev
  REMOVE PLANE M* P1 >$nulldev
#.
```

@expression_generator CHOM_CONCORD

========================================================================== does its best to generate a concord structure for the specified workarea localvar ma p pat msav noth try setvar ma $1 fix indole atom typing problem setvar pat %search2d( %sln( $ma ) NH(:C):C ALL 0 y )

for p in $pat setvar tpat %sln_rgroup_sybid( $ma $p 1 )

modify atom only $tpat N.ar 1 >$nulldev endfor renumber heavy atoms to avoid other problems echo before renumber: %sln( $ma )

setvar mrenum %molempty()

renumber $ma $mrenum %atoms( *-<H> ) >$nulldev | copy $mrenum $ma zap $mrenum setvar msav %molempty()

copy $ma $msav setvar nats %mol_info( $ma NATOMS )

DEFAULT $ma >$nulldev for try in %range( 1 3 )

CONCORD M $ma >$nulldev

Concord can return bond-less structures! or some different structure or do nothing setvar cok TRUE if %not( %eq( %mol_info( $ma NATOMS ) $nats ) )

setvar cok endif if %eq( 0 %mol_info( $ma NBONDS ) )

setvar cok endif if $cok

```
        setvar noth %arg( 1 %atoms( <H> ) )
        if $noth
            measure distance $noth %atom_info( $noth NEIGHBORS ) >$nulldev |
            setvar cok %gt( $measure_distance 0.9 )
        endif
    endif
    if $cok
        break
    endif
    echo Concord failed try $try
#echo %prompt( INT 2 "" "" )
    copy $msav $ma
endfor
    if %not( $cok )
        if %not( $CHOM!Align[ FAST ] )
        echo Concord failed for %sln( $ma ) -- minimizing
        copy $msav $ma
        for try in %range( 1 4 )
            MAXIMIN $ma DONE INTERACTIVE
            if %lt( $maximin2_energy 1000 )
                break
            endif
            %file_delete( junk.his ) >$nulldev
            DYNAMICS m1 SETUP junk.his DONE Interval_Length \
                300.0 DONE FINISHED INTERACTIVE
            if %eq( $try 3 )
                zap $msav
                return
            endif
        endfor
    else
        echo Skipping non-Concord structure
        zap $msav
```

```
            return
        endif
    endif
    zap $msav
    if $CHOM!Align[ CORE_SLN ]
# need to find and record other attachment point for trans_path --
#                standard aligning group
        setvar args $CHOM!Align[ CORE_SLN ]
        setvar msln %string_insert( %arg( 1 $args ) \
            %arg( 3 $args ) %arg( 2 $args ) )
        setvar msln %string_insert( $msln %arg( 4 $args ) R1 )
# can't begin SLN with (
        if %eq( 1 %pos( "(CH2" $msln ) )
            setvar msln %cat( "CH2(" %substr( $msln 5 ) )
        endif
        setvar rid %sln_rgroup_slnid( $msln )
        setvar hit %search2d( %sln( $ma ) $msln NoDup 1 y )
        if %not( $hit )
            while %pos( ":" $msln )
                setvar msln %string_insert( $msln ":" "~" )
            endwhile
            setvar hit %search2d( %sln( $ma ) $msln NoDup 1 y )
        endwhile
        setvar rats %sln_rgroup_sybid( $ma $hit $rid )
        if %not( $rats )
            echo Pattern $msln not found in %sln( $ma ) -- missing core attachment
            return
        endif
        for cat in %set_unpack( $rats )
            if %gt( %count( %atom_info( $cat NEIGHBORS ) ) 1 )
                break
            endif
        endfor
```

```
        setvar CHOM!Align[ ATTACHED ] %set_create( $cat \
            %set_diff( %set_create( %atom_info( $cat NEIGHBORS ) ) $rats ) )
    endif
    %return( TRUE )
#.
@macro INIT_BUILD_3D CHOM
#==========================================================================
# prepare and generate global data about template fragment
globalvar CHOM!patats CHOM!polypat
localvar mcore msln capsln patats ys rat yrat nrat tpat a
# setvar mcore $CHOM!Align[ MCORE ]
    if $1
        setvar mcore $1
    else
        setvar mcore %molempty()
    endif
    default $mcore >$nulldev
    if $CHOM!Align[DEBUG]
        label id *
    endif
    setvar capsln $CHOM!Align[ SLN ]
# use as is
if $CHOM!Align[ ORIENT ]
# orient template so that an R points in the positive X direction
    setvar ys %set_unpack( $CHOM!Align[ ORIENT ] )
    setvar rat %arg( 1 $ys )
    setvar nrat %arg( 2 $ys )
    setvar yrat %arg( 3 $ys )
    ORIENT USER $rat $nrat $yrat >$nulldev
endif
# identify all the atoms for FIT,
# Here we identify the SLN IDs of the polyvalent atoms
```

```
setvar tpat %arg( 1 %search2d( $capsln $capsln NoDup 0 y ) )
setvar polypat
setvar CHOM!patats
echo %sln_to_mol( $mcore $capsln ) >$nulldev
for a in %range(1 %sln_atom_count( $capsln ) )
    setvar CHOM!patats[ $a ] %sln_rgroup_sybid( $mcore $tpat $a )
    if %gt( %count( %atom_info( $CHOM!patats[ $a ] NEIGHBORS ) ) 1 )
        setvar polypat $polypat $a
    endif
endfor
if $CHOM!Align[DEBUG]
 echo %prompt( INT 1 " " " " )
endif
 copy $CHOM!Align[ MCORE ] $mcore
 zap $CHOM!Align[ MCORE ]
 setvar msln %sln( $mcore )
  setvar CHOM!polypat $polypat
  setvar CHOM!Align[ MINIT ] $mcore
  setvar CHOM!Align[ MSLN ] $msln
#.
II-C
/*#module SYB_MGEN_CONN_ATOMS "V1.0"*/
#include <ctype.h>
#include <string.h>
#include <stdio.h>
#include "ta_config.h"
#include "ta_types.h"
#include "utl_mem.h"
#include "uims2.h"
#include "ta_math.h"
#include "utl_geom.h"
#include "utl_str.h"
#include "molecule.h"
```

```
#include "utl_list.h"
#include "syb_uims_def.h"
#include "uims2/macros_proto.h"
#include "syb/expr_p.h"
#include "syb/area_p.h"
#include "syb/atab_p.h"
#include "syb/atom_p.h"
#include "uims2_p.h"
#include "utl_set.h"
/*E+:SYB_MGEN_CONN_BEST*/
/**************************************************************
* int SYB_MGEN_CONN_BEST( identifier, nargs, args, writer )   *
*       Dick Cramer, Apr. 9, 1995 (written for SELECTOR use)  *
*                                                             *
* Expression generator that returns the atoms attached to a given *
*       atom, excepting the second, in a prioritized order.   *
* If there are two arguments, the ordering is by decreasing branch *
*       "size", where "size" is first any path with rings encountered, then
* number of attached atoms, then MW (paths in cycles end when an atom
* in another path is encountered.)
*     If three arguments, the atom that is returned is the one that
* begins the shortest path containing either of up
* to two atoms referred to by the
* third argument. If multiple such paths, ordering is same as for
* two arguments.
*     If last argument is DEBUG, all paths are written to stdout.
*
* User interface:
*     %trans_path( a1 a2 ( a3 ) (DEBUG) )
**************************************************************/
int SYB_MGEN_CONN_BEST( identifier, nargs, args, Writer )
char    *identifier;
int     nargs;
```

```
char    *args[];
PFI     Writer;
{
# define MAX_NP   8
        struct pathrec {
            int root, nrings, chosen, nats, done;
            float mw;
            set_ptr path;
            atom_ptr a;
        } ;
        struct pathrec p[MAX_NP];
        int retval, i, np, toroot, a1, a2, a4, a5, a, pnow, pdone, growing,
            final_pos, area_num, new_rings, nats, nuats, elem, ncycles,
            best, debug, ringclosed, p2do;
        List_Ptr  atom_exp_list=NIL;
        mol_ptr   m1, m2;
        atom_ptr  arec1, arec2, arec, a4rec;
        set_ptr   atom_set1=NIL, a2chk = NIL, nu1s = NIL, cnats = NIL,
                  nxcn = NIL, end_atoms = NIL, scratch = NIL;
        char      tempString[256];
        float     t1, t2, diff, pot1, pot2, podiff;
        retval = 0;
        /* Check the number of arguments */
        if ( nargs < 2 || nargs > 4 ) {
            UIMS2_WRITE_ERROR(
                "Error: %trans_path requires 2 to 4 arguments\n" );
            return 0;
        }
        np = 0;
        debug = (!UTL_STR_CMP_NOCASE( args[ nargs - 1], "DEBUG" ));
        toroot = (debug && nargs == 4) || (!debug && nargs == 3);
/* PARSE THE INPUT */
/* get first atom */
```

```c
        if (!(atom_exp_list = SYB_EXPR_ANALYZE( SYB_EXPR_GET_ATOM_TOKEN,
args[0],
                &final_pos, &area_num )))
            goto error;
        if (!(m1 = SYB_AREA_GET_MOLECULE (area_num)))
            goto cleanup;
        if (!(atom_set1 = SYB_ATOM_FIND_SET ( m1, atom_exp_list)))
            goto error;
        if( atom_exp_list)
                SYB_EXPR_DELETE_RPN_LIST( atom_exp_list);
        atom_exp_list = (List_Ptr) NIL;
        if(!(1 == UTL_SET_CARDINALITY(atom_set1))) {
                UIMS2_WRITE_ERROR(
                    "Error: First argument must be only one atom\n");
                goto error;
        }
        if (!(arec1 = SYB_ATOM_FIND_REC (m1, UTL_SET_NEXT (atom_set1, -1)) )) goto
error;
        a1 = arec1->recno;
        UTL_SET_DESTROY( atom_set1 );
        atom_set1 = NIL;
/* get 2nd atom */
        if (!(atom_exp_list = SYB_EXPR_ANALYZE( SYB_EXPR_GET_ATOM_TOKEN,
args[1],
                &final_pos, &area_num )))
            goto error;
        if (!(m2 = SYB_AREA_GET_MOLECULE (area_num)))
            goto cleanup;
        if (!(end_atoms = SYB_ATOM_FIND_SET ( m2, atom_exp_list)))
            goto error;
        if( atom_exp_list)
                SYB_EXPR_DELETE_RPN_LIST( atom_exp_list);
        atom_exp_list = (List_Ptr) NIL;
```

```
if (m1 != m2 ) {
        UIMS2_WRITE_ERROR(
            "Error: atoms must be in the same molecule\n");
        goto error;
}
if(!(1 == UTL_SET_CARDINALITY(end_atoms))) {
        UIMS2_WRITE_ERROR(
            "Error: Second argument must be only one atom\n");
        goto error;
}
    if (!(arec2 = SYB_ATOM_FIND_REC (m1, UTL_SET_NEXT (end_atoms, -1)) )) goto
error;
    a2 = arec2->recno;
/* get 3rd atom */
 if (toroot) {
    if (!(atom_exp_list = SYB_EXPR_ANALYZE( SYB_EXPR_GET_ATOM_TOKEN,
args[2],
        &final_pos, &area_num )))
        goto error;
    if (!(m2 = SYB_AREA_GET_MOLECULE (area_num)))
        goto cleanup;
    if (!(atom_set1 = SYB_ATOM_FIND_SET ( m2, atom_exp_list)))
        goto error;
    if( atom_exp_list)
        SYB_EXPR_DELETE_RPN_LIST( atom_exp_list);
    atom_exp_list = (List_Ptr) NIL;
    if (m1 != m2 ) {
        UIMS2_WRITE_ERROR(
            "Error: atoms must be in the same molecule\n");
        goto error;
    }
    if (2 < UTL_SET_CARDINALITY(atom_set1)) {
        UIMS2_WRITE_ERROR(
```

```
                "Error: Second argument must be no more than two atoms\n");
            goto error;
        }
        a4 = a5 = -1;
        elem = UTL_SET_NEXT (atom_set1, -1);
        if (!(arec = SYB_ATOM_FIND_REC (m1, elem) )) goto error;
        a4 = arec->recno;
        if ((elem = UTL_SET_NEXT (atom_set1, elem) ) != -1) {
            if (!(arec = SYB_ATOM_FIND_REC (m1, elem) ))  goto error;
            a5 = arec -> recno;
        }
        UTL_SET_DESTROY( atom_set1 );
        atom_set1 = NIL;
    }
/* GENERATE the paths */
/* set up paths */
    if (!(a2chk = UTL_SET_CREATE( m1->max_atoms + 1 ) )) goto error;
    if (!(nuls  = UTL_SET_CREATE( m1->max_atoms + 1 ) )) goto error;
    if (!(cnats = UTL_SET_CREATE( m1->max_atoms + 1 ) )) goto error;
    if (!(nxcn = UTL_SET_CREATE( m1->max_atoms + 1 ) )) goto error;
    if (!(scratch = UTL_SET_CREATE( m1->max_atoms + 1 ) )) goto error;
    if (!syb_mgen_conn_att_atoms( a2chk, m1, a1 )) goto error;
    if (!UTL_SET_MEMBER( a2chk, a2 )) {
        UIMS2_WRITE_ERROR (
            "Error: second argument atom is not bonded to first argument atom/\n");
        goto error;
    }
    UTL_SET_DELETE( a2chk, a2 );
    a = -1;
    np = 0;
    while (np < MAX_NP && (a = UTL_SET_NEXT( a2chk, a)) >= 0 ) {
        if (!(p[np].path = UTL_SET_CREATE( m1->max_atoms + 1 ) )) goto error;
        p[np].root = a;
```

```
      p[np].nrings = p[np].done = 0;
      UTL_SET_INSERT( p[np].path, a );
      if (!(p[np].a = SYB_ATOM_FIND_REC (m1, p[np].root) )) goto error;
      np++;
    }
    /* grow the paths */
    growing = TRUE;
    nats = 0;
    ncycles = 0;
    while (growing ) {
      nuats = 0;
      ringclosed = FALSE;
      for (pnow = 0; pnow < np; pnow++ ) if (!p[pnow].done) {
        UTL_SET_COPY_INPLACE( cnats, p[pnow].path );
        UTL_SET_CLEAR( nxcn );
        elem = -1;
        /* accumnulate this generation of attached atoms into nxcn */
        while ( (elem = UTL_SET_NEXT( cnats, elem)) >= 0 ) {
          UTL_SET_CLEAR( nuls );
          if (!syb_mgen_conn_att_atoms( nuls, m1, elem )) return( FALSE );
          UTL_SET_DELETE( nuls, a1 );
          UTL_SET_DIFF_INPLACE( nuls, end_atoms, nuls );
          UTL_SET_OR_INPLACE( nxcn, nuls, nxcn );
          UTL_SET_DIFF_INPLACE( nxcn, p[pnow].path, nxcn );
        }
        UTL_SET_OR_INPLACE( p[pnow].path, nxcn, p[pnow].path );
        if (toroot) if ((UTL_SET_MEMBER( p[pnow].path, a4 ))
             || ( a5 > -1 && UTL_SET_MEMBER( p[pnow].path, a5 ))) p[pnow].done =
TRUE;
    /* remove and mark ring closures when growing out */
        if (!toroot) for (pdone = 0; pdone < np; pdone++ ) if (pdone != pnow) {
          UTL_SET_AND_INPLACE( p[pnow].path, p[pdone].path, a2chk );
          if ((new_rings = UTL_SET_CARDINALITY( a2chk ))) {
```

```c
            /* we have ring closure(s) */
            p[pnow].nrings += new_rings;
            p[pdone].nrings += new_rings;
            ringclosed = TRUE;
            UTL_SET_OR_INPLACE( end_atoms, a2chk, end_atoms );
    /* if pdone < pnow, two branches are now same lengths, drop common atom from both;
       but if >, branches are different, and must avoid repeated closing */
            if (pdone < pnow) {
    /* remove atom(s) in the previous branch because paths are really same length */
                UTL_SET_DIFF_INPLACE( p[pdone].path, a2chk, p[pdone].path );
                UTL_SET_DIFF_INPLACE( p[pnow].path, a2chk, p[pnow].path );
            }
            else {
    /* must identify and mark each atom in nxcn that is attached to a2chk atom */
                elem = -1;
                while ( (elem = UTL_SET_NEXT( a2chk, elem)) >= 0 ) {
                    UTL_SET_CLEAR( scratch );
                    if (!syb_mgen_conn_att_atoms( scratch, m1, elem ))
                        return( FALSE );
                    UTL_SET_AND_INPLACE( scratch, nxcn, scratch );
                    UTL_SET_OR_INPLACE( end_atoms, scratch, end_atoms );
                }
            }
        }
       }
      }
     }
    }
    /* done growing paths if no more atoms added to any path .. */
    for (pdone = 0, nuats = 0; pdone < np; pdone++ )
        nuats += UTL_SET_CARDINALITY( p[pdone].path );
    if (nuats<=nats && !ringclosed) growing = FALSE;
    nats = nuats;
    /* .. or after 100 atom layers out regardless */
    ncycles++;
```

```
            if (ncycles >= 100) growing = FALSE;
        }
        /* debugging */
        if (debug) for (pdone = 0; pdone < np; pdone++) {
            sprintf( tempString, "Path %d (%d rings, from %d): ",
                pdone+1, p[pdone].nrings, p[pdone].root );
            UBS_OUTPUT_MESSAGE( stdout, tempString );
            ashow( p[pdone].path, m1 );
        }
    /* compute the path properties */
    for (pdone = 0; pdone < np; pdone++) {
        p[pdone].chosen = toroot && (UTL_SET_MEMBER(p[pdone].path, a4)
            || ( a5 > -1 && UTL_SET_MEMBER( p[pdone].path, a5 )));
        p[pdone].nats = UTL_SET_CARDINALITY( p[pdone].path );
        p[pdone].nrings = p[pdone].nrings ? 1 : 0;
        p[pdone].mw = 0.0;
        p[pdone].done = 0;
    }
    /* return all root atoms, ordered best to worst */
    for (p2do = 0; p2do < np; p2do++ ) {
        for (pdone = 0; pdone < np; pdone++) if (!p[pdone].done) {
            best = pdone;
            break;
        }
        for (pdone = 0; pdone < np; pdone++) if (!p[pdone].done && pdone != best) {
            if (!p[best].chosen && p[pdone].chosen) best = pdone;
            if (p[best].chosen == p[pdone].chosen) {
                if (p[pdone].nrings && !p[best].nrings) best = pdone;
                else if (((!p[best].chosen && (p[pdone].nats > p[best].nats)) ||
                    (p[best].chosen && (p[pdone].nats < p[best].nats))) best = pdone;
                else if (p[pdone].nats == p[best].nats) {
                    p[pdone].mw = get_path_mw( p[pdone].path, m1, p[pdone].mw );
                    p[best].mw = get_path_mw( p[best].path, m1, p[best].mw );
```

```
            if (p[pdone].mw > p[best].mw) best = pdone;
            else if (p[pdone].mw == p[best].mw) {
/* checking relative geometries of attachments via "improper" torsion */
/* the phenyl ether problem -- if candidates are 180 degrees apart and we are on the
root side of the torsion, pick the atom to the "right", not the "left", of the main chain */
                if (toroot) {
/* are we 180 apart? */
                    if (!( a4rec = SYB_ATOM_FIND_REC (m1, a4 )) ) goto error;
                    pot1 = UTL_GEOM_TAU ( a4rec->xyz, arec1->xyz, arec2->xyz,
p[best].a->xyz );

pot2 = UTL_GEOM_TAU ( a4rec->xyz, arec1->xyz, arec2->xyz,
p[pdone].a->xyz );

podiff = pot1 - pot2;
                    while (podiff < 0.0) podiff += 360.0;
                    while (pot2 < 0.0) pot2 += 360.0;
                    if (podiff < 190.0 && podiff > 170.0 && pot2 < 180.0)
                        best = pdone;
                }
                if (best != pdone) {
/* if not already set, according to the previous special case, then */
/* if torsions differ by 360 degrees then we have trans, prefer the +180 */
                    t1 = UTL_GEOM_TAU ( p[pdone].a->xyz, arec1->xyz, arec2->xyz,
p[best].a->xyz );
                    t2 = UTL_GEOM_TAU ( p[best].a->xyz, arec1->xyz, arec2->xyz,
p[pdone].a->xyz );
                    diff = t1 - t2;
                    if (diff > 355.0) best = pdone;
                    else if (diff > -355.0) {
                        while (t1 < 0.0) t1 += 360.0;
                        if (t1 > 170.0 && t1 <= 350.0) best = pdone;
                    }
                }
            }
```

```
            }
          }
        }
        arec = SYB_ATOM_FIND_REC( m1, p[best].root );
        sprintf(tempString,"%d ", arec->id );
        if(!(*Writer)(tempString)) goto error;
        p[best].done = TRUE;
    }
    retval = TRUE;
error:
cleanup:
    if( atom_exp_list)
        SYB_EXPR_DELETE_RPN_LIST( atom_exp_list);
    if(atom_set1)
        UTL_SET_DESTROY(atom_set1);
    if(end_atoms)
        UTL_SET_DESTROY(end_atoms);
    if(a2chk)
        UTL_SET_DESTROY(a2chk);
    if(nuls)
        UTL_SET_DESTROY(nuls);
    if(nxcn)
        UTL_SET_DESTROY(nxcn);
    if(cnats)
        UTL_SET_DESTROY(cnats);
    if(scratch)
        UTL_SET_DESTROY(scratch);
    return( retval );
}
static int syb_mgen_conn_att_atoms( aset, m, atid )
/* ors atoms attached to atm into aset */
/* WORKS STRUCTLY WITH RECNOS */
set_ptr aset;
```

```
mol_ptr m;
int atid;
{
  atom_ptr at;
  List_Ptr tohs;
  atom_ptr toh;
  acon_ptr conn1;
  unsigned nbytes1;
  at = SYB_ATOM_FIND_REC( m, atid );
  tohs = at->conn_atom;
  while (tohs) {
      tohs = UTL_LIST_RETRIEVE_P( tohs, &conn1, &nbytes1);
      toh = SYB_ATOM_FIND_REC( m, conn1->target );
      UTL_SET_INSERT( aset, toh->recno );
  }
  return( TRUE );
}
static float get_path_mw( aset, m, mw )
/* returns the total atomic weight of all atoms in aset */
set_ptr aset;
mol_ptr m;
float mw;
{
  int elem = -1;
  float ans = 0.0;
  atom_ptr at;
  if (mw) return( mw );
  elem = -1;
  while ( (elem = UTL_SET_NEXT( aset, elem)) >= 0 ) {
    at = SYB_ATOM_FIND_REC( m, elem );
    ans += (float) SYB_ATAB_ATOMIC_WEIGHT( at->type );
  }
  return( ans );
```

```
}
static void ashow( aset, m )
/* for interactive debugging, shows a set's membership in terms of atom ID */
set_ptr aset;
mol_ptr m;
{
    char buff[1000], *b;
    atom_ptr at;
    int elem;
    *buff = '\0';
    b = buff;
    elem = -1;
    while ( (elem = UTL_SET_NEXT( aset, elem)) >= 0 ) {
        at = SYB_ATOM_FIND_REC( m, elem );
        sprintf( b, " %d", at->id );
        b = buff + strlen( buff );
    }
    sprintf( b, "\n" );
    UBS_OUTPUT_MESSAGE( stdout, buff );
}
```

/* BEGINNING OF SUBROUTINES I-D. Calculation of attenuated fields */

/*+E:QSAR_FIELD_EVAL_RB_ATTEN()*/
/******************************************************************************/
/*                                                                            */
/* int QSAR_FIELD_EVAL_RB_ATTEN( molp, stfldp, elfldp, regp, no_st, no_el, ctp ) */
/*                                                                            */
/* Dick Cramer    May 13, 1995                                                */
/*                                                                            */

```
/*
        "Standard CoMFA" -- except that the contribution of any atom
        to the field falls off with an inverse power of its distance
        from a root atom, measured in NUMBER OF ROTATABLE BONDS!
          This means also that each individual atom's contribution
        has a similarly scaled upper bound, rather than checking
        the upper bound only for the sum over all atoms.
*/

/* This procedure computes vdW 6-12 steric values at each point in region  */
/* and the electrostatic interactions (initially assuming 1/r dielectric). */
/*                                                                         */
/* NOTE:: initially ignoring space averaging, other user knobs.            */
/* note:: assuming valid input here; error checking higher up !            */
/*                                                                         */
/*                                                                         */
/* Input:                                                                  */
/*   molp   - molecule pointer, molecule to place in region.               */
/*   stfldp - steric field pointer, where values will be placed.           */
/*   elfldp - electrostatic field pointer, where values will be placed.    */
/*   regp   - region pointer, locations where values are to be evaluated.  */
/*   no_st  - flag to skip steric evaluations                              */
/*   no_el  - flag to skip electrostatic evaluations                       */
/*   ctp    - ComfaTopPtr, for dummy/lp values                             */
/*                                                                         */
/* Returns 0 on failure, 1 otherwise.                                      */
/*                                                                         */
```

/**********************************************************************/

/*+E:QSAR_FIELD_EVAL_RB_ATTEN()*/

```
int QSAR_FIELD_EVAL_RB_ATTEN ( molp, stfldp, elfldp, regp , no_st, no_el, ctp)
mol_ptr molp;
FieldPtr stfldp, elfldp;
RegionPtr regp;
int no_st, no_el ;
ComfaTopPtr ctp;

{

BoxPtr box;
atom_ptr at, SYB_ATOM_FIND_ID();
int pid, b, ix, iy, iz, nat, vol_avg, repulsive ;
fpt *steric, *elect, SYB_ATAB_VDW_RADII() ;
fpt diff, dis, dis2, x, y, z, sum_steric, sum_elect ;
fpt dis6, dis12 , repuls_val, offs[9][3], atm_ste, atm_ele;
fpt *charge, *ctemp, *coord, *ftemp, *wt, scale_vol_avg, atm_steric, atm_elect;
int *atyp , *itemp,  dohbd, dohba, ishbd, retval, dielectric , off, atid;
static fpt hbond_scal;
fpt hbond_A, hbond_B, *AtWts = NIL, *QSAR_FIELD_RB_WTS();
int *HAs, *HDs, *HAp, *HDp; /* sets would be more efficient but slower */
int do_steric, do_elect;
set_ptr hdonor, SYB_HBOND_DONORS(), pset = NIL, aset = NIL;

#define Q2KC 332.0
#define MIN_SQ_DISTANCE 1.0e-4
```

```
/* ^^^ any atom within 10-2 Angstroms is hereby zapped !
     this is about it: 10^6 / 10^-24 is close to overflow!   */ ftemp = NIL; ctemp = NIL; itemp = NIL; retval = FALSE; HAs = NIL; HDs = NIL;
  hdonor = NIL;

/* for now, make root atom the one closest to 0,0,0 */
  for (nat = 1; nat <= molp->natoms; nat++) {
    at = SYB_ATOM_FIND_ID( molp, nat );
    dis2 = at->xyz[0] * at->xyz[0] + at->xyz[1] * at->xyz[1] +
           at->xyz[2] * at->xyz[2];
    if (nat == 1 || dis2 < dis) {
      dis = dis2;
      atid = nat;
    }
  }

/* following is specific to topomeric fields */
  if (!(AtWts = QSAR_FIELD_RB_WTS( molp, atid ) )) goto cleanup;

if (!no_el)
   {dielectric = elfldp->dielectric ;
    vol_avg = elfldp->vol_avg_type;
    scale_vol_avg = elfldp->scale_vol_avg;
    repulsive = elfldp->repulsive;
    repuls_val=repexp[repulsive]; elect = elfldp -> field_value;}
  if (!no_st)
```

```
{vol_avg   = stfldp->vol_avg_type;
 scale_vol_avg = stfldp->scale_vol_avg;
 repulsive = stfldp->repulsive;
 repuls_val=repexp[repulsive]; steric = stfldp -> field_value;} if (!(ftemp = (fpt *) UTL_MEM_ALLOC(3*sizeof(fpt)*molp->natoms))) goto cleanup;
if (!(ctemp = (fpt *) UTL_MEM_ALLOC( sizeof(fpt)*molp->natoms))) goto cleanup;

if (!(itemp = (int *) UTL_MEM_ALLOC( sizeof(int)*molp->natoms))) goto cleanup;

if (!(HAs = (int *) UTL_MEM_ALLOC( sizeof(int)*molp->natoms))) goto cleanup;

if (!(HDs = (int *) UTL_MEM_ALLOC( sizeof(int)*molp->natoms))) goto cleanup;

/* get just those H's which are capable of Hbonding */
if (!(hdonor = SYB_HBOND_DONORS( molp, NIL ) )) goto cleanup;

for (coord=ftemp,atyp=itemp,charge=ctemp,HAp=HAs,HDp=HDs, nat=1;
        nat<=molp->natoms;nat++)

{ if (NIL ==(at = SYB_ATOM_FIND_ID(molp, nat) ) ) goto cleanup;
  *coord++  = at->xyz[0];
  *coord++  = at->xyz[1];
  *coord++  = at->xyz[2];
  *atyp++   = at->type -1 ;
  *charge++ = at->charge;
  *HAp++    = SYB_ATAB_HBOND_ACCEPT(at->type) ;
  *HDp++    = UTL_SET_MEMBER(hdonor, at->recno) ;
}
```

```
for (b=0; b<regp->n_boxes; b++) {
  box = & regp->box_array[b];
  dohbd = (SYB_ATAB_ATOMIC_NUMBER( box->atom_type) == 1) &&
      (box->pt_charge == 1.0);
  dohba = (SYB_ATAB_ATOMIC_NUMBER( box->atom_type ) == 8) &&
      (box->pt_charge == -1.0);

if (dohbd || dohba) {
    if (!TAILOR_STORE_IT_HERE(
  "TAILOR!FORCE_FIELD!HBOND_RAD_SCALING",
          &hbond_scal, 1)) goto cleanup;
    hbond_A = pow( hbond_scal, 6.0 );
    hbond_B = hbond_A * hbond_A;
  } if (vol_avg)
    QSAR_FIELD_EVAL_GETOFF(offs,box->stepsize,vol_avg,scale_vol_avg);

if ( !no_st )
    QSAR_FIELD_VDWTAB ( box -> atom_type, repuls_val, ctp->du_lp_steric );

for (iz=0, z=box->lo[2] ; iz < box->nstep[2]; iz++, z += box->stepsize[2])
  for (iy=0, y=box->lo[1] ; iy < box->nstep[1]; iy++, y += box->stepsize[1])
  for (ix=0, x=box->lo[0] ; ix < box->nstep[0]; ix++, x += box->stepsize[0])
  {
    for ( coord = ftemp, charge = ctemp, atyp = itemp, HAp=HAs, HDp=HDs,
        do_steric=TRUE, do_elect=TRUE, nat=0, sum_steric = sum_elect = 0.0,
      nat<molp->natoms;
```

```
        nat++, wt++)
{
    if ( ( *atyp == DUMMY-1 || *atyp == LP-1 ) && !ctp->du_lp_elect )
        *charge = 0.0;    /* set charge to 0 since ignoring Du/lp */
    if (!vol_avg) /* the "normal" case */
    {
        dis2 = x - *coord++ ;
        dis2 *= dis2;
        diff = y - *coord++ ;
        diff *= diff;
        dis2 += diff;
        diff = z - *coord++ ;
        diff *= diff;
        dis2 += diff;
        if ( !no_el && elfldp->zap_el==2 && do_elect) {
            dis = sqrt( dis2 );
            if ( dis < SYB_ATAB_VDW_RADII( *atyp+1 ) ) {

/* no shortcircuits! */
/*
                *elect++ = 0.0;
                do_elect = FALSE;
*/
            }
        } if ( dis2 < MIN_SQ_DISTANCE ) {
            if ( !no_st )
                /* if atom has no steric value, we don't care about
```

```
                    MIN_SQ_DISTANCE since it has no contribution anyway */
            if ( vdw_a[*atyp] != 0.0 && vdw_b[*atyp] != 0.0 ) {
                /* set sterics to its max value at current grid pt. */
                atm_steric = (*wt) * stfldp->max_value;
            }
            if ( !no_el && do_elect) {
                if ( !no_st && !do_steric && elfldp->zap_el ) {
                    *elect++ = DAB_F_MISSING;
                }
                else if ( *charge != 0.0 ) {
                    if ( *charge > 0.0 )
                        atm_elect = (*wt) * elfldp->max_value;
                    else atm_elect = (*wt) * -elfldp->max_value;
                }
            } if ( !do_elect && !do_steric )
                break;    /* break out of loop since neither el. or st.
                             need to be calculated for this grid point */

/* setting dis2 to 1 (an arbitrary no.) will prevent a zero
               divide in the sum_steric or sum_elect calculations below */
            dis2 = 1.0;
        } if ( ! no_st && do_steric ) {
            dis6 = dis2 * dis2 * dis2;
            dis12= dis6 * dis6 ;
            if (repulsive)
                dis12 = (repulsive==1) ? dis12 / dis2 : dis12 / dis2 / dis2;
```

```
if (dohbd && *HAp)
    atm_steric = hbond_B * vdw_b[*atyp]/dis12 -
        hbond_A * vdw_a[*atyp]/dis6 ;
else if (dohba && *HDp)
    atm_steric = hbond_B * vdw_b[*atyp]/dis12 -
        hbond_A * vdw_a[*atyp]/dis6 ;
else
    atm_steric = vdw_b[*atyp]/dis12 - vdw_a[*atyp]/dis6 ;
HAp++; HDp++;     }
atm_steric = atm_steric > stfldp->max_value ? stfldp->max_value
        : atm_steric;
atm_steric *= (*wt);

if ( ! no_el && do_elect ) {
atm_elect = *charge++ /
        ( dielectric ? sqrt(dis2) : dis2 ) ;
atm_elect = atm_elect > elfldp->max_value ? elfldp->max_value
        : atm_elect;
atm_elect = atm_elect < -(elfldp->max_value) ? -(elfldp->max_value)
        : atm_elect;
atm_elect *= (*wt);
sum_elect += atm_elect;
} atyp++;
sum_steric += atm_steric;
}
else
{ for (off=0;off<9;off++)
{
}
```

```
        coord += 3;
        atyp ++ ;
        charge ++ ;
        HAp ++ ;
        HDp ++ ;
      }
    } /* atom loop */ doneatoms:
    if ( do_steric || do_elect ) {
      if (vol_avg) { sum_elect /= 9.0; sum_steric /= 9.0 ; }
      if ( !no_el && do_elect )
      { *elect = sum_elect * box-> pt_charge * Q2KC ;
        if ( *elect > elfldp->max_value ) *elect = elfldp->max_value;
        else if ( *elect < - elfldp->max_value ) *elect =
            - elfldp->max_value;
          transform_field(elfldp->max_value,elect,ctp);
          elect ++;
      } if ( !no_st && do_steric )
      { *steric = sum_steric ;
        if ( *steric > stfldp->max_value)
        { *steric = stfldp->max_value;
          if (!no_el && elfldp->zap_el==1 ) *(elect-1) = DAB_F_MISSING; }
          transform_field(stfldp->max_value,steric,ctp);
          steric ++ ; }
    }
  } /* points in box loop */
} /* boxes loop */
```

```
    retval = TRUE;
cleanup:

if ( itemp) UTL_MEM_FREE( itemp);

if ( ftemp) UTL_MEM_FREE( ftemp);

if ( ctemp) UTL_MEM_FREE( ctemp);

if (HAs) UTL_MEM_FREE( HAs );

if (HDs) UTL_MEM_FREE( HDs );

if (hdonor) UTL_SET_DESTROY( hdonor );

if (AtWts) UTL_MEM_FREE( AtWts );

if (pset) UTL_MEM_FREE( pset );

if (aset) UTL_MEM_FREE( aset );
    return retval;
#undef Q2KC
#undef MIN_SQ_DISTANCE
}

/* ---------------------------------------------------------------- */
static fpt *QSAR_FIELD_RB_WTS( molp, rootid )
/* generates rotational-bond wts for each atom */
mol_ptr molp;
```

```
int rootid;
{
/* pseudo code for FIELD_RB_WTS()

while saw new atoms
        uncover atoms that stopped last shell growth
        grow next "rotational shell"
        while adding to shell
            for each atom in shell
                get neighbors not seen
                for each neighbor
                    if bond is rotatable (acyclic, > 1 attached atom, not =,am,#)
                        cover all other atoms attached to atom for this shell
                    add it to shell
*/ fpt      *ansr = NIL, *vals = NIL, factor, nowfact = 1.0;
    int       found, aggcount, atid, aggid, loop, size;
    set_ptr   aggats = NIL, allats = NIL, nuls = NIL, endatms = NIL, end_cands
    atom_ptr  root, SYB_ATOM_FIND_REC(), at, atrec ;
    bond_ptr  b, SYB_BOND_FIND_REC();
    List_Ptr  toats, UTL_LIST_RETRIEVE_P();
    acon_ptr  cptr;
    char      tempString[200];
    void      ashow(), qsar_field_attached_atoms();

if (!( vals = (fpt *) UTL_MEM_ALLOC( sizeof(fpt)*molp->natoms))) return( NI
```

```c
if (!UIMS2_VAR_GET_TOKEN( "TAILOR!COMFA!AGGREG_DESCALE",
    &factor ) ) return( NIL );

if (!(allats = UTL_SET_CREATE( molp->max_atoms + 1 ) )) goto cleanup;

if (!(aggats = UTL_SET_CREATE( molp->max_atoms + 1 ) )) goto cleanup;

if (!(nuls = UTL_SET_CREATE( molp->max_atoms + 1 ) )) goto cleanup;

if (!(endatms = UTL_SET_CREATE( molp->max_atoms + 1 ) )) goto cleanup;

if (!(end_cands = UTL_SET_CREATE( molp->max_atoms + 1 ) )) goto cleanup;

if (!( root = SYB_ATOM_FIND_REC( molp, rootid ) )) goto cleanup;

UTL_SET_INSERT( aggats, root->recno );
UTL_SET_INSERT( allats, root-> recno );
aggcount = loop = 1;
while (TRUE) {
    while (TRUE) {
        aggid = -1;
        while ((aggid = UTL_SET_NEXT( allats, aggid )) >= 0 ) {
            UTL_SET_CLEAR( nuls );
            qsar_field_attached_atoms( nuls, molp, aggid );
            UTL_SET_DIFF_INPLACE( nuls, allats, nuls );
            UTL_SET_DIFF_INPLACE( nuls, endatms, nuls );
            /* identifying any atoms that terminate this aggregate */
            atid = -1;
            while ((atid = UTL_SET_NEXT( nuls, atid )) >= 0 ) {
```

```
            if (!( at = SYB_ATOM_FIND_REC( molp, atid ) )) goto cleanup;

/* skipping monovalent atoms */
            if (at->nbond > 1) {

/* find bond record that attaches to aggid */
                toats = at->conn_atom;
                found = FALSE;
                while (toats && !found ) {
                    toats = UTL_LIST_RETRIEVE_P( toats, &cptr, &size );
                    found = (cptr-> target == aggid );
                }
                if (!found) goto cleanup;
                b = SYB_BOND_FIND_REC (molp, cptr->bond_rec);
                if ( !(b->status & BOND_V_IRING) && !(b->status & BOND_V_ERI
                        && (b->type == SYB_BTAB_MNEM_TO_TYPE("1") ) ) {
/* have an end-of-aggregate atom, mark as end atoms all other attached atoms */
                    UTL_SET_CLEAR( end_cands );
                    qsar_field_attached_atoms( end_cands, molp, at->recno );
                    UTL_SET_DELETE( end_cands, aggid );
                    UTL_SET_OR_INPLACE( endatms, end_cands, endatms );
                }
            }
        }
        UTL_SET_OR_INPLACE( aggats, nuls, aggats );
    }
    if (UTL_SET_CARDINALITY( aggats ) <= aggcount ) break;
    aggcount = UTL_SET_CARDINALITY( aggats );
```

```
        UTL_SET_OR_INPLACE( allats, aggats, allats );
    }

/* debugging stuff .. */
/*
        sprintf( tempString, "Aggregate %d (weight = %f ):", loop, nowfact );
        UBS_OUTPUT_MESSAGE( stdout, tempString );
        ashow( aggats, molp );
*/

/* if no atoms added, we are done! */
        if (UTL_SET_EMPTY( aggats )) break;

/* record scaling factor for atoms in this aggregate */
        atid = -1;
        while ((atid = UTL_SET_NEXT( aggats, atid )) >= 0 ) {
            if (!(atrec = SYB_ATOM_FIND_REC( molp, atid ))) goto cleanup;
            vals[ (atrec->id)-1 ] = nowfact;
        }
        UTL_SET_OR_INPLACE( allats, aggats, allats );
        UTL_SET_CLEAR( aggats );
        UTL_SET_CLEAR( endatms );
        aggcount = 0;
        nowfact *= factor;
        loop++;
    } ansr = vals;
```

```
cleanup:
    if (aggats) UTL_SET_DESTROY( aggats );
    if (allats) UTL_SET_DESTROY( allats );
    if (endatms) UTL_SET_DESTROY( endatms );
    if (end_cands) UTL_SET_DESTROY( end_cands );
    if (nuls) UTL_SET_DESTROY( nuls );
    return( ansr );
} static void qsar_field_attached_atoms( aset, m, atid )
/* ors atoms attached to atm into aset */
/* WORKS STRUCTLY WITH RECNOS */
set_ptr aset;
mol_ptr m;
int atid;
{
    atom_ptr at, SYB_ATOM_FIND_ID();
    List_Ptr tohs, UTL_LIST_RETRIEVE_P();
    atom_ptr toh, SYB_ATOM_FIND_REC();
    acon_ptr conn1;
    int nbytes1;
    at = SYB_ATOM_FIND_REC( m, atid );
    tohs = at->conn_atom;
    while (tohs) {
        tohs = UTL_LIST_RETRIEVE_P( tohs, &conn1, &nbytes1);
        toh = SYB_ATOM_FIND_REC( m, conn1->target );
        UTL_SET_INSERT( aset, toh->recno );
    }
    return;
}
```

```
static void ashow( aset, m )
/* for interactive debugging, shows a set's membership in terms of atom ID */
set_ptr aset;
mol_ptr m;
{
    char buff[1000], *b;
    atom_ptr at, SYB_ATOM_FIND_REC();
    int elem;

*buff = '/0';
    b = buff;
    elem = -1;
    while ( (elem = UTL_SET_NEXT( aset, elem)) >= 0 ) {
        at = SYB_ATOM_FIND_REC( m, elem );
        sprintf( b, " %d", at->id );
        b = buff + strlen( buff );
    } sprintf( b, "\n" );
    UBS_OUTPUT_MESSAGE( stdout, buff );
}
```

```

# Section II-A. SPL invoked shell for computing the diagonal defining the
#       "best" triangle, e.g., the one with the highest density of points below.

@expression_generator LRT_FAST

# Usage:
# lrt_fast rows descriptor_cols bio_col [pls flags like scaling in quotes]
#       rows (*) - rows to take
#       descriptor_cols - which columns are the neighborhood metrics
#       bio_col  - which column has the bio (probably log bio) data
#       [...] - if need to SCAL NONE or anything like that, do it here

# returns a line of the form
#    3.09691 / 0.000546509 = 5666.71 - 496 : 496 :: 15.6981 : 15.6989
#        ^ max bio difference
#              ^ optimal distance division for max bio
#                         ^ slope
#                                    ^number in the lrt
#                                              ^total number
#                                                       ^area in the lrt
#                                                                ^total area
# Significance is related to whether ratio of numbers is
#   much above ratio of areas.

globalvar SAMPLS_IN_PROGRESS DONE_CHECKED_OUT
localvar hold distname rows cols bio
```

```
setvar rows %promptif("$1" ROW_EXP "*" "Rows to use in lrt")
setvar cols %promptif("$2" COL_EXP "COMFA*" "Columns of mol descriptors")
setvar bio  %promptif("$3" COL_EXP "LOGBIO" "Column of bio data")

setvar hold SAMPLS_IN_PROGRESS
setvar SAMPLS_IN_PROGRESS $bio setvar distname TAILOR!HIER!DIST_FNAME
setvar TAILOR!HIER!DIST_FNAME lrt_fort.3 here the information is computed and written to a file
whose name is passed in via a TAILOR value
QSAR ANA DO I >$NULLDEV   $rows $cols HIER $4  | setvar SAMPLS_IN_PROGRESS $hold
setvar TAILOR!HIER!DIST_FNAME $distname contents of the file are returned to the caller
setvar hold %system("cat lrt_fort.3")
%return( "$hold" )

.
```

```

# Section II-B. SPL script for computing the significance of the distribution
#        found by lrt_fast

@expression_generator dochi
# computes the chi-square statistic for the number of points below
# the diagonal, null hyptheses being the area fraction of the total.

#      To be called as: %dochi( %lrt_fast( ) ), i.e., its inputs
# are exactly the output of %lrt_fast as described in the lrt_fast header.

setvar expected  %math( $9 * $11 / $13 )
    setvar sq %math( $7 - $expected )
    setvar sq %math( $sq * $sq / $expected )
    %return( $sq )
```

```c
/* Section II-C. Computes the best diagonal in the "virtual graph" of biological
distances vs property differences. */ int QSHELL_HIER_LRT(table,biocol,dmat,nrow,order,lmsg)
char *table;

int biocol,  /* column in MSS with biological data */
    nrow,    /* dimension of dmat and order */
    *order;  /* array of row IDs to consider */
fpt *dmat;   /* distance matrix for property distances */
char *lmsg;  /* file name for results */
{
fpt *p, *q, fabs(), bmax;
int i,j, count, status_array;
char *fpt_colname;
FILE *out, *UTL_FILE_FOPEN();

/* need to get the bio values
    In the n^2 we can repack into n(n-1)/2 then add the n bio values
    and finish with the bio distances */
/*
    No error handling. Better be data in those rows!
*/ for (count=0, i=0; i<nrow; i++)
  for (j=0; j<i; j++)
    dmat[count++] = dmat[i*nrow + j];

q = p = dmat + ( (nrow-1) * nrow) / 2;
```

```
TBL_ACCESS_INDEX_TO_COLNAME(table, biocol-1, &fpt_colname);
TBL_GRAB_INIT_FPTS(table, 1, &fpt_colname );
for ( i=0;i<nrow;i++, p++)
  TBL_GRAB_GET_FPTS_INV(order[i]-1, &status_array, p);
TBL_GRAB_COMPLETE_FPTS();

bmax = 0.0;
for (count=0, i=0; i<nrow; i++)
 for (j=0; j<i; j++, count++)
  if ( (p[count] = fabs(q[i] - q[j])) > bmax) bmax = p[count];

out = UTL_FILE_FOPEN(lmsg,"w");
QSHELL_HIER_DO_LRT(out,count,dmat,p, bmax);

UTL_FILE_FCLOSE(out);
} int QSHELL_HIER_DO_LRT( out, index, xsort, ysort, bmax )
FILE *out;
fpt *xsort, *ysort, bmax;
int index;
{
int *order, count, j, i, bad;
int bestN, bestI;
fpt den,bestDen;

#define CUTOFF ( bmax * ( xsort[order[i]] / xsort[order[j]] ) )

if (!(order = (int  *) UTL_MEM_ALLOC( index *sizeof(int  )))) return 0;
```

```
for (i=0;i<index;i++) order[i]=i;
bestN = bestI = bad = 0;
bestDen = 0.0;

fpt_heapsort(index, xsort, order);

for (j=0;count=0, bad=0, j<index ;j++)
{
  if (xsort[order[j]] <= 0.0) continue;
  for (i=0;i<=j;i++)
  {
    if (ysort[order[i]] <= CUTOFF) count++;
    else                           bad++;
  } /* loop over all d <= this distance    */
  if ( (den = count/ bmax / xsort[order[j]] *2.0) > bestDen)
      {bestDen = den; bestI = j; bestN = index - bad;}
}    /* loop over all distances           */ den = bmax * xsort[order[index-1]];
sprintf(msg,"%g / %g = %g - %d : %d :: %g : %g\n",
       bmax,xsort[order[bestI]], bmax/xsort[order[bestI]],
       bestN,index,den-xsort[order[bestI]]*bmax/2.0, den);
UBS_OUTPUT_MESSAGE(out,msg);
UTL_MEM_FREE(order);
return 1;
}

/* n is number of elements
   arrin is array of floats to be sorted
``` indx is array of ints initially 0...n-1

*/ int fpt_heapsort(n,arrin,indx)

int n;

fpt *arrin;

int *indx;

{ int l, ir, indxt, i, j;

fpt q;

l = n/2 ;

ir = n -1 ;

while (TRUE)    /* the "10" loop */

{ if (l>0) { indxt = indx[--l]; q = arrin[indxt]; } else

{ indxt = indx[ir];  q = arrin[indxt];

indx[ir--] = indx[0];

if ( ir == 0 )

{ indx[0] = indxt; return 1; }   /* <=== Only way out ! */

} i = l;

i = l;

j = l + 1   +1;

while (j <= ir)   /* the "20" loop */

```
    {
      if ( (j<ir) && (arrin[indx[j]] < arrin[indx[j+1]]) ) j++ ;
      if (q < arrin[indx[j]]) { indx[i] = indx[j]; i = j; j = j+j+1; }
      else                    { j = ir+1;                           }
    } indx[i] = indxt;
  }
}
```

/* SECTION III-A. Declarations for all non-standard data structures referenced in the C code functions shown in Sections I and II. */

```
/**************************************************************/
/*      Molecule and Supporting Structure Definitions         */
/*                                                            */
/*         John McAlister      09-Aug-1985                    */
/*                                                            */
/*  This file contains the definitions for the molecular data struc- */
/*  tures required within SYBYL.  The contents of this file are des- */
/*  described in detail in the document "SYBYL Molecular Data Struc- */
/*  tures".                                                   */
/*                                                            */
/**************************************************************/

/* Define the molecule descriptor template                    */
    typedef struct molecule_struct { char     *name;    /* pointer to molecule name              */
        i32      type;     /* molecule type                         */
        List_Ptr dict;     /* list of dictionaries used with molecule */
        i32      status;   /* molecule status                       */
        char     *comment; /* pointer to comment for molecule       */
        stamp    cre_time; /* creation time/user/version stamp      */
        stamp    mod_time; /* modification time/user/version stamp  */
        int      max_props;/* maximum properties currently allocated */
        int      nprops;   /* number of molecular properties        */
        List_Ptr props;    /* pointer to list of properties         */
        int      max_feats;/* maximum features currently allocated  */
```

```
int       nfeats;    /* number of molecular features       */
List_Ptr  feats;     /* pointer to list of molecular features */
int       max_subst; /* maximum substructures currently allocated*/
int       nsubst;    /* number of substructures in molecule */
List_Ptr  subst;     /* pointer to list of substructures    */
List_Ptr  subst_roots; /* pointer to list of root subst offsets */
int       max_atoms; /* maximum atoms currently allocated   */
int       natoms;    /* number of atoms in molecule         */
List_Ptr  atoms;     /* pointer to atom array segment list  */
int       max_bonds; /* maximum bonds currently allocated   */
int       nbonds;    /* number of bonds in molecule         */
List_Ptr  bonds;     /* pointer to bond array segment list  */
int       charges;   /* type of atomic charges, if present  */
fpt       vector[3]; /* translation vector for molecule     */
fpt       matrix[9]; /* rotation matrix for molecule        */
List_Ptr  assoc_data; /* pointer to list of associated data */
          /*          descriptors                 */
} molecule, *mol_ptr;
```

/******************* ATOM DEFINITION
****************************/

/*                                                                    */

/* Define the atom entry record template                              */
```
    typedef struct atom_struct {
```

```
    char      *name;      /* atom name                                */
    int       type;       /* atom type                                */
    i32       status;     /* atom status                              */
    int       recno;      /* cumulative atom record number            */
    int       id;         /* atom id (logical atom number)            */
    int       link;       /* link to next atom record                 */
    int       subst;      /* offset to substructure containing atom   */
    List_Ptr  property;   /* pointer to list of properties for atom   */
    List_Ptr  feature;    /* pointer to list of features including    */
                          /*   this atom                              */
    int       nbond;      /* number of bonds involving this atom      */
    List_Ptr  conn_atom;  /* pointer to list of bonded atoms          */
    fpt       xyz[3];     /* coordinates of atom                      */
    fpt       charge;     /* point charge on atom                     */
    } atom, *atom_ptr;
```

/* Define the atom array segment descriptor template                  */
```
    typedef struct atom_seg_struct {
```

```
    atom_ptr  seg_head;   /* pointer to head of atom array segment    */
    mol_ptr   molecule;   /* pointer to molecule containing atom seg  */
    int       max_atom;   /* maximum number of atom records in seg    */
```

```
    int     natom;      /* number of filled atom records in seg    */
    int     used_atom;  /* offset to first filled record in segment */
    int     free_atom;  /* offset to first free record in segment   */
} atom_seg, *aseg_ptr;
```

```
/* Define the bond specifier records pointed to by the atom records   */
typedef struct atom_conn_struct { int     target;     /* offset to target atom                  */
    int     bond_rec;   /* offset to bond descriptor record       */
} atom_conn, *acon_ptr;
```

/******************** BOND DEFINITION
*****************************/
/*                                                                    */
/* Define the bond entry record template                              */
    typedef struct bond_struct {

```
    int       type;      /* bond type                                 */
    i32       status;    /* bond status                               */
    int       recno;     /* cumulative bond record number             */
    int       id;        /* bond id (logical bond number)             */
    int       link;      /* link to empty bond record                 */
    List_Ptr  property;  /* pointer to bond property list             */
    List_Ptr  feature;   /* pointer to list of features including     */
                         /* this bond                                 */
    int       o_subst;   /* offset to origin atom substructure        */
    int       origin;    /* offset to atom at bond origin             */
    int       t_subst;   /* offset to target atom substructure        */
    int       target;    /* offset to atom at bond destination        */
    } bond, *bond_ptr;
```

/* Define the bond array segment descriptor template                  */
    typedef struct bond_seg_struct {

```
    bond_ptr  seg_head;   /* pointer to head of bond array segment    */
    mol_ptr   molecule;   /* pointer to molecule containing bond seg  */
    int       max_bond;   /* maximum number of bonds in segment       */
    int       nbond;      /* number of filled bond records in seg     */
    int       used_bond;  /* offset to first filled record in segment */
    int       free_bond;  /* offset to first free record in segment   */
    } bond_seg, *bseg_ptr;
```

```
/*****************************************************************/
/* =====   comfa.h   ======                                     */
/* Regions are the set of points at which energy evaluations are made */
/*      in the CoMFA method of QSAR. A region is defined as the union */
/*      of a set of 3D boxes (which may be a single point in the */
/*      limit) and their associated attributes. Attributes needed for */
/*      CoMFA purposes are outlined below.                       */
/*                                                               */
/*****************************************************************/ ifndef     QSAR_COMFA_DEFINITIONS
define     QSAR_COMFA_DEFINITIONS 1
#include    "ta_types.h"
#define     DUMMY 26    /* dummy atom id */
define     LP  20      /* lone pair atom id */ typedef enum {

FDENGY_UNKNOWN,
    FDENGY_ELECT,
    FDENGY_STERIC,
    FDENGY_HOMO,
    FDENGY_LUMO,
    DOCK_ELECT,
    DOCK_STA_NOHB,
    DOCK_STA_HBD,
    DOCK_STA_HBA,
    DOCK_STB_NOHB,
```

```
    DOCK_STB_HBD,
    DOCK_STB_HBA } FldEngyTyp;

typedef enum {

FDHD_ORIGINAL,
    FDHD_FFIT,
    FDHD_XTERN,
    FDHD_FUNC,
    FDHD_USER,
    FDHD_USR_AVG,
    FDHD_DOCK,
    FDHD_AVG,
    FDHD_SIG,
    FDHD_MAX,
    FDHD_MIN,
    FDHD_COEFF,
    FDHD_AVG_X,
    FDHD_SIG_X,
    FDHD_FLD_X,
    FDHD_RANGE,
    FDHD_PLS_XWT,
    FDHD_PLS_XLOAD,
    FDHD_FAC_LOAD,
    FDHD_FAC_COMM,
    FDHD_FAC_ROTLOAD,
    FDHD_SIMCA_LOAD,
    FDHD_SIMCA_MODEL,
    FDHD_SIMCA_DISCRIM,
```

FDHD_HBD } FldHowTyp;

```
typedef struct { fpt  lo[3],       /* corner with lowest values for each axis    */
         hi[3],       /*    "    "  hi-est    "    "   "    "       */
         stepsize[3]; /* increment between points                   */
    int  nstep[3],    /* derived as 1 + (hi-lo + epsilon) / stepsize */
         n;           /* n = product of nstep[i]                    */
    int  atom_type;   /* SYBYL atom type, for steric energy computation */
    fpt  pt_charge;   /* elemental charge at point, for electrostatics */
    fpt  *weight;     /* weight[n] is applied in all computations,e.g=1 */
    int  avg_type;    /* box of 'scale', sphere, sphere x vdw, ...? */
    fpt  avg_scale;   /* scale whose meaning derived from avg_type  */
    int  arb,         /* arbitrary int for later use                */
         *parb;       /*    "    pointer "    "                     */
} Box, *BoxPtr ;

typedef struct { char *filename ;  /* name of the region's file (if any)         */
    int  n_boxes;     /* number of boxes which make up the region   */
    int  n_points ;   /* number of points in this region altogether */
    BoxPtr box_array; /* box_array[n_regions], each one a Box       */
    int  n_refs   ;   /* number of CURRENT references to this memory */
    long when_made;   /* creation stamp                             */
} Region, *RegionPtr ;

typedef struct {
```

```
char *reg_name;     /* name of the region's file (if any)           */
char *fld_name;     /* name of this field's file (if any)           */
RegionPtr reference; /* the region referenced by this field         */
FldEngyTyp fld;     /* what type of field is referenced here        */
int num_avgd;       /* number of fields averaged into this one      */
int curr_iter;      /* number of iterations in current field fit run */
char *mol_id;       /* unspecified molecule id,
                       e.g. dbname/molname/alignname                */ int n_points ;      /* number of points in associated region        */
int zap_el;         /* whether electrostatics are MISSING when > max_st */
fpt max_value;      /* largest permitted absolute value of energy   */
fpt *field_value;   /* values at each point of the field            */
int n_refs    ;     /* number of CURRENT references to this memory  */
long when_made;     /* creation stamp                               */
int vol_avg_type;   /* added these 4 items 1/30/89 DEP              */
fpt scale_vol_avg;
int dielectric;
int repulsive;

FldHowTyp how_made;   /* perry's way = 1 or old way = 0 */
} Field, *FieldPtr ;
```

/* molecule dependent information solicited by QSAR table operations,
   passed into COMFA column field evaluations                       */ typedef struct { boolean already_field; /* whether a field name exists (otherwise alignment) */

```
char   *some_name;    /* name of alignment;    NIl align==use as is (!) */
char   *steric_name;  /* name of steric       field (if applicable)    */
char   *elect_name;   /* name of electrostatic field (if applicable)   */
FieldPtr sfld_p;      /* points to steric field in memory (when there) */
FieldPtr efld_p;      /* points to elect. field in memory (when there) */
} ComfaMol, *ComfaMolPtr;

/* molecule-independent information for CoMFA evaluations */ typedef struct { int   vol_avg   ;     /* case for volume averaging: 0,1,2=none,box,sphere(0)*/
fpt   vol_scale ;     /* scale for volume averaging (1.0)              */
int   fld_types ;     /* case for what fields: 0,1,2=both,steric,elect.(0) */ fpt   steric_max;     /* maximum steric energy (30)                    */
int   repulsive ;     /* steric repulsive exponent - 12,10,or 8 (12)   */
fpt   elect_max ;     /* maximum electrostatic energy (30)             */
int   dielectric;     /* case for dielectric (AS FORCE FIELD TAILOR)   */
int   elect_out ;     /* case to drop elect inside steric max: 0,1=T,F (1) */ char *region_name;    /* name of region used in the CoMFA computations */

FieldPtr sweight_fld; /* points to MEMORY field for weighting steric PLS */
FieldPtr eweight_fld; /* points to MEMORY field for weighting elect. PLS */
FldHowTyp how_done;   /* perry's way = 1 or old way = 0 */
int du_lp_steric;     /* include dummies and lone pairs in steric field
                         calculations */
int du_lp_elect;      /* include dummies and lone pairs in electrostatic
```

```
                   field calculations */
   int  spare1;    /* As of 6.1comfa , this is TAILOR!COMFA!TRANSFORM*/
   int  spare2;    /* INDICATOR SCALE among other things         */
} ComfaTop, *ComfaTopPtr;

#endif
```

Section III-B. Functional descriptions of external procedures. (Routines that simply return dynamic memory to the heap are not described.)

BOND_V_ERING - TRUE if bond is in an external ring.

BOND_V_IRING - TRUE if bond is in an internal (simple) ring.

QSAR_FIELD_EVAL_GETOFF - provides coordinates for field computation when "volume averaging" is being done.

QSAR_FIELD_VDWTAB - returns steric parameters for the computation of the field contribution from the probe atom and each of the molecule atoms.

SYB_AREA_GET_MOLECULE - returns the internal representation of the molecule in some area or "container", if such exists.

SYB_ATAB_ATOMIC_NUMBER - returns the atomic number of the specified atom type.

SYB_ATAB_ATOMIC_WEIGHT - returns the atomic weight of the specified atom type.

SYB_ATAB_HBOND_ACCEPT - returns TRUE if the specified atomic type is a hydrogen-bond accepting atom.

SYB_ATAB_VDW_RADII - returns the atomic radius of the specified atomic type.

SYB_ATOM_FIND_ID - returns the internal representation of an atom referenced by its atom ID number (Atom IDs are guaranteed to be continuous but the ID of any single atom may change as atoms are added or deleted.)

SYB_ATOM_FIND_REC - returns the internal representation of an atom referenced by its record ID number. (Atom record IDs are invariant but there may be "holes" in their sequence such that the largest record ID may be greater than the number of atoms.)

SYB_ATOM_FIND_SET - returns the bitset of atoms corresponding to a list of atoms.

SYB_BOND_FIND_REC - returns the internal representation of a bond referenced by its (invariant) record ID number.

SYB_BTAB_MNEM_TO_TYPE - converts an ASCII representation of a bond type to its internal representation.

SYB_EXPR_ANALYZE - parses a user-entered ASCII description of atoms (e.g., M2(<H>) for all hydrogen atoms within molecule M2) into internally valid representations of molecule and atoms.

SYB_HBOND_DONORS - returns the set of IDs for atoms which are hydrogen-bonding hydrogens.

TAILOR_STORE_IT_HERE - returns the current value of a user- (and SPL-) accessible variable.

TBL_ACCESS_INDEX_TO_COLNAME - converts a user-provided MSS column ID to a column name (name is guaranteed to be a unique identifier).

TBL_GRAB_COMPLETE_FPTS - done returning multiple (scalar) values in an MSS column to an array.

TBL_GRAB_GET_FPTS_INV - in a multiple value retrieval, returns the value corresponding to a user-provided row ID.

TBL_GRAB_INIT_FPTS - set up for returning multiple (scalar) values in an MSS column to an array.

UBS_OUTPUT_MESSAGE - equivalent to *fprintf()*

UIMS2_VAR_GET_TOKEN - returns the current value of a global SPL variable.

UIMS2_WRITE_ERROR - writes text to the error output stream.

UTL_FILE_FCLOSE, UTL_FILE_FOPEN - equivalent to *fclose()* and *fopen()*.

UTL_LIST_RETRIEVE - returns the next element on a linked list.

UTL_MEM_ALLOC - equivalent to *malloc()*.

UTL_SET_AND_INPLACE - makes the first set logically equivalent to the second set, with only those bits that are also 1 in the third set becoming 1 in the first set.

UTL_SET_CARDINALITY - returns the number of bits that are 1 in a particular bitset.

UTL_SET_CLEAR - sets all bits in the set to 0.

UTL_SET_COPY_INPLACE - makes the first set logically identical to the second.

UTL_SET_CREATE - creates and returns an empty set of requested size.

UTL_SET_DELETE - sets the specified bit to 0.

UTL_SET_DIFF_INPLACE - makes the first set logically equivalent to the second set, with all bits that are 1 in the third set becoming 0 in the first set.

UTL_SET_EMPTY - TRUE if all bits in the set are 0.

UTL_SET_INSERT - sets the requested bit to 1.

UTL_SET_MEMBER - returns TRUE if the requested set bit equals 1.

UTL_SET_NEXT - returns the identity of the next non-zero bit in a set.

UTL_SET_OR_INPLACE - makes the first set logically equivalent to the second set, with all bits that are 1 in the third set becoming 1 in the first set.

UTL_STR_CMP_NOCASE - non-case sensitive version of strcmp().

APPENDIX "B"

```c
/* CODE. This code implements a PHORE_LOC column type and calculates a single
cell value (the Hydrogen Bonding Fingerprint for a molecule) within the SYBYL
Molecular Spreadsheet. It is to be understood that other supporting code handles user input, user output, and disk file
I/O. */
/* data structure for PHORE_LOC column type */
typedef
    struct PHORE {
        char *disco_fn;    /* user name for DISCO feature file - default
appears below */
        int   disco_in;    /* internal flag if DISCO feature file loaded */
        char *region_fn;   /* user name for defining region file */
        RegionPtr rgn;     /* internal reference to region when loaded */
        int   nfuzz;       /* number of extra lattice points (each direction)
for each PHORE feature */
        int   nbits;       /* set length (must agree with rgn contents or EVAL
fails) */
    } PHORE, *PPHORE;
/*+E:QSAR_PROC_EVAL_PHORE_LOC */
/*******************************************************************
**********/
/*    int QSAR_PROC_EVAL_PHORE_LOC(tablename, row, colname)
    */
/*
        */
/*    Dick Cramer 31-Jul-95     (PHORE_LOC   == lattice bitset
)        */
/*
```

```
/*                                                                    */
/*    This module generates bitsets whose cardinality is equal to
                                                                      */
/*    lattice points x 2 (# of sitepoint classes. For each
                                                                      */
/*    instance of a pharmacophoric point in the molecule being
                                                                      */
/*    processed, the geometrically nearest (1+m)^3 bits in the
                                                                      */
/*    bitset will be set to 1 (where m is user supplied).
                                                                      */
/*
                                                                      */
/*    NOTE: this routine explicitly requires that sets begin after
a     */
/*          first element that is the set size!!!
                                                                      */
/*
                                                                      */
/*    Inputs
                                                                      */
/*
                                                                      */
/*    Outputs
                                                                      */
/*
                                                                      */
/*    User Required Definition Files
                                                                      */
/*
                                                                      */
/**************************************************************
**********/
/*-E*/
int QSAR_PROC_EVAL_PHORE_LOC(tablename, row, colname)
char    *tablename, *colname;
int     row;
  {
    mol_ptr     mol;
```

```
    PPHORE      phr;
    int         err, status, nvalid, mol_area;
    char        *dum;
    set_ptr     print, qsar_proc_calc_phore_set();
    FILE *fp;
/* get the molecule */
    if ( !TBL_UTL_GET_MOLECULE(tablename, row, FALSE, &mol) )
    {
       if ( UTL_ERROR_IS_SET() )                             {err=1;
goto
error;}
        else   return FALSE;
    }
/* get the user-provided input data */
    if   (    !TBL_ATTR_FIND_COLUMN_A(tablename,   colname,
"PROC_SUPPORT", &dum,
                                    (int *)&phr) )          {err=3;
goto
error;}
/* retrieve DISCO stuff if not yet present */
    if ( ! phr->disco_in) {
       if ( !phr->disco_fn) {err=1; goto error;}
/* set appropriate tailor value, then initialize DISCO */
       sprintf( str, "SETVAR TAILOR!DISCO!FILE %s", phr->disco_fn
);
       UIMS2_EXEC_COMMAND( str );
       UIMS2_EXEC_COMMAND( "DISCO INIT" );
       phr->disco_in = TRUE;
    }
/* retrieve region if not yet present */
    if (!phr->rgn ) {
         if ( !phr->region_fn) {err=1; goto error;}
         if (!(phr->rgn = QSAR_REGION_RETRIEVE( phr->region_fn )
))
{err=4;goto error;}
         if (phr->rgn->n_boxes > 1 ) {
                sprintf( str, "WARNING: Region %s has %d boxes.
Only first
will be used.\n",
```

```
                phr->region_fn, phr->rgn->n_boxes );
        UBS_OUTPUT_MESSAGE( stdout, str );
    }
    phr->nbits = 2 * phr->rgn->n_points;
  }
/* evaluate this result, first the DISCO call */
    if (!( print = qsar_proc_calc_phore_set( mol, phr, &nvalid ))
) {err=12;
goto error;}
/* go store both the bitset in the MSS "Cell_Support" and the
number of bits
actually set in the "CELL", so there's something for the user to
see */
    if ( !TBL_ACCESS_X_PUT_VALUE(tablename, row, colname,
"CELL_SUPPORT",
                            (int *)&print) )        {err=11;
goto error;}
    if ( !TBL_ACCESS_X_PUT_VALUE(tablename, row, colname, "CELL",
                            (int *)&nvalid) )       {err=11;
goto
error;}
    return TRUE;
error:
    sprintf (str, "QSAR_PROC_EVAL_PHORE_LOC (%d)", err);
    UTL_ERROR_ADD_TRACE (str);
    return FALSE;
}
set_ptr qsar_proc_calc_phore_set( mol, phr, nvalid )
/* creates actual bitset */
    mol_ptr    mol;
    PPHORE     phr;
    int        *nvalid;
{
  set_ptr anset = NIL, pset = NIL, SYB_FEAT_FIND_ID_SET();
  feat_ptr featp, SYB_FEAT_FIND_REC();
  atom_ptr   a, SYB_ATOM_FIND_REC();
  int     err, elem, sitebase, ci, xybase, boff, lt_base[3],
lt_off[3], loff =
0, hioff = 0 ;
```

```
   fpt    tmp;
  BoxPtr          bxptr;
  line_ptr cdp;
    if (!( anset = UTL_SET_CREATE( phr->nbits ) )) {err = 1; goto
error;}
    *nvalid = 0;
    if (phr->nfuzz) {
        loff -= phr->nfuzz / 2;
        hioff += (phr->nfuzz + 1 ) / 2;
    }
    bxptr =  phr->rgn->box_array;
    xybase = bxptr->nstep[0] * bxptr->nstep[1];
/* generate the DISCO sites for this molecule, which .. */
    UIMS2_EXEC_COMMAND( "ECHO %DISCO_SITES()" );
/* .. become "FEATURES" + "dummy atoms" within SYBYL's molecule
data
structure */
    pset = SYB_FEAT_FIND_ID_SET(mol, FEAT_V_LINE, 1, mol->nfeats);
    if (pset ) {
  elem = -1;
  while((elem = UTL_SET_NEXT(pset,elem)) != NO_MORE_ELEM) {
     if (!(featp = SYB_FEAT_FIND_REC (mol,elem)))  goto error;
     if ((featp->name[1] == 'S') && (featp->name[2] == '_')) {
/* have an H-bonding feature, it must represent a line */
        sitebase = featp->name[0] == 'A' ? 0 : phr->rgn->n_points;
/* the dummy atom at the end of the line is our H-bonding locus
*/
        cdp = (line_ptr) featp->dataptr;
        if (!(a = SYB_ATOM_FIND_REC (mol, cdp->positn)) ) {err=2;
goto
error;}
        for (ci = 0; ci < 3; ci++ ) {
            tmp   =   (a->xyz[ci]  -   bxptr->lo[ci])   /
bxptr->stepsize[ci];
            lt_base[ci] = (int) (tmp < 0.0 ? tmp -
bxptr->stepsize[ci] :
tmp );
        }
/* cycle through all points touched by this locus that are also
```

```
within the
region */
        for (lt_off[0] =  lt_base[0] + loff; lt_off[0] <=
lt_base[0] + hioff;
lt_off[0]++)
            if (lt_off[0] >= 0 && lt_off[0] < bxptr->nstep[0])
              for (lt_off[1] = lt_base[1] + loff; lt_off[1] <=
lt_base[1] +
hioff; lt_off[1]++)
                if (lt_off[1] >= 0 && lt_off[1] < bxptr->nstep[1])
                  for (lt_off[2] = lt_base[2] + loff; lt_off[2] <=
lt_base[2] +
hioff; lt_off[2]++)
                    if (lt_off[2] >= 0 && lt_off[2] < bxptr->nstep[2] )
{
                        boff = xybase * lt_off[2] +
                              (bxptr -> nstep[0]) * lt_off[1]
+
                              lt_off[0] + sitebase;
                        UTL_SET_INSERT( anset, boff );
                        (*nvalid)++;
        }
      }
   }
    UTL_SET_DESTROY( pset );
    } /* pset exists */
    return( anset );
error:
    sprintf (str, "qsar_proc_calc_phore_set(%d)", err);
    UTL_ERROR_ADD_TRACE (str);
    return FALSE;
}
#  This file determines the recognition of site points in
Sybyl/DISCO.
#  See the SYBYL DISCO manual for detailed documentation. The
defined types
are
#    (1) HB : the QUERY is searched in the SEARCH mode, and all
occurences
```

```
#                 are assigned DISCO features according to the remaining
#                 specifications -- the three ATOMS refer to the atom number
#                 in QUERY such that the feature is DIST from the first atom
#                 at bond ANGLE with the first and second atom at each of the
#                 TORSIONS formed by the site point and the three ATOMS in order.
#                 A sitepoint of NAME is added at these extension points,
#                 -- and -- the first atom is assigned a feature complimentary
#                 to the extension point (such as HBD_CO_ and RHBD_CO_).
#    (2) HBex:differs from HB in that the angles and torsions are replaced
#                 by two other arguments: whether lone pairs are part of the
#                 extension point placement, and which ATYPE (generally LP
#                 and/or H) determine the direction of the sitepoints.

#TYPE NAME      ATOMS SEARCH DIST ANGLE TORSIONS      QUERY
#====  ====     =====  ======  ==== =====  ========    =====
HB    DS_O2C2_   4 2 1 NoDup   2.9  120   "0.0 180.0"  HevC(Any)=O[f]
HB    DS_O3Car_  1 3 4 All     2.9  119   "0.0 180.0"  O[f]HC(:Hev):Hev
HB    DS_O3Car_  1 2 3 All     2.9  119   "0.0 180.0"  O[f]C(:Hev):Hev
HB    DS_O3Car_  1 3 4 NoDup   2.9  119   "0.0 180.0"  O[f]HC(=O)
HB    DS_O3Car_  1 2 3 NoDup   2.9  119   "0.0 180.0"  O[f]C(=O)
HB    DS_O3Car_  2 1 3 All     2.9  120   "0.0 180.0"  C(:O[f]):O[f]
HB    DS_O3C3_   1 3 6 NoDup   2.9  117   "60 180 300"  O[f]HC(Any)(Any)C(Any)(Any)Any
HB    DS_N3C3_   1 4 5 NoDup   2.9  110   "60 180 300"  N[f]H2ZC{Z:C&!C=O&!C:Hev}
HB    DS_O2S_    3 2 1 All     2.9  120   "0.0 180"   AnyS(=O)(=O)NH
#TYPE NAME      ATOMS   SEARCH DIST LP ATYPE  Query
```

```
#====  ====  =====  ======  ====  ===  =====  ==========
HBex  DS_O3C3_  2 1 3   NoDup    2.9    YES  "LP H"
O[f]HC(Any)(Any)Z{Z:Hev&!C(Any)(Any)Any}
HBex  DS_O3C3_  3 1 2   NoDup    2.9    YES  "LP"    O[f](Z)Z{Z:C&!C=Het}
HBex  DS_N3C3_  2 1 4   Nodup    2.9    ""   "H"
N[f]H2YaZ{Z:Hev&!C}{Ya:C&!C=O&!C:Hev}
HBex  DS_N3C3_  2 1 3         NoDup       2.9      YES     "LP  H"
N[f]H(Ya)Ya{Ya:C&!C=O&!C:Hev}
HBex  DS_N3C3_  3 1 2  NoDup   2.9    YES  "LP"
N[f](Ya)(Ya)Ya{Ya:C&!C=O&!C:Hev}
HBex  DS_N2C2_  2 1 3  NoDup    3.0   YES  "H LP"  N[f]H=C
HBex  DS_N2C2_  1 2 3  NoDup    3.0   YES  "H LP"  Any~N[f]=C
HBex  DS_N2C2_  1 2 3  NoDup    3.0   YES  "LP"    Any~N[r]=C[r]
HBex  DS_N2N2   2 1 3  NoTriv   3.0   YES  "LP H"  N[1]H:C:C:N[f]:C:@1
HBex  DS_N2N2   2 1 3  NoTriv   3.0   YES  "LP H"  N[1]H:C:C:N[f]:C:@1
HBex  DS_N2N2_  3 2 1  NoDup    3.0   YES  "LP"    C:N[f]:Hev
hb    DS_O3S_   3 2 1 NoDup  2.9      128   "0.0 180.0"     HevS=O[f]
hb    DS_O3S_     4 2 1  All  2.9     128    "0.0 180.0"
HevS(=O[f])=O[f]
hb    DS_O3S_     4 2 1  All  2.9     128    "0.0 180.0"
HevS(~O[f])(~O[f])~O[f]
hb    DS_O3N_     3 2 4  All  2.9     128    "0.0 180.0"
HevN(O[f])O[f]
hb    DS_O2N_     4 2 1 NoDup  2.9    128    "0.0 180.0"
HevN(Hev)~O[f]
hbex  DS_N2N2_   3 2 1 NoDup   3.0   YES  "LP"           N:N[f]:N
hb    DS_O3P_     3 1 2  All   2.9    128  "0.0 180.0"
P(~O)(~O)(~O)(~O)
hb    DS_O3P_    3 1 2  All   2.9  128  "0.0 180.0"    P(~O)(~O)(~O)
#    #CLASSNAMES#  Acceptor_site Donor_Atom DL
HB    AS_HO3C2_  1 3 4  All 2.9    119   "0.0 180.0"  O[f]HC(:Hev):Hev
HB    AS_HO3C3_  1 3 6  NoDup 2.9    117    "60 180 300"
O[f]HC(Any)(Any)C(Any)(Any)Any
HB    AS_N3C3_   1 4 7  NoDup 2.9    110  "60 180 300"
N[f]H2C(Any)(Any)C(Any)(Any)Any
HB    AS_N3C3_   1 5 8  NoDup 2.9    110  "60 180 300"
N[f]H3C(Any)(Any)C(Any)(Any)Any
#TYPE   NAME    ATOMS    SEARCH DIST LP  ATYPE  Query
#====  ====   =====    ======  ==== ===  =====   ==========
```

```
HBex AS_HN2C2_   2 1 3 NoDup    3.0  ""  "H"    NHC(Any)=O[f]
HBex AS_HN2C2_   3 2 1 NoDup    3.0  YES "LP H" C:N[f]H:Hev
HBex AS_HN2C2_   6 5 4 NoTriv   3.0  YES "LP"   N[1]H:C:C:N[f]:C:@1
HBex AS_HO3C3_   2 1 3 NoDup    2.9  YES "LP H"
O[f]HC(Any)(Any)Z{Z:Hev&!C(Any)(Any)Any}
HBex AS_HN2C2_   3 2 4 Nodup    3.0  YES "LP H" HevN[f]H=C
HBex AS_HN2C2_   1 2 3 Nodup    3.0  YES "LP"   HevN[f]=C
HBex AS_HN2C2_   2 1 4 Nodup    3.0  ""  "H"    N[f]H2C(N)=N
HBex AS_N3C3_    2 1 4 Nodup    2.9  YES "LP H"
N[f]H2C(Any)(Any)Z{Z:Hev&!C(Any)(Any)Any}
HBex AS_N3C3_    2 1 5 Nodup    2.9  YES "LP H"
N[f]H3C(Any)(Any)Z{Z:Hev&!C(Any)(Any)Any}
HBex  AS_N3C3_    2    1    3    NoDup         2.9      YES     "LP   H"
N[f]H(Ya)Ya{Ya:C&!C=O&!C:Hev}
HBex  AS_N3C3_    2    1    4    NoDup         2.9      YES     "LP   H"
N[f]H2(Ya)Ya{Ya:C&!C=O&!C:Hev}
HBex  AS_N3C3_    2    1    3    NoDup         2.9      YES     "LP   H"
N[f]H(Ya)(Ya)Ya{Ya:C&!C=O&!C:Hev}
HBex   AS_N3C3_    3    1    2    NoDup         2.9      YES     "LP"
N[f](Ya)(Ya)Ya{Ya:C&!C=O&!C:Hev}
HBex AS_HN2C2_   2 1 3 NoDup    3.0  YES "H LP" N[f]H=C
HBex AS_HN2C2_   3 1 2 NoDup    3.0  YES "LP"   N[f]=C~Any
HBex AS_HN2C2_   2 1 4 NoDup    3.0  ""  "H"    N[f]H2Hev(:Hev):Hev
HBex AS_HN2C2_   2 1 3 NoDup    3.0  ""  "H"    N[f]HHev(:Hev):Hev
HBex AS_HN2C2_   1 2 3 NoDup    3.0  ""  "H"    HNC=Any
HBex AS_HNS3_    6 5 2 NoDup    3.0  ""  "H"    AnyS(=O)(=O)N[f]H
HBex AS_HN4_     2 1 3 NoDup   -3.6  ""  "C*"
N[f](Z)(Z)(Z)Z{Z:C&!C=O&!C:Hev}
hbex AS_HN2N2_   3 2 1 NoDup    3.0  YES "LP"             N:N[f]:N
hb   AS_O3P_     3 1 2 All   2.9   128  "0.0 180.0"
P(~O)(~O)(~O)(~O)
hb   AS_O3P_     3 1 2 All   2.9   128  "0.0 180.0"    P(~O)(~O)(~O)
```

APPENDIX "C"

EXPERIMENTAL DATA SETS

| Data Set | No. Of Cpds | Structure, Activity |
|---|---|---|
| 1 Uehling | 9 | camptothecin, DNA fragmentation |
| 2 Strupczewski | 34 | benzisoxazoles, ip Behavioral |
| 3 Siddiqi | 10 | adenosines, Brain A1 binding |
| 4 Garratt1 | 10 | tryptamines, melanophore binding |
| 5 Garratt2 | 14 | tryptamines, melanophore binding |
| 6 Heyl | 11 | deltorphin, opioid receptor (DAMGO) |
| 7 Cristalli | 32 | adenosines, A2a agonists |
| 8 Stevenson | 5 | piperidines, NK1 antagonism |
| 9 Doherty | 6 | triarylbutenolides, endothelin-A antag. |
| 10 Penning | 13 | SC-41930 analogs, LTB4 antagonism |
| 11 Lewis | 7 | oxazolinediones, NK1 binding |
| 12 Krystek | 30 | sulfonamides, endothelin-A antagonism |
| 13 Yokoyama1 | 13 | oxamic acids, T3 binding |
| 14 Yokoyama2 | 12 | oxamic acids, T3 binding |
| 15 Svensson | 13 | benzindoles, 5-HTA agonism |
| 16 Tsutsumi | 13 | peptidyl heterocycles, endopeptidase inhib |
| 17 Chang | 34 | biphenyl sulfonamides, AT1 binding |
| 18 Rosowsky | 10 | trimetrexate analogs, DHFR inhibition |
| 19 Thompson | 8 | peptidomimetic, HIV-1 protease inhibition |
| 20 Depreux | 26 | naphthylethyl amides, melatonin displ. |

Literature References for Data Sets:

1. Uehling, D.E., Nanthakamur, S.S., Croom, D., Emerson, D.L., Leitner, P.P., Luzzio, M.J., et al., Synthesis, Topoisomerase I Inhibitory Activity, and in Vivo Evaluation of 11-Azacamptothecin Analogs. *J. Med. Chem.* 1995, 38, 1106 (Table 2, with $R_2$=Et; $IC_{50}$ data.

2. Strupczewski, J.T., Bordeau, K.J., Chiang, Y., Glamkowski, E.J., Conway, P.G., et al. 3-[[(aryloxy)alkyl]piperidinyl]-1,2-Benzisoxazoles as D2/5-HT2 Antagonists with Potential Atypical Antipsychotic Activity: Antipsychotic Profile of Iloperidone (HP873). *J. Med. Chem.* 1995, 38, 1119. (Tables 2 and 3 with n=3, X=O; $ED_{50}$ for inhibition of apomorphine-induced climbing.)

3. Siddiqi, S.M., Jacobson, K.A., Esker, J.L., Olah, M.E., Ji, Xi.-duo., *et al.*, Search for New Purine- and Ribose-Modified Adenosine Analogs as Selective Agonists and Antagonists at Adenosine Receptors. *J. Med. Chem.* 1995, 38, 1174. (Table 1, $R_2$=H; $K_i$(A1), values estimated from % displacement and stereoisomers averaged as needed.)

4. Garratt, P. J., Jones, R., Tocher, D. A., Sugden, D., Mapping the Melatonin Receptor. 3. Design and Synthesis of Melatonin Agonists and Antagonists Derived from 2-Phenyltryptamines. *J. Med. Chem.* 1995, 38, 1132. (Table 1 and Table 2).

5. Garratt, P. J., Jones, R., Tocher, D. A., Sugden, D., Mapping the Melatonin Receptor. 3. Design and Synthesis of Melatonin Agonists and Antagonists Derived from 2-Phenyltryptamines. *J. Med. Chem.* 1995, 38, 1132. (Table 1 and Table 2).

6. Heyl, D.L., Dandabuthla, M., Kurtz, K.R., Mousigian, C. Opioid Receptor Binding Requirements for the &-Selective Peptide Deltorphin I: $Phe^3$ Replacement with Ring-Substituted and Heterocyclic Amino Acids. *J. Med. Chem.* 1995, 38, 1242. (Table 1; binding $K_1$ to DAMGO.)

7. Cristalli, G., Camaioni, E., Vittori, S., Volpini, R., Borea, P.A., *et al.* 2-Aralkynyl and 2-Heteroalkynyl Derivatives of Adenosine-5'-N-ethyluronamide as Selective A2a Adenosine Receptor Agonists. *J. Med. Chem.* 1995, 38, 1462.

8. Stevenson, G.I., MacLeod, A.M., Huscroft, I., Cascieri, M.A., Sadowski, S., Baker, R. 4,4-Disubstituted Piperidines: A New Class of $NK_1$ Antagonist. *J. Med. Chem.* 1995, 38, 1264. (Table 1.)

9. Doherty, A.M., Patt, W.C., Edmunds, J.J. Berryman, K.A., Reisdorph, B.R., *et al.* Discovery of a Novel Series of Orally Active Non-Peptide Endothelin-A ($ET_A$) Receptor-Selective Antagonists. *J. Med. Chem.* 1995, 38, 1259. (Table 3; $IC_{50}$ $ET_A$.)

10. Penning, T.D., Djuric, S.W., Miyashiro, J.M., Yu, S., Snyder, J.P., *et al.* Second-Generation Leukotriene $B_4$ Receptor Antagonists Related to SC-41930; Heterocyclic Replacement of the Methyl Ketone Pharmacophore. *J. Med. Chem.* 1995, 38, 858. (Table 1, all; $LTB_4$ receptor binding.)

11. Lewis, R.T., MacLeod, A.M., Merchant, K.J. Kelleher, F., Sanderson, I., *et al.* Tryptophan-Derived NK1 Antagonists: Conformationally Constrained Heterocyclic Bioisosteres of the Ester Linkage. *J. Med. Chem.* 1995, 28, 923.

12. Krystek, S.R., Hunt, J.T., Stein, P.D., Stouch, T.R. 3D-QSAR of Sulfonamide Endothelin Inhibitors. *J. Med. Chem.* 1995, 38, 659.

13. Yokoyama, N., Walker, G.N., Main, A.J. Stanton, J.L. Morrissey, M., *et al.* Synthesis and SAR of Oxamic Acid and Acetic Acid Derivatives Related to L-Thyronine. *J. Med. Chem.* 1995, 38, 695.

14. Yokoyama, N., Walker, G.N., Main, A.J. Stanton, J.L. Morrissey, M., *et al.* Synthesis and SAR of Oxamic Acid and Acetic Acid Derivatives Related to L-Thyronine. *J. Med. Chem.* 1995, 38, 695.

15. Haadsma-Svensson, S.R., Svensson, K., Duncan, N., Smith, M.W., Lin, Ch.-H. C-9 and N-Substituted Analogs of cis-(3aR)-(-)-2,3,3a,4,5,9b-Hexahydro-3-propyl-1H-benz[e]indole-9-carboxamide: 5HT1A Receptor Agonists with Various Degrees of Metabolic Stability. *J. Med. Chem.* 1995, 38, 725.

16. Tsutsumi, S., Okonogi, T. Shibahara, S., Ohuchi, S., Hatsushiba, E., *et al.*, Synthesis and Structure Activity Relationships of Peptidyl @-Keto Heterocycles as Novel Inhibitors of Prolyl Endopeptidase. *J. Med. Chem.* 1994, 37, 3492. (Table 2, X=$CH_2CH_2$;$IC_{50}$.)

17. Chang, L.L., Ashton, W.T., Flanagan, K.L., Chen, Ts.-Bau., O'Malley, S.S., *et al.*, Triazolinone Biphenylsulfonamides as Angiotensin II Receptor Antagonists with High Affinity for Both the $AT_1$ and $AT_2$ Subtypes. *J. Med. Chem.*, 1994, 37, 4464. (Table 1, $R^3$ =(2-Cl)$C_6H_5$; $AT_1$ [rabbit aorta] $IC_{50}$.)

18. Rosowsky, A., Mota, C.E., Wright, J.E., Queener, S.F., 2,4-Diamino-5-chloroquinazoline Analogs of Trimetrexate and Piritrexim: Synthesis and Antifolate Activity. *J. Med. Chem.* 1994, 37, 4522. (Table 2; rat liver $IC_{50}$.)

19. Thompson, S.K., Murthy, K.H.M., Zhao, B., Winborne, E., Green, D.W., *et al.* Rational Design, Synthesis, and Crystallographic Analysis of a Hydroxyethylene-Based HIV-1 Protease Inhibitor Containing a Heterocyclic P1'-P2' Amide Bond Isostere. *J. Med. Chem.* 1994, 37, 3100. (Table 2, X-Boc; apparent $K_i$.)

20. Depreux, P., Lesieur, D., Mansour, H.A., Morgan, P., *et al.* Synthesis and Structure-Activity Relationships of Novel Naphthalenic and Bioisosteric Related Amidic Derivatives as Melatonin Receptor Ligands. *J. Med. Chem.* 1994, 37, 3231.

APPENDIX "D"

A list of 736 commercially available thiols broken down into 231 clusters based on topomeric CoMFA field descriptors along with the systematic name applicable to each. The 231 clusters are sorted by proposed name, first by the "root" structure, ie., the fragment attached immediately to the -SH, and then by the substitution pattern on that "root" substructure. The names describe topologically equivalent hydrocarbons, ie., structures in which all monovalent atoms are replaced by hydrogens and the other atoms by carbons.

| Cluster ID | Cluster Size | Struct. Root | Structural Substitution[a] |
|---|---|---|---|
| 1 | 26 | aryl | Simple |
| 144 | 1 | aryl | 2,3,5-Me |
| 177 | 1 | aryl | 2,3,5-Me-4-Pr |
| 163[c] | 1 | aryl | 2,3-(4-(2,3-Pr)5het)5hetO |
| 151 | 1 | aryl | 2,3-(4-Bu)5hetO-5-Me |
| 33 | 5 | aryl | 2,3-Benzo |
| 80 | 2 | aryl | 2,5-Me |
| 192 | 1 | aryl | 2,5-Me-3-iPe |
| 7 | 14 | aryl | 2,6-NoH-3(4/5)-Me |
| 27 | 6 | aryl | 2,6-NoH-3-Ar |
| 107 | 2 | aryl | 2-(2-Bz)PheEt-4,5-Benzo |
| 189 | 1 | aryl | 2-(3,5-Me)Ar-4,5-Benzo |
| 141 | 1 | aryl | 2-(4-Et)PhePr |
| 205 | 1 | aryl | 2-(4-Stilbenyl)Stilbenyl |
| 188 | 1 | aryl | 2-5hetCH2-4,5-Benzo |
| 56 | 3 | aryl | 2-Ar |
| 138 | 1 | aryl | 2-Ar-3,5-Me |
| 190 | 1 | aryl | 2-Ar-4,5-(3,4-Et)Benzo |
| 41 | 6 | aryl | 2-Ar-4,5-Benzo |
| 152 | 1 | aryl | 2-Bz |
| 16 | 9 | aryl | 2-Et |
| 85 | 2 | aryl | 2-NoH-3-Et-5-Me |
| 106 | 2 | aryl | 2-PheEt-4,5-Benzo |
| 77 | 2 | aryl | 2-PhePr |
| 142 | 1 | aryl | 2-R8 |

| | | | |
|---|---|---|---|
| 121 | 2 | aryl | 2-Stilbenyl |
| 97 | 2 | aryl | 3,4-(3-Me)Benzo |
| 218 | 1 | aryl | 3,4-(a,b)IndenO |
| 164 | 1 | aryl | 3,4-(a,b,(8-Ar)IndenO)-6-Me |
| 98 | 2 | aryl | 3,4-(a,b,(c-Me)IndenO) |
| 99 | 3 | aryl | 3,4-(a,b-Naphtho) |
| 157 | 1 | aryl | 3,4-Ar |
| 58 | 3 | aryl | 3,4-Benzo-5-Me |
| 100 | 2 | aryl | 3,4-Benzo-6-tBu |
| 37 | 5 | aryl | 3,5-Me |
| 180 | 1 | aryl | 3-(2,3-Benzo-4-Et)5het |
| 199 | 1 | aryl | 3-(2,3-Benzo-5-Me)5het |
| 182 | 1 | aryl | 3-(2-Me-3-5het-5-Et)5het |
| 115 | 2 | aryl | 3-(3-5het)5het |
| 193 | 1 | aryl | 3-(3-Ar)5het-4-Me |
| 67 | 3 | aryl | 3-Ar |
| 129 | 2 | aryl | 3-Ar-4-(2-Me)5hetCH2 |
| 46 | 4 | aryl | 3-Ar-5-Me |
| 155 | 1 | aryl | 3-Bz |
| 82 | 2 | aryl | 3-Bz-5,6-Benzo |
| 10 | 16 | aryl | 3-Me |
| 70 | 3 | aryl | 3-Naphth |
| 73 | 3 | aryl | 3-Pr-4-sBu-6-Me |
| 95 | 2 | aryl | 3-iPr |
| 88 | 2 | aryl | 4-Ar |

| | | | |
|---|---|---|---|
| 81 | 2 | aryl | 4-Bz |
| 48 | 4 | aryl | 4-Et |
| 2 | 23 | aryl | 4-Me |
| 92 | 2 | aryl | 4-R9+ |
| 90 | 4 | aryl | 4-iBu |
| 19 | 8 | aryl | 6-NoH |
| 148[c] | 1 | aryl | (adenosine) |
| 228 | 1 | aryl | (fluorescein) |
| 12 | 10 | 5het | Simple |
| 50 | 4 | 5het | 2,3-(a,b-Naphtho) |
| 139 | 1 | 5het | 2,3-5hetO-4-Me |
| 89 | 2 | 5het | 2,3-Ar |
| 173 | 1 | 5het | 2-(2,5-Et)Ar-3-Et |
| 69 | 3 | 5het | 2-(2-Me)Ar-3-(2-Me)PheEt |
| 198 | 1 | 5het | 2-(2-Me)Ar-3-R10 |
| 174 | 1 | 5het | 2-(2-sBu)-3-Et |
| 171 | 1 | 5het | 2-(3,5-Me)Ar-3-5het |
| 170 | 1 | 5het | 2-(3,5-Me)Bz-3,4-Benzo |
| 123 | 2 | 5het | 2-(3-Et)Ar-3-Bz |
| 22 | 7 | 5het | 2-(4-Et)Ar |
| 202 | 1 | 5het | 2-(4-Et)Ar-4-(4-Me)Ar |
| 122 | 2 | 5het | 2-(4-iPr)Ar-3-Bz |
| 197 | 1 | 5het | 2-5hetCH2-3-(4-tBu)Ar |
| 6 | 14 | 5het | 2-Ar |
| 225 | 1 | 5het | 2-Ar-3-(2-Ar)5hetBu |

| | | | |
|---|---|---|---|
| 224 | 1 | 5het | 2-Ar-3-(2-Ar)5hetCH2 |
| 63 | 3 | 5het | 2-Ar-3-(2-Bz)Ar |
| 178 | 2 | 5het | 2-Ar-3-(2-Me)5het |
| 72 | 3 | 5het | 2-Ar-3-(3,4-Et)Bz |
| 40 | 5 | 5het | 2-Ar-3-(3-Ar)5HetEt |
| 183 | 1 | 5het | 2-Ar-3-(3-Ar)PhePr |
| 64 | 3 | 5het | 2-Ar-3-(3-Ar-5-Me)5het |
| 105 | 2 | 5het | 2-Ar-3-(3-Me)Ar |
| 160 | 1 | 5het | 2-Ar-3-(4-Ar)Cyhx |
| 146 | 1 | 5het | 2-Ar-3-(4-Ar)CyhxCH2 |
| 203 | 1 | 5het | 2-Ar-3-(4-PheEt)Ar |
| 126 | 2 | 5het | 2-Ar-3-(tBu)Ar |
| 17 | 9 | 5het | 2-Ar-3-Ar |
| 211[c] | 1 | 5het | 2-Ar-3-Benzylidene |
| 124 | 2 | 5het | 2-Ar-3-IndenCH2 |
| 28[b] | 6 | 5het | 2-Ar-3-Me |
| 30 | 6 | 5het | 2-Ar-3-PhePr |
| 204 | 1 | 5het | 2-Ar-5-(4-(2,4-Me)Bz)Ar |
| 79 | 2 | 5het | 2-Bz |
| 78 | 2 | 5het | 2-Bz-3,4-Benzo |
| 117 | 2 | 5het | 2-Cyhx |
| 186 | 1 | 5het | 2-Cyhx-3,4-iPe |
| 68 | 3 | 5het | 2-Et |
| 112 | 2 | 5het | 2-Et-3-(2-Me)PheEt |
| 128 | 2 | 5het | 2-Me-3,4-(3-Me)Benzo |

| | | | |
|---|---|---|---|
| 93 | 2 | 5het | 2-Me-3,4-Benzo |
| 61 | 3 | 5het | 2-Me-3-(2,3,4-Me)5het |
| 181 | 1 | 5het | 2-Me-3-(2,3-Benzo-4-Et)5het |
| 49 | 4 | 5het | 2-Me-3-(3-Ar)5het |
| 86 | 2 | 5het | 2-Me-3-(3-Ar)5hetPr |
| 91 | 2 | 5het | 2-Me-3-(3-Ar-5-Me)5het |
| 4 | 17 | 5het | 2-Me-3-(3-Bz)Ar |
| 172 | 1 | 5het | 2-Me-3-(4-tBu)PheEt |
| 38 | 5 | 5het | 2-Me-3-5Het |
| 13 | 10 | 5het | 2-Me-3-Me |
| 222 | 1 | 5het | 2-Me-3-Pe |
| 66 | 3 | 5het | 2-Me-3-PheEt |
| 29 | 6 | 5het | 2-Me-3-PhePr |
| 71 | 3 | 5het | 2-Me-3-R8+ |
| 108 | 2 | 5het | 2-Me-5-Bu |
| 127 | 2 | 5het | 2-Pe-3-Ar |
| 54 | 3 | 5het | 2-Pr |
| 221 | 1 | 5het | 2-R12 |
| 187 | 1 | 5het | 2-iBu-3,4-iPe |
| 143 | 1 | 5het | 2-iPe-3,4-Benzo |
| 96 | 2 | 5het | 3,4-(2,4-Me)Benzo |
| 162 | 1 | 5het | 3,4-(3-Ar)Benzo |
| 169 | 1 | 5het | 3,4-(3-Hx)Benzo |
| 94 | 2 | 5het | 3,4-(3-Pr)Benzo |
| 210 | 1 | 5het | 3,4-(a,b-Napththo) |

| | | | |
|---|---|---|---|
| 36 | 15 | 5het | 3,4-Benzo |
| 176 | 1 | 5het | 3-(2,4-Me)Bz |
| 196 | 1 | 5het | 3-(3,5-Me)Ar |
| 159 | 1 | 5het | 3-(3-Ar)5het |
| 42 | 4 | 5het | 3-(3-Bz)Ar |
| 200 | 1 | 5het | 3-(3-Me)PheEt |
| 113 | 2 | 5het | 3-(4-Me)Ar |
| 125 | 2 | 5het | 3-(4-tBu)Ar |
| 191 | 1 | 5het | 3-(A1-4-Et)PheEt |
| 145 | 1 | 5het | 3-(B-Ar)PhePr |
| 114 | 2 | 5het | 3-5hetCH2 |
| 18 | 8 | 5het | 3-Ar |
| 59 | 3 | 5het | 3-Ar(2-thia) |
| 65 | 3 | 5het | 3-Bu |
| 24 | 7 | 5het | 3-Me-5-H |
| 44 | 6 | 5het | 3-Me-5-NoH |
| 52 | 5 | 5het | 3-Pe |
| 111 | 2 | 5het | 3-PheEt |
| 153 | 1 | 5het | 3-PhePr |
| 32[b] | 6 | 5het | 3-Pr |
| 223 | 1 | 5het | 3-R13 |
| 185 | 1 | 5het | (chrysenO) |
| 34 | 5 | alkyl | Simple |
| 104 | 2 | alkyl | (3)(B1)(B1) |
| 62 | 3 | alkyl | (3-Me)PhePr |

| | | | |
|---|---|---|---|
| 3 | 18 | alkyl | (3:4) |
| 14 | 9 | alkyl | (3:4)(A1) |
| 60 | 3 | alkyl | (3:4)(B1) |
| 226 | 1 | alkyl | (4)(A1)(A-tBu)(C1)(C1) |
| 45 | 4 | alkyl | (4)(D1)(D1) |
| 35 | 7 | alkyl | (4-Me)PhePr |
| 168 | 1 | alkyl | (4-iPe)PhePr |
| 47 | 4 | alkyl | (5)(A1) |
| 179 | 1 | alkyl | (5)(B1)(E-(2-Ar-5-Me)5het) |
| 103 | 2 | alkyl | (5)(B3) |
| 76 | 2 | alkyl | (5)(C1)(C1) |
| 83 | 2 | alkyl | (5)(C2) |
| 216 | 1 | alkyl | (5)(C2)(D2)(D2) |
| 43 | 8 | alkyl | (5:6)(D1/B1/F1) |
| 5 | 15 | alkyl | (5:7) |
| 158 | 1 | alkyl | (6)(B8)(C1)(E1)(E1) |
| 140 | 1 | alkyl | (6)(F-Ar) |
| 166 | 1 | alkyl | (7)(A8)(F1) |
| 53 | 3 | alkyl | (7)(D3)(D3) |
| 207 | 1 | alkyl | (8)(C3) |
| 8 | 13 | alkyl | (8:11) |
| 206 | 1 | alkyl | (9)(B4)(G3) |
| 75 | 3 | alkyl | (10)(B1)(E5)(E1) |
| 136 | 1 | alkyl | (10)(C1)(E5)(E2) |
| 20 | 8 | alkyl | (10+)(B1) |

| | | | |
|---|---|---|---|
| 39 | 7 | alkyl | (11+)(B1) |
| 154ᶜ | 1 | alkyl | (12)(A-PheEt) |
| 230 | 1 | alkyl | (12)(F6)(F1) |
| 131 | 2 | alkyl | (12)(F6)(F6) |
| 15 | 9 | alkyl | (12+) |
| 137 | 1 | alkyl | (13)(E4) |
| 231 | 1 | alkyl | (A-Ar)(A-Ar)Bz |
| 229 | 1 | alkyl | (A-Bz)(A-Bz)PheEt |
| 184 | 1 | alkyl | (A1)PheEt |
| 227ᶜ | 1 | alkyl | (cholesterol) |
| 214ᶜ | 1 | alkyl | (cryptate) |
| 23 | 7 | alkyl | PheBu |
| 74 | 3 | alkyl | PheEt |
| 25ᵇ | 6 | alkyl | PhePr |
| 11 | 10 | benzyl | Simple |
| 102 | 2 | benzyl | 2,4,5-Me |
| 57 | 3 | benzyl | 2,4,6-Me |
| 217 | 2 | benzyl | 2-(3-(2-Et)Ar)Ar |
| 213 | 1 | benzyl | 2-Et-3-(2,3-Et-5-Me)Ar-5-Me |
| 212 | 1 | benzyl | 2-R8-3-Naphthyl-4,5-Benzo |
| 9 | 13 | benzyl | 2/3-Me |
| 84 | 2 | benzyl | 3,4-Benzo |
| 132 | 2 | benzyl | 3,5-Me |
| 130 | 2 | benzyl | 3-(4-Stilbenyl)Stilbenyl |
| 134 | 2 | benzyl | 4-(3-Ar)Ar |

| | | | |
|---|---|---|---|
| 21 | 7 | benzyl | 4-Et |
| 26[b] | 6 | benzyl | 4-Me |
| 156 | 1 | benzyl | 4-PhePr |
| 201 | 1 | benzyl | 4-tBu |
| 135 | 2 | alkenyl | Ar..(2-Et)Ar |
| 220 | 1 | alkenyl | Ar..(4-Bz)Ar |
| 116 | 2 | alkenyl | Ar..Ar |
| 133 | 2 | alkenyl | Ar..Bz |
| 110 | 2 | alkenyl | Et.CN.CONH2 |
| 87 | 2 | alkenyl | NH2.CN.N=NPh |
| 119 | 2 | alkenyl | P(NMe2)3..Ar |
| 120 | 2 | alkenyl | P(Pr)3..Ar |
| 118 | 2 | alkenyl | P(iPe)3..Ar |
| 51 | 4 | alkenyl | PCyhx3..Ar |
| 195[c] | 1 | alkenyl | PEt3..(2-Bz)Ar |
| 31[b] | 6 | alkenyl | PEt3..Ar |
| 194 | 1 | alkenyl | PEt3..Bz |
| 109 | 2 | alkenyl | PheEt.CN.CONH2 |
| 101 | 2 | cyclohexyl | Simple |
| 149 | 1 | cyclohexyl | 1-Me-2,4-CMe2 |
| 55 | 3 | cyclohexyl | 2,3,4,5-iBu |
| 147 | 1 | cyclohexyl | 2,3,4-iBu-5-iPe |
| 209 | 1 | cyclohexyl | 2-(3,4-PheEt)5het-6-Me |
| 208 | 1 | cyclohexyl | 2-Me-3,5-CMe2 |
| 167 | 1 | cyclohexyl | 2-Me-4-sPe |

| | | | |
|---|---|---|---|
| 165 | 1 | cyclohexyl | 2-iPr-3,5-Me |
| 150 | 1 | cyclohexyl | 3-sPe-6-Me |
| 161 | 1 | cyclohexyl | 4-Et-4-iBu |
| 219 | 1 | cyclohexyl | (complex) |
| 175 | 1 | cyclopentyl | 2-Ar-4-spiro |
| 215 | 1 | cyclopentyl | 3-PhePr |

*To generate these names, <u>all heteroatoms are first replaced by carbon</u> (to produce the simplest common topology) and a particular structure is chosen from among these topologies as the "most typical" of that cluster, if possible to contain the largest substructure that distinguishes that cluster from all others.

Within the name of a substitution, numbers indicate positions when substitution is on a ring, but chain length when substitution is on a chain (numbers separated by a colon indicate a range of chain lengths). Also, within a chain, letters indicate a position of substitution. (For example, (C2) describes a two atom branching from the third position of a chain, while 3-PhePr describes a phenyl propyl skeleton attached to the 3-position of a ring. )

A dot notation (.) separates the three possible substituents on an alkenyl root, the substituent order being same carbon as the -SH substituent, then the position *trans* to the -SH, and finally *cis* to -SH.

The above notwithstanding, <u>any</u> name enclosed completely in parentheses takes its usual structural meaning.

Here are structural descriptions for each name abbreviation in the above table, mostly in SLN (SYBYL Line Notation), listed alphabetically. (SLN extends SMILES with the following concepts, among others. Hydrogens are explicit. Ring openings and closures begin with a number enclosed by [] and end with the matching number preceded by @. Other SLN symbols used in these SLN definitions are: ~ = any bond; - = single bond (used here to provide a reference for [R]) : = aromatic bond; ! = the SLN following (here in parentheses) is <u>not</u> allowed; [F] = no additional atoms may be attached to the preceding atom; [!R] = preceding bond may not be in a ring; [R] = preceding bond must be in a ring.)

5het = 5Het = C[1]:C:C:C:C:@1. alkenyl = C=C. alkyl = C~[!R]C. aryl = Ar = Phe = Ph = C[1]:C:C:C:C:C@1. benzyl = Bz = HSC-[!R]C~[R]C. Bu = C-[!R]C-[!R]C-[!R]C-[!R]C. cyclohexyl = Cyhx = C[1](- | =)C~C~C~C~C~@1. cyclopentyl = C[1]~(- | =)C~C~C~C~@1. Et = C-[!R]C. inden = C[1]:C(~C~X~[2]):C(~@2):C:C@1. iBu = C-[!R]C-[!R]C(-[!R]C)-[!R]C. iPe = C-[!R]C-[!R]C-[!R]C(-[!R]C)-[!R]C. Me = C. naphth = C[1]:C(~C~X~[2]):C(~@2):C:C:C@1. NoH = !(CH). O denotes ring fusion, e.g., benzo fuses a 6-membered aromatic ring. Pe = C-[!R]C-[!R]C-[!R]C-[!R]C-[!R]C. Pr = C-[!R]C-[!R]C-[!R]C. R# = alkyl chain of approximate length #. Simple = !(C~[!R]C). sPe = C(-[!R]C)-[!R]C-[!R]C-[!R]C-[!R]C. Stilbenyl = C=[!R]C-[!R]C[1]:C:C:C:C:C@1. tBu = C(-[!R]C)(-[!R]C)-[!R]C.

Appendix "E"

===================================================================================

The following replaces section E contained in the priority applications. Not all of what was previously in E is included here, because the latest versions of BUILD_3D etc. are provided separately in Section A.

*************************************************************

The first phase of construction of a combinatorial library takes
as input a description of the chemical transformation represented
by that combinatorial library and a list of available reagents such
as the Available Chemical Directory (ACD), and produces as output
all the part structures (aka substructures or fragments), in product
form, found in the list of available reagents which are appropriate for
the chemical transformation, along with all structure-invariant
physicochemical properties of those fragments that might be useful in
diversity design (Optiverse) or searching (VL).

In the course of this process, data are recorded permanently into three
tables:

REACTIONS (a Molecular Spreadsheet) = information about a
reaction scheme. Each record corresponds to a reaction,
where PanLabs or the manager of the VL designates
what is a reaction. A typical reaction would be:
"reaction of each nitrogen of a diamine with various
reagents such as acids (acylation) or ketones (reductive
amnination)".

REAGENTS (a Molecular Spreadsheet) = information about a
particular set of reagents used in some instance of a
reaction. Each record corresponds to a particular logical
reagent structure search in a database such as Available
Chemical Directories, presumably a set of reagent structures
which will all react in the same way. For example, there are sixteen reagent records for the diamine reaction, enumerating
each of eight reactant classes that might react with
each of the two nitrogens. One record for example describes a
reaction with epoxides, that could be ring opened nucleophilically
(and regioselectively) by an amine to yield a beta-amino alcohol.

RDATA (an Oracle Table) = invariant physicochemical data computed about
compound fragments, typically the varying portions in a
cSLN, with one record for each fragment encountered in ANY
cSLN constructed. Thus data need not be recomputed when such
fragments are reencountered, a substantial savings in processing time.
For example, records will be added describing the properties of
a -CH2CH(OH)R chain (product fragment) for each (new) epoxide-R
reagent retrieved by the example record just given for the REAGENTS
spreadsheet.

Entering a new reaction into the system involves adding a new row to
REACTIONS and at least two new rows to REAGENTS, by hand. This data
entry operation is the only required data entry in preparation for virtual
library production.

All other operations on these entities are carried out by the SPL script
getacd.core, executed within SYBYL. This script is reproduced below in its
entirety.

The major overall output of getacd.core is a set of files for a reaction,
whose base (file set) names are constructed by concatenating record numbers
from the REACTIONS and REAGENTS tables, and whose prefixes are as follows:

.files = explicitly contains the names for all other files.

.csln = the template or prototype for the construction of a particular
cSLN. If there is more than one possible core for a particular reaction, their
structures and properties are recorded in the optional .cores file.

.X1,.X2,.. = a "hitlist" having an SLN with property contributions
for each unique fragment or variation at a particular position. Each variation site has its own hitlist file.

.cores = similar to an .Xn file, but describes available variations in a cSLN core. For example, the .cores file for the diamine reaction lists SLNs of the cores and properties that each of the commercially available diamines would contribute.

Two intermediate data tables are used in some of the operations of getacd.core, as molecular spreadsheets:

HITS = results of a particular reagent search, also records information about supplier, catalog number, and price.

RSCRATCH = a "work table" used for calculation of side chain properties.

To aid in understanding the getacd.core SPL script which follows, here are descriptions of the individual "columns" (aka attributes, fields) for each of the tables introduced above.

REACTIONS:
  NAME (text) For user recognition only
  CLASS_ID (integer) A "global" identifier for a particular reaction scheme
  VARIATION (integer) Can be more than one per CLASS_ID, intended to distinguish
     among different reaction conditions for a particular reaction. This
     value is the key linking REACTIONS and REAGENTS
  NREAG (integer) Number of rows in REAGENTS for this reaction. Used only for
     checking self-consistency of user input.
  CORE_SLN (text) The SLN of the core for this reaction, along with information
     needed by the cSLN builder to correctly attach side chains, or, especially,
     to correctly merge polyvalent variations with an invariant core.

example of a record (diamine reaction, producing the R5V2Rn fileset), broken into two lines for clarity:

1        2        3        4

| NAME | CLASS_ID | VARIATION | NREAG |
|---|---|---|---|
| 5 Row5 Piperazine | 5 | 2 | 16 |

CORE_SLN

---

5 Row5 N[1](X1)CH2CH2N(X2)CH2CH2@1 2,X1R1=1;10,X2R1=9

REAGENTS:

ID (integer) invariant identifier for this record

VARIATION (integer) link to REACTIONS by many-to-one relation

SEARCH_SLN (text) SLN for the reactive fragment, which any reactant
molecule (e.g., within ACD) must contain in order to undergo
the particular reaction NOTLIST (text) combination of SLNs and files (of additional SLNs)
for fragments that must NOT be contained within any reactant
to be used in this reaction. (Reasons include interference
with this or other reactions in the sequence, or toxicity
to biological systems.)

PRUNE_SLN (text) similar and usually identical to SEARCH_SLN but
may not contain any atoms or bonds of type "Any", needed
while processing the individual reagent to overcome some
quirks in SLN processing within SYBYL.

SAME_AS (text) a hitlist file name. If present, this file's contents
are used instead of an explicit reagent search that need not
be done. (For example, the list of acids that react with
piperidine are identical for each of the two nitrogens.)

HOW (text) a series of structural modification commands which the
script uses to convert a reactant structure into the corresponding
atoms within the product. Atom ID references within these
commands are sequence numbers of that atom within the PRUNE_SLN, or to names of atoms generated in a previous command.

Example: An isocyanate (PRUNE_SLN is CN=C=O) becomes most of a urea (CNHC(=O)X1) when reacted with an amine. Here is the HOW for this transformation:

BREAKB,2,3 ATYPE,2,N.am ATYPE,3,C.2 FILLV,2,H,A1 FILLV,3,H,A2 MARKX,A2

(reading left to right: the N=C becomes single; the N is made trivalent; the C is made sp2; hydrogen named A1 is added to the N; hydrogen named A2 is added to the C; the A2 is marked as designating a "free valence" whenever a cSLN is expanded.)

ATTACHED (text) the file extension for the output file of cSLN variations that this record produces.

TEMPLATE (text) for polyvalent variations only, information needed to build an aligned topomeric conformation, as follows:

Argument 1: a file containing a pre-aligned 3D structure.

Argument 2: the SLN of the template within the 3D structure produced by joining the reactant molecule to the pre-aligned structure.

Argument 3: the name of an SPL macro that performs any additional structural operations needed to generate the topomeric conformation.

Argument 4: Any additional arguments to be passed to the macro named in argument 3.

Example: aram.mol2 NH=CHCH2C(:Any):CH ACD!FIX_FUSE 10,11

VALENCES (integer) the number of valences within each of these variations.

FGPT_XTRA (text) for optimal fingerprint estimation, the SLN for any atoms that this particular record will ALWAYS add to the core. For example, FGPT_XTRA for the isocyanate acylation example in HOW is: C(=O)NHC EXAMPLE: Here is the record for the reductive amination reaction in which a carbonyl (aldehyde or ketone only) is condensed with a primary or secondary amine and then reduced to the amine with borohydride.

| 1 | 2 | 3 |
|---|---|---|
| ID | VARIATION | SEARCH_SLN |
| 13 ROW13 | 13 | 2 HcC(=O)C(-:Any)-:Any{Hc:H\|C(-:Any)} |

| 4 | 5 |
|---|---|
| | NOTLIST |
| 13 ROW13 bad1s.kal | O=CO[f] O=COH O=CC=O O=CAnyC=O \ HcC(=O)C(-:Any)(-:Any).HcC(=O)C(-:Any)(-:Any){Hc:H\|C(-:Any)-:Any} \ NH(Hc)C(Any)Any{Hc:H\|C(Any)Any} |

| 5 | 6 |
|---|---|
| PRUNE_SLN | SAME_AS |
| 13 ROW13 HcC(=O)C{Hc:H\|C} | ? |

| 7 |
|---|
| HOW |
| 13 ROW13 BREAKB,2,3 DELA,3 ATYPE,2,c.3 FILLV,2,H,A1 MARKX,A1 |

| 8 | 9 | 10 |
|---|---|---|
| ATTACHED | TEMPLATE | VALENCES |
| 13 ROW13 X1 | ? | 1 |

| 11 |
|---|
| FGPT_XTRA |
| 13 ROW13 CHC |

RDATA

CRC (number(10,0), primary key) a "cyclic redundancy code", used most often to verify the integrity of data communication packets, generated here from the SLN to enable fast exact substructure match searching of an Oracle table. (Rare ties in CRC values fOr non-identical SLNs are broken by appending <name=junk> to the duplicate-generating SLN and attempting to reregister until a unique CRC is generated.)

SLN (text) SLN of a fragment, open valence(s) at point(s) of attachment.

LOGP (NUMBER(6,2)) logP of the fragment, calculated for the structure where all open valences are filled with H's. A value of 99.99 denotes "could not be calculated".

MW (NUMBER(10,2)) molecular weight of the fragment exactly as described by the SLN. A value of -1.0 denotes "could not be calculated".

TOPOMERIC (text) a textual representation of the CoMFA steric field for the topomeric conformation of this molecule. (The 3D SLN of this conformation is written to a file in the fileset with extension .fal, for possible future reference.)

NROTBONDS (NUMBER(2,0)) number of bonds whose torsional values were set for this side chain during generation of the topomeric conformation.

PH_AS, PH_DL, PH_DS, PH_AL, PH_AR (NUMBER(2,0)) number of pharmacophoric points within this side chain, of different classes as defined by DISCO and SYBYL 6.3/Unity 2.6.

following are definitions of oracle queries used for referencing table RDATA
within SPL.

RDBMS REFERENCE DEFINE oracle_rdata tripos oracle castor \
    MACHINE_ACCESS_INFO explicit_userid lawless explicit_password j1u8l6y1 \
    RDBMS_ACCESS_INFO EXPLICIT_USERID adsvl explicit_password adsvl \
DONE RDBMS QUERY DEFINE RDATA_DATA oracle_rdata
  select SLN,LOGP,MW,TOPOMERIC,NROTBONDS from RDATA where CRC=:NEW_CRC
.
DONE

ALL THAT REMAINS IS GETACD.CORE AND CERTAIN FILES FROM CHOM_BATCH.CORE

======================================================================

```
# There are only two important user entry points
#     "optiv" for most purposes
#     "cores" for building the .cores file (to be replaced)

@macro optiverse sybylbasic

================================================================
# sets global state variables, then dispatches tasks in order

# $1 is a set of reaction IDs
# $2 is a set of modifiers (variations to be skipped, NoSearch, Test, .. )
#      TEST = only the first item in each hitlist is processed
#             (allows checking out all input data quickly)
#      DEBUG = uims ver on at all times
#      RONLY = only process specified rows in REAGENTS
#      NOSEARCH = skip search (hit lists must already exist in
#                 working directory)
#      NOCAT = skip concatenation of Xn files
#      SEARCH = ONLY do search
#      BUILD = ONLY convert hitlists to Xn files
#      CSLN = ONLY build CSLN template
#      CORES = ONLY do core search and processing
#      numeric values - two interpretatioons
#             if RONLY, these are the ROW IDS in the REAGENT MSS to use
#             if not RONLY, these are VARIATIONS to NOT process
```

```
globalvar ACD!cmd ACD!db ACD!inited CHOM!Err ACD!Pool ACD!Xs \
    ACD!DoSearch ACD!Test ACD!Price ACD!Password \
    ACD!Preferred_supplier ACD!qprop \
    ACD!cost ACD!supplier ACD!FCD ACD!Only_Rs ACD!NoCAT ACD!Sites
localvar nrg rxrow rcrows v vars rxn dosearch dobuild docsln docores setvar args2 %uppercase( "$2" )
  setvar ACD!DoSearch %not( %set_and( NOSEARCH "$args2" ) )
  setvar ACD!Test %set_and( TEST "$args2" )
  setvar ACD!Price %not( %set_and( TEST "$args2" ) )
  setvar ACD!NoCAT %set_and( NOCAT "$args2" )

# initialize other data if not done in a previous optiverse run
  if %not( $ACD!inited )
      ACDinit
      if %not( $ACD!inited )
          return
      endif
  endif
  setvar ACD!only_rs
  if %set_and( RONLY "$args2" )
      setvar ACD!only_rs $args2
  endif
                    .

setvar dosearch TRUE
  setvar dobuild TRUE
# next is obsolete ..
  setvar docsln
  setvar docores TRUE
  setvar procs %set_and( SEARCH,BUILD,CORES,CSLN "$args2" )
  if $procs
# if subprocess(es) specified set all false, only those specified on
      setvar dosearch %set_and( SEARCH "$args2" )
```

```
    setvar dobuild %set_and( BUILD "$args2" )
    setvar docsln %set_and( CSLN "$args2" )
    setvar docores %set_and( CORES "$args2" )
endif for rxn in %set_unpack( $1 )
    setvar vars %tblsrch_val( REACTIONS CLASS_ID $rxn )
    if %not( $vars )
        %dialog_message( ERROR \
"REACTIONS has no entry for a Class ID of: $rxn" "Bad REACTIONS Data" )
        return
    endif if %set_and( DEBUG "$args2" )
        uims ver on
    else
        uims ver off
    endif %file_delete( startup.pho ) >$nulldev
    photo on startup.pho >$nulldev setvar nv 1
    for v in $vars
# allow variations to be skipped
        if %or( "%not( $args2 )" "%not( %set_and( "$v" "$args2" ) )" )
        echo Variation $nv (ID: $v) of %count( $vars )
        setvar nv %math( $nv + 1 )

TABLE DEFAULT REACTIONS
        setvar nrg %rcell( $v NREAG )
        setvar rcts %rcell( $v VARIATION )
        setvar rcrows %tblsrch_val( REAGENTS VARIATION $rcts )
```

```
    if %not( %eq( $nrg %count( $rcrows ) ) )
        %dialog_message( ERROR \
"For Variation $v of Reaction $rxn,\
REAGENTS has %count( $rcrows ) rows\
but REACTIONS specifies $nrg reagents" \
"Bad REACTIONS or REAGENTS Data" )
        return
    endif
    if $ACD!only_rs
        setvar svrows %set_unpack( "%set_and( %set_create( $rcrows ) \
            $ACD!only_rs )" )
        if %not( $svrows )
                echo No reactant classes to be searched or built for Reaction $rxn
        endif
    else
        setvar svrows $rcrows
    endif if $dosearch
            get_acd $rxn $rcts %set_create( $svrows )
        endif
        if $dobuild
            trsl_acd $rxn $rcts %set_create( $svrows )
        endif
        %file_delete( finish.pho ) >$nulldev
        photo on finish.pho >$nulldev

# CSLN file generation is obsolete
        if $docsln
            csln_files $rxn $rcts %set_create( $rcrows )
        endif
        if $docores
            cores $rxn $rcts %set_create( $rcrows )
```

```
      endif
    endif
    ACD!RxnUpdate $rxn $rcts
  endfor
endfor
        uims ver off
        photo off
#.

@macro get_acd sybylbasic

==================================================
=============================================
do reagent searches in ACD for all specified rows in reagents localvar fct rg sfrag buff bf hfname TABLE DEFAULT REAGENTS
    setvar rcrows %set_unpack( $3 )
    for rg in $rcrows
      setvar sfrag %rcell( $rg SEARCH_SLN )
      setvar hfname %cat( R $1 V $2 R %rcell( $rg ID ) )
      setvar ofname %rcell( $rg SAME_AS )
      if %streql( "$ofname" "?" )
         setvar ofname
      endif
      if $ofname
         setvar ofname %substr( $ofname 1 %math( %pos( "." $ofname ) - 1 ) )
      endif
      if %or( "$ACD!DoSearch" "%not( %file_exists( %cat( $hfname .hits ) ) )" )
        if %and( "$ofname" "%file_exists( %cat( $ofname .hits ) )" )
#         dcl /bin/cp %cat( $ofname .hits ) %cat( $hfname .hits )
        else
```

```
# prepare notlist file
        setvar notf %open( %cat( $hfname .bad ) "w" )
        for not in %rcell( $rg NOTLIST )
            if %file_exists( $not )
# write out all bad fragments NOT CONTAINED by SEARCH FRAGMENT
                setvar bf %open( $not "r" )
                while %not( %eof( $bf ) )
                    setvar buff %read( $bf )
                    if %and( "%not( %eof( $bf ) )" \
                    "%not( %streql( "%substr( "$buff" 1 1 )" "#" ) )" )
# Any in $sfarg allows metals to fall through, so Any cannot exclude a frag
                        setvar notin %not( %search2d( $sfrag \
                            "$buff" NoTriv 1 y ) )
                        if %or( "$notin" "%and( "%not( $notin )" \
"%gt( %sln_atom_count( "$buff" ) 1 )" )" )
                            %write( $notf $buff ) >$nulldev
                        else
                            echo Not excluding $not fragment $buff (contained in $sfrag )
                        endif
                    endif
                endwhile
                %close( $bf )
            else
                %write( $notf $not ) >$nulldev
            endif
        endfor
        %close( $notf )
# prepare query file
        setvar notf %open( %cat( $hfname .query ) "w" )
        %write( $notf $sfrag ) >$nulldev
        %close( $notf )

# do search (first time for individual components, second time to filter
```

```
#              umlticomponent cpds retrieved)
            echo .. Searching for %rcell( $rg SEARCH_SLN )
            setvar dbs dcl $ACD!cmd -database $ACD!db -qfile \
                %cat( $hfname .query ) -notlist \
                %cat( $hfname .bad ) -hitlist tmp.hits -coords
            if $ACD!Test
                setvar dbs $dbs -maxhits 10
            endif
            $dbs
            setvar dbs dcl $ACD!cmd -database tmp.hits \
                -dbtype sln -qfile %cat( $hfname .query ) \
                -notlist %cat( $hfname .bad ) -hitlist %cat( $hfname .hits )
            $dbs
          endif
        endif
      endfor
#.

@macro trsl_acd sybylbasic

==================================================
==============================================
prepare Xn files, ensure properties are recorded for all side chains globalvar ACD!CycFrag
localvar rcrows ma xls hfname how patin template xfile fname
localvar f f1 rg valences h nout XRgs allcrc crc setvar rcrows %set_unpack( $3 )
    setvar ma M1
    setvar ACD!Xs
    setvar ACD!Pool
    setvar xls
```

```
setvar xs
TAILOR SET MAXIMIN2 MAXIMUM_ITERATIONS 1000 | |
setvar split_atms
setvar XRgs
setvar supp ACD!INIT_Std_Topomer reset CRC uniqueness checker
    %CRC_NOT_UNIQUE( junk junk ) >$nulldev for all reagents in this variant of this reaction
    for rg in $rcrows
        TABLE DEFAULT REAGENTS
        setvar nout 0
        setvar hfname %cat( R $1 V $2 R %rcell( $rg ID ) )
        %file_delete( %cat( $hfname .pho ) ) >$nulldev
        photo on %cat( $hfname .pho ) >$nulldev setvar xfile %rcell( $rg ATTACHED )
        setvar ACD!Xs %set_or( "$ACD!Xs" $xfile )
        setvar XRgs[ $xfile ] $XRgs[ $xfile ] $rg setvar fname %cat( $hfname "." $xfile )
        setvar ofname %rcell( $rg SAME_AS )
        if %streql( "$ofname" "?" )
                setvar ofname
        endif
        setvar do_copy
        if $ofname
            if %not( %streql( "$ofname" "H.X1" ) )
                setvar p %substr( $ofname %math( %pos( R \
                    %substr( $ofname 2 ) ) + 2 ) \
```

```
                %math( %strlen( $ofname ) - %pos( "." $ofname ) ) )
                setvar rid %tblsrch_val( REAGENTS ID $p )
            endif
            setvar do_copy %file_exists( $ofname )
        endif
# may only need to copy a previous version of *.Xn, if it's there
        if $do_copy
        else
            setvar fgpt_xtra %rcell( $rg FGPT_XTRA )
            setvar uname %rcell( $rg USER_NAME )
            setvar falign %open( %cat( $hfname ".fal" ) "a" )
            setvar foracle %open( %cat( $hfname ".ora" ) "a" )

setvar how %rcell( $rg HOW )
            if %not( $how )
                    echo No HOW specified for row $rg in REACTANT table
                    goto nxtreactant
            endif
            setvar ACD!FixGeom %pos( CLIP "$how" )
            setvar ACD!CycFrag setvar patin %rcell( $rg PRUNE_SLN )
            setvar valences %rcell( $rg VALENCES )
            for ats in %range( 1 $valences )
                setvar xls $xls %cat( X $ats )
            endfor setvar keep_ats
            setvar xats
            if %gt( %count( $patin ) 1 )
                setvar xats %arg( 2 $patin )
                setvar keep_ats %arg( 3 $patin )
                setvar patin %arg( 1 $patin )
``` endif

```
    setvar template %rcell( $rg TEMPLATE )
    if $template
        setvar split_atms %arg( 4 $template )
        setvar CHOM!Align[ FIX_CF_CALLBACK ] %arg( 3 $template )
        setvar CHOM!Align[ SLN ] %arg( 2 $template )
        setvar template %arg( 1 $template )
        mol in m6 $template >$nulldev
        CHOM!INIT_BUILD_3D M5
    endif setvar f %open( $fname "w" )
    if $fgpt_xtra
        %write( $f # %cat( FGPT_X= $fgpt_xtra ) ) >$nulldev
    endif
    if $uname
        %write( $f # %cat( USER_NAME= $uname ) ) >$nulldev
    endif setvar f1
setvar f1 %open( %cat( $hfname ".base." $xfile ) "w" )

echo .. Translating hits for %rcell( $rg SEARCH_SLN )

if %set_and( HITS %set_create( %table_name() ) )
        echo ERror -- HITS table already exists!
        return
    endif read in the hitlist (it better be there!) and add price, FCD# columns
    TABLE CREATE hits unity "" $ma FROM_A_FILE \
        %cat( $hfname .hits ) | >$nulldev
```

```
                if %not( %set_and( HITS %set_create( %table_name() ) ) )
                    echo No HITS exist for  %rcell( $rg SEARCH_SLN ) !
                else
                 if $ACD!Price
                    table column_append rdbms tcd_price first price
                    table column_append rdbms tcd_suppliers first supplier
                    table eval new * PRICE,SUPPLIER
                 endif
                 setvar args %table( * ROW NUM )
                 setvar wrote1
# processing all the hits
                 for h in $args
                    echo $h
                    table default HITS
                    setvar allsln %sln_get_sln_from_table( HITS $h )
# skip isotopically labelled reagents
                    if %pos( "[I=" "$allsln" )
                        echo Skipping isotopically labelled $allsln
                        goto nxt_rxnb
                    endif
                    setvar pat %search2d( $allsln $patin NoTriv 1 y )
# break up compound SLN into molecular components
                        setvar p %pos( "." $allsln )
                        while $p
                            setvar allsln %substr( "$allsln" 1 %math( $p - 1 ) ) \
                                %substr( "$allsln" %math( $p + 1 ) )
                            setvar p %pos( "." "$allsln" )
                        endwhile
# cycle through any components until we get the RELEVANT molecular component
                        for cpsln in $allsln
                            setvar cpsln %fix_acd( $cpsln )
                            setvar pat %search2d( $cpsln $patin NoTriv 1 y )
                            if $pat
```

```
                setvar crc %sln_to_crc( $cpsln )
# check for within-hitlist duplicate of previous reagent providing same side chain
                if %CRC_NOT_UNIQUE( $crc )
                        echo Duplicate reagent SLN skipped \
                                (supplier $supp) $cpsln
                        goto nxt_rxn
                endif
                DEFAULT $MA >$NUlldev
                %sln_to_mol( $ma $cpsln ) >$nulldev
                if $ACD!FixGeom
                        if %not( %chom_concord( $ma ) )
                                goto nxt_rxn
                        endif
                endif
                setvar ats %acd_do_rxn( $ma $patin $how )
                if %not( $ats )
                        goto nxt_rxn
                endif setvar nowsln %sln_labelx( $ma $xls )
                setvar px %pos( X $nowsln )

# convert R's into X's (should probably be in C)
                while $px
# check for isolated X's in ACD input
                        if %not( %set_and( "%substr( $nowsln \
                                %math( $px + 1 ) 1 )" 1,2,3,4,5,6,7,8,9 ) )
                                echo Input contains Isolated X -- reactant discarded
                                goto nxt_rxn
                        endif
                        setvar nowsln %cat( %substr( $nowsln 1 %math( $px - 1 ) ) R \
                                %substr( $nowsln %math( $px + 1 ) ) )
                        setvar px %pos( X $nowsln )
```

```
            endwhile
# must ensure that every Rx is unique
            setvar rct 1
            setvar px %pos( %cat( R $rct ) $nowsln )
            while $px
                setvar xs %set_or( "$xs" %cat( X $rct ) )
                setvar py %pos( %cat( R $rct ) \
                    %substr( $nowsln %math( $px + 1 ) ) )
                while $py
                    setvar nowsln %cat( %substr( $nowsln 1 \
                        %math( $py + $px ) ) %math( $rct + 1 ) \
                        %substr( $nowsln %math( $px + $py + 2 ) ) )
                    setvar py %pos( %cat( R $rct ) \
                        %substr( $nowsln %math( $px + $py ) ) )
                endwhile
                setvar rct %math( $rct + 1 )
                setvar px %pos( %cat( R $rct ) $nowsln )
            endwhile
# check again for within-hitlist duplicate of previous reagent providing same side chain
            setvar crc %sln_to_crc( $nowsln )
            if %CRC_NOT_UNIQUE( $crc )
                echo Duplicate side chain SLN skipped: $nowsln
                goto nxt_rxn
            endif if $ACD!Price
                setvar nowsln %cat( $nowsln "<FCD=" %table( $h ROW NAME ) \
                    ";PRICE=" %rcell( $h PRICE ) ";SUPPLIER=" )
# identify any preferred supplier present
                setvar supp %uppercase( %rcell( $h SUPPLIER ) )
                setvar supp %ACD_Get_Preferred_Supplier( $supp )
                if %not( $supp )
                    setvar nowsln %cat( $nowsln '"""' )
```

```
        else
            setvar nowsln %cat( $nowsln $supp )
        endif
    else
        setvar nowsln %cat( $nowsln "<FCD=" %table( $h ROW NAME ) )
    endif we have our SLN, now need to go off to RDATA to retrieve (find or generate) properties
    copy $ma M2
    default M2 >$nulldev
# generate fragment(s) for identity search
# NOTE -- removal of reagent atoms may have split reagent up into independent fragments
    remove atom %set_create( %atoms( $xs ) ) >$nulldev
    setvar fsln %sln( M2 UNIQUE )
    setvar p %pos( "<" $fsln )
    if $p
        setvar fsln %substr( $fsln 1 %math( $p - 1 ) )
    endif
    setvar p %pos( "." $fsln )
    while $p
        setvar fsln %substr( "$fsln" 1 %math( $p - 1 ) ) \
                    %substr( "$fsln" %math( $p + 1 ) )
        setvar p %pos( "." "$fsln" )
    endwhile
# because there may be multiple fragments per reactant, must sum over
#     these to get property values
    setvar tlogp 0
    setvar tmw 0
    setvar trb 0
    setvar tcmf
# cycle through 1 or more fragments ..
#  for each, search Oracle table via CRC for a previosu occurrence
    for sln in $fsln
```

```
# check for multiple binding of THIS fragment
            setvar ACD!cycfrag
            if %gt( $valences 1 )
                        %sln_to_mol( M4 $sln ) >$nulldev
                        default M4 >$nulldev
                        setvar nat %mol_info( M4 NATOMS )
                        FILLVALENCE * H 1 1.09 1 1.09 1 1.09 >$nulldev
                        setvar ACD!cycfrag %gt( %math( \
                                    %mol_info( M4 NATOMS ) - $nat ) 1 )
            endif
# if a fragment closes a ring, must use the input conformation
            if $ACD!cycfrag
# identify the atoms to be extracted
                        setvar cycpat %search2d( %sln( $ma ) $sln NoDup 1 y )
                        setvar extract %set_create( %sln_rgroup_sybid( \
                          $ma $cycpat %range( 1 %sln_atom_count( $sln ) ) ) )
                        EXTRACT %cat( $ma "(" $extract ")" ) M4 >$nulldev
                        if %not( $ACD!FixGeom )
                              echo WARNING: Side Chains are joined \
                                    in a reactant $allsln but CLIP is not in HOW
                        endif
            else
                        %sln_to_mol( M4 $sln ) >$nulldev
            endif
            setvar sln %sln( M4 UNIQUE )
            setvar ct 0
sln_modified:
            setvar crc %sln_to_crc( $sln )
# find RDATA record -- have properties already if present
                        if %not( %streql( %RDBMS_SetBindValue( \
                                    $ACD!qprop NEW_CRC $crc ) TRUE ) )
                              echo RDBMS Set Bind VAlue failed -- quitting
                              return
```

```
                )
                        endif
                        setvar have1
                        setvar matches %RDBMS_BindQuery( $ACD!qprop )
                        setvar EOQ
                        while %not( $EOQ )
                                setvar rdata %RDBMS_ReadQuery( $ACD!qprop \
                                        "%s %f %f %s %f" )
                                if %RDBMS_Error()
                                        setvar EOQ true
                                else
# trim previously stored SLN of any <name= before checking for string match
                                        setvar sln_noname %arg( 1 $rdata )
                                        setvar p %pos( "<" $sln_noname )
                                        if $p
                                                setvar sln_noname %substr( \
                                                        $sln_noname 1 %math( $p - 1 ) )
                                        endif
                                        if %streql( $sln $sln_noname )
                                                setvar have1 TRUE
                                                break
                                        else
                                                echo Different structures have same CRC's - renaming
                                                setvar p %pos( "<" $sln )
                                                if $p
                                                        setvar sln \
                                                                %substr( $sln 1 %math( $p - 1 ) )
                                                endif
                                                setvar ct %math( $ct + 1 )
                                                setvar sln %cat( $sln "<name=DUP" $ct ">" )
                                                goto sln_modified
                                        endif
                                endif
                        endwhile
```

```
!
# if fragment not in Oracle table, calculate, then store, fragment properties
        if %not( $have1 )
            echo Adding $sln to RDATA
            if %streql( SH $sln )
                goto nxt_rxn
            endif
            setvar vals %ACDcalcprop( $sln $ma \
                    $valences $falign $split_atms )

if %not( $vals )
                echo Physical data not calculable for $sln
                goto nxt_rxn
            endif
            setvar rdata $sln $vals %set_size( "$CHOM!Align[ RBDS ]" )
            if %not( %rdbms_transactionstart( oracle_rdata ) )
                echo RDMBS_TRANSACTIONSTART failed -- quitting
                return
            endif
# building SQL command to do Oracle INSERT
            setvar cmd %cat( "(" $crc ",'" $sln "'," $valences "," \
                    %arg( 1 $vals ) "," %arg( 2 $vals ) ",'" \
                    %arg( 3 $vals ) "'," %set_size( \
                    "$CHOM!Align[ RBDS ]" )
",NULL,NULL,NULL,NULL,NULL)" )
            setvar cmd insert into RDATA VALUES $cmd ;
            if %not( %rdbms_transactionCommand( oracle_rdata " $cmd " ) )
                echo Addition of side chain to Oracle RDATA table failed --
Quitting
                return
            endif
            if %not( %rdbms_transactioncommit( oracle_rdata ) )
                echo Transaction Commit failed -- quitting
                return
```

```
            endif
        endif
# accumulate Logp, MW, rotatable bonds -- if any is NULL, overall value is NULL
        setvar tlogp %ACD_add( $tlogp %arg( 2 $rdata ) 99.99 )
        setvar tmw %ACD_Add( $tmw %arg( 3 $rdata ) -1.0 )
        setvar trb %ACD_Add( $trb %arg( 5 $rdata ) -1.0 )
        if %and( "%not( %streql( "$tcmf" NULL ) )" \
                "%not( %streql( "%arg( 4 $rdata )" NULL ) )" )
            setvar tcmf %cat( $tcmf %arg( 4 $rdata ) )
        else
            setvar tcmf NULL
        endif
    endfor
finished checking all fragments within a reagent from HITS output side chain structure for CSLN construction on 1st pass only
    if $f1
        %write( $f1 %substr( $nowsln 1 %math( %pos( \
            "<" $nowsln ) - 1 ) ) ) >$nulldev
        %close( $f1 ) >$nulldev
        setvar f1
    endif keep building output string for .Xn file -- Null values are represented by blanks setvar ACD!SLN $nowsln
    ACD!addval MW -1.0 $tmw
    ACD!addval RBD -1 $trb
    ACD!addval LOGP 99.99 $tlogp
    ACD!addval CTOPS NULL $tcmf STRCMP setvar nowsln %cat( $ACD!sln ">" )
    %write( $f $nowsln ) >$nulldev
```

```
            setvar nout %math( $nout + 1 )
            setvar wrote1 TRUE write out data for future Oracle table matching RDATA to its uses in CSLN libraries
            if %not( $supp )
                setvar supp NULL
            endif
            TABLE DEFA HITS
            setvar price %rcell( $h PRICE )
            if %not( $price )
                setvar price NULL
            endif
            %write( $foracle $crc $1 $2 $rg %table( $h ROW NAME ) \
                $PRICE $supp ) >$nulldev
# only record first occurrence of a component containing the fragment
            break
        endif
nxt_rxn:
        endfor
        if %and( "$wrote1" "$ACD!Test" )
            break
        endif
nxt_rxnb:
        endfor
# finished all HITS !!

if $template
            ACD!INIT_Std_Topomer
            setvar template
        endif
        %close( $falign )
        %close( $foracle )
        %close( $f ) >$nulldev
```

```
        ACD!record REAGENTS $fname $rg VARIANTS UPDATED
        TABLE CLOSE hits NO >$nulldev
        echo $nout variations written to $fname
     endif
nxtreactant:
        photo off
     endif
    endfor
#   %rdbms_close( oracle_RDATA ) >$nulldev

#.

@macro record ACD

=================================================
================================
# count how many variations are referenced by the new CSLN
        if %not( $ACD!Test )
            TABLE DEFAULT $1
            dcl "wc $2 >junk.txt"
            setvar f %open( junk.txt r )
            setvar buff %read( $f )
            echo %wcell( $3 $4 %arg( 1 $buff ) ) >$nulldev
            echo %wcell( $3 $5 "%time()" ) >$nulldev
            %close( $f ) >$nulldev
            setvar f %table_attribute( FILENAME )
            echo SAVING $f
            %file_delete( $f ) >$nulldev
            TABLE SAVE $f
        endif
.

@macro RxnUpdate ACD
```

```

=========================================
=====================================
# count and save how many products
    if %not( $ACD!Test )
        setvar nprod 1
        setvar xrg %tblsrch_val( REACTIONS CLASS_ID $1 )
        if $xrg
            if %eq( 1 %rcell( $xrg MORE_CORES ) )
                table default cores
                setvar nprod %rcell( %tblsrch_val( \
                    CORES CLASS_ID $1 ) VARIANTS )
                if %not( $nprod )
                    echo No VARIANTS value for CORES file for CLASS_ID $1
                    return
                endif
            endif
        endif
    endif
    TABLE DEFAULT REAGENTS
    setvar ACD!Xs
    setvar XRgs
    for rg in %tblsrch_val( REAGENTS VARIATION $2 )
        setvar x %rcell( $rg ATTACHED )
        setvar ACD!Xs %set_or( "$ACD!Xs" $x )
        setvar XRgs[ $x ] $XRgs[ $x ] $rg
    endfor
    for x in %set_unpack( $ACD!Xs )
        setvar nvar 0
        for var in $XRgs[ $x ]
            setvar nxvar %rcell( $var VARIANTS )
            if %or( "%not( $nxvar )" "%lt( "$nxvar" 1 )" )
                setvar nxvar %rcell( $var SAME_AS )
                if %streql( "$nxvar" "?" )
```

```
            setvar nxvar
        endif
        if %not( $nxvar )
            echo No variants value found or \
                derivable for ID $var in REACTANTS
            return
        endif
        if %streql( $nxvar "H.X1" )
            setvar nxvar 1
        else
            setvar rg %pos( R %substr( $nxvar 2 ) )
            setvar rg %substr( $nxvar %math( $rg + 2 ) \
                %math( %pos( "." $nxvar ) - $rg - 2 ) )
            setvar nxvar %rcell( %tblsrch_val( REAGENTS ID $rg ) \
                VARIANTS )
            if %not( $nxvar )
                echo No variants value found or derivable \
                    for ID $nxvar in REACTANTS
                return
            endif
        endif
    endif
    setvar nvar %math( $nvar + $nxvar )
  endfor
  setvar nprod %math( $nprod * $nvar )
endfor
TABLE DEFAULT REACTIONS
echo Generated $nprod products
echo %wcell( $xrg SIZE  $nprod ) >$nulldev
echo %wcell( $xrg UPDATED "%time()" ) >$nulldev
setvar f %table_attribute( FILENAME )
echo SAVING $f
```

```
        %file_delete( $f ) >$nulldev
      TABLE SAVE $f
    endif
.

@macro delval ACD

===============================================
=========================================
# removes all instances of an attribute/value pair from an SLN
globalvar ACD!SLN
localvar p p1 setvar p %pos( $1 $ACD!SLN )
    while $p
        setvar p1 %pos( ";" %substr( $ACD!SLN $p ) )
        if %not( $p1 )
            setvar p1 %pos( ">" %substr( $ACD!SLN $p ) )
        endif
        setvar ACD!SLN %cat( %substr( "$ACD!SLN" 1 %math( $p - 1 ) ) \
            %substr( "$ACD!SLN" %math( $p1 + $p ) )
        setvar p %pos( $1 $ACD!SLN )
    endwhile
#.

@macro addval ACD

================================================
===============================
# appends attribute value pair to ACD!SLN in UNITY format, checking
# for input values which simulate null values
globalvar ACD!SLN
localvar isnull
```

```
# first remove all existing references/data
    ACD!delval $1 setvar ACD!SLN %cat( $ACD!SLN ";" $1 "=" )
    if %eq( $# 4 )
        setvar isnull %streql( $2 $3 )
    else
        setvar isnull %eq( $2 $3 )
    endif
    if $isnull
        setvar ACD!SLN %cat( $ACD!SLN '""' )
    else
        setvar ACD!SLN %cat( $ACD!SLN $3 )
    endif
.

@expression_generator ACD_Add

=================================================================
=============================================
# adds a new value and returns sum, or returns the supplied code for NIL
if either old or new value already codes for NIL need to truncate values retrieved from Oracle DB
    setvar arg2 $2
    setvar p %pos( "." $arg2 )
    if $p
      if %gt( %strlen( $arg2 ) %math( $p + 2 ) )
         setvar arg2 %substr( $arg2 1 %math( $p + 2 ) )
      endif
    endif
    if %streql( $arg2 $3 )
         %return( $3 )
```

```
    else
        %return( %math( $arg2 + $1 ) )
    endif
    return
.

@expression_generator ACD_Get_Preferred_Supplier

==========================================================
===================================================
# identify "best" supplier, edit name as needed
localvar p prefs supp
        setvar prefs %set_and( "$1" $ACD!Preferred_Supplier )
        if $prefs
# if ANY suppliers are preferred, pick the best
            for p in %set_unpack( $ACD!Preferred_Supplier )
                setvar supp %set_and( $p $prefs )
                if $supp
                    break
                endif
            endfor
        else
# else just grab the first one
            setvar supp %arg( 1 %set_unpack( "$1" ) )
            if %streql( "-" "$supp" )
                setvar supp
            endif
        endif
# can't tolerate hyphens
        setvar p %pos( "-" "$supp" )
        if $p
            setvar supp %cat( %substr( $supp 1 %math( $p - 1 ) ) \
                %substr( $supp %math( $p + 1 ) ) )
```

```
        endif
        %return( $supp )
#.

@expression_generator ACD_core_props

==========================================
=====================================
# generate physicochemical data
    table default RSCRATCH
    echo %wcell( 1 1 %sln( M1 ) ) >$nulldev
    TABLE EVAL ALL 1 MW
# note that Xn each have an "AW" of 12.011 -- back these out!
    setvar mw %math( %rcell( 1 3 ) - %count( $* ) * 12.011 )
# replace Xn by Me groups for best LogP estimate
    setvar sln %sln( M1 )
    setvar p %pos( "X" $sln )
    while $p
        setvar sln %cat( %substr( $sln 1 %math( $p - 1 ) ) \
            CH3 %substr( $sln %math( $p + 2 ) ) )
        setvar p %pos( "X" $sln )
    endwhile
    echo %wcell( 1 1 $sln ) >$nulldev
    table eval all 1 CLOGP >$nulldev
    setvar logp %rcell( 1 2 )
    if %not( $logp )
        echo LogP not calculated for $sln
        setvar logp 99.99
    endif
    %return( "$mw $logp" )
#.

@expression_generator SybID2SLN
```

```

=============================================
========================================
# returns the (first) atom in the SLN that corresponds to a SYBYL ID #
    setvar targ %arg( 1 %set_unpack( 3 ) )
    for i in %range( 1 %mol_info( $1 NATOMS ) )
        if %eq( $targ %arg( 1 %set_unpack( %sln_rgroup_sybid( $1 $2 $i ) ) ) )
            %return( $i )
            return
        endif
    endfor
#.

@macro ACDinit sybylbasic

=============================================
========================================
read in MSS's, initiate database location and dbsearch engine globalvar ACD!cmd ACD!db CHOM!Align ACD!inited ACD!SLNin ACD!SLNout setvar ACD!db /common3/lawless/acd/acd_udb
other one is /ads/lawless/ACD
    setvar ACD!cmd /home5/jilek/bin/dbsearch.ads
    set CGQ_timeout 0
    setvar TA_RDBMS_READ_TIMEOUT 50000
odd bond types get created, later overridden by Concord table recall reactions
    table recall reagents
    table recall cores

# Oracle setup
```

```
take /home8/lawless/tcd  > $nulldev
take /tmp_mnt/net/sn/home4/cramer/panlabs/synplan/rdata  > $nulldev
if %not( %RDBMS_Open( oracle_rdata ) )
    echo could not open Oracle table: RDATA with side chain data
    return
endif
setvar ACD!qprop  %RDBMS_SetupQuery( oracle_rdata RDATA_DATA )
if %not( $ACD!qprop )
    echo RDATA query could not be Setup
    return
endif
if $ACD!Price
    if %not( %rdbms_open( oracle_tcd) )
        echo ACD Price Oracle table not opened
        return
    endif
endif

ACD!INIT_TOPOMER setvar ACD!SLNin N[+1](=O)(O[-1]) N[+1](=O)O[-1]
setvar ACD!SLNout N(=O)(=O) N(=O)=O
setvar ACD!Preferred_supplier \
    ALDRICH,SIGMA,FLUKA,LANCASTER,TCI-US,TRANSWLD,JANSSEN setvar ACD!inited TRUE
.

@macro INIT_TOPOMER ACD
# initializes topomer calculations

================================================================
==========================================
```

```
globalvar ACD!TopInited ACD!Sites if %not( $ACD!TopInited)
    table recall %cat( $DSERV_TB RSCRATCH ) m3 >$nulldev
    table CONF SLN
    setvar CHOM!Align[ DEBUG ]
    setvar CHOM!Align[ BUMPS ]
    setvar CHOM!Align[ ALICYC ] All_trans
    setvar CHOM!Align[ CHARGE ] None
    setvar CHOM!Align[ MCORE ] M6
    setvar CHOM!Align[ ORIENT ]
    setvar CHOM!Align[ FITRMS ] 0.6
    setvar CHOM!Align[ ATTACHED ]
    setvar CHOM!Align[ CORE_SLN ]
    uims load %cat( $DSERV_TB chom_batch.core ) >$nulldev ACD!INIT_STD_TOPOMER
    set CGQ_timeout 0
    setvar ACD!Sites[FILE] $TA_DEMO/disco_file.dat
    setvar ACD!Sites[FILE] /view/sybBDFR4K/vob/src/sybyl/demo/disco_file.dat param modi >$nulldev atom_def F F 4 TH F 9 1.30 GREEN 0.0 \
        4.0 N N 3 12.63 18 16 F | |
    parameter add bond_type C.3 O.2 1 NO O.3 C.2 1 NO N.ar H 1 \
        NO S.o2 N.3 1 NO  S.o2 N.2 1 NO S.O2 N.pl3 1 NO \
        N.1 H 1 NO S.o2 S.3 1 NO | | >$nulldev
    parameter add bond_length C.3 O.2 1 1.5 O.3 C.2 1 1.5 \
        N.ar H 1 1.0 S.o2 N.3 1 1.5 S.o2 N.2 1 1.5 S.o2 \
        N.pl3 1 1.5 N.1 H 1 1.0 S.o2 S.3 1 1.6 | | >$nulldev endif
setvar ACD!TopInited TRUE
#.
```

@macro INIT_STD_TOPOMER ACD
(re)sets standard topomer template info after a TEMPLATE was supplied by a REAGENT

================================================================================= setvar CHOM!Align[ SLN ] NH=CHCH2Any
   mol in m6 %cat( $DSERV_TB amidine.mol2 ) >$nulldev
   setvar CHOM!Align[FIX_CF_CALLBACK] ACD!AMID_TORS
   CHOM!INIT_BUILD_3D M5
.

@expression_generator tblsrch_val

=================================================================================
performs a search by value within some column of an MSS,
returns space separated row IDs localvar rows table defa $1
   if %eq( $# 3 )
      setvar rows %table( %cat( "{RANGE(" $2 "," \
         %math( $3 - 0.0001 ) "," %math( $3 + 0.0001 ) ")}" ) ROW NUM )
   else
      setvar rows %table( %cat( "{RANGE(" $2 "," $3 "," $4 ")}" ) ROW NUM )
   endif
   %return( "$rows" )
   return
.

@expression_generator ACD_DO_RXN

==================================================
=============================================
$1 = molecule area; $2 = SLN pattern, $3 and following are transformations
which convert the reactant in $1 to its product form,
attachment point atoms being named by Xn
returns TRUE if all went well

globalvar ACD!recnos
localvar ma sln tsf recno ats atm fd1 nx setvar ma $1
DEFAULT $ma >$nulldev
setvar sln $2
shift
shift setvar pat %search2d( %sln( $ma ) $sln NoDup 1 y )
if %not( %eq( 1 %count( $pat ) ) )
    echo ACD_DO_RXN: $sln not found in %sln( $ma )
    return
endif set up mapping of SLN IDs to invariant RECNO's
    setvar ats %sln_rgroup_sybid( $ma $pat %range( 1 %sln_atom_count( $sln ) ) )
    for atm in %range( 1 %sln_atom_count( $sln ) )
        setvar anow %arg( 1 %set_unpack( %arg( $atm $ats ) ) )
        setvar ACD!recno[ $atm ] %atom_info( $anow RECNO )
    endfor setvar nx 0
execute reaction, step-by-step
    for tsfm in $*

```
setvar tsfm %set_unpack( $tsfm )
switch %uppercase( %arg( 1 $tsfm ) )
case ATYPE)
    modify atom type %recno_to_id( $ma $ACD!recno[ %arg( 2 $tsfm ) ] ) \
        %arg( 3 $tsfm ) 1 1.5 1 1.5 1 1.5 1 1.5 >$nulldev
;;
case BREAKB)
    setvar a1 %recno_to_id( $ma $ACD!recno[ %arg( 2 $tsfm ) ] )
    setvar a2 %recno_to_id( $ma $ACD!recno[ %arg( 3 $tsfm ) ] )
    setvar bond %bonds( %cat( $a1 "=" $a2 ) )
    if $bond
        switch %bond_info( $bond TYPE )
    case 1)
    case am)
        remove bond $bond >$nulldev
    ;;
    case 2)
    case ar)
        modify bond type $bond 1 >$nulldev
    ;;
        endswitch
    else
        echo ACD_DO_RXN: $tsfm but no bond exists
        return
    endif
;;
case SPLIT)
    setvar a1 %recno_to_id( $ma $ACD!recno[ %arg( 2 $tsfm ) ] )
    setvar a2 %recno_to_id( $ma $ACD!recno[ %arg( 3 $tsfm ) ] )
    SPLIT $a1 $a2 >$nulldev
;;
case DELA)
    remove atom %recno_to_id( $ma $ACD!recno[ %arg( 2 $tsfm ) ] ) >$nulldev
```

```
;;
case FILLV)
        fillvalence %recno_to_id( $ma $ACD!recno[ %arg( 2 $tsfm ) ] ) \
                %arg( 3 $tsfm ) 1 1.5 1 1.5 1 1.5 >$nulldev
        setvar ACD!recno[ %arg( 4 $tsfm ) ] %atom_info( $NEW_ATOM_ID RECNO )
;;
case ADDAT)
        add atom %recno_to_id( $ma $ACD!recno[ %arg( 2 $tsfm ) ] ) \
                %arg( 3 $tsfm ) 1 1.5 >$nulldev
        setvar ACD!recno[ %arg( 4 $tsfm ) ] %atom_info( $NEW_ATOM_ID RECNO )
;;
case MARKX)
        setvar nx %math( $nx + 1 )
        setvar aname %arg( 3 $tsfm )
        if %not( $aname )
                setvar aname %cat( X $nx )
        endif
        if %gt( %count( %atom_info( %recno_to_id( $ma \
                $ACD!recno[ %arg( 2 $tsfm ) ] ) ) ) 1 )
            echo WARNING: Multivalent attachment atom in %sln( $ma )
        endif
        modify atom name %recno_to_id( $ma $ACD!recno[ %arg( 2 $tsfm ) ] ) \
                $aname >$nulldev
;;
case MAKEB)
        setvar a1 %recno_to_id( $ma $ACD!recno[ %arg( 2 $tsfm ) ] )
        setvar a2 %recno_to_id( $ma $ACD!recno[ %arg( 3 $tsfm ) ] )
        setvar bond %bonds( %cat( $a1 "=" $a2 ) )
        if $bond
            switch %bond_info( $bond TYPE )
    case 1)
    case am)
        modify bond type $bond 2 >$nulldev
```

```
    ;;
    case 2)
        modify bond type $bond 3  > $nulldev
    ;;
    case )
        echo ACD_DO_RXN: $tsfm now has type: %bond_info( $bond TYPE )
        return
    ;;
        endswitch
    else
        add bond $a1 $a2 1 1.5  > $nulldev
    endif
;;
case CLIP)
# prune some atoms in recognition SLN
# use remaining atoms in recognition SLN to control mapping of
#      reactant side chains to product side chains
    setvar lp %pos( "(" "$tsfm" )
    setvar rp %pos( ")" "$tsfm" )
    if %or( "%not( $lp )" "%not( $rp )" )
        echo Missing parentheses in CLIP command
        return
    endif
    setvar ats
    for at in %substr( "$tsfm" %math( $lp + 1 ) %math( $rp - $lp - 1 ) )
        setvar ats $ats %sln_rgroup_sybid( $ma $pat $at )
    endfor
    setvar rs
    for at in %substr( "$tsfm" %math( $rp + 1 ) )
        setvar rs $rs %atom_info( %arg( 1 %set_unpack( \
            %sln_rgroup_sybid( $ma $pat $at ) ) ) RECNO )
    endfor
# following routine: removes all $ats in ats EXCEPT for those directly
``` attached to atoms NOT removed. The latter will be labelled X1 if $rs is empty,
otherwise $rs is to contain RECNO's (invariant after deletions) for all
attached atoms NOT removed.
    %chom_rmv_ats( %cat( $ma "(" %set_create( $ats ) ")" ) $rs )
;;
case )
    echo ACD_DO_RXN: Unknown HOW operator: $tsfm
    return
;;
  endswitch
 endfor
 %return( $nx )
 return
.

@macro FIX_FUSE ACD

==================================================================
================================================
specific callback for aligning topomer confs of tryptanthrin variants
ensure that NH=CH-CH2-C bond is 180 degrees and CH-CH2-C:C
is 0 before FIT is done regardless of what Concord did to it.
localvar a
  setvar a %set_unpack( $2 )
  modify torsion %arg( 1 $a ) %arg( 3 $a ) \
    %arg( 5 $a ) %arg( 8 $a ) 180  >$nulldev
  modify torsion %arg( 3 $a ) %arg( 5 $a ) \
    %arg( 8 $a ) %arg( 10 $a ) 0  >$nulldev
.

@macro AMID_TORS ACD

==================================================================

```
# default callback, ensures that NH=CHCH2Any torsion is set to 180
# (minimization will change it) so that MATCH can work
localvar a
    setvar a %set_unpack( $2 )
    modify torsion %arg( 1 $a ) %arg( 3 $a ) \
              %arg( 5 $a ) %arg( 8 $a ) 180  >$nulldev
#.

@expression_generator ACDcalcprop

=================================================
=============================================
# calculates physical properties of a previously unknown side chain
#   logP, MW, topmer field (via call to CHOM!THis_Build_3D for conformer)
# uses RSCRATCH as workspace MSS

globalvar ACD!CycFrag
localvar split_atms buildhow TABLE DEFAULT Rscratch
    TABLE CONFORMER SLN set up NULL values so we can tell if calculation failed
    echo %wcell( 1 CLOGP 99.99 )  >$nulldev
    echo %wcell( 1 MW -1.0 )  >$nulldev
    echo %wcell( 1 SLN H<NAME="UNNAMED";COORD3D=(0.000,0.000,0.000)> )
>$nulldev
    TABLE EVAL ALL 1 TOPOMERIC molecular weight for frag as is
    echo %wcell( 1 SLN $1 )  >$nulldev
    TABLE EVAL ALL 1 MW  >$nulldev
```

```
# LogP is for structure with H instead of open valence
# echo %sln_to_mol( M4 $1 ) >$nulldev
    default M4 >$nulldev setvar nat %mol_info( M4 NATOMS )
fix bad S=O typing
    if %search2d( $1 S=O NoDup 1 y )
        for pat in %search2d( $1 O=S=O NoDup 0 y )
            modify atom type %sln_rgroup_sybid( M4 $pat 2 ) \
                S.o2 1 1.5 >$nulldev
        endfor
        for pat in %search2d( $1 O=S[F]Any NoDup 0 y )
            modify atom type %sln_rgroup_sybid( M4 $pat 2 ) \
                S.o 1 1.5 >$nulldev
        endfor
    endif
# following replaces (and greatly simplifies) code that is believed to be obsolete
    FILLVALENCE * H 1 1.09 1 1.09 1 1.09 >$nulldev
    if %not( %gt( %mol_info( M4 NATOMS ) $nat ) )
        echo ERROR: NO unfilled valences in new fragment $1
        return
    endif
    modify atom name $NEW_ATOM_ID X1 >$nulldev echo %wcell( 1 SLN %sln( M4 ) ) >$nulldev
    TABLE EVAL ALL 1 CLOGP >$nulldev
# should check result here and go to simpler evaluation if CLOGP fails

# Add aligning group for Topomeric, to be found in $CHOM!Align[ MINIT ]
    JOIN %cat( "M4(" %atoms( X1 ) ")" ) \
        %cat( $CHOM!Align[ MINIT ] "(6)" ) 1 1.54 >$nulldev setvar cfa
```

```
    setvar CHOM!Align[ ALICYC ] All_trans
    setvar buildhow CONCORD
    if $ACD!CycFrag
        setvar buildhow NOBUILD
        setvar CHOM!Align[ ALICYC ] None
    endif if %CHOM_THIS_BUILD_3D( M4 $buildhow $1 A )
remove aligning group before saving & doing CoMFA
        setvar pat %search2d( %sln( M4 ) $CHOM!align[ SLN ] NoTriv 0 y )
        if $5
# need to save recnos of standard split before doing custom split
            setvar split_atms %atom_info( \
                %sln_rgroup_sybid( M4 $pat 8 ) RECNO ) \
                %atom_info( %sln_rgroup_sybid( M4 $pat 5 ) RECNO )
            SPLIT %sln_rgroup_sybid( M4 $pat %set_unpack( $4 ) ) >$nulldev
            SPLIT %recno_to_id( M4 %arg( 1 $split_atms ) ) \
                %recno_to_id( M4 %arg( 2 $split_atms ) ) >$nulldev
        else
            SPLIT %sln_rgroup_sybid( M4 $pat 8 5 ) >$nulldev
        endif
# evaluate and save CoMFA field
        setvar fsln %cat( %sln( M4 FULL ) )
        echo %wcell( 1 SLN $fsln ) >$nulldev
        %write( $3 $fsln ) >$nulldev
        TABLE CONF SLN
        TABLE ENTER CELL 1 TOPOMERIC NO NO >$nulldev
        TABLE EVAL ALL 1 TOPOMERIC >$nulldev
        setvar cfa %rcell( 1 TOPOMERIC )
    else
        setvar cfa NULL
    endif
```

```
# round up and return all the results
    setvar logp %rcell( 1 CLOGP )
    setvar mw %rcell( 1 MW )
    if %not( %streql( "$cfa" NULL ) )
        if %eq( "$cfa" 1.00 )
            setvar cfa NULL
        else
            setvar cfa %comfa_hex( 1 TOPOMERIC )
        endif
    endif
    %return( "$logp $mw $cfa" )
#.

@expression_generator FIX_ACD

=========================================
  .
=====================================
# does string search/replace for groups -- specifically nitro
globalvar ACD!SLNin ACD!SLNout
localvar ans p arg ct
    setvar ans $*
    setvar ct 1
    for arg in $ACD!SLNin
        setvar p %pos( "$arg" "$ans" )
        while $p
            setvar ans %cat( %substr( "$ans" 1 %math( $p - 1 ) ) \
                    %arg( $ct $ACD!SLNout ) %substr( "$ans" \
                    %math( $p + %strlen( $arg ) ) ) )
            setvar p %pos( "$arg" "$ans" )
        endwhile
        setvar ct %math( $ct + 1 )
    endfor
    %return( "$ans" )
```

.

@macro cores sybylbasic

==========================================
===================================
Converts a hit list of core reactanst into a hit list with cores, properties
The side chains will be identical to those in some prototype rxn localvar f buff files cct fct core_sln fcore weird xweird setvar Xs
    setvar Xlist
    setvar xls
    setvar weird Na K Ca setvar fcore %cat( R $1 V $2 )
    TABLE DEFAULT REACTIONS
    setvar vars %tblsrch_val( REACTIONS CLASS_ID $1 )
    setvar how_core %eq( 1 "%rcell( $vars MORE_CORES )" )
    setvar coreflag NO
    if $how_core
        setvar coreflag YES
    endif setvar fout %open( %cat( $fcore ".cores" ) "w" )
    if %not( $ACD!NoCat )
      setvar rx %rcell( $vars CLASS_ID )
      setvar uname %rcell( $vars NAME )
      if %not( %eq( 1 %count( $uname ) ) )
        echo Not a one-word reaction NAME in row $vars : $uname
        return
      endif

```
echo Preparing %cat( $fcore ".files" )
TABLE DEFAULT REAGENTS
setvar rcrows %set_unpack( $3 )
for rg in $rcrows
    setvar x %rcell( $rg ATTACHED )
    setvar Xs %set_or( $x "$Xs" )
    setvar Xlist[ $x ] $Xlist[ $x ] $rg
endfor
setvar f %open( %cat( $fcore ".files" ) "w" )
# following generates all combinations of all calls (no recursion in SPL)
setvar npos %set_size( $Xs )
setvar n2make 1
for nx in %sort( %set_unpack( $Xs ) )
    setvar smax[ $nx ] %count( $XList[ $nx ] )
    setvar n2make %math( $n2make * $smax[ $nx ] )
    setvar idx[ $nx ] 1
endfor
for i in %range( 0 %math( $n2make - 1 ) )
    setvar idx %cat( R $rx "." ) $coreflag \
        $uname %cat( $fcore .cores )
    setvar base $i
# establish indexes at each position
    for j in %set_unpack( $Xs )
        setvar rg %arg( %math( ( $base % $smax[ $j ] ) + 1 ) \
            $XList[ $j ] )
        setvar rf %rcell( $rg SAME_AS )
        if %and( "$rf" "%not( %streql( "$rf" "?" ) )" )
            setvar idx $idx $rf
        else
            setvar idx $idx %cat( $fcore R %rcell( $rg ID ) \
                "." %rcell( $rg ATTACHED ) )
        endif
        setvar base %math( $base / $smax[ $j ] )
```

```
    endfor
        %write( $f $idx ) >$nulldev
    endfor
    %close( $f )
endif now recover additional cores, if needed if $how_core
    setvar cvars %tblsrch_val( CORES CLASS_ID \
        %rcell( $vars CLASS_ID ) )
    setvar how_core %rcell( $cvars HOW_CORE )

setvar valences %rcell( $cvars VALENCES )
    setvar xls
    for ats in %range( 1 $valences )
        setvar xls $xls %cat( X $ats )
    endfor setvar core_sln %rcell( $cvars MORE_CORE )
    if %not( $core_sln )
        echo No MORE_CORE for reaction $vars
        return
    endif
    setvar xrlist %rcell( $cvars XRLIST )
    if %not( %eq( %count( $xrlist ) $VALENCES ) )
        echo mismatch between VALENCES and XRLIST for reaction $vars
        return
    endif
    setvar opat %string_insert( %string_insert( %rcell( $cvars XRCORE ) \
        %arg( 1 $xls ) %arg( 1 $weird ) ) \
        %arg( 2 $xls ) %arg( 2 $weird ) )
    setvar xrcore %rcell( $cvars XRCORE )
```

```
core_get_acd $1 $2 $3 setvar fhits %cat( $fcore core.hits )
start processing hits
    if %not( %file_exists( $fhits ) )
        echo $fhits (hitlist of core reactants) not found
        return
    endif
    setvar cct 1
    TABLE CREATE hits unity "" M5 FROM_A_FILE "$fhits" | >$nulldev
    if $ACD!Price
       table column_append rdbms tcd_price first price
       table column_append rdbms tcd_suppliers first supplier
       table eval new * PRICE,SUPPLIER
    endif
    %CRC_NOT_UNIQUE( junk junk ) >$nulldev
    setvar choices %table( * ROW NUM )
else
    setvar choices %arg( 1 %rcell( $vars CORE_SLN ) )
endif for h in $choices
        if $how_core
          table default HITS
          setvar allsln %sln_get_sln_from_table( HITS $h )
        else
          setvar allsln $h
        endif
# cycle through RELEVANT molecular component
        setvar p %pos( "." $allsln )
        while $p
            setvar allsln %substr( "$allsln" 1 %math( $p - 1 ) ) \
                %substr( "$allsln" %math( $p + 1 ) )
```

```
        setvar p %pos( "." "$allsln" )
    endwhile
  for cpsln in $allsln
    setvar cpsln %fix_acd( $cpsln )

if $how_core
    setvar pat %search2d( $cpsln $core_sln NoDup 1 y )
    if %not( $pat )
          break
    endif
    setvar crc %sln_to_crc( $cpsln )
    if %CRC_NOT_UNIQUE( $crc )
          echo Skipping duplicate $cpsln
          break
    endif
    if %pos( "[I=" "$cpsln" )
      echo Isotope skipping $cpsln
      break
    endif
     echo Core $cct -- $cpsln %sln_to_mol( M1 $cpsln ) >$nulldev
    if %not( %acd_do_rxn( m1 $core_sln $how_core ) )
          goto nxt_core
    endif
    setvar outsln %sln_labelx( m1 $xls )

# build XRLIST
        setvar osln %string_insert( %string_insert( \
            $outsln %arg( 1 $xls ) \
            %arg( 1 $weird ) ) %arg( 2 $xls ) %arg( 2 $weird ) )
        setvar patx %search2d( $osln $opat NoDup 1 y )
        if %not( $patx )
```

```
            echo $opat not found in $osln -- skipping core
            goto nxt_core
        endif
        setvar xrl
        for x in $xrlist
            setvar x %set_unpack( $x )
            if $xrl
                setvar xrl %cat( $xrl ";" )
            endif
            setvar xrl %cat( $xrl %SLN_ID( $patx %arg( 2 $x ) ) "," \
                %arg( 1 $x ) "=" %SLN_ID( $patx %arg( 3 $x ) ) )
        endfor is core symmetric?
        setvar sym 0
        %sln_to_mol( M2 $osln ) >$nulldev
        %sln_to_mol( M3 %string_insert( %string_insert( \
            $outsln %arg( 1 $xls ) \
            %arg( 2 $weird ) ) %arg( 2 $xls ) \
            %arg( 1 $weird ) ) ) >$nulldev
        if %streql( %sln( M2 UNIQUE ) %sln( M3 UNIQUE ) )
            setvar sym 1
        endif
    else
        setvar outsln $cpsln
        setvar sym 0
        setvar xrl %arg( 2 %rcell( $vars CORE_SLN ) )
    endif

At this point $outsln is the SLN with X1, X2, etc for the
variation sites.

```

Calculate number of rotatable bonds WITHOUT X1, X2 attachment
points.
```
    setvar newsln1 $outsln
    setvar ct 1
    setvar offset 2
    setvar p1 %pos( %cat( X $ct ) $newsln1 )
    while $p1
        setvar newsln1 %cat( %substr( $newsln1 1 %math( $p1 - 1 ) ) \
            %substr( $newsln1 %math( $p1 + $offset ) ) )
        setvar ct %math( $ct + 1 )
        if %eq( $ct 10 )
            setvar offset 3
        endif
        setvar p1 %pos( %cat( X $ct ) $newsln1 )
    endwhile
    setvar scratch_molarea %molempty()
    %sln_to_mol( $scratch_molarea $newsln1 ) >$nulldev
    setvar old_default $default_area
    default $scratch_molarea >$nulldev
    setvar bds %set_create( %bonds( (*-{RINGS()})&<1> ) )
    setvar mval %set_create( \
        %atoms( 
<H>+<o.2>+<F>+<I>+<Cl>+<Br>+<n.1>+<LP>+<Du> ) )
    setvar pds %set_create( %bonds( %cat( "{TO_ATOMS(" $mval ")}" ) ) )
    setvar bds %set_diff( $bds $pds )
    if $bds
        setvar bds %set_size( $bds )
    else
        setvar bds 0
    endif
    zap $scratch_molarea
    default $old_default >$nulldev
```

```

$outsln can also be sent to acd_core_props1 to generate MW and CLOGP

    setvar props %ACD_Core_Props1( $outsln )

Change all X into Y_0 setvar ct 1
    setvar ypfx Y_0
    while TRUE
        if %pos( %cat( X $ct ) $outsln )
            setvar outsln %string_insert( \
                $outsln %cat( X $ct ) %cat( $ypfx $ct ) )
        else
            break
        endif
        setvar ct %math( $ct + 1 )
        if %eq( $ct 10 )
            setvar ypfx Y_
        endif
    endwhile if $how_core
      TABLE DEFAULT HITS
      setvar sln %cat( $outsln "<FCD=" %table( $h ROW NAME ) \
            ";PRICE=" %rcell( $h PRICE ) ";SUPPLIER=" %uppercase( \
            %ACD_Get_Preferred_Supplier( %rcell( $h SUPPLIER ) ) ) \
            ";MW=" %arg( 1 $props ) ";RBD=" $bds ";LOGP=" \
            %arg( 2 $props ) ";SYM=" $sym ";XRLIST=" '"' $xrl '"' ">")
    else
      setvar sln %cat( $outsln "<MW=" %arg( 1 $props ) ";RBD=" $bds \
```

```
                    ";LOGP=" %arg( 2 $props ) ";SYM=" $sym ";XRLIST=" '"' \
                  $xrl '"' " > ")
        endif
           %write( $fout $sln ) > $nulldev
        if $ACD!Test
             goto alldone
           endif
nxt_core:
        setvar cct %math( $cct + 1 )
        break
      endfor
    endfor alldone:
    %close( $fout) > $nulldev
    if $how_core
      TABLE CLOSE hits NO > $nulldev
      ACD!Record CORES %cat( $fcore ".cores" ) $cvars VARIANTS UPDATED
    endif
.

@expression_generator string_insert

================================================
==============================================
  setvar p %pos( $2 $1 )
  if $p
    if $3
      setvar ans %cat( "%substr( $1 1 %math( $p - 1 ) )" \
            $3 "%substr( $1 %math( $p + %strlen( $2 ) ) )" )
      %return( $ans )
    else
      setvar ans %cat( "%substr( $1 1 %math( $p - 1 ) )" \
```

```
            "%substr( $1 %math( $p + %strlen( $2 ) ) )" )
        %return( $ans )
      endif
   else
        %return( $1 )
   endif
.

@expression_generator ACD_extract_ridX

==================================================
=============================================
backs out the row id and X from the input file name get rid of first few chars
    setvar arg %substr( $1 4 )
    setvar r %pos( R $arg )
    setvar p %pos( "." $arg )
    %return( %set_create( %substr( $arg %math( $r + 1 ) %math( $p - $r - 1 ) ) \
        %substr( $arg %math( $p + 1 ) ) ) )
#.

@macro core_get_acd sybylbasic

==================================================
=========================================
do reagent searches in ACD for all specified rows in reagents localvar fct rg sfrag buff bf hfname setvar rg    %tblsrch_val( CORES CLASS_ID $1 )
        setvar sfrag %rcell( $rg MORE_CORE )
        setvar hfname %cat( R $1 V $2 core )
```

```
        if %or( "$ACD!DoSearch" "%not( %file_exists( %cat( $hfname .hits ) ) )" )
# prepare notlist file
            setvar notf %open( %cat( $hfname .bad ) "w" )
            for not in %rcell( $rg CORE_NOTLIST )
                if %file_exists( $not )
# write out all bad fragments NOT CONTAINED by SEARCH FRAGMENT
                    setvar bf %open( $not "r" )
                    while %not( %eof( $bf ) )
                        setvar buff %read( $bf )
                        if %and( "%not( %eof( $bf ) )" "%not( %streql( \
                            "%substr( "$buff" 1 1 )" "#" ) )" )
                            if %not( %search2d( $sfrag "$buff" NoTriv 0 y ) )
                                %write( $notf $buff ) >$nulldev
                            else
                                echo Not excluding $not \
                                    fragment $buff (contained in $sfrag )
                            endif
                        endif
                    endwhile
                    %close( $bf )
                else
                    %write( $notf $not ) >$nulldev
                endif
            endfor
            %close( $notf )
# prepare query file
            setvar notf %open( %cat( $hfname .query ) "w" )
            %write( $notf $sfrag ) >$nulldev
            %close( $notf )

# do search (first time for individual components,
#            second time to filter umlticomponent cpds retrieved)
            echo .. Searching for $sfrag
```

```
setvar dbs dcl $ACD!cmd -database $ACD!db -qfile \
    %cat( $hfname .query ) -notlist %cat( $hfname .bad ) \
    -hitlist tmp.hits -coords
if $ACD!Test
    setvar dbs $dbs -maxhits 10
endif
$dbs
setvar dbs dcl $ACD!cmd -database tmp.hits -dbtype sln -qfile \
    %cat( $hfname .query ) -notlist %cat( $hfname .bad ) \
    -hitlist %cat( $hfname .hits )
$dbs
endif
.
```

Appendix "F"

```
/*E+:SYB_MGEN_GPLS_COMFA_HEX */
/*****************************************************************
*                                                                 *
* int SYB_MGEN_GPLS_COMFA_HEX( identifier, nargs, args, writer )   *
*                                                                 *
* Expression generator that returns hex version of a fingerprint  *
*                                                                 *
* interface:                                                      *
*                                                                 *
* %comfa_hex(Row ( CoMFA_col)                                     *
* with Row being a row to dump                                    *
*      CoMFA_col being a column selection for the topomer fingerprint*
* handles steric field or if 3 args electrostatic                 *
*                    , converts fpt to 4 bits                     *
*                                                                 *
*****************************************************************/
int SYB_MGEN_GPLS_COMFA_HEX(identifier, nargs, args, writer )
char    *identifier;
int     nargs;
char    *args[];
PFI     writer;
{
  int row, type, present;
  int err, i;
  set_ptr ref;
  ROWCOL_SEL_PTR row_sel;
  char *dum, *cname, *parname, *table;
  FieldPtr ofield;
  ComfaMolPtr cmp;
  if (! LM_ACCESS_CHECK_CmpdSel("CmpdSel","CmpdSel") )
      { UBS_OUTPUT_MESSAGE(stdout,"This requires a license to CmpdSel.\n");
```

```
        return 0; }
    if (nargs < 2 || nargs > 3 )
    {
        UIMS2_WRITE_ERROR(
            "Error: %comfa_hex (Row PrintCol (field 2 ) )\n" );
        return 0;
    }

/* get the column */
    if (!(table=TSH_APLINT_GET_DEFAULT_TABLE() ) ) goto badcol;
    if (!(UIMS2_VARTYPE_CALC_VALUE("COL_SEL",args[1], &row_sel)) ||
        !TBL_ACCESS_INDEX_TO_COLNAME( table , row_sel->id -1, &cname ) ||
        !TBL_ATTR_SAMPLE_COLUMN_A(table, cname, "FIELD", &dum, &present)
            || !present)
        { UBS_OUTPUT_MESSAGE(stdout,"Not a valid CoMFA column.\n");
          goto badcol; }

/* get the reference row */
    if (!(UIMS2_VARTYPE_CALC_VALUE("ROW_SEL",args[0], &row_sel)) ||
        !TBL_ACCESS_X_GET_VALUE(table, row_sel->id -1, cname,
                    "CELL_SUPPORT", (int *)&cmp, &err ) )
    {
        UIMS2_WRITE_ERROR(
            "Error: Invalid reference row selection for %fp_hex\n" );
        return 0;
    }
    if(!cmp || !(ofield = (nargs == 3) ? cmp->efld_p : cmp->sfld_p) ) {  /*
the data is not there */
        UBS_OUTPUT_MESSAGE(stdout,"Not a valid CoMFA cell.\n");
        goto badcol;}
    dum = UIMS2_MessageBuffer;
    for (i=0;i<ofield->n_points ;i++, dum +=1 )
        sprintf(dum, "%.1x", lookup_my_comfa_code(ofield->field_value[i]) );
```

```
        (*writer)( UIMS2_MessageBuffer );

return 1;
badcol:
    UIMS2_WRITE_ERROR(
        "Error: Invalid column selection for %comfa_hex\n" );
    return 0;
}
int lookup_my_comfa_code(value)
fpt value;
{
  static fpt cutoff[16] = {9999., 0., 2., 4., 6., 8., 10., 12.,
                14., 16., 18., 20., 22., 24., 26., 30.
};
  int i;
  if (!DABS_DUT_OKDATA(value)) return 0;
  for (i=1;i<16;i++) if (value <= cutoff[i]) return i;
  UBS_OUTPUT_MESSAGE(stdout,"Invalid field value above 30.0 set to
missing.\n");
  return 0;
}

/*E+:SYB_MGEN_GPLS_FP_HEX */
/******************************************************************
*                                                                 *
* int SYB_MGEN_GPLS_FP_HEX( identifier, nargs, args, writer )     *
*                                                                 *
* Expression generator that returns hex version of a fingerprint  *
*                                                                 *
* interface:                                                      *
*                                                                 *
* %fp_hex(Row (Finger_col)                                        *
* with Row being a row to dump                                    *
```

```
*    Finger_col being a column selection for the fingerprint    *
*                                                               *
****************************************************************/
int SYB_MGEN_GPLS_FP_HEX(identifier, nargs, args, writer )
char    *identifier;
int     nargs;
char    *args[];
PFI     writer;
{
    int row, type, present;
    int err, i;
    set_ptr ref;
    ROWCOL_SEL_PTR row_sel;
    char *dum, *cname, *parname, *table;
    if (! LM_ACCESS_CHECK_CmpdSel("CmpdSel","CmpdSel") )
        { UBS_OUTPUT_MESSAGE(stdout,"This requires a license to CmpdSel.\n");
          return 0; }
    if (nargs != 2 )
    {
        UIMS2_WRITE_ERROR(
            "Error: %fp_hex (Row PrintCol )\n" );
        return 0;
    }

/* get the column */
    if (!(table=TSH_APLINT_GET_DEFAULT_TABLE() ) ) goto badcol;
    if (!(UIMS2_VARTYPE_CALC_VALUE("COL_SEL",args[1], &row_sel)) ||
        !TBL_ACCESS_INDEX_TO_COLNAME( table , row_sel->id -1,
                &cname ))
        goto badcol;
    if (! TBL_UTL_COL_TO_FUNCTION(table, cname, &parname))
        goto badcol;
    if (!TBL_ATTR_FIND_COLUMN_A ( table, parname,
```

```c
                "TYPE", &dum, &type ))
        goto badcol;
    type = TBL_IO_TYPE_TO_KEY( type );
    if ( type != PROC_V_PRINT &&
        !(TBL_ATTR_SAMPLE_COLUMN_A(table, cname, "FINGERPRINT",
            &dum, &present) && present ) )
        goto badcol;
    /* get the reference row */
    if (!(UIMS2_VARTYPE_CALC_VALUE("ROW_SEL",args[0], &row_sel)) ||
        !TBL_ACCESS_X_GET_VALUE(table, row_sel->id -1, cname,
                "CELL_SUPPORT", (int *)&ref, &err ) ||
        !ref )
    {
        UIMS2_WRITE_ERROR(
            "Error: Invalid reference row selection for %fp_hex\n" );
        return 0;
    }
    dum = UIMS2_MessageBuffer;
    err = (ref[0]+31) / 32;
    for (i=1;i<=err ;i++, dum +=8 )
        sprintf(dum, "%.8x", ref[i] );
    (*writer)( UIMS2_MessageBuffer );

return 1;
badcol:
    UIMS2_WRITE_ERROR(
        "Error: Invalid column selection for %fp_hex\n" );
    return 0;
}
```

Appendix "G"

```
/****************************************************************
*/
/*              power
*/
/****************************************************************
*/
/*      David E. Patterson
*/
/****************************************************************
*/

/*   substantially changed 6/96 for cores-based reorganization of operation
 *   updated to include more reaction info (Dick Cramer -- 10/24/96)
 *   updated to use DB_CT_CCT_GET_PRD routines 10/29/96 DEP)
 *
 * This program performs the following functions:
 *   (1) read in one line from a ".files" file, one line per cores/X1/X2 file
 *   (2) read in one core to process (core / X1 / X2 file) = = a cSLN
 *   (3) for each cSLN, open a fp file to contain fingerprints
 *       (a) first is fingerprint size in bits
 *       (b) 2cd is number of records in segment (header + core + n1 + n2)
 *       (c) 3rd record notes size of record in bytes
 *       (d) 4th is number of cSLN segments included (= = 1 here always)
 *       (e) 5th and following ints contain the ASCII .2DRULES filename
 *       (A) next (second) record represents an "augmented fingerprint"
 *           which is made by attaching invariant pieces of X1 and X2 to core
 *           -> cardinality plus bitset is the record for every fp <-
 *       (B) then N1 + N2 augmented fingerprints records for all of the
 *           structural variations
```

```
*    (4) compute MBITS and LBITS estimates of worst case missing bits
*    (5) write out a "master record" entry for the result
*
*
* power -file <name> -line <m> -core <n> -fraction <f> -screendef <file>
*       -prefix <file> +debug
*
* Options:
*
*       -file   name        - name is file with names of cores/X1/X2 that
*                             determines what gets built
*
*       -line   number      - which line in file to process
*
*       -core   number      - which core in corefile named in line to process
*
*       -fraction f         - fraction of products to be evaluated, 0.0 - 1.0
*                             or if more than 1.0, it is the NUMBER desired
*                             and an appropriate fraction is computed to
yield
*                             approximately this number
*
*       -screendef file     - name of a file containing the fingerprint
*                             definition rules.
*
*       -prefix file        - name from which output filenames will be formed
*                             (i.e. -prefix Hi --> Hi.fp and Hi.mf
*
*       +debug              - writes irrelevant info to stderr
*
*       -#                  This flag forces the display of all
*                           options
*
```

```
/
/* use 3db
 * dbcc  power.c  -o power */
#include <stdio.h>
include <signal.h>
#include <ctype.h>
#include <unistd.h>
#include <string.h>
#include <sys/stat.h>
#include <math.h>
#include "parseopt.h"
#include "utl_str.h"
#include "utl_mem.h"
#include "utl_file.h"
#include "utl_math.h"
#include "ct.h"
#include "ct_expr.h"
#include "ct_proto.h"
#include "import_proto.h"

#define GoodExit 0
#define ErrorExit 1
#define Visual(s) {             fprintf s; }
static int              (*ExploderFunction)();
static char             *ScreenFileName;
static char             DefaultScreenFileName[32]
                            = "standard.2DRULES";
static int              *ScreenStructure;
static int              **fingerPointer;
static int              *fingerPrint = 0;
static int              *fingerMask  = 0;
static int              fingerBits;
```

```
static int          Mbits;
static int          Lbits;
static double       Fraction = 1.0 ;
static int          TopNumber = 0;
static char         *FileOfFiles;
static char         *Corefile, *X1file, *X2file;
static char         *PrefixForFiles;
static char         *ReactionCode;
static char         *UserRxnName;
static char         DefaultPrefixForFiles[20]
                        = "csln_preprocess";
static FILE         *InputSourceFile;
static FILE         *FileOfFilesFile;
static FILE         *fpFile;
static int          nbits[256];
static char         *fullQuery;
static char         **FGPT_X;
static char         *Xrlist;
static int          WordsPerFingerprint = 0;
static int          BytesPerFingerPrint = 0;
static int          CurrentSlnId = 0;
static int          DebugLevel;
static int          UserAborted;
static int          NullCore;
static int          MoreRxnInfo;
static int          StartCore = 0;
static int          LineFile = 0;
static char         *CombNameTemplate;
static int          CombCounter;
static int          **Y_01; /* fingerprints */
static int          **Y_02; /*      "      */
static int          nY_01; /* number of structures */
static int          nY_02; /*      "              */
```

```c
static int              nProcessed = 0;
static void *fullCsln, *xcoreCsln, *temp1Csln, *temp2Csln;
static char *CoreSln;
static char *X1xfile, *X2xfile;
static struct ParseOptions Options[] = {
/***
*** DO NOT MOVE ENTRIES IN THIS TABLE.  ADD ENTRIES ONLY AT THE END.
***/
        {"file",      ParseOptString,    &FileOfFiles,
            "File listing all input files" },
        {"fraction",  ParseOptDouble,    &Fraction,
            "Proportion of products(0 to 1) or Number to test" },
        {"screendef", ParseOptOldFile,   &ScreenFileName,
            "File which defines the UNITY screen" },
        {"line",      ParseOptInt,       &LineFile,
            "Sequential entry to use in Files file" },
        {"core",      ParseOptInt,       &StartCore,
            "Sequential core to use in Cores file" },
        {"prefix",    ParseOptString,    &PrefixForFiles,
            "Filename root for output files" },
        {"debug",     ParseOptBoolean,   &DebugLevel,
            "Use +debug to enable debugging messages" },
};
int UBS_OUTPUT_MESSAGE() { return 0; }   /* just for compiling OK */
int UIMS2_WRITE_PHOTO() { return 0; }
int lowercase (s) char *s; {while (*s) { if isupper(*s) *s = tolower(*s); s++;}}
static void UserHitControlC()
/*+I
*
* This function is the signal handler for user initiated program termination.
```

```
 * It's only role is to set a flag indicating that the user wishes to abort
the program.
 *
 * Author     Date          Description
 * ======     ========      ============
 * G. B. Smith   02-09-93      Original Version
 *
 */
{
        UserAborted = 1;
} static int ParseArguments( argc, argv )
/*+I
 *
 * This function parses the command line arguments.
 *
 * Returns: 1 on a successful command line parse, 0 otherwise.
 *
 * Warnings:
 *
 * Errors:
 *
 * See Also:
 *
 *
 * Author     Date          Description
 * ======     ========      ============
 * G. B. Smith   02-09-93      Original Version
 *
 */
int     argc;
```

```
char    **argv;
{
        int     nargs,
                noptions = sizeof( Options )/sizeof(Options[0]);

nargs = UTL_PARSE_OPT( argc, argv, noptions, Options );

if( !nargs ) goto SyntaxError;

if ( (!StartCore) || (!LineFile)) return 0;

if (!PrefixForFiles) PrefixForFiles = DefaultPrefixForFiles;

return 1;
SyntaxError:
        return 0;
} int main( argc, argv )
/*+E
 *
 */
int     argc;
char    **argv;
{
        long                    startTime,
                                totalTime,
                                finishTime;
/***
 *** Establish handler for a user interrupt.
 ***/
        signal( SIGINT, UserHitControlC);
#ifdef SIGHUP
        signal( SIGHUP, UserHitControlC);
#endif
        if( !ParseArguments( argc, argv ) )
                goto SyntaxError;
        time( &startTime );
```

```
    Visual((stderr,"Begin reading csln : %s",ctime(&startTime)));
/* Let's actually do something now */
    WarmUp();
    if(!(FileOfFilesFile = UTL_FILE_FOPEN(FileOfFiles,"r"))) return 0;
    GetFileSet (FileOfFilesFile);   /* getcSLN info - core, X1, X2 */
        if (! FGPT_X[0] || ! FGPT_X[1] ) goto FailureExit;
        if (!*FGPT_X[0] || !*FGPT_X[1] ) goto FailureExit;
        if (!ReadTheCslnInfo())    goto FailureExit;
    time( &finishTime );
    Visual((stderr,"Begin computations: %s",ctime(&finishTime)));
    time( &finishTime );
    if (!UserAborted && !DoPiecewiseFingerprints()) goto FailureExit;
    totalTime = finishTime - startTime;
    if( !totalTime ) totalTime = 1;
    Visual((stderr, "Created %d Finger Processed reagents in ",
        nProcessed = nY_01+nY_02 ));
    Visual((stderr,"%d Hours, %d min, %d secs\n",
            totalTime/(60*60),
            (totalTime%(60*60))/60,
            (totalTime%60)));
    Visual((stderr,"Each comparison required %.8f seconds to calculate\n",
        (totalTime/((double)(nProcessed?nProcessed:1)))));

time( &finishTime );
    Visual((stderr,"\nNow evaluating missing bits distribution at %s\n",
            ctime(&finishTime)));
    if (!UserAborted && !CheckMissingBits()) goto FailureExit;
    CoolDown();
    time( &finishTime );
    Visual((stderr,"End bits checking: %s",ctime(&finishTime)));
    Visual((stderr,"End cSLN preparation : %s",ctime(&finishTime)));
    UserAborted ? exit(ErrorExit) : exit(GoodExit);
SyntaxError:
```

```
            exit(1);
FailureExit:
            exit(ErrorExit);
}
int GetFileSet(f)
FILE *f;
{
    char *three_files, *hold, *pch;
    int i;
    /* does not read the core itself */ for (i=0;i<LineFile;i++)
        if( -1 == UTL_SCAN_GETS(FileOfFilesFile, "\\","#",&three_files)) return
0;
    /* see how many tokens there are -- if >5, new format with rxn data */
    for (i = 0, pch = three_files; *pch; pch++) if (*pch == ' ') i++;
    if ((MoreRxnInfo = i>4) ) {
        for (pch = three_files; *pch != ' '; pch++); *pch++ = '\0';
        if(!(ReactionCode = UTL_STR_SAVE( three_files ) )) return 0;
        for (hold = pch ; *pch != ' '; pch++); *pch++ = '\0';
        NullCore = (int) strstr( "YES", hold );

for (hold = pch; *pch != ' '; pch++); *pch++ = '\0';
        if (!(UserRxnName = UTL_STR_SAVE( hold ) )) return 0;
    }
    else pch = three_files;
    for (Corefile = pch; *Corefile == ' '; Corefile++) ;
    for (X1file = Corefile ; *X1file != ' '; X1file++) ;
    *X1file++ = '\0';
    for (                ; *X1file == ' '; X1file++) ;
    for (X2file =   X1file ; *X2file != ' '; X2file++) ;
    *X2file++ = '\0';
    for (                ; *X2file == ' '; X2file++) ;
```

```
Corefile = UTL_STR_SAVE(Corefile);
X1file   = UTL_STR_SAVE( X1file);
X2file   = UTL_STR_SAVE( X2file);

hold = 0;
nY_01 = testread(X1file,hold,1);
nY_02 = testread(X2file,hold,2);
return 1;
}
/* free up the arrays in the loop */
int CoolDown()
{
char *hold;
int i;
for (i=0;i<nY_01;i++) UTL_MEM_FREE(Y_01[i]);
UTL_MEM_FREE(Y_01);
for (i=0;i<nY_02;i++) UTL_MEM_FREE(Y_02[i]);
UTL_MEM_FREE(Y_02);
UTL_FILE_DELETE(X1xfile);
UTL_FILE_DELETE(X2xfile);

UTL_MEM_FREE(Corefile);
UTL_MEM_FREE( X1file);
UTL_MEM_FREE( X2file);
return 1;
}
int WarmUp()
{
int i;
FILE *fp;
for (i=0;i<256;i++) nbits[i] = (i&1) + (i&2)/2 + (i&4)/4 + (i&8)/8 +
                (i&16)/16 + (i&32)/32 + (i&64)/64 +
(i&128)/128 ;
```

```c
if (!ScreenFileName) ScreenFileName = DefaultScreenFileName;
if (!(fp = UTL_FILE_FOPEN(ScreenFileName,"r"))) return 0;
ScreenStructure = (int *) DB_BIT2_PARSE_2DSCREEN(fp);
UTL_FILE_FCLOSE(fp); fp = 0;
if (!ScreenStructure) return 0;
BytesPerFingerPrint = DB_BIT2_GET_SIZE( ScreenStructure );
WordsPerFingerprint = (BytesPerFingerPrint + 3) / 4;
fingerPrint = (int    *) UTL_MEM_ALLOC( BytesPerFingerPrint);
fingerMask  = (int    *) UTL_MEM_ALLOC( BytesPerFingerPrint);
if (Fraction > 1.0) TopNumber = Fraction;
Get_BY_SLN_Mask();    /* Set up for LBITS by ignoring the counts */

FGPT_X = (char**) UTL_MEM_ALLOC( sizeof(char *) * 2 );
return 1;
}
int Get_BY_SLN_Mask()
{
/* placeholder until a general one is written.
    This is correct for standard.2DRULES as of 6/96    */
int i;
unsigned char *foo;
foo = (unsigned char *) fingerMask;
for (i= 0;i<116;i++) *foo++ = 0xFF;
for (i=116;i<124;i++) *foo++ =    0;
return 1;
}
char *GenerateMySln(core)
char *core;
{
/*              ??? CONVERT THE Y_0x to Xn in core ??? */
            char *foo, *oof, *goo;
            goo = UTL_STR_SAVE(core);
            foo =strstr(goo,"Y_01");
```

```
        foo[1]=foo[2]=' ';  foo[0]='X';
        oof =strstr(goo,"Y_02");
        oof[1]=oof[2]=' ';  oof[0]='X';
        for (oof=foo=goo; *oof; oof++)
            if (*oof != ' ') *foo++ = *oof;
        *foo = '\0';

return goo;
}

/* THis routine should open the fp output file
            generate the full cSLN
                generate the augmented core SLN
                    write header and augmented core fp to fp file
                    generate *.rgroup files later fp work. */
int ReadTheCslnInfo()
{
    int i;
    char *junk, *hold, *line, *one, *two, *thr, *fou, *fiv, *six ,*legion;
    char *my_concatenate(), *augment();
    char *my_how_youve_grown();
    FILE *tfil;
    if (! (InputSourceFile = fopen(Corefile,"r")))          return 0;
    for (i=0;i<StartCore;i++)
        if (-1 == UTL_SCAN_GETS( InputSourceFile, "\\", "#", &line)) return 0;
    fclose(InputSourceFile);
    if (!GrabXrlist(line)) return 0;
    one = strstr(line,"<");
    *one= '\0';                 /* zap the parameters at the end of the line*/
    CoreSln = GenerateMySln(line);
    if (!(hold = UTL_STR_CONCATENATE(PrefixForFiles,".fp"))) return 0;
    if (! (fpFile = fopen(hold,"w")))          return 0;
    UTL_MEM_FREE(hold);
    i = BytesPerFingerPrint * 8 ;
```

```
UTL_FILE_FWRITE(     &i ,sizeof(int),     1     ,fpFile);
fingerPrint[0] = 2 + nY_01 + nY_02;
fingerPrint[1] = sizeof(int)*(WordsPerFingerprint + 1);
fingerPrint[2] = 1;
junk = ScreenFileName;
hold = (char *) &(fingerPrint[3]) ;
for (i=0; i < (WordsPerFingerprint-3)*sizeof(int); i++, junk++)
  { *hold++ = *junk;
     if ( ! *junk ) break;  }
UTL_FILE_FWRITE(fingerPrint,sizeof(int),WordsPerFingerprint,fpFile);
if (!(X1xfile = UTL_STR_CONCATENATE(PrefixForFiles,".FGPT.1"))) return 0;
tfil = fopen(X1xfile,"w");
fprintf(tfil,"%s\n",FGPT_X[0]);
fclose(tfil);
if (!(X2xfile = UTL_STR_CONCATENATE(PrefixForFiles,".FGPT.2"))) return 0;
tfil = fopen(X2xfile,"w");
fprintf(tfil,"%s\n",FGPT_X[1]);
fclose(tfil);
if (!sln_defines_csln( &xcoreCsln, X1xfile, X2xfile)) return 0;
if (!sln_defines_csln( &temp1Csln, X1file , X2xfile)) return 0;
if (!sln_defines_csln( &temp2Csln, X1xfile, X2file)) return 0;
if (!sln_defines_csln( &fullCsln,  X1file,  X2file)) return 0;
return 1;
} int GrabXrlist(string)
char *string;
{
  /* find XRLIST= and grab what's in there ! */
  char *foo, *strip_down();
  if (!(string = strstr(string,"XRLIST="))) return 0;
  Xrlist = strip_down(string);
  return 1;
```

```
} int testread(old, new, which)
char *old, *new;
int which;
{
 FILE *file, *elif;
 int i;
 char *line;
 char *strip_down();
/* get and hold FGPT_X info here
   Expect it to be at top of file preceded by a #   */
 if (!(file = fopen(old,"r"))) return 0;
 if (new && !(elif = fopen(new,"w"))) return 0;
 which--;
 FGPT_X[which] = 0;
 while (!FGPT_X[which])
 { if (-1 == UTL_SCAN_GETS( file, "\\", "", &line)) return 0;
   if ( line = strstr(line,"FGPT_X=") ) FGPT_X[which] = strip_down(line);
 }
/* this won't really work if the attachment point is NOT the first atom
listed*/
 FGPT_X[which] = UTL_STR_CONCATENATE("R1", FGPT_X[which]);
 for(i=0; ;i++)
 {
  if (-1 == UTL_SCAN_GETS( file, "\\", "#", &line)) break;
  if (new)
  { UTL_SCAN_TOKENIZE(line,'<','\\');
    fprintf(elif,"%s\n",line); }
 }
 fclose(file); if (new) fclose(elif);
 return i;
}
```

```
char *strip_down(string)
char *string;
{
  int i;
  char foo, *retme;
  string = strstr(string,"=") ;
  for ( ; *string == '=' || *string == '"'; string++) foo = *string;
  if ( foo != '"')
   {for ( i=0; ; i++)
      if ( (string[i] == ';') || (string[i] == '>')) break; }
  else
   {for ( i=0; ; i++)
      if ( (string[i] == '"')) break; }
  foo = string[i];
  string[i]= '\0';
  retme = UTL_STR_SAVE(string);
  string[i] = foo;
  return retme;
}
/* Assume that the fp file is opened and written to earlier */
int DoPiecewiseFingerprints()
{
  char *hold, *line1, *line2;
  int i;
  if (!(Y_01 = (int **) UTL_MEM_ALLOC( nY_01 * sizeof(int *))))
       return 0;
  if (!(Y_02 = (int **) UTL_MEM_ALLOC( nY_02 * sizeof(int *))))
       return 0;

MakeAllPrints( xcoreCsln , 1, 1, &fingerPrint);
  DB_CT_CCT_GET_PRD_CLEANUP( xcoreCsln );

for(i=0;i<nY_01;i++)
```

```c
{
    if (!(Y_01[i] = (int *) UTL_MEM_ALLOC(WordsPerFingerprint * sizeof(int))))
        return 0;
}
MakeAllPrints( temp1Csln , nY_01, 1, Y_01);
DB_CT_CCT_GET_PRD_CLEANUP( temp1Csln );
for(i=0;i<nY_02;i++)
{
    if (!(Y_02[i] = (int *) UTL_MEM_ALLOC(WordsPerFingerprint * sizeof(int))))
        return 0;
}
MakeAllPrints( temp2Csln , 1, nY_02, Y_02);
DB_CT_CCT_GET_PRD_CLEANUP( temp2Csln );
return 1;
} int WritefpFunc(struct CtConnectionTable *ct, int num, int**indexes)
{
int nbits;
int *fprint;
fprint = *fingerPointer++;
    memset ( fprint, 0, BytesPerFingerPrint );
    if( !DB_BIT2_EVALUATE( ct, ScreenStructure, fprint, &nbits ))
        return 0 ;

UTL_FILE_FWRITE( &nbits ,sizeof(int),    1       ,fpFile);
    UTL_FILE_FWRITE(fprint,sizeof(int),WordsPerFingerprint,fpFile);
    return 1;
}
int GrabfpFunc(struct CtConnectionTable *ct, int num, int**indexes)
{
```

```
int *fprint;
fprint = *fingerPointer++;
 memset ( fprint, 0, BytesPerFingerPrint );
 if( !DB_BIT2_EVALUATE( ct, ScreenStructure, fprint, &fingerBits ))
        return 0 ;

return 1;
}
int MakeOnePrint( void *CsIn , int i, int j, int *fp)
{
 static int **productIndexes = 0;
 if (!productIndexes)
 { productIndexes = (int **)UTL_MEM_CALLOC(2,sizeof(int *));
   productIndexes[0] = (int *)UTL_MEM_CALLOC(1,sizeof(int));
   productIndexes[1] = (int *)UTL_MEM_CALLOC(1,sizeof(int));
 }
        productIndexes[0][0] = i+1;
        productIndexes[1][0] = j+1;
 fingerPointer = &fp;
 DB_CT_CCT_GET_PRD_PRODUCT(CsIn, 1, productIndexes, GrabfpFunc);
 return 1;
}
int MakeAllPrints(void *CsInThing, int n1, int n2, int **pfp)
{
 int numProducts, **productIndexes, i, j, nProcessed;
 int numConnections = 2;
 numProducts = n1 * n2;
 nProcessed = 0;
 productIndexes = (int **)UTL_MEM_CALLOC(numConnections,sizeof(int *));
        for ( i = 0 ; i < numConnections ; i++ )
            productIndexes[i] = (int *)UTL_MEM_CALLOC(numProducts,sizeof(int));

for (i=0;i<n1;i++) for (j=0;j<n2;j++)
```

```
            {productIndexes[0][nProcessed] = i+1;
            productIndexes[1][nProcessed] = j+1;
            nProcessed++;
            }
    fingerPointer = pfp;
    DB_CT_CCT_GET_PRD_PRODUCT(CsInThing, numProducts, productIndexes,
WritefpFunc);
    for ( i = 0 ; i < numConnections ; i++ ) UTL_MEM_FREE(productIndexes[i]);
    UTL_MEM_FREE(productIndexes);
    return 1;
}

/*  Also find Mbits and Lbits
    and write them where they belong */
/*
        Should reorganize to find worst cases rather than pure random
*/
int CheckMissingBits()
{
        int argCount, err =1, i, j;
        int counts[21];
    nProcessed = 0;
    for (i=0;i<21;i++) counts[i]=0;
    if (TopNumber) Fraction = (double) TopNumber / (double) (nY_01 * nY_02);
    for (i=0;i<nY_01;i++) for (j=0;j<nY_02;j++)
    {
      if (UTL_MATH_URAND() >  Fraction) continue;
      nProcessed++;
      MakeOnePrint( fullCsIn , i, j, fingerPrint);
      CompareFingerPrint(Y_01[i],Y_02[j],20,counts);
    }
    WriteMissingBits(20,counts);
    WriteMasterRecord();
```

```
    return 1;
}

CompareFingerPrint( one, two, Nbins, bins)
int *one, *two, Nbins, *bins;
{
  unsigned char *h1, *h2, *h3, *fing;
  int i, product, card, lcard, lbits;
  h1 = (unsigned char *) one;
  h2 = (unsigned char *) two;
  h3 = (unsigned char *) fingerMask;
  fing = (unsigned char *) fingerPrint;
  lcard = card = lbits = 0;
  for (i=0;i<BytesPerFingerPrint;i++, h1++,h2++,h3++,fing++)
  { card += nbits[ *h1  | *h2  ];
    lbits += nbits[ *h3  & *fing ];
    lcard += nbits[ (*h1  | *h2 ) & *h3 ]; }
  if ((card = fingerBits - card) < 0) goto NoWay; /* should be impossible */
  if ((lcard = lbits - lcard)    < 0) goto NoWay; /* should be impossible */
  if ( card > Mbits) Mbits = card;
  if (lcard > Lbits) Lbits = lcard;
  if (card >Nbins) card = Nbins;
  bins[card] += 1;
  return 1;
NoWay:
   return 0;
}
WriteMissingBits(n,counts)
int n, *counts;
{
  int i, sum;
  sum = 0;
  for(i=0;i<=n;i++) {printf("%d - %d;   ",i,counts[i]); sum += counts[i]; }
```

```
printf("\n");
if (sum != nProcessed)
  fprintf(stderr,
"Mismatch indicates possible error in core entry.\nOnly %d of %d found.\n",
    sum, nProcessed);
}
/* File format of the "master record" is
    Reaction class name
    Reaction specific name
    Number of varying sites == 2 so far
    Mbits
    Lbits
    *.core filename
    *.core index
    prefix.fp
    number of fp records before 1st == 0 in this program
    X1 filename
    X2 filename
*/
WriteMasterRecord()
{
  FILE *fp;
  char *hold;
  if (!(hold = UTL_STR_CONCATENATE(PrefixForFiles,".mf"))) return 0;
  if (!(fp = UTL_FILE_FOPEN(hold,"w"))) return 0;
  UTL_MEM_FREE(hold);
  if (!(hold = UTL_STR_CONCATENATE(PrefixForFiles,".fp"))) return 0;
  if (MoreRxnInfo)
    fprintf(fp,"Reaction class %s%s\n%s\n%d\n%d\n%d\n%s\n%d\n%s\n%d\n%s\n%s\n",
        ReactionCode, NullCore ? " NO_core" : "", UserRxnName, 2, Mbits,
        Lbits, Corefile, StartCore, hold, 0, X1file, X2file);
```

```c
        else fprintf(fp,"Reaction class
Unknown\n%s\n%d\n%d\n%d\n%s\n%d\n%s\n%d\n%s\n%s\n",
    PrefixForFiles, 2, Mbits, Lbits, Corefile, StartCore, hold, 0, X1file,
X2file);
    UTL_MEM_FREE(hold);
    UTL_FILE_FCLOSE(fp);
}
int sln_defines_csln(void **c, char *file1, char *file2)
{
int numConnections = 0;
char *connectionFiles[2];
    if (file1) { connectionFiles[ numConnections++ ] = file1; }
    if (file2) { connectionFiles[ numConnections++ ] = file2; }
    if (numConnections < 2) { fprintf(stderr,"\nNo X1 or X2 file - failure.\n");
                return 0; }

*c = (void *) DB_CT_CCT_GET_PRD_INIT(CoreSln, Xrlist, numConnections,
                        connectionFiles);
if ( !*c )
    { fprintf(stderr,"\nUnable to init"); return 0 ; }
return 1;
}
```

Appendix "H"

```
/***********************************************************************
*/
/*            Similarity   - formerly dbcslnsim              */
/* mod to read from the master file format (DEP 6/26/96)     */
/* mod to read/write bitset files      (DEP 9/19/96)         */
/* mod to read $TA_MOLTABLES  screendef file if not where fp file points */
/* mod to take the "-q" format of input SLN                  */
/* mod to use fp mask to improve searches    (DEP 10/24/96)  */
/***********************************************************************
*/
/*+C                                           *
* This program evaluates (approximate) Tanimoto 2D similarity vs one cSLN
* based on preprocessing of the substituent reagents.
*
* Input file is a master file with one multiline record per cSLN.
* Record format is
*   Reaction class xxxx        (where "Reaction class" is a literal)
*   reaction_name
*   number_of_sv_sites
*   missing_bits_count         (may be overridden by mask)
*   hashed_only_missing_bits_count
*   core_filename
*   core_filename_index_of_core
*   fingerprint_filename
*   offset_into_fingerprint_file
*   first_sv_file_X1
*   secod_sv_file_X2           (etc if more than two sv_sites)
*
* Queries are input as SLN repeatedly from stdin; ending on ^D or X
*
* The optional ASCII output file contains one line per hit, of the form
*   Y1 Y2 T Tmax
```

* where Y1 = index of the substituent in X1.pro file
*      Y2 = index of the substituent in X2.pro file
*      T = apparent Tanimoto similarity
*      Tmax = maximum possible Tanimoto, given the slop bits (see below)
*
* The (required) checkpoint file is in the standard CSR format, which can
*   also be used instead of the master file to start a search.
*
* Similarity   -master <name> -bitset <name> -Tanimoto <real> -range <exp>
*              -index <int> -maxhits <int> -output <name> -checkpoint <name>
*              +debug
*
* Options:
*
*    -master name      - name is the file with master file records
*    -bitset name      - name is a result of an earlier search operation
*                        (use EITHER master or bitset)
*
*    -index number     - which sequential record in master file to use
*                        OR offset into bitset in a bitset file
*
*    -Tanimoto tan     - tan is a Tanimoto similarity 0.0 - 1.0
*                        (default is 0.85)
*
*    -maxhits max      - stop when max hits are found (default infinity)
*
*    -input filename   - name of file with queries (default stdin)
*
*    -q                - single SLN query string
*
*    -output filename  - specifies the output file for the hit info
*                        (Mainly used for debugging - otherwise obsolete)
*

```
*      -checkpoint name    -file to which bitset results will be written
*
*      -mask hex           - hex format bitmask of missing bits (tan_hex form)
*
*      -range range_exp    - set of internal cSLN ids (Y_01 varies slowest)
*                            for which similarity will be computed. Range_exp
*                            is a comma separated list of one or more of the
*                            following primitives:
*
*                            *      - everything in the cSLN
*                            1-18   - ids 1,2,3,....,18
*                            5-*    - ids from 5 to the last in the
*                                     cSLN.
*                            17     - id 17 only
*
*      -append             - append results to an existing output file
*                            By default an output file is overwritten.
*
*      +debug              - writes irrelevant info to stderr
*
*      -#                  This flag forces the display of all
*                          options
*
***************************************************************************
/
/* use 3db
 * dbcc Similarity.c -o Similarity  */
#include <stdio.h>
include <signal.h>
#include <ctype.h>
#include <unistd.h>
#include <string.h>
#include <sys/stat.h>
```

```c
#include <math.h>
#include "parseopt.h"
#include "utl_str.h"
#include "utl_mem.h"
#include "utl_file.h"
#include "ct.h"
#include "ct_expr.h"
#include "ct_proto.h"
#include "import_proto.h"
#include "commonData.h"
static char        *OutputFileName =0;
static char        *MasterFile =0;
static int         MasterRecord;
static FILE        *MasterFile_File;
static char        *FngrFile;
static int         FingerCore_Card;
static int         *FingerCore_FP;
static char        *InputSource = 0;
static char        *fullQuery;
static char        *BitsetFile;
static char        *CheckPointFileName;
static char        *directQuery = 0;
static double      Tanimoto = 0.85;
static int         AppendToOutputFile = 0;
static int         WordsPerFingerprint = 0;
static int         BytesPerFingerPrint = 0;
static int         CurrentSlnId = 0;
static int         NoMorehitsPlease = 999999999;
static char        *DatabaseRangeString = "*";
static int         DebugLevel;
static int         UserAborted;
static int         First, Last;
static int         Pro_size ;
```

```c
static char *mASCII = 0;
static int *MaskMissingBits = 0;
static int *MaskQueryBits = 0;
static struct ParseOptions Options[] = {
/***
*** DO NOT MOVE ENTRIES IN THIS TABLE.  ADD ENTRIES ONLY AT THE END.
***/
    {"master",     ParseOptString,     &MasterFile,
        "Name is the file with master file records" },
    {"bitset",     ParseOptString,     &BitsetFile,
        "Name is the file with bitset records" },
    {"Tanimoto",   ParseOptDouble,     &Tanimoto,
        "Similarity threshold (0.0 to 1.0)" },
    {"index",      ParseOptInt,        &MasterRecord,
        "Which MasterRecord entry 1-n" },
    {"maxhits",    ParseOptInt,        &NoMorehitsPlease,
        "Maximum number of hits before stopping" },
    {"input",      ParseOptString,     &InputSource,
        "File from which queries will be read( default stdin). "},
    {"q",          ParseOptString,     &directQuery,
        "Query string to use instead of a file or stdin"},
    {"output",     ParseOptString,     &OutputFileName,
        "File to which ASII hit info will be written. OBSOLETE "},
    {"checkpoint", ParseOptString,     &CheckPointFileName,
        "File to which bitset info will be written."},
    {"mask",       ParseOptString,     &mASCII,
        "Hex mask of missing bits" },
    {"range",      ParseOptString,     &DatabaseRangeString,
        "Range of cSLN ids to compare to query" },
    {"append",     ParseOptNoArg,      &AppendToOutputFile,
        "Use -append to append results to an existing file" },
    {"debug",      ParseOptBoolean,    &DebugLevel,
```

"Use +debug to enable debugging messages" },
};
int UBS_OUTPUT_MESSAGE() { return 0; }   /* just for compiling OK */
int UIMS2_WRITE_PHOTO() { return 0; }
int lowercase (s) char *s; {while (*s) { if isupper(*s) *s = tolower(*s); s++;}}
static void UserHitControlC()
/*+I
*
* This function is the signal handler for user initiated program termination.
* It's only role is to set a flag indicating that the user wishes to abort the program.
*
* Author    Date         Description
* ======    ========     ============
* G. B. Smith   02-09-93     Original Version
*
*/
{
        UserAborted = 1;
} static int ParseArguments( argc, argv )
/*+I
*
* This function parses the command line arguments.
*
* Returns:  1 on a successful command line parse, 0 otherwise.
*
* Warnings:
*
* Errors:
*
* See Also:
*

```
 *
 * Author    Date         Description
 * ======    ========     ============
 * G. B. Smith    02-09-93    Original Version
 *
 */
int     argc;
char    **argv;
{
        int     nargs,
                noptions = sizeof( Options )/sizeof(Options[0]);
        nargs = UTL_PARSE_OPT( argc, argv, noptions, Options );
        if( !nargs ) goto SyntaxError;
        return 1;
SyntaxError:
        return 0;
} static int OpenOutputFile()
/*+I
 *
 * Returns: 1 on sucesss, else 0
 *
 */
{
        char    *msg;
        FILE    *fp;
        if( OutputFileName )
        {
/*
** We need to create output files under the ownership of the REAL user not the
** EFFECTIVE user.  This only applies if setuid options are activated.
*/
```

```
{
struct stat statBuff ;
int    uid ;
int    euid ;
        uid = getuid() ;
        euid = geteuid();
    stat(OutputFileName, &statBuff);
/*
** There are two cases
** (1) the file to output to exists
**     Use the ownership of the current owner of the file or if you cant do that
**     do not do anything.
** (2) The file is being created.
**     use the ownership of the REAL user.
*/
        if ( access(OutputFileName, F_OK) == 0 )
        { /* If the file exist and the real user is the owner of the file */
                if ( statBuff.st_uid == uid )
                        seteuid(uid);
        }
        else
        { /* Create the file as the REAL user */
                seteuid(uid);
        }
}
        OutputFile = fopen( OutputFileName, (AppendToOutputFile?"a":"wb"));
        if( !OutputFile ) {
                fprintf(stderr,"Error: Failed to open output file \"%s\"\n",
                    OutputFileName );
                goto ErrorReturn;
        }
    }
        return 1;
```

ErrorReturn:

return 0;

} static int ParseRangeExpr( expr, maximum, low, high )
/*+I
 *
 * Function evaluates a structure range expression. See the module
 * description in this file for a definition of structure range expressions.
 *
 * Returns: Function returns 1 if the expression is correct. If the
 *          expression is incorrect 0 is returned.
 *
 * Author      Date         Description
 * ======      ========     =============
 * G. B. Smith 02-12-91     Original Version
 *
 */
```
char    *expr;     /* A structure range expression   */
int     maximum;   /* Maximum structure number. 999999999   */
int     *low;      /* RETURN: low value in the range */
int     *high;     /* RETURN: High value in the range */
{
        char    *p;
        for( p=expr; *p && isdigit(*p); p++ );
        if( !*p ) {
                sscanf( expr, "%d", low );
                *high = *low;
        } else if( 2 == sscanf( expr, "%d-%d", low, high)){
                ;
        } else if( 1 == sscanf(expr,"%d-*",low )) {
                *high = maximum;
        } else if( !strcmp( expr, "*" )) {
```

```
                *low = 1; *high = maximum;
        } else {
                fprintf(stderr, "ERROR: Invalid structure range \"%s\"\n",
                        expr );
                goto BadExpression;
        }
        if( *low < 1 ) {
                fprintf(stderr,
                        "ERROR: Structure range must be greater than zero\n" );
                goto BadExpression;
        }
        if( *high > maximum ) {
                fprintf(stderr,
                        "INFO: Specified range (%d-%d) is greated than the total number of
structures\n", *low, *high );
                *high = maximum;
        }
        if( *high < *low ) {
                fprintf(stderr, "ERROR: Low range value (%d) is larger than high value
(%d)\n",
                        *low, *high );
                goto BadExpression;
        }
        return 1;
BadExpression:
        return 0;
}
int main( argc, argv )
/*+E
*
*/
int     argc;
char    **argv;
```

```
{
    char        comline[2048];
    long        startTime,
                totalTime,
                finishTime;
/***
*** Establish handler for a user interrupt.
***/
    signal( SIGINT, UserHitControlC);
#ifdef SIGHUP
    signal( SIGHUP, UserHitControlC);
#endif
    if( !ParseArguments( argc, argv ) )
        goto SyntaxError;
    if (!ParseRangeExpr(DatabaseRangeString, 999999999, &First, &Last))
        goto SyntaxError;
    First--; Last--;
    if (!OpenOutputFile()) goto FailureExit;
    time( &startTime );
    Visual((stderr,"Begin reading files: %s",ctime(&startTime)));
/* Let's actually do something now */
    if (!ReadEverything())   goto FailureExit;
        time( &finishTime );
        Visual((stderr,"Begin comparison: %s",ctime(&finishTime)));
    if (!UserAborted && !CompareEverything()) goto FailureExit;
    if (OutputFile) fclose(OutputFile);
    time( &finishTime );
    totalTime = finishTime - startTime;
    if( !totalTime ) totalTime = 1;
    Visual((stderr, "Created %d Finger Prints in ", nProcessed ));
    Visual((stderr,"%d Hours, %d min, %d secs\n",
        totalTime/(60*60),
        (totalTime%(60*60))/60,
```

```
        (totalTime%60)));
    Visual((stderr,"Each comparison required %.8f seconds to calculate\n",
        (totalTime/((double)(nProcessed?nProcessed:1)))));
    MakeComLine(comline, 2048, argc, argv);
    CheckPointProgram(comline);
    Visual((stderr,"End Finger Print Computation: %s",ctime(&finishTime)));
    UserAborted ? exit(ErrorExit) : exit(GoodExit);
SyntaxError:
        exit(1);
FailureExit:
        exit(ErrorExit);
}
int ReadEverything()
{
 char *hold;
 char buff[256];
 int i;
 int j, offset, size;
 void *bitset=0;
/* because failure here means end program run, no effort to clean up
   memory on error is included. */
 if (!MasterFile && !BitsetFile ) return 0;
 setbits_nbits_Init();
 TotalInputs = 1;   /* no provision for concatenated */
 InputNames[0] = MasterFile ? MasterFile : BitsetFile;
 InputStartRec[0] = MasterRecord;
 if (MasterFile && !MasterRecord) InputStartRec[0]=1;
 if (CheckPointFileName)
   OutputCheckpointNames[0] = CheckPointFileName;
 else
  { sprintf(buff,"%s_%d_chk.bs",InputNames[0],0);
    OutputCheckpointNames[0] = UTL_STR_SAVE(buff);
  }
```

```
nY_01 = nY_02 = 0;
if (MasterFile)
            {  if ( !RetrieveMasterFile(InputNames[0],
                            MasterFile_File ,
                            InputStartRec[0],
                            &(NumMissingBits[0]),
                            &(BitsInAbsentiaNoCount[0]),
                            &(CoreFileNames[0]),
                            &(CoreStart[0]),
                            &FngrFile,
                            &(X1file[0]),
                            &(X2file[0]),
                            &(Y_01_Length[0]),
                            &(Y_02_Length[0]),
                            &fingerFP[0],
                            &fingerOffsets[0],
                            &ScreenFileName,
                            &BytesPerFingerPrint,
                            &WordsPerFingerprint,
                            &query,
                            &FingerCore_FP,
                            &FingerCore_Card  ) )
                            goto UnableToReadMaster ; }
else
{
            if ( !( bitset  =  CS_PRDCT_BITSET_OPEN(InputNames[0],
                            InputStartRec[0])) )
                            goto UnableToReadBitset ;
            if ( !RetrieveMasterFileFromBitset(bitset,
                            &(MasterFile_Bitset[0]),
                            &(StartRec_Bitset[0]),
                            &(NumMissingBits[0]),
                            &(BitsInAbsentiaNoCount[0]),
```

```
                    &(CoreFileNames[0]),
                    &(CoreStart[0]),
                    &FngrFile,
                    &(X1file[0]),
                    &(X2file[0]),
                    &(Y_01_Length[0]),
                    &(Y_02_Length[0]),
                    &fingerFP[0],
                    &fingerOffsets[0],
                    &ScreenFileName,
                    &BytesPerFingerPrint,
                    &WordsPerFingerprint,
                    &query,
                    &FingerCore_FP,
                    &FingerCore_Card  ) )
                goto UnableToReadBitset ;
        }
        nY_01 += Y_01_Length[0] ;
        nY_02 += Y_02_Length[0] ;
    if (!WarmUp()) goto UnableToWarmUp;
    RemainingInput[0] =SomeLeft = Y_01_Length[0] * Y_02_Length[0] ;
    Pro_size = ( 31 + SomeLeft )/32 * 4;
    BitMapStartPoint[0] = 0;
        if (!Good_Products) /* initialize iff not already done */
        {if (!(Good_Products = (int *) UTL_MEM_ALLOC(Pro_size))) return 0;
                memset( Good_Products,0,Pro_size); }
        if (!Dead_Products) /* initialize iff not already done */
        {if (!(Dead_Products = (int *) UTL_MEM_ALLOC(Pro_size))) return 0;
                memset( Dead_Products,0,Pro_size);
            if (bitset) /* assumes actuallsizes matches current sizes!*/
            { CS_PRDCT_BITSET_TO_RAW( bitset, Dead_Products, 0);
                not_here(Dead_Products,Pro_size );
            }
```

```c
    }
    if (! (Y_01 = (int **) UTL_MEM_ALLOC(sizeof(int *) * nY_01))) return 0;
    if (!(cY_01 = (int  *) UTL_MEM_ALLOC(sizeof(int  ) * nY_01))) return 0;
    if (!(iY_01 = (int  *) UTL_MEM_ALLOC(sizeof(int  ) * nY_01))) return 0;
    for (i=0;i<nY_01;i++)
    {
      if (! GetNextLine(   cY_01+i,Y_01+i ))    return 0;
    } if (! (Y_02 = (int **) UTL_MEM_ALLOC(sizeof(int *) * nY_02))) return 0;
    if (!(cY_02 = (int  *) UTL_MEM_ALLOC(sizeof(int  ) * nY_02))) return 0;
    if (!(iY_02 = (int  *) UTL_MEM_ALLOC(sizeof(int  ) * nY_02))) return 0;
    for (i=0;i<nY_02;i++)
    {
      if (! GetNextLine(   cY_02+i,Y_02+i ))    return 0;
    } return 1;
UnableToWarmUp:
        fprintf(stderr,"Unable to Read screen file\n");
        return 0;
UnableToReadMaster:
        fprintf(stderr,"Unable to Read master file\n");
        return 0;
UnableToReadBitset:
        fprintf(stderr,"Unable to Read bitset file\n");
        return 0;
}
int WarmUp()
{
 FILE *fp;
 char *where_else,*name, *ext;
 int words;
```

```
if (!(fp = fopen(ScreenFileName,"r")))
{
  where_else = UTL_FILE_PARSE(ScreenFileName,4);
  name = UTL_STR_CONCATENATE("sybylbase/tables/",where_else);
  UTL_MEM_FREE(where_else);
  ext = UTL_FILE_PARSE(ScreenFileName,5);
  where_else = UTL_FILE_COMPOSE_SPEC( "TA_ROOT", name, ext);
  if (!(fp = fopen(where_else,"r"))) return 0;
  UTL_MEM_FREE(where_else);
  UTL_MEM_FREE(name);
  UTL_MEM_FREE(ext);
}
ScreenStructure = (int *) DB_BIT2_PARSE_2DSCREEN(fp);
fclose(fp); fp = 0;
if (!ScreenStructure) return 0;
CurrentInput = 0;
if (mASCII)        /* generate binary missing bits */
{
  if ( (strlen(mASCII) / 8) != WordsPerFingerprint) return 0;
  if (!(MaskMissingBits = (int *) UTL_MEM_ALLOC( BytesPerFingerPrint)))
        return 0;
  if (!(MaskQueryBits = (int *) UTL_MEM_ALLOC( BytesPerFingerPrint)))
        return 0;
  for (words=0;words<WordsPerFingerprint;words++)
  {
    memcpy(next8,mASCII,8);
    mASCII += 8;
    sscanf(next8,"%8x", MaskMissingBits + words);
  }
}
return 1;
}
int MakeAFingerprint( sln, fingerPrint)
```

```c
char *sln;

int *fingerPrint;

{ struct CtConnectionTable *ct;

int nBitsSet;

if (!(ct = DB_IMPORT_SLN(sln))) return 0;

memset ( fingerPrint, 0, BytesPerFingerPrint );

if( !DB_BIT2_EVALUATE( ct, ScreenStructure, fingerPrint, &nBitsSet ))

return 0 ;

return nBitsSet;

} int GetNextLine( pCard, pFP)

int *pCard, **pFP;

{ if (!(*pFP = (int    *) UTL_MEM_ALLOC( BytesPerFingerPrint))) return 0;

if (!UTL_FILE_FREAD( pCard,sizeof(int), 1 ,fingerFP[0])) return 0;

if (!UTL_FILE_FREAD( *pFP  ,sizeof(int), WordsPerFingerprint ,fingerFP[0]))

return 0;

return 1;

} int IntersectQuery( pIntr, pFP)

int *pIntr, **pFP;

{ unsigned char *ptr ,*qtr;

int i, count;

ptr = (unsigned char *) *pFP;

qtr = (unsigned char *) query;

for(count=0, i=0; i<WordsPerFingerprint*4;i++)

count += nbits[ *ptr++ & *qtr++];

*pIntr = count;

return 1;

} int CompareEverything()
```

```c
{
  int cqt, q_lo, q_hi, i, j, carhold, inthold, onion, intsc, countinput;
  double max;
 countinput = 0;
 if ( ! directQuery )
 {if (!InputSource) InputSourceFile = stdin;
  else
   if (! (InputSourceFile = fopen(InputSource,"r")))         return 0;
 }
 while ( directQuery ?
                 ((fullQuery = directQuery) && countinput == 0) :
                 (-1 != UTL_SCAN_GETS( InputSourceFile, "\\", "#", &fullQuery)))
 {
  countinput++;
  if (! (c_query = MakeAFingerprint(fullQuery,query) ))         return 0;
  if (MaskMissingBits) ReNumMissingBits(1);

for (i=0;i<nY_01;i++)
    if (! IntersectQuery( iY_01+i,Y_01+i ))     return 0;
  for (i=0;i<nY_02;i++)
    if (! IntersectQuery( iY_02+i,Y_02+i ))     return 0;
  CurrentSlnId = 0;
  cqt = floor( (double) c_query / Tanimoto);
  q_lo = floor( (double) c_query * Tanimoto - (double) NumMissingBits[0]);
  q_hi = ceil( (double) ( c_query + NumMissingBits[0]) / Tanimoto);
  /* should convert test of Dead_Products to a "UTL_SET_NEXT" approach ?? */
  for(i=0;i<nY_01;i++)
   {
     if (CurrentSlnId > Last) break;
     if (cY_01[i] > cqt)    { CurrentSlnId += nY_02; continue;}
     carhold = q_lo - cY_01[i];
     inthold = q_lo - iY_01[i];
     for (j=0;j<nY_02;j++)
```

```
    {
        if (UserAborted) return 1;

if (CurrentSlnId > Last)  break;
        if (CurrentSlnId < First)    { CurrentSlnId++; continue; }
        if (cY_02[j] > cqt)          { CurrentSlnId++; continue; }
        if (cY_02[j] < carhold)      { CurrentSlnId++; continue; }
        if (inthold > iY_02[j])      { CurrentSlnId++; continue; }
        if (TestDead(0,CurrentSlnId)) { CurrentSlnId++; continue; }
        ActuallyCompute( i, j, &onion, &intsc, &max);
        if (max >= Tanimoto)
        {
            OutputThisHit(i,j,onion, intsc, max);
            nProcessed++;
            if (nProcessed >= NoMorehitsPlease) return 1;
        }
        CurrentSlnId++;
    } /* Y_02 loop */
  } /* Y_01 loop */
 } /* while stil queries left */
 return 1;
}
int ReNumMissingBits( int howmany )
{
 for ( ; howmany ; howmany--)
   ReNum(MaskMissingBits,query,WordsPerFingerprint,&(NumMissingBits[howmany-1])
);
}
int ReNum(int *mask, int*query, int len, int *missed)
{
 unsigned char *one, *two;
 unsigned char *masq;
 masq = (unsigned char *) MaskQueryBits;
```

```
  one = (unsigned char *) mask;
  two = (unsigned char *) query;
  *missed = 0;
  len *= 4;
  for ( ; len ; len--) *missed += nbits[ (*masq++ = *one++ & *two++) ];
  return 1;
}
int ActuallyCompute( index1, index2, pUnion, pIntersection, pMaxTan)
int index1, index2, *pUnion, *pIntersection;
double *pMaxTan;
{
  int i, product;
  unsigned char *h1, *h2, *hquery, *masq;
  int nuMissing;
  if (DebugLevel)
      fprintf( stderr," ActuallyCompute at %d , %d\n", index1, index2);
  h1 = (unsigned char *) Y_01[index1];
  h2 = (unsigned char *) Y_02[index2];
  hquery = (unsigned char *) query;
  *pUnion = *pIntersection = 0;
  if (mASCII) {nuMissing = 0; masq = (unsigned char *) MaskQueryBits; }
  else     {nuMissing = NumMissingBits[0];}
  for( i=0; i<WordsPerFingerprint*4;i++)
   {
      product = *h1++ | *h2++ ;
      *pUnion     += nbits[ product | *hquery];
      if (mASCII)
        nuMissing  += nbits[ ~product & *masq++];
      *pIntersection += nbits[ product & *hquery++];
   }
  if (DebugLevel > 9) fprintf(stderr,"%d / %d %6.3f\n",
              *pIntersection, *pUnion,
              (double) *pIntersection / *pUnion);
```

```c
  return (*pMaxTan = (double) (*pIntersection + nuMissing) / (double) *pUnion);
}
int OutputThisHit( index1, index2, onion, intsc, maxtan)
int index1, index2, onion, intsc;
double maxtan;
{
  if (OutputFile)
    fprintf(OutputFile,"%6d %6d %5.3f %5.3f\n", index1+1 ,index2+1 ,
                                    (double) intsc / (double) onion,
                                    maxtan);
        /* just note in bitset as a hit */
  FlagProduct(Good_Products, index1, index2, 0);
  return 1;
}
static int not_here( what, nbytes )
unsigned char *what;
int nbytes;
{
  for ( ; nbytes; --nbytes) *what++ = ~ *what;
  return 1;
}
/* this belongs in the utl module, actually */
int MakeComLine( char *line, int len, int argc, char **argv)
{
  int i;
  sprintf(line,"%s ",argv[0]);
  for(i=1;i<argc;i++)
  {
    line += strlen(line);
    sprintf(line,"%s ",argv[i]);
  }
}
CheckPointProgram(programName)
```

```
char *programName ;
{
int sizes[2] , size;
int allocSizes[2] ;
int numInSites[2] ;
char hold[81] ;
int i ;
void *compressed ;
int total ;
        for ( i = 0 ; i < TotalInputs ; i++ )
        {
                sizes[0] = Y_01_Length[i] ;
                sizes[1] = Y_02_Length[i] ;
                numInSites[0] = numInSites[1] = -1 ;
                allocSizes[0] = allocSizes[1] = -1 ; /* should keep bitset
                                                        allocSizes if present?*/
                compressed = NIL;
                total      = 0;
                WriteOutCheckPointFile(OutputCheckpointNames[i],
                        MasterFile ? InputNames[i]
                                : MasterFile_Bitset[i],
                        MasterFile ? InputStartRec[i]
                                : StartRec_Bitset[i],
                                        programName,
                                        Good_Products,
                                        BitMapStartPoint[i],
                                        2,
                                        sizes,
                                        allocSizes,
                                        Selections[i],
                                        numInSites,
                                        total,
                                        compressed);
```

```
        }
    }
```

Appendix "I"

```
/************************************************************
*/
/*              dbcslnquickselect                    */
/************************************************************
*/
/*+C
*
* This program evaluates (approximate) Tanimoto 2D similarity vs cSLNs
* based on preprocessing of the substituent reagents. Using this, it
* selects a diverse set of products while trying to maximize use of
* some groups.
*
* To Do:
*    Following ADS group suggestions, order the reagent fp by size (fpcard).
*
* To be added: restart capability and reagent blackout.
*
* The input files, one per X1, X2,           have one line per
* structure and contain the elements "fpcard=xxx;" and "fp=zzz;" where
* the terminating ";" may also be ">". The integer value of fpcard is
* the cardinality of the fingerprint; the hex value of fp is the
* fingerprint bitstring as two ascii bytes per bitset byte.
*
* Queries are input as SLN repeatedly from stdin; ending on ^D or X
*
* The resultant file contains one line per hit, of the form
*   Y1 Y2 T Tmax
* where Y1 = index of the substituent in X1.pro file
*       Y2 = index of the substituent in X2.pro file
*       T  = apparent Tanimoto similarity
*       Tmax = maximum possible Tanimoto, given the slop bits (see below)
```

```
*
* dbcslnquickselect -prefix <name> -Tanimoto <real> -prefer <what> -append
*                   -slop <int> -maxhits <int> -output <name> +debug
*
* Options:
*
*       -prefix name      - name is the prefix for a set of 2 files
*                           with extensions .X1.pro .X2.pro
*                           ; files have fingerprints
*            (someday)     will reload from prefix.RELOAD if present
*
*       -Tanimoto tan     - tan is a Tanimoto similarity 0.0 - 1.0
*                           (default is 0.85)
*
*       -prefer           - one of R1,R2 else random. R1 maximizes use of R1
*
*       -slop bitcount    - bitcount is the number of bits in the
*                           product fingerprint that may not be
*                           represented by ORinf X1 X2  (default 0)
*
*       -maxhits max      - stop when max hits are found (default infinity)
*
*       -output filename  - specifies the output file for the hit info
*                           by default results are sent to stdout.
*
*       -append           - append results to an existing output file
*                           By default an output file is overwritten.
*
*       +debug            - writes irrelevant info to stderr
*
*       -rangevar         - List of field names and ranges to filter
*                           the final list with.
*       -oneof            - List of field names and values that the product
```

```
*                     should match in order to be considered.
*
*     -#              This flag forces the display of all
*                     options
*
```

```
*************************************************************
/
/* use 3db
 * dbcc dbcslnquickselect.c -o dbcslnquickselect     */ include <stdio.h>
include <signal.h>
#include <ctype.h>
#include <unistd.h>
#include <string.h>
#include <sys/stat.h>
#include <math.h>
#include "parseopt.h"
#include "utl_str.h"
#include "utl_mem.h"
#include "utl_file.h"
#include "utl_math.h"
#include "ct.h"
#include "ct_expr.h"
#include "ct_proto.h"
#include "import_proto.h"

#define GoodExit 0
#define ErrorExit 1
define Visual(s) {                    fprintf s; } define ALLOCATE_INCREMENT 5
```

```
#define MISSING_FLOAT_VALUE    -100000000.00
#define MISSING_INT_VALUE      -1
define NOT_A_MATCH_VALUE      -2 define SMALL_FLOAT            0.00001

/*
** Command line argument -rangevar and -oneof are kept here.
*/
static char     *RangeVar ;
static char     *OneOfVar ;

/*
** Structure to hold the field name(inside the nnn.x? files) and the allowed
** range for that field.
*/
typedef struct RangeStruct
{
    char  *RangeFieldName ;
    float lowValue ;
    float highValue ;
} RangeStruct ;

int       NumRangeFields ;
int       NumRangeFieldsAllocated ;
RangeStruct *RangeFields ;

/*
** Structure to hold the field name and a list of values for the selection
** type fields.
*/
typedef struct OneOfStruct
```

```c
{
    char *OneOfFieldName ;
    int  numValues ;
    int  numValuesAlloc ;
    char **values ;
} OneOfStruct ;

int         NumOneOfFieldsAllocated ;
int         NumOneOfFields ;
OneOfStruct *OneOfValues ;

float **RangeValues_Y01 ; /* Actual values read in from  nnn.X1 file,
                If MW is the first and logp is the second value
                specified on the -rangevar argument list then
                RangeValues_Y01[n][0] would keep the value for MW
                for the nth line in the nnn.X1 file and
                RangeValues_Y01[n][1] would keep the value for
                logp for that line*/ float **RangeValues_Y02 ; /* same */ int **OneOfValues_Y01 ; /*Actual values read from nnn.X1 files but translated
                into an index of OneOfValues[i].values so
                we dont have to waist memory and time doing strcmp*/
int **OneOfValues_Y02 ; /* Same */ static FILE             *OutputFile;
static char             *OutputFileName;

static char             *WhatFirst;
static int              What1 = -1;
static int              What2;
```

```
static char         *PrefixForFiles;
static char         *InputSource = 0;
static FILE         *InputSourceFile;

/* Code presumes that an int is 32 bits, ASCII-ed into %.8x format */
static int          **Y_01;     /* fingerprints */
static int          **Y_02;     /*      "       */
static int          *query;     /*      "       */
static int          nY_01;      /* number of structures */
static int          nY_02;      /*      "       */
static int          *cY_01;     /* cardinality of fingerprints */
static int          *cY_02;     /*      "       */
static int          c_query;    /*      "       */
static int          *iY_01;     /* intersection count of fprints */
static int          *iY_02;     /*      "       */ static int          *Good_1;
static int          *Good_2;
static int          *Dead_1;
static int          *Dead_2;
static int          *Good_Products;
static int          *Dead_Products;

static int          nbits[256];
static int          setbits[8];

static double       Tanimoto = 0.85;
static int          BitsInAbsentia = 0;
static int          AppendToOutputFile = 0;
static int          WordsPerFingerprint = 0;
static int          BytesPerFingerPrint = 0;
static int          NoMorehitsPlease = 999999999;
```

```c
static int          DebugLevel = 0 ;
static int          UserAborted;

static int          nProcessed = 0;
static int          SomeLeft;
static char         next8[10] = "01234567\0";

static struct ParseOptions Options[] = {

/***
*** DO NOT MOVE ENTRIES IN THIS TABLE.  ADD ENTRIES ONLY AT THE END.
***/

{"prefix",   ParseOptString,    &PrefixForFiles,
        "Prefix for all input files" }, {"Tanimoto", ParseOptDouble,    &Tanimoto,
        "Similarity threshold (0.0 to 1.0)" }, {"slop",     ParseOptInt,       &BitsInAbsentia,
        "Number of potentially missing bits in product fp" }, {"maxhits",  ParseOptInt,       &NoMorehitsPlease,
        "Maximum number of hits before stopping" }, {"input",    ParseOptString,    &InputSource,
        "File from which queries will be read( default stdin). "}, {"output",   ParseOptString,    &OutputFileName,
        "File to which hit info will be written. "}, {"prefer",   ParseOptString,    &WhatFirst,
```

"One of R1, R2 to maximize us of."},

{"append", ParseOptNoArg, &AppendToOutputFile,
"Use -append to append results to an existing file" }, {"debug", ParseOptBoolean, &DebugLevel,
"Use +debug to enable debugging messages" },
{"rangevar", ParseOptString, &RangeVar,
"Scalar field name and range to filter out, i.e. logp -1.0 8.0 MW 200 500 price 0 12.50" },
{"oneof", ParseOptString, &OneOfVar,
"Field name and list of values that the product should match\n, i.e. supplier Aldrich,Sigma,Fluka,SALOR taste SWEET,Salty" },

};

int UBS_OUTPUT_MESSAGE() { return 0; }   /* just for compiling OK */
int UIMS2_WRITE_PHOTO() { return 0; }
int lowercase (s) char *s; {while (*s) { if isupper(*s) *s = tolower(*s); s++;}} static void UserHitControlC()
/*+I
*
* This function is the signal handler for user initiated program termination.
* It's only role is to set a flag indicating that the user wishes to abort the program.
*

*
*/

{
    UserAborted = 1;
}

```
/*
**+E:
**
**
** Abstract    : Function parses range field string for ADS design programs.
**               It takes a string of the form
**               "logp -1.0 8.0 MW 200 500 price 0 12.50" and fills in the
**               global array  RangeFields.
**
**
** Usage       :
**
** Returns     : 1 on success, 0 for failure.
**
** Algorithms  : None.
**
** Revision History :
**

**
**-E:
*/
int ParseRangeVar(rangeVar,numRangeFieldsAllocated,numRangeFields,rangeFields)
char   *rangeVar ;
int    *numRangeFieldsAllocated ;
int    *numRangeFields ;
struct RangeStruct **rangeFields;
{
static int stat = 0 ;
char *buffer = (char *)NULL ;
char *name ;
char *low ;
char *high ;
```

```c
int i ;

*numRangeFieldsAllocated = 0 ;
    *numRangeFields = 0 ;
    *rangeFields = (struct RangeStruct *)NULL ;

if ( !(buffer = UTL_STR_SAVE(RangeVar)) )
                goto Failure ;

name = strtok(buffer," ");
    while ( name )
    {
        if ( !(low  = strtok(NULL," ")) )
                    goto UnableToParse ;
        if ( !(high = strtok(NULL," ")) )
                    goto UnableToParse ;
        if ( *numRangeFields >= *numRangeFieldsAllocated )
        {
                if ( !*rangeFields )
                {
                        if (!(*rangeFields = (struct RangeStruct
*)UTL_MEM_CALLOC(

ALLOCATE_INCREMENT, sizeof(struct RangeStruct))))
                                goto Failure ;
                        else
                                *numRangeFieldsAllocated =
ALLOCATE_INCREMENT ;
                }
                else
                {
                        if (!( *rangeFields = (struct RangeStruct
```

```
*)UTL_MEM_RECALLOC(
                    RangeFields,
                    (*numRangeFieldsAllocated *sizeof(struct RangeStruct)),
                    ((*numRangeFieldsAllocated + ALLOCATE_INCREMENT) *
                        sizeof(struct RangeStruct)) )) )
                    goto Failure ;
                else
                    *numRangeFieldsAllocated +=
ALLOCATE_INCREMENT ;

}
        }
            RangeFields[*numRangeFields].RangeFieldName =
UTL_STR_SAVE(name);
            RangeFields[*numRangeFields].lowValue = atof(low);
            RangeFields[*numRangeFields].highValue = atof(high);
        (*numRangeFields)++ ;
            name = strtok(NULL," ");
    }
if (DebugLevel)
{
        for ( i = 0 ; i < *numRangeFields ; i++ )
        {
            fprintf(stderr,"\n%s %f -- %f",
            RangeFields[i].RangeFieldName,
            RangeFields[i].lowValue,
            RangeFields[i].highValue);
        }
}
    stat = 1 ;
    goto CleanUp ;

UnableToParse:
```

```
            fprintf(stderr,"Unable to parse -rangevar %s\n",RangeVar);
        stat = 0 ;
    goto CleanUp ;
Failure :
    stat = 0 ;
    goto CleanUp ;
CleanUp :
        if ( buffer )
            UTL_MEM_FREE(buffer);
    return stat ;
}

/*
**+E:
**
**
** Abstract    : Function parses one of field string for ADS design programs.
**              It takes a string of the form
**              "supplier Aldrich,Sigma,Fluka,SALOR taste SWEET,Salty"
**              global array  OneOfValues.
**
**
** Usage       :
**
** Returns     : 1 on success, 0 for failure.
**
** Algorithms  : None.
**
** Revision History :
**

**
**-E:
```

```
*/
static int
ParseOneOfVar(oneOfVar,numOneOfFieldsAllocated,numOneOfFields,oneOfValues)
    char    *oneOfVar ;
    int     *numOneOfFieldsAllocated ;
    int     *numOneOfFields ;
    struct OneOfStruct **oneOfValues;
{
    static int stat = 0 ;
    char *buffer = (char *)NULL ;
    char *name ;
    char *choices ;
    char *choice ;
    int i ;
    int j ;
    char *cp ;
    char *end ;

*numOneOfFieldsAllocated = 0 ;
        *numOneOfFields = 0 ;
        (*oneOfValues) = (struct OneOfStruct *)NULL ;

if ( !(buffer = UTL_STR_SAVE(OneOfVar)) )
                    goto Failure ;
/*
** Start off by reading the field name .
*/
        name = strtok(buffer," ");
        while ( name )
        {
            if ( *numOneOfFields >= *numOneOfFieldsAllocated )
            {
```

```
            if ( !(*oneOfValues) )
            {
                    if (!(*oneOfValues = (struct OneOfStruct
*)UTL_MEM_CALLOC( ALLOCATE_INCREMENT,
                                    sizeof(struct OneOfStruct))))
                            goto Failure ;
                    else
                            *numOneOfFieldsAllocated =
ALLOCATE_INCREMENT ;
            }
                    else
                    {
                            if (!( *oneOfValues = (struct OneOfStruct
*)UTL_MEM_RECALLOC(
                                    *oneOfValues,
                            (*numOneOfFieldsAllocated *sizeof(struct OneOfStruct)),
                            ((*numOneOfFieldsAllocated + ALLOCATE_INCREMENT) *
                                    sizeof(struct OneOfStruct)) )) )
                                    goto Failure ;
                            else
                                    *numOneOfFieldsAllocated +=
ALLOCATE_INCREMENT ;

}
            }
                    (*oneOfValues)[*numOneOfFields].OneOfFieldName =
UTL_STR_SAVE(name);
                            (*oneOfValues)[*numOneOfFields].numValues = 0 ;
                            (*oneOfValues)[*numOneOfFields].numValuesAlloc =
ALLOCATE_INCREMENT ;
                            if ( !((*oneOfValues)[*numOneOfFields].values = (char **)
```

```
                UTL_MEM_CALLOC(ALLOCATE_INCREMENT, sizeof(char *)) ) )
                                goto Failure ;
/*
** Now look at the choices this field could have.
*/
                        choices = strtok(NULL," ");
                        if ( !choices )
                                goto UnableToParse ;
                        choice  = strtok(choices,",");
                        while ( choice )
                        {
                                if ( (*oneOfValues)[*numOneOfFields].numValues > =
                                        (*oneOfValues)[*numOneOfFields].numValuesAlloc )
                                {
                                        if ( !((*oneOfValues)[*numOneOfFields].values = (char **)

UTL_MEM_RECALLOC((*oneOfValues)[*numOneOfFields].values,
                                                                (
(*oneOfValues)[*numOneOfFields].numValuesAlloc *
                        sizeof(char *)),
                                        ( ((*oneOfValues)[*numOneOfFields].numValuesAlloc +
                                                        ALLOCATE_INCREMENT )
*sizeof(char *)) ) ))
                                                goto Failure ;
                                        (*oneOfValues)[*numOneOfFields].numValuesAlloc+ =
ALLOCATE_INCREMENT;
                                }

(*oneOfValues)[*numOneOfFields].values[(*oneOfValues)[*numOneOfFields].numValues]
= UTL_STR_SAVE(choice);
```

```c
                    (*oneOfValues)[*numOneOfFields].numValues++ ;
                    end = choice + strlen(choice) + 1 ;
                    choice = strtok(NULL,",");
        }
                    (*numOneOfFields)++;
                    name = strtok(end," ");
    }
if (DebugLevel)
{
        for ( i = 0 ; i < *numOneOfFields ; i++ )
        {
                fprintf(stderr,"\n%s ", (*oneOfValues)[i].OneOfFieldName) ;
                for ( j = 0 ; j < (*oneOfValues)[i].numValues ; j++ )
                        fprintf(stderr,"\n     %s",(*oneOfValues)[i].values[j]);
        }
        fprintf(stderr,"\n");
} stat = 1 ;
    goto CleanUp ;

UnableToParse:
        fprintf(stderr,"Unable to parse -oneof %s\n",OneOfVar);
        stat = 0 ;
    goto CleanUp ;
Failure :
    stat = 0 ;
    goto CleanUp ;
CleanUp :
        if ( buffer )
                UTL_MEM_FREE(buffer);
    return stat ;
}
```

```
/*
**+E:
**
**
** Abstract    : Function parses a line from the input file and extracts
**               out any rangevar or oneof fields.
**
**
** Usage       :
**
** Returns     : Always returns 1 ;
**
** Algorithms  : None.
**
** Revision History :
**

**
**-E:
*/
int ReadLineAttributes(line,numRangeFields,rangeValues,rangeFields,numOneOfFields,
oneOfValues,oneOfFields)
char   *line ;
int    numRangeFields ;
float  **rangeValues;
struct RangeStruct *rangeFields;
int    numOneOfFields ;
int    **oneOfValues;
struct OneOfStruct *oneOfFields;
{
   int i ;
   int j ;
   char *cp ;
```

```
/*
** Now read in the salar selection fields if any.
*/
    if ( numRangeFields )
    {
        if ( !(*rangeValues = (float *)UTL_MEM_CALLOC(numRangeFields, sizeof(float)) ) )
            return 0 ;
    }
    if ( numOneOfFields )
    {
        if ( !(*oneOfValues = (int *)UTL_MEM_CALLOC(numOneOfFields, sizeof(int)) ) )
            return 0 ;
    }
    for ( i = 0 ; i < numRangeFields ; i++ )
    {
        if ( ( cp = strstr(line,rangeFields[i].RangeFieldName ) ) )
        {
/*
** Move past the logp= to get the value of this field, if the value is
** a ';' then it is a missing value.
*/
            cp = cp + strlen(rangeFields[i].RangeFieldName) + 1 ;
            if ( *cp == ';' )
                (*rangeValues)[i] = MISSING_FLOAT_VALUE ;
            else
                (*rangeValues)[i] = atof(cp);
        }
        else
        {
```

```
                    (*rangeValues)[i] = MISSING_FLOAT_VALUE ;
                }
            }
        }
/*
** Parse the -oneof field, we are looking for something looking like
** "supplier=Aldrich"
*/
        for ( i = 0 ; i < numOneOfFields ; i++ )
        {
            if ( ( cp = strstr(line,oneOfFields[i].OneOfFieldName ) ) )
            {
                cp = cp + strlen(oneOfFields[i].OneOfFieldName) + 1 ;
                if ( *cp == ';' )
                    (*oneOfValues)[i] = MISSING_INT_VALUE ;
                else
                {
                    for ( j = 0 ; j < OneOfValues[i].numValues ; j++ )
                    {
                        if ( UTL_STR_NCMP_NOCASE(cp,
                        oneOfFields[i].values[j],
                        strlen(oneOfFields[i].values[j])) == 0)
                        {
                            (*oneOfValues)[i] = j ;
                            break;
                        }
                    }
                    if ( j == oneOfFields[i].numValues )
                        (*oneOfValues)[i] = NOT_A_MATCH_VALUE ;
                }
            }
            else
                (*oneOfValues)[i] = MISSING_INT_VALUE ;
```

```
        }
}

/*
**+E:
**
**
** Abstract    : Function Checks to see if the given product passes the
**              user supplied filters.
**
**
** Usage       :
**
** Returns     : 1 if the product is not within range, 0 otherwise.
**
** Algorithms  : None.
**
** Revision History :
**

**
**-E:
*/
static int
NotWithinScalarRange(firstIndex,secondIndex,numRangeFields,rangeValues_Y01,rangeVal
ues_Y02,rangeFields,numOneOfFields,oneOfValues_Y01,oneOfValues_Y02,oneOfValues)
int firstIndex ;   /* Index into Y_01 data */
int secondIndex ;  /* Index into Y_02 data */
int numRangeFields ;
float **rangeValues_Y01 ;
float **rangeValues_Y02 ;
struct RangeStruct *rangeFields;
int   numOneOfFields   ;
```

```c
int    **oneOfValues_Y01 ;
int    **oneOfValues_Y02 ;
struct OneOfStruct *oneOfValues ;
{
int i ;
float total ;

/*
** First check the range values.
*/
        for ( i = 0 ; i < numRangeFields ; i++ )
        {
/*
** If one of the regions has a missing value, then we do not filter this
** product.
*/
                if ((( rangeValues_Y01[firstIndex][i] - MISSING_FLOAT_VALUE )
                        == SMALL_FLOAT ) ||
                    (( rangeValues_Y02[secondIndex][i] - MISSING_FLOAT_VALUE )
                        == SMALL_FLOAT ) )
                    return 0 ;

total=rangeValues_Y01[firstIndex][i] + rangeValues_Y02[secondIndex][i];
                if ((total > rangeFields[i].highValue ) ||
                    (total < rangeFields[i].lowValue ) )
                {
                    return 1 ;
                }
        }
        for ( i = 0 ; i < numOneOfFields ; i++ )
        {
/*
** If the value is missing then we dont mess with this guy.
```

```
*/
        if ( ( oneOfValues_Y01[firstIndex][i] == MISSING_INT_VALUE ) ||
            ( oneOfValues_Y02[secondIndex][i] == MISSING_INT_VALUE ) )
            return 0 ;
/*
** If any of the regions in the product does not match the selection
** criteria, then the product is rejected.
*/
        if ( ( oneOfValues_Y01[firstIndex][i] == NOT_A_MATCH_VALUE ) ||
            (oneOfValues_Y02[secondIndex][i] == NOT_A_MATCH_VALUE ) )
            return 1 ;
    } return 0 ;
} static int ParseArguments( argc, argv )
/*+I
*
* This function parses the command line arguments.
*
* Returns: 1 on a successful command line parse, 0 otherwise.
*
* Warnings:
*
* Errors:
*
* See Also:
*
*
*
*/
```

```
int     argc;
char    **argv;
{
        int     nargs,
                noptions = sizeof( Options )/sizeof(Options[0]);

OutputFile = stdout;

nargs = UTL_PARSE_OPT( argc, argv, noptions, Options );
        if( !nargs ) goto SyntaxError;

if (WhatFirst)
        { if (strstr(WhatFirst,"R1")) WhatFirst[0]='1';
          if (strstr(WhatFirst,"R2")) WhatFirst[0]='2';
        } else {
          WhatFirst=UTL_MEM_ALLOC(2); WhatFirst[0]='0';  } if ( RangeVar && !
ParseRangeVar(RangeVar,&NumRangeFieldsAllocated,&NumRangeFields,&RangeFields))
                goto SyntaxError ;
        if ( OneOfVar &&
!ParseOneOfVar(&OneOfVar,&NumOneOfFieldsAllocated,&NumOneOfFields,&OneOfVal
ues))
                goto SyntaxError ;

return 1;

SyntaxError:
        return 0;
} static int OpenOutputFile()
/*+I
```

```
 *
 * Returns: 1 on sucesss, else 0
 *
 */

{
    char    *msg;
    FILE    *fp;

OutputFile = stdout;
    if( OutputFileName )
    {
/*
** We need to create output files under the ownership of the REAL user not the
** EFFECTIVE user.  This only applies if setuid options are activated.
*/
{
struct stat statBuff ;
int    uid ;
int    euid ;

uid = getuid() ;
        euid = geteuid();
    stat(OutputFileName, &statBuff);
/*
** There are two cases
** (1) the file to output to exists
**     Use the ownership of the current owner of the file or if you cant do that
**     do not do anything.
** (2) The file is being created.
**     use the ownership of the REAL user.
*/
```

```
        if ( access(OutputFileName, F_OK) == 0 )
        { /* If the file exist and the real user is the owner of the file */
                if ( statBuff.st_uid == uid )
                        seteuid(uid);
        }
        else
        { /* Create the file as the REAL user */
                seteuid(uid);
        }
    }

OutputFile = fopen( OutputFileName, (AppendToOutputFile?"a":"wb"));

if( !OutputFile ) {
                fprintf(stderr,"Error: Failed to open output file \"%s\"\n",
                        OutputFileName );
                goto ErrorReturn;
        }
    } return 1;

ErrorReturn:
        return 0;
} static void CloseOutputFile()
/*+I
```

```
*
* This function closes the output file. It is included just for cleanliness.
*

*
*/

{
        fclose( OutputFile );
} int main( argc, argv )
/*+E
*
*/ int     argc;
char    **argv;
{ long            startTime,
                        totalTime,
                        finishTime;

int numFiltered = 0 ;

/***
*** Establish handler for a user interrupt.
***/
        signal( SIGINT, UserHitControlC);
#ifdef SIGHUP
```

```
        signal( SIGHUP, UserHitControlC);
#endif
        if( !ParseArguments( argc, argv ) )
            goto SyntaxError;

if( !OpenOutputFile() ) goto FailureExit;

/*      if (!RestartState()) goto FailureExit;   */ time( &startTime );
        Visual((stderr,"Begin reading files: %s",ctime(&startTime)));

/* Let's actually do something now */
        if (!ReadEverything())    goto FailureExit;
            time( &finishTime );

Visual((stderr,"Begin filtering: %s",ctime(&finishTime)));
#if 0
        DumpBitSet(Good_Products,nY_01,nY_02);
        DumpBitSet(Dead_Products,nY_01,nY_02);
#endif
        if (!FilterProducts(&numFiltered))
            goto FailureExit;
#if 0
        DumpBitSet(Dead_Products,nY_01,nY_02);
#endif
        time( &finishTime );

Visual((stderr,"Filtered out %d out of %d possible products\n",numFiltered, nY_02
* nY_01 ));
        Visual((stderr,"Begin selection: %s",ctime(&finishTime)));

if (!UserAborted && !SelectEverything()) goto FailureExit;
```

```
CloseOutputFile();

time( &finishTime );

totalTime = finishTime - startTime;
if( !totalTime ) totalTime = 1;

Visual((stderr, "Created %d Selections in ", nProcessed ));

Visual((stderr,"%d Hours, %d min, %d secs\n",
        totalTime/(60*60),
        (totalTime%(60*60))/60,
        (totalTime%60)));

Visual((stderr,"Each comparison required %.8f seconds to calculate\n",
        (totalTime/((double)(nProcessed?nProcessed:1)))));

Visual((stderr,"End Quick Select Computation: %s",ctime(&finishTime)));

UserAborted ? exit(ErrorExit) : exit(GoodExit);

SyntaxError:
        exit(1);

FailureExit:
        exit(ErrorExit);
} int ReadEverything()
{
char *hold;
```

```c
int i;

/* because failure here means end program run, no effort to clean up
   memory on error is included. */ if (!PrefixForFiles ) return 0;
if (!WarmUp())       return 0;

if (!(hold = UTL_STR_CONCATENATE(PrefixForFiles,".X1.pro"))) return 0;
if (! (InputSourceFile = fopen(hold,"r")))           return 0;
if (! (nY_01 = CountLines()))                        return 0;
if (! (Y_01 = (int **) UTL_MEM_ALLOC(sizeof(int *) * nY_01))) return 0;
if (!(cY_01 = (int *) UTL_MEM_ALLOC(sizeof(int ) * nY_01))) return 0;
if (!(iY_01 = (int *) UTL_MEM_ALLOC(sizeof(int ) * nY_01))) return 0;

if ( NumRangeFields )
{
  if(!(RangeValues_Y01 = (float **) UTL_MEM_ALLOC(sizeof(float *) * nY_01)))
      return 0;
}
if ( NumOneOfFields )
{
  if (!(OneOfValues_Y01 = (int **) UTL_MEM_ALLOC(sizeof(int *) * nY_01)))
      return 0;
} for (i=0;i<nY_01;i++)
{
  if (!GetNextLine( cY_01+i,Y_01+i, RangeValues_Y01 + i, OneOfValues_Y01 + i ))
        return 0;
}
fclose(InputSourceFile); UTL_MEM_FREE(hold);
```

```
if (!(hold = UTL_STR_CONCATENATE(PrefixForFiles,".X2.pro"))) return 0;
if (! (InputSourceFile = fopen(hold,"r")))           return 0;
if (! (nY_02 = CountLines()))                         return 0;
if (! (Y_02 = (int **) UTL_MEM_ALLOC(sizeof(int *) * nY_02))) return 0;
if (!(cY_02 = (int *) UTL_MEM_ALLOC(sizeof(int ) * nY_02))) return 0;
if (!(iY_02 = (int *) UTL_MEM_ALLOC(sizeof(int ) * nY_02))) return 0;

if ( NumRangeFields )
{
  if(!(RangeValues_Y02 = (float **) UTL_MEM_ALLOC(sizeof(float *) * nY_02)))
     return 0;
}
if ( NumOneOfFields )
{
  if (!(OneOfValues_Y02 = (int **) UTL_MEM_ALLOC(sizeof(int *) * nY_02)))
     return 0;
} for (i=0;i<nY_02;i++)
{
  if (! GetNextLine(cY_02+i,Y_02+i,RangeValues_Y02 + i, OneOfValues_Y02 + i ))
      return 0;
}
fclose(InputSourceFile); UTL_MEM_FREE(hold);

if (!Good_1) /* not reloaded */
{ i= (nY_01+31)/32 * 4;
   if (!(Good_1 = (int *) UTL_MEM_ALLOC(i))) return 0; memset( Good_1,0,i);
   if (!(Good_2 = (int *) UTL_MEM_ALLOC(i))) return 0; memset( Good_2,0,i);
   i= (nY_02+31)/32 * 4;
   if (!(Dead_1 = (int *) UTL_MEM_ALLOC(i))) return 0; memset( Dead_1,0,i);
   if (!(Dead_2 = (int *) UTL_MEM_ALLOC(i))) return 0; memset( Dead_2,0,i);
```

```
    i= (nY_01*nY_02+31)/32 * 4;
    if (!(Good_Products = (int *) UTL_MEM_ALLOC(i))) return 0;
            memset( Good_Products,0,i);
    if (!(Dead_Products = (int *) UTL_MEM_ALLOC(i))) return 0;
            memset( Dead_Products,0,i);
    SomeLeft = nY_01 * nY_02;
  }
return 1;
} int WarmUp()
{
 int i;
 for (i=0;i<256;i++) nbits[i] = (i&1) + (i&2)/2 + (i&4)/4 + (i&8)/8 +
            (i&16)/16 + (i&32)/32 + (i&64)/64 + (i&128)/128 ;
 for (i=0;i<8;i++) setbits[i] = ( 1 << i) & 255;

return 1;
} int CountLines()
{
 int i;
 char *foo;

i=0;
 while ( -1 != UTL_SCAN_GETS( InputSourceFile, "\\", "#", &foo)) i++;

rewind(InputSourceFile);
 return i;
} static int FilterProducts(numFiltered)
```

```
int *numFiltered ;
{
int numProducts ;
int i ;
int index1 ;
int index2 ;

*numFiltered = 0 ;

numProducts = nY_02 * nY_01 ;

for ( i = 0 ; i < numProducts ; i++ )
        {
                index1 = i / nY_02 ; /*Y_01 index */
                index2 = i % nY_02 ; /*Y_02 index */ if ( NotWithinScalarRange(index1,
                                index2,
                                NumRangeFields ,
                                RangeValues_Y01 ,
                                RangeValues_Y02 ,
                                RangeFields,
                                NumOneOfFields   ,
                                OneOfValues_Y01 ,
                                OneOfValues_Y02 ,
                                OneOfValues ))
                {
                        FlagProduct(Dead_Products,0,0,i);
                        SomeLeft--;
                        *numFiltered += 1 ;
if (DebugLevel)
    fprintf(stderr,"Filtered %d %d %d\n",i+1,index1+1,index2+1);
```

}

}
        return 1 ;
}

/*
**+I:
**
**
** Abstract    : Function will read the next line pointed to by global
**              InputSourceFile and parses out finger print and any other
**              scalar attributes we are filtering on.
**
**
** Usage       :
**
** Returns     : 1 on success, 0 for failure.
**
** Algorithms  : None.
**
** Revision History :
**

**
**-I:
*/
int GetNextLine( pCard, pFP, rangeValues, oneOfValues )
int    *pCard;      /*(OUT) returns the cardinality of the finger print */
int    **pFP;       /*(OUT) returns the finger print */
float **rangeValues;/*(OUT */
int    **oneOfValues;/*(OUT */
{

```c
char *line;

int words;

int i ;

int j ;

char *cp ;

if (-1 == UTL_SCAN_GETS( InputSourceFile, "\\", "#", &line)) return 0;

ReadLineAttributes(line,
                NumRangeFields,
                rangeValues,
                RangeFields,
                NumOneOfFields,
                oneOfValues,
                OneOfValues) ;

line = strstr(line,"fpcard=")+strlen("fpcard=");
if (! UTL_STR_EXTRACT_INT(line, pCard)) return 0;
line = strstr(line,"fp=")+strlen("fp=");
UTL_SCAN_TOKENIZE(line,';','\\');
UTL_SCAN_TOKENIZE(line,'>','\\');
words =    strlen(line)  / 8; /* must have 32 bit int multiple */
if (!WordsPerFingerprint)
  { BytesPerFingerPrint = words*4;
    query = (int   *) UTL_MEM_ALLOC( BytesPerFingerPrint);
    WordsPerFingerprint = words;}
if ( words != WordsPerFingerprint) return 0;
*pFP = (int *) UTL_MEM_ALLOC(words * sizeof(int));
for (words=0;words<WordsPerFingerprint;words++)
 {
    memcpy(next8,line,8);
    line += 8;
```

```
        sscanf(next8,"%8x", *pFP+words);
    }
    return 1;
} int IntersectQuery( pIntr, pFP)
int *pIntr, **pFP;
{
    unsigned char *ptr ,*qtr;
    int i, count;

ptr = (unsigned char *) *pFP;
    qtr = (unsigned char *) query;
    for(count=0, i=0; i<WordsPerFingerprint*4;i++)
        count += nbits[ *ptr++ & *qtr++];

*pIntr = count;
    return 1;
} int SelectEverything()
{
    int cqt, q_lo, q_hi, i, j, carhold, inthold, onion, intsc;
    double max;

while (nProcessed < NoMorehitsPlease && SomeLeft )
    {
    /*
    ** What we would like to do is first select any selections that were found
    ** in a previous run.
    */
            if ( !InputSource || !( c_query = SelectFromInputFile(query)) )
            {
```

344
```
            if (! (c_query =  SelectIt(query) ))        return 0;
        }
    nProcessed++;
    SomeLeft--;
5   /* then zap its neighbors and continue! */ for (i=0;i<nY_01;i++)
        if (! IntersectQuery( iY_01+i,Y_01+i ))    return 0;
    for (i=0;i<nY_02;i++)
10      if (! IntersectQuery( iY_02+i,Y_02+i ))    return 0;

cqt  = floor( (double) c_query / Tanimoto);
    q_lo = floor( (double) c_query * Tanimoto - (double) BitsInAbsentia);
    q_hi = ceil(  (double) ( c_query +BitsInAbsentia) / Tanimoto);

if ( DebugLevel )
15      DumpValues(nY_01,nY_02);

for(i=0;i<nY_01;i++)
    {
        if (cY_01[i] > cqt)        {            continue;} carhold = q_lo - cY_01[i];
20      inthold = q_lo - iY_01[i];
        for (j=0;j<nY_02;j++)
        {
            if (UserAborted) return 1;

25          if (cY_02[j] > cqt)        {            continue; }
            if (cY_02[j] < carhold)    {            continue; }
            if (inthold > iY_02[j])    {            continue; }
    /*
    ** Do not need to look at it, if it has already been used, eliminated.
```

```
*/
            if (TestBit(Dead_Products,i*nY_02+j)) continue;

ActuallyCompute( i, j, &onion, &intsc, &max);
            if (max >= Tanimoto)
            {
                    FlagProduct(Dead_Products, i,j, 0);
                    SomeLeft--;
if ( DebugLevel )
{
fprintf(stderr,"\nZapping %d %d",i+1,j+1);
DumpBitSet(Dead_Products,nY_01,nY_02);
}
            }
        } /* Y_02 loop */
    } /* Y_01 loop */

} /* while still stuff left */
   return 1;
} int TestBit(bitset, bit)
int *bitset, bit;
{
  int what, this;
  unsigned char *bytes;

bytes = (unsigned char *) bitset;

what = bit % 8;
  this = bit / 8;
  return (bytes[this] & setbits[what] );
}
```

```
int FlagProduct(TheProducts, index1,index2, this)
int *TheProducts;
int index1,index2, this;
{
int what;
unsigned char *Products;

/*      if (DebugLevel)
            printf("%d %d, %d, %x\n",index1,index2,this,TheProducts);*/
Products = (unsigned char *) TheProducts;

if (!this ) this = index1*nY_02 + index2;      /* bit index */
what = this % 8;
this /= 8;
Products[this] |= setbits[what];
return 1;
} int DumpBitSet(bitSet,numY01,numY02)
int *bitSet ;
int numY01 ;
int numY02 ;
{
int i , j ;
unsigned char *Products = (unsigned char *)bitSet ;
int   pos ;
int   byte ;
int   bit ;
int   index1 ;
int   index2 ;

fprintf(stderr,"\n----------------------------Y_02----------------------------\n
```

```
");
        for ( i = 0 ; i < nY_02 ; i++ )
            fprintf(stderr," %3d ",i+1);
    fprintf(stderr,"\n------------------------------------------------------------\n
");

for ( i = 0 ; i < (numY01 * numY02) ; i++ )
        {
            index1 = i / numY02 ;
            index2 = i % numY02 ;

byte = i / 8 ;
            bit  = i % 8 ;

if (( index2 == 0 ) )
                    fprintf(stderr,"\n%3d  |",index1+1);
            fprintf(stderr," %3d ",(Products[byte] & setbits[bit])?1:0 );
        }
        fprintf(stderr,"\n------------------------------------------------------------\n");

} int DumpValues(numY01,numY02)
int numY01 ;
int numY02 ;
{
int i , j ;
int   pos ;
int   byte ;
int   bit ;
int   index1 ;
int   index2 ;
int onion ;
```

```
int intsc ;
double max ;

fprintf(stderr,"\n---------------------------------Y_02--------------------------------\n
");
        for ( i = 0 ; i < nY_02 ; i++ )
                fprintf(stderr," %5d ",i+1);
        fprintf(stderr,"\n----------------------------------------------------------------------\n
");

for ( i = 0 ; i < (numY01 * numY02) ; i++ )
        {
                index1 = i / numY02 ;
                index2 = i % numY02 ;

ActuallyCompute( index1, index2, &onion, &intsc, &max);

if (( index2 == 0 ) )
                        fprintf(stderr,"\n%5d  |",index1+1);
                fprintf(stderr," %0.3f ",max);
        }
        fprintf(stderr,"\n----------------------------------------------------------------------\n");

} int FlagReagent(TheReagent, size, index)
int *TheReagent;
int size, index;
{
  int what, this;
  unsigned char *Reagent;

Reagent = (unsigned char *) TheReagent;
```

```
what = index % 8;
this = index / 8;
Reagent[this] |= setbits[what];
return 1;
} int SelectFromInputFile(query)
int *query ;
{
static int firstTime = 1 ;
static FILE *fp = (FILE *)NULL ;

unsigned char *p, *q ;
int index1;
int index2;
int index ;
char *line ;
char *cp ;
unsigned char *queryPtr ;

if ( firstTime )
    {
        if ( !(fp = fopen(InputSource,"r")))
            goto UnableToOpenFile ;
        firstTime = 0 ;
    } if (-1 == UTL_SCAN_GETS( fp, "", "", &line)) return 0;

if ( !( cp = strtok(line," ")) )
        goto UnableToParseLine ;
```

```c
    if ( !( cp = strtok(NULL," ")) )
            goto UnableToParseLine ;

index1 = atoi(cp) - 1 ;

if ( !( cp = strtok(NULL," ")) )
            goto UnableToParseLine ;
    index2 = atoi(cp) - 1 ;

if (( index1 < 0 ) || ( index2 < 0 ))
            goto UnableToParseLine ;
/*
** If we are reading back in a selection that might have already been filtered
** out we better adjust our counts.
*/
    if (TestBit(Dead_Products,index1*nY_02+index2))
            SomeLeft++;

p  = (unsigned char *) Y_01[index1];
    q  = (unsigned char *) Y_02[index2];

c_query = 0;
    queryPtr = (unsigned char *)query ;
    for (index=0;index<BytesPerFingerPrint;index++,queryPtr++)
    {
            *queryPtr = *p++ | *q++ ;
            c_query += nbits[*queryPtr & 255];
    }

OutputThisHit(index1,index2); /* both print it and note it in bitsets */ return c_query;
```

UnableToParseLine :

fprintf(stderr,"Unable to Parse %s\n",line);

return 0 ;

UnableToOpenFile :

fprintf(stderr,"Unable to open file %s\n",InputSource);

return 0 ;

}

/* Here the intent is to select the next compound "intelligently".

We try to maximize use of one or the other reagent.

*/ int SelectIt(query)

int *query;

{ int i,j;

if (What1 < 0) {GrabRandom( &i, &j, query); goto out; } switch (WhatFirst[0])

{ case '0':

GrabRandom( &i, &j, query);

break;

case '1':

GrabThis( &i, &j, 1, query);

break;

case '2':

GrabThis( &i, &j, 2, query);

break;

} out:

OutputThisHit(i,j); /* both print it and note it in bitsets */

```c
    return c_query;
} int GrabThis( p1, p2, type, fp)
int *p1, *p2, type, *fp;
{
  unsigned char *p, *q, *pro;
  int index;

switch (type)
  {
    case 1:
            if (!findOne(Dead_Products, What1*nY_02, 1, nY_02) &&
                !findOne(Dead_Products, What2 , nY_02, nY_01) &&
                !GrabRandom( p1, p2, fp)  )             return 0;
            break;
    case 2:
            if (!findOne(Dead_Products, What2 , nY_02, nY_01) &&
                !findOne(Dead_Products, What1*nY_02, 1, nY_02) &&
                !GrabRandom( p1, p2, fp)  )             return 0;
            break;
  }
  *p1 = What1; *p2 = What2;
  pro = (unsigned char *) fp;
  p   = (unsigned char *) Y_01[What1];
  q   = (unsigned char *) Y_02[What2];

c_query = 0;
  for (index=0;index<BytesPerFingerPrint;index++,pro++)
  {     *pro = *p++ | *q++ ;
        c_query += nbits[*pro & 255]; }
  return 1;
}
```

```c
/* This can be done more efficiently when we KNOW we are walking a vector */
int findOne(bitset,start,incr,max)
int *bitset, start, incr, max;
{
  int i;
  for (i=0;i<max;i++, start += incr )
  {
    if ( TestBit(bitset, start)) continue;
    What1 = start / nY_02;
    What2 = start % nY_02;
    return 1;
  }
  return 0;
} int GrabRandom( p1, p2, fp)
int *p1, *p2, *fp;
{
  int index, sum;
  int value1, value2;
  unsigned char *p, *q, *pro;

p = (unsigned char *) Dead_Products;
  index = UTL_MATH_RAND() * SomeLeft + 1;
  value1 = sum = 0;

while (sum < index)
   {sum += nbits[ ~(*p++) & 255];
    value1 += 8; } p -= 1; sum -= nbits[ ~(*p) &255 ]; value1 -= 9; value2 = (~(*p) & 255);
  while (sum < index)
```

```c
{value1++;
 if ( value2 & 1) sum++;
 value2 = value2 >> 1; } value2 = value1 % nY_02;
value1 /= nY_02 ;

*p1 = What1 = value1;
*p2 = What2 = value2;

pro = (unsigned char *) fp;
p   = (unsigned char *) Y_01[What1];
q   = (unsigned char *) Y_02[What2];

c_query = 0;
for (index=0;index<BytesPerFingerPrint;index++,pro++)
{      *pro = *p++ | *q++ ;
       c_query += nbits[*pro & 255]; }
  return 1;
} int ActuallyCompute( index1, index2, pUnion, pIntersection, pMaxTan)
int index1, index2, *pUnion, *pIntersection;
double *pMaxTan;
{
  int i, product;
  unsigned char *h1, *h2, *hquery;

/* if (DebugLevel)
     fprintf( stderr," ActuallyCompute at %d , %d\n", index1, index2);*/ h1 = (unsigned char *) Y_01[index1];
  h2 = (unsigned char *) Y_02[index2];
```

```
hquery = (unsigned char *) query;
*pUnion = *pIntersection = 0;
for( i=0; i<WordsPerFingerprint*4;i++)
  {
     product = *h1++ | *h2++ ;
     *pUnion       += nbits[ product | *hquery];
     *pIntersection += nbits[ product & *hquery++];
  }
/* if (DebugLevel > 9) fprintf(stderr,"%d / %d %6.3f\n",
                   *pIntersection, *pUnion,
                     (double) *pIntersection / *pUnion); */
return (*pMaxTan = (double) (*pIntersection + BitsInAbsentia) / (double) *pUnion);
} int OutputThisHit( index1, index2)
int index1, index2;
{
  int which;

which = index1*nY_02+index2;
  fprintf(OutputFile,"%s%d %d %d\n", PrefixForFiles, which+1,
                    index1+1 ,index2+1);
  FlagProduct(Good_Products,0,0, which);
  FlagProduct(Dead_Products,0,0, which);  /* can only be selected once */
     /* note use of reagents; this is slightly wasteful of time */
  FlagReagent(Good_1, nY_01, index1);
  FlagReagent(Good_2, nY_02, index2);

return 1;
}
```

Appendix "J"

```
/*********************************************************************
*/
/*                    dbcsln_qstop                                   */
/*********************************************************************
*/
/*+C
*
* This program evaluates topomeric shape similarity vs cSLNs
* based on preprocessing of the substituent reagents. Using this, it
* selects a diverse set of products while trying to maximize use of
* some groups. A key assumption: D^2(i,j) = Dr1^2(i,j) + Dr2^2(i,j)
* i.e. the distance between products from any one reaction is the
* root mean square distance of their corresponding reactants.
*
* To be added: restart capability and reagent blackout.
*
* The input files, one per X1, X2,         have one line per
* structure and contain the element "tp=zzz;" where
* the terminating ";" may also be ">".
* The hex value of fp is the condensed representation of a CoMFA grid
* value, 4 bits (one hex char) per grid, with interpretation as in
* routine WhatsTheDifference().
*
* The resultant file contains one line per hit, of the form
*    Y1 Y2 D D1 D2
* where Y1 = index of the substituent in X1.prT file
*       Y2 = index of the substituent in X2.prT file
*       D = apparent Tanimoto similarity
*    D1,D2 = R1, R2 distance
*
* dbcsln_stop     -prefix <name> -distance <real> -prefer <what> -append
```

```
*                   -maxhits <int> -output <name> +debug
*
* Options:
*
*    -prefix name      - name is the prefix for a set of 2 files
*                       with extensions .X1.prT .X2.prT
*                       ; files have fingerprints
*             (someday)  will reload from prefix.RELOAD if present
*
*    -distance dmin    - dmin is the closest allowed approach
*                       (default is 80)
*
*    -prefer           - one of R1,R2 else random. R1 maximizes use of R1
*
*    -maxhits max      - stop when max hits are found (default infinity)
*
*    -output filename  - specifies the output file for the hit info
*                       by default results are sent to stdout.
*
*    -append           - append results to an existing output file
*                       By default an output file is overwritten.
*
*    +debug            - writes irrelevant info to stderr
*
*    -#                This flag forces the display of all
*                      options
*

*********************************************************************
/
/* use 3db
 * dbcc dbcslnquickselect.c -o dbcslnquickselect   */
```

```c
#include <stdio.h>
include <signal.h>
#include <ctype.h>
#include <unistd.h>
#include <string.h>
#include <sys/stat.h>
#include <math.h>
#include "parseopt.h"
#include "utl_str.h"
#include "utl_mem.h"
#include "utl_file.h"
#include "utl_math.h"
#include "ct.h"
#include "ct_expr.h"
#include "ct_proto.h"
#include "import_proto.h"

#define GoodExit 0
#define ErrorExit 1
define Visual(s) {            fprintf s; } static FILE            *OutputFile;
static char            *OutputFileName;

static char            *WhatFirst;
static int             What1 = -1;
static int             What2;

static char            *PrefixForFiles;
static char            *InputSource = 0;
static FILE            *InputSourceFile;

/* Code presumes that an int is 32 bits, ASCII-ed into %.8x format */
```

```
static unsigned char    **Y_01;     /* fingerprints */
static unsigned char    **Y_02;     /*      "       */
static int              nY_01;      /* number of structures */
static int              nY_02;      /*      "               */
static double           *iY_01;     /* intersection count of fprints */
static double           *iY_02;     /*      "                        */ static int              *Good_1;
static int              *Good_2;
static int              *Dead_1;
static int              *Dead_2;
static int              *Good_Products;
static int              *Dead_Products;

static double           boundary[16];
static double           Dist[16][16];
static int              setbits[8];
static int              nbits[256];

static double           Distance = 80.0 ;
static int              AppendToOutputFile = 0;
static int              BytesPerFingerPrint[2] ;
static int              NoMorehitsPlease = 999999999;
static int              DebugLevel;
static int              UserAborted;

static int              nProcessed = 0;
static int              SomeLeft;
static char             next8[10] = "01\0";

static struct ParseOptions Options[] = {

/***
```

*** DO NOT MOVE ENTRIES IN THIS TABLE. ADD ENTRIES ONLY AT THE END.
***/

{"prefix",   ParseOptString,        &␣PrefixForFiles,
        "Prefix for all input files" }, {"distance", ParseOptDouble,   &␣Distance,
        "Topomer distance (typically 75 to 100)" }, {"maxhits", ParseOptInt,   &␣NoMorehitsPlease,
        "Maximum number of hits before stopping" }, {"input",   ParseOptString,   &␣InputSource,
        "File from which queries will be read( default stdin). "}, {"output",  ParseOptString,   &␣OutputFileName,
        "File to which hit info will be written. "}, {"prefer",  ParseOptString,   &␣WhatFirst,
        "One of R1, R2 to maximize us of."}, {"append",  ParseOptNoArg,   &␣AppendToOutputFile,
        "Use -append to append results to an existing file" }, {"debug",   ParseOptBoolean, &␣DebugLevel,
        "Use +debug to enable debugging messages" },

};

int UBS_OUTPUT_MESSAGE() { return 0; }   /* just for compiling OK */
int UIMS2_WRITE_PHOTO() { return 0; }
int lowercase (s) char *s; {while (*s) { if isupper(*s) *s = tolower(*s); s++;}}

```
static void UserHitControlC()
/*+I
*
* This function is the signal handler for user initiated program termination.
* It's only role is to set a flag indicating that the user wishes to abort the program.
*
*
*
*/

{
        UserAborted = 1;
} static int ParseArguments( argc, argv )
/*+I
*
* This function parses the command line arguments.
*
* Returns:  1 on a successful command line parse, 0 otherwise.
*
* Warnings:
*
* Errors:
*
* See Also:
*
*
```

```
 *
 */ int     argc;
char    **argv;
{
        int     nargs,
                noptions = sizeof( Options )/sizeof(Options[0]);

OutputFile = stdout;

nargs = UTL_PARSE_OPT( argc, argv, noptions, Options );
        if( !nargs ) goto SyntaxError;

if (WhatFirst)
        { if (strstr(WhatFirst,"R1")) WhatFirst[0]='1';
          if (strstr(WhatFirst,"R2")) WhatFirst[0]='2';
        } else {
          WhatFirst=UTL_MEM_ALLOC(2); WhatFirst[0]='0'; } return 1;

SyntaxError:
        return 0;
} static int OpenOutputFile()
/*+I
 *
 * Returns:  1 on sucesss, else 0
 *
 */
```

```
{
    char    *msg;
    FILE    *fp;

OutputFile = stdout;
    if( OutputFileName )
    {
/*
** We need to create output files under the ownership of the REAL user not the
** EFFECTIVE user.  This only applies if setuid options are activated.
*/
{
struct stat statBuff ;
int    uid ;
int    euid ;

uid = getuid() ;
    euid = geteuid();
    stat(OutputFileName, &statBuff);
/*
** There are two cases
** (1) the file to output to exists
**     Use the ownership of the current owner of the file or if you cant do that
**     do not do anything.
** (2) The file is being created.
**     use the ownership of the REAL user.
*/ if ( access(OutputFileName, F_OK) == 0 )
    { /* If the file exist and the real user is the owner of the file */
        if ( statBuff.st_uid == uid )
            seteuid(uid);
    }
```

```
        else
        { /* Create the file as the REAL user */
                seteuid(uid);
        }
    }

OutputFile = fopen( OutputFileName, (AppendToOutputFile?"a":"wb"));

if( !OutputFile ) {
                fprintf(stderr,"Error: Failed to open output file \"%s\"\n",
                        OutputFileName );
                goto ErrorReturn;
        }
    } return 1;

ErrorReturn:
        return 0;
}
```

```
static void CloseOutputFile()
/*+I
*
* This function closes the output file. It is included just for cleanliness.
*

*
```

```
*/

{
    fclose( OutputFile );
} int main( argc, argv )
/*+E
 *
 */ int     argc;
char    **argv;
{ long            startTime,
                        totalTime,
                        finishTime;

/***
 *** Establish handler for a user interrupt.
 ***/
    signal( SIGINT, UserHitControlC);
#ifdef SIGHUP
    signal( SIGHUP, UserHitControlC);
#endif
    if( !ParseArguments( argc, argv ) )
        goto SyntaxError;

if( !OpenOutputFile() ) goto FailureExit;
```

```
/*      if (!RestartState()) goto FailureExit; */ time( &startTime );
        Visual((stderr,"Begin reading files: %s",ctime(&startTime)));

/* Let's actually do something now */
        if (!ReadEverything())    goto FailureExit;
            time( &finishTime );
            Visual((stderr,"Begin selection: %s",ctime(&finishTime)));

if (!UserAborted && !SelectEverything()) goto FailureExit;

CloseOutputFile();

time( &finishTime );

totalTime = finishTime - startTime;
        if( !totalTime ) totalTime = 1;

Visual((stderr, "Created %d Selections in ", nProcessed ));

Visual((stderr,"%d Hours, %d min, %d secs\n",
                totalTime/(60*60),
                (totalTime%(60*60))/60,
                (totalTime%60)));

Visual((stderr,"Each comparison required %.8f seconds to calculate\n",
                (totalTime/((double)(nProcessed?nProcessed:1)))));

Visual((stderr,"End Quick Select Computation: %s",ctime(&finishTime)));
```

UserAborted ? exit(ErrorExit) : exit(GoodExit);

SyntaxError:
    exit(1);

FailureExit:
    exit(ErrorExit);
} int ReadEverything()
{
char *hold;
int i;

/* because failure here means end program run, no effort to clean up
   memory on error is included. */ if (!PrefixForFiles ) return 0;
if (!WhatsTheDifference())      return 0;

if (!(hold = UTL_STR_CONCATENATE(PrefixForFiles,".X1.prT"))) return 0;
if (! (InputSourceFile = fopen(hold,"r")))        return 0;
if (! (nY_01 = CountLines()))        return 0;
if (! (Y_01 = (unsigned char **)
        UTL_MEM_ALLOC(sizeof(unsigned char *)*nY_01))) return 0;
if (!(iY_01 = (double *) UTL_MEM_ALLOC(sizeof(double ) * nY_01))) return 0;
for (i=0;i<nY_01;i++)
    if (! GetNextLine( Y_01+i, 0 ))     return 0;

fclose(InputSourceFile); UTL_MEM_FREE(hold);

if (!(hold = UTL_STR_CONCATENATE(PrefixForFiles,".X2.prT"))) return 0;
if (! (InputSourceFile = fopen(hold,"r")))        return 0;

```
if (! (nY_02 = CountLines()))                        return 0;
if (! (Y_02 = (unsigned char **)
        UTL_MEM_ALLOC(sizeof(unsigned char *) * nY_02))) return 0;
if (!(iY_02 = (double *) UTL_MEM_ALLOC(sizeof(double ) * nY_02))) return 0;
for (i=0;i<nY_02;i++)
  if (! GetNextLine( Y_02+i ,1))    return 0;

fclose(InputSourceFile); UTL_MEM_FREE(hold);

if (!Good_1) /* not reloaded */
{  i= (nY_01+31)/32 * 4;
   if (!(Good_1 = (int *) UTL_MEM_ALLOC(i))) return 0; memset( Good_1,0,i);
   if (!(Good_2 = (int *) UTL_MEM_ALLOC(i))) return 0; memset( Good_2,0,i);
   i= (nY_02+31)/32 * 4;
   if (!(Dead_1 = (int *) UTL_MEM_ALLOC(i))) return 0; memset( Dead_1,0,i);
   if (!(Dead_2 = (int *) UTL_MEM_ALLOC(i))) return 0; memset( Dead_2,0,i);
   i= (nY_01*nY_02+31)/32 * 4;
   if (!(Good_Products = (int *) UTL_MEM_ALLOC(i))) return 0;
            memset( Good_Products,0,i);
   if (!(Dead_Products = (int *) UTL_MEM_ALLOC(i))) return 0;
            memset( Dead_Products,0,i);
   SomeLeft = nY_01 * nY_02;
}
return 1;
} int WhatsTheDifference()
{
int i, j;

define pow2(a) ( (a) * (a) )

/* the assignment of codes is based on the following (from gen_pls.c):
```

```
    static fpt cutoff[16] = {9999.,  0.,   2.,   4.,   6.,   8.,  10.,  12.,
                              14.,  16.,  18.,  20.,  22.,  24.,  26.,  30. };
*/
boundary[0] = 9999.;  /* missing data ought never to occur. */
boundary[1] = -0.1 ;

for (i=2;i< 15;i++)
  boundary[i] = 2*i-3;
boundary[15] = 30.0;  /* this is a steep curve with a cutoff at 30! */
for (i=0;i<16;i++) for (j=0;j<16;j++)
  Dist[i][j] = pow2( boundary[i] - boundary[j]);

for (i=0;i<256;i++) nbits[i] = (i&1) + (i&2)/2 + (i&4)/4 + (i&8)/8 +
                (i&16)/16 + (i&32)/32 + (i&64)/64 + (i&128)/128 ;
for (i=0;i<8;i++) setbits[i] = ( 1 << i) & 255;

Distance *= Distance;  /* want to test D^2 directly */ return 1;
} int CountLines()
{
int i;
char *foo;

i=0;
while ( -1 != UTL_SCAN_GETS( InputSourceFile, "\\", "#", &foo)) i++;

rewind(InputSourceFile);
return i;
}
```

```
int GetNextLine( pFP, index)
unsigned char **pFP;
int index;
{
char *line;
int words, hold;

if (-1 == UTL_SCAN_GETS( InputSourceFile, "\\", "#", &line)) return 0;
line = strstr(line,"tp=")+strlen("tp=");
UTL_SCAN_TOKENIZE(line,';','\\');
UTL_SCAN_TOKENIZE(line,'>','\\');
words =    strlen(line)   / 2; /* must have 8 bit bytes */
if (!BytesPerFingerPrint[index])
  { BytesPerFingerPrint[index] = words;

}
if ( words != BytesPerFingerPrint[index]) return 0;
*pFP = (unsigned char *) UTL_MEM_ALLOC(words);
for (words=0;words<BytesPerFingerPrint[index];words++)
{
   memcpy(next8,line,2);
   line += 2;
   sscanf(next8,"%2x", &hold);
   *(*pFP+words) = (unsigned char *) hold;
} return 1;
} int IntersectQuery( pIntr, pFP, query, index)
double *pIntr;
unsigned char **pFP, **query;
int index;
```

```
{
    unsigned char *ptr ,*qtr;
    int i;
    double count;

ptr = (unsigned char *) *pFP;
    qtr = (unsigned char *) *query;
    for(count=0.0, i=0; i<BytesPerFingerPrint[index];i++, ptr++, qtr++)
        count += Dist[ *ptr & 0x0F    ][ *qtr & 0x0F    ]
               + Dist[ (*ptr & 0xF0) >> 4][ (*qtr & 0xF0) >> 4] ;

*pIntr = count;
    return 1;
} int SelectEverything()
{
    int cqt, q_lo, q_hi, i, j, carhold, inthold, onion, intsc;
    double max;

while (nProcessed < NoMorehitsPlease && SomeLeft )
    {
        if (! SelectIt() )         return 0;
        nProcessed++;
        SomeLeft--;
        /* then zap its neighbors and continue! */ for (i=0;i<nY_01;i++)
            if (! IntersectQuery( iY_01+i,Y_01+i, Y_01 + What1,0 ))    return 0;
        for (i=0;i<nY_02;i++)
            if (! IntersectQuery( iY_02+i,Y_02+i, Y_02 + What2,1 ))    return 0;

for(i=0;i<nY_01;i++)
```

```
   {
     if (iY_01[i] > Distance)      {                continue;} for (j=0;j<nY_02;j++)
       {
         if (UserAborted) return 1;

if (iY_02[j] > Distance)   {                continue; }
         if ( iY_01[i] + iY_02[j] <= Distance &&
             ! TestBit(Dead_Products,i*nY_02+j)          )
         {
             FlagProduct(Dead_Products, i,j, 0);
             SomeLeft--;
         }
       } /* Y_02 loop */
   } /* Y_01 loop */

} /* while still stuff  left */
 return 1;
} int TestBit(bitset, bit)
int *bitset, bit;
{
  int what, this;
  unsigned char *bytes;

bytes = (unsigned char *) bitset;

what = bit % 8;
  this = bit / 8;
  return (bytes[this] & setbits[what] );
}
```

```
int FlagProduct(TheProducts, index1,index2, this)
int *TheProducts;
int index1,index2, this;
{
  int what;
  unsigned char *Products;

/*    if (DebugLevel)
          printf("%d %d, %d, %x\n",index1,index2,this,TheProducts);*/
  Products = (unsigned char *) TheProducts;

if (!this ) this = index1*nY_02 + index2;      /* bit index */
  what = this % 8;
  this /= 8;
  Products[this] |= setbits[what];
  return 1;
} int FlagReagent(TheReagent, size, index)
int *TheReagent;
int size, index;
{
  int what, this;
  unsigned char *Reagent;

Reagent = (unsigned char *) TheReagent;

what = index % 8;
  this = index / 8;
  Reagent[this] |= setbits[what];
  return 1;
}
```

```
/* Here the intent is to select the next compound "intelligently".
   We try to maximize use of one or the other reagent.
*/
int SelectIt()
{
  int i,j;

if (What1 < 0) {GrabRandom( &i, &j); goto out; } switch (WhatFirst[0])
  {
    case '0':
            GrabRandom( &i, &j);
            break;
    case '1':
            GrabThis( &i, &j, 1);
            break;
    case '2':
            GrabThis( &i, &j, 2);
            break;
  } out:
  OutputThisHit(i,j); /* both print it and note it in bitsets */ return 1;
} int GrabThis( p1, p2, type)
int *p1, *p2, type;
{
  unsigned char *p, *q, *pro;
  int index;
```

```
switch (type)
{
  case 1:
          if (!findOne(Dead_Products, What1*nY_02, 1, nY_02) &&
              !findOne(Dead_Products, What2  , nY_02, nY_01) &&
              !GrabRandom( p1, p2)   )              return 0;
          break;
  case 2:
          if (!findOne(Dead_Products, What2  , nY_02, nY_01) &&
              !findOne(Dead_Products, What1*nY_02, 1, nY_02) &&
              !GrabRandom( p1, p2)   )              return 0;
          break;
}
*p1 = What1;
*p2 = What2;

return 1;
} if 0
/* This can be done more efficiently when we KNOW we are walking a vector */
int findOne(bitset,start,incr,max)
int *bitset, start, incr, max;
{
  int i;
  for (i=0;i<max;i++, start += incr )
  {
    if ( TestBit(bitset, start)) continue;
    What1 = start / nY_02;
    What2 = start % nY_02;
    return 1;
  }
  return 0;
```

```
}
else
int findOne(bitset,start,incr,max)
int *bitset, start, incr, max;
{
  static int oldstart = -1234,
              oldincr,
              old_i;
  int i;

if ( (start != oldstart) || (incr != oldincr) ) old_i = -1 ;
  oldstart = start; oldincr = incr;
  old_i ++;
  start += incr * old_i;
  for (i=old_i;i<max;i++, start += incr )
  {
    if ( TestBit(bitset, start)) continue;
    What1 = start / nY_02;
    What2 = start % nY_02;
    old_i = i;
    return 1;
  }
  oldstart = -1234;
  return 0;
}
endif int GrabRandom( p1, p2, fp)
int *p1, *p2, *fp;
{
  int index, sum;
  int value1, value2;
  unsigned char *p, *q, *pro;
```

```
p = (unsigned char *) Dead_Products;
index = UTL_MATH_RAND() * SomeLeft + 1;
value1 = sum = 0;

while (sum < index)
 {sum += nbits[ ~(*p++) & 255];
  value1 += 8; } p -= 1; sum -= nbits[ ~(*p) &255 ]; value1 -= 9; value2 = (~(*p) & 255);
while (sum < index)
 {value1++;
  if ( value2 & 1) sum++;
  value2 = value2 >> 1; } value2 = value1 % nY_02;
value1 /= nY_02 ;

*p1 = What1 = value1;
*p2 = What2 = value2;

return 1;
} int OutputThisHit( index1, index2)
int index1, index2;
{
 int which;

which = index1*nY_02+index2;
 fprintf(OutputFile,"%s%d %d %d\n", PrefixForFiles, which+1,
                  index1+1 ,index2+1);
 FlagProduct(Good_Products,0,0, which);
 FlagProduct(Dead_Products,0,0, which);  /* can only be selected once */
```

```
/* note use of reagents; this is slightly wasteful of time */
FlagReagent(Good_1, nY_01, index1);
FlagReagent(Good_2, nY_02, index2);

if (DebugLevel) printf("Selection %d is %d , %d\n",
                nProcessed+1,index1+1 ,index2+1);

return 1;
}
```

Appendix "K"

```
/*********************************************************************
*/
/*                    dbcsln_design                              */
/*********************************************************************
*/
/*+C
*
* This program evaluates (approximate) Topomer+Tanimoto similarity vs cSLNs
* based on preprocessing of the substituent reagents. Using this, it
* selects a diverse set of products while trying to maximize use of
* some groups. Diversity is achieved by zapping all neighbors after each
* new selection, so that any non-zapped product can freely be selected.
*
* To be added: restart capability and reagent blackout.
*            (i.e. to recomplete an earlier design and/or to remove
*                 all occurences of Y_01= 37 and so on when they
*                 prove to be unavailable or otherwise unsuitable).
* Limitations: currently exactly 2 R groups are assumed. Need to extend
*              to more than 2 and to handle X groups.
*
*
* The resultant file contains one line per hit, of the form
*   Y1 Y2
* where Y1 = index of the substituent in X1.pro file
*       Y2 = index of the substituent in X2.pro file
*
*
* Options:   Look at the array Options below.
*                                                                    *

**********************************************************************
```

```c
/
#include <stdio.h>
include <signal.h>
#include <ctype.h>
#include <unistd.h>
#include <string.h>
#include <sys/stat.h>
#include <math.h>
#include "parseopt.h"
#include "utl_str.h"
#include "utl_mem.h"
#include "utl_file.h"
#include "utl_math.h"
#include "ct.h"
#include "ct_expr.h"
#include "ct_proto.h"
#include "import_proto.h"
#include "io_fprint.h"
#include "commonData.h" /* Globals use by most functions, we will clean this
                          up soon */
#include "dbcsln_bs_proto.h"
#include "dbcsln_hlm_proto.h"
#define OBSOLETE_IS_OK 1
FILE *debugFile = (FILE *) NULL ;

#ifdef OBSOLETE_IS_OK
/* these sections retain the filtering capabilities now also present
   in db_filter.c -- at some point they should exist ONLY in db_filter.
*/
static struct RangeInfoStruct  RangeValuesData ;
static struct OneOfInfoStruct  OneOfValuesData ;
static struct InputInfoStruct  InputData ;
static int         NumRangeFields ;
```

```c
static int        NumRangeFieldsAllocated ;
static RangeStruct *RangeFields ;
static int        NumOneOfFieldsAllocated ;
static int        NumOneOfFields ;
static OneOfStruct *OneOfValues ;
static float **RangeValues_Y01 ; /* Actual values read in from  nnn.X1 file,
            If MW is the first and logp is the second value
            specified on the -rangevar argument list then
            RangeValues_Y01[n][0] would keep the value for MW
            for the nth line in the nnn.X1 file and
            RangeValues_Y01[n][1] would keep the value for
            logp for that line*/
static float **RangeValues_Y02 ; /* same */
static int   **OneOfValues_Y01 ; /*Actual values read from nnn.X1 files but translated
            into an index of OneOfValues[i].values so
            we dont have to waist memory and time doing strcmp*/
static int   **OneOfValues_Y02 ; /* Same */
endif static char *MasterFile ;
static char *MasterFileList ;
static char *BitsetFileList ;
static char *MasterRecord ;
static FILE           *MasterFile_File;
static char           *FngrFile;
static int            FingerCore_Card;
static int            *FingerCore_FP;

static char *RangeVar ;
static char *OneOfVar ;
static double    Tanimoto = 0.85;

static int       WordsPerFingerprint = 0;
```

```
static int          BytesPerFingerPrint = 0;
static int          NoMorehitsPlease = 999999999;
static int          DebugLevel;
static int          UserAborted;
static char         *OutputFileName;
static char         *CheckPointFileName;
static char         *WhatFirst;
static char         *InputSource = 0;
static char         *BitsetSource = 0;
static char         *DatabaseNames = (char *)0 ;
static char         *HitlistNames  = (char *)0 ;
static int          BitOffsets[MAX_INPUT_CSLNS];  /* why recompute? */
int TotalProducts ;
static int          Pro_size;
static struct ParseOptions Options[] = {
/***
*** DO NOT MOVE ENTRIES IN THIS TABLE.  ADD ENTRIES ONLY AT THE END.
***/
    {"master",     ParseOptString,      &MasterFile,
        "Name is the file with master file records" },
    {"masterlist", ParseOptString,      &MasterFileList,
        "Name of the file containing master input/result file names" },
    {"bitsetlist", ParseOptString,      &BitsetFileList,
        "Name of the file containing bitset input/result file names" },
    {"index",      ParseOptString,      &MasterRecord,
        "Which MasterRecord or Bitset entry 1-n" },
    {"Tanimoto",   ParseOptDouble,      &Tanimoto,
        "Similarity threshold (0.0 to 1.0)" },
    {"distance",   ParseOptDouble,      &Distance,
        "Topomer distance (typically 75 to 100)" },
    {"maxhits",    ParseOptInt,         &NoMorehitsPlease,
        "Maximum number of hits before stopping" },
```

```
    {"bitset",     ParseOptString,     &BitsetSource,
        "Bitset file to start from"},
    {"output",     ParseOptString,     &OutputFileName,
        "File to which hit info will be written. "},
    {"checkpoint", ParseOptString,     &CheckPointFileName,
        "File to which bitset info will be written. "},
    {"prefer",     ParseOptString,     &WhatFirst,
        "One of R1, R2 to maximize us of."},
    {"debug",      ParseOptBoolean,    &DebugLevel,
        "Use +debug to enable debugging messages" },
ifdef OBSOLETE_IS_OK
    {"rangevar",   ParseOptString,     &RangeVar,
        "Scalar field name and range to filter out, i.e. logp -1.0 8.0 MW 200 500 price 0 12.50" },
    {"oneof",      ParseOptString,     &OneOfVar,
        "Field name and list of values that the product should match\n, i.e. supplier Aldrich,Sigma,Fluka,SALOR taste SWEET,Salty" },
endif
    {"database",   ParseOptString,     &DatabaseNames,
        "Unity database to use to exclude possible products" },
    {"hitlist",    ParseOptString,     &HitlistNames,
        "Unity hitlist to use to exclude possible products" },
};

static int WarmUp()
{
int i;
for (i=0;i<65536;i++) BigBits[i] = (i&1) + (i&2)/2 + (i&4)/4 + (i&8)/8 +
            (i&16)/16 + (i&32)/32 + (i&64)/64 + (i&128)/128
        + (i&256)/256 +(i&512)/512 +(i&1024)/1024
        + (i&2048)/2048
        + (i&4096)/4096 + (i&8192)/8192 + (i&16384)/16384
```

+ (i&32768)/32768 ;

setbits_nbits_Init();

return 1;

} static int WhatsTheDifference()

{ int i, j;

define pow2(a) ( (a) * (a) )

/* the assignment of codes is based on the following (from gen_pls.c):

static fpt cutoff[16] = {9999., 0., 2., 4., 6., 8., 10., 12.,

14., 16., 18., 20., 22., 24., 26., 30. };

*/ boundary[0] = 9999.; /* missing data ought never to occur. */ boundary[1] = -0.1 ;

for (i=2;i< 15;i++)

boundary[i] = 2*i-3;

boundary[15] = 30.0; /* this is a steep curve with a cutoff at 30! */ for (i=0;i<16;i++) for (j=0;j<16;j++)

Dist[i][j] = pow2( boundary[i] - boundary[j]);

Distance *= Distance; /* want to test D^2 directly */ return 1;

} static int CalcualteProductFingurePrint(product,firstPart,secondPart)

int *product ;

int *firstPart ;

int *secondPart ;

{ int index ;

int totalBitsSet = 0 ;

unsigned char *prod , *y01, *y02 ;

prod = ( unsigned char *)product ;

y01 = ( unsigned char *)firstPart ;

```
        y02 = ( unsigned char *)secondPart ;
        for (index=0;index<BytesPerFingerPrint;index++,prod++)
        {
                *prod = *y01++ | *y02++ ;
                totalBitsSet += nbits[*prod & 255];
        }
        return totalBitsSet ;
} static int IntersectQuery( pIntr, pFP, pXntr, pXP, xuery, index)
int *pIntr, **pFP;
double *pXntr;
unsigned char **pXP, **xuery;
int index;
{
 unsigned char *ptr ,*qtr;
 int i, count;
 double xount;
        if ( !(*pFP) || !(*pXP) )
                return 1 ;
 ptr = (unsigned char *) *pFP;
 qtr = (unsigned char *) query;
 for(count=0, i=0; i<WordsPerFingerprint*4;i++)
    count += nbits[ *ptr++ & *qtr++];
 *pIntr = count;
 if ( xuery )
 {
 ptr = (unsigned char *) *pXP;
 qtr = (unsigned char *) *xuery;
 for(xount=0.0, i=0; i<XytesPerFingerPrint[index];i++, ptr++, qtr++)
      xount += Dist[ *ptr & 0x0F    ][ *qtr & 0x0F    ]
           + Dist[ (*ptr & 0xF0) >> 4][ (*qtr & 0xF0) >> 4] ;
 *pXntr = xount;
```

```
}
    return 1;
}
static int ActuallyCompute( index1, index2, pUnion, pIntersection, pMaxTan,currentInput)
int index1, index2, *pUnion, *pIntersection;
double *pMaxTan;
{
  int i;
  unsigned short *h1, *h2, *hquery, product;
  int numberOfMissingBits ;
  if ( currentInput == -1 )
        numberOfMissingBits = NumMissingBits[0] ;
  else
        numberOfMissingBits = NumMissingBits[currentInput] ;

h1 = (unsigned short *) Y_01[index1];
  h2 = (unsigned short *) Y_02[index2];
  hquery = (unsigned short *) query;
  *pUnion = *pIntersection = 0;
  for( i=0; i<WordsPerFingerprint*2 ;i++,h1++,h2++,hquery++)
    {
/*     product = (*h1 | *h2) ;*/
        *pUnion       += BigBits[ (*h1 | *h2) | *hquery];
        *pIntersection += BigBits[ (*h1 | *h2) & *hquery];
    }
  *pMaxTan = (double) (*pIntersection + numberOfMissingBits )/ (double) *pUnion;
  return 1;
} static int
ZapAllNeighbors(thisQuery,thisC_Query,numZapped,doCTOPS,index1,index2,currentInput
)
int *thisQuery ;
```

```
int thisC_Query ;

int *numZapped ;

int doCTOPS ;

int currentInput ;

{
  int cqt, q_lo, q_hi, i, j, carhold, inthold, onion, intsc;
    double max;
int k ;
int Y_01_Offset, Y_02_Offset ;
  int pos ;
int numberOfMissingBits ;

if ( currentInput == -1 )
            numberOfMissingBits = NumMissingBits[0] ;
      else
            numberOfMissingBits = NumMissingBits[currentInput] ;
  if ( thisQuery )
  {
            memcpy(query,thisQuery,BytesPerFingerPrint) ;
            c_query = thisC_Query ;
  }
  *numZapped = 0 ;
      Y_01_Offset = Y_02_Offset = 0 ;
      for ( k = 0 ; k < CurrentInput ; k++ )
      {
            Y_01_Offset += Y_01_Length[k];
            Y_02_Offset += Y_02_Length[k];
      }
  for (i=0;i<nY_01;i++)
    if (! IntersectQuery( iY_01+i,
                                          Y_01+i,
                                          iX_01+i,
                                          X_01+i,
```

```
                                                  (doCTOPS)?X_01 + index1 + Y_01_Offset :
NULL ,
                                                  0 ))
        return 0;
    for (i=0;i<nY_02;i++)
      if (! IntersectQuery( iY_02+i,
                                                  Y_02+i,
                                                  iX_02+i,
                                                  X_02+i,
                                                  (doCTOPS)?X_02 + index2 + Y_02_Offset
: NULL ,
                                                  1 ))
        return 0;
    /* now zap topomer neighbors */
/*
** Only do topomer neighbors if CTOPS was present in the input.
*/
        if ( doCTOPS )
        {
        Y_01_Offset = Y_02_Offset = 0 ;
        for ( k = 0 ; k < TotalInputs ; k++ )
        {
                for(i= 0 ;i< Y_01_Length[k];i++)
                {
                    if (iX_01[ i + Y_01_Offset ] > Distance)
                        continue;
                    for (j=0 ;j< Y_02_Length[k];j++)
                    {
                        if (UserAborted)
                            return 1;
                        if (iX_02[j+Y_02_Offset] > Distance)
                            continue;
                        if (iX_01[i+Y_01_Offset] + iX_02[j+Y_02_Offset] <=
```

```
                            Distance &&
                                    !TestBit(Dead_Products,
                                            BitMapStartPoint[k] + i
*Y_02_Length[k] +j) )
                                    {
if (DebugLevel == 69)
   printf("Distance kill %d %d - %f , %f + %f\n",
        i+1,j+1, iX_01[i] + iX_02[j], iX_01[i] , iX_02[j]);
                                    pos = BitMapStartPoint[k] + i *Y_02_Length[k] +j ;
                                    FlagProduct(Dead_Products, 0,0, pos );
         SomeLeft--;
                                    RemainingInput[k]-- ;
                                    (*numZapped)++;
                                    }
                            } /* Y_02 loop */
                        } /* Y_01 loop */
                        Y_01_Offset += Y_01_Length[k] ;
                        Y_02_Offset += Y_02_Length[k] ;
        }
    }
    cqt = floor( (double) c_query / Tanimoto);
    q_lo = floor( (double) c_query * Tanimoto - (double) numberOfMissingBits );
    q_hi = ceil( (double) ( c_query + numberOfMissingBits )/ Tanimoto);
        inTestBit = inActually = 0;
        Y_01_Offset = Y_02_Offset = 0 ;
/*
** Run thru all the input files, one at a time.
*/
        for ( k = 0 ; k < TotalInputs ; k++ )
        {
    for(i= 0 ;i< Y_01_Length[k];i++)
    {
       if (cY_01[i+Y_01_Offset] > cqt)            {                        continue;}
```

```
            carhold = q_lo - cY_01[i+Y_01_Offset];
            inthold = q_lo - iY_01[i+Y_01_Offset];
            for (j=0 ;j< Y_02_Length[k];j++)
            {
                if (UserAborted) return 1;

if (cY_02[j+Y_02_Offset] > cqt)          {           continue; }
                if (cY_02[j+Y_02_Offset] < carhold)      {           continue; }
                if (inthold > iY_02[j+Y_02_Offset])      {           continue; }
#ifdef Waste_time
                time( &waste_time );
#endif
                if (TestBit(Dead_Products,BitMapStartPoint[k] + i *Y_02_Length[k] +j))
                    continue;
#ifdef Waste_time
                inTestBit += time( &trash_time ) - waste_time;
#endif
                ActuallyCompute( Y_01_Offset + i, Y_02_Offset + j, &onion, &intsc, &max,k);
#ifdef Waste_time
                inActually += time( &waste_time )- trash_time;
#endif
                if (max >= Tanimoto)
                {
if (DebugLevel == 69)
    printf("Tanimoto kill %d %d - %6.3f , %d + %d, %d + %d\n",
        i+1,j+1, max, cY_01[i],cY_02[j], iY_01[i],iY_02[j]);
                    pos = BitMapStartPoint[k] + i *Y_02_Length[k] +j ;
                        FlagProduct(Dead_Products, 0,0, pos );
                        SomeLeft--;
                    RemainingInput[k]-- ;
                        (*numZapped)++;
if ( DebugLevel )
    fprintf(stderr,"\nZapping %d %d %d",k+1,i+1,j+1);
```

```
            }
        } /* Y_02 loop */
    } /* Y_01 loop */
        Y_01_Offset += Y_01_Length[k] ;
        Y_02_Offset += Y_02_Length[k] ;
    } /* Number of Inputfile loop */
#ifdef Waste_time
        Visual((stderr,"ActuallyCompute : %d",inActually));
        Visual((stderr," TestBit      : %d",inTestBit ));
endif if ( DebugLevel )
{
int fred ;
for ( fred = 0 ; fred < TotalInputs ; fred++ )
        DumpValues(fred,Y_01_Length[fred],Y_02_Length[fred],ActuallyCompute);
}
}

/*
**+I:
**
**
** Abstract    : Function zapps products who are missing CTOPS or FP fields.
**
**
**
** Usage       :
**
** Returns     : 1 if the data value is missing or zero if the values exist.
**
** Algorithms  : None.
**
```

```
** Revision History :
**
** Author              Date        Description
** ==================  ==========
==================
** Fred Soltanshahi    05/21/96    Original version.
**
**-I:
*/
static int IsItMissingAValue(index1,index2,currentInput)
int index1 ;
int index2 ;
{
int Y_01_Offset = 0 ;
int Y_02_Offset = 0 ;
int k ;
     for ( k = 0 ; k < currentInput ; k++ )
     {
          Y_01_Offset += Y_01_Length[k] ;
          Y_02_Offset += Y_02_Length[k] ;
     }
     if ( ( Y_01[index1+Y_01_Offset] == NULL ) ||
          ( Y_02[index2+Y_02_Offset] == NULL ) ||
          ( X_01[index1+Y_01_Offset] == NULL ) ||
          ( X_02[index2+Y_02_Offset] == NULL ) )
     {
          return 1 ;
     }
     return 0 ;

} static int GetNextLine( FILE *filePointer,FILE *fingerfp,int *pCard,int **pFP,
```

```c
                    unsigned char **pXP, int index
#ifdef OBSOLETE_IS_OK
                                    , float rangeValues, int oneOfValues
#endif
                                                                        )
{
    char *line, *fpcard, *fp, *CTOPS ;
    int words, hold;
    int pos ;
    if (-1 == UTL_SCAN_GETS( filePointer, "\\", "#", &line))
        goto AddTraceback ;

#ifdef OBSOLETE_IS_OK
    ReadLineAttributes(line,
                NumRangeFields,
                rangeValues,
                RangeFields,
                NumOneOfFields,
                oneOfValues,
                OneOfValues) ;
endif /* CTOPS = strstr(line,"CTOPS=")+strlen("CTOPS="); */
    CTOPS = strstr(line,"CTOPS=") ;

if (!(*pFP = (int   *) UTL_MEM_ALLOC( BytesPerFingerPrint)))
        goto AddTraceback ;
    if (!UTL_FILE_FREAD( pCard,sizeof(int), 1 ,fingerfp))
        goto AddTraceback ;
    if (!UTL_FILE_FREAD( *pFP ,sizeof(int), WordsPerFingerprint ,fingerfp))
        goto AddTraceback ;
    if ( CTOPS )
    {
```

```
CTOPS += strlen("CTOPS");
UTL_SCAN_TOKENIZE(CTOPS,';','\\');
UTL_SCAN_TOKENIZE(CTOPS,'>','\\');
words =    strlen(CTOPS)  / 2; /* must have 8 bit bytes */
if (!XytesPerFingerPrint[index])
  { XytesPerFingerPrint[index] = words;
  }
if ( words != XytesPerFingerPrint[index]) goto MissingValue;
*pXP = (unsigned char *) UTL_MEM_ALLOC(words);
for (words=0;words<XytesPerFingerPrint[index];words++)
{
   memcpy(next2,CTOPS,2);
   CTOPS += 2;
   sscanf(next2,"%2x", &hold);
   *(*pXP+words) = (unsigned char ) hold;
}
} return 1;
MissingValue :
      *pCard = 0 ;
      *pFP = (int *)NULL ;
      *pXP = (unsigned char *)NULL ;
      return 1 ;
AddTraceback :
      return 0 ;
} static int not_here( what, nbytes )
unsigned char *what;
int nbytes;
{
  for ( ; nbytes; --nbytes) *what++ = ~ *what;
```

```
   return 1;
}
/* this belongs in the utl module, actually */
int MakeComLine( char *line, int len, int argc, char **argv)
{
  int i;
  sprintf(line,"%s ",argv[0]);
  for(i=1;i<argc;i++)
  {
    line += strlen(line);
    sprintf(line,"%s ",argv[i]);
  }
} static void UserHitControlC()
/*+I
*
* This function is the signal handler for user initiated program termination.
* It's only role is to set a flag indicating that the user wishes to abort the program.
*
* Author     Date          Description
* ======     ========      ============
* G. B. Smith   02-09-93      Original Version
*
*/
{
        UserAborted = 1;
} static int ReadEverything()
{
  char *hold;
  char buff[255];
```

```c
int i;
int j;
char *cp ;
char *mp ;
int offset ;
int size ;
char *input ;
FILE *fp ;
char *line ;
void *bitset[MAX_INPUT_CSLNS] ;
/* because failure here means end program run, no effort to clean up
   memory on error is included. */
offset=0;
if (!WarmUp() || !WhatsTheDifference())     return 0;

if ( MasterFileList || BitsetFileList )
    {
            if ( ! ( fp = fopen(MasterFileList?MasterFileList:BitsetFileList,"r")) )
                    return 0 ;
            TotalInputs = 0 ;
            while ( UTL_SCAN_GETS( fp, "\\", "#", &line) != -1 )
            {
                    strcpy(buff,line);
                    cp = strtok(buff," ");
        InputNames[TotalInputs] = UTL_STR_SAVE(cp);
                    cp = strtok(NULL," ");
                    InputStartRec[TotalInputs] = atoi(cp);
                    cp = strtok(NULL," ");
                    OutputCheckpointNames[TotalInputs++] = UTL_STR_SAVE(cp);
            }
    }
    else
    {
```

```c
if ( !MasterFile && !BitsetSource && !MasterFileList )
{
        fprintf(stderr,"An input file(master or bitset) must be specified\n");
        return 0 ;
}
if ( MasterFile && BitsetSource )
{
        fprintf(stderr,"A design run can be run from either a master or a bitset file\n");
        return 0 ;
}
if (MasterFile && !MasterRecord )
{
        fprintf(stderr,"A Bitset (or Master) record number must be specified\n");
        return 0 ;
}

/*
** Special case where we want to process all the records in the
** master file.
*/
   if ( atoi(MasterRecord) == -1 )
   {
      if ( ( TotalInputs = CountMasterRecords(MasterFile)) == 0 )
         goto UnableToReadMaster ;
      for ( i = 0 ; i < TotalInputs ; i++ )
      {
         InputNames[i] = UTL_STR_SAVE(MasterFile);
         InputStartRec[i] = i+1 ;
      }
   }
   else
   {
```

```
                if ( MasterFile )
                        input = UTL_STR_SAVE(MasterFile);
                else
                        input = UTL_STR_SAVE(BitsetSource);
/*
** If there are more than one input file, process them all.
*/
                cp = strtok(input," ");
                while ( cp )
                {
                        InputNames[TotalInputs++] = UTL_STR_SAVE(cp);
                        cp = strtok(NULL," ");
                }
                mp = strtok(MasterRecord," ");
                for ( i = 0 ; i < TotalInputs ; i++ )
                {
/*
** If the user specified record numbers for all the master files, then use them
** otherwise we will use the first record.
*/
                        if ( mp )
                        {
                                InputStartRec[i] = atoi(mp);
                                mp = strtok(NULL," ");
                        }
                        else
                                InputStartRec[i] = 1 ;
                }
        }
        mp = strtok(CheckPointFileName," ");
        for ( i = 0 ; i < TotalInputs ; i++ )
        {
                if ( mp )
```

```
            {
                    OutputCheckpointNames[i] = UTL_STR_SAVE(mp);
                    mp = strtok(NULL," ");
            }
            else
            {
                    sprintf(buff,"%s_%d_chk.bs",basename(InputNames[i],NULL),i);
                    OutputCheckpointNames[i] = UTL_STR_SAVE(buff);
            }
        }
    }
nY_01 = nY_02 = 0 ;
    for ( i = 0 ; i < TotalInputs ; i++ )
    {
            if ( MasterFile || MasterFileList )
            {
                    if ( !RetrieveMasterFile(InputNames[i],
                                            MasterFile_File,
                                            InputStartRec[i],
                                            &(NumMissingBits[i]),
                                            &(BitsInAbsentiaNoCount[i]),
                                            &(CoreFileNames[i]),
                                            &(CoreStart[i]),
                                            &FngrFile,
                                            &(X1file[i]),
                                            &(X2file[i]),
                                            &(Y_01_Length[i]),
                                            &(Y_02_Length[i]),
                                            &(fingerFP[i]),
                                            &(fingerOffsets[i]),
                                            &ScreenFileName,
                                            &BytesPerFingerPrint,
                                            &WordsPerFingerprint,
```

```
                            &query,
                            &FingerCore_FP,
                            &FingerCore_Card) )
        goto UnableToReadMaster ;
    RemainingInput[i] = Y_01_Length[i] * Y_02_Length[i];
}
else
{
    if ( !( bitset[i] = CS_PRDCT_BITSET_OPEN(InputNames[i],
                                InputStartRec[i])) )
        goto UnableToReadBitset ;
    if ( !RetrieveMasterFileFromBitset(bitset[i],
                            &(MasterFile_Bitset[i]),
                            &(StartRec_Bitset[i]),
                            &(NumMissingBits[i]),
                            &(BitsInAbsentiaNoCount[i]),
                            &(CoreFileNames[i]),
                            &(CoreStart[i]),
                            &FngrFile,
                            &(X1file[i]),
                            &(X2file[i]),
                            &(Y_01_Length[i]),
                            &(Y_02_Length[i]),
                            &(fingerFP[i]),
                            &(fingerOffsets[i]),
                            &ScreenFileName,
                            &BytesPerFingerPrint,
                            &WordsPerFingerprint,
                            &query,
                            &FingerCore_FP,
                            &FingerCore_Card) )
        goto UnableToReadBitset ;
    RemainingInput[i] = CS_PRDCT_BITSET_SELECTED(bitset[i]);
```

```
            }
            nY_01 += Y_01_Length[i] ;
            nY_02 += Y_02_Length[i] ;
        }
        if (! (Y_01 = (int **) UTL_MEM_ALLOC(sizeof(int *) * nY_01)))
            goto UnableToAllocateMemory ;
        if (!(cY_01 = (int *) UTL_MEM_ALLOC(sizeof(int ) * nY_01)))
            goto UnableToAllocateMemory ;
        if (!(iY_01 = (int *) UTL_MEM_ALLOC(sizeof(int ) * nY_01)))
            goto UnableToAllocateMemory ;
        if (! (X_01 = (unsigned char **)
            UTL_MEM_ALLOC(sizeof(unsigned char *)*nY_01)))
            goto UnableToAllocateMemory ;
        if (!(iX_01 = (double *) UTL_MEM_ALLOC(sizeof(double ) * nY_01)))
            goto UnableToAllocateMemory ;
#ifdef OBSOLETE_IS_OK
 if ( NumRangeFields )
 {
   if(!(RangeValues_Y01 = (float **) UTL_MEM_ALLOC(sizeof(float *) * nY_01)))
            goto UnableToAllocateMemory ;
 }
 if ( NumOneOfFields )
 {
    if (!(OneOfValues_Y01 = (int **) UTL_MEM_ALLOC(sizeof(int *) * nY_01)))
            goto UnableToAllocateMemory ;
 }
endif
/*
** Read all the values for the X1 file.
*/
        for ( j = 0 ; j < TotalInputs ; j++ )
        {
            if ( !(fileHandles[j] =  fopen(X1file[j],"r")) )
```

```
                    goto UnableToOpenX1File ;
            for (i=0;i<Y_01_Length[j];i++)
            {
                    if (! GetNextLine( fileHandles[j],
                                       fingerFP[j],
                                       cY_01+i + offset ,
                                       Y_01+i + offset ,
                                       X_01+i + offset ,
                                       0
#ifdef OBSOLETE_IS_OK
                                       ,RangeValues_Y01 + i + offset ,
                                        OneOfValues_Y01 + i  + offset
#endif
                                       ))      return 0;
            }
            offset += Y_01_Length[j] ;
            fclose(fileHandles[j]);
    }
    if (! (Y_02 = (int **) UTL_MEM_ALLOC(sizeof(int *) * nY_02)))
            goto UnableToAllocateMemory ;
    if (!(cY_02 = (int *) UTL_MEM_ALLOC(sizeof(int ) * nY_02)))
            goto UnableToAllocateMemory ;
    if (!(iY_02 = (int *) UTL_MEM_ALLOC(sizeof(int ) * nY_02)))
            goto UnableToAllocateMemory ;
    if (! (X_02 = (unsigned char **)
        UTL_MEM_ALLOC(sizeof(unsigned char *) * nY_02)))
            goto UnableToAllocateMemory ;
    if (!(iX_02 = (double *) UTL_MEM_ALLOC(sizeof(double ) * nY_02)))
            goto UnableToAllocateMemory ;

#ifdef OBSOLETE_IS_OK
    if ( NumRangeFields )
    {
```

```c
            if(!(RangeValues_Y02 = (float **) UTL_MEM_ALLOC(sizeof(float *) *
nY_02)))
                        goto UnableToAllocateMemory ;
        }
        if ( NumOneOfFields )
        {
            if (!(OneOfValues_Y02 = (int **) UTL_MEM_ALLOC(sizeof(int *) *
nY_02)))
                        goto UnableToAllocateMemory ;
        }
endif
        offset = 0 ;
        for ( j = 0 ; j < TotalInputs ; j++ )
        {
            if ( !(fileHandles[j] = fopen(X2file[j],"r")) )
                        goto UnableToAllocateMemory ;
            for (i=0;i<Y_02_Length[j];i++)
            {
                if (! GetNextLine( fileHandles[j],
                                    fingerFP[j],
                                    cY_02+i+offset ,
                                    Y_02+i+offset,
                                    X_02+i+offset ,
                                    1
#ifdef OBSOLETE_IS_OK
                                    ,RangeValues_Y02 + i + offset ,
                                        OneOfValues_Y02 + i + offset
#endif
                                            ))    return 0;
            }
            offset += Y_02_Length[j] ;
            fclose(fileHandles[j]);
        }
```

```
if (!Good_1) /* note: Good_1 is never used but triggers other allocations */
{
    i= (nY_01+31)/32 * 4;
    if (!(Good_1 = (int *) UTL_MEM_ALLOC(i))) return 0; memset( Good_1,0,i);
    if (!(Dead_1 = (int *) UTL_MEM_ALLOC(i))) return 0; memset( Dead_1,0,i);
    i= (nY_02+31)/32 * 4;
    if (!(Good_2 = (int *) UTL_MEM_ALLOC(i))) return 0; memset( Good_2,0,i);
    if (!(Dead_2 = (int *) UTL_MEM_ALLOC(i))) return 0; memset( Dead_2,0,i);

for ( size = 0 , j = 0 ; j < TotalInputs ; j++ )
    {   BitOffsets[j] = size;
        size += ( Y_01_Length[j] * Y_02_Length[j] ) ;
    }
    Pro_size = size = ( size + 31 )/32 * 4 ;
    if (!(Good_Products = (int *) UTL_MEM_ALLOC(size))) return 0;
            memset( Good_Products,0,size);
    if (!(Dead_Products = (int *) UTL_MEM_ALLOC(size))) return 0;
            memset( Dead_Products,0,size);
    if ( !( MasterFile || MasterFileList ) ) /* gather the dead together.... */
            Mortuary(bitset, TotalInputs, Dead_Products, size, BitOffsets);
}
offset = SomeLeft = 0 ;
/*
** Figure out the number of products for each input set and the total
** number of products.
*/
for ( j = 0 ; j < TotalInputs ; j++ )
{
        BitMapStartPoint[j] = offset ;
        offset += Y_01_Length[j] * Y_02_Length[j] ;
        SomeLeft += RemainingInput[j];
}
```

```
TotalProducts = offset ;
#ifdef OBSOLETE_IS_OK
/*
** Initialize the needed structures to pass around.
*/
        RangeValuesData.numRangeFields =   NumRangeFields ;
        RangeValuesData.rangeValues_Y01 = RangeValues_Y01 ;
        RangeValuesData.rangeValues_Y02 = RangeValues_Y02 ;
        RangeValuesData.rangeFields =     RangeFields ;
        OneOfValuesData.numOneOfFields  = NumOneOfFields ;
        OneOfValuesData.oneOfValues_Y01 = OneOfValues_Y01 ;
        OneOfValuesData.oneOfValues_Y02 = OneOfValues_Y02 ;
        OneOfValuesData.oneOfFields     = OneOfValues ;
#endif
        InputData.totalInputs = TotalInputs ;
        InputData.Y_01_Length = Y_01_Length ;
        InputData.Y_02_Length = Y_02_Length ;
/*
** Read in the -rangevar values if they are present in the csln file.
*/ ifdef OBSOLETE_IS_OK
        if( !ReadRangeVarFromCoreFiles(TotalInputs,
                                                CoreFileNames,
                                                CoreStart,
                                                NumRangeFields,
                                                RangeFields) )
                return 0 ;
#endif
return 1;
UnableToOpenX1File :
        fprintf(stderr,"Unable to open reagant file\n");
        goto AddTraceback ;
```

```
UnableToAllocateMemory :
        fprintf(stderr,"Unable to allocate memory\n");
        goto AddTraceback ;
UnableToReadBitset :
        fprintf(stderr,"Unable to Read bitset file\n");
        goto AddTraceback ;
UnableToReadMaster :
        fprintf(stderr,"Unable to Read master file\n");
        goto AddTraceback ;
AddTraceback :
        return 0 ;
}

/* concatenate a series of compressed bitsets into one big raw bitset
   --> AND <-- destroy those compressed bitsets                     */
int Mortuary(void *bitset[], int nsets, int *rawbits,int byte_size, int *offset)
{
int i ;
for (i=0; i< nsets; i++)
   {  CS_PRDCT_BITSET_CONCAT_RAW( bitset[i], rawbits, offset[i], 0);
      CS_PRDCT_BITSET_DESTROY_BIT_STRING(bitset[i]);
      bitset[i] = NULL;
   }
  not_here( rawbits,byte_size );
} static int ParseArguments( argc, argv )
/*+I
*
* This function parses the command line arguments.
*
* Returns: 1 on a successful command line parse, 0 otherwise.
*
```

```
 * Warnings:
 *
 * Errors:
 *
 * See Also:
 *
 *
 * Author     Date          Description
 * ======     ========      ===========
 * G. B. Smith   02-09-93    Original Version
 *
 */
int     argc;
char    **argv;
{
        int     nargs,
                noptions = sizeof( Options )/sizeof(Options[0]);
        OutputFile = stdout;
        nargs = UTL_PARSE_OPT( argc, argv, noptions, Options );
        if( !nargs ) goto SyntaxError;
        if (WhatFirst)
        { if (strstr(WhatFirst,"R1")) WhatFirst[0]='1';
          if (strstr(WhatFirst,"R2")) WhatFirst[0]='2';
        } else {
          WhatFirst=UTL_MEM_ALLOC(2); WhatFirst[0]='0'; }
#ifdef OBSOLETE_IS_OK
        if ( RangeVar && !
ParseRangeVar(RangeVar,&NumRangeFieldsAllocated,&NumRangeFields,&RangeFields))
                goto SyntaxError ;
        if ( OneOfVar &&
!ParseOneOfVar(OneOfVar,&NumOneOfFieldsAllocated,&NumOneOfFields,&OneOfValues))
                goto SyntaxError ;
```

```
endif
        return 1;
SyntaxError:
        return 0;
}
static int OpenOutputFile()
/*+I
 *
 * Returns:  1 on sucesss, else 0
 *
 */
{
        char    *msg;
        FILE    *fp;
        OutputFile = stdout;
        if( OutputFileName )
        {
/*
** We need to create output files under the ownership of the REAL user not the
** EFFECTIVE user.  This only applies if setuid options are activated.
*/
{
struct stat statBuff ;
int    uid ;
int    euid ;
        uid = getuid() ;
        euid = geteuid();
    stat(OutputFileName, &statBuff);
/*
** There are two cases
** (1) the file to output to exists
**     Use the ownership of the current owner of the file or if you cant do that
**     do not do anything.
```

```
** (2) The file is being created.
**    use the ownership of the REAL user.
*/
        if ( access(OutputFileName, F_OK) == 0 )
        { /* If the file exist and the real user is the owner of the file */
                if ( statBuff.st_uid == uid )
                        seteuid(uid);
        }
        else
        { /* Create the file as the REAL user */
                seteuid(uid);
        }
    }

OutputFile = fopen( OutputFileName, "wb");
        if( !OutputFile ) {
                fprintf(stderr,"Error: Failed to open output file \"%s\"\n",
                        OutputFileName );
                goto ErrorReturn;
        }
    } return 1;
ErrorReturn:
        return 0;
} static CloseOutputFile()
/*+I
*
* This function closes the output file. It is included just for cleanliness.
*
```

```
 * Author    Date         Description
 * ======    ========     ============
 * G. B. Smith  02-09-93  Original Version
 *
 */
{
    fclose( OutputFile );
}

CheckPointProgram(programName)
char *programName ;
{
int sizes[2] ;
int allocSizes[2] ;
int numInSites[2] ;
char hold[81] ;
int i ;
void *compressed ;
int total ;

for ( i = 0 ; i < TotalInputs ; i++ )
        {
                sizes[0] = Y_01_Length[i] ;
                sizes[1] = Y_02_Length[i] ;
                numInSites[0] = numInSites[1] = -1 ;
                allocSizes[0] = allocSizes[1] = -1 ;
/*
** Lets get a compressed version of the dead products before we write it out
** to file.
*/
                compressed = CS_PRDCT_BITSET_CREATE_BIT_STRING(
                                        Dead_Products,
                                        BitMapStartPoint[i],
```

```
                                            2,
                                        sizes,
                                        sizes,
                                        &total);
            WriteOutCheckPointFile(OutputCheckpointNames[i],
                    ( MasterFile || MasterFileList ) ? InputNames[i]
                        : MasterFile_Bitset[i],
                    ( MasterFile || MasterFileList ) ? InputStartRec[i]
                        : StartRec_Bitset[i],
                                        programName,
                                        Good_Products,
                                        BitMapStartPoint[i],
                                        2,
                                        sizes,
                                        allocSizes,
                                        Selections[i],
                                        numInSites,
                                        total,
                                        compressed);
            CS_PRDCT_BITSET_DESTROY_BIT_STRING(compressed);
        }
} int main( argc, argv )
/*+E
 *
 */
int     argc;
char    **argv;
{
        long            startTime,
                        totalTime,
                        finishTime;
```

```
        int numFiltered ;
        int numEliminated ;
        int tmp ;
        char comline[2048];
/***
*** Establish handler for a user interrupt.
***/
        signal( SIGINT, UserHitControlC);
#ifdef SIGHUP
        signal( SIGHUP, UserHitControlC);
#endif
        if( !ParseArguments( argc, argv ) )
                goto SyntaxError;
        if( !OpenOutputFile() ) goto FailureExit;
/*      if (!RestartState()) goto FailureExit;  */
        time( &startTime );
        Visual((stderr,"Begin reading files: %s",ctime(&startTime)));
/* Let's actually do something now */
        if (!ReadEverything(NoMorehitsPlease))    goto FailureExit;
                time( &finishTime );

Visual((stderr,"Begin filtering: %s",ctime(&finishTime)));
        if
(!FilterProducts(&InputData,&RangeValuesData,&OneOfValuesData,&numFiltered,IsItMiss
ingAValue))
                goto FailureExit;
        CurrentInput = 0 ;
        time( &finishTime );
        Visual((stderr,"Filtered out %d out of %d possible products\n",numFiltered,
TotalProducts ));

#if 0
/*
```

```
** Now see if there are any hitlists or databases that you should filter
** for.
*/
        time( &finishTime );
        Visual((stderr,"Begin eliminating selections in Unity database
%s",ctime(&finishTime)));
        if ( !EliminateProductsFromDatabase(DatabaseNames,
                                                &numEliminated,
                                                ZapAllNeighbors))
            goto FailureExit;
        time( &finishTime );
        time( &finishTime );
        Visual((stderr,"Begin eliminating selections in Unity hitlist
%s",ctime(&finishTime)));
        if ( !EliminateProductsFromHitlist(HitlistNames, ScreenFileName?ScreenFileName:DefaultScreenFileName,
                                                &tmp,
                                                ZapAllNeighbors))
            goto FailureExit;
        time( &finishTime );
        Visual((stderr,"Eliminated %d out of %d possible products\n",numEliminated+tmp,
TotalProducts ));
#endif
            Visual((stderr,"Begin selection: %s",ctime(&finishTime)));
        if (!UserAborted &&
            !SelectEverything(InputSource,
                                                NoMorehitsPlease,
                                                WhatFirst,
                                                CalcualteProductFingurePrint,
                                                ActuallyCompute,
                        ZapAllNeighbors)) goto FailureExit;
        CloseOutputFile();
```

```
time( &finishTime );

totalTime = finishTime - startTime;
if( !totalTime ) totalTime = 1;
Visual((stderr, "Created %d Selections in ", nProcessed ));
Visual((stderr,"%d Hours, %d min, %d secs\n",
        totalTime/(60*60),
        (totalTime%(60*60))/60,
        (totalTime%60)));
Visual((stderr,"Each comparison required %.8f seconds to calculate\n",
        (totalTime/((double)(nProcessed?nProcessed:1)))));

Visual((stderr,"End Quick Select Computation: %s",ctime(&finishTime)));
MakeComLine(comline, 2048, argc, argv);
CheckPointProgram(comline);
UserAborted ? exit(ErrorExit) : exit(GoodExit);
SyntaxError:
        exit(1);
FailureExit:
        exit(ErrorExit);
}
```

Appendix "L"

```
/******************************************************************
*/
/*          dbcsln_both                              */
/******************************************************************
*/
/* differs from dbcsln_design ONLY in combining topomers and fp as 1 metric */
/*   combined as D^2 = (Ratio * CoMFA)^2 + (1-Tanimoto)^2              */
/******************************************************************
*/
/*+C
*
* This program evaluates (approximate) Topomer+Tanimoto similarity vs cSLNs
* based on preprocessing of the substituent reagents. Using this, it
* selects a diverse set of products while trying to maximize use of
* some groups. Diversity is achieved by zapping all neighbors after each
* new selection, so that any non-zapped product can freely be selected.
*
* To be added: restart capability and reagent blackout.
*           (i.e. to recomplete an earlier design and/or to remove
*               all occurences of Y_01= 37 and so on when they
*               prove to be unavailable or otherwise unsuitable).
* Limitations: currently exactly 2 R groups are assumed. Need to extend
*           to more than 2 and to handle X groups.
*
* The OBSOLETE file contains one line per hit, of the form
*   Y1 Y2
* where Y1 = index of the substituent in X1.pro file
*       Y2 = index of the substituent in X2.pro file
*
* The REAL output is a ChemSpace bitset file.
*
```

```
*
* Options:    Look at the array Options below.
*                                                        *

**************************************************************
/
#include <stdio.h>
include <signal.h>
#include <ctype.h>
#include <unistd.h>
#include <string.h>
#include <sys/stat.h>
#include <math.h>
#include "parseopt.h"
#include "utl_str.h"
#include "utl_mem.h"
#include "utl_file.h"
#include "utl_math.h"
#include "ct.h"
#include "ct_expr.h"
#include "ct_proto.h"
#include "import_proto.h"
#include "io_fprint.h"
#include "commonData.h" /* Globals use by most functions, we will clean this
                          up soon */
#include "dbcsln_bs_proto.h"
#include "dbcsln_hlm_proto.h"
#define OBSOLETE_IS_OK 1
FILE *debugFile = (FILE *) NULL ;

#ifdef OBSOLETE_IS_OK
/* these sections retain the filtering capabilities now also present
   in db_filter.c -- at some point they should exist ONLY in db_filter.
```

```
*/
static struct RangeInfoStruct  RangeValuesData ;
static struct OneOfInfoStruct  OneOfValuesData ;
static struct InputInfoStruct  InputData ;
static int       NumRangeFields ;
static int       NumRangeFieldsAllocated ;
static RangeStruct *RangeFields ;
static int       NumOneOfFieldsAllocated ;
static int       NumOneOfFields ;
static OneOfStruct *OneOfValues ;
static float **RangeValues_Y01 ; /* Actual values read in from  nnn.X1 file,
            If MW is the first and logp is the second value
            specified on the -rangevar argument list then
            RangeValues_Y01[n][0] would keep the value for MW
            for the nth line in the nnn.X1 file and
            RangeValues_Y01[n][1] would keep the value for
            logp for that line*/
static float **RangeValues_Y02 ; /* same */
static int   **OneOfValues_Y01 ; /*Actual values read from nnn.X1 files but translated
            into an index of OneOfValues[i].values so
            we dont have to waist memory and time doing strcmp*/
static int   **OneOfValues_Y02 ; /* Same */
endif static char *MasterFile ;
static char *MasterRecord ;
static FILE               *MasterFile_File;
static char               *FngrFile;
static int                FingerCore_Card;
static int                *FingerCore_FP;

static char *RangeVar ;
static char *OneOfVar ;
```

```
static double        Ratio = 0.003 ;

static int           WordsPerFingerprint = 0;
static int           BytesPerFingerPrint = 0;
static int           NoMorehitsPlease = 999999999;
static int           DebugLevel;
static int           UserAborted;
static char          *OutputFileName;
static char          *CheckPointFileName;
static char          *WhatFirst;
static char          *InputSource = 0;
static char          *BitsetSource = 0;
static char          *DatabaseNames = (char *)0 ;
static char          *HitlistNames = (char *)0 ;
static int           BitOffsets[MAX_INPUT_CSLNS];   /* why recompute? */
static int           CoreSym[MAX_INPUT_CSLNS];
static double        *jX_01, *jX_02;
int TotalProducts ;
static int           Pro_size;
static struct ParseOptions Options[] = {
/***
*** DO NOT MOVE ENTRIES IN THIS TABLE.  ADD ENTRIES ONLY AT THE END.
***/
    {"master",   ParseOptString,    &MasterFile,
        "Name is the file with master file records" },
    {"index",    ParseOptString,    &MasterRecord,
        "Which MasterRecord or Bitset entry 1-n" },
    {"comfa",    ParseOptDouble,    &Ratio ,
        "Weighting for CoMFA fields (0.003)" },
    {"distance", ParseOptDouble,    &Distance,
        "Weighted neighborhood distance (0.240)" },
    {"maxhits",  ParseOptInt,       &NoMorehitsPlease,
```

"Maximum number of hits before stopping" },

{"bitset",   ParseOptString,   &BitsetSource,

"Bitset file to start from"},

{"output",   ParseOptString,   &OutputFileName,

"File to which hit info will be written. "},

{"checkpoint",   ParseOptString,   &CheckPointFileName,

"File to which bitset info will be written. "},

{"prefer",   ParseOptString,   &WhatFirst,

"One of R1, R2 to maximize us of."},

{"debug",   ParseOptBoolean,   &DebugLevel,

"Use +debug to enable debugging messages" }, ifdef OBSOLETE_IS_OK

{"rangevar",   ParseOptString,   &RangeVar,

"Scalar field name and range to filter out, i.e. logp -1.0 8.0 MW 200 500 price 0 12.50" }, {"oneof",   ParseOptString,   &OneOfVar, "Field name and list of values that the product should match\n, i.e. supplier Aldrich,Sigma,Fluka,SALOR taste SWEET,Salty" }, endif

{"database",   ParseOptString,   &DatabaseNames,

"Unity database to use to exclude possible products" },

{"hitlist",   ParseOptString,   &HitlistNames,

"Unity hitlist to use to exclude possible products" },

};

static int WarmUp()
{
int i;
for (i=0;i<65536;i++) BigBits[i] = (i&1) + (i&2)/2 + (i&4)/4 + (i&8)/8 +
    (i&16)/16 + (i&32)/32 + (i&64)/64 + (i&128)/128
    + (i&256)/256 +(i&512)/512 +(i&1024)/1024
    + (i&2048)/2048
    + (i&4096)/4096 + (i&8192)/8192 + (i&16384)/16384

+ (i&32768)/32768 ;

setbits_nbits_Init();

return 1;

} static int WhatsTheDifference()

{ int i, j;

define pow2(a) ( (a) * (a) )

/* the assignment of codes is based on the following (from gen_pls.c):

static fpt cutoff[16] = {9999., 0., 2., 4., 6., 8., 10., 12.,

14., 16., 18., 20., 22., 24., 26., 30. };

*/ boundary[0] = 9999.; /* missing data ought never to occur. */ boundary[1] = -0.1 * Ratio;

for (i=2;i< 15;i++)

boundary[i] = (2*i-3) * Ratio;

boundary[15] = 30.0 * Ratio; /* this is a steep curve with a cutoff at 30! */ for (i=0;i<16;i++) for (j=0;j<16;j++)

Dist[i][j] = pow2( boundary[i] - boundary[j]);

Distance *= Distance; /* want to test D^2 directly */ return 1;

} static int CalcualteProductFingurePrint(product,firstPart,secondPart)

int *product ;

int *firstPart ;

int *secondPart ;

{ int index ;

int totalBitsSet = 0 ;

unsigned char *prod , *y01, *y02 ;

prod = ( unsigned char *)product ;

y01 = ( unsigned char *)firstPart ;

```
        y02 = ( unsigned char *)secondPart ;
        for (index=0;index<BytesPerFingerPrint;index++,prod++)
        {
                *prod = *y01++ | *y02++ ;
                totalBitsSet += nbits[*prod & 255];
        }
        return totalBitsSet ;
} static int IntersectQuery( pIntr, pFP,  pXntr, pXP, xuery, index,
                 symmetric, yuery, pXntr2)
int *pIntr, **pFP;
double *pXntr, *pXntr2;
unsigned char **pXP, **xuery,  **yuery;
int index, symmetric;
{
unsigned char *ptr ,*qtr;
int i, count;
double xount;
        if ( !(*pFP) || !(*pXP) )
                return 1 ;
ptr = (unsigned char *) *pFP;
qtr = (unsigned char *) query;
for(count=0, i=0; i<WordsPerFingerprint*4;i++)
    count += nbits[ *ptr++ & *qtr++];
*pIntr = count;
if ( xuery )
{
ptr = (unsigned char *) *pXP;
qtr = (unsigned char *) *xuery;
for(xount=0.0, i=0; i<XytesPerFingerPrint[index];i++, ptr++, qtr++)
     xount += Dist[  *ptr & 0x0F    ][ *qtr & 0x0F    ]
         + Dist[ (*ptr & 0xF0) >> 4][ (*qtr & 0xF0) >> 4] ;
```

```
*pXntr = xount;
if ( !symmetric) return 1;

ptr = (unsigned char *) *pXP;
qtr = (unsigned char *) *yuery;
for(xount=0.0, i=0; i<XytesPerFingerPrint[index];i++, ptr++, qtr++)
     xount += Dist[ *ptr & 0x0F   ][ *qtr & 0x0F   ]
         + Dist[ (*ptr & 0xF0) >> 4][ (*qtr & 0xF0) >> 4] ;
*pXntr2 = xount ;
}
return 1;
}
static int ActuallyCompute( index1, index2, pUnion, pIntersection, pMaxTan,currentInput)
int index1, index2, *pUnion, *pIntersection;
double *pMaxTan;
{
 int i;
 unsigned short *h1, *h2, *hquery, product;
 int numberOfMissingBits ;
 if ( currentInput == -1 )
      numberOfMissingBits = NumMissingBits[0] ;
 else
      numberOfMissingBits = NumMissingBits[currentInput] ;

h1 = (unsigned short *) Y_01[index1];
 h2 = (unsigned short *) Y_02[index2];
 hquery = (unsigned short *) query;
 *pUnion = *pIntersection = 0;
 for( i=0; i<WordsPerFingerprint*2 ;i++,h1++,h2++,hquery++)
   {
/*    product = (*h1 | *h2) ;*/
      *pUnion      += BigBits[ (*h1 | *h2) | *hquery];
      *pIntersection += BigBits[ (*h1 | *h2) & *hquery];
```

```
}
*pMaxTan = (double) (*pIntersection + numberOfMissingBits )/ (double) *pUnion;
return 1;
} static int
ZapAllNeighbors(thisQuery,thisC_Query,numZapped,doCTOPS,index1,index2,currentInput
)
int *thisQuery ;
int thisC_Query ;
int *numZapped ;
int doCTOPS ;
int currentInput ;
{
  int cqt, q_lo, q_hi, i, j, carhold, inthold, onion, intsc ;
  double max, test,test2;
int k ;
int Y_01_Offset, Y_02_Offset ;
 int pos ;
int  numberOfMissingBits ;
if (DebugLevel == 69)
    printf(" ------------ time to zap %d - %d\n", index1+1, index2+1);
  if ( currentInput == -1 )
            numberOfMissingBits = NumMissingBits[0] ;
      else
            numberOfMissingBits = NumMissingBits[currentInput] ;
  if ( thisQuery )
  {
            memcpy(query,thisQuery,BytesPerFingerPrint) ;
            c_query = thisC_Query ;
  }
  *numZapped = 0 ;
      Y_01_Offset = Y_02_Offset = 0 ;
```

```
        for ( k = 0 ; k < CurrentInput ; k++ )
        {
                Y_01_Offset += Y_01_Length[k];
                Y_02_Offset += Y_02_Length[k];
        }
    for (i=0;i<nY_01;i++)
        if (! IntersectQuery( iY_01+i,
                              Y_01+i,
                              iX_01+i,
                              X_01+i,
                              (doCTOPS)?X_01 + index1 + Y_01_Offset : NULL ,
                              0,
                              CoreSym[CurrentInput],
                              (doCTOPS)?X_02 + index2 + Y_02_Offset : NULL , jX_01+i))
            return 0;
    for (i=0;i<nY_02;i++)
        if (! IntersectQuery( iY_02+i,
                              Y_02+i,
                              iX_02+i,
                              X_02+i,
                              (doCTOPS)?X_02 + index2 + Y_02_Offset : NULL ,
                              1,
                              CoreSym[CurrentInput],
                              (doCTOPS)?X_01 + index1 + Y_01_Offset : NULL, jX_02+i))
            return 0;
    /* now zap topomer neighbors */
/*
** Only do topomer neighbors if CTOPS was present in the input.
*/
        if ( doCTOPS )
        {
        Y_01_Offset = Y_02_Offset = 0 ;
        for ( k = 0 ; k < TotalInputs ; k++ )
```

```
{
    for(i= 0 ;i< Y_01_Length[k];i++)
    { if ( !CoreSym[CurrentInput] && (iX_01[ i + Y_01_Offset ] > Distance) )
            continue;
        for (j=0 ;j< Y_02_Length[k];j++)
        {
            if (UserAborted)
                return 1;
            switch (CoreSym[CurrentInput])
            { case 0: if ( iX_02[j+Y_02_Offset] > Distance) continue;
                    test = iX_01[i+Y_01_Offset] + iX_02[j+Y_02_Offset];

break;
                case 1:
                    test = iX_01[i+Y_01_Offset] + iX_02[j+Y_02_Offset];
                    test2= jX_01[i+Y_01_Offset] + jX_02[j+Y_02_Offset];

if (test2 < test) test=test2;
                    break;
            }
            if ( test <= Distance &&
                !TestBit(Dead_Products,
                        BitMapStartPoint[k] + i *Y_02_Length[k] +j) &&
                Am_I_Close(i + Y_01_Offset ,j + Y_02_Offset , test ,currentInput) )
            {
                if (DebugLevel == 69)
                    printf("Distance kill %d %d - %f , %f + %f OR %f , %f + %f\n",
                        i+1,j+1, iX_01[i] + iX_02[j], iX_01[i] , iX_02[j],
```

```
                                  jX_01[i] + jX_02[j], jX_01[i] , jX_02[j] );
                                       pos = BitMapStartPoint[k] + i *Y_02_Length[k] +j ;
                                       FlagProduct(Dead_Products, 0,0, pos );
                              SomeLeft--;
                                       RemainingInput[k]-- ;
                                       (*numZapped)++;
                                     }
                                 } /* Y_02 loop */
                          } /* Y_01 loop */
                          Y_01_Offset += Y_01_Length[k] ;
                          Y_02_Offset += Y_02_Length[k] ;
               }
             }
   }
   static int Am_I_Close(i,j,test,currentInput)
   int i,j;
   double test;
   int    currentInput ;
   {
     int onion, intsc;
     double max, Tanimoto;
        Tanimoto = 1. - sqrt( Distance - test);
        ActuallyCompute( i, j, &onion, &intsc, &max,currentInput);
        return( max >= Tanimoto);
   }

/*
   **+I:
   **
   **
   ** Abstract    : Function zapps products who are missing CTOPS or FP fields.
   **
   **
```

```
**
** Usage        :
**
** Returns      : 1 if the data value is missing or zero if the values exist.
**
** Algorithms   : None.
**
** Revision History :
**
** Author              Date        Description
** ==================  ========    ===============
** Fred Soltanshahi    05/21/96    Original version.
**
**-I:
*/
static int IsItMissingAValue(index1,index2,currentInput)
int index1 ;
int index2 ;
{
int Y_01_Offset = 0 ;
int Y_02_Offset = 0 ;
int k ;
        for ( k = 0 ; k < currentInput ; k++ )
        {
                Y_01_Offset += Y_01_Length[k] ;
                Y_02_Offset += Y_02_Length[k] ;
        }
        if ( ( Y_01[index1+Y_01_Offset] == NULL ) ||
             ( Y_02[index2+Y_02_Offset] == NULL ) ||
             ( X_01[index1+Y_01_Offset] == NULL ) ||
             ( X_02[index2+Y_02_Offset] == NULL ) )
        {
```

```
            return 1 ;
    }
        return 0 ;

} static int GetNextLine( FILE *filePointer,FILE *fingerfp,int *pCard,int **pFP,
            unsigned char **pXP, int index
#ifdef OBSOLETE_IS_OK
                    , float rangeValues, int oneOfValues
#endif
                                )
{
 char *line, *fpcard, *fp, *CTOPS ;
 int words, hold;
 int pos ;
 if (-1 == UTL_SCAN_GETS( filePointer, "\\", "#", &line))
        goto AddTraceback ;

#ifdef OBSOLETE_IS_OK
  ReadLineAttributes(line,
            NumRangeFields,
            rangeValues,
            RangeFields,
            NumOneOfFields,
            oneOfValues,
            OneOfValues) ;
endif /* CTOPS  = strstr(line,"CTOPS=")+strlen("CTOPS="); */
   CTOPS  = strstr(line,"CTOPS=") ;

if (!(*pFP = (int    *) UTL_MEM_ALLOC( BytesPerFingerPrint)))
```

```
        goto AddTraceback ;
if (!UTL_FILE_FREAD( pCard,sizeof(int), 1 ,fingerfp))
        goto AddTraceback ;
if (!UTL_FILE_FREAD( *pFP ,sizeof(int), WordsPerFingerprint ,fingerfp))
        goto AddTraceback ;
if ( CTOPS )
{
  CTOPS += strlen("CTOPS");
UTL_SCAN_TOKENIZE(CTOPS,';','\\');
UTL_SCAN_TOKENIZE(CTOPS,'>','\\');
words =     strlen(CTOPS)   / 2; /* must have 8 bit bytes */
if (!XytesPerFingerPrint[index])
  { XytesPerFingerPrint[index] = words;
  }
if ( words != XytesPerFingerPrint[index]) goto MissingValue;
*pXP = (unsigned char *) UTL_MEM_ALLOC(words);
for (words=0;words<XytesPerFingerPrint[index];words++)
{
   memcpy(next2,CTOPS,2);
   CTOPS += 2;
   sscanf(next2,"%2x", &hold);
   *(*pXP+words) = (unsigned char ) hold;
}
} return 1;
MissingValue :
        *pCard = 0 ;
        *pFP = (int *)NULL ;
        *pXP = (unsigned char *)NULL ;
        return 1 ;
AddTraceback :
        return 0 ;
```

```
} static int not_here( what, nbytes )
unsigned char *what;
int nbytes;
{
  for ( ; nbytes; --nbytes) *what++ = ~ *what;
  return 1;
}
/* this belongs in the utl module, actually */
int MakeComLine( char *line, int len, int argc, char **argv)
{
  int i;
  sprintf(line,"%s ",argv[0]);
  for(i=1;i<argc;i++)
  {
    line += strlen(line);
    sprintf(line,"%s ",argv[i]);
  }
} static void UserHitControlC()
/*+I
*
* This function is the signal handler for user initiated program termination.
* It's only role is to set a flag indicating that the user wishes to abort the program.
*
* Author    Date         Description
* ======    ========     ============
* G. B. Smith   02-09-93    Original Version
*
*/
{
```

```
        UserAborted = 1;
} static int ReadEverything()
{
 char *hold;
 char buff[255];
 int i;
 int j;
 char *cp ;
 char *mp ;
 int offset ;
 int size ;
 char *input ;
 void *bitset[MAX_INPUT_CSLNS] ;
 /* because failure here means end program run, no effort to clean up
    memory on error is included. */
 offset=0;
        if ( !MasterFile && !BitsetSource )
        {
                fprintf(stderr,"An input file(master or bitset) must be specified\n");
                return 0 ;
        }
        if ( MasterFile && BitsetSource )
        {
                fprintf(stderr,"A design run can be run from either a master or a bitset
file\n");
                return 0 ;
        }
        if (MasterFile && !MasterRecord )
        {
                fprintf(stderr,"A Bitset (or Master) record number must be specified\n");
```

```
            return 0 ;
    }
if (!WarmUp() || !WhatsTheDifference())     return 0;
/*
** Special case where we want to process all the records in the
** master file.
*/
    if ( atoi(MasterRecord) == -1 )
    {
        if ( ( TotalInputs = CountMasterRecords(MasterFile)) == 0 )
            goto UnableToReadMaster ;
        for ( i = 0 ; i < TotalInputs ; i++ )
        {
            InputNames[i] = UTL_STR_SAVE(MasterFile);
            InputStartRec[i] = i+1 ;
        }
    }
    else
    {
            if ( MasterFile )
                    input = UTL_STR_SAVE(MasterFile);
            else
                    input = UTL_STR_SAVE(BitsetSource);
/*
** If there are more than one input file, process them all.
*/
            cp = strtok(input," ");
            while ( cp )
            {
                    InputNames[TotalInputs++] = UTL_STR_SAVE(cp);
                    cp = strtok(NULL," ");
            }
            mp = strtok(MasterRecord," ");
```

```c
        for ( i = 0 ; i < TotalInputs ; i++ )
        {
/*
** If the user specified record numbers for all the master files, then use them
** otherwise we will use the first record.
*/
            if ( mp )
            {
                    InputStartRec[i] = atoi(mp);
                    mp = strtok(NULL," ");
            }
            else
                    InputStartRec[i] = 1 ;
        }
    }
    mp = strtok(CheckPointFileName," ");
    for ( i = 0 ; i < TotalInputs ; i++ )
    {
        if ( mp )
        {
                OutputCheckpointNames[i] = UTL_STR_SAVE(mp);
                mp = strtok(NULL," ");
        }
        else
        {
                sprintf(buff,"%s_%d_chk.bs",basename(InputNames[i],NULL),i);
                OutputCheckpointNames[i] = UTL_STR_SAVE(buff);
        }
    }
nY_01 = nY_02 = 0 ;
if (TotalInputs > 1)
    fprintf(stderr,"All files assumed to be for same core.\n");
    for ( i = 0 ; i < TotalInputs ; i++ )
```

```
{
    if ( MasterFile )
    {
        if ( !RetrieveMasterFile(InputNames[i],
                                MasterFile_File,
                                InputStartRec[i],
                                &(NumMissingBits[i]),
                                &(BitsInAbsentiaNoCount[i]),
                                &(CoreFileNames[i]),
                                &(CoreStart[i]),
                                &FngrFile,
                                &(X1file[i]),
                                &(X2file[i]),
                                &(Y_01_Length[i]),
                                &(Y_02_Length[i]),
                                &(fingerFP[i]),
                                &(fingerOffsets[i]),
                                &ScreenFileName,
                                &BytesPerFingerPrint,
                                &WordsPerFingerprint,
                                &query,
                                &FingerCore_FP,
                                &FingerCore_Card) )
            goto UnableToReadMaster ;
        RemainingInput[i] = Y_01_Length[i] * Y_02_Length[i];
    }
    else
    {
        if ( !( bitset[i] =  CS_PRDCT_BITSET_OPEN(InputNames[i],
                                                 InputStartRec[i])) )
            goto UnableToReadBitset ;
        if ( !RetrieveMasterFileFromBitset(bitset[i],
                                           &(MasterFile_Bitset[i]),
```

```
                    &(StartRec_Bitset[i]),
                    &(NumMissingBits[i]),
                    &(BitsInAbsentiaNoCount[i]),
                    &(CoreFileNames[i]),
                    &(CoreStart[i]),
                    &FngrFile,
                    &(X1file[i]),
                    &(X2file[i]),
                    &(Y_01_Length[i]),
                    &(Y_02_Length[i]),
                    &(fingerFP[i]),
                    &(fingerOffsets[i]),
                    &ScreenFileName,
                    &BytesPerFingerPrint,
                    &WordsPerFingerprint,
                    &query,
                    &FingerCore_FP,
                    &FingerCore_Card) )
            goto UnableToReadBitset ;
        RemainingInput[i] = CS_PRDCT_BITSET_SELECTED(bitset[i]);
    }
    nY_01 += Y_01_Length[i] ;
    nY_02 += Y_02_Length[i] ;
    RetrieveSymmetry(CoreFileNames[i],CoreStart[i],&(CoreSym[i]) );
}
if (! (Y_01 = (int **) UTL_MEM_ALLOC(sizeof(int *) * nY_01)))
    goto UnableToAllocateMemory ;
if (!(cY_01 = (int *) UTL_MEM_ALLOC(sizeof(int ) * nY_01)))
    goto UnableToAllocateMemory ;
if (!(iY_01 = (int *) UTL_MEM_ALLOC(sizeof(int ) * nY_01)))
    goto UnableToAllocateMemory ;
if (! (X_01 = (unsigned char **)
    UTL_MEM_ALLOC(sizeof(unsigned char *)*nY_01)))
```

```
            goto UnableToAllocateMemory ;
    if (!(iX_01 = (double *) UTL_MEM_ALLOC(sizeof(double ) * nY_01)))
            goto UnableToAllocateMemory ;
    if (!(jX_01 = (double *) UTL_MEM_ALLOC(sizeof(double ) * nY_01)))
            goto UnableToAllocateMemory ;
#ifdef OBSOLETE_IS_OK
 if ( NumRangeFields )
 {
   if(!(RangeValues_Y01 = (float **) UTL_MEM_ALLOC(sizeof(float *) * nY_01)))
            goto UnableToAllocateMemory ;
 }
 if ( NumOneOfFields )
 {
   if (!(OneOfValues_Y01 = (int **) UTL_MEM_ALLOC(sizeof(int *) * nY_01)))
            goto UnableToAllocateMemory ;
 }
endif
/*
** Read all the values for the X1 file.
*/
    for ( j = 0 ; j < TotalInputs ; j++ )
    {
        if ( !(fileHandles[j] = fopen(X1file[j],"r")) )
                goto UnableToOpenX1File ;
        for (i=0;i<Y_01_Length[j];i++)
        {
            if (! GetNextLine( fileHandles[j],
                    fingerFP[j],
                        cY_01+i + offset ,
                        Y_01+i + offset ,
                        X_01+i + offset ,
                        0
#ifdef OBSOLETE_IS_OK
```

```
                        ,RangeValues_Y01 + i + offset ,
                                OneOfValues_Y01 + i  + offset
#endif
                            ))      return 0;
                }
                offset += Y_01_Length[j] ;
                fclose(fileHandles[j]);
        }
        if (! (Y_02 = (int **) UTL_MEM_ALLOC(sizeof(int *) * nY_02)))
                goto UnableToAllocateMemory ;
        if (!(cY_02 = (int *) UTL_MEM_ALLOC(sizeof(int ) * nY_02)))
                goto UnableToAllocateMemory ;
        if (!(iY_02 = (int *) UTL_MEM_ALLOC(sizeof(int ) * nY_02)))
                goto UnableToAllocateMemory ;
        if (! (X_02 = (unsigned char **)
            UTL_MEM_ALLOC(sizeof(unsigned char *) * nY_02)))
                goto UnableToAllocateMemory ;
        if (!(iX_02 = (double *) UTL_MEM_ALLOC(sizeof(double ) * nY_02)))
                goto UnableToAllocateMemory ;
        if (!(jX_02 = (double *) UTL_MEM_ALLOC(sizeof(double ) * nY_02)))
                goto UnableToAllocateMemory ;

#ifdef OBSOLETE_IS_OK
        if ( NumRangeFields )
        {
                if(!(RangeValues_Y02 = (float **) UTL_MEM_ALLOC(sizeof(float *) * nY_02)))
                        goto UnableToAllocateMemory ;
        }
        if ( NumOneOfFields )
        {
                if (!(OneOfValues_Y02 = (int **) UTL_MEM_ALLOC(sizeof(int *) * nY_02)))
```

```
                goto UnableToAllocateMemory ;
        }
endif
        offset = 0 ;
        for ( j = 0 ; j < TotalInputs ; j++ )
        {
                if ( !(fileHandles[j] = fopen(X2file[j],"r")) )
                        goto UnableToAllocateMemory ;
                for (i=0;i<Y_02_Length[j];i++)
                {
                        if (! GetNextLine( fileHandles[j],
                                        fingerFP[j],
                                                cY_02+i+offset ,
                                                Y_02+i+offset,
                                                X_02+i+offset ,
                                                1
#ifdef OBSOLETE_IS_OK
                                                ,RangeValues_Y02 + i + offset ,
                                                        OneOfValues_Y02 + i + offset
#endif
                                                ))     return 0;
                }
                offset += Y_02_Length[j] ;
                fclose(fileHandles[j]);
        } if (!Good_1) /* note: Good_1 is never used but triggers other allocations */
        {
                i= (nY_01+31)/32 * 4;
                if (!(Good_1 = (int *) UTL_MEM_ALLOC(i))) return 0; memset( Good_1,0,i);
                if (!(Dead_1 = (int *) UTL_MEM_ALLOC(i))) return 0; memset( Dead_1,0,i);
                i= (nY_02+31)/32 * 4;
                if (!(Good_2 = (int *) UTL_MEM_ALLOC(i))) return 0; memset( Good_2,0,i);
```

```
        if (!(Dead_2 = (int *) UTL_MEM_ALLOC(i))) return 0; memset( Dead_2,0,i);

for ( size = 0 , j = 0 ; j < TotalInputs ; j++ )
            {       BitOffsets[j] = size;
                    size += ( Y_01_Length[j] * Y_02_Length[j] ) ;
            }
            Pro_size = size = ( size + 31 )/32 * 4 ;
        if (!(Good_Products = (int *) UTL_MEM_ALLOC(size))) return 0;
                memset( Good_Products,0,size);
        if (!(Dead_Products = (int *) UTL_MEM_ALLOC(size))) return 0;
                memset( Dead_Products,0,size);
        if ( !MasterFile ) /* gather the dead together....   */
                Mortuary(bitset, TotalInputs, Dead_Products, size, BitOffsets);
    }
    offset = SomeLeft = 0 ;
/*
** Figure out the number of products for each input set and the total
** number of products.
*/
    for ( j = 0 ; j < TotalInputs ; j++ )
    {
                BitMapStartPoint[j] = offset ;
                offset += Y_01_Length[j] * Y_02_Length[j] ;
                SomeLeft += RemainingInput[j];
    }
TotalProducts = offset ;
#ifdef OBSOLETE_IS_OK
/*
** Initialize the needed structures to pass around.
*/
            RangeValuesData.numRangeFields = NumRangeFields ;
            RangeValuesData.rangeValues_Y01 = RangeValues_Y01 ;
            RangeValuesData.rangeValues_Y02 = RangeValues_Y02 ;
```

```
            RangeValuesData.rangeFields =     RangeFields ;
            OneOfValuesData.numOneOfFields =  NumOneOfFields ;
            OneOfValuesData.oneOfValues_Y01 = OneOfValues_Y01 ;
            OneOfValuesData.oneOfValues_Y02 = OneOfValues_Y02 ;
            OneOfValuesData.oneOfFields    = OneOfValues ;
#endif
            InputData.totalInputs =  TotalInputs ;
            InputData.Y_01_Length =  Y_01_Length ;
            InputData.Y_02_Length =  Y_02_Length ;
#if 0
/*
** Read in the -rangevar values if they are present in the csln file.
*/
            if( !ReadRangeVarFromCoreFile( Corefile,
                                           NumRangeFields,
                                           RangeFields) )
                    return 0 ;
#endif
            return 1;
UnableToOpenX1File :
            fprintf(stderr,"Unable to open reagant file\n");
            goto AddTraceback ;
UnableToAllocateMemory :
            fprintf(stderr,"Unable to allocate memory\n");
            goto AddTraceback ;
UnableToReadBitset :
            fprintf(stderr,"Unable to Read bitset file\n");
            goto AddTraceback ;
UnableToReadMaster :
            fprintf(stderr,"Unable to Read master file\n");
            goto AddTraceback ;
AddTraceback :
            return 0 ;
```

```c
} int RetrieveSymmetry( char *FileName, int Start, int *pSym )
{
  FILE *tmp;
  char *line;
  if (!(tmp = fopen(FileName, "r"))) return 0;
  for ( ; Start; Start--)
    if (-1 == UTL_SCAN_GETS( tmp, "\\", "#", &line)) return 0 ;
  fclose(tmp);
  if (strstr(line,"SYM=1")) *pSym = 1; else *pSym = 0;
  return 1;

}
/* concatenate a series of compressed bitsets into one big raw bitset
    --> AND <-- destroy those compressed bitsets                    */
int Mortuary(void *bitset[], int nsets, int *rawbits,int byte_size, int *offset)
{
int i ;
for (i=0; i< nsets; i++)
   { CS_PRDCT_BITSET_CONCAT_RAW( bitset[i], rawbits, offset[i], 0);
     CS_PRDCT_BITSET_DESTROY_BIT_STRING(bitset[i]);
     bitset[i] = NULL;
   }
  not_here( rawbits,byte_size );
} static int ParseArguments( argc, argv )
/*+I
 *
 * This function parses the command line arguments.
 *
```

```
* Returns:  1 on a successful command line parse, 0 otherwise.
*
* Warnings:
*
* Errors:
*
* See Also:
*
*
* Author     Date         Description
* ======     ========     ============
* G. B. Smith   02-09-93   Original Version
*
*/
int     argc;
char    **argv;
{
        int     nargs,
                noptions = sizeof( Options )/sizeof(Options[0]);
        OutputFile = stdout;
        nargs = UTL_PARSE_OPT( argc, argv, noptions, Options );
        if( !nargs ) goto SyntaxError;
        if (WhatFirst)
        { if (strstr(WhatFirst,"R1")) WhatFirst[0]='1';
          if (strstr(WhatFirst,"R2")) WhatFirst[0]='2';
        } else {
          WhatFirst=UTL_MEM_ALLOC(2); WhatFirst[0]='0'; }
#ifdef OBSOLETE_IS_OK
        if ( RangeVar && ! ParseRangeVar(RangeVar,&NumRangeFieldsAllocated,&NumRangeFields,&RangeFields))
                goto SyntaxError ;
        if ( OneOfVar &&
!ParseOneOfVar(OneOfVar,&NumOneOfFieldsAllocated,&NumOneOfFields,&OneOfValue
```

```
    s))
                goto SyntaxError ;
#endif
        return 1;
SyntaxError:
        return 0;
}
static int OpenOutputFile()
/*+I
 *
 * Returns:  1 on sucesss, else 0
 *
 */
{
        char    *msg;
        FILE    *fp;
        OutputFile = stdout;
        if( OutputFileName )
        {
/*
** We need to create output files under the ownership of the REAL user not the
** EFFECTIVE user.  This only applies if setuid options are activated.
*/
{
struct stat statBuff ;
int    uid ;
int    euid ;
        uid = getuid() ;
        euid = geteuid();
    stat(OutputFileName, &statBuff);
/*
** There are two cases
** (1) the file to output to exists
```

```
**    Use the ownership of the current owner of the file or if you cant do that
**    do not do anything.
**    (2) The file is being created.
**    use the ownership of the REAL user.
*/
        if ( access(OutputFileName, F_OK) == 0 )
        { /* If the file exist and the real user is the owner of the file */
                if ( statBuff.st_uid == uid )
                        seteuid(uid);
        }
        else
        { /* Create the file as the REAL user */
                seteuid(uid);
        }
    }

OutputFile = fopen( OutputFileName, "wb");
        if( !OutputFile ) {
                fprintf(stderr,"Error: Failed to open output file \"%s\"\n",
                        OutputFileName );
                goto ErrorReturn;
        }
    } return 1;
ErrorReturn:
        return 0;
} static CloseOutputFile()
/*+I
*
```

* This function closes the output file. It is included just for cleanliness.
*
* Author      Date           Description
* ======      ========       ============
* G. B. Smith    02-09-93     Original Version
*
*/
{
    fclose( OutputFile );
}

CheckPointProgram(programName)

char *programName ;

{ int sizes[2] ;

int allocSizes[2] ;

int numInSites[2] ;

char hold[81] ;

int i ;

void *compressed ;

int total ;

for ( i = 0 ; i < TotalInputs ; i++ )
    {
        sizes[0] = Y_01_Length[i] ;
        sizes[1] = Y_02_Length[i] ;
        numInSites[0] = numInSites[1] = -1 ;
        allocSizes[0] = allocSizes[1] = -1 ;
/*
** Lets get a compressed version of the dead products before we write it out
** to file.
*/
        compressed = CS_PRDCT_BITSET_CREATE_BIT_STRING(

```
                    Dead_Products,
                    BitMapStartPoint[i],
                    2,
                    sizes,
                    sizes,
                    &total);
    WriteOutCheckPointFile(OutputCheckpointNames[i],
            MasterFile ? InputNames[i]
                    : MasterFile_Bitset[i],
            MasterFile ? InputStartRec[i]
                    : StartRec_Bitset[i],
                    programName,
                    Good_Products,
                    BitMapStartPoint[i],
                    2,
                    sizes,
                    allocSizes,
                    Selections[i],
                    numInSites,
                    total,
                    compressed);
    CS_PRDCT_BITSET_DESTROY_BIT_STRING(compressed);
        }
    }
} int main( argc, argv )
/*+E
 *
 */
int     argc;
char    **argv;
```

```c
{
    long        startTime,
                totalTime,
                finishTime;
    int numFiltered ;
    int numEliminated ;
    int tmp ;
    char comline[2048];
/***
*** Establish handler for a user interrupt.
***/
    signal( SIGINT, UserHitControlC);
#ifdef SIGHUP
    signal( SIGHUP, UserHitControlC);
#endif
/*
** Initialize variables.
*/
    Distance = 0.240;
    if( !ParseArguments( argc, argv ) )
        goto SyntaxError;
    if( !OpenOutputFile() ) goto FailureExit;
/*  if (!RestartState()) goto FailureExit; */
    time( &startTime );
    Visual((stderr,"Begin reading files: %s",ctime(&startTime)));
/* Let's actually do something now */
    if (!ReadEverything(NoMorehitsPlease))   goto FailureExit;
        time( &finishTime );

Visual((stderr,"Begin filtering: %s",ctime(&finishTime)));
    if (!FilterProducts(&InputData,&RangeValuesData,&OneOfValuesData,&numFiltered,IsItMissingAValue))
```

```
        goto FailureExit;
    CurrentInput = 0 ;
    time( &finishTime );
    Visual((stderr,"Filtered out %d out of %d possible products\n",numFiltered,
TotalProducts ));

#if 0
/*
** Now see if there are any hitlists or databases that you should filter
** for.
*/
    time( &finishTime );
    Visual((stderr,"Begin eliminating selections in Unity database
%s",ctime(&finishTime)));
        if ( !EliminateProductsFromDatabase(DatabaseNames,
                                            &numEliminated,
                                            ZapAllNeighbors))
            goto FailureExit;
    time( &finishTime );
    time( &finishTime );
    Visual((stderr,"Begin eliminating selections in Unity hitlist
%s",ctime(&finishTime)));
        if ( !EliminateProductsFromHitlist(HitlistNames, ScreenFileName?ScreenFileName:DefaultScreenFileName,
                                           &tmp,
                                           ZapAllNeighbors))
            goto FailureExit;
    time( &finishTime );
    Visual((stderr,"Eliminated %d out of %d possible products\n",numEliminated+tmp,
TotalProducts ));
#endif
            Visual((stderr,"Begin selection: %s",ctime(&finishTime)));
```

```
if (!UserAborted &&
    !SelectEverything(InputSource,
                      NoMorehitsPlease,
                      WhatFirst,
                      CalcualteProductFingurePrint,
                      ActuallyCompute,
        ZapAllNeighbors)) goto FailureExit;
CloseOutputFile();
time( &finishTime );

totalTime = finishTime - startTime;
if( !totalTime ) totalTime = 1;
Visual((stderr, "Created %d Selections in ", nProcessed ));
Visual((stderr,"%d Hours, %d min, %d secs\n",
        totalTime/(60*60),
        (totalTime%(60*60))/60,
        (totalTime%60)));
Visual((stderr,"Each comparison required %.8f seconds to calculate\n",
        (totalTime/((double)(nProcessed?nProcessed:1)))));

Visual((stderr,"End Quick Select Computation: %s",ctime(&finishTime)));
MakeComLine(comline, 2048, argc, argv);
CheckPointProgram(comline);
UserAborted ? exit(ErrorExit) : exit(GoodExit);
SyntaxError:
    exit(1);
FailureExit:
    exit(ErrorExit);
}
```

Appendix "M"

```
/********************************************************************/
/*                    listbitset                                    */
/********************************************************************/
#include <stdio.h>
include <signal.h>
#include <ctype.h>
#include <unistd.h>
#include <string.h>
#include <sys/stat.h>
#include <math.h>
#include "parseopt.h"
#include "utl_str.h"
#include "utl_mem.h"
#include "utl_file.h"
#include "utl_math.h"
#include "ct.h"
#include "ct_expr.h"
#include "ct_proto.h"
#include "import_proto.h"
#include "io_fprint.h"
#include "hits.h"
#include "hits_proto.h"
#include "commonData.h" /* Globals use by most functions, we will clean this
                          up soon */
#include "dbcsln_bs_proto.h"
#include "dbcsln_hlm_proto.h"
extern char *basename() ;
extern char *DB_CT_CCT_FIX_SLN();
```

```c
typedef enum
{
    HeaderOnly,
    FullListing,
    DetailListing,
    Hitlist
} ListingOptions ;
static char *OptionsNames[] = { "header", "full", "detail" , "str_list" } ;
static ListingOptions listOption = HeaderOnly ;
static char *HitlistFile ;
static char *BitsetFile ;
static int      UserAborted;
static char     *CombNameTemplate= (char *)NULL ;
static int      CombCounter;
char *HitlistName  = "listbitset.hits" ;
FILE  *HitFile ;
static char *Prefix ;
static struct ParseOptions Options[] =
{
/***
*** DO NOT MOVE ENTRIES IN THIS TABLE.  ADD ENTRIES ONLY AT THE END.
***/
    {"hitlist",    ParseOptString,        &HitlistFile,
        "Name is the file with hitlist records. ie. xxxxx.hits file" },
    {"bitset",     ParseOptString,        &BitsetFile,
        "Name is the bitset file . ie. xxxxx.csr file" },
    {"list",       ParseOptEnum,          (void *)OptionsNames ,
        "Type of output" },
    {"output",     ParseOptString,        &HitlistName,
        "Name is the file with hitlist records. ie. xxxxx.hits file" },
    {"prefix",     ParseOptString,        &Prefix,
        "Prefix for naming the products.Product name will be Prefix_Y01_Y02_n"},
```

};

static void UserHitControlC()
/*+I
*
* This function is the signal handler for user initiated program termination.
* It's only role is to set a flag indicating that the user wishes to abort the program.
*
* Author     Date           Description
* ======     ========       ============
* G. B. Smith    02-09-93    Original Version
*
*/
{
    UserAborted = 1;
} static int ParseArguments( argc, argv )
/*+I
*
* This function parses the command line arguments.
*
* Returns: 1 on a successful command line parse, 0 otherwise.
*
* Warnings:
*
* Errors:
*
* See Also:
*
*

```
* Author      Date          Description
* ======      ========      ===========
* G. B. Smith 02-09-93      Original Version
*
*/
int     argc;
char    **argv;
{
char *fileTypeName ;
        int     nargs,
                noptions = sizeof( Options )/sizeof(Options[0]);
        nargs = UTL_PARSE_OPT( argc, argv, noptions, Options );
        if( !nargs ) goto SyntaxError;
        fileTypeName = *((char**)Options[2].value);
        if( !strcmp( "detail", fileTypeName ))
                listOption = DetailListing;
        else if( !strcmp( "full", fileTypeName ))
                listOption = FullListing;
        else if( !strcmp( "str_list", fileTypeName ))
                listOption = Hitlist;
        else
                listOption = HeaderOnly;
        return 1;
SyntaxError:
        return 0;
} int CallbackFunc(ct,numAttachments,indexes)
struct CtConnectionTable *ct ;
int numAttachments ;
int indexes[] ;
{
        static char *sln = 0;
```

```
        static char nameBuffer[41];
CombCounter += 1;
    if ( CombNameTemplate && *CombNameTemplate )
        {
            if ( !DB_CT_CT_ATTR_EXISTS( ct, CtCtName ) &&
                 !DB_CT_CT_ATTR_EXISTS( ct, CtCtRegId ))
                {
                    (void)sprintf( nameBuffer, "%.30s_%d_%d_%0d", CombNameTemplate,
                                                                indexes[0],
                                                                indexes[1],
                            CombCounter);
                    if (!DB_CT_SET_CT_ATTR( ct, CtCtName, nameBuffer ))
                            goto trc;
                }
        }
    if ( sln = DB_CT_SLN_GENERATE( ct ))
    {
    fprintf( (FILE*)HitFile, "%s\n", sln );
            UTL_MEM_FREE( sln );
    }
    else {
            if ( UTL_ERROR_IS_SET())
                    goto trc;
    }
    return 1;
trc: UTL_ERROR_ADD_TRACE( "CallbackFunc" );
    return 0;
} static struct HitsHitList *CreateHitlist( hName, cSln, core )
char *hName;
```

```
char *cSln;
char *core;
{
    struct HitsHitList *hitlist;
        char *bname;
        int  len;

hitlist = DB_HITS_CREATE( "STRLIST" );
        if ( !hitlist ) goto trc;
        if (!hName || !*hName ) hName = "SCRATCH";
        bname = (char *) basename( hName, (char*)0 );
        DB_HITS_SET_ATTR( hitlist, HitsAttrName, bname );
        if ( Prefix )
        {
                CombNameTemplate = UTL_STR_SAVE(Prefix);
        }
        else
        {
            if ( ! CombNameTemplate && bname )
            {
                CombNameTemplate = bname;
                for (len = 0, bname = CombNameTemplate+1; *bname; ++bname, ++len )
                {
                    if ( !isalnum( *bname ) || len == 36 )
                    {
                        *bname = 0;
                        break;
                    }
                }
            } else {
                if (bname) UTL_MEM_FREE(bname);
            }
```

```
    }
    DB_HITS_SET_ATTR ( hitlist, HitsAttrFilename, hName );
    DB_HITS_SET_ATTR (hitlist, HitsAttrDatabase, "NONE" );
    DB_HITS_SET_ATTR ( hitlist, HitsAttrSource, "SLN_EXPLODER" );
    if ( cSln && *cSln)
        DB_HITS_SET_ATTR ( hitlist, HitsAttrQuery, cSln );

if ( core && *core )
        DB_HITS_SET_ATTR ( hitlist, HitsAttrCore, core );

DB_HITS_SYNC_FILE( hitlist, hName, (void*)0 );
    return hitlist;

trc: UTL_ERROR_ADD_TRACE( "CreateHitlist" );
    return 0;
}

DumpBitsetInfo(char *bitsetName,int bIndex,char *core )
{
void *bitset ;
int numProducts ;
int *sizes= (int *)NULL ;
int *numUsed= (int *)NULL ;
int i ;
char *masterName ;
int masterRec ;
char *coreInfo ;
char *xrString ;
int numSites ;
char **xNames ;
char *bName ;
char *newCore ;
char *cp ;
```

```
char buffer[1024] ;
int  **productIndexes ;
void *c ;
struct HitsHitList *h, *CreateHitlist();
char *fixedCore ;
    if ( !(bitset = CS_PRDCT_BITSET_OPEN(bitsetName,bIndex)))
    {
        fprintf(stderr,"Unable to open %s %d\n",bitsetName,bIndex);
        return 0 ;
    }
    if (!CS_PRDCT_BITSET_GET_STATS(bitset,
                                              &numSites,
                                              &numProducts,
                                              &sizes,
                                              &numUsed))
    {
        fprintf(stderr,"Unable to get stat on %s %d\n",bitsetName,bIndex);
        return 0 ;
    }
    if ( numProducts == -1 )
        numProducts = 0 ;
    if ( ! core )
    {
        CS_PRDCT_BITSET_CORE_INFO(bitset,
                                              &masterName,
                                              &masterRec,
                                              &coreInfo ,
                                              &xrString,
                                              &numSites,
                                              &xNames);
        newCore = Replace_Y_0x_With_Xx(coreInfo);
    }
    else
```

```
        {
                newCore = Replace_Y_0x_With_Xx(core);
        }
        if ( listOption == Hitlist )
        {
                fixedCore = DB_CT_CCT_FIX_SLN(newCore,1);
            if (!(h = CreateHitlist( HitlistName, "query_sln", "core_sln")))
                    return 0;
            if (!(HitFile = fopen(HitlistName,"a")))
                    return 0;
/*
** Allocate the arrays.
*/
        productIndexes = (int **)UTL_MEM_CALLOC(numSites,sizeof(int *));
        for ( i = 0 ; i < numSites ; i++ )
        {
            productIndexes[i] = (int *)UTL_MEM_CALLOC(numProducts,sizeof(int ));
        }
/*
** Figure out what indexes compose a product.
*/
                CS_PRDCT_BITSET_GET_HITS(bitset,productIndexes);
/*
        productIndexes[0][nProcessed] = Y_01 ;
        productIndexes[1][nProcessed] = Y_02 ;
*/
        c = (void *) DB_CT_CCT_GET_PRD_INIT(fixedCore,
                                            xrString,
                                            numSites,
                                            xNames);
        if ( !c )
        {
                fprintf(stderr,"\nUnable to init");
```

```
            return -1 ;
    }
    DB_CT_CCT_GET_PRD_PRODUCT(c,
                                numProducts,
                                productIndexes,
                                CallbackFunc) ;
    DB_CT_CCT_GET_PRD_CLEANUP(c);
    DB_HITS_CLOSE( h );
    if ( CombNameTemplate )
        UTL_MEM_FREE( CombNameTemplate ),
    CombNameTemplate = 0;
    fclose(HitFile);

}
    else
    {
    fprintf(stdout,"%s %d\n",bitsetName,bIndex);
    cp = strtok(newCore,"<");
    bName = basename(bitsetName,NULL);
    if ( cp )
        sprintf(buffer, "%s<CS_PRD_BITSET_FILE=\"%s\";CS_PRD_BITSET_OFFSET=\"%d\">",
            cp,bName,bIndex);
    else
        sprintf(buffer, "%s<CS_PRD_BITSET_FILE=\"%s\";CS_PRD_BITSET_OFFSET=\"%d\">",
            newCore,bName,bIndex);
    fprintf(stdout,"%s\n",buffer);

fprintf(stdout,"Num Products : %d of %d\n",numProducts,sizes[0]*sizes[1]);
    for ( i = 0 ; i < numSites ; i++ )
```

```
            fprintf(stdout,"Num Y_0%d : %d of %d\n",i+1,numUsed[i],sizes[i]);
        if ( ( listOption == FullListing ) || ( listOption == DetailListing ) )
            CS_PRDCT_BITSET_DUMP(bitset);
        return 1 ;
        }
    }
}

CheckPointProgram()
{
        fprintf(stderr,"CheckPointProgram() is a lonely stub in listbitset.c!\n");
} int main( argc, argv )
/*+E
 *
 */
int     argc;
char    **argv;
{
int totalHits ;
int i ;
int j ;
int hId ;
int bIndex ;
char bitsetName[1024] ;
char hold[81];
char *cp ;
char *pRet ;
char *dir ;
char *fullPath ;
int n ;
char *core ;
/***
```

```
*** Establish handler for a user interrupt.
***/
        signal( SIGINT, UserHitControlC);
#ifdef SIGHUP
        signal( SIGHUP, UserHitControlC);
#endif
        if( !ParseArguments( argc, argv ) )
                goto SyntaxError;
        if ( !HitlistFile && !BitsetFile )
        {
                fprintf(stderr,"An input (bitset or hitlist) file is required\n");
                goto SyntaxError ;
        }
        if ( HitlistFile )
        {
                if ( !(hId = CS_HLM_OPEN_HITLIST(HitlistFile)) )
                        goto UnableToOpenHitlist ;
                dir = dirname(HitlistFile);
                totalHits = CS_HLM_GET_HITS_TOTAL(hId) ;
                for ( i =0 ; i < totalHits ; i++ )
                {
                        pRet = CS_HLM_GET_HITS(hId, i, 1);
/*
** Grab the bitset file name and the offset from the csln.
*/
                        cp = strstr(pRet,"CS_PRD_BITSET_FILE=");
                        if ( !cp )
                                goto InvalidCsln ;
                        cp += 20 ;
                        j = 0 ;
                        while ( *cp != '"' )
                                bitsetName[j++] = *cp++ ;
                        bitsetName[j] = 0 ;
```

```
                cp = strstr(pRet,"CS_PRD_BITSET_OFFSET=");
                if ( !cp )
                        goto InvalidCsln ;
                cp += 21 ;
                j = 0 ;
                while ( *cp != ';' )
                        hold[j++] = *cp++ ;
                hold[j] = 0 ;
                bIndex = atoi(hold);
                if ( dir )
                        fullPath =
UTL_FILE_ADD_DIR_TO_DIRSPEC(dir,bitsetName);
                else
                        fullPath = bitsetName ;
                core = strtok(pRet,"\n");
                core = strtok(NULL,"\n");
                DumpBitsetInfo(fullPath,bIndex,core);
            }
        }
        else
        {
                n = CountBitSets(BitsetFile);
                for ( i = 0 ; i < n ; i++ )
                        DumpBitsetInfo(BitsetFile,n,NULL);
        }
        UserAborted ? exit(ErrorExit) : exit(GoodExit);
SyntaxError:
        exit(1);
FailureExit:
UnableToOpenHitlist :
InvalidCsln :
        exit(ErrorExit);
}
```

Appendix "N"
CODATA

```c
#include <stdio.h>
include <signal.h>
#include <ctype.h>
#include <unistd.h>
#include <string.h>
#include <sys/stat.h>
#include <math.h>
#include "parseopt.h"
#include "utl_str.h"
#include "utl_mem.h"
#include "utl_file.h"
#include "utl_math.h"
#include "ct.h"
#include "ct_expr.h"
#include "ct_proto.h"
#include "import_proto.h"
#include "io_fprint.h"

#include "dservTypes.h"

#if 0
int     NumRangeFields ;
int     NumRangeFieldsAllocated ;
RangeStruct *RangeFields ;

int         NumOneOfFieldsAllocated ;
int         NumOneOfFields ;
OneOfStruct *OneOfValues ;

float **RangeValues_Y01 ; /* Actual values read in from  nnn.X1 file, if MW is the first
``` and logp is the second value specified on the -rangevar argument list then RangeValues_Y01[n][0] would keep the value for MW for the nth line in the nnn.X1 file and RangeValues_Y01[n][1] would keep the value for logp for that line*/ float **RangeValues_Y02 ; /* same */ int **OneOfValues_Y01 ; /*Actual values read from nnn.X1 files but translated into an index of OneOfValues[i].values so we dont have to waist memory and time doing strcmp*/int **OneOfValues_Y02 ; /* Same */
endif

```
int  TotalInputs = 0 ;
int  CurrentInput = 0 ;
FILE *fileHandles[255] ;
char *InputNames[255] ;
int  Y_01_Length[255] ;
int  Y_02_Length[255] ;
int  BitMapStartPoint[255] ;
int  RemainingInput[255] ;
```

/*************************************************************************
**/
FILE            *OutputFile;

FILE            *InputSourceFile;

/* Code presumes that an int is 32 bits, ASCII-ed into %.8x format */
```
int         **Y_01;   /* fingerprints */
int         **Y_02;   /*     "       */
```

```
int            *query;              /*        "              */
int            nY_01;               /* number of structures */
int            nY_02;               /*        "              */
int            *cY_01;              /* cardinality of fingerprints */
int            *cY_02; /*           "              */
int            c_query;/*           "              */
int            *iY_01; /* intersection count of fprints */
int            *iY_02; /*           "              */ unsigned char  **X_01; /* topomers */
unsigned char  **X_02; /*          "    */
double         *iX_01; /* distance of topomers to selection */
double         *iX_02; /*          "    */ int            *Good_1;
int            *Good_2;
int            *Dead_1;
int            *Dead_2;
int            *Good_Products;
int            *Dead_Products;

int            nbits[256];
int            BigBits[65536];
int            setbits[8];
double         boundary[16];
double         Dist[16][16];

double         Distance = 80.0 ;
int            XytesPerFingerPrint[2] ;

int            nProcessed = 0;
int            SomeLeft;
```

801                                    802
char            next8[10] = "01234567\0";
char            next2[10] = "01\0";

char            *ScreenFileName;
char            DefaultScreenFileName[32] ="$TA_MOLTABLES/standard.2DRULES";

long            waste_time, trash_time, inTestBit, inActually;

Appendix "O"
DB_UTL

```c
#include <stdio.h>
include <signal.h>
#include <ctype.h>
#include <unistd.h>
#include <string.h>
#include <sys/stat.h>
#include <math.h>
#include "parseopt.h"
#include "utl_str.h"
#include "utl_mem.h"
#include "utl_file.h"
#include "utl_math.h"
#include "ct.h"
#include "ct_expr.h"
#include "ct_proto.h"
#include "import_proto.h"
#include "io_fprint.h"

#include "commonData.h" /* Globals use by most functions, we will clean this
                          up soon */ static  int        What1 = -1;
static  int        What2 = 0 ;

static int   (*CalcFingerPrintFunc)();
static int   (*ActuallyComputeFunc)();

extern FILE *debugFile ;

int CountLines(fp)
```

```
FILE *fp ;
{
int i;
char *foo;

i=0;
while ( -1 != UTL_SCAN_GETS( fp, "\\", "#", &foo)) i++;

rewind(fp);
return i;
} int SelectEverything(inputSource,maxHits,whatFirst,calcFP,computeFP,zapNeighbors)
char  *inputSource ;
int   maxHits ;
char  *whatFirst ;
int   (*calcFP)();
int   (*computeFP)();
int   (*zapNeighbors)();

{
  int cqt, q_lo, q_hi, i, j, carhold, inthold, onion, intsc;
  double max;
int k ;
int Y_01_Offset, Y_02_Offset ;
 int pos ;
 int numZapped = 0 ;

CalcFingerPrintFunc = calcFP ;
        ActuallyComputeFunc = computeFP ;
  while (nProcessed < maxHits && ( SomeLeft > 0 ) )
  {
/*
```

```
** What we would like to do is first select any selections that were found
** in a previous run.
*/
        if ( !inputSource || !( c_query = SelectFromInputFile(inputSource,query)) )
        {
                if (! (c_query =  SelectIt(query,whatFirst) ))           return 0;
                nProcessed++;
                SomeLeft--;
                RemainingInput[CurrentInput]-- ;
        }

/* then zap its neighbors and continue! */

(*zapNeighbors)(NULL,0,&numZapped,1,What1,What2);

} /* while still stuff  left */
  return 1;
} int TestBit(bitset, bit)
int *bitset, bit;
{
  int what, this;
  unsigned char *bytes;

bytes = (unsigned char *) bitset;

what = bit % 8;
  this = bit / 8;
  return (bytes[this] & setbits[what] );
}
```

```c
int ZapInputProduct(inputIndex,whichProduct,index1,index2)
int inputIndex ;   /* which input are we currently processing */
int whichProduct;  /* This will be a direct index into the bitmap vector */
int index1 ;       /* if whichProduct is not given we will calcualte it */
int index2 ;       /* from these two values */
{
        if ( !whichProduct )
                whichProduct = index1 * Y_02_Length[inputIndex] + index2 ;

whichProduct += BitMapStartPoint[inputIndex] ;

FlagProduct(Dead_Products,index1, index2, whichProduct );

SomeLeft-- ;
        RemainingInput[inputIndex]-- ;
} int FlagProduct(TheProducts, index1,index2, this)
int *TheProducts;
int index1,index2, this;
{
 int what;
 unsigned char *Products;

/*      if (DebugLevel)
                printf("%d %d, %d, %x\n",index1,index2,this,TheProducts);*/
 Products = (unsigned char *) TheProducts;

if (!this ) this = index1*Y_02_Length[CurrentInput] + index2;      /* bit index */
 what = this % 8;
 this /= 8;
```

```
    Products[this] |= setbits[what];
    return 1;
} int FlagReagent(TheReagent, size, index)
int *TheReagent;
int size, index;
{
    int what, this;
    unsigned char *Reagent;

Reagent = (unsigned char *) TheReagent;

what = index % 8;
    this = index / 8;
    Reagent[this] |= setbits[what];
    return 1;
} int SelectFromInputFile(inputSource,query)
char *inputSource ;
int  *query ;
{
static int firstTime = 1 ;
static FILE *fp = (FILE *)NULL ;

unsigned char *p, *q ;
    int index1;
    int index2;
    int index ;
    char *line ;
```

```
char *cp ;

unsigned char *queryPtr ;

int which ;

int i ;

char *name = (char *)NULL ;

char hold[81];

int OldIndex ;

int Y_01_Offset , Y_02_Offset ;

OldIndex = CurrentInput ;

if ( firstTime )
    {
        if ( !(fp = fopen(inputSource,"r")))
            goto UnableToOpenFile ;
        firstTime = 0 ;
    } if (-1 == UTL_SCAN_GETS( fp, "", "", &line)) return 0;

if ( !( cp = strtok(line," ")) )
        goto UnableToParseLine ;
/*
** Hold on to this for now.
*/
    name = UTL_STR_SAVE(cp);

if ( !( cp = strtok(NULL," ")) )
        goto UnableToParseLine ;

index1 = atoi(cp) - 1 ;
```

```
        if ( !( cp = strtok(NULL," ")) )
                goto UnableToParseLine ;
        index2 = atoi(cp) - 1 ;

if (( index1 < 0 ) || ( index2 < 0 ))
                goto UnableToParseLine ;
/*
** Must get the input from a file that we are processing now to work.
*/
        for ( CurrentInput = -1 , i = 0 ; i < TotalInputs ; i++ )
        {
#if 0
                which = index1 * Y_02_Length[i] + index2 ;
                sprintf(hold,"%s%d", InputNames[i], which+1) ;
                if ( UTL_STR_CMP_NOCASE(name,hold) == 0 )
                {
                        CurrentInput = i ;
                        break;
                }
endif
                if ( UTL_STR_NCMP_NOCASE(name,InputNames[i],strlen(InputNames[i]))
== 0 )
                {
                        CurrentInput = i ;
                        break;
                }
        }
        if ( i >= TotalInputs )
                goto InvalidInput ;
/*
** If we are reading back in a selection that might have already been filtered
** out we better adjust our counts.
```

```
*/
    if (!TestBit(Dead_Products,
                 BitMapStartPoint[CurrentInput] +
                     index1 *Y_02_Length[CurrentInput] + index2 ))
    {
        nProcessed++;
        SomeLeft--;
        RemainingInput[CurrentInput]-- ;
    }

Y_01_Offset = Y_02_Offset = 0 ;
    for ( i = 0 ; i < CurrentInput ; i++ )
    {
        Y_01_Offset += Y_01_Length[i] ;
        Y_02_Offset += Y_02_Length[i] ;
    } c_query = (*CalcFingerPrintFunc)(query,
                                                    Y_01[index1 +
Y_01_Offset ],
                                                    Y_02[index2 +
Y_02_Offset ]);

#if 0
    p       = (unsigned char *) Y_01[index1];
    q       = (unsigned char *) Y_02[index2];
    c_query = 0;
    queryPtr = (unsigned char *)query ;

for (index=0;index<BytesPerFingerPrint;index++,queryPtr++)
    {
        *queryPtr = *p++ | *q++ ;
```

```
                c_query += nbits[*queryPtr & 255];
        }
endif

OutputThisHit(index1,index2); /* both print it and note it in bitsets */

CurrentInput = OldIndex ; /* reset this back to the begining */
        if ( name )
                UTL_MEM_FREE(name);
        return c_query;

UnableToParseLine :
        fprintf(stderr,"Unable to Parse %s\n",line);
        return 0 ;
UnableToOpenFile : .
        fprintf(stderr,"Unable to open file %s\n",inputSource);
        return 0 ;
InvalidInput :
        fprintf(stderr,"Input %s does not match one of the -prefix files\n", name);
        return 0 ;
}

CountFingerPrintBits(fingerPrint,length)
int *fingerPrint ;
int length ;
{
int i ;
int count = 0 ;

for ( i = 0 ; i < length ; i++ )
        {
```

```
                count += nbits[fingerPrint[i] & 255];
        } return count ;
}

/* Here the intent is to select the next compound "intelligently".
   We try to maximize use of one or the other reagent.
*/
int SelectIt(query,whatFirst)
int *query;
char *whatFirst ;
{
  int i,j;

if (What1 < 0) {GrabRandom( &i, &j, query); goto out; } switch (whatFirst[0])
  {
    case '0':
                GrabRandom( &i, &j, query);
                break;
    case '1':
                GrabThis( &i, &j, 1, query);
                break;
    case '2':
                GrabThis( &i, &j, 2, query);
                break;
  } out:
    OutputThisHit(i,j); /* both print it and note it in bitsets */
```

```
    return c_query;
} int GrabThis( p1, p2, type, fp)
int *p1, *p2, type, *fp;
{
  unsigned char *p, *q, *pro;
  int index;
  int Y_01_Offset , Y_02_Offset ;
  int i ;

int NY02 ;

int NY01 ;

while ( CurrentInput < = TotalInputs )
  {
/*
** Process each one of the inputs walking down the data array.
*/
        NY02 = Y_02_Length[CurrentInput] ;
        NY01 = Y_01_Length[CurrentInput] ;
    switch (type)
    {
      case 1:

if (!findOne(Dead_Products, What1*NY02, 1, NY02) &&
                    !findOne(Dead_Products, What2 , NY02, NY01) &&
                    !GrabRandom( p1, p2, fp)   )
                {
                        CurrentInput++ ;
                        continue ;
                }
```

```
                break;
        case 2:
                if (!findOne(Dead_Products, What2 , NY02, NY01) &&
                    !findOne(Dead_Products, What1*NY02, 1, NY02) &&
                    !GrabRandom( p1, p2, fp)   )
            {
                        CurrentInput++ ;
                        continue ;
            }
                break;
    }
/*
** If we are at the end of this input set, we need to advance to the
** next one.
*/
        if ( ( What1 >= Y_01_Length[CurrentInput] ) ||
             ( What2 >= Y_02_Length[CurrentInput] ) )
        {
                What1 = 0 ;
                What2 = 0 ;
                CurrentInput++ ;
                continue ;
        }
    break;
    }
    if ( CurrentInput == TotalInputs )
        return 0 ;

*p1 = What1; *p2 = What2;

Y_01_Offset = Y_02_Offset = 0 ;
    for ( i = 0 ; i < CurrentInput ; i++ )
    {
```

```
      Y_01_Offset += Y_01_Length[i] ;
      Y_02_Offset += Y_02_Length[i] ;
  } c_query = (*CalcFingerPrintFunc)(fp,
                                                                  Y_01[What1 +
Y_01_Offset ],
                                                                  Y_02[What2 +
Y_02_Offset ]);
#if 0
  pro = (unsigned char *) fp;
  p   = (unsigned char *) ( Y_01[What1 + Y_01_Offset] ) ;
  q   = (unsigned char *) ( Y_02[What2 + Y_02_Offset] ) ;

c_query = 0;
  for (index=0;index<BytesPerFingerPrint;index++,pro++)
  {    *pro = *p++ | *q++ ;
       c_query += nbits[*pro & 255]; }
#endif
  return 1;
}

/* This can be done more efficiently when we KNOW we are walking a vector */
int findOne(bitset,start,incr,max)
int *bitset, start, incr, max;
{
  static int oldstart = -1234,
             oldincr,
             old_i;
  int i;

if ( (start != oldstart) || (incr != oldincr) ) old_i = -1 ;
  oldstart = start; oldincr = incr;
```

```
old_i ++;
start += incr * old_i;
for (i=old_i;i<max;i++, start += incr )
{
  if ( TestBit(bitset, BitMapStartPoint[CurrentInput] + start)) continue;
  What1 = start / Y_02_Length[CurrentInput] ;
  What2 = start % Y_02_Length[CurrentInput] ;
  old_i = i;
  return 1;
}
oldstart = -1234;
return 0;
}

/*
**+E:
**
**
** Abstract    : Function will randomly select a product from the current
**               input file, if there are no more selections left in the
**               current input then the next one is searched.
**
**               Currently we deal with two reaction sites(two points of
**               variability Y1 and Y2). A product is one of possible
**               combination of Y1.Y2.
**               The bit maps that are used to track the selections/eliminated
**               products are a vector of length numY01*numY02, where every
**               bit represents a product. Since we are dealing with multiple
**               slns then we just use one bitmap vector and string the
**               representations for a set of product together.
**
**               [ reaction1(csln1) products][reaction2(csln2) products] ...
```

```
**
**              where each reaction products are layed out in a row major
**              format :
**
**              Y1(0).Y2(0), Y1(0).Y2(1) .. |Y1(1)Y2(0),Y1(1)Y2(1)...
**
** Usage       :
**
** Returns     : 1 on success, 0 for failure.
**
** Algorithms  : None.
**
** Revision History :
**
   Modified to work with multiple csln
**                              processing and documented.
**
**-E:
*/
int GrabRandom( p1, p2, fp)
int *p1, *p2, *fp;
{
  int index, sum;
  int i ;
  int value1, value2;
  unsigned char *p, *q, *pro;

int byteOffset, bitsToSkip ;
  int Y_01_Offset , Y_02_Offset ;
  fpt f ;
/*
** Lets start at the begining portion of the bitmap for this input, our products
** are layed out like :
```

```
**
**
** global varaible CurrentInput tells us which reaction we are look at now
** and BitMapStartPoint[] has the starting points in the bitmap for each
** input.
*/

/*
** We know how many products are left in the current input, if we get to
** zero here we need to move on to the next input set.
*/
    for ( i = CurrentInput ; i < TotalInputs ; i++ )
        if ( RemainingInput[CurrentInput] > 0 )
            break;
        else
            CurrentInput++ ;
    if ( CurrentInput >= TotalInputs )
        return 0 ;
/*
** Figure out which byte in the bitmap the products for this input start.
**/
    byteOffset = BitMapStartPoint[CurrentInput] / 8 ;

p = (unsigned char *) ( Dead_Products );
    p += byteOffset ;
    index = (( f = UTL_MATH_RAND()) * RemainingInput[CurrentInput]) + 1 ;

value1 = sum = 0;

while (sum < index)
    {
        sum += nbits[ ~(*p++) & 255];
```

```
        value1 += 8;
    } p -= 1; sum -= nbits[ ~(*p) &255 ]; value1 -= 9; value2 = (~(*p) & 255);
    while (sum < index)
    {
        value1++;
        if ( value2 & 1)
                sum++;
        value2 = value2 >> 1;
    }
/*
** We found where our random(not selected) product is, now we need to go
** back so many bits to be able to translate the address in a one dimentional
** bitmap vector into a 2D index.
** (This is becuase our bitmap representation for this input did not start
** from 0(or a byte boundary).
*/
    bitsToSkip = BitMapStartPoint[CurrentInput] - ( byteOffset * 8 )  ;

value1 -= bitsToSkip ;
    What2 = ( value1 ) % Y_02_Length[CurrentInput];
    What1 = ( value1 ) / Y_02_Length[CurrentInput] ;

*p1 = What1 ;
    *p2 = What2 ;
/*
** Find out where the values for this product is.
*/
    Y_01_Offset = Y_02_Offset = 0 ;
    for ( i = 0 ; i < CurrentInput ; i++ )
    {
        Y_01_Offset += Y_01_Length[i] ;
```

```
      Y_02_Offset += Y_02_Length[i] ;
} c_query = (*CalcFingerPrintFunc)(fp,
                                               Y_01[What1 +
Y_01_Offset ],
                                               Y_02[What2 +
Y_02_Offset ]);
#if 0
 pro = (unsigned char *) fp;
 p   = (unsigned char *) ( Y_01[What1 +  Y_01_Offset ] ) ;
 q   = (unsigned char *) ( Y_02[What2 +  Y_02_Offset ] ) ;

/*
** Calculate the approximate fingure print by ORing the fingure print
** for the two pieces.
*/
 c_query = 0;
 for (index=0;index<BytesPerFingerPrint;index++,pro++)
 {     *pro = *p++ | *q++ ;
       c_query += nbits[*pro & 255]; }
#endif
  return 1;
} int OutputThisHit( index1, index2)
int index1, index2;
{
 int which;

which = index1 * Y_02_Length[CurrentInput] + index2;
 fprintf(OutputFile,"%s%d %d %d\n", InputNames[CurrentInput], which+1,
```

```
            index1+1 ,index2+1);
  which = BitMapStartPoint[CurrentInput] + index1 *Y_02_Length[CurrentInput]
+index2 ;
  FlagProduct(Good_Products,0,0, which);
  FlagProduct(Dead_Products,0,0, which);   /* can only be selected once */
        /* note use of reagents; this is slightly wasteful of time */
  FlagReagent(Good_1, nY_01, index1);
  FlagReagent(Good_2, nY_02, index2);

fflush(OutputFile);
  return 1;
} int DumpBitSet(bitSet,offset,numY01,numY02)
int *bitSet ;
int offset ;
int numY01 ;
int numY02 ;
{
int i , j ;
unsigned char *Products = (unsigned char *)bitSet ;
int   pos ;
int   byte ;
int   bit ;
int   index1 ;
int   index2 ;

fprintf(stderr,"\n--------------------------------Y_02--------------------------------\n
");
        for ( i = 0 ; i < numY02 ; i++ )
                fprintf(stderr," %3d ",i+1);
        fprintf(stderr,"\n-----------------------------------------------------------------\n
```

```
      ");

for ( i = 0 ; i <  (numY01 * numY02) ; i++ )
            {
                    index1 = i / numY02 ;
                    index2 = i % numY02 ;

byte = ( i + offset ) / 8 ;
                    bit  = ( i + offset ) % 8 ;

if ((( ( i % numY02 ) == 0 ) )
                            fprintf(stderr,"\n%3d  |",index1+1);
                    fprintf(stderr," %3d ",(Products[byte] & setbits[bit])?1:0 );
            }
            fprintf(stderr,"\n-------------------------------------------------------------------------\n");

} int DumpValues(inputSet,numY01,numY02,computeFunc)
int inputSet ;
int numY01 ;
int numY02 ;
int (*computeFunc)();
{
int i , j ;
int   pos ;
int   byte ;
int   bit ;
int   index1 ;
int   index2 ;
int onion ;
int intsc ;
double max ;
```

```
int Y2_Offset ;
int Y1_Offset ;

fprintf(stderr,"\n---------------------------------Y_02----------------------------------\n
");
        for ( i = 0 ; i < numY02 ; i++ )
                fprintf(stderr," %5d ",i+1);
        fprintf(stderr,"\n-------------------------------------------------------------------------\n
");

for ( Y1_Offset = Y2_Offset = i = 0 ; i < inputSet ; i++ )
{
Y1_Offset += Y_01_Length[i];
Y2_Offset += Y_02_Length[i];
}
        for ( i = 0 ; i < (numY01 * numY02) ; i++ )
        {
                index1 = Y1_Offset + i / numY02 ;
                index2 = Y2_Offset + i % numY02 ;

(*computeFunc)( index1, index2, &onion, &intsc, &max);

if ((( ( index2 - Y2_Offset )== 0 ) )
                        fprintf(stderr,"\n%5d |",index1+1- Y1_Offset );
                fprintf(stderr," %0.3f ",max);
        }
        fprintf(stderr,"\n-------------------------------------------------------------------------\n");

DumpBitSet(Dead_Products,BitMapStartPoint[inputSet],numY01,numY02);
}
```

Appendix "P"

ELIMATE

```
#include <stdio.h>
include <signal.h>
#include <ctype.h>
#include <unistd.h>
#include <string.h>
#include <sys/stat.h>
#include <math.h>
#include "parseopt.h"
#include "utl_str.h"
#include "utl_mem.h"
#include "utl_file.h"
#include "utl_math.h"
#include "ct.h"
#include "ct_expr.h"
#include "ct_proto.h"
#include "import_proto.h"
#include "io_fprint.h"

#include "dservTypes.h"

/*
**+E:
**
**
** Abstract    : Function zapps products who are in the same neighborhood
**              as the SLNs in the Unity hitlist files.
**
**
** Usage       :
**
```

```
** Returns      : 1 on success, 0 on error
**
** Algorithms   : None.
**
** Revision History :
**

**
**-E:
*/
int EliminateProductsFromDatabase(DatabaseNames,numEliminated,zapNeighbors)
char *DatabaseNames ;
int *numEliminated ;
int (*zapNeighbors)();
{
int i ;
char *cp ;
struct IoDataBase    *database  = 0 ;
struct IoFingerPrint *fingerPrint = 0 ;
struct IoFingerPrintInfo   fprintInfo;
struct IoFprintDef        *fprintDef=0;
int          fingerPrintFile ;
int          bytesPerFingerPrint ;
long         slnId ;
char         *databaseDirectory ;
char         *databaseName ;
int          numZapped = 0 ;
int          c_query ;

*numEliminated = 0 ;
    if ( DatabaseNames )
    {
        cp = strtok(DatabaseNames," ");
```

```
                while ( cp )
                {

/*
** Open the database.
*/
                    databaseDirectory = dirname( cp );
                        databaseDirectory = databaseDirectory?databaseDirectory:".";
                        databaseName = basename(cp,(char*)0);

if ( !( database = DB_IO_DBSTART_USER_PSWD(
databaseDirectory,
                                                                    databaseName,
                                                                    "r",
                                                                    NULL,
                                                                    NULL,
                                                                    0,
                                                                    0)) )
                                goto UnableToOpenDatabase ;

if( !(fprintDef = DB_IO_FPDEF_VREAD( database, "standard" )))
                                goto NoSuchScreen;

if ( !DB_IO_FPRINT_GETINFO( database,
fprintDef->fpdFprintDir,
fprintDef->fpdFprintFileName,
                                                                    &fprintInfo ) )
                                goto UnableToGetScreenInfo ;

if( !(fingerPrintFile = DB_IO_FPRINT_OPEN( database,
```

```
                fprintDef->fpdFprintDir, fprintDef->fpdFprintFileName )))
                                                goto NoSuchScreen;

bytesPerFingerPrint = fprintInfo.fpFingerLength / 8 ;
   fprintf(stderr,"Processing database %s %d\n",cp,bytesPerFingerPrint);
                if ( (fprintInfo.fpFingerLength % 8 ) )
                        bytesPerFingerPrint++;

fingerPrint = (struct IoFingerPrint *) UTL_MEM_ALLOC (
                        sizeof (*fingerPrint) + bytesPerFingerPrint + 1 );
/*
** Read all compounds in the database.
*/
                for ( slnId=fprintInfo.fpStartSlnNo;
                        slnId<=fprintInfo.fpLastSlnNo;
                        slnId++ )
                {
                        if ( !DB_IO_FPRINT_READ ( database,
                                                                fingerPrintFile,
                                                                (long) slnId,
                                                                fingerPrint ) )
                                                                goto
UnableToReadFromDatabase;
/*
** Zap all the neighbors in the current run.
*/
                                c_query = CountFingerPrintBits(&fingerPrint->fpPrint,
bytesPerFingerPrint);
fprintf(stderr,"Reading sln %d\r",slnId++);
```

```
            (*zapNeighbors)(&fingerPrint->fpPrint,c_query,&numZapped,0,-1,-1);
                    (*numEliminated) += numZapped ;

}
/*
** CLOSING DATABASES TRASHES MEMORY, DO THIS AFTER YOU CAN SPEND SOME
** TIME TO DEBUG THIS PROBLEM.
** F.S. 05-14-96
*/
#if 0
/*
** Close the database and do it again!
*/
                    DB_IO_DBCLOSE(database);
/*
** Get the next database to process.
*/
                    if ( fingerPrint )
                            UTL_MEM_FREE( fingerPrint );
                    DB_IO_FPRINT_CLOSE( database, fingerPrintFile );
#endif
                    cp = strtok(NULL," ");
            }
        }
        fprintf(stderr,"\n");

return 1 ;

UnableToOpenDatabase :
        fprintf(stderr,"Unable to open database %s\n",cp);
```

```
            goto Error ;
NoSuchScreen:
            fprintf(stderr,"Unable to open screen 'standard'\n");
            goto Error ;
UnableToGetScreenInfo:
            fprintf(stderr,"Unable to read screen information\n");
            goto Error ;
UnableToReadFromDatabase:
            fprintf(stderr,"Unable to read fingerprint for sln id %d\n",slnId);
            goto Error ;
Error :
            return 0 ;
}

/*
**+E:
**
**
** Abstract   : Function zapps products who are in the same neighborhood
**              as the SLNs in the Unity hitlist files.
**
**
** Usage      :
**
** Returns    : 1 on success, 0 on error
**
** Algorithms : None.
**
**

**
**-E:
*/
```

```c
int EliminateProductsFromHitlist(HitlistNames,screenName,numEliminated,zapNeighbors)
char *HitlistNames ;
char *screenName ;
int *numEliminated ;
int (*zapNeighbors)();
{
int i ;
char *cp ;
struct IoFingerPrint *fingerPrint = 0 ;
FILE            *fingerPrintFile = 0 ;
int             bytesPerFingerPrint ;
long            slnId ;
char            *databaseDirectory ;
char            *databaseName ;
int             numZapped = 0 ;
struct          CtConnectionTable *ct;
int             nBitsSet;
char            *sln ;
FILE            *handle ;
int             c_query ;
int        *ScreenStructure;

*numEliminated = 0 ;
    if ( !HitlistNames )
            return 1 ;
/*
** Read in the screen information first.
*/
    if (!(fingerPrintFile = UTL_FILE_FOPEN(screenName,"r")))
            goto UnableToOpenFingureprintFile ;
    ScreenStructure = (int *) DB_BIT2_PARSE_2DSCREEN(fingerPrintFile);
    UTL_FILE_FCLOSE(fingerPrintFile);
```

```
        if (!ScreenStructure)
                goto UnableToReadScreenStructure ;

bytesPerFingerPrint = DB_BIT2_GET_SIZE( ScreenStructure );
fingerPrint = (struct IoFingerPrint *) UTL_MEM_ALLOC( bytesPerFingerPrint);

*numEliminated = 0 ;
if ( HitlistNames )
{
        cp = strtok(HitlistNames," ");
        while ( cp )
        {
                slnId = 0 ;

fprintf(stderr,"Processing hitlist %s\n",cp);

/*
** Open the database.
*/
                if ( !(handle = fopen(cp,"r")) )
                        goto UanbleToOpenHitlist ;

/*
** Read all the hits in the hitlist.
*/
                while ( UTL_SCAN_GETS ( (FILE *) handle, "\\", "#", &sln) != -1
)
                {
                        if (!(ct = DB_IMPORT_SLN(sln)))
                                goto UnableToGetCtFromSln ;
                        memset ( fingerPrint, 0, bytesPerFingerPrint );
                        if( !DB_BIT2_EVALUATE( ct,
                                                ScreenStructure,
```

```
                              fingerPrint,
                              &nBitsSet ))
                    goto UnableToGenerateFingerprint ;
/*
** Zap all the neighbors in the current run.
*/
                    c_query = 0 ;
                    c_query =
CountFingerPrintBits(&fingerPrint->fpPrint,bytesPerFingerPrint);
fprintf(stderr,"Reading sln %d\r",slnId++);

(*zapNeighbors)(&fingerPrint->fpPrint,c_query,&numZapped,0,-1,-1);
                    (*numEliminated) += numZapped ;

}
/*
** Close the database and do it again!
*/
                fclose(handle);
/*
** Get the next hitlist to process.
*/
                cp = strtok(NULL," ");
            }
        }
        fprintf(stderr,"\n");

if ( fingerPrint )
            UTL_MEM_FREE( fingerPrint );

return 1 ;
```

UnableToOpenFingureprintFile :

fprintf(stderr,"Unable to open fingure print file %s\n",screenName);

goto Error ;

UnableToReadScreenStructure :

fprintf(stderr,"Unable read screen info for %s\n",screenName);

goto Error ;

UanbleToOpenHitlist :

fprintf(stderr,"Unable to open hitlist %s\n",cp);

goto Error ;

UnableToGenerateFingerprint:

fprintf(stderr,"Unable to generate fingureprint for \n%s\n",sln);

goto Error ;

UnableToGetCtFromSln:

fprintf(stderr,"Unable to generate ct for \n%s\n",sln);

goto Error ;

Error :

return 0 ;

}

Appendix "Q"
FILTER

```c
#include <stdio.h>
include <signal.h>
#include <ctype.h>
#include <unistd.h>
#include <string.h>
#include <sys/stat.h>
#include <math.h>
#include "parseopt.h"
#include "utl_str.h"
#include "utl_mem.h"
#include "utl_file.h"
#include "utl_math.h"
#include "ct.h"
#include "ct_expr.h"
#include "ct_proto.h"
#include "import_proto.h"
#include "io_fprint.h"

#include "dservTypes.h"

/*
**+E:
**
**
** Abstract    : Function parses range field string for ADS design programs.
**               It takes a string of the form
**               "logp -1.0 8.0 MW 200 500 price 0 12.50" and fills in the
**               global array   RangeFields.
**
**
```

```
** Usage     :
**
** Returns   : 1 on success, 0 for failure.
**
** Algorithms : None.
**
**
**
**-E:
*/
int ParseRangeVar(rangeVar,numRangeFieldsAllocated,numRangeFields,rangeFields)
char   *rangeVar ;
int    *numRangeFieldsAllocated ;
int    *numRangeFields ;
struct RangeStruct **rangeFields;
{
static int stat = 0 ;
char *buffer = (char *)NULL ;
char *name ;
char *low ;
char *high ;
int  i ;

*numRangeFieldsAllocated = 0 ;
    *numRangeFields = 0 ;
    *rangeFields = (struct RangeStruct *)NULL ;

if ( !(buffer = UTL_STR_SAVE(rangeVar)) )
            goto Failure ;

name = strtok(buffer," ");
    while ( name )
    {
```

```
if ( !(low = strtok(NULL," ")) )
        goto UnableToParse ;
if ( !(high = strtok(NULL," ")) )
        goto UnableToParse ;
if ( *numRangeFields >= *numRangeFieldsAllocated )
{
    if ( !*rangeFields )
    {
        if (!(*rangeFields = (struct RangeStruct *)UTL_MEM_CALLOC(
                ALLOCATE_INCREMENT,
                sizeof(struct RangeStruct))))
            goto Failure ;
        else
            *numRangeFieldsAllocated = ALLOCATE_INCREMENT ;
    }
    else
    {
        if (!( *rangeFields = (struct RangeStruct *)UTL_MEM_RECALLOC(
                rangeFields,
                (*numRangeFieldsAllocated *sizeof(struct RangeStruct)),
                ((*numRangeFieldsAllocated + ALLOCATE_INCREMENT) *
                    sizeof(struct RangeStruct)) ) )
            goto Failure ;
        else
            *numRangeFieldsAllocated += ALLOCATE_INCREMENT ;
    }
}
```

```
                (*rangeFields)[*numRangeFields].RangeFieldName =
UTL_STR_SAVE(name);
                (*rangeFields)[*numRangeFields].lowValue = atof(low);
                (*rangeFields)[*numRangeFields].highValue = atof(high);
        (*numRangeFields)++ ;
                name = strtok(NULL," ");
    }
    stat = 1 ;
    goto CleanUp ;

UnableToParse:
        fprintf(stderr,"Unable to parse -rangevar %s\n",rangeVar);
    stat = 0 ;
    goto CleanUp ;
Failure :
    stat = 0 ;
    goto CleanUp ;
CleanUp :
        if ( buffer )
                UTL_MEM_FREE(buffer);
    return stat ;
}

/*
**+E:
**
**
** Abstract     : Function parses one of field string for ADS design programs.
**               It takes a string of the form
**               "supplier Aldrich,Sigma,Fluka,SALOR taste SWEET,Salty"
**               global array OneOfValues.
**
**
```

```
**  Usage       :
**
**  Returns     : 1 on success, 0 for failure.
**
**  Algorithms  : None.
**
**
**
**-E:
*/
int ParseOneOfVar(oneOfVar,numOneOfFieldsAllocated,numOneOfFields,oneOfValues)
char   *oneOfVar ;
int    *numOneOfFieldsAllocated ;
int    *numOneOfFields ;
struct OneOfStruct **oneOfValues;
{
static int stat = 0 ;
char *buffer = (char *)NULL ;
char *name ;
char *choices ;
char *choice ;
int i ;
int j ;
char *cp ;
char *end ;
   *numOneOfFieldsAllocated = 0 ;
   *numOneOfFields = 0 ;
   (*oneOfValues) = (struct OneOfStruct *)NULL ;

if ( !(buffer = UTL_STR_SAVE(oneOfVar)) )
            goto Failure ;
/*
** Start off by reading the field name .
```

```
*/
    name = strtok(buffer," ");
    while ( name )
    {
        if ( *numOneOfFields >= *numOneOfFieldsAllocated )
        {
            if ( !(*oneOfValues) )
            {
                if (!(*oneOfValues = (struct OneOfStruct *)UTL_MEM_CALLOC(
                        ALLOCATE_INCREMENT,
                                sizeof(struct OneOfStruct))))
                    goto Failure ;
                else
                    *numOneOfFieldsAllocated = ALLOCATE_INCREMENT ;
            }
            else
            {
                if (!( *oneOfValues = (struct OneOfStruct *)UTL_MEM_RECALLOC(
                        *oneOfValues,
                    (*numOneOfFieldsAllocated *sizeof(struct OneOfStruct)),
                    ((*numOneOfFieldsAllocated + ALLOCATE_INCREMENT) *
                        sizeof(struct OneOfStruct)) )) )
                    goto Failure ;
                else
                    *numOneOfFieldsAllocated += ALLOCATE_INCREMENT ;
            }
        }
```

```
            (*oneOfValues)[*numOneOfFields].OneOfFieldName =
UTL_STR_SAVE(name);
            (*oneOfValues)[*numOneOfFields].numValues = 0 ;
            (*oneOfValues)[*numOneOfFields].numValuesAlloc =
ALLOCATE_INCREMENT ;
            if ( !((*oneOfValues)[*numOneOfFields].values = (char **)

UTL_MEM_CALLOC(ALLOCATE_INCREMENT, sizeof(char *)) ) )
                    goto Failure ;
/*
** Now look at the choices this field could have.
*/
            choices = strtok(NULL," ");
            if ( !choices )
                    goto UnableToParse ;
            choice = strtok(choices,",");
            while ( choice )
            {
                    if ( (*oneOfValues)[*numOneOfFields].numValues >=
                            (*oneOfValues)[*numOneOfFields].numValuesAlloc )
                    {
                            if ( !((*oneOfValues)[*numOneOfFields].values = (char **)

UTL_MEM_RECALLOC((*oneOfValues)[*numOneOfFields].values,
                                                                            (
(*oneOfValues)[*numOneOfFields].numValuesAlloc *
                    sizeof(char *)),
                            ( ((*oneOfValues)[*numOneOfFields].numValuesAlloc +
                                            ALLOCATE_INCREMENT )
*sizeof(char *)) ) ))
                            goto Failure ;
```

```
                    (*oneOfValues)[*numOneOfFields].numValuesAlloc+=
ALLOCATE_INCREMENT;
                }

(*oneOfValues)[*numOneOfFields].values[(*oneOfValues)[*numOneOfFields].numValues]
= UTL_STR_SAVE(choice);
                    (*oneOfValues)[*numOneOfFields].numValues++ ;
                    end = choice + strlen(choice) + 1 ;
                    choice = strtok(NULL,",");
        }
                (*numOneOfFields)++;
                name = strtok(end," ");
        } stat = 1 ;
    goto CleanUp ;

UnableToParse:
        fprintf(stderr,"Unable to parse -oneof %s\n",oneOfVar);
        stat = 0 ;
    goto CleanUp ;
Failure :
    stat = 0 ;
    goto CleanUp ;
CleanUp :
        if ( buffer )
                UTL_MEM_FREE(buffer);
    return stat ;
}

/*
**+E:
```

```
**
**
** Abstract    : Function parses a line from the input file and extracts
**               out any rangevar or oneof fields.
**
**
** Usage       :
**
** Returns     : Always returns 1 ;
**
** Algorithms  : None.
**
**
**
**-E:
*/
int ReadLineAttributes(line,numRangeFields,rangeValues,rangeFields,numOneOfFields,
oneOfValues,oneOfFields)
char    *line ;
int     numRangeFields ;
float   **rangeValues;
struct RangeStruct *rangeFields;
int     numOneOfFields ;
int     **oneOfValues;
struct OneOfStruct *oneOfFields;
{
   int i ;
   int j ;
   char *cp ;
/*
** Now read in the salar selection fields if any.
*/
     if ( numRangeFields )
```

```
        {
                if ( !(*rangeValues = (float *)UTL_MEM_CALLOC(numRangeFields,
sizeof(float)) ) )
                        return 0 ;
        }
        if ( numOneOfFields )
        {
                if ( !(*oneOfValues = (int *)UTL_MEM_CALLOC(numOneOfFields,
sizeof(int)) ) )
                        return 0 ;
        }
        for ( i = 0 ; i < numRangeFields ; i++ )
        {
                if ( ( cp = strstr(line,rangeFields[i].RangeFieldName ) ) )
                {
/*
** Move past the logp= to get the value of this field, if the value is
** a ';' then it is a missing value.
*/
                        cp = cp + strlen(rangeFields[i].RangeFieldName) + 1 ;
                        if ( *cp == ';' )
                                (*rangeValues)[i] = MISSING_FLOAT_VALUE ;
                        else
                                (*rangeValues)[i] = atof(cp);
                }
                else
                {
                        (*rangeValues)[i] = MISSING_FLOAT_VALUE ;
                }
        }
/*
```

```
** Parse the -oneof field, we are looking for something looking like
** "supplier=Aldrich"
*/
        for ( i = 0 ; i < numOneOfFields ; i++ )
        {
                if ( ( cp = strstr(line,oneOfFields[i].OneOfFieldName ) ) )
                {
                        cp = cp + strlen(oneOfFields[i].OneOfFieldName) + 1 ;
                        if ( *cp == ';' )
                                (*oneOfValues)[i] = MISSING_INT_VALUE ;
                        else
                        {
                                for ( j = 0 ; j < oneOfFields[i].numValues ; j++ )
                                {
                                        if ( UTL_STR_NCMP_NOCASE(cp,
                                        oneOfFields[i].values[j],
                                        strlen(oneOfFields[i].values[j])) == 0)
                                        {
                                                (*oneOfValues)[i] = j ;
                                                break;
                                        }
                                }
                                if ( j == oneOfFields[i].numValues )
                                        (*oneOfValues)[i] = NOT_A_MATCH_VALUE ;
                        }

}
                else
                        (*oneOfValues)[i] = MISSING_INT_VALUE ;
        }
}

/*
```

```
**+E:
**
**
** Abstract    : Function Checks to see if the given product passes the
**               user supplied filters.
**
**
** Usage      :
**
** Returns    : 1 if the product is not within range, 0 otherwise.
**
** Algorithms : None.
**
**
**-E:
*/
static int
NotWithinScalarRange(firstIndex,secondIndex,numRangeFields,rangeValues_Y01,rangeValues_Y02,rangeFields,numOneOfFields,oneOfValues_Y01,oneOfValues_Y02,oneOfValues)
int firstIndex ;  /* Index into Y_01 data */
int secondIndex ; /* Index into Y_02 data */
int numRangeFields ;
float **rangeValues_Y01 ;
float **rangeValues_Y02 ;
struct RangeStruct *rangeFields;
int   numOneOfFields  ;
int   **oneOfValues_Y01 ;
int   **oneOfValues_Y02 ;
struct OneOfStruct *oneOfValues ;
{
int i ;
float total ;
```

```
/*
** First check the range values.
*/
    for ( i = 0 ; i < numRangeFields ; i++ )
    {
/*
** If one of the regions has a missing value, then we do not filter this
** product.
*/
        if ((( rangeValues_Y01[firstIndex][i] - MISSING_FLOAT_VALUE )
            == SMALL_FLOAT ) ||
            (( rangeValues_Y02[secondIndex][i] - MISSING_FLOAT_VALUE )
            == SMALL_FLOAT ) )
            return 0 ;

total=rangeValues_Y01[firstIndex][i] + rangeValues_Y02[secondIndex][i];
        if ((total > rangeFields[i].highValue ) ||
            (total < rangeFields[i].lowValue ) )
        {
            return 1 ;
        }
    }
    for ( i = 0 ; i < numOneOfFields ; i++ )
    {
/*
** If the value is missing then we dont mess with this guy.
*/
        if ( ( oneOfValues_Y01[firstIndex][i] == MISSING_INT_VALUE ) ||
            ( oneOfValues_Y02[secondIndex][i] == MISSING_INT_VALUE ) )
            return 0 ;
/*
** If any of the regions in the product does not match the selection
** criteria, then the product is rejected.
```

```
*/
            if ( ( oneOfValues_Y01[firstIndex][i] == NOT_A_MATCH_VALUE ) ||
                (oneOfValues_Y02[secondIndex][i] == NOT_A_MATCH_VALUE ) )
                    return 1 ;
        } return 0 ;
}

/*
**+E:
**
**
** Abstract    : Function zapps products who are not within the user supplied
**                selection criteria.
**
**
** Usage       :
**
** Returns     : 1 on success or 0 on failure.
**
** Algorithms  : None.
**
**
**-E:
*/
int FilterProducts(inputInfo,rangeData,oneOfData,numFiltered)
struct InputInfoStruct *inputInfo ;
struct RangeInfoStruct *rangeData ;
struct OneOfInfoStruct *oneOfData ;
int                    *numFiltered ;
{
int numProducts ;
```

```
int i ;
int index1 ;
int index2 ;
int Y01_Offset = 0 ;
int Y02_Offset = 0 ;
int k ;

*numFiltered = 0 ;

for ( k = 0 ; k < inputInfo->totalInputs ; k++ )
    {
        numProducts = inputInfo->Y_01_Length[k] * inputInfo->Y_02_Length[k]
;

for ( i = 0 ; i < numProducts ; i++ )
        {
            index1 = i / inputInfo->Y_02_Length[k]  ; /*Y_01 index */
            index2 = i % inputInfo->Y_02_Length[k]  ; /*Y_02 index */ if ( NotWithinScalarRange(index1,
                index2,
                rangeData->numRangeFields ,
                rangeData->rangeValues_Y01 + Y01_Offset ,
                rangeData->rangeValues_Y02 + Y02_Offset ,
                rangeData->rangeFields,
                oneOfData->numOneOfFields   ,
                oneOfData->oneOfValues_Y01 + Y01_Offset ,
                oneOfData->oneOfValues_Y02 + Y02_Offset ,
                oneOfData->oneOfFields ))
            {
                ZapInputProduct(k,i,0,0);
/*              FlagProduct(dead_Products,0,0,i  + bitMapStartPoint[k]  ); */
/*              someLeft--;
```

```
                        remainingInput[k]-- ;  */
                    *numFiltered += 1 ;
                }
            }
            Y01_Offset += inputInfo->Y_01_Length[k] ;
            Y02_Offset += inputInfo->Y_02_Length[k] ;
        }
        return 1 ;
    }
```

Appendix "R"

```
/*+M: dbcsln_bitset.c
******************************************************************
**
**
** Author           Date            Description
** ===================   ==============
=====================
** Fred Soltanshahi    07-30-96       Routines to access a ChemSpace
**                                    bitset.
** Entry Points :
**       CS_PRDCT_BITSET_OPEN() -- Opens a CS bitset file.
**       CS_PRDCT_BITSET_CLOSE()-- Closes and cleansup after a bitset file.
**       CS_PRDCT_BITSET_WRITE()-- Writes a bitset file.
**       CS_PRDCT_BITSET_CREATE()-- Creates a bitset in memory.
**       CS_PRDCT_BITSET_DUMP() -- Dumps the content of the file.
**       CS_PRDCT_BITSET_GETHITS-- Returns the indexes for the requested
**          number of hits.
**       CS_PRDCT_BITSET_SETBITS() -- Copies a raw bitset into ChemSpace
**                                    compressed bitset.
**       CS_PRDCT_BITSET_INDEXES_TO_INDEX -- get bitset index from
**                                    Y_01,Y_02 etc.
**       CS_PRDCT_BITSET_TO_RAW() -- Copies a ChemSpace bitset back into
**                                    a raw bitset
**       CS_PRDCT_BITSET_CONCAT_RAW() -- Copies a ChemSpace bitset
**                                    into part of a raw bitset
**       CS_PRDCT_BITSET_SELECTED() -- returns totalSelected
**       CS_PRDCT_BITSET_REVEAL()  -- Returns elements of hidden bitset
**                                    data structure to external program.
**       CS_PRDCT_BITSET_SET_PRD_BIT() -- Sets a bit in ChemSpace bitset.
**       CS_PRDCT_BITSET_GET_STATS()  -- Returns totals for the bitset.
**       CS_PRDCT_BITSET_CORE_INFO()  -- Gets core information from a bitset
``` file.
```
**      CS_PRDCT_MSTR_CORE_INFO() -- Gets core information from a master file.
**      CS_PRDCT_BITSET_GETHITS() -- Gets the indexes for the requested set of
**                                   hits.
**      CS_PRDCT_BITSET_CREATE_BIT_STRING() -- Creates a compressed
bitstring in memory
**      CS_PRDCT_BITSET_DESTROY_BIT_STRING()-- Deletes a compressed bitset
in memory.
**
********************************************************************
**
-M*/ include <stdio.h>
include <unistd.h>
#include <string.h>
#include <math.h>
#include "utl_str.h"
#include "utl_mem.h"
extern char *GetFullPathName();
extern char *basename();

#define VERSION_NUMBER 1.001
#define ALLOCATION_FACTOR 1.25  /*Extra room in each variation site for growth*/
define MAX_VARIATION_SITES 255 extern int    setbits[8] ;
extern int    nbits[256] ;

typedef struct MasterFileStruct
{
        char *masterFilePathName ;
        int  masterRecNo ;
```

```c
        char *prefixForFiles;
        int numVariationSites ;
        int numberOfMissingBits;
        int lbits;
        char *corefilePathName;
        int startCore;
        char *fingerFileName;
        int fingerOffset ;
        char **x_FileName ;
        char **reagentInfo ;
} MasterFileStruct ;
typedef struct ProgramInfoStruct
{
        char *programName ;
        int bufferSize ;
        int *buffer ;
} ProgramInfoStruct ;
typedef struct BitSetFileStruct
{
        struct MasterFileStruct masterFileInfo ;
        struct ProgramInfoStruct programInfo ;
        int    numVariationSites ;
        int    *actuallSizes ;
        int    *allocSizes ;
        int    *numFragsInEachSite ;
        int    totalSelected ;
        int    *bitset ;
        int    firstHitAddress ;
     unsigned char **fragmentBitset;
} BitSetFileStruct ;
typedef struct
{
        struct BitSetFileStruct *bitset;
```

```c
    int numVariations;
    int *choices;
    void *call_udata;          /* callback callback's udata */
    int (*funcptr)(void *udata, int numVariants, int *choices );
    int totalExcluded;
} BIT_TRACKING;
static int RangeCallback ( void *udata, int startRange, int endRange );

static int BitSetAddressToIndexes(struct BitSetFileStruct *bitset,int address,int **indxs,int *notUsedFlag)
{
int    numVariations;
int *allPtr;           /* alloced Sizes Ptr */
int *actPtr;           /* actual sizes Ptr */
int *choices;
int *chPtr ;
int x ;
int i ;
int skip = 1;
int skipcnt = 0;
        numVariations = bitset->numVariationSites;
    x = address ;
/*
** If the caller did not give us space to put in the indexes, allocate our
** own.
*/
    if ( ! (*indxs) )
            (*indxs) = (int *) UTL_MEM_CALLOC(numVariations, sizeof(int) );
    choices = *indxs ;
    if ( notUsedFlag)
            *notUsedFlag = 0 ;
        for ( allPtr = bitset->allocSizes + (numVariations - 1),
                        actPtr = bitset->actuallSizes + (numVariations
```

```
                                            -1 ),
                                                    chPtr = choices + (numVariations - 1 ),
                                                    i = numVariations;
                                    i-- ;
                                    allPtr--, actPtr--, chPtr-- )
        {
                    *chPtr = x % *allPtr;
                    if ( *chPtr >= *actPtr )
                    {
                                if ( !skipcnt )
                                {
                                            skipcnt = 1;
                                            skip *= ( *allPtr - *chPtr );
                                }
/*
** If we are rejecting things out of bounds of the actual sizes then we
** are out of here.
*/
                                if ( notUsedFlag )
                                {.
                                            *notUsedFlag = 1 ;
                                            break;
                                }
                    }
                    x = x / *allPtr;
                    if ( !skipcnt )
                                skip *= *allPtr;
        }
        if ( !skipcnt )
                    skip = 0;
        return skip;
}
```

```
static int TestDump(DumpCode, Parameter, DumpInt)
int DumpCode ;
void *Parameter ;
int DumpInt ;
{
FILE *File = (FILE *)Parameter ;
        fprintf(File, "%d\n", DumpInt);
} static int CalculateAllocatedSizes(int numSites,int *sizes,int *allocSizes)
{
int i ;
        for ( i = 0 ; i < numSites ; i++ )
                allocSizes[i] = sizes[i] * ALLOCATION_FACTOR ;
} static int Init()
{
static int    firstTime = 1 ;
int    i ;
        if ( firstTime )
        {
                for (i=0;i<8;i++) setbits[i] = ( 1 << i) & 255;
                firstTime = 0 ;
                for (i=0;i<256;i++) nbits[i] = (i&1) + (i&2)/2 + (i&4)/4 + (i&8)/8 +
                                                (i&16)/16 + (i&32)/32
+ (i&64)/64 + (i&128)/128 ;
        }
} int setbits_nbits_Init()
{
```

```
Init();
  return 1;
} void *CreateCompressedBitSet(bitset,offset,numVariations,sizes,allocSizes)
int  *bitset ;
int  offset ;
int  numVariations ;
int  *sizes ;
int  *allocSizes ;
{
void *compressed ;
int   byte ;
int   bit ;
int   size ;
int   total ;
int   i ;
int   index1 ;
int   index2 ;
int   newPos ;
int   rowLength ;
unsigned char *bs = (unsigned char *)bitset ;
        Init();

#if 0
/*
** Always calculate the allocated sizes, we are the only one who can set this.
*/
        if ( allocSizes[0] <= 0 )
                CalculateAllocatedSizes(numVariations,sizes,allocSizes);
#endif
/*
```

```
** Make the allocated size the same as the real size.
*/
        for ( i = 0 ; i < numVariations ; i++ )
                allocSizes[i] = sizes[i] ;
        size = allocSizes[0] ;
        for ( i = 1 ; i < numVariations ; i++ )
                size *= allocSizes[i] ;
        total = sizes[0] ;
        for ( i = 1 ; i < numVariations ; i++ )
                total *= sizes[i] ;
        if ( sizes[0] != allocSizes[0] )
        {
                if ( !( compressed = (void *)IHBDeclare( size ) ) )
                        goto AddTraceback ;
/*
** Set the bitset if the caller supplied us with one.
*/
                if ( bitset )
                {
                        rowLength = sizes[1] ;
                        for ( i = 0 ; i < total ; i++ )
                        {
                                index1 = i / rowLength ;
                                index2 = i % rowLength ;
                                byte = ( i + offset ) / 8 ;
                                bit  = ( i + offset ) % 8 ;
                                if ( bs[byte] & setbits[bit] )
                                {
                                        newPos = ( index1 * allocSizes[1] ) + index2 ;
                                        IHBSet(compressed, newPos );
                                }
                        }
                        IHBOptimize(compressed);
```

```
                }
        }
            else
            {
                if ( bitset )
                {
                    if ( !( compressed = (void *)IHBDeclareWithInit(offset, size , bs )))
                        goto AddTraceback ;
                }
                else
                {
                    if ( !( compressed = (void *)IHBDeclare( size ) ) )
                        goto AddTraceback ;
                }
        }
            return compressed ;
AddTraceback :
            return (void *)NULL ;
}
/*
** This routine will create a compressed bitset that is bigger in every
** dimension.
*/ void *CreateCompressedBitSetExp(bitset,offset,numVariations,sizes,allocSizes)
int  *bitset ;
int  offset ;
int  numVariations ;
int  *sizes ;
int  *allocSizes ;
{
void *compressed ;
int   byte ;
```

```
int    bit ;
int    size ;
int    total ;
int    i ;
int    index1 ;
int    index2 ;
int    newPos ;
int    rowLength ;
unsigned char *bs = (unsigned char *)bitset ;
        Init();
/*
** Always calculate the allocated sizes, we are the only one who can set this.
*/
        if ( allocSizes[0] <= 0 )
                CalculateAllocatedSizes(numVariations,sizes,allocSizes);
        size = allocSizes[0] ;
        for ( i = 1 ; i < numVariations ; i++ )
                size *= allocSizes[i] ;
        total = sizes[0] ;
        for ( i = 1 ; i < numVariations ; i++ )
                total *= sizes[i] ;
        if ( sizes[0] != allocSizes[0] )
        {
                if ( !( compressed = (void *)IHBDeclare( size ) ) )
                        goto AddTraceback ;
/*
** Set the bitset if the caller supplied us with one.
*/
        if ( bitset )
        {
                rowLength = sizes[1] ;
                for ( i = 0 ; i < total ; i++ )
                {
```

```
                    index1 = i / rowLength ;
                    index2 = i % rowLength ;
                    byte = ( i + offset ) / 8 ;
                    bit  = ( i + offset ) % 8 ;
                    if ( bs[byte] & setbits[bit] )
                    {
                            newPos = ( index1 * allocSizes[1] ) + index2 ;
                            IHBSet(compressed, newPos );
                    }
                }
            }
        }
        else
        {
            if ( bitset )
            {
            if ( !( compressed = (void *)IHBDeclareWithInit(offset, size , bs )))
                    goto AddTraceback ;
            }
            else
            {
            if ( !( compressed = (void *)IHBDeclare( size ) ) )
                    goto AddTraceback ;
            }
        }
        IHBOptimize(compressed);
        return compressed ;
AddTraceback :
        return (void *)NULL ;
}
CountBitSets(char *inputFileName)
{
FILE *inputFile ;
```

```c
int i ;
char *line ;
long length ;
long next ;
long here ;
        if ( !(inputFile = fopen(inputFileName,"r")))
                goto UnableToOpenFile ;
        i = 0 ;
        while ( 1 )
        {
                here = ftell(inputFile);
                if ( -1 == UTL_SCAN_GETS( inputFile, "\\", "#", &line))
                        break;
                if ( UTL_STR_NCMP_NOCASE(line,"@BITSET_LENGTH:",15) != 0 )
                {
/*
** Kludge for dbsearch old format.
*/
                        if ( UTL_STR_NCMP_NOCASE(line,"@BITSET_START:",14) != 0 )
                                break;
                }
                i++ ;
            length = (long ) atoi(line+15) ;
            next = here + length ;
                fseek(inputFile,next,SEEK_SET);
        }
        return i ;
UnableToOpenFile :
AddTraceback :
        return 0 ;
}
```

```
/*
**+E:
**
**
** Function Name : WriteOutCompressedBSFile()
**
** Purpose    : Function will write out a compressed bitset to disk.
**
** Usage :     To be used by dbsearch/design programs to write out check
**             points.
**
** Returns    : 1 on success, 0 for failure.
**
** Algorithms : None.
**
** Revision History :
**
** Author            Date       Description
** ==================           =========
** ==============
** Fred Soltanshahi      07/25/96   Original version.
**
**-E:
*/
int
WriteOutCompressedBSFile(outputFileName,masterFileName,masterRec,programName,compressed,numVariations,sizes,allocSizes,numSelected,numInSites,bufferSize,buffer)
char *outputFileName ;  /* Name of output file */
char *masterFileName ;  /* Name of master file */
int  masterRec ;        /* Which record in the master file */
char *programName ;     /* Name of program generating this. */
void *compressed ;      /* Compressed bitset */
int  numVariations ;    /* Num X01, X02 ... variation sites */
```

```
int *sizes ;        /* Actuall sizes in each dimension */
int *allocSizes ;   /* Allocated sizes(bitset size) in each dimension */
int numSelected ;   /* Number of products selected */
int *numInSites ;   /* Number of selections in each Y_0? site */
int bufferSize ;    /* Program specific buffer size */
int *buffer ;       /* Arbitrary data written by the program */
{
FILE *outputFile ;
float version = VERSION_NUMBER ;
long bitsetSize ;
time_t startTime ;
int i ;
int numBytes ;
long bitsetStart = 0 ;
long endOfFile  = 0 ;
long length ;
long beginingOfFile = 0 ;
char *dir ;
char *base ;
char *fullPathName ;
/*
** Calcualte the total size of the bitset.
*/
        bitsetSize = sizes[0] ;
        for ( i = 1 ; i < numVariations ; i++ )
            bitsetSize = bitsetSize * sizes[i] ;
        if ( !(outputFile = fopen(outputFileName,"w")))
            goto UnableToOpenFile ;
/*
** File format is :
** Version Number
** Date/Time Stamp
** "Location of the master file"  "Record Number in the file".
```

** A copy of master file records(one line at a time)

** Number of Variation sites

** Actual(current) number of choices for each site.

** Allocated number of choices for each site.

** Source -- program that generated this file.i.e. dbsearch, dbcsln_des,etc

** program command line parameters -- ASCII representation of parameters

** Program specific info       -- ASCII line of info specific to program.

** Number of products selected.

** Number of selections in each dimension -- num_Y_01_choices num_y_02_choices ...

** Bitset size -- The compressed bitset size in bytes.

** Bitset -- Row major bitset of products selected.

*/

```
/*     fprintf(outputFile,"@NEXT_SLOT:%010ld\n",endOfFile); */
       beginingOfFile = ftell(outputFile);
       fprintf(outputFile,"@BITSET_LENGTH:%010ld\n",bitsetStart);
       fprintf(outputFile,"@VERSION:%f\n",version);
       time( &startTime );
       fprintf(outputFile,"%s",ctime(&startTime));
       dir = GetFullPathName(masterFileName);
       base = basename(masterFileName,NULL);
       fullPathName = UTL_FILE_ADD_DIR_TO_DIRSPEC(dir,base);
       fprintf(outputFile,"%s %d\n",fullPathName,masterRec);
       UTL_MEM_FREE(fullPathName);
       if ( !DumpMasterFileInfo(outputFile,masterFileName,masterRec))
              goto UnableToDumpMaster ;
       fprintf(outputFile,"%d\n",numVariations);
       for ( i = 0 ; i < numVariations ; i++ )
              fprintf(outputFile,"%d ",sizes[i]);
       fprintf(outputFile,"\n");
       if ( allocSizes[0] == - 1 )
              CalculateAllocatedSizes(numVariations,sizes,allocSizes);
       for ( i = 0 ; i < numVariations ; i++ )
              fprintf(outputFile,"%d ",allocSizes[i]);
```

```
            fprintf(outputFile,"\n");
            fprintf(outputFile,"%s\n",programName);
            fprintf(outputFile,"%d\n",numSelected);
            for ( i = 0 ; i < numVariations ; i++ )
                    fprintf(outputFile,"%d ",numInSites[i]);
            fprintf(outputFile,"\n");
/*
** Now the product bitset.
*/
            bitsetStart = ftell(outputFile);
            fprintf(outputFile,"@PRODUCT_BITSET\n");
            IHBDump(compressed,TestDump,outputFile);
            fprintf(outputFile,"@PROGRAM_INFO\n");
            fprintf(outputFile,"%d\n",bufferSize);
            if ( buffer )
                    fwrite(buffer,bufferSize,1,outputFile);
            endOfFile = ftell(outputFile);
            length    = endOfFile - beginingOfFile ;
            fseek(outputFile,beginingOfFile,SEEK_SET);
            fprintf(outputFile,"@BITSET_LENGTH:%010ld\n",length);
/*
** Go back to the begining and write out the header info for the file
*/
            rewind(outputFile);
/*          fprintf(outputFile,"@NEXT_SLOT:%010ld\n",endOfFile);*/
            fclose(outputFile);
            return 1 ;
UnableToDumpMaster :
            fprintf(stderr,"WriteOutCompressedBSFile()--Unable to dump master file %s\n",masterFileName);
            goto AddTraceback ;
UnableToOpenFile :
            fprintf(stderr,"WriteOutCompressedBSFile()--Unable to open
```

%s\n",outputFileName);

goto AddTraceback ;

UnableToWriteToFile :

fprintf(stderr,"WriteOutCompressedBSFile()--Unable to write to output file\n");

goto AddTraceback ;

UnableToCreateBitSet :

fprintf(stderr,"WriteOutCompressedBSFile()--Unable to create compressed bitset\n");

goto AddTraceback ;

AddTraceback :

return 0 ;

}

/*
**+E:
**
**
** Function Name : WriteOutCheckPointFile()
**
** Purpose    : Function will write out a check point(bitset file to
**              the given file.
**
** Usage :       To be used by dbsearch/design programs to write out check
**               points.
**
** Returns    : 1 on success, 0 for failure.
**
** Algorithms : None.
**
** Revision History :
**
** Author            Date         Description
** ==================            ========

```
==============
** Fred Soltanshahi      07/25/96    Original version.
**
**-E:
*/
int
WriteOutCheckPointFile(outputFileName,masterFileName,masterRec,programName,bitSet,
offset,numVariations,sizes,allocSizes,numSelected,numInSites,bufferSize,buffer)
char *outputFileName ;  /* Name of output file */
char *masterFileName ;  /* Name of master file */
int  masterRec ;        /* Which record in the master file */
char *programName ;     /* Name of program generating this. */
int  *bitSet ;          /* Actual bitset */
int  offset ;           /* Offset into the bitset */
int  numVariations ;    /* Num X01, X02 ... variation sites */
int  *sizes ;           /* Actuall sizes in each dimension */
int  *allocSizes ;      /* Allocated sizes(bitset size) in each dimension */
int  numSelected ;      /* Number of products selected */
int  *numInSites ;      /* Number of selections in each Y_0? site */
int  bufferSize ;       /* Program specific buffer size */
int  *buffer ;          /* Arbitrary data written by the program */
{
void *compressed ;
/*
** Created a compressed bitset.
*/
        if ( !(compressed = CreateCompressedBitSet(bitSet,
                                                   offset,
                                                   numVariations,
                                                   sizes,
                                                   allocSizes) ) )
```

```
            goto UnableToCreateBitSet ;
    if ( !WriteOutCompressedBSFile(outputFileName,
                                                    masterFileName,
                                                    masterRec,
                                                    programName,
                                                    compressed,
                                                    numVariations,
                                                    sizes,
                                                    allocSizes,
                                                    numSelected,
                                                    numInSites,
                                                    bufferSize,
                                                    buffer))
            goto UnableToWriteToFile ;
        IHBDestroy(compressed);
        return 1 ;
UnableToWriteToFile :
        fprintf(stderr,"WriteOutCheckPointFile()--Unable to write to output file\n");
        goto AddTraceback ;
UnableToCreateBitSet :
        fprintf(stderr,"WriteOutCheckPointFile()--Unable to create compressed bitset\n");
        goto AddTraceback ;
AddTraceback :
        return 0 ;
}
static int TestRestore(DumpCode, Parameter, DumpInt)
int DumpCode;
void *Parameter;
int *DumpInt;
{
FILE *fp = (FILE *)Parameter ;
    fscanf(fp, "%d\n", DumpInt);
    return 1 ;
```

```c
}
static int GetReagentInfo(char *fileName,char **reagentInfo)
{
FILE *fp ;
char  buffer[4096] ;
int   i = 0 ;
char  *cp ;
        if ( !(fp = fopen(fileName,"r")) )
                return 0 ;
        while ( fgets(buffer,sizeof(buffer)-1,fp))
        {
                buffer[strlen(buffer)-1] = 0 ;
                if ( ( cp = strstr(buffer,"# USER_NAME=")) )
                {
                        (*reagentInfo) = UTL_STR_SAVE(buffer+12);
                        return 1;
                }
/*
** Only read the first 10 lines.
*/
                if ( i++ > 10 )
                        break;
        }
/*
** We did not find the reagent info, lets save an empty string and
** assume the file is old and does not contain the info.
*/
        reagentInfo = UTL_STR_SAVE("");
        return 1 ;
}

/*
**+I:
```

```
**
**
** Function Name : ReadCheckPointFile()
**
** Purpose    : Function will write out a check point(bitset file to
**             the given file.
**
** Usage :     To be used by dbsearch/design programs to write out check
**             points.
**
** Returns    : 1 on success, 0 for failure.
**
** Algorithms : None.
**
** Revision History :
**
** Author          Date       Description
** ================    ========
================
** Fred Soltanshahi    07/25/96    Original version.
**
**-I:
*/
static int
ReadCheckPointFile(inputFileName,inputOffset,masterFileName,masterRec,programName,
bitSet,numVariations,sizes,allocSizes,numSelected,numInSites,masterInfo,bufferSize,progBu
ff)
char *inputFileName ; /* Name of input file */
int  inputOffset ;    /* Offset into the input file where the bitset starts*/
char **masterFileName ; /* Name of master file */
int  *masterRec ;     /* Which record in the master file */
char **programName ;  /* Name of program generating this. */
int  **bitSet ;       /* Actual bitset */
```

```
int  *numVariations ;   /* Num X01, X02 ... variation sites */
int  **sizes ;          /* Actuall sizes in each dimension */
int  **allocSizes ;     /* Allocated sizes(bitset size) in each dimension */
int  *numSelected ;     /* Number of products selected */
int  **numInSites ;     /* Number of selections in each Y_0? site */
struct MasterFileStruct *masterInfo ;
int  *bufferSize ;      /* program specific buffer size */
int  **progBuff   ;     /* Program specific buffer */
{
FILE  *inputFile ;
float version ;
long  bitsetSize ;
time_t startTime ;
int  i ;
int  numBytes ;
char buffer[4096] ;
char hold[81] ;
char *cp ;
        if ( !(inputFile = fopen(inputFileName,"r")))
                goto UnableToOpenFile ;
/*
** File format is :
** @BITSET_START:Where In the File The bitset starts
** @VERSION:Version Number:currentVersion Number
** Date/Time Stamp
** "Location of the master file"  "Record Number in the file".
** @MASTER NumberOfLines : Number of lines used for the master file.
** A copy of master file records(one line at a time,currently 11 lines )
** Number of Variation sites
** Actual(current) number of choices for each site.
** Allocated number of choices for each site.
** Source -- program that generated this file.i.e. dbsearch, dbcsln_des,etc
** Number of products selected.
```

```
** Number of selections in each dimension -- num_Y_01_choices num_y_02_choices ...
** @PRODUCT_BITSET
** Bitset -- Row major bitset of products selected.
** @PROGRAM_INFO
** size of program specific buffer
** program specific buffer
*/
/*
** BITSET_START:
*/
        if ( !fgets(buffer,sizeof(buffer)-1,inputFile))
                goto UnableToReadFile ;
/*
** VERSION.
*/
        if ( !fgets(buffer,sizeof(buffer)-1,inputFile))
                goto UnableToReadFile ;
        cp = strstr(buffer,"@VERSION:");
        if ( !cp )
                goto VersionMissing ;
        version = atof(buffer);
        if ( !fgets(buffer,sizeof(buffer)-1,inputFile))
                goto UnableToReadFile ;
        if ( !fgets(buffer,sizeof(buffer)-1,inputFile))
                goto UnableToReadFile ;
        sscanf(buffer,"%s %d",hold,masterRec);
        (*masterFileName) = UTL_STR_SAVE(hold);
        if ( masterInfo )
        {
                masterInfo->masterFilePathName = UTL_STR_SAVE(hold);
                masterInfo->masterRecNo = *masterRec ;
/*
** @MASTER 11 thing.
```

```
                    */
                            if ( !fgets(buffer,sizeof(buffer)-1,inputFile))
                                    goto UnableToReadFile ;
    /*
    ** Reaction class
    */
                            if ( !fgets(buffer,sizeof(buffer)-1,inputFile))
                                    goto UnableToReadFile ;
    /*
    ** Prefix
    */
                            if ( !fgets(buffer,sizeof(buffer)-1,inputFile))
                                    goto UnableToReadFile ;
                            buffer[strlen(buffer)-1] = 0 ;
                            masterInfo->prefixForFiles =
    UTL_STR_SAVE(UTL_FILE_PARSE(buffer,4));
    /*
    ** number of sites
    */
                            if ( !fgets(buffer,sizeof(buffer)-1,inputFile))
                                    goto UnableToReadFile ;
                            masterInfo->numVariationSites = atoi(buffer);
    /*
    ** missing bits
    */
                            if ( !fgets(buffer,sizeof(buffer)-1,inputFile))
                                    goto UnableToReadFile ;
                            masterInfo->numberOfMissingBits = atoi(buffer);
    /*
    ** Lbits
    */
                            if ( !fgets(buffer,sizeof(buffer)-1,inputFile))
                                    goto UnableToReadFile ;
```

```
                masterInfo->lbits = atoi(buffer);
/*
** core file
*/
                if ( !fgets(buffer,sizeof(buffer)-1,inputFile))
                        goto UnableToReadFile ;
                buffer[strlen(buffer)-1] = 0 ;
                masterInfo->corefilePathName = UTL_STR_SAVE(buffer);
/*
** Start core
*/
                if ( !fgets(buffer,sizeof(buffer)-1,inputFile))
                        goto UnableToReadFile ;
                masterInfo->startCore = atoi(buffer);
/*
** fingure print file name
*/
                if ( !fgets(buffer,sizeof(buffer)-1,inputFile))
                        goto UnableToReadFile ;
                buffer[strlen(buffer)-1] = 0 ;
                masterInfo->fingerFileName = UTL_STR_SAVE(buffer);
/*
** start fingure print
*/
                if ( !fgets(buffer,sizeof(buffer)-1,inputFile))
                        goto UnableToReadFile ;
                masterInfo->fingerOffset = atoi(buffer);
                if (!(masterInfo->x_FileName = (char **)UTL_MEM_CALLOC(
                                        masterInfo->numVariationSites,
                                        sizeof(char *))) )
                        goto AddTraceback ;
                if (!(masterInfo->reagentInfo = (char **)UTL_MEM_CALLOC(
                                        masterInfo->numVariationSites,
```

```
                                    sizeof(char *))) )
              goto AddTraceback ;
/*
** X1 file pathname
*/
              if ( !fgets(buffer,sizeof(buffer)-1,inputFile))
                      goto UnableToReadFile ;
              buffer[strlen(buffer)-1] = 0 ;
              masterInfo->x_FileName[0] = UTL_STR_SAVE(buffer);
              if ( !GetReagentInfo(buffer,&masterInfo->reagentInfo[0]))
                      goto UnableToReadReagentInfo0 ;
/*
** X2 file pathname
*/
              if ( !fgets(buffer,sizeof(buffer)-1,inputFile))
                      goto UnableToReadFile ;
              buffer[strlen(buffer)-1] = 0 ;
              masterInfo->x_FileName[1] = UTL_STR_SAVE(buffer);
              if ( !GetReagentInfo(buffer,&masterInfo->reagentInfo[1]))
                      goto UnableToReadReagentInfo1;
       }
       else
       {
/*
** just skip the 12 lines.
*/
              for ( i = 0 ; i < 12 ; i++ )
              {
                      if ( !fgets(buffer,sizeof(buffer)-1,inputFile))
                              goto UnableToReadFile ;
              }
       }
       if ( !fgets(buffer,sizeof(buffer)-1,inputFile))
```

```
            goto UnableToReadFile ;
    *numVariations = atoi(buffer);
    if ( !fgets(buffer,sizeof(buffer)-1,inputFile))
            goto UnableToReadFile ;
/*
** We have to allocate the arrays for sizes, allocSizes and fragSizes .
*/
    if ( !( (*sizes) = (int *)UTL_MEM_CALLOC(*numVariations,
                                                            sizeof(int))
))
            goto AddTraceback ;
    if ( !( (*allocSizes) = (int *)UTL_MEM_CALLOC(*numVariations,
                                                            sizeof(int))
))
            goto AddTraceback ;
    if ( !( (*numInSites) = (int *)UTL_MEM_CALLOC(*numVariations,
                                                            sizeof(int))
))
            goto AddTraceback ;
    cp = buffer ;
    for ( i = 0 ; i < *numVariations ; i++ )
    {
            sscanf(cp,"%d",&((*sizes)[i]));
            cp = strstr(cp," ");
    }
    if ( !fgets(buffer,sizeof(buffer)-1,inputFile))
            goto UnableToReadFile ;
    cp = buffer ;
    for ( i = 0 ; i < *numVariations ; i++ )
    {
            sscanf(cp,"%d",&((*allocSizes)[i]));
            cp = strstr(cp," ");
    }
```

```c
        if ( !fgets(buffer,sizeof(buffer)-1,inputFile))
                goto UnableToReadFile ;
        buffer[strlen(buffer)-1] = 0 ;
    (*programName) = UTL_STR_SAVE(buffer);

if ( !fgets(buffer,sizeof(buffer)-1,inputFile))
                goto UnableToReadFile ;
    *numSelected = atoi(buffer);
        if ( !fgets(buffer,sizeof(buffer)-1,inputFile))
                goto UnableToReadFile ;
   cp = buffer ;
        for ( i = 0 ; i < *numVariations ; i++ )
        {
                sscanf(cp," %d",&((*numInSites)[i]));
                cp = strstr(cp," ");
        }
/*
** @PRODUCT_BITSET
*/
        if ( !fgets(buffer,sizeof(buffer)-1,inputFile))
                goto UnableToReadFile ;
        IHBRestore(bitSet,TestRestore,inputFile);
/*
** @PROGRAM_INFO
*/
        if ( !fgets(buffer,sizeof(buffer)-1,inputFile))
                goto UnableToReadFile ;
        fclose(inputFile);
        return 1 ;
VersionMissing :
        fprintf(stderr,"ReadCheckPointFile()--File %s is not a valid ChemSpace file\n",inputFileName);
        goto AddTraceback ;
```

UnableToReadFile :

fprintf(stderr,"ReadCheckPointFile()--Unable to read from file\n");

goto AddTraceback ;

UnableToDumpMaster :

fprintf(stderr,"ReadCheckPointFile()--Unable to dump master file %s\n",masterFileName);

goto AddTraceback ;

UnableToReadReagentInfo0 :

fprintf(stderr,"ReadCheckPointFile()--Unable to read reagent info in %s\n", masterInfo->x_FileName[0]);

UnableToReadReagentInfo1 :

fprintf(stderr,"ReadCheckPointFile()--Unable to read reagent info in %s\n", masterInfo->x_FileName[1]);

goto AddTraceback ;

UnableToOpenFile :

fprintf(stderr,"ReadCheckPointFile()--Unable to open %s\n",inputFileName);

goto AddTraceback ;

UnableToWriteToFile :

fprintf(stderr,"ReadCheckPointFile()--Unable to write to output file\n");

goto AddTraceback ;

AddTraceback :

return 0 ;

} static struct BitSetFileStruct *ReadAndAllocateMaster(char *masterFileName,int masterRecNumber,int *initBitset)

{ struct BitSetFileStruct *bitset ;

FILE *mfFP ;

/*

** First allocate everything we need.

*/ if ( !(bitset = (struct BitSetFileStruct *)UTL_MEM_CALLOC(1,

```
                sizeof(struct BitSetFileStruct ))))
        goto AddTraceback ;
    bitset->masterFileInfo.masterFilePathName = UTL_STR_SAVE(masterFileName);
    bitset->masterFileInfo.masterRecNo = masterRecNumber;
/*
** Some if this info is fixed for now.
*/
    bitset->programInfo.programName = (char *)NULL ;
    bitset->masterFileInfo.numVariationSites = bitset->numVariationSites = 2 ;
    bitset->totalSelected        = 0 ;
    if (!(bitset->masterFileInfo.x_FileName = (char **)UTL_MEM_CALLOC(
                                bitset->numVariationSites,
                                sizeof(char *))) )
        goto AddTraceback ;
    if (!(bitset->actualSizes = (int *)UTL_MEM_CALLOC(
                                bitset->numVariationSites,
                                sizeof(int ))) )
        goto AddTraceback ;
    if (!(bitset->allocSizes = (int *)UTL_MEM_CALLOC(
                                bitset->numVariationSites,
                                sizeof(int ))) )
        goto AddTraceback ;
    if (!(bitset->numFragsInEachSite = (int *)UTL_MEM_CALLOC(
                                bitset->numVariationSites,
                                sizeof(int ))) )
        goto AddTraceback ;
    if ( !RetrieveMasterFile(masterFileName,
                                mfFP,
                                masterRecNumber, &(bitset->masterFileInfo.numberOfMissingBits),
                                &(bitset->masterFileInfo.lbits),
```

```
                    &(bitset->masterFileInfo.corefilePathName),
                                                    &(bitset->masterFileInfo.startCore), &(bitset->masterFileInfo.fingerFileName), &(bitset->masterFileInfo.x_FileName[0]), &(bitset->masterFileInfo.x_FileName[1]),
                                                    &(bitset->actuallSizes[0]),
                                                    &(bitset->actuallSizes[1]),
                                                    NULL,
                                                    &(bitset->masterFileInfo.fingerOffset),
                                                    NULL,
                                                    NULL,
                                                    NULL,
                                                    NULL,
                                                    NULL,
                                                    NULL))
            goto AddTraceback ;
        if ( !( bitset->bitset = CreateCompressedBitSet(initBitset,
                    0,
                    bitset->numVariationSites,
                    bitset->actuallSizes,
                    bitset->allocSizes)) )
            goto AddTraceback ;
        return bitset ;
AddTraceback :
        fprintf(stderr,"ReadAndAllocateMaster()--Unable to read master file\n");
        return (struct BitSetFileStruct *) NULL ;
} static int CalculateFragsInSties( struct BitSetFileStruct *bitset )
{
```

```
unsigned char **bitArray ;
int i ;
int j ;
int size ;
int address ;
int *indxs = 0 ;
int what ;
int this ;
        Init();
        if ( !( bitArray = (unsigned char
**)UTL_MEM_CALLOC(bitset->numVariationSites, sizeof(unsigned char *))) )
                goto AddTraceback ;
        for ( i = 0 ; i < bitset->numVariationSites ; i++ )
        {
                size = ( bitset->actuallSizes[i] + 7 ) / 8 ;
                if ( !(bitArray[i] = (unsigned char
*)UTL_MEM_CALLOC(size,sizeof(unsigned char))))
                        goto AddTraceback ;
        }
        for ( address = -1 , i = 0 ; i < bitset->totalSelected ; i++ )
        {
                address = IHBFindNextOne(bitset->bitset,address+1);
                BitSetAddressToIndexes(bitset,address,&indxs,0);
/*
** For every hit and every variation site address set the bit to 1.
*/
                for ( j = 0 ; j < bitset->numVariationSites ; j++ )
                {
                        what = indxs[j] % 8;
                        this = indxs[j] / 8;
                        bitArray[j][this] |= setbits[what];
```

```
            }
        }
        for ( i = 0 ; i < bitset->numVariationSites ; i++ )
        {
            size = ( bitset->actuallSizes[i] + 7 ) / 8 ;
            bitset->numFragsInEachSite[i] = 0 ;
            for ( j = 0 ; j < size ; j++ )
                bitset->numFragsInEachSite[i] += nbits[bitArray[i][j] & 255];

}
/*
** Get read of memory we allocated for calculating the hits the last time.
*/
        if ( bitset->fragmentBitset )
        {
            for ( i = 0 ; i < bitset->numVariationSites ; i++ )
                UTL_MEM_FREE(bitset->fragmentBitset[i]);
            UTL_MEM_FREE(bitset->fragmentBitset );
        }
        bitset->fragmentBitset = bitArray ;
        UTL_MEM_FREE(indxs);
        return 1 ;
AddTraceback :
        return 0 ;
} static int GetPartialProductsAddresses(struct BitSetFileStruct *bitset,int numFixedSites, int
*fixedSitesIndexes, int site, int **hitIndexes)
{
int i ;
int j ;
```

```
int k ;
int address ;
int *indxs = 0 ;
int skipIt ;
int numHits = 0 ;
unsigned char **bitArray ;
int size ;
int what ;
int this ;
        Init();
        if ( !( bitArray = (unsigned char
**)UTL_MEM_CALLOC(bitset->numVariationSites, sizeof(unsigned char *))) )
                goto AddTraceback ;
        for ( i = 0 ; i < bitset->numVariationSites ; i++ )
        {
/*
** We only want to count the fragments for the site that is being exploded.
*/
                if ( ( ( site != -1 ) && ( i != site ) )
                        continue ;
                size = ( bitset->actuallSizes[i] + 7 ) / 8 ;
                if ( !(bitArray[i] = (unsigned char
*)UTL_MEM_CALLOC(size,sizeof(unsigned char))))
                        goto AddTraceback ;
        }
        for ( address = -1 , i = 0 ; i < bitset->totalSelected ; i++ )
        {
                address = IHBFindNextOne(bitset->bitset,address+1);
                BitSetAddressToIndexes(bitset,address,&indxs,0);
/*
** The sites that have already been expanded will constraint what hits
```

```
** we find.
*/
                if ( numFixedSites )
                {
                        skipIt = 0 ;
                        for ( k = 0 ; k < bitset->numVariationSites ; k++ )
                        {
                                if ( fixedSitesIndexes[k] == -1 )
                                        continue ;
/*
** our hit index matches our constraint index.
*/
                                if ( fixedSitesIndexes[k] != indxs[k] )
                                {
                                        skipIt = 1 ;
                                        break;
                                }
                        }
                        if ( skipIt )
                                continue ;
                }
                numHits++ ;
                for ( j = 0 ; j < bitset->numVariationSites ; j++ )
                {
                        if ( ( site != -1 ) && ( j != site ) )
                                continue ;
                        what = indxs[j] % 8;
                        this = indxs[j] / 8;
                        bitArray[j][this] |= setbits[what];
                }
        }
if 0
/*
```

```
** Figure out how many hits there are for this site.
*/
        for ( k = 0 ; k < bitset->numVariationSites ; k++ )
        {
                if ( site != k )
                        continue ;
                size = ( bitset->actuallSizes[k] + 7 ) / 8 ;
                numFragmentsPerSite[k] = 0 ;
                for ( j = 0 ; j < size ; j++ )
                        numFragmentsPerSite[k] += nbits[bitArray[k][j] & 255];
        }
endif
/*
** Now get the indexes for all the hits.
*/
        if ( !( (*hitIndexes) = (int *)UTL_MEM_CALLOC(numHits,
                                                                sizeof(int)))
)
                goto AddTraceback ;
        numHits = 0 ;
        for ( k = 0 ; k < bitset->numVariationSites ; k++ )
        {
        if ( site == -1 )
                {
                        if ( fixedSitesIndexes[k] != -1 )
                                continue ;
                }
                else
                {
                        if ( site != k )
                                continue ;
                }
                size = ( bitset->actuallSizes[k] + 7 ) / 8 ;
```

```
                for ( i = 0 ; i < size ; i++ )
                {
                        if ( bitArray[k][i] )
                        {
/*
** If any bit is set in the byte then we need to figure out what the hits are.
*/
                                for ( j = 0 ; j < 8 ; j++ )
                                {
                                        if ( bitArray[k][i] & setbits[j] )
                                        {
                                                (*hitIndexes)[numHits++] = i * 8 + j ;
                                        }
                                }
                        }
                }
        }
        for ( i = 0 ; i < bitset->numVariationSites ; i++ )
                if ( bitArray[i] )
                        UTL_MEM_FREE(bitArray[i]);
        UTL_MEM_FREE(bitArray );
        return numHits ;

AddTraceback :
        return 0 ;
} static int GetPartialProductsStats( struct BitSetFileStruct *bitset , int numFixedSites, int *fixedSitesIndexes, int *numProducts, int *numFragmentsPerSite)
{
int i ;
int j ;
```

```
int k ;
int address ;
int *indxs = 0 ;
int skipIt ;
int numHits = 0 ;
unsigned char **bitArray ;
int size ;
int what ;
int this ;
        Init();
        if ( !( bitArray = (unsigned char
**)UTL_MEM_CALLOC(bitset->numVariationSites,
sizeof(unsigned char *))) )
                goto AddTraceback ;
        for ( i = 0 ; i < bitset->numVariationSites ; i++ )
        {
/*
** We only want to count the fragments for the sites that are not being
** exploded.
*/
                if ( fixedSitesIndexes[i] != -1 )
                        continue ;
                size = ( bitset->actuallSizes[i] + 7 ) / 8 ;
                if ( !(bitArray[i] = (unsigned char
*)UTL_MEM_CALLOC(size,sizeof(unsigned char))))
                        goto AddTraceback ;
        }
        for ( address = -1 , i = 0 ; i < bitset->totalSelected ; i++ )
        {
                address = IHBFindNextOne(bitset->bitset,address+1);
                BitSetAddressToIndexes(bitset,address,&indxs,0);
/*
```

```
** The sites that have already been expanded will constraint what hits
** we find.
*/
            if ( numFixedSites )
            {
                skipIt = 0 ;
                for ( k = 0 ; k < bitset->numVariationSites ; k++ )
                {
                    if ( fixedSitesIndexes[k] == -1 )
                        continue ;
/*
** our hit index matches our constraint index.
*/
                    if ( fixedSitesIndexes[k] != indxs[k] )
                    {
                        skipIt = 1 ;
                        break;
                    }
                }
                if ( skipIt )
                    continue ;
            }
            numHits++ ;
            for ( j = 0 ; j < bitset->numVariationSites ; j++ )
            {
                if ( fixedSitesIndexes[j] != -1 )
                    continue ;
                what = indxs[j] % 8;
                this = indxs[j] / 8;
                bitArray[j][this] |= setbits[what];
            }
        }
        for ( k = 0 ; k < bitset->numVariationSites ; k++ )
```

```
        {
                if ( fixedSitesIndexes[k] != -1 )
                        continue ;
                size = ( bitset->actuallSizes[k] + 7 ) / 8 ;
                numFragmentsPerSite[k] = 0 ;
                for ( j = 0 ; j < size ; j++ )
                        numFragmentsPerSite[k] += nbits[bitArray[k][j] & 255];

}
        *numProducts = numHits ;
        for ( i = 0 ; i < bitset->numVariationSites ; i++ )
                if ( bitArray[i] )
                        UTL_MEM_FREE(bitArray[i]);
        UTL_MEM_FREE(bitArray );
        return numHits ;

AddTraceback :
        return 0 ;
} static int GetPartialProducts( struct BitSetFileStruct *bitset , int numFixedSites, int *fixedSitesIndexes, int whichSite, int **siteIndexes)
{
int i ;
int j ;
int k ;
int address ;
int *indxs = 0 ;
int skipIt ;
int numHits = 0 ;
        Init();
        for ( address = -1 , i = 0 ; i < bitset->totalSelected ; i++ )
```

```
            {
                    address = IHBFindNextOne(bitset->bitset,address+1);
                    BitSetAddressToIndexes(bitset,address,&indxs,0);
/*
** The sites that have already been expanded will constraint what hits
** we find.
*/
                    if ( numFixedSites )
                    {
                            skipIt = 0 ;
                            for ( k = 0 ; k < bitset->numVariationSites ; k++ )
                            {
                                    if ( fixedSitesIndexes[k] == -1 )
                                            continue ;
/*
** our hit index matches our constraint index.
*/
                                    if ( fixedSitesIndexes[k] != indxs[k] )
                                    {
                                            skipIt = 1 ;
                                            break;
                                    }
                            }
                            if ( skipIt )
                                    continue ;
                    }
                    numHits++ ;
fprintf(stderr,"Got a hit on %d %d %d\n",address,indxs[0],indxs[1]);
            }
            return numHits ;

AddTraceback :
    return 0 ;
```

}

```
static GetFragmentsUsedInASite( struct BitSetFileStruct *bitset , int whichSite , int ** indxs)
{
unsigned char *bitArray ;
int i ;
int j ;
int size ;
int *address ;
int numHits = 0 ;
int bit ;
        if (!(address = (int *)UTL_MEM_CALLOC(bitset->numFragsInEachSite[whichSite],
                                                                        sizeof(int))) )
                goto AddTraceback ;
/*
** Figure out how many ints there are in this bitset.
*/
        size = ( bitset->actuallSizes[whichSite] + 7 ) / 8 ;
        for ( bitArray = bitset->fragmentBitset[whichSite], i = 0 ; i < size ; i++ )
        {
                if ( bitArray[i] )
                {
/*
** If any bit is set in the byte then we need to figure out what the hits are.
*/
                        for ( j = 0 ; j < 8 ; j++ )
                        {
                                if ( bitArray[i] & setbits[j] )
                                {
                                        address[numHits++] = i * 8 + j ;
                                }
```

```
                    }
                }
            }
            (*indxs) = address ;
            return numHits ;
AddTraceback :
            return 0 ;
} static struct BitSetFileStruct *ReadAndAllocate(char *fileName ,int offset )
{
struct BitSetFileStruct *bitset ;
        if ( !(bitset = (struct BitSetFileStruct *)UTL_MEM_CALLOC(1,
                        sizeof(struct BitSetFileStruct ))))
                goto AddTraceback ;
        if ( !ReadCheckPointFile(fileName,
                                    offset,
&(bitset->masterFileInfo.masterFilePathName), &(bitset->masterFileInfo.masterRecNo),
                                    &(bitset->programInfo.programName),
                                    &(bitset->bitset),
                                    &(bitset->numVariationSites),
                                    &(bitset->actuallSizes),
                                    &(bitset->allocSizes),
                                    &(bitset->totalSelected),
                                    &(bitset->numFragsInEachSite),
                                    &(bitset->masterFileInfo),
                                    &(bitset->programInfo.bufferSize),
                                    NULL))
                goto AddTraceback ;
```

```
            return bitset ;
AddTraceback :
            return ( struct BitSetFileStruct *)NULL ;
} static int ReadBitsetCoreInfo(void *bs, char **masterFileName, int *masterRecno, char
core, char xrString, int *numSites, char ***xFileNames )
{
struct BitSetFileStruct *bitset = (struct BitSetFileStruct *) bs;
int    recNo ;
FILE   *fp ;
int    i ;
int       found = 0 ;
char   *line ;
char   *cp ;
char   *cp1 ;
            *numSites = bitset->numVariationSites ;
            *masterFileName = bitset->masterFileInfo.masterFilePathName;
            *masterRecno   = bitset->masterFileInfo.masterRecNo;
            if ( !((*xFileNames) = (char **)UTL_MEM_CALLOC(*numSites, sizeof(char *)) ))
                    goto AddTraceback ;
            for ( i = 0 ; i < *numSites ; i++ )
                    (*xFileNames)[i] =
UTL_STR_SAVE(bitset->masterFileInfo.x_FileName[i]);
/*
** Open the core file and read in the core and parse out the XRstring.
*/
            if ( !(fp = fopen(bitset->masterFileInfo.corefilePathName,"r")) )
                    goto UnableToReadCore ;
            recNo = 0 ;
            found = 0 ;
```

```
        while ( -1 != UTL_SCAN_GETS( fp, "\\", "#", &line))
        {
                recNo++ ;
                if ( recNo ==      bitset->masterFileInfo.startCore )
                {
                        found = 1 ;
                        break;
                }
        }
        if (!found )
                goto UnableToReadCore ;
/*
** Replace all occurances of Y_0x with Xx.
*/
        (*core ) = UTL_STR_SAVE(line);
        cp = strstr(line,"XRLIST=");
        if ( !cp )
                (*xrString) = UTL_STR_SAVE("");
        else
        {
/*
** Skip the first double quote.
*/
                cp += 8 ;
/*
** Go find the end of double quotes.
*/
                cp1 = cp ;
                while ( (*cp) != '"')
                        cp++ ;
                *cp = 0 ;
                (*xrString) = UTL_STR_SAVE(cp1);
        }
```

```c
        fclose(fp);
        return 1 ;
UnableToReadCore :
        fprintf(stderr,"ReadBitsetCoreInfo() -- Unable to read core %s %d\n",
        bitset->masterFileInfo.corefilePathName,
        bitset->masterFileInfo.startCore);
AddTraceback :
        fprintf(stderr,"ReadBitsetCoreInfo() -- Unable to read core info\n");
        return 0 ;
} static int ReadMasterCoreInfo(char *masterFile, int index, char core, char xrString,
int *numSites, char ***xFileNames )
{
int    recNo ;
FILE   *fp ;
int    i ;
int        found = 0 ;
char   *line ;
char   *cp ;
char   *cp1 ;
char *prefix = (char *)NULL ;
char *coreFile = (char *)NULL ;
char *fpFileName = (char *)NULL ;
int  fpOffset ;
int  mBits ;
int  lBits ;
int  startCore ;
        *numSites = 2 ; /* fixed for now */
        if ( !((*xFileNames) = (char **)UTL_MEM_CALLOC(*numSites, sizeof(char *)) ))
```

```
                    goto AddTraceback ;
/*
** Get the master file info.
*/
        if ( !GetMasterRecordHeader(masterFile,
                                                index,
                                                &prefix,
                                                &mBits,
                                                &lBits,
                                                &coreFile,
                                                &startCore,
                                                &(*xFileNames)[0],
                                                &(*xFileNames)[1],
                                                numSites,
                                                &fpFileName,
                                                &fpOffset))
                    goto AddTraceback ;
/*
** Open the core file and read in the core and parse out the XRstring.
*/
        if ( !(fp = fopen(coreFile,"r")) )
                goto UnableToReadCore ;
        recNo = 0 ;
        found = 0 ;
        while ( -1 != UTL_SCAN_GETS( fp, "\\", "#", &line))
        {
                recNo++ ;
                if ( recNo ==      startCore )
                {
                        found = 1 ;
                        break;
                }
        }
```

```
          if (!found )
                  goto UnableToReadCore ;
          (*core ) = UTL_STR_SAVE(line);
          cp = strstr(line,"XRLIST=");
          if ( !cp )
                  (*xrString) = UTL_STR_SAVE("");
          else
          {
/*
** Skip the first double quote.
*/
                  cp += 8 ;
/*
** Go find the end of double quotes.
*/
                  cp1 = cp ;
                  while ( (*cp)  != '"')
                          cp++ ;
                  *cp = 0 ;
                  (*xrString) = UTL_STR_SAVE(cp1);
          } fclose(fp);
   if ( coreFile )
           UTL_MEM_FREE(coreFile);
   if ( fpFileName )
           UTL_MEM_FREE(fpFileName);
   if ( prefix )
           UTL_MEM_FREE(prefix);
   return 1 ;
UnableToReadCore :
       fprintf(stderr,"ReadMastersetCoreInfo() -- Unable to read core %s %d\n",
               coreFile,startCore);
```

AddTraceback :

```
        fprintf(stderr,"ReadMastersetCoreInfo() -- Unable to read core info\n");
    if ( coreFile )
            UTL_MEM_FREE(coreFile);
    if ( fpFileName )
            UTL_MEM_FREE(fpFileName);
    if ( prefix )
            UTL_MEM_FREE(prefix);
    return 0 ;
} static void DeallocateBitset( struct BitSetFileStruct *bitset )
{
int i ;
    if ( bitset->masterFileInfo.masterFilePathName )
            UTL_MEM_FREE(bitset->masterFileInfo.masterFilePathName);
    if ( bitset->masterFileInfo.corefilePathName )
            UTL_MEM_FREE(bitset->masterFileInfo.corefilePathName);
    if ( bitset->masterFileInfo.fingerFileName )
            UTL_MEM_FREE(bitset->masterFileInfo.fingerFileName);
    if ( bitset->masterFileInfo.prefixForFiles )
            UTL_MEM_FREE(bitset->masterFileInfo.prefixForFiles);
    for ( i = 0 ; i < bitset->masterFileInfo.numVariationSites ; i++ )
            UTL_MEM_FREE(bitset->masterFileInfo.x_FileName[i]);
    if ( bitset->masterFileInfo.x_FileName)
            UTL_MEM_FREE(bitset->masterFileInfo.x_FileName);
    if ( bitset->programInfo.programName )
            UTL_MEM_FREE(bitset->programInfo.programName);
    if ( bitset->programInfo.buffer )
            UTL_MEM_FREE(bitset->programInfo.buffer);
    IHBDestroy(bitset->bitset);
    if ( bitset->actuallSizes )
            UTL_MEM_FREE(bitset->actuallSizes);
```

```c
        if ( bitset->allocSizes )
                UTL_MEM_FREE(bitset->allocSizes);
        if ( bitset->numFragsInEachSite )
                UTL_MEM_FREE(bitset->numFragsInEachSite);
        UTL_MEM_FREE(bitset);
        bitset = (struct BitSetFileStruct *) NULL ;
}
void CS_PRDCT_BITSET_DUMP( struct BitSetFileStruct *bitset )
{
int i ;
int indx ;
int indx1 ;
int indx2 ;
        fprintf(stderr,"Master file name : %s\n",bitset->masterFileInfo.masterFilePathName);
        fprintf(stderr,"Master file rec  : %d\n",bitset->masterFileInfo.masterRecNo);
        fprintf(stderr,"Program Name     : %s\n",bitset->programInfo.programName);
        fprintf(stderr,"Number of Sites  : %d\n",bitset->numVariationSites);
        fprintf(stderr,"Number Selected  : %d\n",bitset->totalSelected);
        fprintf(stderr,"Actual Sizes     : ");
        for ( i = 0 ; i < bitset->numVariationSites ; i++ )
                fprintf(stderr," %d ",bitset->actuallSizes[i]);
        fprintf(stderr,"\n");
        fprintf(stderr,"Alloc Sizes      : ");
        for ( i = 0 ; i < bitset->numVariationSites ; i++ )
                fprintf(stderr," %d ",bitset->allocSizes[i]);
        fprintf(stderr,"\n");
        fprintf(stderr,"Num Frags in X?  : ");
/*
** If the number of fragments is zero then we will write -1 to tell others
** to calculate this themselves.
*/
        for ( i = 0 ; i < bitset->numVariationSites ; i++ )
```

```c
            fprintf(stderr,"%d ",(bitset->numFragsInEachSite[i] == 0 )?-1:
                                                bitset->numFragsInEachSite[i]);
    fprintf(stderr,"\n");
    fprintf(stderr,"Selections     : \n");
    indx = -1 ;
    do
    {
            indx = IHBFindNextOne(bitset->bitset,indx+1);
            if ( indx == -1 )
                    break;
            indx1 = indx / bitset->allocSizes[1] ;
            indx2 = indx % bitset->allocSizes[1] ;
            fprintf(stderr,"%d %d\n",indx1 + 1 ,indx2 + 1 );
    } while ( 1 );
}
void CS_PRDCT_BITSET_GET_HITS( struct BitSetFileStruct *bitset , int **indexes)
{
int i ;
int indx ;
int indx1 ;
int indx2 ;
int hitNo = 0 ;
    indx = -1 ;
    do
    {
            indx = IHBFindNextOne(bitset->bitset,indx+1);
            if ( indx == -1 )
                    break;
            indx1 = indx / bitset->allocSizes[1] ;
            indx2 = indx % bitset->allocSizes[1] ;
            indexes[0][hitNo] = indx1 + 1 ;
            indexes[1][hitNo] = indx2 + 1 ;
            hitNo++ ;
```

```
        } while ( 1 );
}

/*
**+E:
**
**
** Function Name : CS_PRDCT_BITSET_OPEN()
**
** Purpose    : Function will read in the header for a CS product bitset.
**
** Usage :
**
** Returns    : A handle to the product bitset info structure or NULL on
**             error.
**
** Algorithms  : None.
**
** Revision History :
**
** Author           Date       Description
** ==================    ========
================
** Fred Soltanshahi    07/26/96    Original version.
**
**-E:
*/
void *CS_PRDCT_BITSET_OPEN( char *bitsetFileName , int offset )
{
struct BitSetFileStruct *bitset ;
        if ( !(bitset = ReadAndAllocate(bitsetFileName,offset)) )
                return (void *)NULL ;
        bitset->totalSelected = IHBCountOnes(bitset->bitset,
```

```
                            0, IHBBitSize(bitset->bitset));
/*
** If the program did not keep track of and output this to the file then we
** need to calculate it ourselves.
*/
    if ( ( bitset->numFragsInEachSite[0] == 0 ) || ( bitset->numFragsInEachSite[0] == -1 ) )
    {
        CalculateFragsInSties(bitset);
    }
    return (void *)bitset ;
}

/*
**+E:
**
**
** Function Name : CS_PRDCT_BITSET_CLOSE()
**
** Purpose      : Function will close a bitset file and cleanup allocated.
**                 memory.
**
** Usage        :
**
** Returns      : None.
**
** Algorithms   : None.
**
** Revision History :
**
** Author          Date        Description
** =================== ========
===============
```

```
** Fred Soltanshahi      07/26/96    Original version.
**
**-E:
*/
void CS_PRDCT_BITSET_CLOSE( struct BitSetFileStruct *bitset )
{
        DeallocateBitset(bitset);
}

/*
**+E:
**
**
** Function Name : CS_PRDCT_BITSET_WRITE()
**
** Purpose    : Function will write a bitset into the given file.
**
** Usage :
**
** Returns    : 1 on success or 0 on failure.
**
** Algorithms : None.
**
** Revision History :
**
** Author              Date        Description
** ===================  ========
================
** Fred Soltanshahi      08/02/96    Original version.
**
**-E:
*/
int CS_PRDCT_BITSET_WRITE(char *fileName,char *programName,struct
```

```
            BitSetFileStruct *productBitset,int progBufferSize,int *progBuffer)
            {
                    if ( !WriteOutCompressedBSFile(fileName, productBitset->masterFileInfo.masterFilePathName,
                                            productBitset->masterFileInfo.masterRecNo,
                                            programName,
                                            productBitset->bitset,
                                            productBitset->numVariationSites,
                                            productBitset->actuallSizes,
                                            productBitset->allocSizes,
                                            productBitset->totalSelected,
                                            productBitset->numFragsInEachSite,
                                            progBufferSize,
                                            progBuffer))
                            goto AddTraceback ;
                    return 1 ;
            AddTraceback :
                    fprintf(stderr,"CS_PRDCT_BITSET_WRITE()--Unable to write bitset file\n");
                    return 0 ;
            }

/*
**+E:
**
**
** Function Name : CS_PRDCT_BITSET_CREATE()
**
** Purpose     : Function will create an in-memory product bitset from a
**               master file.
**
** Usage :
**
```

```
** Returns       : A handle to the product bitset info structure or NULL on
**                 error.
**
** Algorithms    : None.
**
** Revision History :
**
** Author              Date        Description
** ==================  ========    ===============
** Fred Soltanshahi    08/02/96    Original version.
**
**-E:
*/
void *CS_PRDCT_BITSET_CREATE(char *masterFileName,
                             int masterRecNumber,
                             int *initRawBitset)
{
struct BitSetFileStruct *bitset ;
    if ( !(bitset = ReadAndAllocateMaster(masterFileName,
                                          masterRecNumber,
                                          initRawBitset)) )
        return (void *)NULL ;
    else
        return (void *)bitset ;
}

/*
**+E:
**
**
** Function Name : CS_PRDCT_BITSET_SETBITS()
```

```
**
** Purpose      : Function will copy a raw bitset into the ChemSpace product
**                bitset format.
**
** Usage :
**
** Returns      : 1 on success or zero on failure.
**
** Algorithms   : None.
**
** Revision History :
**
** Author            Date        Description
** =================  ========
================
** Fred Soltanshahi   08/02/96    Original version.
**
**-E:
*/
int  CS_PRDCT_BITSET_SETBITS(void *bs, int *rawBS, int numProducts)
{
struct BitSetFileStruct *bitset = (struct BitSetFileStruct *)bs ;
void   *compressed ;
static int    firstTime = 1 ;
int    i ;
int    total;
char   *cp = (char *)rawBS ;
int rowLength ;
int index1 ;
int index2 ;
int byte ;
int bit ;
int totalSelected = 0 ;
```

```
if ( firstTime )
{
    Init();
    firstTime = 0 ;
}
/*
** Just create a new one.
*/
if ( bitset->bitset )
        IHBDestroy(bitset->bitset ) ;
if ( !(bitset->bitset  = CreateCompressedBitSet(rawBS,
                                                                    0,
bitset->numVariationSites, bitset->actuallSizes, bitset->allocSizes) ) )
            goto UnableToCreateBitSet ;
total = bitset->actuallSizes[0] ;
for ( i = 1 ; i < bitset->numVariationSites ; i++ )
        total *= bitset->actuallSizes[i] ;
if ( numProducts == -1 )
/*
** Calculate what products are being set.
*/
{
        numProducts = 0 ;
        rowLength = bitset->actuallSizes[1] ;
        for ( i = 0 ; i < total ; i++ )
        {
                byte = ( i ) / 8 ;
```

```
                    bit = ( i ) % 8 ;
                    if ( cp[byte] & setbits[bit] )
                        numProducts++ ;
            }
        }
        bitset->totalSelected = numProducts ;
        return 1 ;
UnableToCreateBitSet :
        fprintf(stderr,"CS_PRDCT_BITSET_SETBITS-- Unable to set bit\n");
        return 0 ;
}
```

```
/*
**+E:
**
**
** Function Name : CS_PRDCT_BITSET_TO_RAW ()
**
** Purpose    : Function will copy a ChemSpace product bitset to a
**               raw bitset format.
**
** Usage :    calloc rawBS before call. useAlloc nonzero to use allocated
**               rather than actual dimensions
**
** Returns    : 1 on success or zero on failure.
**
** Algorithms   : None.
**
** Revision History :
**
** Author              Date        Description
** ==================       =========
==================
```

```
** David Patterson        09/09/96    Original version.
**
**-E:
*/
int CS_PRDCT_BITSET_TO_RAW (void *bs, int *rawBS, int useAlloc)
{
  CS_PRDCT_BITSET_CONCAT_RAW(bs, rawBS, 0, useAlloc);
  return 1;
} int CS_PRDCT_BITSET_CONCAT_RAW(void *bs, int *rawBS, int offset,
                int useAlloc)
{
  int *indxs = 0;
  int address, sum, b;
  struct BitSetFileStruct *bitset = (struct BitSetFileStruct *) bs;
  for ( address = -1 , b = 0 ; b < bitset->totalSelected ; b++ )
  {
          address = IHBFindNextOne(bitset->bitset,address+1);
          BitSetAddressToIndexes(bitset,address,&indxs,0);
          if (useAlloc)
            FlagProduct(rawBS, 0,0, address+offset);
          else /* must explicitly calculate the address */
            {sum= CS_PRDCT_BITSET_INDEXES_TO_INDEX( bitset, indxs) ;
              FlagProduct(rawBS, 0,0, sum+offset);
            }
  }
  UTL_MEM_FREE(indxs);
  return 1;
}

/*
**+E:
```

```
**
**
** Function Name : CS_PRDCT_BITSET_SELECTED ()
**
** Purpose     : Function will return a ChemSpace bitset's totalSelected
**
** Usage :
**
** Returns     : integet count of selected bits in bitset
**
** Algorithms  : None.
**
** Revision History :
**
** Author              Date          Description
** ==================  ========
 ===============
** David Patterson     09/24/96      Original version.
**
**-E:
*/
int CS_PRDCT_BITSET_SELECTED (void *bsvoid )
{
struct BitSetFileStruct *bs = (struct BitSetFileStruct *) bsvoid;
    return bs->totalSelected;
}

/*
**+E:
**
**
** Function Name : CS_PRDCT_BITSET_REVEAL ()
**
```

```
** Purpose      : Function will return a ChemSpace bitset's struct info to
**                external calling program.
**
** Usage :
**
** Returns      : 1 on success or zero on failure.
**
** Algorithms   : None.
**
** Revision History :
**
** Author            Date         Description
** ==================    ========    ==============
** David Patterson     09/10/96    Original version.
**
**-E:
*/
int   CS_PRDCT_BITSET_REVEAL (void *bsvoid,
      char **MasterFile_Bitset,
      int  *StartRec_Bitset,
      int  *BitsInAbsentia,
      int  *BitsInAbsentiaNoCount,
      char **CoreFile,
      int  *StartCore,
      char **FngrFile,
      char ***Xfiles,
      int  **nY,
      FILE **FngrFile_File,
      int  *FingerOff,
      char **ScreenFileName,
      int  *BytesPerFingerPrint,
      int  *WordsPerFingerprint,
```

```c
        int **query,
        int **FingerCore_FP,
        int *FingerCore_Card   )
{
int i, size;
int *fooi;
struct BitSetFileStruct *bs = (struct BitSetFileStruct *) bsvoid;
if (MasterFile_Bitset)
    *MasterFile_Bitset   = bs->masterFileInfo.masterFilePathName ;
if (StartRec_Bitset)
    *StartRec_Bitset     =bs->masterFileInfo.masterRecNo ;
if (BitsInAbsentia)
    *BitsInAbsentia      = bs->masterFileInfo.numberOfMissingBits;
if (BitsInAbsentiaNoCount)
    *BitsInAbsentiaNoCount = bs->masterFileInfo.lbits;
if (CoreFile)       -
    *CoreFile            = bs->masterFileInfo.corefilePathName;
if (StartCore)
    *StartCore           = bs->masterFileInfo.startCore;
if (FngrFile)
    *FngrFile            = bs->masterFileInfo.fingerFileName;
if (Xfiles)
    *Xfiles              = bs->masterFileInfo.x_FileName;
if (nY)
    *nY                  = bs->actuallSizes;
if ( FngrFile_File)
{   if (!((*FngrFile_File) = UTL_FILE_FOPEN((*FngrFile),"r"))) return 0;
        if (!UTL_FILE_FREAD(&i,sizeof(int),1,*FngrFile_File)) return 0; /* nbits in fp */
        *BytesPerFingerPrint = ( i + 7 ) / 8 ;
        *WordsPerFingerprint = (*BytesPerFingerPrint + 3) / 4;
        (*query) = (int    *) UTL_MEM_ALLOC( *BytesPerFingerPrint);
```

```
            if (!UTL_FILE_FREAD(&i,sizeof(int),1,*FngrFile_File)) return 0; /* record
cnt */
            if (!UTL_FILE_FREAD(&i,sizeof(int),1,*FngrFile_File)) return 0; /* record
size */
            rewind(*FngrFile_File);
            if (!(fooi = (int *) UTL_MEM_ALLOC( i          ))) return 0;
            size = (3+i)/4 ;
            for ( i=0; i< = *FingerOff; i++)
                    if (!UTL_FILE_FREAD( fooi,sizeof(int),size,*FngrFile_File))
                            return 0;
/* if ( fooi[1] != 2 + nY_01 * nY_02 ) return 0; */
            if ( ScreenFileName )
            {
                    if (!((*ScreenFileName) = UTL_STR_SAVE(fooi+4))) return 0 ;
            } if ( FingerCore_FP )
            {
                    *FingerCore_FP = fooi;
                    if (!UTL_FILE_FREAD( FingerCore_Card,sizeof(int),1,
*FngrFile_File))
                            return 0;
                    if (!UTL_FILE_FREAD(*FingerCore_FP ,
                                        sizeof(int),
                                        *WordsPerFingerprint,
                                        *FngrFile_File))
                            return 0;
            }
    }
        return 1;
}

/*
```

```
**+E:
**
**
** Function Name : CS_PRDCT_BITSET_INDEXES_TO_INDEX()
**
** Purpose     : Function will return the right bit given a set of indices
**
** Usage :      all indexes are 0 based.
**
** Returns     : index to use in bitset.
**
** Algorithms  : None.
**
** Revision History : extracted from CS_PRDCT_BITSET_SET_PRD_BIT by
**                    David Patterson
**
** Author            Date        Description
** ===================           ========
** ================
** Fred Soltanshahi    08/02/96    Original version.
**
**-E:
*/
int  CS_PRDCT_BITSET_INDEXES_TO_INDEX( struct BitSetFileStruct *bitset,
                    int *indexes)
{
int   i ;
int   j ;
int   rowLength[MAX_VARIATION_SITES] ;
int   indx = 0 ;
      for ( i = 0 ; i < bitset->numVariationSites ; i++ )
      {
              rowLength[i] = 1 ;
```

```
            for ( j = i + 1 ; j < bitset->numVariationSites ; j++ )
                rowLength[i] *= bitset->actualSizes[j] ;
        }
        for ( i = 0 ; i < bitset->numVariationSites ; i++ )
        {
            indx += indexes[i] * rowLength[i] ;
        }
        return indx ;
}

/*
**+E:
**
**
** Function Name : CS_PRDCT_BITSET_ALLOC_SIZE_INDEXES_TO_INDEX()
**
** Purpose      : Function will return the right bit given a set of indices
**                it uses the allocated sizes in the bitset to get the info.
**
*/
int  CS_PRDCT_BITSET_ALLOC_SIZE_INDEXES_TO_INDEX( struct BitSetFileStruct *bitset,
                int *indexes)
{
int    i ;
int    j ;
int    rowLength[MAX_VARIATION_SITES] ;
int    indx = 0 ;
        for ( i = 0 ; i < bitset->numVariationSites ; i++ )
        {
            rowLength[i] = 1 ;
            for ( j = i + 1 ; j < bitset->numVariationSites ; j++ )
                rowLength[i] *= bitset->allocSizes[j] ;
```

```
        }
        for ( i = 0 ; i < bitset->numVariationSites ; i++ )
        {
                indx += indexes[i] * rowLength[i] ;
        }
        return indx ;
}

/*
**+E:
**
**
** Function Name : CS_PRDCT_BITSET_SET_PRD_BIT()
**
** Purpose    : Function will set a product bit with the given indexes.
**
** Usage :
**
** Returns    : none.
**
** Algorithms : None.
**
** Revision History :
**
** Author              Date       Description
** ==================         =========
================
** Fred Soltanshahi    08/02/96   Original version.
**
**-E:
*/
int  CS_PRDCT_BITSET_SET_PRD_BIT(void *bs, int *indexes)
{
```

```
struct BitSetFileStruct *bitset = (struct BitSetFileStruct *)bs ;
int   indx = 0 ;
      indx = CS_PRDCT_BITSET_ALLOC_SIZE_INDEXES_TO_INDEX(bitset,
indexes);
      IHBSet(bitset->bitset, indx );
      bitset->totalSelected++ ;
      return 1 ;
}

/*
**+E:
**
**
** Function Name : CS_PRDCT_BITSET_GET_RINFO()
**
** Purpose    : Function will return the Reaction/Reagent info from
**              the bitset file.
**
** Usage :
**
** Returns    : none.
**
** Algorithms : None.
**
** Revision History :
**
** Author            Date       Description
** ==================           ========
================
** Fred Soltanshahi     01/03/97   Original version.
**
**-E:
*/
```

```
int CS_PRDCT_BITSET_GET_RINFO(void *bs, char **reactionInfo,char ***reagentInfo)
{
struct BitSetFileStruct *bitset = (struct BitSetFileStruct *)bs ;
    *reactionInfo = bitset->masterFileInfo.prefixForFiles ;
    *reagentInfo  = bitset->masterFileInfo.reagentInfo ;
    return 1 ;
}
```

```
/*
**+E:
**
**
** Function Name : CS_PRDCT_BITSET_GET_STATS()
**
** Purpose    : Function will return the statistics for a bitset file,
**               these will include numberOfSites, originalSizes,
**               numberOfProducts and Number of fragments used at each
**               variation site.
**
** Usage :
**
** Returns    : none.
**
** Algorithms : None.
**
** Revision History :
**
** Author              Date         Description
** ==================  ========  ===============
** Fred Soltanshahi    08/05/96   Original version.
**
**-E:
```

```
*/
int CS_PRDCT_BITSET_GET_STATS(void *bs, int *numSites, int *numProducts,
int **sizes, int **numUsed )
{
struct BitSetFileStruct *bitset = (struct BitSetFileStruct *)bs ;
        *numSites = bitset->numVariationSites ;
        *numProducts = bitset->totalSelected ;
/*
** Allocate buffers, if they have not been.
*/
        if ( !(*sizes) )
        {
                if ( !((*sizes) = (int *)UTL_MEM_CALLOC(*numSites,sizeof(int))))
                        goto UnableToAllocateMemory ;
        }
        if ( !(*numUsed) )
        {
                if ( !((*numUsed) = (int *)UTL_MEM_CALLOC(*numSites,sizeof(int))))
                        goto UnableToAllocateMemory ;
        }
        memcpy(*sizes, bitset->actuallSizes, sizeof(int) * *numSites );
        memcpy(*numUsed, bitset->numFragsInEachSite, sizeof(int) * *numSites );
        return 1 ;
UnableToAllocateMemory :
        fprintf(stderr,"CS_PRDCT_BITSET_GET_STATS() -- Unable to allocate memory\n");
        return 0 ;
}

/*
**+E:
**
```

```
**
** Function Name : CS_PRDCT_BITSET_CORE_INFO()
**
** Purpose    : Function will get the xfile and core and xrstring info
**              from the bitset file.
**
** Usage :
**
** Returns    : 1 on success or 0 on error.
**
** Algorithms : None.
**
** Revision History :
**
** Author              Date        Description
** ===================  ========
================
** Fred Soltanshahi    08/09/96    Original version.
**
**-E:
*/
int CS_PRDCT_BITSET_CORE_INFO(void *bs, char **masterName, int *masterRecno,
char **core, char **xrString, int *numSites, char ***xFileNames )
{
        return ( ReadBitsetCoreInfo(bs,masterName,masterRecno,
                core,xrString,numSites,xFileNames));
}

/*
**+E:
**
**
** Function Name : CS_PRDCT_BITSET_PROG_NAME()
```

```
**
** Purpose      : Function will get the program name that produced this bitset.
**
** Usage :
**
** Returns      : 1 on success or 0 on error.
**
** Algorithms   : None.
**
** Revision History :
**
** Author             Date       Description
** ==================  ========
================
** Fred Soltanshahi    08/09/96   Original version.
**
**-E:
*/
int CS_PRDCT_BITSET_PROG_NAME(void *bs, char **programName)
{
     *programName = ((struct BitSetFileStruct *)bs)->programInfo.programName ;
     return 1 ;
}

/*
**+E:
**
**
** Function Name : CS_PRDCT_MSTR_CORE_INFO()
**
** Purpose      : Function will get the xfile and core and xrstring info
**                from the master file.
**
```

```
** Usage :

**

** Returns       : 1 on success or 0 on error.

**

** Algorithms    : None.

**

** Revision History :

**

** Author              Date        Description

** ==================  ========

================

** Fred Soltanshahi    08/09/96    Original version.

**

**-E:

*/
int CS_PRDCT_MSTR_CORE_INFO(char *masterFile, int index, char **core, char **xrString, int *numSites, char ***xFileNames )
{
        return ( ReadMasterCoreInfo(masterFile,index
,core,xrString,numSites,xFileNames));
}

/*
**+E:

**

**

** Function Name : CS_PRDCT_BITSET_CREATE_BIT_STRING()

**

** Purpose    : Function will create a compressed version of a raw bit set.
**             It returns the memory size needed to hold the bitset.
**

** Usage :
```

```
**
** Returns      : pointer to a compressed bitset(this is not a ChemSpace
**                product bitset but just a compressed bitstring)
**
** Algorithms   : None.
**
** Revision History :
**
** Author              Date      Description
** ==================  ========  ===============
** Fred Soltanshahi    08/06/96  Original version.
**
**-E:
*/
void *CS_PRDCT_BITSET_CREATE_BIT_STRING( int *rawBits, int offset, int numVariations, int *sizes, int *allocSizes, int *totalSize)
{
void *compressed ;
    if ( !(compressed = CreateCompressedBitSet(rawBits,
                                                offset,
                                                numVariations,
                                                sizes,
                                                allocSizes) ) )
        goto UnableToCreateBitSet ;
    *totalSize = IHBRealSize(compressed);
    return compressed ;
UnableToCreateBitSet :
    fprintf(stderr,"CS_PRDCT_BITSET_CREATE_BIT_STRING() -- Unable to create bitset\n");
    return ( void *)NULL ;
```

}

```
/*
**+E:
**
**
** Function Name : CS_PRDCT_BITSET_DESTROY_BIT_STRING()
**
** Purpose      : Function will destroy the memory for a bitstring
**                allocate by the CREATE call above.
**
** Usage :
**
** Returns      : none
**
** Algorithms   : None.
**
** Revision History :
**
** Author              Date        Description
** ==================  ========
** ================
** Fred Soltanshahi    08/06/96    Original version.
**
**-E:
*/
void CS_PRDCT_BITSET_DESTROY_BIT_STRING( void *bitset)
{
    IHBDestroy(bitset);
}

/*
**+E:
```

```
**
**
** Function Name : CS_PRDCT_BITSET_GETHITS()
**
** Purpose    : Function will return the indexes(into the original X1,X2 files
**              for the requested number of hits.
**
** Usage :
**
** Returns    : Number of hits found or -1 for error.
**
** Algorithms : None.
**
** Revision History :
**
** Author              Date        Description
** ==================  ========
** ===============
** Fred Soltanshahi    08/07/96    Original version.
**
**-E:
*/
int CS_PRDCT_BITSET_GETHITS( void *bs, int offset, int numberOfHits, int ***hitIndexes)
{
struct BitSetFileStruct *bitset = (struct BitSetFileStruct *)bs ;
int numFound ;
int numConnections ;
static int *bitAddresses = (int *)NULL ;
static int numBitAddresses = 0 ;
int *indxs = (int *)NULL ;
int start ;
int count ;
```

```
int i ;

int j ;

(*hitIndexes) = (int **)NULL ;

numConnections = bitset->numVariationSites ;

/*
** Local housekeeping .
*/ if ( numberOfHits > numBitAddresses )

{ if ( !bitAddresses )

{ if ( !(bitAddresses = (int *)UTL_MEM_CALLOC(numberOfHits, sizeof(int))) )

goto UnableToAllocate ;

} else

{ if ( !(bitAddresses = (int *)UTL_MEM_REALLOC(bitAddresses, numberOfHits* sizeof(int))) )

goto UnableToAllocate ;

} numBitAddresses = numberOfHits ;

}

/*
** Figure out if we have the number of hits he wanted and what their addresses
** are in the bitset file.
**
** We will have to come back and speed this up if it is to slow, but for now
** lets get it working.
**
```

```
*/
/*      start = bitset->firstHitAddress ; */
        start = -1 ; /* start from the begining */
        for ( count = 0 ; count < offset ; count++ )
        {
                start = IHBFindNextOne(bitset->bitset,start+1);
/*
** Lets remember where the first hit is, this should save us some time later.
*/
                if ( bitset->firstHitAddress <= 0 )
                        bitset->firstHitAddress = start ;
                if ( start == -1 )
                {
                        return 0 ;
                }
        }
/*
** Now lets see how many bits are set from here on.
*/
        for ( numFound = 0 ; numFound < numberOfHits ; numFound++ )
        {
                start= IHBFindNextOne(bitset->bitset,start+1);
                if ( start == -1 )
                        break;
                bitAddresses[numFound] = start ;
        }
/*
** Allocate the arrays.
*/
        if ( !(*hitIndexes = (int **)UTL_MEM_CALLOC(numConnections,sizeof(int *))) )
                goto UnableToAllocate ;
        for ( i = 0 ; i < numConnections ; i++ )
        {
```

```
                if ( !((*hitIndexes)[i] = (int *)UTL_MEM_CALLOC(numFound,
sizeof(int ))) )
                        goto UnableToAllocate ;
        }
/*
** Now translate each one of the bitset addresses to the variation site
** indexes.
*/
        for ( i = 0 ; i < numFound ; i++ )
        {
                BitSetAddressToIndexes(bitset,bitAddresses[i],&indxs,0);
                for ( j = 0 ; j < numConnections ; j++ )
                        (*hitIndexes)[j][i] = indxs[j] + 1 ; /* Translate to 1 based indexes */
        }
        if ( indxs )
                UTL_MEM_FREE( indxs );
        return numFound ;
UnableToAllocate :
AddTraceback :
        if ( indxs )
                UTL_MEM_FREE( indxs );
        return -1 ;
}

/*
**+E:
**
**
** Function Name : CS_PRDCT_BITSET_GET_PARTIAL_HITS()
**
** Purpose      : Function will return the indexes(into the original X1,X2 files
**                for the requested number of hits.
```

```
**
** Usage :
**
** Returns     : Number of hits found or -1 for error.
**
** Algorithms  : None.
**
** Revision History :
**
** Author           Date       Description
** ==================    ========
================
** Fred Soltanshahi      08/07/96    Original version.
**
**-E:
*/
int CS_PRDCT_BITSET_GET_PARTIAL_HITS( void *bs, int *numProducts, int site, int
numFixedSites, int *fixedSitesIndexes, int *numFragmentsPerSite, int **hitIndexes )
{
struct BitSetFileStruct *bitset = (struct BitSetFileStruct *)bs ;
int   total ;
        (*hitIndexes) = (int *)NULL ;
        GetPartialProductsStats( bitset ,
                                            numFixedSites,
                                            fixedSitesIndexes,
                                            &total,
                                            numFragmentsPerSite);

(*numProducts ) = GetPartialProductsAddresses(bitset,
                                            numFixedSites,
                                            fixedSitesIndexes,
                                            site,
                                            hitIndexes);
```

```
            return 1 ;
}

/*
**+E:
**
**
** Function Name : CS_PRDCT_BITSET_GET_PRDCT_PARTIAL_HITS()
**
** Purpose      : Function will return the indexes(into the original X1,X2 files
**                for the requested number of hits.
**
** Usage :       This works when the csln is actually being exploded.
**
** Returns      : Number of hits found or -1 for error.
**
** Algorithms   : None.
**
** Revision History :
**
** Author            Date        Description
** ==================      ========
================
** Fred Soltanshahi     08/07/96    Original version.
**
**-E:
*/
int  CS_PRDCT_BITSET_GET_PRDCT_PARTIAL_HITS( void *bs, int *numProducts, int site, int numFixedSites, int *fixedSitesIndexes, int *numFragmentsPerSite, int **hitIndexes
)
{
struct BitSetFileStruct *bitset = (struct BitSetFileStruct *)bs ;
int    total ;
```

```
    (*hitIndexes) = (int *)NULL ;
    GetPartialProductsStats( bitset ,
                                          numFixedSites,
                                          fixedSitesIndexes,
                                          &total,
                                          numFragmentsPerSite);

(*numProducts ) = GetPartialProductsAddresses(bitset,
                                          numFixedSites,
                                          fixedSitesIndexes,
                                          site,
                                          hitIndexes);
    (*numProducts ) = total ;
        return 1 ;
}

/* +E
Abstract: For Chemspace bitset file call callback with products choices not selected.
Input:
1. This function takes a BitSetFileStruct returned most likely from:
        CS_PRDCT_BITSET_OPEN(char *filename)
2. A void pointer which is passed to callback function.  This is for
        whatever you want.
3. A pointer to function returning:
                int (void *udata, int numVariants, int *choices ).
    choices is of size numVariants, the choices are zero based, and
    choices[0] is the choice for markush Y_01, choice[1] for Y_02 etc.
    NOTE 1: numVariants of -1 and a null for choices is passed to signify
        the end of the choices excluded, just in case the function
        want to do some special processing at the end.
    NOTE 2: The return value from the callback function is ignored.
Returns:
    Total number of bits excluded.
```

-1 upon error.
```
** Author              Date        Description
** ==================  ==========  ================
** Rob Jilek           07/26/96    Original version.
*/
int CS_PRDCT_BITSET_ZERO(struct BitSetFileStruct *bitset, void *udata,
int (*ZeroProducts)(void *udata, int numVariants, int *choices ) )
{
    BIT_TRACKING bt[1];
    if ( bitset->numVariationSites <= 0 )
            return -1;
    bt->numVariations = bitset->numVariationSites;
    bt->bitset = bitset;
    bt->call_udata = udata;
    bt->funcptr = ZeroProducts;
    bt->choices = (int *) UTL_MEM_CALLOC(bt->numVariations, sizeof(int) );
    bt->totalExcluded = 0;
        /* The sequence is as follows:
                IHBRange has a loop to find zeros/ones.
                    It calls RangeCallback
                        RangeCallback calls ZeroProducts callback.
                while ( not end of list )
                    call RangeCallback with start and end Range.
                        for ( i = startRange; i <= EndRange; i++ ) // RangeCallback
                            calculate product array.
                            call ZeroProducts                       // ZeroCallback
        */

IHBRange(bitset->bitset, 0, (void *) bt, RangeCallback );
    UTL_MEM_FREE((char *) bt->choices );
```

```
            return bt->totalExcluded;
}
/*+I
Synopsis: Gets called for each range of bits set. It then
converts each bit to a product array and calls callback for each.
*/
static int RangeCallback ( void *udata, int startRange, int endRange )
{
        BIT_TRACKING *bt = (BIT_TRACKING *) udata;
        int indx;
        int oor;
        int skip;
        void *call_udata;
        int numVar;
        int *choices;
        void *bitset;
        call_udata = bt->call_udata;
        numVar = bt->numVariations;
        choices = bt->choices;
        bitset = bt->bitset;
        for ( indx = startRange; indx <= endRange; )
        {
                skip = BitSetAddressToIndexes(bitset,indx,&choices,&oor);
                if ( !oor )
                {
                        (*bt->funcptr)(call_udata, numVar, choices );
                        bt->totalExcluded++;
                        indx++;
                }
                else
                {
                        if ( skip > 0 )
                                indx += skip;
```

```
                    else
                        indx++;
            }
        }
        (*bt->funcptr)(call_udata,-1, (int *) 0 );        /* Signify end of zeros. */
        return 0;
}

/* +E
Abstract: For Chemspace bitset file call callback with products choices selected.
Input:
    1. This function takes a BitSetFileStruct returned most likely from:
            CS_PRDCT_BITSET_OPEN(char *filename)
    2. A void pointer which is passed to callback function.  This is for
        whatever you want.
    3. A pointer to function returning:
                        int (void *udata, int numVariants, int *choices ).
        choices is of size numVariants, the choices are zero based, and
        choices[0] is the choice for markush Y_01, choice[1] for Y_02 etc.
        NOTE 1: numVariants of -1 and a null for choices is passed to signify
            the end of the choices excluded, just in case the function
            want to do some special processing at the end.
        NOTE 2: The return value from the callback function is ignored.
Returns:
    Total number of bits included.
    -1 upon error.
See Also: CS_PRDCT_BITSET_ZERO
** Author             Date        Description
** ====================           =========
====================
** Rob Jilek           08/19/96    Original version.
*/
int CS_PRDCT_BITSET_ONE(struct BitSetFileStruct *bitset, void *udata,
```

```c
int (*OneProducts)(void *udata, int numVariants, int *choices ) )
{
        BIT_TRACKING bt[1];
        if ( bitset->numVariationSites <= 0 )
                return -1;
        bt->numVariations = bitset->numVariationSites;
        bt->bitset = bitset;
        bt->call_udata = udata;
        bt->funcptr = OneProducts;
        bt->choices = (int *) UTL_MEM_CALLOC(bt->numVariations, sizeof(int) );
        bt->totalExcluded = 0;
        IHBRange(bitset->bitset, 1, (void *) bt, RangeCallback );
        UTL_MEM_FREE((char *) bt->choices );
        return bt->totalExcluded;
} if 0
main(argc,argv)
int argc ;
char *argv[] ;
{
void *h ;
char *masterFileName =
"/home7/fred/work/ADS/dserv/source/dbcsln_des/TestData/Di_300_400.mf" ;
int   masterRecNumber = 1 ;
int  *bitset ;
int size = ( 300 * 400 + 7 ) / 8 ;
int  i ;
int  j ;
int  indexes[2] ;
char hold[81];
#if 1
        if ( !(h = CS_PRDCT_BITSET_OPEN(argv[1],0)))
```

```
        {
                fprintf(stderr,"Unable to open the bitset file %s\n",argv[1]);
                exit ;
        }
        CS_PRDCT_BITSET_DUMP(h);
        CS_PRDCT_BITSET_CLOSE(h);
#else
        if ( !( h = CS_PRDCT_BITSET_CREATE(masterFileName,masterRecNumber,NULL) ) )
        {
                fprintf(stderr,"Unable to create bitset for %s\n",masterFileName);
                exit ;
        }
        CS_PRDCT_BITSET_WRITE("Test.bs","MyProg",h,0,NULL);

indexes[0] = 59 ;
        indexes[1] = 129 ;
        CS_PRDCT_BITSET_SET_PRD_BIT(h,indexes);
        indexes[0] = 159 ;
        indexes[1] = 241 ;
        CS_PRDCT_BITSET_SET_PRD_BIT(h,indexes);
        CS_PRDCT_BITSET_WRITE("Test2.bs","MyProg",h,0,NULL);
        bitset = (int *)UTL_MEM_CALLOC(size,sizeof(int));
        bitset[5] = 49 ;
        bitset[1] = 99 ;
        CS_PRDCT_BITSET_SETBITS(h,bitset,-1);
        CS_PRDCT_BITSET_WRITE("Test1.bs","MyProg",h,0,NULL);
        CS_PRDCT_BITSET_CLOSE(h);
#endif
}
endif
```

Appendix "S"

```
/***************************************************************
*/
/*                    topsim                                  */
/***************************************************************
*/
/*+C
*
* This program determines which csln "products" are similar to an input
* structure, where similarity occurs if the sum of differences in encoded
* "CoMFA" fields is less than some threshold.
*
* The csln components are referenced in a master file with
* one multiline record per cSLN. Record format is
*   Reaction class xxxx          (where "Reaction class" is a literal)
*   reaction_name
*   number_of_sv_sites
*   missing_bits_count
*   hashed_only_missing_bits_count
*   core_filename
*   core_filename_index_of_core
*   fingerprint_filename
*   offset_into_fingerprint_file
*   first_sv_file_X1
*   secod_sv_file_X2             (etc if more than two sv_sites)
*
* NOTE -- ALL subsequent entries in the master file whose Reaction class
* matches the Reaction class of the record referenced by -index are also
* processed! ("Matching" implies matching of possible other input symbols
* to components of the Reaction class line.)
*
* The input structure is read as encoded fields from stdin (or
* a named file if provided), one field per line. There
```

```
* must be provided (by a SYBYL SPL script), in order:
*
* "number_of_sv_sites" * "number_of_field_types" fields describing the "core" of the query
* "number_of_sv_sites" - 1 sextets of relative coordinates of core attachment atoms
* "number_of_sv_sites" * "number_of_field_types" fields describing the "side chains"
*
* Options:
*
*    -master  name        - name is the file with master file records
*    -bitset  name        - name is a result of an earlier search operation
*                           (use EITHER master or bitset)
*
*    -index   number      - which sequential record in master file to begin at
*                           OR offset into bitset in a bitset file
*                           (default = 1)
*
*    -reaction name       - records in master file to be processed must have this
*                           class name
*
*    -details  name       - if provided, records in master file to be processed
*                               must have any one of these tokens following its class name
*
*    -distance tan        - tan is the overall similarity threshold
*                           (default is 90.0)
*
*    -cooweight cwt       - weight of the core attachment coordinates,
*                               relative to fields
*
*    -nocore nocore       - do not consider core topomer differences
*                           By default these are considered (required)
*
*    -allcores allc       - process all cores in the core file
```

```
*                       By default only one core (index in the master file) is processed
*
*    -maxhits max       - stop when max hits are found (default infinity)
*
*    -input filename    - name of file with queries (default stdin)
*
*    -output filename   - specifies the output file for the hit info
*
*    -#                 This flag forces the display of all
*                       options
*
*

**********************************************************************
/
#include <stdio.h>
include <signal.h>
#include <ctype.h>
#include <unistd.h>
#include <string.h>
#include <sys/stat.h>
#include <math.h>
#include "parseopt.h"
#include "utl_str.h"
#include "utl_mem.h"
#include "utl_file.h"
#include "utl_math.h"
#include "ct.h"
#include "ct_expr.h"
#include "ct_proto.h"
#define GoodExit 0
#define ErrorExit 1
#define Visual(s) {           fprintf s; }
```

```
static FILE      *OutputFile = 0;
static char      *OutputFileBase;
static char      OutputFileName[200];
static int       nOutFiles = 0;  /* number of output files */
static char      *MasterFile = 0;
static char      *BitsetFile = 0;
void             *bitset;
static int       MasterRecord = 1;
static FILE      *MasterFile_File;
static int       StartCore;
static char      *InputSource = 0;
static FILE      *InputSourceFile;
static char      *ReactionNeeded = 0;
static char      *ScratchDetails = 0;
static int       nDetail = 0;
static char      **ReactionDetails = 0;
static char      *XWeights = 0;
static double    *RWeights = 0;
static double    CoreWeight;
static char      *FieldTypes = 0;
static int       nFType = 0;
static char      **FTypes = 0;
static double    *FWeights = 0;
static char      **FOrder = 0;  /* temp, for recording L->R order of data
                                   in side chain SLN */
static char      **FROrder = 0;
static char      *Corefile = 0;
static FILE      *CoreFile_File;
static char      *CoreNow;
static char      **Xfile;
static char      **Xname;
static double    Distance = 90.0;
static double    CoreDistance = 0.0;
```

```
static double        DWeight = 1.0;
static double        Dist[16][16];
static double        boundary[16];
static double        CXcoords[6], CXdiffsq[6];
static double        searched = 0.0; /* number searched */
static double        combi = 1.0; /* number of side chain combos */
static int           totnout = 0, nout = 0; /* number of products */
static int           *Good_Products = 0; /* product bit set */
static int           *Dead_Products = 0; /* forbidden product bit set */
static int           nR;      /* number of R positions (usually 2) */
static int           *nX;     /* number of product dimensions */
static int           *Xct;    /* used for indexing over all products */
static int           **Xsize; /* bytes per field */
static unsigned char ****X = 0;   /* csln field (F x R x nX )*/
static unsigned char ***Xin;      /* target fields */
static unsigned char ***Y;        /* csln core fields (F x R ) */
static unsigned char ***Yin;      /* target core fields */
static double        ***X2Y;      /* distances between X and X' */
static int           nSym,   /* number of symmetries in this core */
                     *CoreSyms, /* flags for all matching core symmetries */
                     **SymList; /* symmetry mappings */
static int           DefaultSym[9] = {0, 1, 2, 3, 4, 5, 6, 7, 8};
static int           ReverseSym[2] = {1, 0};
static int           AppendToOutputFile = 0;
static int           NoMorehitsPlease = 0;
static int           UserAborted;
static int           NoCore = 0;
static int           AllCores = 0;
static int           CoreOK = 0;
static int           CoreIsSame = 0;
static int           SideChainOnly = 0;
static int           SideChainsAreSame = 0;
static int           NotBitOutput = 0;
```

```
static char              comline[2048];
static struct ParseOptions Options[] = {
        {"master",   ParseOptString,   &MasterFile,
                "Prefix for all input files" },
        {"bitset",   ParseOptString,   &BitsetFile,
                "Name is the file with bitset records" },
        {"distance", ParseOptDouble,   &Distance,
                "Field similarity threshold (default 90.0)" },
        {"cooweight", ParseOptDouble,  &DWeight,
                "Core coord wt, relative to fields (default )" },
        {"index",    ParseOptInt,      &MasterRecord,
                "Which MasterRecord entry 1-n" },
        {"maxhits",  ParseOptInt,      &NoMorehitsPlease,
                "Maximum number of hits before stopping" },
        {"nocore",   ParseOptInt,      &NoCore,
                "Use -nocore to override inclusion of the core differences" },
        {"allcores", ParseOptInt,      &AllCores,
                "Use -allcores to search all cores provided" },
        {"input",    ParseOptString,   &InputSource,
                "File from which queries will be read( default stdin). "},
        {"output",   ParseOptString,   &OutputFileBase,
                "File to which hit info will be written. "},
        {"notbits",  ParseOptInt,      &NotBitOutput,
                "Use notbits to output as index ASCII instead of std bitset." },
        {"reaction", ParseOptString,   &ReactionNeeded,
                "Reaction class for topomer search. "},
        {"details",  ParseOptString,   &ScratchDetails,
                "Details further discriminating the reaction class. "},
        {"sidechain", ParseOptInt,     &SideChainOnly,
                "Use sidechain to search for similiarity in a single sidechain only. "},
        {"fieldtypes", ParseOptString, &FieldTypes,
                "Names of all field types (optional prefix =weight), space separated. Does
CTOPS if none provided."},
```

{"xweights", ParseOptString, &XWeights,
"Weights of varying sites. Must be nR(+core?) individual weights present (if any)."},
};

```
int UBS_OUTPUT_MESSAGE() { return 0; }   /* just for compiling OK */
int UIMS2_WRITE_PHOTO() { return 0; }
int lowercase (s) char *s; {while (*s) { if isupper(*s) *s = tolower(*s); s++;}}
static int ParseArguments( argc, argv )
/*+I
 *
 * This function parses the command line arguments.
 *
 * Returns:  1 on a successful command line parse, 0 otherwise.
 *
 * Warnings:
 *
 * Errors:
 *
 * Author     Date         Description
 * ======     ========     ===========
 * G. B. Smith  02-09-93   Original Version
 *
 */
int     argc;
char    **argv;
{
    int     nargs,
            noptions = sizeof( Options )/sizeof(Options[0]);

nargs = UTL_PARSE_OPT( argc, argv, noptions, Options );

if( !nargs ) goto SyntaxError;

return 1;
SyntaxError:
    fprintf( stderr, "Bad command line argument(s)\n" );
```

```
        return 0;
}
static int OpenOutputFile()
/*+I
 *
 * Returns:  1 on sucesss, else 0
 *
 */
{
        char    *msg;
        FILE    *fp;
        OutputFile = stdout;
        if( OutputFileBase)
        {
                MakeOutputFileName();
/*
** We need to create output files under the ownership of the REAL user not the
** EFFECTIVE user.  This only applies if setuid options are activated.
*/
{
struct stat statBuff ;
int     uid ;
int     euid ;
        uid = getuid() ;
        euid = geteuid();
   stat(OutputFileName, &statBuff);
/*
** There are two cases
** (1) the file to output to exists
**     Use the ownership of the current owner of the file or if you cant do that
**     do not do anything.
** (2) The file is being created.
**     use the ownership of the REAL user.
```

```c
        */
            if ( access(OutputFileName, F_OK) == 0 )
            { /* If the file exist and the real user is the owner of the file */
                if ( statBuff.st_uid == uid )
                    seteuid(uid);
            }
            else
            { /* Create the file as the REAL user */
                seteuid(uid);
            }
        }
            OutputFile = fopen( OutputFileName, (AppendToOutputFile?"a":"wb"));
            if( !OutputFile ) {
                fprintf(stderr,"Error: Failed to open output file \"%s\"\n",
                    OutputFileName );
                goto ErrorReturn;
            }
        }
            return 1;
ErrorReturn:
            return 0;
}
static int WhatsTheDifference()
/* builds distance lookup table and initializes default symmetry data structure */
{
int i, j;
define pow2(a) ( (a) * (a) )
/* the assignment of codes is based on the following (from gen_pls.c):
   static fpt cutoff[16] = {9999.,  0.,   2.,   4.,   6.,   8.,  10.,  12.,
                             14.,  16.,  18.,  20.,  22.,  24.,  26.,  30.  };
*/
boundary[0] = 9999.; /* missing data ought never to occur. */
boundary[1] = -0.1 ;
```

```
for (i=2;i< 15;i++)
  boundary[i] = 2*i-3;
boundary[15] = 30.0;  /* this is a steep curve with a cutoff at 30! */
for (i=0;i<16;i++) for (j=0;j<16;j++)
  Dist[i][j] = pow2( boundary[i] - boundary[j]);
Distance *= Distance;  /* want to test D^2 directly */
DWeight *= DWeight;
/* allocate once for all conceivable symmetry reorderings */
if (!(SymList = (int **) UTL_MEM_ALLOC( sizeof( int *) * nR * (nR - 1) / 2) ))
        return 0;
if (!(CoreSyms = (int *) UTL_MEM_ALLOC( sizeof( int ) * nR * (nR - 1) / 2) ))
        return 0;
SymList[ 0 ] = DefaultSym;
SymList[ 1 ] = ReverseSym;
return 1;
}
static int ReadAField( hex, index, pXP )
/* converts field from external (ASCii hex) format to internal */
char *hex;
int *index;
unsigned char **pXP;
{
  int words, hold;
  char next2[10], *nxhx;
  words = strlen( hex ) / 2;  /* assuming 8-bit bytes */
  if (! *index ) *index = words;
  if ( words != *index ) {
/* bad field (most likely NULL), continue anyway */
        *pXP = (unsigned char *) NULL;
        return 1;
  }
  if (!(*pXP = (unsigned char *) UTL_MEM_ALLOC(words) )) return 0;
  for (words=0, nxhx = hex; words< *index ; words++) {
```

```c
        memcpy(next2, nxhx, 2);
        nxhx += 2;
        sscanf( next2, "%2x", &hold );
        *(*pXP + words) = (unsigned char) hold;
    }
    return 1;
}
static int RetrieveInput() {
/* reads the search pattern fields (generated by SYBYL script) */
    int index, R, F;
    char *line;
    double atof();
    if (!InputSource) InputSourceFile = stdin;
        else if (!(InputSourceFile = fopen( InputSource, "r" ) )) {
            fprintf( stdout, "Could not open -input file %s\n", InputSource );
            return 0;
    }
    if (!(Yin = (unsigned char ***) UTL_MEM_ALLOC( sizeof( unsigned char **) * nFType
)))
        return 0;
    for (F = 0; F < nFType; F++) {
        if (!(Yin[ F ] = (unsigned char **) UTL_MEM_ALLOC( sizeof( unsigned char *) * nR
)))
            return 0;
        memset( Yin[F], 0, sizeof( unsigned char *) * nR );
    }
    if (!NoCore) {
/* field types are paired closest! */
    for (index = 0; index < nR; index++) for (F = 0; F < nFType; F++) {
/* a Field is on a single line, no parsing needed */
        if (-1 == UTL_SCAN_GETS( InputSourceFile, "\\", "#", &line))
                return 0;
        if (!ReadAField( line, Xsize[ F ] + index, Yin[ F ] + index )) return 0;
```

```c
}
for (index = 0; index < 6; index++) {
    if (-1 == UTL_SCAN_GETS( InputSourceFile, "\\", "#", &line))
        return 0;
    CXcoords[ index ] = atof( line );
}
if (!(Xin = (unsigned char ***) UTL_MEM_ALLOC( sizeof( unsigned char **) * nFType
)))
    return 0;
for (F = 0; F < nFType; F++) {
    if (!(Xin[F] = (unsigned char **) UTL_MEM_ALLOC( sizeof( unsigned char *) * nR
)))
        return 0;
    memset( Xin[F], 0, sizeof( unsigned char *) * nR );
}
for (index = 0; index < nR; index++) for (F = 0; F < nFType; F++ ) {
/* a Field is on a single line, no parsing needed */
    if (-1 == UTL_SCAN_GETS( InputSourceFile, "\\", "#", &line))
        return 0;
    if (!ReadAField( line, Xsize[ F ] + index, Xin[ F ] + index )) return 0;
}
}
fclose( InputSourceFile );
return 1;
}
static int InitCore() {
/* readies core file and its input arrays */
int R, i, F;
char *foo;

if (! (CoreFile_File = fopen(Corefile,"r"))) {
    fprintf( stderr, "%s Core file not found.\n", Corefile );
    return 0;
```

```
  }
  i=0;
  while ( i < StartCore )
  {
    if ( -1 == UTL_SCAN_GETS( CoreFile_File, "\\", "#", &foo)) return 0;
    if (AllCores) break;
    i++;
  }
  CoreNow = UTL_STR_SAVE( foo );
/* initialize core data structures */
  if (!(Y = (unsigned char ***) UTL_MEM_ALLOC( sizeof( unsigned char **) *
nFType)) )
            return 0;
  for (F = 0; F < nFType; F++) {
    if (!(Y[F] = (unsigned char **) UTL_MEM_ALLOC( sizeof( unsigned char *) * nR)) )

return 0;
    for (R = 0; R < nR; R++)
      if (!( *( (Y[F]) + R ) = (unsigned char *) UTL_MEM_ALLOC( sizeof( unsigned
char )
            * (*Xsize[F ]) + R ) )) return 0;
  }
  return 1;
}
int CountLines()
{
int i;
char *foo;
/* note that CountLines returns one less than the actual number */
i=0;
while ( -1 != UTL_SCAN_GETS( InputSourceFile, "\\", "#", &foo)) i++;
rewind(InputSourceFile);
return i;
```

```
}
static int initXarrays ()
{
    int F, i;
    if (!(Xfile = (char **) UTL_MEM_ALLOC( sizeof( char* ) * nR ))) return 0;
    if (!(Xname = (char **) UTL_MEM_ALLOC( sizeof( char* ) * nR ))) return 0;
    if (!(nX = (int*) UTL_MEM_ALLOC( sizeof( int ) * nR ))) return 0;
    if (!(Xct = (int*) UTL_MEM_ALLOC( sizeof( int ) * nR ))) return 0;
    for (i = 0; i < nR; i++) { Xfile[i] = 0; Xname[i] = 0; nX[i] = 0; Xct[i] = 0; }
    if (!(X = (unsigned char ****) UTL_MEM_ALLOC( sizeof( unsigned char ***) * nFType)) )
            return 0;
        for (F = 0; F < nFType; F++) {
            if (!(X[F] = (unsigned char ***) UTL_MEM_ALLOC( sizeof( unsigned char **) * nR)) )
                return 0;
            memset( X[F], 0, sizeof( unsigned char **) * nR );
        }
        if (!(Xsize = (int **) UTL_MEM_ALLOC( sizeof( int * ) * nFType ))) return 0;
        for (F = 0; F < nFType; F++) {
            if (!(Xsize[F] = (int *) UTL_MEM_ALLOC( sizeof( int ) * nR ))) return 0;
            for (i = 0; i < nR; i++) *(Xsize[F] + i) = 0;
        }
        return 1;
}
static int initXfiles( i, SideChainsAreSame )
/* reads X file data (reactant descriptors from 2nd comment line of X file ) */
int i, *SideChainsAreSame;
{
    char *foo, *pch;
    if ( -1 == UTL_SCAN_GETS( MasterFile_File, "\\", "#", &foo)) return 0;
    if (Xfile[i]) {
/* if this X file is same as last, nothing to do */
```

```c
            if (!strcmp( Xfile[ i ], foo ) ) return 1;
            *SideChainsAreSame = FALSE;
            UTL_MEM_FREE( Xfile[i] );
        }
        Xfile[ i ] = UTL_STR_SAVE(foo);
        if (! (InputSourceFile = fopen(Xfile[i],"r"))) {
            fprintf( stdout, "Could not open variation file %s\n", Xfile[i] );
            return 0;
        }
/* reading COMMENT lines to get USER_NAME value for matching */
        if ( -1 == UTL_SCAN_GETS( InputSourceFile, "\\", "", &foo)) return 0;
        if ( -1 == UTL_SCAN_GETS( InputSourceFile, "\\", "", &foo)) return 0;
        if (Xname[i]) UTL_MEM_FREE( Xname[i] );
        Xname[i] = 0;
        pch = strstr( foo, "USER_NAME=" );
        pch += strlen( "USER_NAME=" );
        if (!(Xname[i] = UTL_STR_SAVE( pch ) )) return 0;
        fclose( InputSourceFile );
        return 1;
}
int StartFromBitset()
{
    void *CS_PRDCT_BITSET_OPEN();
    if ( !( bitset = CS_PRDCT_BITSET_OPEN( BitsetFile, MasterRecord))) return 0;

if ( !RetrieveMasterFileFromBitset(bitset,
                    &MasterFile,
                    &MasterRecord, /*in master file*/
                    0,
                    0,
                    0,
                    0,
                    0,
```

0,
0,
0,
0,
0,
0,
0,
0,
0,
0,
0,
0 ) ) return 0;

return 1;

}

/* 1/7/97 DEP: allow reading of bitsets. Since the masterfile must be
        read in any case, the bitset only generates "Dead_Products" */
int InitMasterFile()
/* Read the master file record which is requested;
        failure if it does not match the input line info */
{
  int i, d, size, rxMatch, irx, ns, *Sym;
  char *foo;
  int *fooi;
  if (BitsetFile && ! StartFromBitset()) return 0;
  if (! (MasterFile_File = fopen(MasterFile,"r"))) {
        fprintf( stdout, "%s (master file) not found.\n", MasterFile );
        return 0;
  }
  rxMatch = irx = 0;
  while ( !rxMatch) {
        if ( -1 == UTL_SCAN_GETS( MasterFile_File, "\\", "#", &foo)) return 0;
        if ( strstr(foo,"Reaction class ")) {
              irx++;

```c
        if (bitset && irx > MasterRecord) return 0; /* the right record did not match */
/* preliminary match if (1) Reaction Needed matches and (2)
        NO_core must be present if NoCore is TRUE (or vice versa) */
    rxMatch = ( irx >= MasterRecord && strstr( foo, ReactionNeeded )
            && ((!NoCore && !strstr( foo, "NO_core" ) )
            || ( NoCore && strstr( foo, "NO_core" ) ) ) );
    }
/* if preliminary match, check rest of .mf record -- first # reactants */
    if (rxMatch) {
/* skip name, record / compare number of reagents */
        if ( -1 == UTL_SCAN_GETS( MasterFile_File, "\\", "#", &foo)) return 0;
        if ( -1 == UTL_SCAN_GETS( MasterFile_File, "\\", "#", &foo)) return 0;
        if ( ! UTL_STR_ATOI(foo, &d) )          return 0;
        if (!nR) {
            if (SideChainOnly && d != 1) {
                fprintf( stdout, "Side Chain only but .mf file references more than one side chain.\n" );
                return 0;
            }
            nR = d;
            if (!initXarrays()) return 0;
        }
        rxMatch = nR == d;
    }
    if (rxMatch) {
/* skip fgpt stuff, record core and side chain file stuff */
        if ( -1 == UTL_SCAN_GETS( MasterFile_File, "\\", "#", &foo)) return 0;
        if ( -1 == UTL_SCAN_GETS( MasterFile_File, "\\", "#", &foo)) return 0;
        if ( -1 == UTL_SCAN_GETS( MasterFile_File, "\\", "#", &foo)) return 0;
        if (Corefile) UTL_MEM_FREE( Corefile );
        Corefile = UTL_STR_SAVE(foo);
        if ( -1 == UTL_SCAN_GETS( MasterFile_File, "\\", "#", &foo)) return 0;
        if ( ! UTL_STR_ATOI(foo, &StartCore   ) )          return 0;
```

```
    if ( -1 == UTL_SCAN_GETS( MasterFile_File, "\\", "#", &foo)) return 0;
    if ( -1 == UTL_SCAN_GETS( MasterFile_File, "\\", "#", &foo)) return 0;
    for (i = 0; i < nR; i++) if (!initXfiles( i, &SideChainsAreSame ) ) return 0;
  }
 } /* read .mf file until we have a matching reaction */
 return 1;
}
static int ReadXs() {
/* reads all topmer fields from all current Xn files */
 int R, F, i, n, ns, realloc, Fd;
 char *CTOPS, *line, *fptr;
 double *dp, **sdptr;
 unsigned char **uc;
 combi = 1.0;
/* skip the following lengthy stuff if side chains are all the same */
 if (SideChainsAreSame && X[0]) return 1;
 for (R = 0; R < nR; R++) {
  if (! (InputSourceFile = fopen(Xfile[R],"r"))) return 0;
  n = CountLines();
  realloc = n != nX[ R ];
  combi *= (double) n;
  if (realloc && nX[ R ] )
    for (F = 0; F < nFType; F++) {
      for (i = 0; i < nX[R]; i++) UTL_MEM_FREE( *(X[F] + R) + i );
      UTL_MEM_FREE( X[F] + R );
    } nX[ R ] = n;
  if (realloc) for (F = 0; F < nFType; F++)
      if (!(*(X[F] + R) = (unsigned char **)
           UTL_MEM_ALLOC( sizeof( unsigned char *) * nX[R]) )) return 0;
/* starts reading at line 2! */
  for (i = 0; i < nX[R]; i++) {
```

```c
        if (-1 == UTL_SCAN_GETS( InputSourceFile, "\\", "#", &line))
            goto error;
/* generate info for left-to-right read */
        for (F = 0; F < nFType; F++) FOrder[ F ] = strstr( line, FTypes[ F ] );
        do {
            for (Fd = -1, F = 0, fptr = 0; F < nFType; F++)
                if (FOrder[F] && (!fptr || FOrder[F] < fptr)) {fptr = FOrder[F]; Fd = F;}
            if (fptr) {
                fptr += strlen( FTypes[ Fd ] ) + 1; /*skipping "CTOPS="*/
                UTL_SCAN_TOKENIZE(fptr,';','\\');
                UTL_SCAN_TOKENIZE(fptr,'>','\\');
                if (!ReadAField( fptr, Xsize[ Fd ] + R, *(X[Fd] + R) + i )) goto error;
                FOrder[ Fd ] = 0;
            }
        } while (fptr);
    }
    fclose( InputSourceFile );
/* set up X - Y distance vectors */
    if (realloc) for (F = 0; F < nFType; F++) for (ns = 0; ns < nSym; ns++) {
        sdptr = X2Y[ns];
        if (sdptr[R]) UTL_MEM_FREE( sdptr[R] );
        if (!( sdptr[ R ] = (double *) UTL_MEM_ALLOC( sizeof( double ) * nX[R] ) ))
            return 0;
        for (i = 0, dp = sdptr[R]; i < nX[R]; i++) *dp++ = -1.0;
    }
  }
}
return 1;
error:
    fprintf( stdout, "topsim failed reading line %d of %s.\nLast line read was %s.\n",
        i, Xfile[R], line );
    return 0;
}
```

```
char **ParseQuotedString( SDetails, nDetail, Weights )
char *SDetails;
int *nDetail;
double **Weights;
{
  char *pch, **ppch, *wch, **Details;
  int i;
  double *wt;
/* first trim string to remove leading/trailing spaces and quotes */
    while (*SDetails == '"' || *SDetails == ' ') SDetails++;
    pch = SDetails + strlen( SDetails ) - 1;
    while (*pch == '"' || *pch == ' ') *pch-- = '\0';
/* each space is token delimiter */
    for (i = 0, pch = SDetails; *pch; pch++)
      if (*pch == ' ') i++;
    *nDetail = i+1;
    if (!(Details = (char **) UTL_MEM_ALLOC( sizeof( char * ) * (*nDetail) ) ))
           return 0;
    if (Weights) {
       if (!(*Weights = (double *) UTL_MEM_ALLOC( sizeof( double ) * (*nDetail) ) ))
return 0;
       wt = *Weights;
    }
    pch = SDetails;
    if (*pch == '"') pch++;
    for (i = 0, ppch = Details; i < *nDetail; i++, ppch++) {
       UTL_SCAN_TOKENIZE(pch,' ','\\');
       *ppch = UTL_STR_SAVE( pch );
       if (Weights) {
/* note, the copy is now being modified */
           if ((wch = strstr( *ppch, "=" )) ) {
               if (!isweight( wch + 1 )) return FALSE;
               *wt = atof( wch + 1 );
```

```
        *wch = '\0';
      }
      else *wt = 1.0;
      wt++;
    }
    pch += strlen( pch ) + 1;
  }
  return( Details );
}
int isweight( s )
/* returns true if value is a positive decimal value */
char *s ;
{
  char *c;
  for (c = s; *c; c++) if (!isdigit( *c ) && ( *c != '.' )) {
      fprintf( stdout, "Bad weight value: %s. Aborting.\n", s );
      return( FALSE );
  }
  return( TRUE );
}
int ParseRxn()
/* parses complex input descriptions */
{
  char **ParseQuotedString(), **scratch;
  int nRW, i, nX;
  double wtsum;
/* parse field type information or set up standard (steric) type only */
  if (FieldTypes) {
      if (!(FTypes = ParseQuotedString( FieldTypes, &nFType, &FWeights ) )) return 0;
/* scale to average weight of unity */
      for (i = 0, wtsum = 0.0; i < nFType; i++) wtsum += FWeights[i];
      wtsum /= (double) nFType;
      for (i = 0; i < nFType; i++) FWeights[ i ] /= wtsum;
```

```
}
else {
  nFType = 1;
  if (!( FTypes = (char **) UTL_MEM_ALLOC( sizeof( char * ) ) )) return 0;
  if (!( *FTypes = UTL_STR_SAVE( "CTOPS" ) )) return 0;
  if (!( FWeights = (double *) UTL_MEM_ALLOC( sizeof( double ) ) )) return 0;
  *FWeights = 1.0;
}
if (!(FOrder = (char **) UTL_MEM_ALLOC( sizeof(char *) * nFType ) )) return 0;
/* parse any reaction type information present */
nR = 0;
if (SideChainOnly) {
    NoCore = TRUE;
    return 1;
}
if (!ReactionNeeded) return 0;
if (ScratchDetails) {
  if (!(ReactionDetails = ParseQuotedString( ScratchDetails, &nDetail, NIL ) )) return 0;
  nR = nDetail;
  if (!initXarrays()) return 0;
}
if (!(FROrder = (char **) UTL_MEM_ALLOC( sizeof(char *) * nFType * nR ) )) return 0;
/* parse any user-provided variation weighting */
CoreWeight = 1.0;
if (!( RWeights = (double *) UTL_MEM_ALLOC( sizeof( double ) * nR ) )) return 0;
if (XWeights) {
    if (!(scratch = ParseQuotedString( XWeights, &nRW, NIL ) )) return 0;
/* scratch will just be unfreed memory */
    nX = nR + (NoCore ? 0 : 1);
    if (nRW != nX ) {
        fprintf( stdout, "Mismatch between count of xweights (%d) and needed (%d).\n", nRW, nX );
```

```
        return 0;
    }
    for (i = 0, wtsum = 0.0; i < nR; i++) if (!isweight( scratch[ i ] )) return FALSE;
        else {
            RWeights[ i ] = atof( scratch[ i ] );
            wtsum += RWeights[ i ];
        }
    if (!NoCore) if (!isweight( scratch[ nR ])) return FALSE;
        else {
            CoreWeight = atof( scratch[ nR ] );
            wtsum += CoreWeight;
        }
    wtsum /= (double) nX;
    for (i = 0; i < nR; i++ ) RWeights[ i ] /= wtsum;
    if (!NoCore) CoreWeight /= wtsum;
  }
  else for (i = 0; i < nR; i++) RWeights[ i ] = 1.0;
  return 1;
}
int ReadEverything()
{
  if (!MasterFile && !BitsetFile) return 0;
  if (!ParseRxn()) return 0;
  setbits_nbits_Init();
  if (!InitMasterFile() ) return 0;
  if (!InitCore() ) return 0;
  if (!WhatsTheDifference()) return 0;
  if (!RetrieveInput() ) return 0;
  return 1;
}
static int InitSym( nsym )
int nsym;
```

```c
{
/* sets up symmetries to consider as described for core
   ONLY 2 reactants considered for now!
   assumes that CoreNow is pointing to the appropriate structure */
    int i, F, maxsym;
    double **x2y;
/* get symmetry from current core molecule if not supplied by caller */
    nSym = nsym;
    if ( !nSym ) {
        if ((!strstr( CoreNow, "SYM=" )) || (strstr(CoreNow, "SYM=0")) ) nSym = 1;
        if (strstr(CoreNow, "SYM=1")) nSym = 2;
/* add more categories here */
    }
        for (i = 0; i<nSym; i++) CoreSyms[ i ] = 1;
/* allocate distance arrays to max possible for nR */
    if (!X2Y) {
        for (maxsym = 1, i = 0; i < nR; i++) maxsym *= (i+1);
        if (!(X2Y = (double ***) UTL_MEM_ALLOC( sizeof( double **) * nFType ) ))
return 0;
        for (i = 0; i < maxsym; i++) {
            if (!(X2Y[i] = (double**) UTL_MEM_ALLOC( sizeof( double *) * nR) )) return 0;
            memset( X2Y[i], 0, sizeof( double *) * nR );
        }
    }
    return nSym;
}
int ReadCoreTopomers( CoreOK )
int *CoreOK;
{
/* returns 1 unless fatal error. Sets CoreOK to TRUE if this mf entry is OK
   Also sets up symmetry considerations (which are core structure dependent).
   assumes that CoreNow is pointing to the appropriate structure */
    int foo, i, R, F, Fd, Rd, rf, skipcore, ns, *Sym;
```

```c
char label[15], *nxTop, *cstart, *fptr;
char *cnames[] = {"NX=","NY=","NZ=","CX=","CY=","CZ="};
double coo;
double atof();
skipcore = NoCore;
/* always consider both matches iff no core */
if(skipcore) InitSym( nR );
    else skipcore = ! InitSym(0);
/* check for any symmetry-allowed rxn by rxn match of all reactant name "details" */
for (ns = 0; ns < nSym; ns++) if (CoreSyms[ns]) {
    Sym = *(SymList + ns);
    *CoreOK = TRUE;
    if (!SideChainOnly)
        for (i = 0; i < nR && *CoreOK; i++)
            if (!strstr( ReactionDetails[ Sym[ i ] ], Xname[ i ] ))
                *CoreOK = FALSE;
    if (*CoreOK) break;
}
if (skipcore || CoreIsSame || !(*CoreOK )) return 1;
nxTop = CoreNow;
/* read left-to-right, so record all starting points;
   assume that coords are bunched and appear only once
*/
for (F = 0; F < nFType; F++) for (R = 0; R < nR; R++) {
    sprintf( label, "%s%d", FTypes[ F ], R + 1 );
    if (!( FROrder[ F * nR + R ] = strstr( nxTop, label ) ) ) {
/* some requested datum missing; then this core entry has no topomer data; use it */
        *CoreOK = 0;
        return 1;
    }
}
cstart = strstr( nxTop, cnames[ 0 ] );
do {
```

```c
/* find next datum in left-to-right order */
    for (F = 0, fptr = 0; F < nFType; F++) for (R = 0; R < nR; R++) {
        rf = F * nR + R;
        if (FROrder[rf] && (!fptr || FROrder[rf] < fptr)) {fptr = FROrder[rf]; Fd = F; Rd = R;}
    }
    if (cstart && (!fptr || cstart < fptr)) {fptr = cstart; Fd = -1; }
    if (fptr) {
/* unpack next piece of data to proper location */
        if (Fd >= 0) {
/* then datum is a field */
            fptr += strlen( FTypes[ Fd ] ) + 2; /*skipping "CTOPn=" */
            UTL_SCAN_TOKENIZE(fptr,';','\\');
            UTL_SCAN_TOKENIZE(fptr,'>','\\');
            if (!ReadAField( fptr, Xsize[ Fd ] + Rd, Y[Fd] + Rd )) return 0;
            FROrder[ Fd * nR + Rd ] = 0;
        }
        else {
            for (i = 0; i < 6; i++) {
/* the next data are coordinates */
/* read coords, save as distances squared */
                cstart = strstr( cstart, cnames[i]);
                if (!cstart) {
/* then this core entry has no topomer data */
                    *CoreOK = 0;
                    return 1;
                }
                cstart += strlen(cnames[i]);
                UTL_SCAN_TOKENIZE(cstart,';','\\');
                UTL_SCAN_TOKENIZE(cstart,'>','\\');
                coo = CXcoords[ i ] - atof(cstart);
                CXdiffsq[ i ] = coo * coo * DWeight;
                cstart += strlen( cstart ) + 1;
```

```
        }
        cstart = 0;
       }
    }
} while (fptr);
 return 1;
}
int CoreMatches( CoreOK )
int *CoreOK;
{
/* returns 1 unless fatal error. Sets CoreOK to FALSE if no compound having
       this core can possibly match */
  int F, R, i, ns, *Xct, ct;
  double sqrt(), totd, xount, cdiff;
  unsigned char *ptr, *qtr;
  if (NoCore || CoreIsSame) {
       *CoreOK = TRUE;
       return 1;
  }
  /* can check for coordinate discrepancy fast! */
  for (i = 0, cdiff = 0.0; i < 6; i++) cdiff += CXdiffsq[i];
  if (cdiff > Distance) {
       *CoreOK = FALSE;
       return 1;
  }
  for (F = 0, totd = cdiff; F < nFType; F++) for (R = 0; R < nR; R++) {
       if (totd > Distance) break;
       ptr = (unsigned char *) *(Y[ F ] + R);
       qtr = (unsigned char *) *(Yin[F] + R);
       if (!ptr || !qtr) xount = 999999.0;
       else for(xount=0.0, i=0; i < *(Xsize[F] + R); i++, ptr++, qtr++)
           xount += Dist[ *ptr & 0x0F   ][ *qtr & 0x0F   ]
              + Dist[ (*ptr & 0xF0) >> 4][ (*qtr & 0xF0) >> 4] ;
```

```
        totd += xount * FWeights[ F ] / (double) nR;
   }
   CoreDistance = totd * CoreWeight;
   *CoreOK = totd <= Distance;
   return 1;
}
int FindXMatches () {
   int R, F, i, ns, ct, *Sym, size, what ;
   double totd, d, **sdptr, *dptr, xount;
   unsigned char *ptr, *qtr;
/* reinitialize indices for permuting over all products --
       code is general for any number of variable positions */
   for (i = 0; i < nR; i++) Xct[i] = 0;
               AddressSize(nR, nX, &size);
               size = (size + 31 )/32 * 4;
   if (bitset) /* assumes actuallsizes matches current sizes!*/
           {
               if (!(Dead_Products = (int *) UTL_MEM_ALLOC(size))) return 0;
               CS_PRDCT_BITSET_TO_RAW( bitset, Dead_Products, 0);
               not_here(Dead_Products,size );
           } while ( TRUE ) {
/* exit elsewhere when all products are enumerated */
           IndexesToAddress( nR, nX, &what, Xct);
           if (Dead_Products &&
               TestDead(0, what) ) goto tupledone; /* not doing this one! */ for (ns = 0; ns < nSym; ns++) if (CoreSyms[ns]) {
/* process all symmetries of current side chain combo */
                   Sym = *(SymList + ns);
                   sdptr = *(X2Y + ns);
                   for (R = 0, totd = CoreDistance;  R < nR; R++) {
```

```
            if (totd > Distance) break;
/* compute next distance if not already done -- DEP knows how this works! */
            dptr = (*(sdptr + R )+Xct[R]);
            if ((*dptr) < 0.0) for (F = 0; F < nFType; F++ ) {
                ptr = (unsigned char *) *( *(X[F] + R) + Xct[ R ]);
                qtr = (unsigned char *)   *(Xin[ F ] + Sym[ R ]) ;
                if (!ptr || !qtr) {*dptr = 999999.0; break;}
                else {
                    for(xount=0.0, i=0; i < *(Xsize[F] + R); i++, ptr++, qtr++)
                        xount += Dist[ *ptr & 0x0F   ][ *qtr & 0x0F   ]
                            + Dist[ (*ptr & 0xF0) >> 4][ (*qtr & 0xF0) >> 4] ;
                    *dptr += xount * FWeights[ F ];
                }
            }
            totd += *dptr * RWeights[ R ];
        }
/* if hit, write it out */
        if (totd <= Distance) {
            if (NotBitOutput || nR != 2) {
/* ASCII index form of output -- also REQUIRED if more than 2 varying elements */
                if (!OutputFile && !OpenOutputFile() ) return 0;
                for (R = 0; R < nR; R++) fprintf( OutputFile, "%6d ", Xct[R] + 1 );
                fprintf( OutputFile, "%6d%8.2f%8.2f%8.2f\n", StartCore,
                    sqrt(totd), sqrt(CoreDistance), sqrt(totd - CoreDistance) );
            }
            else {
                if (!Good_Products ) {
                    if (!(Good_Products = (int *) UTL_MEM_ALLOC( size ) )) return 0;
                    memset( Good_Products, 0, size );
                }
                FlagProduct(Good_Products, 0, 0, what );
            }
```

```
        nout++;
        if (NoMorehitsPlease && nout >= NoMorehitsPlease) goto done;
/* output only one acceptable symmetry per product */
        goto tupledone;
      }
    }
/* generate next index tuple, AKA candidate product */
tupledone:
      ct = nR - 1;
      while ( TRUE ) {
        Xct[ ct ] ++;
        if (Xct[ ct ] < nX[ ct ]) break;
/* finished when first index exceeds limit -- the other exit */
        if (ct == 0) goto done;
        Xct[ ct ] = 0;
        ct--;
      }
  }
done:
/* output any products from this dataset */
  if (NotBitOutput || nR != 2) {
    if (OutputFile) fclose(OutputFile);
    OutputFile = 0;
  }
  else if (Good_Products) {
      WriteStdFile();
      UTL_MEM_FREE( Good_Products );
      Good_Products = (int*) 0;
  }
  return 1;
}
int MakeOutputFileName() {
/* a run may produce multiple files, and the user probably can't tell,
``` so append a sequence _# to subsequent base names */

```
if (!nOutFiles) {
    sprintf( OutputFileName, "%s", OutputFileBase );
/* get base name ready for next call */
    strtok( OutputFileBase, "." );
}
    else sprintf( OutputFileName, "%s_%d.%s", OutputFileBase,
        nOutFiles, OutputFileBase + strlen(OutputFileBase) + 1 );
nOutFiles++;
}
int WriteStdFile() {
/* writes out the bit set of products */
int sizes[2];
int allocSizes[2] ;
int numInSites[2] ;
void *compressed ;
int total ;
    sizes[0] = nX[0] ;
    sizes[1] = nX[1] ;
    numInSites[0] = numInSites[1] = -1 ;
    allocSizes[0] = allocSizes[1] = -1 ;
    compressed = NIL;
    total    = 0;
    MakeOutputFileName();
    WriteOutCheckPointFile( OutputFileName,
        MasterFile,
        MasterRecord,
        comline,
        Good_Products,
        0,
        2,
        sizes,
        allocSizes,
```

```
            nout,
            numInSites,
            total,
            compressed);
}
int ReadNextCore( SideChainsAreSame, CoreIsSame )
int *SideChainsAreSame;
int *CoreIsSame;
{
/* continues reading through master file for more matching Reaction Classes.
        If the side chain files have the same name, can skip rebuild of X diffs */
    char *foo;
    int i, d, rxMatch = 0, val;
    if (AllCores) {
        if ( -1 == UTL_SCAN_GETS( CoreFile_File, "\\", "#", &foo)) fclose( CoreFile_File );
        else {
/* get next core ready and quit */
            CoreNow = UTL_STR_SAVE(foo);
            *SideChainsAreSame = TRUE;
            StartCore++;
            return 1;
        }
    }
    while ( !rxMatch ) {
        if ( -1 == UTL_SCAN_GETS( MasterFile_File, "\\", "#", &foo)) return 0;
/* preliminary match if (1) Reaction Needed matches and (2)
        NO_core must be present if NoCore is TRUE (or vice versa) */
        rxMatch = ( strstr(foo,"Reaction class ") && strstr(foo, ReactionNeeded)
            && ((!NoCore && !strstr( foo, "NO_core" ) )
                || ( NoCore && strstr( foo, "NO_core" ) ) ) );
        if (feof(MasterFile_File)) return 0;
/* skip name, record number of reagents */
```

```
if (rxMatch) {
    if ( -1 == UTL_SCAN_GETS( MasterFile_File, "\\", "#", &foo)) return 0;
    if ( -1 == UTL_SCAN_GETS( MasterFile_File, "\\", "#", &foo)) return 0;
    if ( ! UTL_STR_ATOI(foo, &val) ) return 0;
    if (val != nR) rxMatch = 0;
} if (rxMatch) {
/* skip fgpt stuff, record core and side chain file stuff */
    if ( -1 == UTL_SCAN_GETS( MasterFile_File, "\\", "#", &foo)) return 0;
    if ( -1 == UTL_SCAN_GETS( MasterFile_File, "\\", "#", &foo)) return 0;
    if ( -1 == UTL_SCAN_GETS( MasterFile_File, "\\", "#", &foo)) return 0;
    *CoreIsSame = TRUE;
    if (strcmp( foo, Corefile )) {
        *CoreIsSame = FALSE;
        UTL_MEM_FREE( Corefile );
        Corefile = UTL_STR_SAVE(foo);
    }
    if ( -1 == UTL_SCAN_GETS( MasterFile_File, "\\", "#", &foo)) return 0;
    if ( ! UTL_STR_ATOI(foo, &val ) )           return 0;
    if (val != StartCore ) *CoreIsSame = FALSE;
    StartCore = val;
    if (! *CoreIsSame ) {
        if (CoreFile_File) fclose(CoreFile_File);
        if (! (CoreFile_File = fopen(Corefile,"r"))) return 0;
        i=0;
        while ( i < StartCore ) {
            if ( -1 == UTL_SCAN_GETS( InputSourceFile, "\\", "#", &foo)) return 0;
            if (AllCores) break;
            i++;
        }
        CoreNow = UTL_STR_SAVE( foo );
    }
```

```
      if ( -1 == UTL_SCAN_GETS( MasterFile_File, "\\", "#", &foo)) return 0;
      if ( -1 == UTL_SCAN_GETS( MasterFile_File, "\\", "#", &foo)) return 0;
      *SideChainsAreSame = TRUE;
      for (i = 0; i < nR; i++) if (!initXfiles( i, SideChainsAreSame ) ) return 0;
    }
  }
  return 1;
}
/* this belongs in the utl module, actually */
int MakeComLine( char *line, int len, int argc, char **argv)
{
  int i, nch, totch = 0;
  sprintf(line,"%s ",argv[0]);
  for(i=1;i<argc && totch <= len;i++)
  {
    nch = strlen(line);
    line += nch;
    totch += nch;
    if (totch < len ) sprintf(line,"%s ",argv[i]);
  }
}
int CheckPointProgram(void) {
  fprintf(stderr,"CheckPointProgram() is a lonely stub in topsim.c!\n");
}
int main( argc, argv )
int     argc;
char    **argv;
{
        int processing;
        if( !ParseArguments( argc, argv ) )
                goto SyntaxError;
        MakeComLine( comline, 2048, argc, argv );
        if (!ReadEverything())   goto FailureExit;
```

```
        processing = 1;
        while (processing) {
            if (!ReadCoreTopomers( &CoreOK )) goto FailureExit;
            if (CoreOK && !CoreMatches( &CoreOK )) goto FailureExit;
            if (CoreOK && !ReadXs()) goto FailureExit;
            searched += combi;
            if (CoreOK && !FindXMatches()) goto FailureExit;
            totnout += nout;
            nout = 0;
            processing = ReadNextCore( &SideChainsAreSame, &CoreIsSame ) &&
                (!NoMorehitsPlease || nout < NoMorehitsPlease);
        }
        fprintf(stdout, "Normal Exit: %d of %f are neighbors\n", totnout, searched );
        UserAborted ? exit(ErrorExit) : exit(GoodExit);
SyntaxError:
        exit(1);
FailureExit:
        exit(ErrorExit);
}
/*
    numVariations is number of dimensions Y_01, Y_02 etc (normally 2)
    dsize contains the nY_01, nY_02 etc
    address is the bit number (0 to N-1)
    choices will contain the offsets (0 based) of Y_01, Y_02 etc. on return
*/
int AddressToIndexes(int numVariations, int *allPtr, int address, int *chPtr )
{
        for ( chPtr += (numVariations - 1 ), allPtr += (numVariations - 1) ;
            numVariations-- ;
            allPtr--, chPtr-- )
        {
            *chPtr = address % *allPtr;
            address = address / *allPtr;
```

```
        }
        return 1;
} int IndexesToAddress(int numVariations, int *allPtr, int *address, int *ind)
{
int   i ;
int   indx = 0 ;
        for (i=0;i<numVariations;i++)
           indx += indx * allPtr[i] + ind[i];
        *address = indx;
        return 1 ;
}
int AddressSize(int numVariations, int *allPtr, int *size)
{
  for ( *size = 1 ; --numVariations; allPtr++) *size *= *allPtr;
  return 1;
} int not_here( what, nbytes )
unsigned char *what;
int nbytes;
{
  for ( ; nbytes; --nbytes) *what++ = ~ *what;
  return 1;
}
```

Appendix "T"

```
@macro FragCTOPS ChSp

#=================================================================
=============================================
# Entry point for Web-based topomeric search initialization

# sets up a set of topomeric searches, by identifying topomer data arising from
# substructural searching of SLN patterns found in topfrag.tbl to the
# query structure and generating the topomeric data and search command file entry
# for all resulting fragmentations of the query structure.

#    The Query SLN(s) are assumed to be referenced by $CS_QUERY;
#    The file(s) to be searched are referenced by $CS_DATASET (space separated)
#    The directory where command files are to be written is $CS_TEMPDIR
#    The GUI parameters are to be in $CS_PARAMETERS
#    The name of the output file(s) is to be in $CS_OUTPUT
# read in the data
globalvar CTOP
globalvar ACD!TopInited
localvar fcmdn fcmd tsln dist t base mf mfo nln nxid ferr ferrn rxids doit
# check the input parameters
    setvar ferrn %cat( $CS_TEMPDIR "/CSerror.log" )
    setvar ferr %open( $ferrn "w" )
    setvar flogn %cat( $CS_TEMPDIR "/topfrag.log" )
    setvar flog %open( $flogn "w" )
    setvar fcmdn %cat( $CS_TEMPDIR "/CSCommands.cmd" )
    setvar fcmd %open( $fcmdn "w" )
    if %not( $fcmd )
        %write( $ferr could not open temp file $fcmdn to write ChemSpace search
```

```
cmds. Quitting ) >$nulldev
       return
    endif
  for tsln in $CS_QUERY
    if %pos( "." $tsln )
       setvar nogood TRUE
       if %pos( "<" $tsln )
          if %gt( %pos( "." $tsln ) %pos( "<" $tsln ) )
             setvar nogood
          endif
       endif
    endif
    if $nogood
       %write( $ferr Topomeric searches require a monomolecular search target.
Quitting ) >$nulldev
       goto error
    endif
  endif
  %write( $flog QUERY: $tsln >$nulldev
  setvar dist %CS_param_parse( distance $CS_PARAMETERS 91.0 )
  if %not( $dist )
     %write( $ferr No topomeric distance provided. Quitting ) >$nulldev
     goto error
  endif
  setvar priority %CS_param_parse( priority $CS_PARAMETERS 3.0 )
  if %not( $priority )
     %write( $ferr No reaction priority provided. Quitting ) >$nulldev
     goto error
  endif
  %write( $flog Fragment Priority: $priority ) >$nulldev
  setvar CTOP[ ONLY1 ] %CS_param_parse( only_subs $CS_PARAMETERS )
  if $CTOP[ ONLY ]
     %write( $flog Matching Side Chain Only ) >$nulldev
  endif
```

```
setvar CTOP[ WEIGHTS ] %CS_param_parse( xweights $CS_PARAMETERS )
if $CTOP[ WEIGHTS ]
    %write( $flog User Specified Weighting as: $CTOP[ WEIGHTS ] ) >$nulldev
    for w in $CTOP[ WEIGHTS ]
        setvar pats %search2d( $tsln %arg( 1 %set_unpack( $w ) ) NoDup 0 y )
        if %not( $pats )
            %write( $ferr Weighted search for fragment %arg( 1 %set_unpack( $w ) )
not
in $tsln -- can't happen! ) >$nulldev
            goto error
        else
            if %gt( %count( $pats ) 1 )
                %write( $flog NOTE: Multiple hits for weighting fragment %arg( 1
%set_unpack( $w ) ) in $tsln ) >$nulldev
            endif
        endif
    endfor
endif
setvar CTOP[ CHBD ] %CS_param_parse( hbonding $CS_PARAMETERS )
if $CTOP[ CHBD ]
    %write( $flog FIELDS include Hydrogen Bonding with weight of $CTOP[ CHBD ]
)
>$nulldev
endif
zap m1 >$nulldev
%sln_to_mol( m1 $tsln ) >$nulldev
if %molempty( m1 )
    %write( $ferr SYBYL cannot handle search target (SLN is: $tsln ).
Quitting ) >$nulldev
    goto error
endif
setvar t %mol_info( m1 NATOMS )
FILLVALENCE M1(*) H 1.0 1.5 1.0 1.5 >$nulldev
```

```
if $CTOP[ ONLY1 ]
    if %neq( %mol_info( m1 NATOMS ) %math( $t + 1 ) )
        %write( $ferr Side chain search but target $tsln has other than one
unfilled valence ) >$nulldev
        goto error
    endif
else
    if %neq( %mol_info( m1 NATOMS ) $t )
        %write( $ferr Search Target $tsln has unfilled valences. Quitting )
>$nulldev
        goto error
    endif
endif if $CTOP[ ONLY1 ]
only one side chain to model is a special case
    CTOP!SideChainOnly $fcmd $ferr $flog $dist
else
# check for custom topomer fragmentation table or selection
    setvar tftabn
    setvar tfrows
    if $CS_TOPFRAG
        setvar t %pos( "_" $CS_TOPFRAG )
        if %not( $t )
            %write( $ferr Custom table name $CS_TOPFRAG missing an "_" ) >$nulldev
            goto error
        else
            setvar tftabn %substr( $CS_TOPFRAG 1 %math( $t - 1 ) )
            setvar tfrows %substr( $CS_TOPFRAG %math( $t + 1 ) )
        endif
    endif
    if %set_and( "%set_create( %table_name() )" TOPFRAG )
        table close TOPFRAG
    endif
```

```
if %not( $tftabn )
    setvar tftabn %cat( $DSERV_TB topfrag.tbl )
endif
table recall $tftabn > $nulldev
if %not( %set_and( "%set_create( %table_name() )" TOPFRAG ) )
    %write( $ferr $tftabn not found. Quitting ) > $nulldev
    goto error
endif
%write( $flog Topomer fragmentation table is %cat( $DSERV_TB topfrag.tbl
) ) > $nulldev
# initialize random file name sequence generator
    setvar t %time()
    setvar base %rand( %substr( "$t" %math( %strlen( "$t" ) - 6 ) 2 ) )
    TAILOR SET MAXIMIN2 MAXIMUM_ITERATIONS 1000 | |
    %write( $flog Master file(s): $CS_DATASET ) > $nulldev
    %write( $flog TOPFRAG table: $tftabn -- Row selection: $tfrows )
> $nulldev
    if %not( $tfrows )
        setvar tfrows %set_create( %range( 1 %table_attribute( NROWS ) ) )
    endif
    for rxid in %set_unpack( $tfrows )
# processing ...
        %write( $flog - - - - - - - - - - - - - - - - - - - - - - - ) > $nulldev
# chcek priority
            TABLE Default TOPFRAG
            if %gt( %rcell( $rxid PRIORITY ) $priority )
                %write( $flog TOPFRAG entry $rxid priority > $priority. ) > $nulldev
                break
            endif
            setvar CTOP[RxnCount][$rxid] 0
            if %CS_ReactantMatch( $rxid $fcmd $ferr $tsln $flog )
                %write( $flog > > > Topomer search queueing (TOPFRAG row $rxid) )
> $nulldev
```

```
            CS!Queue_Search $fcmd $rxid $dist $flog
        endif
    endfor
  endif
endfor
# may need to purge or rename error file here!
    %close( $fcmd )
    %close( $ferr )
    %close( $flog )
    return
error:
    %close( $fcmd )
# ensure nothing in search command file !
    %file_delete( $fcmdn ) > $nulldev
```

The invention claimed is:

1. A virtual library stored on computer readable medium of possible combinatorially derived product molecules generated by the following process:
   a) creating one or more files identifying one or more combinatorial reactions for one or more core structures;
   b) creating separate structural variation files (associated with the reaction identifying files) in which are listed together the structural variations representative of those reactants which will react at each variation site of each combinatorial reaction;
   c) associating with each structural variation, data, characterizing each structural variation including:
      1) characterizing data, taking into account when necessary the structures of the cores with which the structural variations would be combined in the listed combinatorial syntheses, which has not been derived from the application of molecular structural descriptors, validated as possessing a neighborhood property; and
      2) characterizing data, taking into account when necessary the structures of the cores with which the structural variations would be combined in the listed combinatorial syntheses, which has been derived from applying molecular structural descriptors, validated as possessing a neighborhood property, to the structural variations
   wherein the virtual library can be searched for product molecules having desired properties without the necessity of generating the product structures during the search.

2. A virtual library stored on computer readable medium of possible combinatorially derived product molecules generated by the following process:
   a) creating one or more files identifying one or more combinatorial reactions for one or more core structures;
   b) creating separate structural variation files (associated with the reaction identifying files) in which are listed together the structural variations representative of those reactants which will react at each variation site of each combinatorial reaction;
   c) associating with each structural variation, data, characterizing each structural variation including:
      (1) characterizing data, taking into account when necessary the structures of the cores with which the structural variations would be combined in the listed combinatorial syntheses which has not been derived from the application of molecular structural descriptors, validated as possessing a neighborhood property; and
      (2) characterizing data, taking into account when necessary the structures of the cores with which the structural variations would be combined in the listed combinatorial syntheses, which has been derived from applying molecular structural descriptors, validated as possessing a neighborhood property, to the structural variation; and
   d) associating with each core, data characterizing each core including:
      (1) characterizing data which has not been derived from application of molecular structural descriptors, validated as possessing a neighborhood property; and
      (2) characterizing data which is derived by the following additional steps:
         (a) selecting a first core;
         (b) selecting an attachment bond on the core;
         (c) topomerically aligning the core;
         (d) characterizing the core with CoMFA fields and the coordinates of the end points of the other attachment bonds;
         (e) repeating steps (b) through (d) for all attachment bonds on the core;
         (f) selecting a next core; and
         (g) repeating steps (b) through (1') for all cores
   wherein the virtual library can be searched for product molecules having desired properties without the necessity of generating the product structures during the search.

3. A virtual library stored on computer readable medium of possible combinatorially derived product molecules generated by the following process:
   a) defining chemical transformations and reagents and cores to be used to generate product molecules; and
   b) using appropriate molecular descriptors to precalculate characteristics of the component parts of all possible product molecules
   wherein the virtual library can be searched for product molecules having desired properties without the necessity of generating the product structures during the search.

4. A virtual library stored on computer readable medium of component parts of molecules and their characteristics generated by the following process:
   a) defining chemical transformations and reagents and cores to be used to specify possible product molecules; and
   b) using appropriate molecular descriptors, validated as possessing a neighborhood property, to precalculate characteristics of the component parts of all possible product molecules
   wherein all possible product molecules combinatorially derived from the component parts can be searched for, without the necessity of generating the product structures during the search, for product molecules having desired properties by searching through only a combination of the descriptors of the component parts of the product molecules.

5. A virtual library stored on computer readable medium of structural variations, cores, and their associated molecular structural descriptors generated by the following process:
   a) creating one or more files identifying one or more combinatorial reactions for one or more core structures;
   b) creating separate structural variation files, associated with the reaction identifying files, in which are listed together the structural variations representative of those reactants which will react at each variation site of each combinatorial reaction;
   c) associating with each structural variation, data, characterizing each structural variation including:
      (1) characterizing data, which has not been derived from applying at least one molecular structural descriptor, validated as possessing a neighborhood property, to the structural variations, taking into account when necessary the structures of the cores with which the structural variations would be combined in the combinatorial syntheses; and
      (2) characterizing data, which has been derived from applying at least one molecular structural descriptor, validated as possessing a neighborhood property, to the structural variations taking into account to the extent appropriate for application of the descriptor the structures of the cores with which the structural variation would be combined in the combinatorial syntheses wherein the virtual library can be searched for product molecules derived from the combinatorial assembly of the structural variations and cores having desired properties, by combining descriptors of the structural variations and cores to generate descriptors representative of the product molecules, without the necessity of generating the product structures during the search.

6. A virtual library stored on computer readable medium of structural variations, cores, and their associated molecular structural descriptors generated by the following process:
   a) creating one or more files identifying one or more combinatorial reactions for one or more core structures;
   b) creating separate structural variation files, associated with the reaction identifying files, in which are listed together the structural variations representative of those reactants which will react at each variation site of each combinatorial reaction;
   c) associating with each structural variation, data, characterizing each structural variation including:
      (1) characterizing data, which has not been derived from applying at least one molecular structural descriptor, validated as possessing a neighborhood property, to the structural variations, taking into account when necessary the structures of the cores with which the structural variations would be combined in the combinatorial syntheses; and
      (2) characterizing data, which has been derived from applying at least one molecular structural descriptor, validated as possessing a neighborhood property, to the structural variations taking into account to the extent appropriate for application of the descriptor the structures of the cores with which the structural variation would be combined in the combinatorial syntheses; and
   d) associating with each core, data characterizing each core including:
      (1) characterizing data which has not been derived from application of molecular descriptors, validated as possessing a neighborhood property; and
      (2) characterizing data which is derived by the following additional steps:
         (a) selecting a first core;
         (b) selecting an attachment bond on the core;
         (c) topomerically aligning the core;
         (d) characterizing the core with CoMFA fields and the coordinates of the end points of the other attachment bonds;
         (e) repeating steps (b) through (d) for all attachment bonds on the core;
         (f) selecting a next core; and
         (g) repeating steps (b) through (1') for all cores
   wherein the virtual library can be searched for product molecules derived from the combinatorial assembly of the structural variations and cores having desired properties, by combining descriptors of the structural variations and cores to generate descriptors representative of the product molecules, without the necessity of generating the product structures during the search.

7. A system for identifying from a virtual library stored on computer readable medium of structural variations, cores, and their associated molecular structural descriptors, product molecules derived from the combinatorial assembly of the structural variations and cores having desired properties, without the necessity of generating the product structures during the search, comprising:
   a) a general purpose programmable digital computer further comprising:
      (1) a central processing unit;
      (2) random access memory;
      (3) additional memory means for storing and accessing data; and
   b) a virtual library stored in accessible memory of structural variations, cores, and their associated molecular structural descriptors, which can be searched for product molecules derived from the combinatorial assembly of the structural variations and cores having desired properties, by combining descriptors of the structural variations and cores to generate descriptors representative of the product molecules, without the necessity of generating the product structures during the search, generated by the following process:
      (1) creating one or more files identifying one or more combinatorial reactions for one or more core structures;
      (2) creating separate structural variation files, associated with the reaction identifying files, in which are listed together the structural variations representative of those reactants which will react at each variation site of each combinatorial reaction;
      (3) associating with each structural variation, data, characterizing each structural variation including:
         (a) characterizing data, which has not been derived from applying at least one molecular structural descriptor, validated as possessing a neighborhood property, to the structural variations, taking into account when necessary the structures of the cores with which the structural variations would be combined in the combinatorial syntheses; and
         (b) characterizing data, which has been derived from applying at least one molecular structural descriptor, validated as possessing a neighborhood property, to the structural variations taking into account to the extent appropriate for application of the descriptor the structures of the cores with which the structural variation would be combined in the combinatorial syntheses.

* * * * *